US006875760B2

(12) United States Patent
Lau et al.

(10) Patent No.: US 6,875,760 B2
(45) Date of Patent: Apr. 5, 2005

(54) GLUCAGON ANTAGONISTS/INVERSE AGONISTS

(75) Inventors: Jesper Lau, Farum (DK); Peter Madsen, Bagsværd (DK); Christian Sams, Frederiksberg (DK); Carsten Behrens, Copenhagen (DK); Inge Thøger Christensen, Lyngby (DK); Behrend Frederik Lundt, Kokkedal (DK); Ulla Grove Sidelmann, Vedbæk (DK); Henning Thøgersen, Farum (DK); Anthony L. Ling, San Diego, CA (US); Michael Bruno Plewe, San Diego, CA (US); Larry Kenneth Truesdale, San Diego, CA (US); Anker Steen Jøgensen, Copenhagen (DK); Janos Tibor Kodra, Copenhagen (DK); Shenghua Shi, San Diego, CA (US)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/233,851

(22) Filed: Aug. 30, 2002

(65) Prior Publication Data

US 2003/0220350 A1 Nov. 27, 2003

Related U.S. Application Data

(62) Division of application No. 09/572,553, filed on May 16, 2000, now Pat. No. 6,503,949.
(60) Provisional application No. 60/191,685, filed on Mar. 23, 2000, and provisional application No. 60/134,415, filed on May 17, 1999.

(30) Foreign Application Priority Data

May 17, 1999 (DK) ........................................ 1999 00684
Mar. 21, 2000 (DK) ........................................ 2000 00478

(51) Int. Cl.[7] ...................... A61K 31/33; A61K 31/695; C07D 257/00; C07D 209/48
(52) U.S. Cl. ...................... 514/183; 514/63; 514/617; 514/383; 514/417; 514/562; 514/567; 548/250; 548/253; 548/473; 548/481; 562/430; 562/439
(58) Field of Search .................... 514/183, 63, 381, 514/417, 562, 567, 617; 548/250, 253, 473, 481; 562/430, 439

(56) References Cited

U.S. PATENT DOCUMENTS

| 4,359,474 A | 11/1982 | Anderson et al. ........ 424/273 P |
| 4,374,130 A | 2/1983 | Barcza ........................ 424/184 |
| 5,776,954 A | 7/1998 | de Laszlo et al. ........... 514/340 |
| 5,837,719 A | 11/1998 | de Laszlo et al. ........... 514/343 |

FOREIGN PATENT DOCUMENTS

| EP | 0 000 816 A1 | 2/1979 |
| EP | 0 387 771 A1 | 9/1990 |
| EP | 0 847 992 A1 | 6/1998 |
| EP | 0 657 423 B1 | 12/1998 |
| WO | WO 94/14426 | 7/1994 |
| WO | WO 95/09021 | 4/1995 |
| WO | WO 96/10559 | 4/1996 |
| WO | WO 97/16442 | 5/1997 |
| WO | WO 98/04528 | 2/1998 |
| WO | WO 98/21957 | 5/1998 |
| WO | WO 98/22108 | 5/1998 |
| WO | WO 98/22109 | 5/1998 |
| WO | WO 98/24780 | 6/1998 |
| WO | WO 98/24782 | 6/1998 |
| WO | WO 98/50029 | 11/1998 |
| WO | WO 98/50030 | 11/1998 |
| WO | 9901423 | * 1/1999 |
| WO | WO 99/01423 | 1/1999 |

OTHER PUBLICATIONS

Brand et al., Diabetologia, vol. 37, pp. 985–993 (1994).
Brand et al., Am. J. Physiol., vol. 269 (Endocrinol. Metab. 32), pp. E469–E477 (1995).
Brand et al., Diabetes, vol. 45, pp. 1076–1083 (1996).
Jelinek et al., Science, vol. 259, pp. 1614–1616 (1993).
Unson et al., Peptides, vol. pp. 1171–1177 (1989).
Post et al., Biochemistry, vol. 90, pp. 1662–1666 (1993).
Madsen et al., J. Med. Chem., vol. 41, 41 pp. 5150–5157 (1998).
Collins et al., Bioorganic & Medicinal Chemistry Letters, vol. 2, pp. 915–918 (1992).
Azizeh et al., Bioorganic & Medicinal Chemistry Letters, vol. 5 pp. 15–30 (1998).
Tanaka et al., Bioorganic & Medicinal Chemistry Letters, vol. 6, pp. 15–30 (1998).
Unson et al., The Journal of Biological Chemistry, vol. 269, pp. 12548–12551 (1994).
Abstract of Japanese Patent JP 11302173.
Abstract of Brand et al., Diabetes, vol. 43, p. 172A (1994).
Abstract of Brand et al., Diabetes, vol. 44 Supplementary, p. 134A (1995).

* cited by examiner

*Primary Examiner*—Richard L. Raymond
*Assistant Examiner*—Sudhaker B. Patel
(74) *Attorney, Agent, or Firm*—Richard W. Boak, Esq.; Reza Green, Esq.; Marc A. Began, Esq.

(57) ABSTRACT

A novel class of compounds, which act to antagonize the action of the glucagon hormone on the glucagon receptor. Owing to their antagonizing effect of the glucagon receptor the compounds may be suitable for the treatment and/or prevention of any glucagon-mediated conditions and diseases such as hyperglycemia, Type 1 diabetes, Type 2 diabetes and obesity.

80 Claims, No Drawings

GLUCAGON ANTAGONISTS/INVERSE AGONISTS

CROSS-REFERENCE TO RELATED APPLICATIONS

This application is a divisional of application Ser. No. 09/572,553, filed May 16, 2000 and now U.S. Pat. No. 6,503,949 and claims priority under 35 U.S.C. 119 of U.S. provisional applications 60/134,415 filed May 17, 1999 and 60/191,685 filed Mar. 23, 2000 and Danish applications PA 1999 00684 filed May 17, 1999 and PA 2000 00478 filed Mar. 21, 2000, the contents of which are fully incorporated herein by reference.

FIELD OF THE INVENTION

The present invention relates to agents that act to antagonize the action of the glucagon peptide hormone. More particularly, it relates to glucagon antagonists or inverse agonists.

BACKGROUND OF THE INVENTION

Glucagon is a key hormonal agent that, in co-operation with insulin, mediates homeostatic regulation of the amount of glucose in the blood. Glucagon primarily acts by stimulating certain cells (mostly liver cells) to release glucose when blood glucose levels fall. The action of glucagon is opposite to that of insulin, which stimulates cells to take up and store glucose whenever blood glucose levels rise. Both glucagon and insulin are peptide hormones. Glucagon is produced in the alpha islet cells of the pancreas and insulin in the beta islet cells. Diabetes mellitus is a common disorder of glucose metabolism. The disease is characterized by hyperglycemia and may be classified as Type 1 diabetes, the insulin-dependent form, or Type 2 diabetes, which is non-insulin-dependent in character. Subjects with Type 1 diabetes are hyperglycemic and hypoinsulinemic, and the conventional treatment for this form of the disease is to provide insulin. However, in some patients with Type 1 or Type 2 diabetes, absolute or relative elevated glucagon levels have been shown to contribute to the hyperglycemic state. Both in healthy control animals as well as in animal models of Type 1 and Type 2 diabetes, removal of circulating glucagon with selective and specific antibodies has resulted in reduction of the glycemic level (Brand et al., Diabetologia 37, 985 (1994); Diabetes 43, [suppl 1], 172A (1994); Am. J. Physiol. 269, E469–E477 (1995); Diabetes 44 [suppl 1], 134A (1995); Diabetes 45, 1076 (1996)). These studies suggest that glucagon suppression or an action that antagonizes glucagon could be a useful adjunct to conventional antihyperglycemia treatment of diabetes. The action of glucagon can be suppressed by providing an antagonist or an inverse agonist, ie substances that inhibit or prevent glucagon induced responses. The antagonist can be peptidic or non-peptidic in nature. Native glucagon is a 29 amino acid peptide having the sequence:

His-Ser-Glu-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-$NH_2$.

Glucagon exerts its action by binding to and activating its receptor, which is part of the Glucagon-Secretin branch of the 7-transmembrane G-protein coupled receptor family (Jelinek et al., Science 259, 1614, (1993)). The receptor functions by an activation of the adenylyl cyclase second messenger system and the result is an increase in cAMP levels.

Several publications disclose peptides that are stated to act as glucagon antagonists. Probably, the most thoroughly characterized antagonist is DesHis$^1$[Glu$^9$]-glucagon amide (Unson et al., Peptides 10, 1171 (1989); Post et al., Proc. Natl. Acad. Sci. USA 90, 1662 (1993)). Other antagonists are eg DesHis$^1$,Phe$^6$[Glu$^9$]-glucagon amide (Azizh et al., Bioorganic & Medicinal Chem. Lett. 16, 1849 (1995)) or NLeu$^9$,Ala$^{11,16}$-glucagon amide (Unson et al., J. Biol. Chem. 269(17), 12548 (1994)).

Peptide antagonists of peptide hormones are often quite potent; however, they are generally known not to be orally available because of degradation by physiological enzymes, and poor distribution in vivo. Therefore, orally available non-peptide antagonists of the peptide hormones are preferred. Among the non-peptide glucagon antagonists, a quinoxaline derivative, (2-styryl-3-[3-(dimethylamino) propylmethylamino]-6,7-dichloroquinoxaline was found to displace glucagon from the rat liver receptor (Collins, J. L. et al., Bioorganic and Medicinal Chemistry Letters 2(9):915–918 (1992)). West, R. R. et al., WO 94/14426 (1994) discloses use of skyrin, a natural product comprising a pair of linked 9,10-anthracenedione groups, and its synthetic analogues, as glucagon antagonists. Anderson, P. L., U.S. Pat. No. 4,359,474 discloses the glucagon antagonistic properties of 1-phenyl pyrazole derivatives. Barcza, S., U.S. Pat. No. 4,374,130, discloses substituted disilacyclohexanes as glucagon antagonists. WO 98/04528 (Bayer Corporation) discloses substituted pyridines and biphenyls as glucagon antagonists. WO 97/16442 and U.S. Pat. No 5,776,954 (Merck & Co., Inc.) disclose substituted pyndyl pyrroles as glucagon antagonists and WO 98/21957, WO 98/22108, WO 98/22109 and U.S. Pat. No. 5,880,139 (Merck & Co., Inc.) disclose 2,4-diaryl-5-pyridylimidazoles as glucagon antagonists. Furthermore, WO 97/16442, U.S. Pat. Nos 5,837,719 and 5,776,954 (Merck & Co., Inc.) discloses 2,5-substituted aryl pyrroles as glucagon antagonists. WO 98/24780, WO 98/24782, WO 99/24404 and WO 99/32448 (Amgen Inc.) disclose substituted pyrimidinone and pyridone compounds and substituted pyrimidine compounds, respectively, which are stated to posses glucagon antagonistic activity. Madsen et al (J. Med. Chem. 1998 (41) 5151–7) discloses a series of 2-(benzimidazol-2-ylthio)-1-(3,4-dihydroxyphenyl)-1-ethanones as competitive human glucagon receptor antagonists. WO 99/01423 (Novo Nordisk A/S) discloses a series of acylhydrazones as glucagon antagonists/inverse agonists.

These known glucagon antagonists differ structurally from the present compounds.

DEFINITIONS

The following is a detailed definition of the terms used to describe the compounds of the invention:

"Halogen" designates an atom selected from the group consisting of F, Cl, Br or I.

The term "$C_{1-6}$-alkyl" in the present context designates a branched or straight hydrocarbon group having from 1 to 6 carbon atoms. Representative examples include, but are not limited to, methyl, ethyl, n-propyl, isopropyl, butyl, isobutyl, sec-butyl, tert-butyl, n-pentyl, isopentyl, neopentyl, tert-pentyl, n-hexyl, isohexyl and the like.

The term "$C_{2-6}$-alkenyl" as used herein represents a branched or straight hydrocarbon group having from 2 to 6 carbon atoms and at least one double bond. Examples of such groups include, but are not limited to, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, 5-hexenyl and the like.

The term "$C_{2-6}$-alkynyl" as used herein represents a branched or straight hydrocarbon group having from 2 to 6 carbon atoms and at least one triple bond. Examples of such groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 5-hexynyl, 2,4-hexadiynyl and the like.

The term "$C_{1-6}$-alkoxy" as used herein, alone or in combination, refers to the radical —O—$C_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{1-6}$-alkanoyl" as used herein denotes a group —C(O)H or —C(O)—$C_{1-5}$-alkyl. Representative examples are formyl, acetyl, propionyl, butyryl, valeryl, hexanoyl and the like.

The term "$C_{3-8}$-cycloalkyl" as used herein represents a carbocyclic group having from 3 to 8 carbon atoms. Representative examples are cyclopropyl, cyclobutyl, cyclopentyl, cyclohexyl, cycloheptyl, cyclooctyl and the like.

The term "$C_{3-8}$-cycloalkenyl" as used herein represents a carbocyclic group having from 3 to 8 carbon atoms containing a least one double bond. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "$C_{4-8}$-cycloalkenyl" as used herein represents a carbocyclic group having from 4 to 8 carbon atoms containing a least one double bond. Representative examples are 1-cyclopentenyl, 2-cyclopentenyl, 3-cyclopentenyl, 1-cyclohexenyl, 2-cyclohexenyl, 3-cyclohexenyl, 2-cycloheptenyl, 3-cycloheptenyl, 2-cyclooctenyl, 1,4-cyclooctadienyl and the like.

The term "heterocyclyl" as used herein represents a saturated or partially unsaturated 3 to 10 membered ring containing one or more heteroatoms selected from nitrogen, oxygen and sulfur. Representative examples are pyrrolidinyl, piperidyl, piperazinyl, morpholinyl, thiomorpholinyl, aziridinyl, tetrahydrofuranyl and the like.

The term "aryl" as used herein is intended to include carbocyclic aromatic ring systems such as phenyl, biphenyl, naphthyl, anthracenyl, phenanthrenyl, fluorenyl, indenyl, pentalenyl, azulenyl, and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "aryloxy" as used herein denotes a group —O-aryl, wherein aryl is as defined above.

The term "aroyl" as used herein denotes a group —C(O)-aryl, wherein aryl is as defined above.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, benzothiophenyl (thianaphthenyl), indazolyl, benzimidazolyl, benzthiazolyl, benzisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indolinyl, oxazolidinyl, oxazolinyl, oxazepinyl and the like.

"Aryl-$C_{1-6}$-alkyl", "heteroaryl-$C_{1-6}$-alkyl", "aryl-$C_{2-6}$-alkenyl" etc. mean $C_{1-6}$-alkyl or $C_{2-6}$-alkenyl as defined above, substituted by an aryl or heteroaryl as defined above, for example:

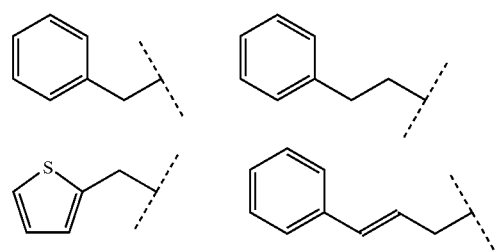

The term "optionally substituted" as used herein means that the groups in question are either unsubstituted or substituted with one or more of the substituents specified. When the groups in question are substituted with more than one substituent the substituents may be the same or different.

Certain of the above defined terms may occur more than once in the structural formulae, and upon such occurrence each term shall be defined independently of the other.

Furthermore, when using the terms "independently are" and "independently selected from" it should be understood that the groups in question may be the same or different.

The present invention is based on the unexpected observation that the compounds of the general formula (I) disclosed below antagonize the action of glucagon.

DESCRIPTION OF THE INVENTION

Accordingly, the invention is concerned with compounds of the general formula (I):

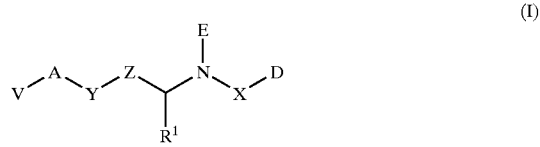

(I)

wherein
V is —C(O)OR$^2$, —C(O)NR$^2$R$^3$, —C(O)NR$^2$OR$^3$, —S(O)$_2$OR$^2$,

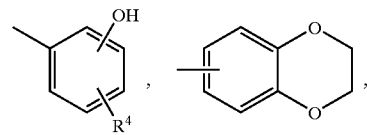

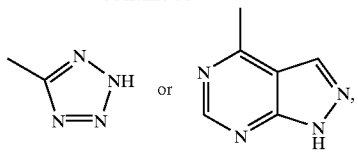 or wherein $R^2$ and $R^3$ independently are hydrogen or $C_{1-6}$-alkyl,
$R^4$ is hydrogen, halogen, —CN, —$CF_3$, —$OCF_3$, —$NO_2$, —$OR^5$, —$NR^5R^6$ or $C_{1-6}$-alkyl,
 wherein $R^5$ and $R^6$ independently are hydrogen or $C_{1-6}$-alkyl,
A is

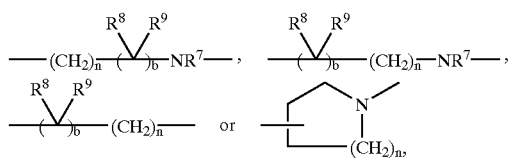

wherein b is 0 or 1,
n is 0, 1, 2 or 3,
$R^7$ is hydrogen, $C_{1-6}$-alkyl or $C_{3-8}$-cycloalkyl-$C_{1-6}$-alkyl,
$R^8$ and $R^9$ independently are hydrogen or $C_{1-6}$-alkyl,
Y is —C(O)—, —S(O)$_2$—, —O— or a valence bond,
Z is phenylene or a divalent radical derived from a 5 or 6 membered heteroaromatic ring containing 1 or 2 heteroatoms selected from nitrogen, oxygen and sulfur,
 which may optionally be substituted with one or two groups $R^{46}$ and $R^{47}$ selected from hydrogen, halogen, —CN, —$CF_3$, —$OCF_3$, —$NO_2$, —$OR^{10}$, —$NR^{10}R^{11}$ and $C_{1-6}$-alkyl,
 wherein $R^{10}$ and $R^{11}$ independently are hydrogen or $C_{1-6}$-alkyl,
or —A—Y—Z— together are

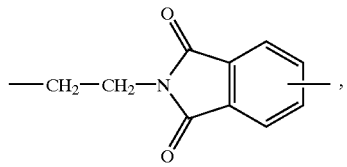

$R^1$ is hydrogen or $C_{1-6}$-alkyl,
X is

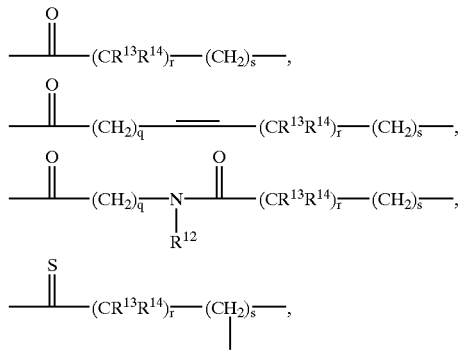

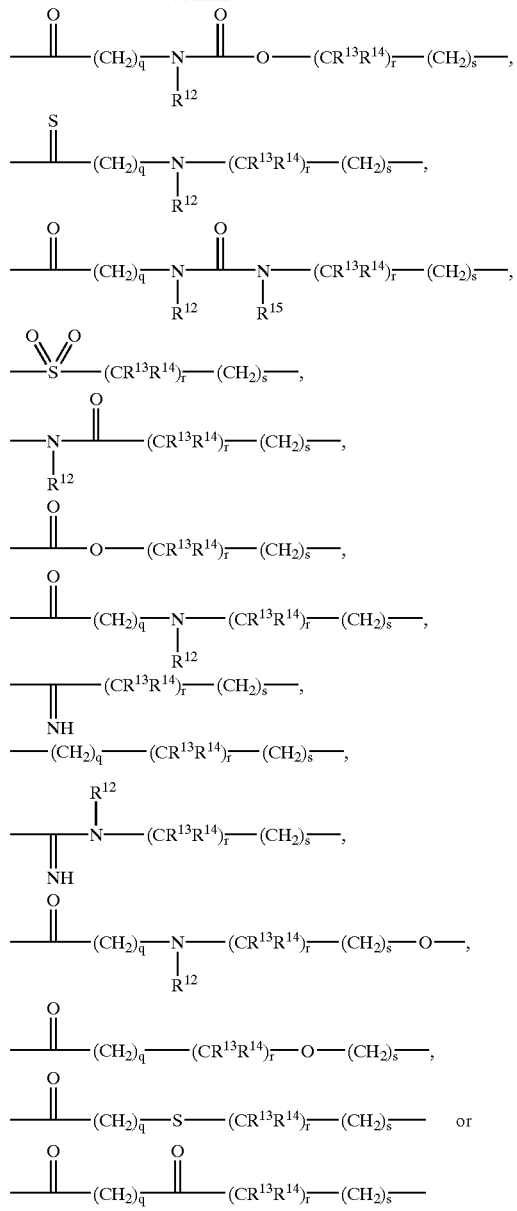

wherein
r is 0 or 1,
q and s independently are 0, 1, 2 or 3,
$R^{12}$, $R^{13}$, $R^{14}$ and $R^{15}$ independently are hydrogen or $C_{1-6}$-alkyl,
D is

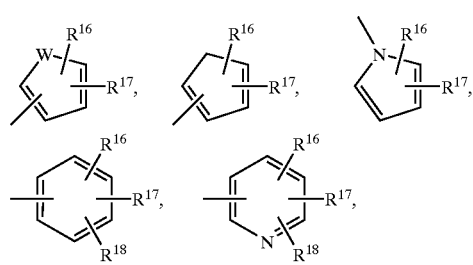

-continued

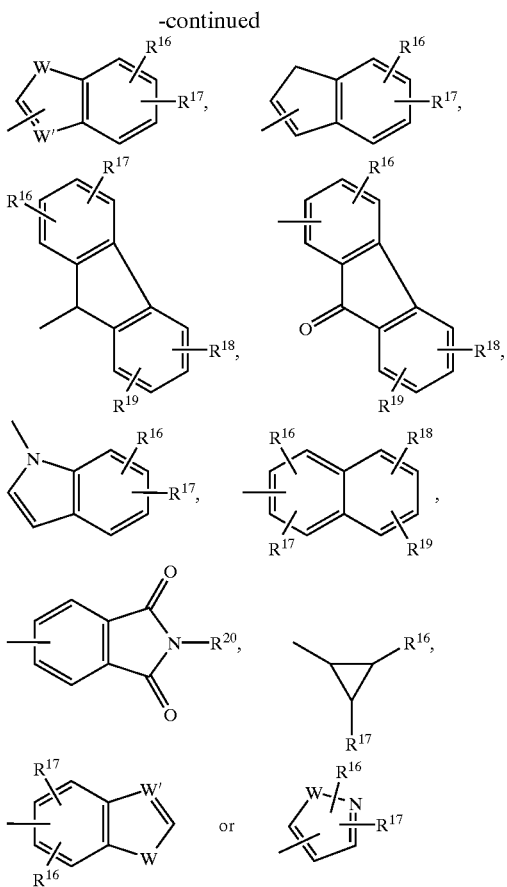

wherein
W is —O—, —S—, —S(O)$_2$— or —NR$^{20}$—,
W' is =CR$^{20'}$— or =N—,
R$^{16}$, R$^{17}$, R$^{18}$ and R$^{19}$ independently are
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)$_2$R$^{21}$, —S(O)$_2$R$^{21}$, —OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{22}$, —OC(O)R$^{21}$, —C(O)R$^{21}$ or —C(O)CR$^{21}$,
C$_{1-6}$-alkyl, C$_{2-6}$-alkenyl or C$_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$,
C$_{3-8}$-cycloalkyl, C$_{4-8}$-cycloalkenyl, heterocyclyl, C$_{3-8}$-cycloalkyl-C$_{1-6}$-alkyl, C$_{3-8}$-cycloalkyl-C$_{1-6}$-alkoxy, C$_{3-8}$-cycloalkyloxy, C$_{3-8}$-cycloalkyl-C$_{1-6}$-alkylthio, C$_{3-8}$-cycloalkylthio, C$_{3-8}$-cycloalkyl-C$_{2-6}$-alkenyl, C$_{3-8}$-cycloalkyl-C$_{2-6}$-alkynyl, C$_{4-8}$-cycloalkenyl-C$_{1-6}$-alkyl, C$_{4-8}$-cycloalkenyl-C$_{2-6}$-alkenyl, C$_{4-8}$-cycloalkenyl-C$_{2-6}$-alkynyl, heterocyclyl-C$_{1-6}$-alkyl, heterocyclyl-C$_{2-6}$-alkenyl or heterocyclyl-C$_{2-6}$-alkynyl,
of which the cyclic moieties optionally may be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, C$_{1-6}$-alkyl, C$_{2-6}$-alkenyl and C$_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$,
aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl,
of which the aryl and heteroaryl moieties optionally may be substituted with one or more substituents selected from
halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ and —C(O)OR$^{21}$,
C$_{1-6}$-alkyl, C$_{2-6}$-alkenyl and C$_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$,
wherein R$^{21}$ and R$^{22}$ independently are hydrogen, —CF$_3$, C$_{1-6}$-alkyl, tri-C$_{1-6}$-alkylsilyl, C$_{3-8}$-cycloalkyl, C$_{3-8}$-cycloalkyl-C$_{1-6}$-alkyl, aryl, aryl-C$_{1-6}$-alkyl or heteroaryl,
or R$^{21}$ and R$^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
or two of the groups R$^{16}$ to R$^{19}$ when placed in adjacent positions together may form a bridge —(CR$^{16'}$R$^{17'}$)$_a$—O—(CR$^{18'}$R$^{19'}$)$_c$—O—,
wherein
a is 0, 1 or 2,
c is 1 or 2,
R$^{16'}$, R$^{17'}$, R$^{18'}$ and R$^{19'}$ independently are hydrogen, C$_{1-6}$-alkyl or halogen,
R$^{20}$ and R$^{20'}$ independently are hydrogen, C$_{1-6}$-alkyl, C$_{3-8}$-cycloalkyl or C$_{3-8}$-cycloalkyl-C$_{1-6}$-alkyl,
E is a 3 to 9 membered mono- or bicyclic ring which may optionally contain one or two double bonds and which may optionally contain one or two heteroatoms selected from nitrogen, oxygen and sulfur, wherein one or two groups R$^{23}$ and R$^{24}$ may be attached to the same or different ring carbon atoms and wherein a group R$^{31}$ may be attached to a ring nitrogen atom when present, or

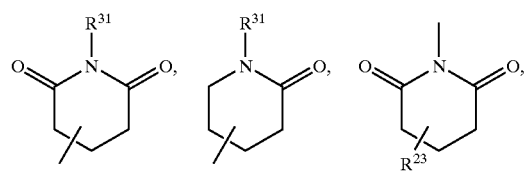

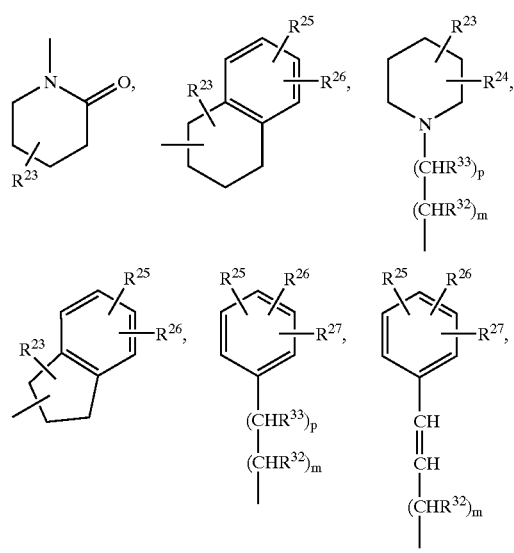

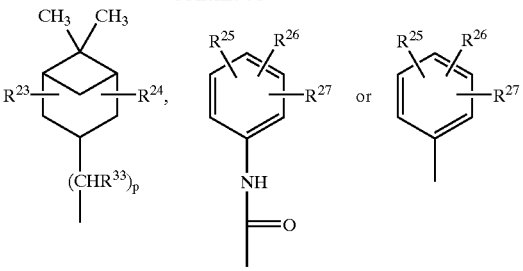

wherein m and p independently are 0, 1, 2, 3 or 4, with the proviso that when both m and p are present in the same formula at least one of m and p is different from 0, $R^{23}$ and $R^{24}$ independently are hydrogen, —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ or —$C(O)OR^{36}$, $C_{1-6}$-alkyl, $C_{2-6}$-alkenyl or $C_{2-6}$-alkynyl,
which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, $C_{3-8}$-cycloalkyl, $C_{3-8}$-cycloalkylidene, $C_{4-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl or heterocyclyl-$C_{2-6}$-alkynyl, of which the cyclic moieties optionally may be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, $C_{1-6}$-alkyl, $C_{2-6}$-alkenyl and $C_{2-6}$-alkynyl,
which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, of which the aryl and heteroaryl moieties optionally may be substituted with one or more substituents selected from halogen, —CN, —$CH_2CN$, —$CHF_2$, —$CF_3$, —$OCF_3$, —$OCHF_2$, —$OCH_2CF_3$, —$OCF_2CHF_2$, —$OS(O)_2CF_3$, —$SCF_3$, —$NO_2$, —$OR^{36}$, —$NR^{36}R^{37}$, —$SR^{36}$, —$NR^{36}S(O)_2R^{37}$, —$S(O)_2NR^{36}R^{37}$, —$S(O)NR^{36}R^{37}$, —$S(O)R^{36}$, —$S(O)_2R^{36}$, —$OS(O)_2R^{36}$, —$C(O)NR^{36}R^{37}$, —$OC(O)NR^{36}R^{37}$, —NR³⁶C(O)R³⁷, —CH₂C(O)NR³⁶R³⁷, —CH₂C(O)NR³⁶R³⁷, —CH₂OR³⁶, —CH₂NR³⁶R³⁷, —OC(O)R³⁶, —C(O)R³⁶ and —C(O)OR³⁶, $C_{1-6}$-alkyl, $C_{2-6}$-alkenyl and $C_{2-6}$-alkynyl,
which may optionally be substituted with one or more substituents selected from —CHF₂, —CF₃, —OCF₃, —OCHF₂, —OCH₂CF₃, —OCF₂CHF₂, —SCF₃, —OR³⁶, —NR³⁶R³⁷, —SR³⁶, —S(O)R³⁶, —S(O)₂R³⁶, —C(O)NR³⁶R³⁷, —OC(O)NR³⁶R³⁷, —NR³⁶C(O)R³⁷, —OCH₂C(O)NR³⁶R³⁷, —C(O)R³⁶ and —C(O)OR³⁶, wherein R³⁶ and R³⁷ independently are hydrogen, $C_{1-6}$-alkyl or aryl,
of which the aryl moiety optionally may be substituted with one or more substituents selected from halogen, —CN, —CF₃, —OCF₃, —NO₂, —OR³⁸, —NR³⁸R³⁹ and $C_{1-6}$-alkyl,
wherein R³⁸ and R³⁹ independently are hydrogen or $C_{1-6}$-alkyl,
or R³⁶ and R³⁷ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
or R²³ and R²⁴ when attached to the same ring carbon atom or different ring carbon atoms together may form a radical —O—(CH₂)$_t$—CR⁴⁰R⁴¹—(CH₂)$_l$—O—, —(CH₂)$_t$—CR⁴⁰R⁴¹—(CH₂)$_l$— or —S—(CH₂)$_t$—CR⁴⁰R⁴¹—(CH₂)$_l$—S—,
wherein
t and l independently are 0, 1, 2, 3, 4 or 5,
R⁴⁰ and R⁴¹ independently are hydrogen or $C_{1-6}$-alkyl,
R²⁵ to R³⁰ independently are hydrogen, halogen, —CN, —CF₃, —NO₂, —OR⁴², —NR⁴²R⁴³, $C_{1-6}$-alkyl, $C_{3-8}$-cycloalkyl or $C_{4-8}$-cycloalkenyl,
wherein R⁴² and R⁴³ independently are hydrogen or $C_{1-6}$-alkyl, or
R⁴² and R⁴³ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
R³¹, R³² and R³³ independently are hydrogen or $C_{1-6}$-alkyl,
R³⁴ and R³⁵ independently are
hydrogen, $C_{1-6}$-alkyl, $C_{1-6}$-alkoxy, $C_{1-6}$-alkanoyl, —C(O)NR⁴⁴R⁴⁵ or —S(O)₂R⁴⁵,
aryl, aroyl, aryl-$C_{1-6}$-alkoxy, aryl-$C_{1-6}$-alkanoyl or aryl-$C_{1-6}$-alkyl,
of which the aryl moieties optionally may be substituted with one or more substituents selected from halogen, —CN, —CF₃, —OCF₃, —OR⁴⁴, —NR⁴⁴R⁴⁵ and $C_{1-6}$-alkyl,
wherein R⁴⁴ and R⁴⁵ independently are hydrogen or $C_{1-6}$-alkyl, or
R³⁴ and R³⁵ when attached to a carbon atom together with the said carbon atom may form a 3 to 8 membered cyclic ring optionally containing one or two heteroatoms selected from nitrogen, oxygen or sulfur, and optionally containing one or two double bonds, or
R³⁴ and R³⁵ when attached to a nitrogen atom together with the said nitrogen atom may form a 3 to 8 membered heterocyclic ring optionally containing one or two further heteroatoms selected from nitrogen, oxygen or sulfur, and optionally containing one or two double bonds,
as well as any optical or geometric isomer or tautomeric form thereof including mixtures of these or a pharmaceutically acceptable salt thereof.

The compounds according to the invention preferably have an $IC_{50}$ value of no greater than 5 μM as determined by the Glucagon Binding Assay (I), Glucagon Binding Assay (II) or Glucagon Binding Assay (III) disclosed herein.

More preferably, the compounds according to the invention have a glucagon antagonistic activity as determined by the Glucagon Binding Assay (I), Glucagon Binding Assay (II) or Glucagon Binding Assay (III) disclosed herein corresponding to an $IC_{50}$ value of less than 1 μM, preferably of less than 500 nM and even more preferred of less than 100 nM.

The compounds according to the invention are useful for the treatment and/or prevention of an indication selected from the group consisting of hyperglycemia, IGT (impaired glucose tolerance), Type 2 diabetes, Type 1 diabetes and obesity.

In a further aspect the invention relates to compounds of the general formula (I'):

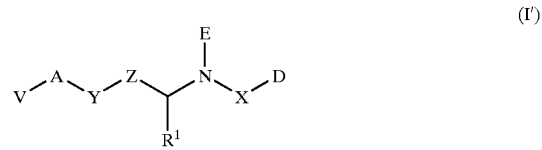

(I')

wherein
V is —C(O)OR², —C(O)NR²R³, —C(O)NR²OR³,

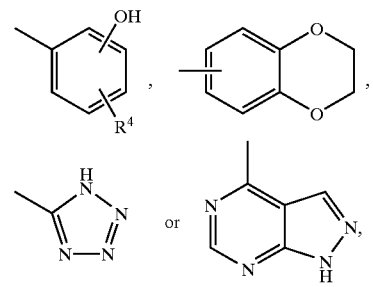

wherein
R² and R³ independently are hydrogen or $C_{1-6}$-alkyl,
R⁴ is hydrogen, halogen, —CN, —CF₃, —OCF₃, —NO₂, —OR⁵, —NR⁵R⁶ or $C_{1-6}$-alkyl,
wherein R⁵ and R⁶ independently are hydrogen or $C_{1-6}$-alkyl;
A is

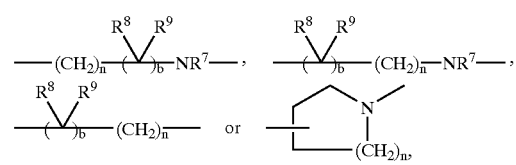

wherein
b is 0 or 1,
n is 0, 1, 2 or 3,
R⁷ is hydrogen, $C_{1-6}$-alkyl or $C_{3-8}$-cycloalkyl-$C_{1-6}$-alkyl,
R⁸ and R⁹ independently are hydrogen or $C_{1-6}$-alkyl;
Y is —C(O)—, —S(O)₂— or —O—;
Z is phenylene or a divalent radical derived from a 5 or 6 membered heteroaromatic ring containing 1 or 2 heteroatoms selected from nitrogen, oxygen and sulfur,
which may optionally be substituted with one or more substituents selected from halogen, —CN, —CF₃, —OCF₃, —NO₂, —OR¹⁰, —NR¹⁰R¹¹ and $C_{1-6}$-alkyl, wherein $R^{10}$ and $R^{11}$ independently are hydrogen or $C_{1-6}$-alkyl;
or —A—Y—Z— together is

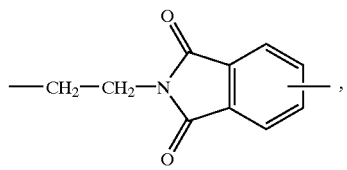

$R^1$ is hydrogen or $C_{1-6}$-alkyl;
X is

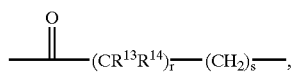

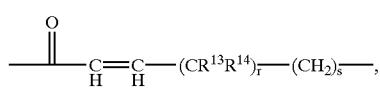

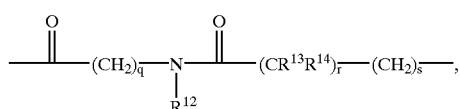

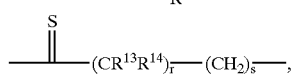

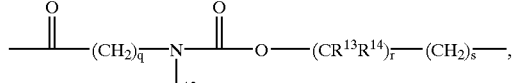

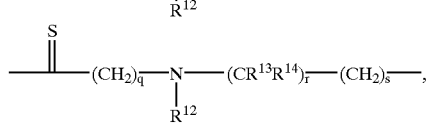

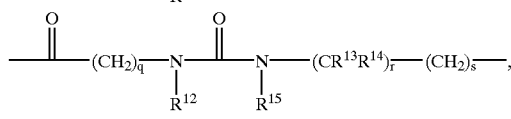

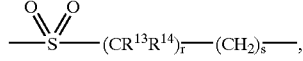

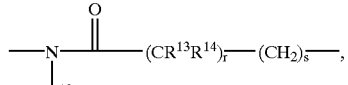

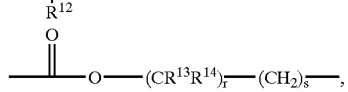

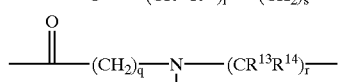

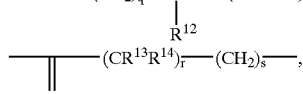

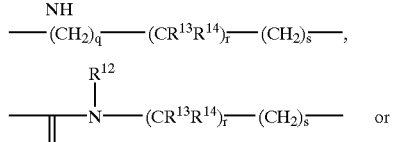

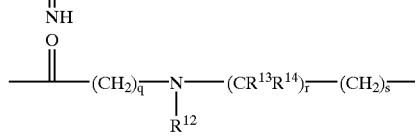

wherein
r is 0 or 1,
q and s independently are 0, 1, 2 or 3,
$R^{12}$, $R^{13}$, $R^{14}$ and $R^{15}$ independently are hydrogen or $C_{1-6}$-alkyl;
D is

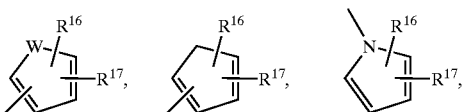

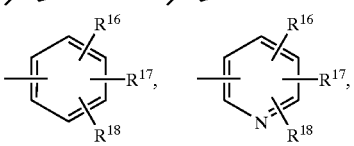

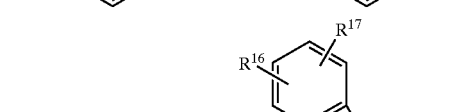

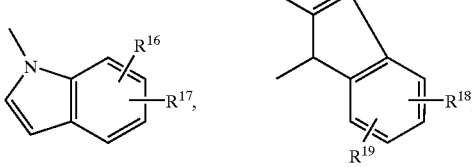

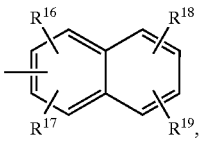

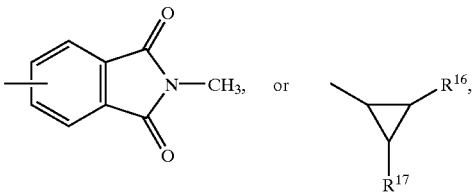

wherein
W is —O—, —S— or —NR$^{20}$—,
wherein $R^{20}$ is hydrogen or $C_{1-6}$-alkyl,
$R^{16}$, $R^{17}$, $R^{18}$ and $R^{19}$ independently are
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ or —C(O)OR$^{21}$,
$C_{1-6}$-alkyl, $C_{2-6}$-alkenyl or $C_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$,
$C_{3-8}$-cycloalkyl, $C_{3-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$- cycloalkyl-$C_{2-6}$-alkynyl, $C_{3-8}$-cycloalkenyl-$C_{1-6}$-alkyl, $C_{3-8}$-cycloalkenyl-$C_{2-6}$-alkenyl, $C_{3-8}$-cycloalkenyl-$C_{2-6}$-alkynyl, heterocyclyl-$C_{1-6}$-alkyl, heterocyclyl-$C_{2-6}$-alkenyl or heterocyclyl-$C_{2-6}$-alkynyl, of which the cyclic moieties optionally may be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{21}$, —$NR^{21}R^{22}$, —$SR^{21}$, —$S(O)R^{21}$, —$S(O)_2R^{21}$, —$C(O)NR^{21}R^{22}$, —$OC(O)NR^{21}R^{22}$, —$NR^{21}C(O)R^{22}$, —$OCH_2C(O)NR^{21}R^{22}$, —$C(O)R^{21}$ and —$C(O)OR^{21}$, $C_{1-6}$-alkyl, $C_{2-6}$-alkenyl and $C_{2-6}$-alkynyl,
which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{21}$, —$NR^{21}R^{22}$, —$SR^{21}$, —$S(O)R^{21}$, —$S(O)_2R^{21}$, —$C(O)NR^{21}R^{22}$, —$OC(O)NR^{21}R^{22}$, —$NR^{21}C(O)R^{22}$, —$OCH_2C(O)NR^{21}R^{22}$, —$C(O)R^{21}$ and —$C(O)OR^{21}$, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, of which the aryl and heteroaryl moieties optionally may be substituted with one or more substituents selected from halogen, —CN, —$CH_2CN$, —$CHF_2$, —$CF_3$, —$OCF_3$, —$OCHF_2$, —$OCH_2CF_3$, —$OCF_2CHF_2$, —$OS(O)_2CF_3$, —$SCF_3$, —$NO_2$, —$OR^{21}$, —$NR^{21}R^{22}$, —$SR^{21}$, —$NR^{21}S(O)_2R^{22}$, —$S(O)_2NR^{21}R^{22}$, —$S(O)NR^{21}R^{22}$, —$S(O)R^{21}$, —$S(O)R^{21}$, —$OS(O)_2R^{21}$, —$C(O)NR^{21}R^{22}$, —$OC(O)NR^{21}R^{22}$, —$NR^{21}C(O)R^{22}$, —$CH_2C(O)NR^{21}R^{22}$, —$OCH_2C(O)NR^{21}R^{22}$, —$CH_2OR^{21}$, —$CH_2NR^{21}R^{22}$, —$OC(O)R^{21}$, —$C(O)R^{21}$ and —$C(O)OR^{21}$, $C_{1-6}$-alkyl, $C_{2-6}$-alkenyl and $C_{2-6}$-alkynyl,
which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{21}$, —$NR^{21}R^{22}$, —$SR^{21}$, —$S(O)R^{21}$, —$S(O)_2R^{21}$, —$C(O)NR^{21}R^{22}$, —$OC(O)NR^{21}R^{22}$, —$NR^{21}C(O)R^{22}$, —$OCH_2C(O)NR^{21}R^{22}$, —$C(O)R^{21}$ and —$C(O)OR^{21}$, wherein $R^{21}$ and $R^{22}$ independently are hydrogen or $C_{1-6}$-alkyl, or $R^{21}$ and $R^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{16}$ to $R^{19}$ when placed in adjacent positions together may form a bridge —$OCH_2O$— or —$OCH_2CH_2O$—;

E is a 3 to 9 membered mono- or bicyclic ring which may optionally contain one or two double bonds and which may optionally contain one or two heteroatoms selected from nitrogen, oxygen and sulfur, wherein one or two groups $R^{23}$ and $R^{24}$ may be attached to the same or different ring carbon atoms and wherein a group $R^{31}$ may be attached to a ring nitrogen atom when present, or

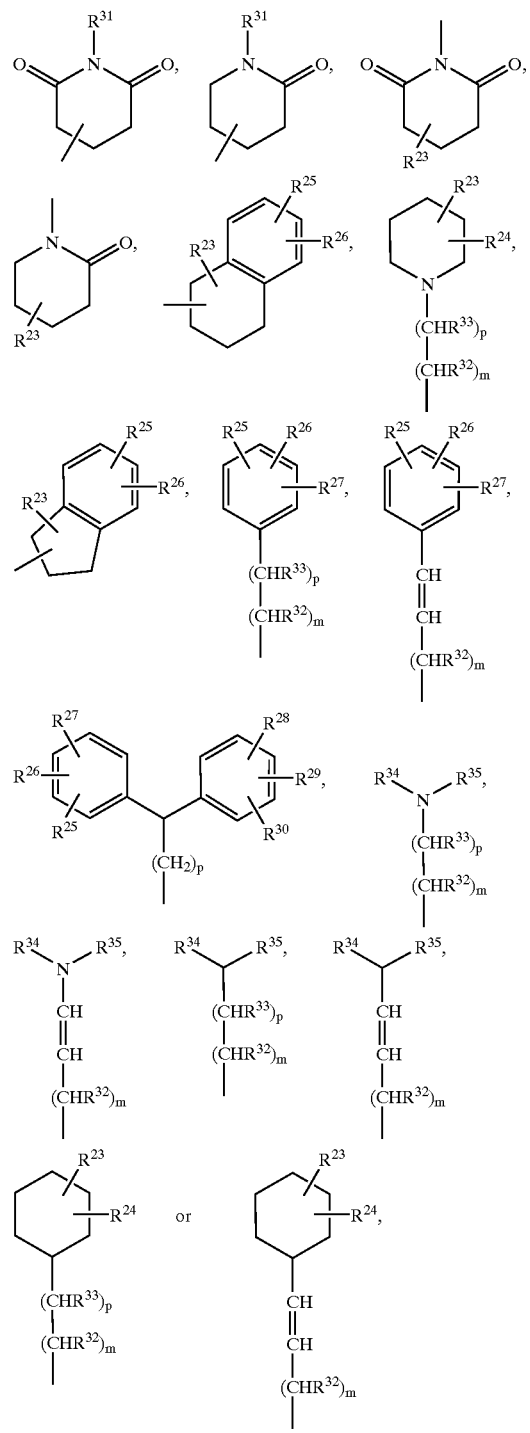

wherein
m and p independently are 0, 1, 2, 3 or 4,
$R^{23}$ and $R^{24}$ independently are hydrogen, —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ or —$C(O)OR^{36}$, $C_{1-6}$-alkyl, $C_{2-6}$-alkenyl or $C_{2-6}$-alkynyl,
which may optionally be substituted with one or more substituents selected from —$CHF_2$, —$CF_3$, —$OCF_3$,

17

—OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ and —C(O)OR$^{36}$, C$_{3-8}$-cycloalkyl, C$_{3-8}$-cycloalkenyl, heterocyclyl, C$_{3-8}$-cycloalkyl-C$_{1-6}$-alkyl, C$_{3-8}$-cycloalkyl-C$_{2-6}$-alkenyl, C$_{3-8}$-cycloalkyl-C$_{2-6}$-alkynyl, C$_{3-8}$-cycloalkenyl-C$_{1-6}$-alkyl, C$_{3-8}$-cycloalkenyl-C$_{2-6}$-alkenyl, C$_{3-8}$-cycloalkenyl-C$_{2-6}$-alkynyl, heterocyclyl-C$_{1-6}$-alkyl, heterocyclyl-C$_{2-6}$-alkenyl or heterocyclyl-C$_{2-6}$-alkynyl, of which the cyclic moieties optionally may be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ and —C(O)OR$^{36}$, C$_{1-6}$-alkyl, C$_{2-6}$-alkenyl and C$_{2-6}$-alkynyl, which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ and —C(O)OR$^{36}$, aryl, aryloxy, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl, of which the aryl and heteroaryl moieties optionally may be substituted with one or more substituents selected from halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{36}$, —NR$^{36}$R$^{37}$, —SR$^{36}$, —NR$^{36}$S(O)$_2$R$^{37}$, —S(O)$_2$NR$^{36}$R$^{37}$, —S(O)NR$^{36}$R$^{37}$, —S(O)R$^{36}$, —S(O)$_2$R$^{36}$, —OS(O)$_2$R$^{36}$, —C(O)NR$^{36}$R$^{37}$, —OC(O)NR$^{36}$R$^{37}$, —NR$^{36}$C(O)R$^{37}$, —CH$_2$C(O)NR$^{36}$R$^{37}$, —CH$_2$C(O)NR$^{36}$R$^{37}$, —CH$_2$OR$^{36}$, —CH$_2$NR$^{36}$R$^{37}$, —OC(O)R$^{36}$, —C(O)R$^{36}$ and —C(O)OR$^{36}$, C$_{1-6}$-alkyl, C$_{2-6}$-alkenyl and C$_{2-6}$-alkynyl, which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ and —C(O)OR$^{36}$, wherein R$^{36}$ and R$^{37}$ independently are hydrogen, C$_{1-6}$-alkyl or aryl, of which the aryl moiety optionally may be substituted with one or more substituents selected from halogen, —CN, —CF$_3$, —OCF$_3$, —NO$_2$, —OR$^{38}$, —NR$^{38}$R$^{39}$ and C$_{1-6}$-alkyl, wherein R$^{38}$ and R$^{39}$ independently are hydrogen or C$_{1-6}$-alkyl, or R$^{36}$ and R$^{37}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or R$^{23}$ and R$^{24}$ when attached to the same ring carbon atom or different ring carbon atoms together may form a radical —O—(CH$_2$)$_t$—CR$^{40}$R$^{41}$—(CH$_2$)$_l$—O—, —(CH$_2$)$_t$—CR$^{40}$R$^{41}$—(CH$_2$)$_l$— or —S—(CH$_2$)$_t$—CR$^{40}$R$^{41}$—(CH$_2$)$_l$—S—,

18 wherein t and l independently are 0, 1, 2, 3, 4 or 5,

R$^{40}$ and R$^{41}$ independently are hydrogen or C$_{1-6}$-alkyl,

R$^{25}$ to R$^{30}$ independently are hydrogen, halogen, —CN, —CF$_3$, —NO$_2$, —OR$^{42}$, —NR$^{42}$R$^{43}$, C$_{1-6}$-alkyl or C$_{3-8}$-cycloalkyl, wherein R$^{42}$ and R$^{43}$ independently are hydrogen or C$_{1-6}$-alkyl, R$^{31}$, R$^{32}$ and R$^{33}$ independently are hydrogen or C$_{1-6}$-alkyl, R$^{34}$ and R$^{35}$ independently are hydrogen, C$_{1-6}$-alkyl, C$_{1-6}$-alkoxy, C$_{1-6}$-alkanoyl, —C(O)NR$^{44}$R$^{45}$ or —S(O)$_2$R$^{45}$, aryl, aroyl, aryl-C$_{1-6}$-alkoxy, aryl-C$_{1-6}$-alkanoyl or aryl-C$_{1-6}$-alkyl, of which the aryl moieties optionally may be substituted with one or more substituents selected from halogen, —CN, —CF$_3$, —OCF$_3$, —OR$^{44}$, —NR$^{44}$R$^{45}$ and C$_{1-6}$-alkyl, wherein R$^{44}$ and R$^{45}$ independently are hydrogen or C$_{1-6}$-alkyl, or R$^{34}$ and R$^{35}$ when attached to the carbon atom together with the said carbon atom may form a 3 to 8 membered cyclic ring optionally containing one or two heteroatoms selected from nitrogen, oxygen or sulfur, and optionally containing one or two double bonds, or R$^{34}$ and R$^{35}$ when attached to the nitrogen atom together with the said nitrogen atom may form a 3 to 8 membered heterocyclic ring optionally containing one or two further heteroatoms selected from nitrogen, oxygen or sulfur, and optionally containing one or two double bonds;

as well as any optical or geometric isomer or tautomeric form thereof including mixtures of these or a pharmaceutically acceptable salt thereof;

having an IC$_{50}$ value of no greater than 5 µM as determined by the Glucagon Binding Assay (I), Glucagon Binding Assay (II) or Glucagon Binding Assay (III) disclosed herein.

By a compound of the general formula (I') having an IC$_{50}$ value of no greater than 5 µM as determined by the Glucagon Binding Assay (I), Glucagon Binding Assay (II) or Glucagon Binding Assay (III) is meant any compound of the defined formula having such activity, without limitation to any utility or usefulness for treating any specific indication.

In a further aspect the invention relates to compounds of the general formula (I''):

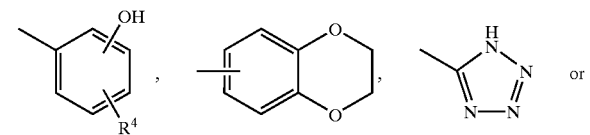

(I'')

wherein

V is —C(O)OR$^2$, —C(O)NR$^2$R$^3$, —C(O)NR$^2$OR$^3$, —S(O)$_2$OR$^2$,

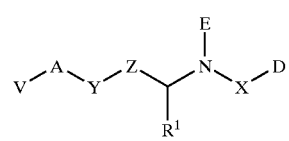

-continued

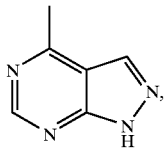

wherein
$R^2$ and $R^3$ independently are hydrogen or $C_{1-6}$-alkyl,
$R^4$ is hydrogen, halogen, —CN, —$CF_3$, —$OCF_3$, —$NO_2$, —$OR^5$, —$NR^5R^6$ or $C_{1-6}$-alkyl,
wherein $R^5$ and $R^6$ independently are hydrogen or $C_{1-6}$-alkyl,
A is

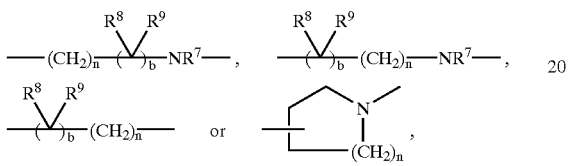

wherein
b is 0 or 1,
n is 0, 1, 2 or 3,
$R^7$ is hydrogen, $C_{1-6}$-alkyl or $C_{3-8}$-cycloalkyl-$C_{1-6}$-alkyl,
$R^8$ and $R^9$ independently are hydrogen or $C_{1-6}$-alkyl,
Y is —C(O)—, —S(O)$_2$—, —O— or a valence bond,
Z is phenylene or a divalent radical derived from a 5 or 6 membered heteroaromatic ring containing 1 or 2 heteroatoms selected from nitrogen, oxygen and sulfur,
which may optionally be attached to one or two groups $R^{46}$ and $R^{47}$ selected from hydrogen, halogen, —CN, —$CF_3$, —$OCF_3$, —$NO_2$, —$OR^{10}$, —$NR^{10}R^{11}$ and $C_{1-6}$-alkyl,
wherein $R^{10}$ and $R^{11}$ independently are hydrogen or $C_{1-6}$-alkyl, or —A—Y—Z— together are

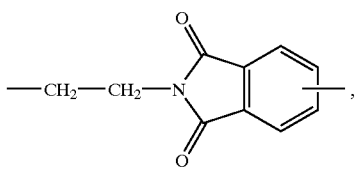

$R^1$ is hydrogen or $C_{1-6}$-alkyl,
X is

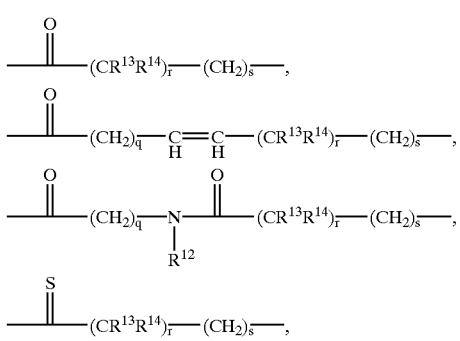

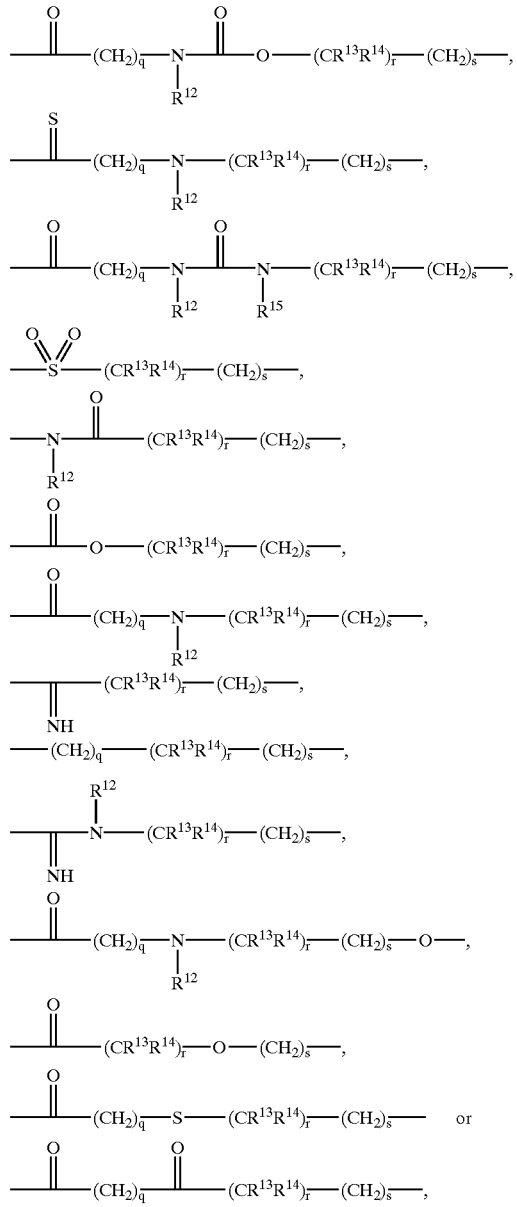

wherein
r is 0 or 1,
q and s independently are 0, 1, 2 or 3,
$R^{12}, R^{13}, R^{14}, R^{15}$ independently are hydrogen or $C_{1-6}$-alkyl,
D is

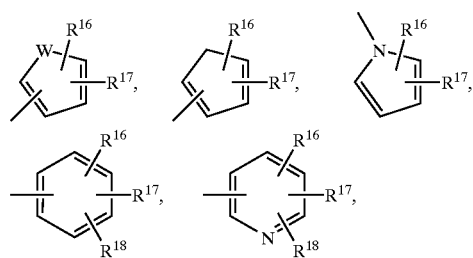

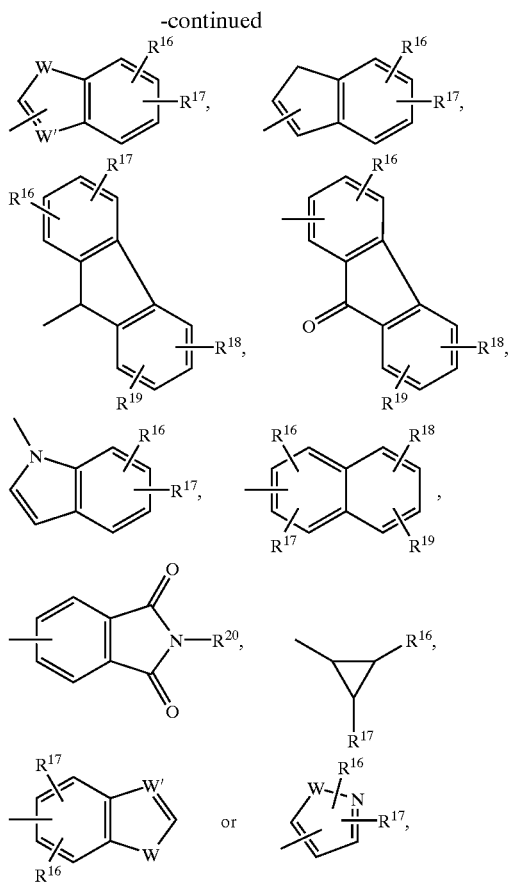

wherein
W is —O—, —S—, —S(O)$_2$— or —NR$^{20}$—,
W' is =CR$^{20'}$— or =N—,
R$^{20}$ and R$^{20'}$ are hydrogen, C$_{1-6}$-alkyl or C$_{3-8}$-cycloalkyl-C$_{1-6}$-alkyl,
R$^{16}$, R$^{17}$, R$^{18}$ and R$^{19}$ independently are hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ or —C(O)OR$^{21}$, C$_{1-6}$-alkyl, C$_{2-6}$-alkenyl or C$_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, C$_{3-8}$-cycloalkyl, C$_{3-8}$-cycloalkenyl, heterocyclyl, C$_{3-8}$-cycloalkyl-C$_{1-6}$-alkyl, C$_{3-8}$-cycloalkyl-C$_{1-6}$-alkoxy, C$_{3-8}$-cycloalkyloxy, C$_{3-8}$-cycloalkyl-C$_{1-6}$-alkylthio, C$_{3-8}$-cycloalkylthio, C$_{3-8}$-cycloalkyl-C$_{2-6}$-alkenyl, C$_{3-8}$-cycloalkyl-C$_{2-6}$-alkynyl, C$_{3-8}$-cycloalkenyl-C$_{1-6}$-alkyl, C$_{3-8}$-cycloalkenyl-C$_{2-6}$-alkenyl, C$_{3-8}$-cycloalkenyl-C$_{2-6}$-alkynyl, heterocyclyl-C$_{1-6}$-alkyl, heterocyclyl-C$_{2-6}$-alkenyl or heterocyclyl-C$_{2-6}$-alkynyl, of which the cyclic moieties optionally may be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, C$_{1-6}$-alkyl, C$_{2-6}$-alkenyl and C$_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, aryl, aryloxy, aryloxycarbonyl, aroyl, aryl-C$_{1-6}$-alkoxy, aryl-C$_{1-6}$-alkyl, aryl-C$_{2-6}$-alkenyl, aryl-C$_{2-6}$-alkynyl, heteroaryl, heteroaryl-C$_{1-6}$-alkyl, heteroaryl-C$_{2-6}$-alkenyl or heteroaryl-C$_{2-6}$-alkynyl,
of which the aryl and heteroaryl moieties optionally may be substituted with one or more substituents selected from halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ and —C(O)OR$^{21}$, C$_{1-6}$-alkyl, C$_{2-6}$-alkenyl and C$_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, wherein R$^{21}$ and R$^{22}$ independently are hydrogen, —CF$_3$, C$_{1-6}$-alkyl, tri-C$_{1-6}$-alkylsilyl, C$_{3-8}$-cycloalkyl, C$_{3-8}$-cycloalkyl-C$_{1-6}$-alkyl, aryl, aryl-C$_{1-6}$-alkyl or heteroaryl, or R$^{21}$ and R$^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups R$^{16}$ to R$^{19}$ when placed in adjacent positions together may form a bridge —(CR$^{16'}$R$^{17'}$)$_a$—O—(CR$^{18'}$R$^{19'}$)$_c$—O—, wherein
a is 0, 1 or 2,
c is 1 or 2,
R$^{16'}$, R$^{17'}$, R$^{18'}$ and R$^{19'}$ independently are hydrogen, C$_{1-6}$-alkyl or halogen,
E is a 3 to 9 membered mono- or bicyclic ring which may optionally contain one or two double bonds and which may optionally contain one or two heteroatoms selected from nitrogen, oxygen and sulfur, wherein one or two groups R$^{23}$ and R$^{24}$ may be attached to the same or different ring carbon atoms and wherein a group R$^{31}$ may be attached to a ring nitrogen atom when present, or

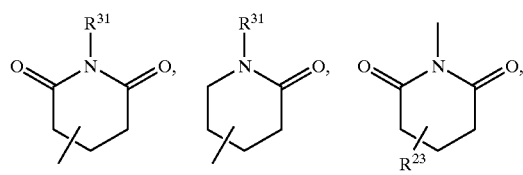
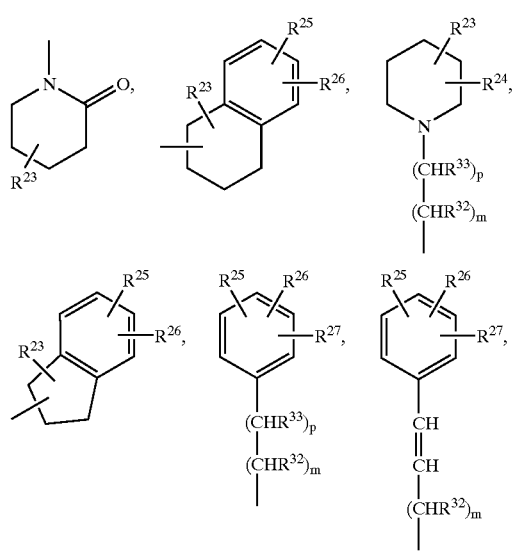
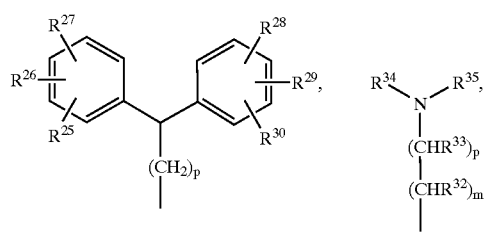
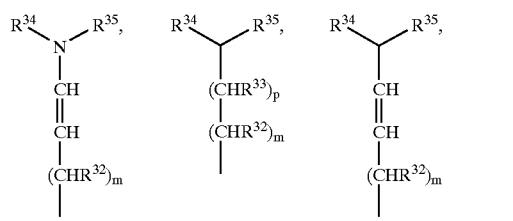
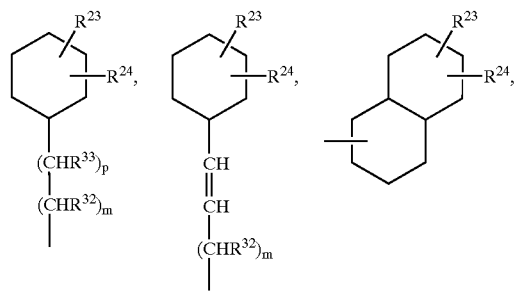
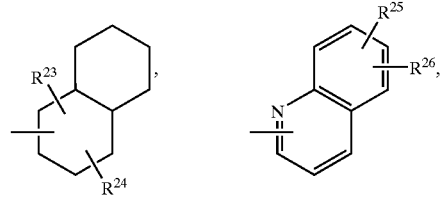
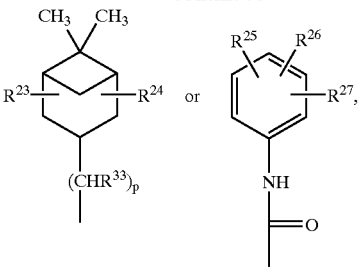

wherein m and p independently are 0, 1, 2, 3 or 4, with the proviso that when both m and p are present in the same formula at least one of m and p is different from 0, $R^{23}$ and $R^{24}$ independently are hydrogen, —CHF$_2$, —CF$_3$, —OCF$_3$, —OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ or —C(O)OR$^{36}$, $C_{1-6}$-alkyl, $C_{2-6}$-alkenyl or $C_{2-6}$-alkynyl, which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ and —C(O)OR$^{36}$, $C_{3-8}$-cycloalkyl, $C_{3-8}$-cycloalkylidene, $C_{3-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{3-8}$-cycloalkenyl-$C_{1-6}$-alkyl, $C_{3-8}$-cycloalkenyl-$C_{2-6}$-alkenyl, $C_{3-8}$-cycloalkenyl-$C_{2-6}$-alkynyl, heterocyclyl-$C_{1-6}$-alkyl, heterocyclyl-$C_{2-6}$-alkenyl or heterocyclyl-$C_{2-6}$-alkynyl, of which the cyclic moieties optionally may be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ and —C(O)OR$^{36}$, $C_{1-6}$-alkyl, $C_{2-6}$-alkenyl and $C_{2-6}$-alkynyl, which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{36}$, —NR$^{36}$R$^{37}$, —SR$^{36}$, —S(O)R$^{36}$, —S(O)$_2$R$^{36}$, —C(O)NR$^{36}$R$^{37}$, —OC(O)NR$^{36}$R$^{37}$, —NR$^{36}$C(O)R$^{37}$, —OCH$_2$C(O)NR$^{36}$R$^{37}$, —C(O)R$^{36}$ and —C(O)OR$^{36}$, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, of which the aryl and heteroaryl moieties optionally may be substituted with one or more substituents selected from halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{36}$, —NR$^{36}$R$^{37}$, —SR$^{36}$, —NR$^{36}$S(O)$_2$R$^{37}$, S(O)$_2$NR$^{36}$R$^{37}$, —S(O)NR$^{36}$R$^{37}$, —S(O)R$^{36}$, —S(O)$_2$R$^{36}$, —OS(O)$_2$R$^{36}$, —C(O)NR$^{36}$R$^{37}$, —OC(O)NR$^{36}$R$^{37}$, —NR$^{36}$C(O)

$R^{37}$, —$CH_2C(O)NR^{36}R^{37}$, —$CH_2C(O)NR^{36}R^{37}$, —$CH_2OR^{36}$, —$CH_2NR^{36}R^{37}$, —$OC(O)R^{36}$, —$C(O)R^{36}$ and —$C(O)OR^{36}$, $C_{1-6}$-alkyl, $C_{2-6}$-alkenyl and $C_{2-6}$-alkynyl,
  which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, wherein $R^{36}$ and $R^{37}$ independently are hydrogen, $C_{1-6}$-alkyl or aryl,
  of which the aryl moiety optionally may be substituted with one or more substituents selected from halogen, —CN, —$CF_3$, —$OCF_3$, —$NO_2$, —$OR^{38}$, —$NR^{38}R^{39}$ and $C_{1-6}$-alkyl, wherein $R^{38}$ and $R^{39}$ independently are hydrogen or $C_{1-6}$-alkyl, or $R^{36}$ and $R^{37}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or $R^{23}$ and $R^{24}$ when attached to the same ring carbon atom or different ring carbon atoms together may form a radical —O—$(CH_2)_t$—$CR^{40}R^{41}$—$(CH_2)_l$—O—, —$(CH_2)_t$—$CR^{40}R^{41}$—$(CH_2)_l$— or —S—$(CH_2)_t$—$CR^{40}R^{41}$—$(CH_2)_l$—S—, wherein
t and l independently are 0, 1, 2, 3, 4 or 5,
$R^{40}$ and $R^{41}$ independently are hydrogen or $C_{1-6}$-alkyl,
$R^{25}$ to $R^{30}$ independently are hydrogen, halogen, —CN, —$CF_3$, —$NO_2$, —$OR^{42}$, —$NR^{42}R^{43}$, $C_{1-6}$-alkyl, $C_{3-8}$-cycloalkyl or $C_{3-8}$-cycloalkenyl, wherein $R^{42}$ and $R^{43}$ independently are hydrogen or $C_{1-6}$-alkyl, or $R^{42}$ and $R^{43}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, $R^{31}$, $R^{32}$ and $R^{33}$ independently are hydrogen or $C_{1-6}$-alkyl,
$R^{34}$ and $R^{35}$ independently are
  hydrogen, $C_{1-6}$-alkyl, $C_{1-6}$-alkoxy, $C_{1-6}$-alkanoyl, —$C(O)NR^{44}R^{45}$ or —$S(O)_2R^{45}$,
  aryl, aroyl, aryl-$C_{1-6}$-alkoxy, aryl-$C_{1-6}$-alkanoyl or aryl-$C_{1-6}$-alkyl,
    of which the aryl moieties optionally may be substituted with one or more substituents selected from halogen, —CN, —$CF_3$, —$OCF_3$, —$OR^{44}$, —$NR^{44}R^{45}$ and $C_{1-6}$-alkyl, wherein $R^{44}$ and $R^{45}$ independently are hydrogen or $C_{1-6}$-alkyl, or $R^{34}$ and $R^{35}$ when attached to the carbon atom together with the said carbon atom may form a 3 to 8 membered cyclic ring optionally containing one or two heteroatoms selected from nitrogen, oxygen or sulfur, and optionally containing one or two double bonds, or $R^{34}$ and $R^{35}$ when attached to the nitrogen atom together with the said nitrogen atom may form a 3 to 8 membered heterocyclic ring optionally containing one or two further heteroatoms selected from nitrogen, oxygen or sulfur, and optionally containing one or two double bonds, as well as any optical or geometric isomer or tautomeric form thereof including mixtures of these or a pharmaceutically acceptable salt thereof.

In a preferred embodiment V is —$C(O)OH$, —$S(O)_2OH$, —$C(O)NHOH$ or 5-tetrazolyl, and more preferred —$C(O)OH$ or 5-tetrazolyl.

In a preferred embodiment A is

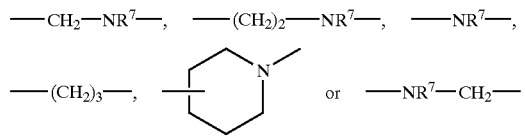

wherein $R^7$ is as defined for formula (I).

More preferred A is

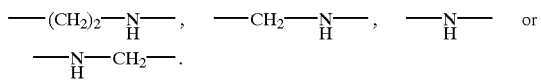

In a preferred embodiment Y is —$C(O)$—.

In another preferred embodiment Y is a valence bond.

In a preferred embodiment Z is

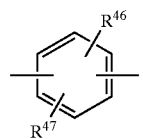

wherein $R^{46}$ and $R^{47}$ are as defined for formula (I).

More preferably, Z is

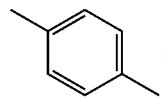

In a preferred embodiment $R^1$ is hydrogen.
In another preferred embodiment $R^1$ is methyl.
In a preferred embodiment X is

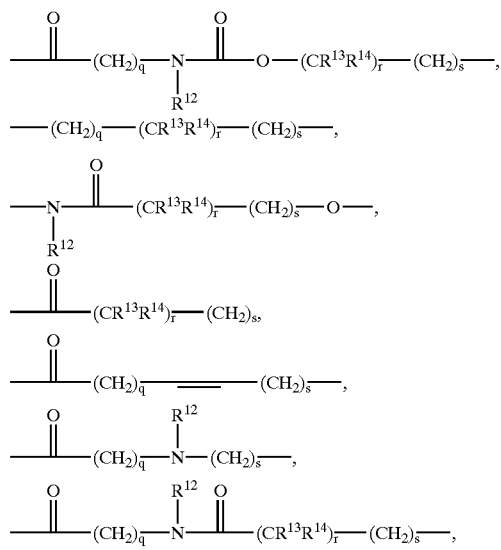

-continued

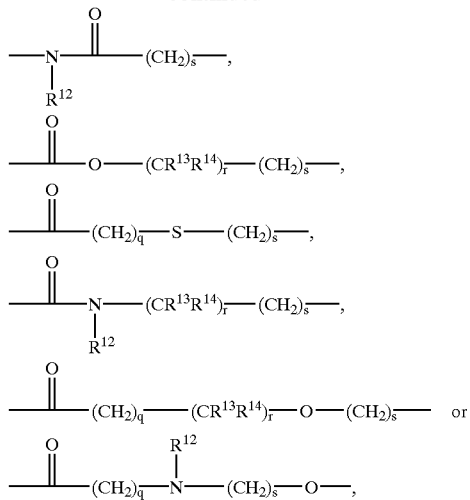

wherein q, r, s, $R^{12}$, $R^{13}$ and $R^{14}$ are as defined for formula (I).

More preferably, X is

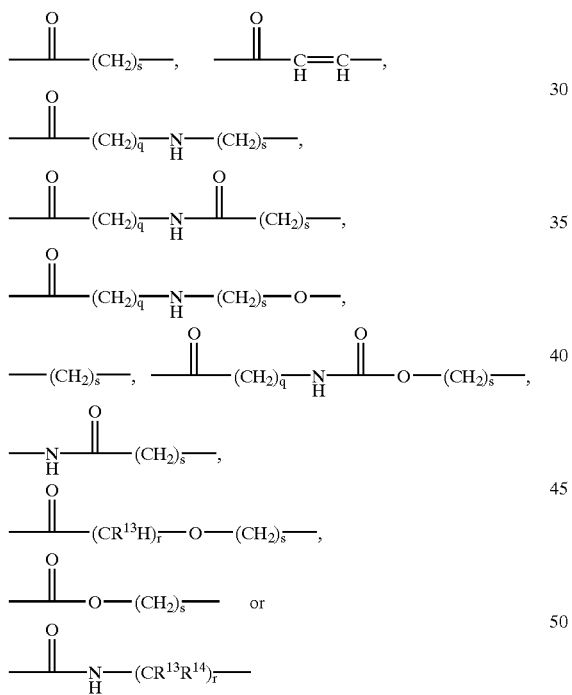

wherein q is 0 or 1, r is 0 or 1, s is 0, 1 or 2, and $R^{13}$ is hydrogen or $C_{1-6}$-alkyl.

Even more preferably, X is —C(O)NH—, —C(O)NHCH$_2$—, —C(O)NHCH(CH$_3$)—, —C(O)NHCH$_2$CH$_2$—, —C(O)CH$_2$—, —C(O)CH=CH—, —(CH$_2$)$_s$—, —C(O)—, —C(O)O— or —NHC(O)—, wherein s is 0 or 1.

Still more preferably, X is —C(O)NH—, —C(O)NHCH$_2$—, —C(O)NHCH(CH$_3$)—, —C(O)NHCH$_2$CH$_2$—, —C(O)CH$_2$—, —(CH$_2$)—, —C(O)— or —NHC(O)—.

Of these X is preferably —C(O)NH— or —C(O)NHCH(CH$_3$)—.

In a preferred embodiment D is

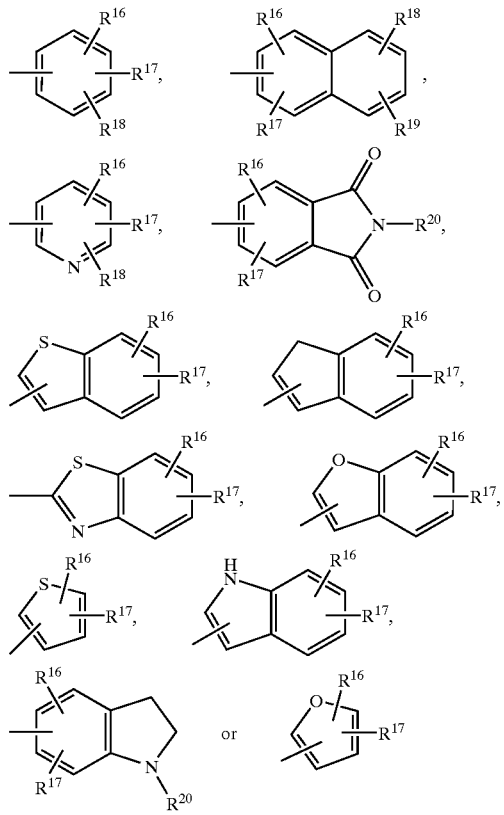

wherein $R^{16}$, $R^{17}$, $R^{18}$, $R^{19}$ and $R^{20}$ are as defined for formula (I).

In a preferred embodiment D is

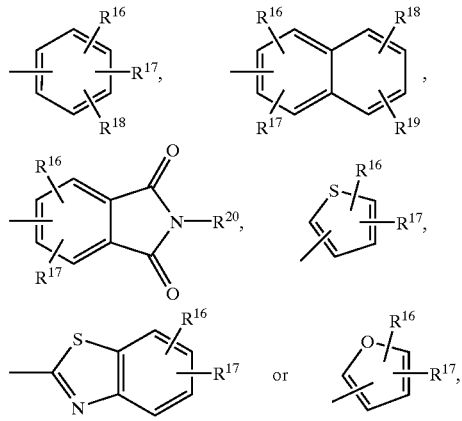

wherein $R^{16}$, $R^{17}$, $R^{18}$ and $R^{20}$ are as defined for formula (I).

In a preferred embodiment D

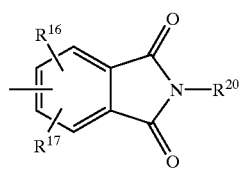

wherein $R^{16}$, $R^{17}$ and $R^{20}$ are as defined for formula (I).

More preferably, $R^{16}$ and $R^{17}$ are both hydrogen and $R^{20}$ is $C_{1-6}$-alkyl or $C_{3-8}$-cycloalkyl-$C_{1-6}$-alkyl. Even more preferably, $R^{20}$ is cyclopropylmethyl, butyl or isopropyl, especially preferred isopropyl.

In another preferred embodiment D is

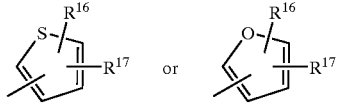

wherein $R^{16}$ and $R^{17}$ are as defined for formula (I).

In yet another preferred embodiment D is

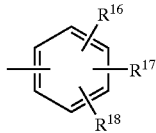

wherein $R^{16}$, $R^{17}$ and $R^{18}$ are as defined for formula (I).

Preferably, $R^{16}$, $R^{17}$ and $R^{18}$ are independently hydrogen, halogen, —CN, —NO$_2$, —CF$_3$, —OCF$_3$, hydroxy, —SCF$_3$, $C_{1-6}$-alkyl, $C_{1-6}$-alkyl substituted with hydroxy, $C_{1-6}$-alkyl substituted with —S(O)$_2$R$^{21}$, $C_{1-6}$-alkoxy, —S—$C_{1-6}$-alkyl, —C(O)OR$^{21}$, —C(O)R$^{21}$, —CH$_2$(O)R$^{21}$, —C(O)NR$^{21}$R$^{22}$, —S(O)R$^{21}$, —S(O)$_2$R$^{21}$, —S(O)$_2$CF$_3$, —S(O)$_2$NR$^{21}$R$^{22}$, $C_{3-8}$-cycloalkyl, $C_{3-8}$-cycloalkyl-$C_{1-6}$-alkoxy, $C_{3-8}$-cycloalkyl-$C_{1-6}$-alkylthio or $C_{3-8}$-cycloalkylthio, wherein $R^{21}$ and $R^{22}$ independently are hydrogen, $C_{1-6}$-alkyl, tri-$C_{1-6}$-alkylsilyl, $C_{3-8}$-cycloalkyl, $C_{3-8}$-cycloalkyl-$C_{1-6}$-alkyl, phenyl, phenyl-$C_{1-6}$-alkyl, 2,3-dihydroindolyl or isoindolyl, or $R^{21}$ and $R^{22}$ together with the nitrogen atom to which they are attached form a piperidine ring, phenoxy, phenoxycarbonyl, phenyl, phenyl-$C_{1-6}$-alkoxy, phenyl-$C_{1-6}$-alkyl, furanyl, tetrazolyl, benzoxazolyl or oxadiazolyl, of which the ring systems optionally may be substituted with halogen, —CN, —CF$_3$, —OCF$_3$, —NO$_2$, —C(O)OR$^{21}$, —OR$^{21}$, —NR$^{21}$R$^{22}$ or $C_{1-6}$-alkyl, wherein $R^{21}$ and $R^{22}$ independently are hydrogen or $C_{1-6}$-alkyl, or wherein $R^{16}$ and $R^{17}$ in adjacent positions form the radical —O—CH$_2$—O—, —CF$_2$—O—CF$_2$—O— or —O—CF$_2$—CF$_2$—O—, and $R^{18}$ is hydrogen.

More preferably, $R^{16}$, $R^{17}$ and $R^{18}$ are independently hydrogen, halogen, —CN, —NO$_2$, —CF$_3$, —OCF$_3$, —SCF$_3$, $C_{1-6}$-alkyl, $C_{1-6}$-alkyl substituted with hydroxy, $C_{1-6}$-alkyl substituted with —S(O)$_2$R$^{21}$, $C_{1-6}$-alkoxy, —S—$C_{1-6}$-alkyl, —C(O)OR$^{21}$, —C(O)R$^{21}$, —CH$_2$(O)R$^{21}$, —C(O)NR$^{21}$R$^{22}$, —S(O)R$^{21}$, —S(O)$_2$R$^{21}$, —S(O)$_2$CF$_3$, —S(O)$_2$NR$^{21}$R$^{22}$, $C_{3-6}$-cycloalkyl-$C_{1-6}$-alkoxy, $C_{3-8}$-cycloalkyl-$C_{1-6}$-alkylthio or $C_{3-8}$-cycloalkylthio, wherein $R^{21}$ and $R^{22}$ independently are hydrogen, $C_{1-6}$-alkyl, tri-$C_{1-6}$-alkylsilyl, $C_{3-8}$-cycloalkyl, $C_{3-8}$-cycloalkyl-$C_{1-6}$-alkyl, phenyl or 2,3-dihydroindolyl, or $R^{21}$ and $R^{22}$ together with the nitrogen atom to which they are attached form a piperidine ring, phenoxy, phenyl, benzyl, furanyl, tetrazolyl, benzoxazolyl or oxadiazolyl, of which the ring systems optionally may be substituted with halogen, —C(O)OR$^{21}$ or $C_{1-6}$-alkyl, wherein $R^{21}$ is hydrogen or $C_{1-6}$-alkyl, or wherein $R^{16}$ and $R^{17}$ in adjacent positions form the radical —CF$_2$—O—CF$_2$—O— or —O—CF$_2$—CF$_2$—O—, and $R^{18}$ is hydrogen.

Even more preferably, $R^{16}$, $R^{17}$ and $R^{18}$ independently are hydrogen, halogen, —CN, —NO$_2$, —CF$_3$, —OCF$_3$, —SCF$_3$, $C_{1-6}$-alkyl, $C_{1-6}$-alkyl substituted with hydroxy, $C_{1-6}$-alkoxy, —S—$C_{1-6}$-alkyl, —C(O)OR$^{21}$, —C(O)R$^{21}$, —CH$_2$(O)R$^{21}$, —C(O)NR$^{21}$R$^{22}$, —S(O)$_2$R$^{21}$, —(O)$_2$CF$_3$ or —S(O)$_2$NR$^{21}$R$^{22}$, wherein $R^{21}$ and $R^{22}$ independently are hydrogen, $C_{1-6}$-alkyl, tri-$C_{1-6}$-alkylsilyl, phenyl or 2,3-dihydroindolyl, phenoxy, phenyl, benzyl, furanyl, tetrazolyl, benzoxazolyl or oxadiazolyl, of which the ring systems optionally may be substituted with halogen, —C(O)OR$^{21}$ or $C_{1-6}$-alkyl, wherein $R^{21}$ is hydrogen or $C_{1-6}$-alkyl, or wherein $R^{16}$ and $R^{17}$ in adjacent positions form the radical —CF$_2$—O—CF$_2$—O— or —O—CF$_2$—CF$_2$—O—, and $R^{18}$ is hydrogen.

Still more preferably, $R^{16}$, $R^{17}$ and $R^{18}$ are independently hydrogen, halogen, —CN, —NO$_2$, —CF$_3$, —OCF$_3$, —SCF$_3$, $C_{1-6}$-alkyl, $C_{1-6}$-alkoxy, —S—$C_{1-6}$-alkyl, —C(O)OC$_{1-6}$-alkyl, —S(O)$_2$C$_{1-6}$-alkyl, —S(O)$_2$CF$_3$, —C(O)N(C$_{1-6}$-alkyl)(C$_{1-6}$-alkyl), —S(O)$_2$N(phenyl)(C$_{1-6}$-alkyl), —C(=O)C$_{1-6}$-alkyl, —CH$_2$OH, —CH$_2$O(tri-C$_{1-6}$-alkylsilyl), 2,3-dihydroindol-1-ylsulfonyl, phenoxy, phenyl, 4-chlorophenyl, 1,3,5-trimethylbenzyl, benzoxazolyl, 2-methyltetrazol-5-yl, 2-methyl-3-methoxycarbonylfuran-5-yl or 3-isopropyl-[1,2,4]oxadiazol-5-yl).

In a preferred embodiment one of $R^{16}$ to $R^{18}$ is hydrogen.

In another preferred embodiment two of $R^{16}$ to $R^{18}$ are hydrogen.

In yet another preferred embodiment $R^{16}$ and $R^{17}$ are both hydrogen and $R^{18}$ is —OCF$_3$, —SCF$_3$ —CF$_3$, —S(O)$_2$CH$_3$, phenyl, halogen, $C_{1-6}$-alkyl, nitro, —S—$C_{1-6}$-alkyl or —S(O)$_2$NR$^{21}$R$^{22}$, wherein $R^{21}$ is $C_{1-6}$-alkyl and $R^{22}$ is phenyl.

In still another preferred embodiment $R^{16}$ and $R^{17}$ are both hydrogen and $R^{18}$ is —OCF$_3$ or halogen.

In a further embodiment $R^{16}$ is hydrogen and $R^{17}$ and $R^{18}$ are both halogen or are both —CF$_3$.

In yet a further embodiment $R^{16}$ is hydrogen, $R^{17}$ is —CF$_3$ and $R^{18}$ is halogen, —CN, $C_{1-6}$-alkoxy or —OCF$_3$.

In still a further embodiment $R^{16}$ is hydrogen, $R^{17}$ is —OCF$_3$ and $R^{18}$ is —S(O)$_2$CH$_3$, —CH$_2$O-tri-C$_{1-6}$-alkylsilyl, benzoxazolyl or —CH$_2$OH.

In another embodiment $R^{16}$ is hydrogen, $R^{17}$ is C$_6$-alkyl and $R^{18}$ is —S(O)$_2$NR$^{21}$R$^{22}$, wherein $R^{21}$ is C$_{1-6}$-alkyl and $R^{22}$ is phenyl.

In still another embodiment $R^{16}$, $R^{17}$ and $R^{18}$ are selected from hydrogen, —OCF$_3$, —CF$_3$, —Br, —F and —Cl.

In a preferred embodiment E is

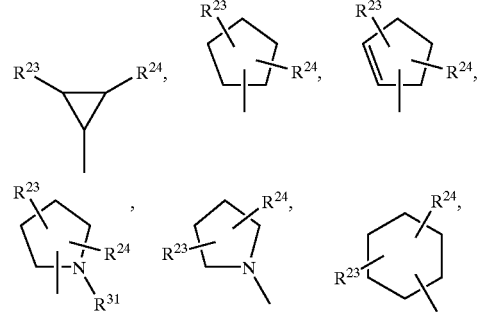

-continued
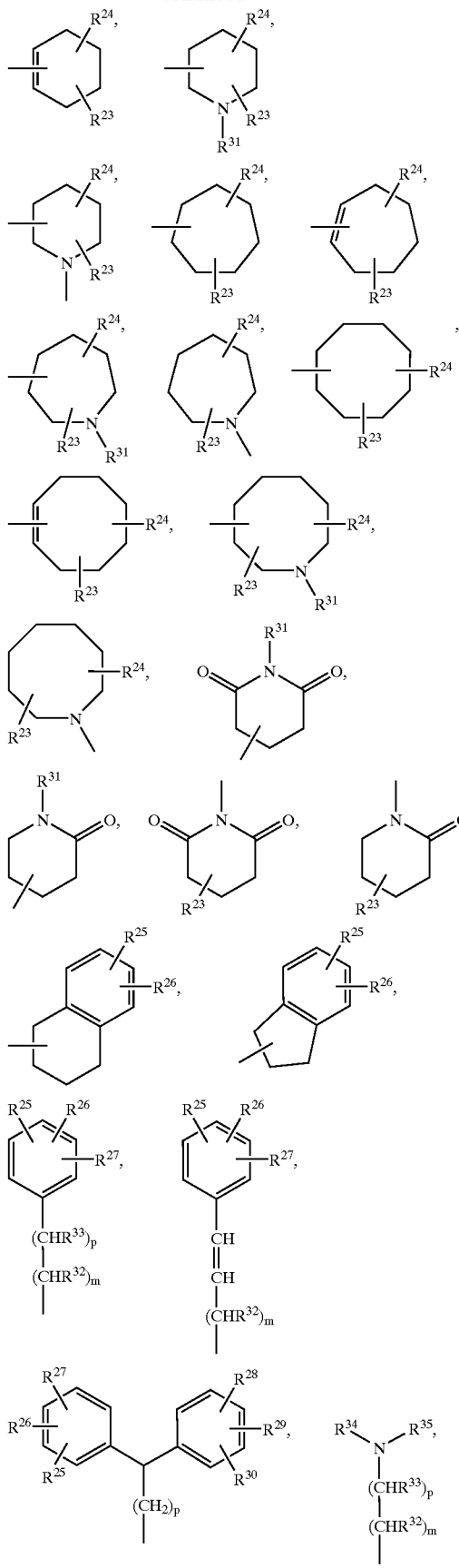
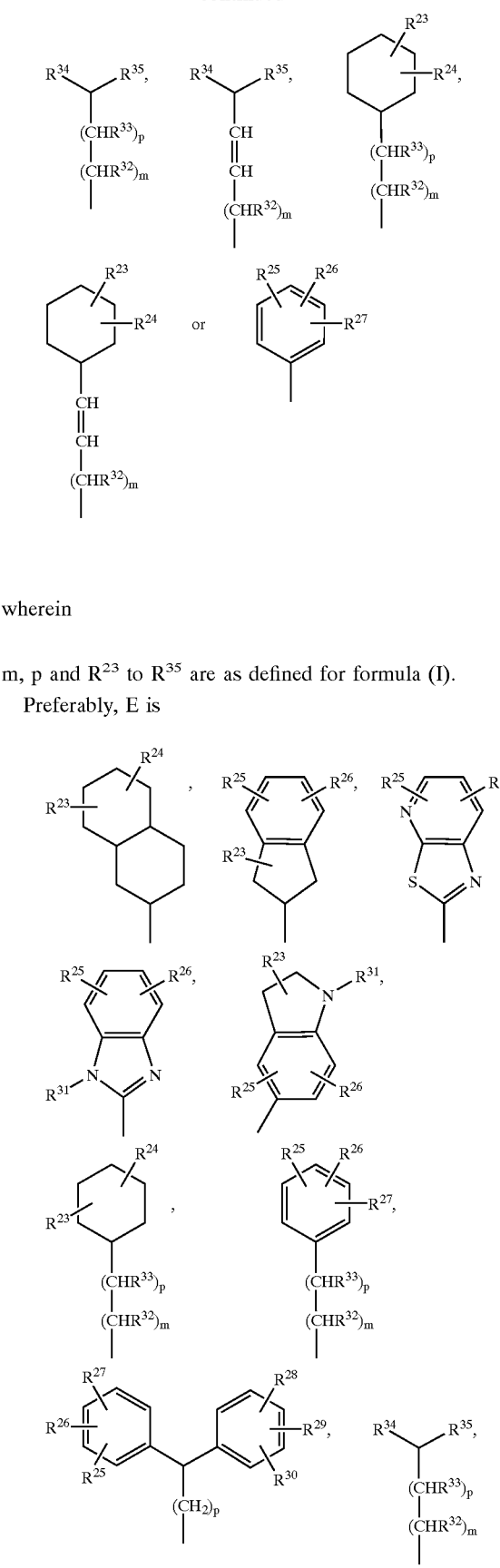
wherein
m, p and $R^{23}$ to $R^{35}$ are as defined for formula (I).
Preferably, E is

33

-continued

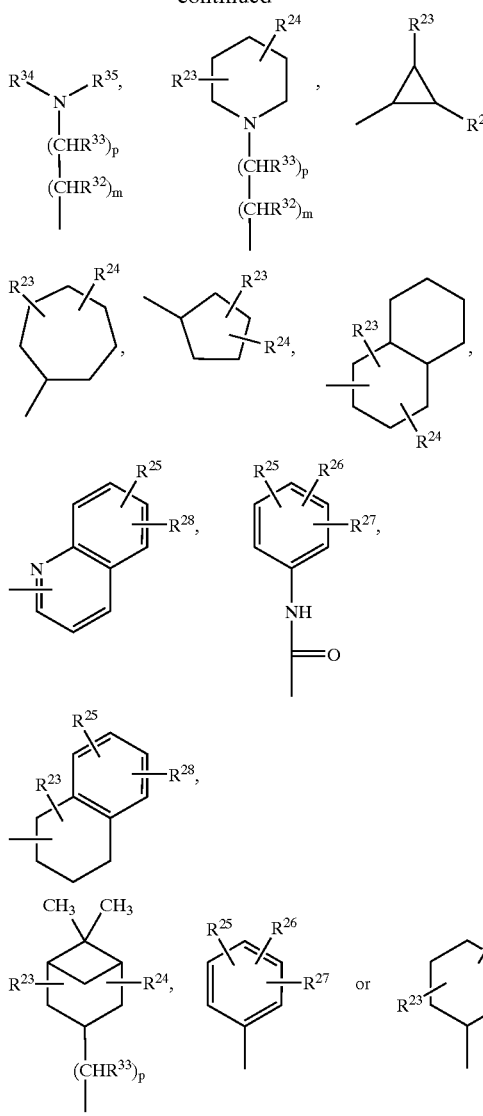

wherein m, p and $R^{23}$ to $R^{35}$ are as defined for formula (I).

More preferably, E is

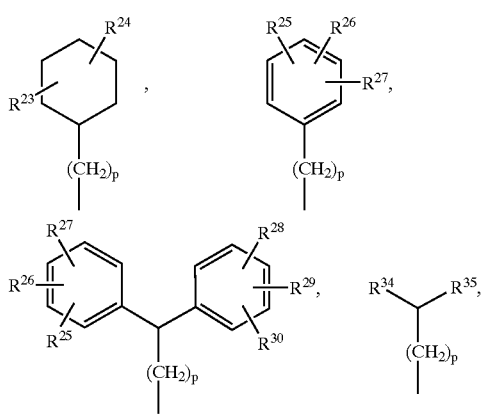

34

-continued

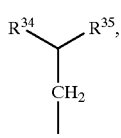

wherein p, $R^{23}$, $R^{24}$, $R^{25}$, $R^{26}$, $R^{27}$, $R^{28}$, $R^{29}$, $R^{30}$, $R^{34}$ and $R^{35}$ are as defined for formula (I).

Even more preferably, E is wherein $R^{23}$, $R^{24}$, $R^{25}$, $R^{26}$, $R^{27}$, $R^{34}$ and $R^{35}$ are as defined for formula (I).

When E is $R^{34}$ and $R^{35}$ are preferably independently $C_{1-6}$-alkyl, hydrogen or $C_{1-6}$-alkoxy. More preferably, $R^{34}$ and $R^{35}$ are both $C_{1-6}$-alkyl.

In another preferred embodiment E is

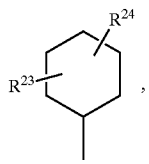

wherein $R^{23}$ and $R^{24}$ are as defined for formula (I).
Preferably, E is

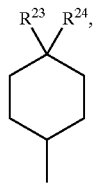

wherein $R^{23}$ and $R^{24}$ are as defined for formula (I).
Preferably, $R^{23}$ and $R^{24}$ are independently selected from hydrogen, $C_{1-6}$-alkyl, $C_{3-8}$-cycloalkyl, $C_{3-8}$-cycloalkylidene, phenoxy, phenyl, —C(O)NR$^{36}$R$^{37}$ and —OC(O)NH-phenyl, of which the phenyl moiety optionally may be substituted with —OCF$_3$, wherein $R^{36}$ and $R^{37}$ are as defined in claim 1, or $R^{23}$ and $R^{24}$ together form the radical —(CH$_2$)$_t$—CR$^{40}$R$^{41}$—(CH$_2$)$_l$—, —O—(CH$_2$)$_t$—CR$^{40}$R$^{41}$—(CH$_2$)$_l$—O—, —S—(CH$_2$)$_t$—CR$^{40}$R$^{41}$—(CH$_2$)$_l$—S—, wherein t, l, $R^{40}$ and $R^{41}$ are as defined for formula (I).
More preferably, $R^{23}$ is hydrogen and $R^{24}$ is $C_{1-6}$-alkyl such as tert-butyl or $C_{3-8}$-cycloalkyl such as cyclohexyl, wherein $R^{23}$ and $R^{24}$ are both $C_{1-6}$-alkyl or wherein $R^{23}$ and $R^{24}$ together form the radical —(CH$_2$)$_5$—.

In yet another preferred embodiment E is

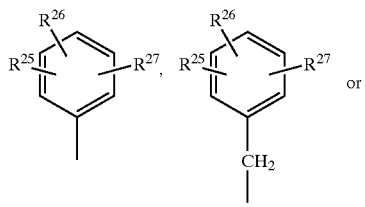

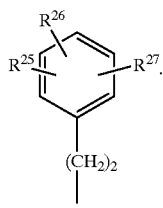

wherein $R^{25}$, $R^{26}$ and $R^{27}$ are as defined for formula (I).
Preferably, E is

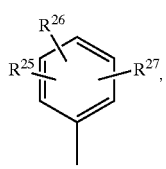

wherein $R^{25}$, $R^{26}$ and $R^{27}$ are as defined for formula (I).
Preferably, $R^{25}$, $R^{26}$ and $R^{27}$ are independently selected from hydrogen, halogen, $C_{1-6}$-alkyl, $C_{1-6}$-alkoxy, $C_{3-8}$-cycloalkyl, $C_{4-8}$-cycloalkenyl, —CF$_3$, —OCF$_3$ or —NR$^{42}$R$^{43}$, wherein $R^{42}$ and $R^{43}$ are as defined for formula (I).

More preferably, E is

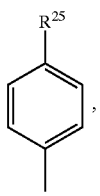

wherein $R^{25}$ is —OCF$_3$, —CF$_3$, $C_{1-6}$-alkyl such as tert-butyl, piperidyl, $C_{3-8}$-cycloalkyl such as cyclohexyl or $C_{4-8}$-cycloalkenyl such as cyclohexenyl.

In another preferred embodiment E is

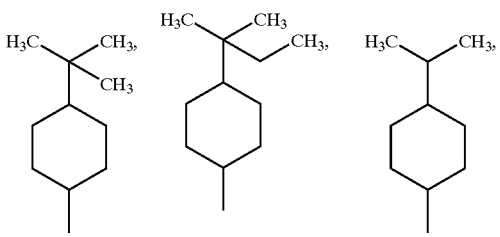

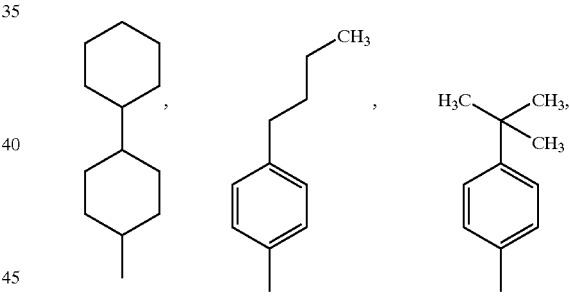

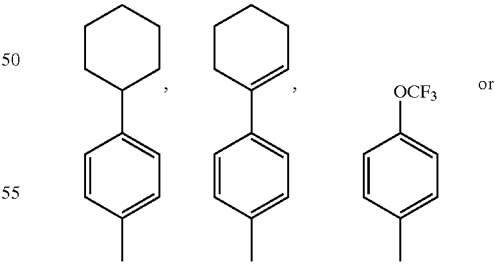

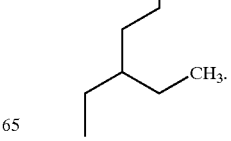

Of these E is preferably

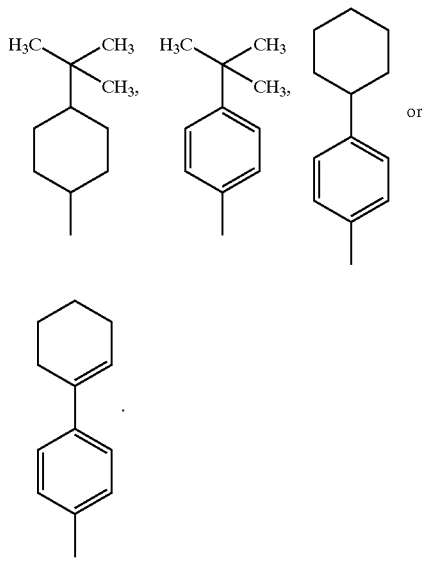

In one preferred embodiment the present invention relates to compounds of the general formula (I₁):

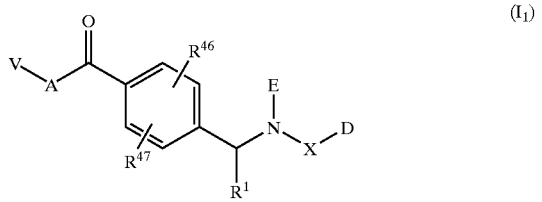

(I₁)

wherein V, A, R⁴⁶, R⁴⁷, R¹, E, X and D are as defined for formula (I) or in any one of the above preferred embodiments.

In another preferred embodiment the present invention relates to compounds of the general formula (I₂):

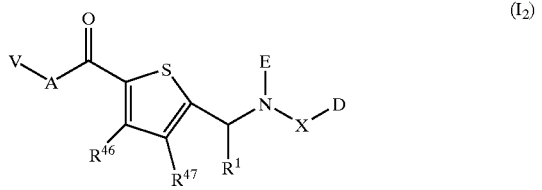

(I₂)

wherein V, A, R⁴⁶, R⁴⁷, R¹, E, X and D are as defined for formula (I) or in any one of the above preferred embodiments.

In still another preferred embodiment the present invention relates to compounds of the general formula (I₃):

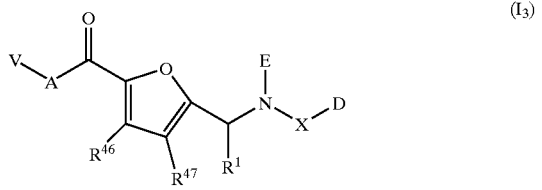

(I₃)

wherein V, A, R⁴⁶, R⁴⁷, R¹, E, X and D are as defined for formula (I) or in any one of the above preferred embodiments.

In yet another preferred embodiment the present invention relates to compounds of the general formula (I₄):

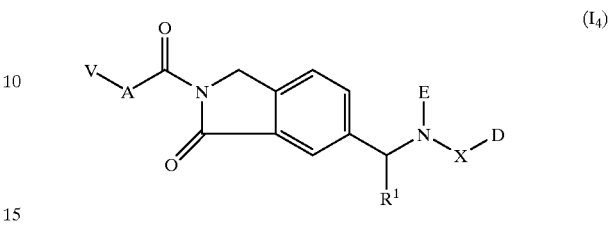

(I₄)

wherein V is —C(O)OR², —C(O)NR²R³ or —C(O)NR²OR³, and R¹, R², R³, E, X and D are as defined for formula (I) or in any one of the above preferred embodiments.

In a further preferred embodiment the present invention relates to compounds of the general formula (I₅):

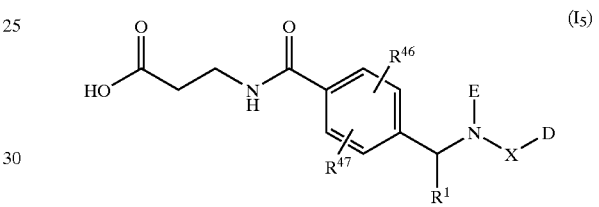

(I₅)

wherein R⁴⁶, R⁴⁷, R¹, E, X and D are as defined for formula (I) or in any one of the above preferred embodiments.

In still a further preferred embodiment the present invention relates to compounds of the general formula (I₆):

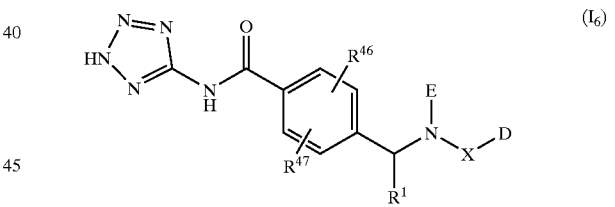

(I₆)

wherein R⁴⁶, R⁴⁷, R¹, E, X and D are as defined for formula (I) or in any one of the above preferred embodiments.

In yet a further preferred embodiment the present invention relates to compounds of the general formula (I₇):


(I₇)

wherein R⁴⁶, R⁴⁷, R¹, E, X and D are as defined for formula (I) or in any one of the above preferred embodiments.

In another preferred embodiment the present invention relates to compounds of the general formula (I₈):

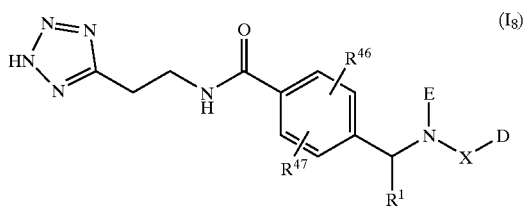

wherein $R^{46}$, $R^{47}$, $R^1$, E, X and D are as defined for formula (I) or in any one of the above preferred embodiments.

In still another preferred embodiment the present invention relates to compounds of the general formula ($I_9$):

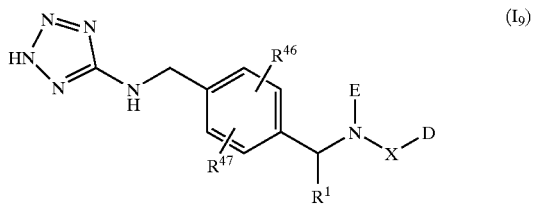

wherein $R^{46}$, $R^{47}$, $R^1$, E, X and D are as defined for formula (I) or in any one of the above preferred embodiments.

In the above formulae ($I_1$) to ($I_3$) and ($I_5$) to ($I_9$), $R^{46}$ and $R^{47}$ are preferably both hydrogen.

The compounds of the present invention may have one or more asymmetric centres and it is intended that any optical isomers, as separated, pure or partially purified optical isomers or racemic mixtures thereof are included within the scope of the invention.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms which the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methyl-, dimethyl-, trimethyl-, ethyl-, hydroxyethyl-, diethyl-, butyl-, tetramethylammonium salts and the like.

Also intended as pharmaceutically acceptable acid addition salts are the hydrates, which the present compounds, are able to form.

Furthermore, the pharmaceutically acceptable salts comprise basic amino acid salts such as lysine, arginine and ornithine.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming pharmacologically active substances. In general, such prodrugs will be functional derivatives of the compounds of the general formula (I), which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds according to the present invention act to antagonize the action of glucagon and are accordingly useful for the treatment and/or prevention of disorders and diseases in which such an antagonism is beneficial.

Accordingly, in a further aspect the invention relates to a compound according to the invention for use as a medicament.

The invention also relates to pharmaceutical compositions comprising, as an active ingredient, at least one compound according to the invention together with one or more pharmaceutically acceptable carriers or excipients.

The pharmaceutical composition is preferably in unit dosage form, comprising from about 0.05 mg to about 1000 mg, preferably from about 0.1 mg to about 500 mg and especially preferred from about 0.5 mg to about 200 mg of the compound according to the invention.

Furthermore, the invention relates to the use of a compound according to the invention for the preparation of a pharmaceutical composition for the treatment and/or prevention of a disorder or disease, wherein a glucagon antagonistic action is beneficial.

The invention also relates to a method for the treatment and/or prevention of disorders or diseases, wherein a glucagon antagonistic action is beneficial the method comprising administering to a subject in need thereof an effective amount of a compound according to the invention.

Owing to their antagonizing effect of the glucagon receptor the present compounds may be suitable for the treatment and/or prevention of any glucagon-mediated conditions and diseases.

Accordingly, the present compounds may be applicable for the treatment and/or prevention of hyperglycemia, IGT, insulin resistance syndromes, syndrome X, Type 1 diabetes, Type 2 diabetes, hyperlipidemia, dyslipidemia, hypertriglyceridemia, glucagonomas, acute pancreatitis, cardiovascular diseases, hypertension, cardiac hypertrophy, gastrointestinal disorders, obesity, diabetes as a consequence of obesity, diabetic dyslipidemia, etc. Furthermore, they may be applicable as diagnostic agents for identifying patients having a defect in the glucagon receptor, as a therapy to increase gastric acid secretions and to reverse intestinal hypomobility due to glucagon administration.

In a preferred embodiment of the invention the present compounds are used for the manufacture of a medicament for the treatment and/or prevention of hyperglycemia.

In yet a preferred embodiment of the invention the present compounds are used for the manufacture of a medicament for lowering blood glucose in a mammal.

In another preferred embodiment of the invention the present compounds are used for the preparation of a pharmaceutical composition for the treatment and/or prevention of IGT.

In still another preferred embodiment of the invention the present compounds are used for the preparation of a pharmaceutical composition for the treatment and/or prevention of Type 2 diabetes.

In yet another preferred embodiment of the invention the present compounds are used for the preparation of a pharmaceutical composition for the delaying or prevention of the progression from IGT to Type 2 diabetes.

In yet another preferred embodiment of the invention the present compounds are used for the preparation of a pharmaceutical composition for the delaying or prevention of the progression from non-insulin requiring Type 2 diabetes to insulin requiring Type 2 diabetes.

In a further preferred embodiment of the invention the present compounds are used for the preparation of a pharmaceutical composition for the treatment and/or prevention of Type 1 diabetes. Such treatment and/or prevention is normally accompanied by insulin therapy.

In a further preferred embodiment of the invention the present compounds are used for the preparation of a pharmaceutical composition for the treatment and/or prevention of obesity.

In still a further embodiment of the invention the present compounds are used for the preparation of a pharmaceutical composition for the treatment and/or prevention of an appetite regulation or energy expenditure disorder.

In a further aspect of the invention the present compounds may be administered in combination with one or more pharmacologically active substances eg selected from antidiabetics, antiobesity agents, antihypertensive agents and agents for the treatment and/or prevention of complications resulting from or associated with diabetes.

Suitable antidiabetics comprise insulin, GLP-1 derivatives such as those disclosed in WO 98/08871 to Novo Nordisk A/S, which is incorporated herein by reference, as well as orally active hypoglycaemic agents.

The orally active hypoglycaemic agents preferably comprise sulphonylureas, biguanides, meglitinides, oxadiazolidinediones, thiazolidinediones, glucosidase inhibitors, glucagon antagonists, GLP-1 agonists, potassium channel openers such as those disclosed in WO 97/26265 and WO 99/03861 to Novo Nordisk A/S which are incorporated herein by reference, insulin sensitizers, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents, compounds lowering food intake, PPAR (peroxisome proliferator-activated receptor) and RXR (retinoid X receptor) agonists and agents acting on the ATP-dependent potassium channel of the β-cells.

In one embodiment of the invention the present compounds are administered in combination with insulin.

In a further embodiment the present compounds are administered in combination with a sulphonylurea eg tolbutamide, glibenclamide, glipizide or glicazide.

In another embodiment the present compounds are administered in combination with a biguanide eg metformin.

In yet another embodiment the present compounds are administered in combination with a meglitinide eg repaglinide.

In still another embodiment the present compounds are administered in combination with a thiazolidinedione eg troglitazone, ciglitazone, pioglitazone, rosiglitazone or the compounds disclosed in WO 97/41097 to Dr. Reddy's Research Foundation.

Furthermore, the present compounds may be administered in combination with the insulin sensitizers disclosed in WO 99/19313 to Dr. Reddy's Research Foundation.

In a further embodiment the present compounds are administered in combination with an α-glucosidase inhibitor eg miglitol or acarbose.

In another embodiment the present compounds are administered in combination with an agent acting on the ATP-dependent potassium channel of the β-cells eg tolbutamide, glibenclamide, glipizide, glicazide or repaglinide.

Furthermore, the present compounds may be administered in combination with nateglinide. In still another embodiment the present compounds are administered in combination with an antihyperlipidemic agent or antilipidemic agent eg cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg in combination with a sulphonylurea and metformin, a sulphonylurea and acarbose, repaglinide and metformin, insulin and a sulphonylurea, insulin and metformin, insulin and troglitazone, insulin and lovastatin, etc.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

It should be understood that any suitable combination of the compounds according to the invention with one or more of the above-mentioned compounds and optionally one or more pharmacologically active substances are considered to be within the scope of the present invention.

PHARMACUETICAL COMPOSITIONS

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
| --- | --- |
| Active compound (as free compound or salt thereof) | 5.0 mg |
| Lactosum Ph. Eur. | 67.8 mg |
| Cellulose, microcryst. (Avicel) | 31.4 mg |
| Amberlite | 1.0 mg |
| Magnesii stearas Ph. Eur. | q.s. |
| Coating: | |
| HPMC approx. | 9 mg |
| Mywacett 9-40 T* approx. | 0.9 mg |

*Acylated monoglyceride used as plasticizer for film coating.

If desired, the pharmaceutical composition of the invention may comprise the compound of the formula (I) in combination with further pharmacologically active substances such as those described in the foregoing.

EXPERIMENTAL

In the following section binding assays as well as functional assays useful for evaluating the efficiency of the compounds of the invention are described.

Binding of compounds to the glucagon receptor was determined in a competition binding assay using the cloned human glucagon receptor.

Antagonism was determined as the ability of the compounds to inhibit the amount of cAMP formed in the presence of 5 nM glucagon.

For further characterization, antagonism was determined in a functional assay, measured as the ability of the compounds to right-shift the glucagon dose-response curve. Using at least 3 different antagonist concentrations, the $K_i$ was calculated from a Schild plot.

Glucagon Binding Assay (I)

Receptor binding was assayed using cloned human receptor (Lok et al., Gene 140, 203–209 (1994)). The receptor inserted in the pLJ6' expression vector using EcoRI/SSt1 restriction sites (Lok et al.) was expressed in a baby hamster kidney cell line (A3 BHK 570-25). Clones were selected in the presence of 0.5 mg/mL G-418 and were shown to be stable for more than 40 passages. The Kd was shown to be 0.1 nM.

Plasma membranes were prepared by growing cells to confluence, detaching them from the surface and resuspending the cells in cold buffer (10 mM tris/HCl, pH 7.4 containing 30 mM NaCl, 1 mM dithiothreitol, 5 mg/L leupeptin (Sigma), 5 mg/L pepstatin (Sigma), 100 mg/L bacitracin (Sigma) and 15 mg/L recombinant aprotinin (Novo Nordisk A/S)), homogenization by two 10-s bursts using a Polytron PT 10-35 homogenizer (Kinematica), and centrifugation upon a layer of 41 w/v % sucrose at 95.000×g for 75 min. The white band located between the two layers was diluted in buffer and centrifuged at 40.000×g for 45 min. The precipitate containing the plasma membranes was suspended in buffer and stored at −80° C. until use. Glucagon was iodinated according to the chloramine T method (Hunter and Greenwood, Nature 194, 495 (1962)) and purified using anion exchange chromatography (Jørgensen et al., Hormone and Metab. Res. 4, 223–224 (1972). The specific activity was 460 μCi/μg on the day of iodination. Tracer was stored at −18° C. in aliquots and were used immediately after thawing.

Binding assays were carried out in triplicate in filter microtiter plates (MADV N65, Millipore). The buffer used in this assay was 50 mM HEPES, 5 mM EGTA, 5 mM MgCl$_2$, 0.005% tween 20, pH 7.4. Glucagon was dissolved in 0.05 M HCl, added an equal amount (w/w) of HSA and freeze-dried. On the day of use, it was dissolved in water and diluted in buffer to the desired concentrations.

Test compounds were dissolved and diluted in DMSO. 140 μL buffer, 25 μL glucagon or buffer, and 10 μL DMSO or test compound were added to each well. Tracer (50.000 cpm) was diluted in buffer and 25 μL were added to each well. 1–4 μg freshly thawed plasma membrane protein diluted in buffer was then added in aliquots of 25 μL to each well. Plates were incubated at 30° C. for 2 hours. Non-specific binding was determined with $10^{-6}$ M of glucagon. Bound tracer and unbound tracer were then separated by vacuum filtration (Millipore vacuum manifold). The plates were washed with 2×100 μL buffer/well. The plates were air dried for a couple of hours, whereupon the filters were separated from the plates using a Millipore Puncher. The filters were counted in a gamma counter.

Functional Assay (I)

The functional assay was carried out in 96 well microtiter plates (tissue culture plates, Nunc). The resulting buffer concentrations in the assay were 50 mM tris/HCl, 1 mM EGTA, 1.5 mM MgSO$_4$, 1.7 mM ATP, 20 μM GTP, 2 mM IBMX (isobutyl-methyl-xanthine), 0.02% tween-20 and 0.1% HSA. pH was 7.4. Glucagon and proposed antagonist were added in aliquots of 35 μL diluted in 50 mM tris/HCl, 1 mM EGTA, 1.85 mM MgSO$_4$, 0.0222% tween-20 and 0.111% HSA, pH 7.4. 20 μL of 50 mM tris/HCl, 1 mM EGTA, 1.5 mM MgSO$_4$, 11.8 mM ATP, 0.14 mM GTP, 14 mM IBMX and 0.1% HSA, pH 7.4 was added. GTP was dissolved immediately before the assay.

50 μL containing 5 μg of plasma membrane protein was added in a tris/HCl, EGTA, MgSO$_4$, HSA buffer (the actual concentrations were dependent upon the concentration of protein in the stored plasma membranes).

The total assay volume was 140 μL. The assay was incubated for 2 hours at 37° C. with continuous shaking. Reaction was terminated by addition of 25 μL 0.5 N HCl. cAMP was measured by the use of a scintillation proximity kit (Amersham).

Glucagon Binding Assay (II)

Receptor binding was assayed using the cloned human receptor (Lok et al., Gene 140, 203–209 (1994)). The receptor inserted in the pLJ6' expression vector using EcoRI/SSt1 restriction sites (Lok et al.) was expressed in a baby hamster kidney cell line (A3 BHK 570-25). Clones were selected in the presence of 0.5 mg/mL G-418 and were shown to be stable for more than 40 passages. The Kd was shown to be 0.1 nM.

Plasma membranes were prepared by growing cells to confluence, detaching them from the surface and resuspending the cells in cold buffer (50 mM tris base, pH 7.4 containing 0.32 mM sucrose, 2 mM EGTA, 1 µg/mL leupeptin, 5 µg/mL pepstatin A, 5 µg/mL aprotinin, 1 mM phenylmethylsulfonylfluoride (all from Sigma)), homogenization by two 10-s bursts using a Polytron PT 10-35 homogenizer (Kinematica), and centrifugation. The homogenate was resuspended and centrifuged again. The final precipitate containing the plasma membranes was suspended in buffer and stored at −80° C. until use.

Binding assays were carried out in duplicate in polypropylene tubes or microtiter plates. The buffer used in this assay was 50 mM HEPES pH 7.4 containing 5 mM EGTA, 5 mM MgCl$_2$ and 0.005% Tween 20. Sample (glucagon (Bachem CA) or test compounds) was added to each tube or well. Tracer (~25.000 cpm) was diluted in buffer and was added to each tube or well. 0.5 mg freshly thawed plasma membrane protein diluted in buffer was then added in aliquots to each tube or well. Tubes or plates were incubated at 37° C. for 1 hour. Non-specific binding was determined with 10$^{-7}$ M of glucagon. Bound tracer and unbound tracer were then separated by vacuum filtration. The tubes or wells were washed twice with 0.01% Triton X-100 buffer. Scintillation fluid was added to the plates and radioactivity was quantified using a scintillation counter.

Functional Assay (II)

The functional assay determined the ability of the compounds to antagonize glucagon-stimulated formation of cAMP in a whole-cell assay. The assay was carried out in borosilicate glass 12×75 tubes. The buffer concentrations in the assay were 10 mM HEPES, 1 mM EGTA, 1.4 mM MgCl$_2$, 0.1 mM IBMX, 30 mM NaCl, 4.7 mM KCl, 2.5 mM NaH$_2$PO$_4$, 3 mM glucose and 0.2% BSA. The pH was 7.4. Loose whole cells (0.5 mL, 10$^6$/mL) were pretreated with various concentrations of compounds for 10 min at 37° C., then challenged with glucagon for 20 min. Some aliquots (500 µL) of cells were treated with test compounds (55 µL) alone to test for agonist activity. The reactions were terminated by centrifugation, followed by cell lysis with the addition of 500 µL 0.1% HCl. Cellular debris was pelleted and the supernatant containing cAMP evaporated to dryness. cAMP was measured by the use of an RIA kit (NEN, NEK-033). Some assays were carried out utilizing the adenylate cyclase FlashPlate system from NEN.

Glucagon Binding Assay (III)

BHK (baby hamster kidney cell line) cells were transfected with the human glucagon receptor and a membrane preparation of the cells was prepared. Wheat Germ Agglutinin derivatized SPA beads containing a scintillant (WGA beads) (Amersham) bound the membranes. $^{125}$I-glucagon bound to human glucagon receptor in the membranes and excited the scintillant in the WGA beads to light emission. Glucagon or samples binding to the receptor competed with $^{125}$I-glucagon.

All steps in the membrane preparation were kept on ice or performed at 4° C. BHK cells were harvested and centrifuged. The pellet was resuspended in homogenisation buffer (25 mM HEPES pH=7.4, 2.5 mM CaCl$_2$, 1.0 mM MgCl$_2$, 250 mg/L bacitracin), homogenised 2×10 sec using Polytron 10-35 homogenizer (Kinematica) and added the same amount of homogenisation buffer as used for resuspension. After centrifugation (15 min at 1000×g) the supernatant was transferred to cold centrifuge tubes and centrifuged for 45 min at 40.000×g. The pellet was resuspended in homogenisation buffer, homogenised 2×10 sec (Polytron) and additional homogenisation buffer was added. The suspension was centrifuged for 45 min at 40.000×g and the pellet was resuspended in resuspension buffer (25 mM HEPES pH=7.4, 2.5 mM CaCl$_2$, 1.0 mM MgCl$_2$) and homogenised 2×10 sec. (Polytron). The protein concentration was normally around 1.75 mg/mL. Stabilisation buffer (25 mM HEPES pH=7.4, 2.5 mM CaCl$_2$, 1.0 mM MgCl$_2$, 1% BSA, 500 mg/L bacitracin, 2.5 M sucrose) was added and the membrane preparation was stored at −80° C.

The glucagon binding assay was carried out in opti plates (Polystyrene Microplates, Packard). 50 µL assay buffer (25 mM HEPES pH=7.5, 2.5 mM CaCl$_2$, 1.0 mM MgCl$_2$, 0.003% Tween-20, 0.005% bacitracin, 0.05% sodium azide) and 5 µL glucagon or test compound (in DMSO) were added to each well. 50 µL tracer ($^{125}$I-porcine glucagon, 70.000 cpm) and 50 µL membranes (12.5 µg) containing the human glucagon receptor were then added to the wells. Finally 50 µL WGA beads containing 1 mg beads were transferred to the well. The assay was incubated for 4 hours on a shaker and then settled for 8–48 hours. The opti plates were counted in a Topcounter. Non-specific binding was determined with 500 nM of glucagon.

Synthesis Methods

The following synthesis protocols refer to intermediate compounds and final products identified in the specification and in the synthetic schemes. The preparation of the compounds of the present invention is described in detail using the following examples, but the chemical reactions described are disclosed in terms of their general applicability to the preparation of the glucagon antagonists of the invention. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, that is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

Some of the NMR data shown in the following examples are only selected data.

Unless otherwise specified in the examples, the cis/trans isomeric compounds were obtained as mixtures of cis and trans isomers, which may be separated by chromatography. Thus, the present invention comprises the compounds in form of mixtures of cis and trans isomers as well as the pure isomeric forms.

In the examples the following terms are intended to have the following meanings:

| | |
|---|---|
| DMF: | N,N-dimethylformamide |
| DMSO: | dimethyl sulfoxide |

-continued

| Fmoc: | 9-fluorenylmethyloxycarbonyl |
| HBTU: | 2-(1H-Benzotriazol-1-yl)-1,1,3,3-tetramethyluronium hexafluorophosphate |
| M.p.: | melting point |
| NCS: | N-Chlorosuccinimide |
| NMP: | N-methylpyrrolidone |
| -OSu: | 2,5-dioxo-pyrrolidin-1-yloxy |
| TFA: | trifluoroacetic acid |
| THF: | tetrahydrofuran |

The final products obtained were characterized by analytical RP-HPLC (retention time) and/or by HPLC-MS (molecular mass and/or retention time).

The RP-HPLC analyses were performed on a Waters HPLC system consisting of Waters™ 600S Controller, Waters™ 996 Photodiode Array Detector, Waters™ 717 Autosampler, Waters™ 616 Pump, Waters™ 3 mm×150 mm 3.5µ C-18 Symmetry column and Millenium QuickSet Control Ver. 2.15 using UV detection at 214 nm. A linear gradient was applied from 5% to 90% acetonitrile/0.1% TFA/water over 15 min at a flow rate of 1 mL/minute.

HPLC-MS (Method A)

The following instrumentation was used:

Sciex API 100 Single quadropole mass spectrometer

Perkin Elmer Series 200 Quard pump

Perkin Elmer Series 200 autosampler

Applied Biosystems 785A UV detector

Sedex 55 evaporative light scattering detector

A Valco column switch with a Valco actuator controlled by timed events from the pump.

The Sciex Sample control software running on a Macintosh PowerPC 7200 computer was used for the instrument control and data acquisition.

The HPLC pump was connected to four eluent reservoirs containing:

| A: | Acetonitrile |
| B: | Water |
| C: | 0.5% TFA in water |
| D: | 0.02 M ammonium acetate |

The requirements for samples are that they contain approximately 500 µg/mL of the compound to be analysed in an acceptable solvent such as methanol, ethanol, acetonitrile, THF, water and mixtures thereof. (High concentrations of strongly eluting solvents will interfere with the chromatography at low acetonitrile concentrations.)

The analysis was performed at room temperature by injecting 20 µL of the sample solution on the column, which was eluted with a gradient of acetonitrile in either 0.05% TFA or 0.002 M ammonium acetate. Depending on the analysis method varying elution conditions were used.

The eluate from the column was passed through a flow splitting T-connector, which passed approximately 20 µL/min (1/50) through approx. 1 m. 75µ fused silica capillary to the API interface of API 100 spectrometer.

The remaining 1.48 mL/min (49/50) was passed through the UV detector and to the ELS detector.

During the LC-analysis the detection data were acquired concurrently from the mass spectrometer, the UV detector and the ELS detector.

The LC conditions, detector settings and mass spectrometer settings used for the different methods are given in the following tables.

| Column | Waters Symmetry $C_{18}$ 3 mm × 150 mm |
| Gradient | 5%–90% acetonitrile in 0.05% TFA linearly during 15 min at 1 mL/min |
| Detection | UV: 214 nm           ELS: 40° C. |
| MS | Experiment:   Start: 100 amu Stop: 800 amu Step: 0.2 amu |
| | Dwell:    0.571 msec |
| | Method:   Scan 284 times = 9.5 min |

HPLC-MS (Method B)

This method was identical to METHOD A but using the following conditions and settings:

| Column | YMC ODS-A 120 Å s - 5µ 3 mm × 50 mm id |
| Gradient | 5%–90% acetonitrile in 0.05% TFA linearly during 7.5 min at 1.5 mL/min |
| Detection | UV: 214 nm           ELS: 40° C. |
| MS | Experiment:   Start: 100 amu Stop: 800 amu Step: 0.2 amu |
| | Dwell:    0.571 msec |
| | Method:   Scan 284 times = 9.5 min |

HPLC-MS (Method C)

The following instrumentation was used:

Hewlett Packard series 1100 MSD G1946A Single quadropole mass spectrometer

Hewlett Packard series 1100 MSD G1312A Bin pump

Hewlett Packard series 1100 MSD G1313A ALS autosampler

Hewlett Packard series 1100 MSD G1315A DAD diode array detector

The HP LC/MSD ChemStation control software running on a HP Vectra computer was used for the instrument control and data acquisition.

The HPLC pump was connected to two eluent reservoirs containing:

A: 0.05% TFA in water

B: Acetonitrile

The analysis was performed at room temperature by injecting 1 µL of the sample solution on the column which was eluted with a gradient of acetonitrile in 0.05% TFA.

The HPLC conditions, detector settings and mass spectrometer settings used are given in the following table.

| Column | Grom Nucleosil 100 C18, 3 µm, 2 mm × 60 mm |
| Gradient | 10%–100% acetonitrile in 0.05% TFA linearly during 5.8 min at 0.6 mL/min |
| Detection | UV: 210 nm (diode array) |
| MS | Ionisation mode: API-ES |
| | Experiment: Start: 100 amu Stop: 1000 amu Step: 0.1 amu |

HPLC-MS (Method D)

The following instrumentation was used:

Hewlett Packard series 1100 G1312A Bin Pump

Hewlett Packard series 1100 G13 15A DAD diode array detector

Sciex 300 triplequadropole mass spectrometer

Gilson 215 micro injector

Sedex 55 evaporative light scattering detector

Pumps and detectors were controlled by MassChrom 1.1.1 software running on a Macintosh G3 computer. Gilson Unipoint Version 1.90 controls the auto-injector.

The HPLC pump was connected to two eluent reservoirs containing:
A: 0.01% TFA in water
B: 0.01% TFA in acetonitrile The analysis was performed at room temperature by injecting an appropriate volume of the sample (preferably 1 μL) onto the column that was eluted with a gradient of acetonitrile.

The HPLC conditions, detector settings and mass spectrometer settings used are:

| | |
|---|---|
| Column | YMC ODS-A 120 Å s 5μ 3 mm × 50 mm id |
| Gradient | 5%–90% acetonitrile linearly during 7.5 min at 1.5 ml/min |
| Detection | 210 nm (analog output from DAD) |
| MS | Ionisation mode: API-ES |
| | Scan 100–1000 amu step 0.1 amu |

HPLC-MS (Method E)

The following instrumentation was used:

Hewlett Packard series 1100 MSD G1946A Single quadropole mass spectrometer

Hewlett Packard series 1100 MSD G1312A Bin pump

Hewlett Packard series 1100 MSD G1313A ALS autosampler

Hewlett Packard series 1100 MSD G1315A DAD diode array detector

The HP LC/MSD ChemStation control software running on a HP Vectra computer was udes for the instrument control and data acquisition.

The HPLC pump was connected to two eluent reservoirs containing:
A: 0.01% TFA in water
B: Acetonitrile The analysis was performed at room temperature by injecting 1 μL of the sample solution on the column which was eluted with a gradient of acetonitrile in 0.01% TFA.

The HPLC conditions, detector settings and mass spectrometer settings used are given in the following table.

| | |
|---|---|
| Column | Waters Xterra 100 A MS C-18 3.5 μm, 2 mm × 50 mm |
| Gradient | 10%–100% acetonitrile in 0.05% TFA linearly during 4.5 min at 1.5 mL/min |
| Detection | UV: 210 nm (diode array) |
| MS | Ionisation mode: API-ES |
| | Experiment: Start: 100 amu Stop: 1000 amu Step: 0.1 amu |

HPLC-MS (Method F)

The following instrumentation was used:

Hewlett Packard series 1100 G1312A Bin Pump

Hewlett Packard series 1100 Column compartment

Hewlett Packard series 1100 G1315A DAD diode array detector

Hewlett Packard series 1100 MSD

The instrument was controlled by HP Chemstation software.

The HPLC pump was connected to two eluent reservoirs containing:
A: 0.01% TFA in water
B: 0.01% TFA in acetonitrile The analysis was performed at 40° C. by injecting an appropriate volume of the sample (preferably 1 μL) onto the column, which was eluted with a gradient of acetonitrile.

The HPLC conditions, detector settings and mass spectrometer settings used are given in the following table.

| | |
|---|---|
| Column | Waters Xterra MS C-18 × 3 mm id |
| Gradient | 10%–100% acetonitrile lineary during 7.5 min at 1.0 mL/min |
| Detection | UV: 210 nm (analog output from DAD) |
| MS | Ionisation mode: API-ES |
| | Scan 100–1000 amu step 0.1 amu |

The compounds of the present invention may be purified using one of the following HPLC methods:

Hit Fractionation Method I

HPLC purification/fractionation of hits is performed on Nucleosil C-18 7 μm 8×100 mm columns (packed by Grom). A standard gradient with water/acetonitrile added 0.01% TFA is used. Flow rate 9 mL/min starting at 10% organic modifier ending after 18 min on 100% organic modifier. This condition is kept for 1 min. Fractions of 4 mL are collected in a deep well collection plate.

Equipment:

2 Gilson 306 pumps equipped with 25 mL SC pump heads, Gilson 806 manometer and Gilson 811c dynamic mixing chamber. UV detection is performed with Gilson 119 UV/VIS detector. Gilson 215 Nebula is used as combined injector and fraction collector.

Hit Fractionation Method II

HPLC purification/fractionation of hits is performed on Waters Xterra columns MS $C_{18}$ 5 μm 7.8×100 mm columns. A standard gradient with water/acetonitrile added 0.01% TFA is used. Flow rate 15 mL/min starting at 10% organic modifier ending after 11 min on 100% modifier. This condition is kept for 1 min. Fractions of 4 mL are collected in a deep well collection plate.

Equipment:

1 Gilson 321 pump equipped with 15 mL H1 pumping heads. UV detection is performed with Gilson 119 UV/VIS detector. Gilson 215 Nebula is used as combined injector and fraction collector.

General Procedure (A) for the Solid Phase Synthesis of Compounds of the General Formula (Ia)

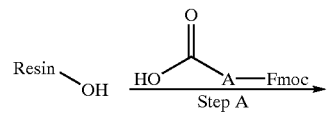

-continued

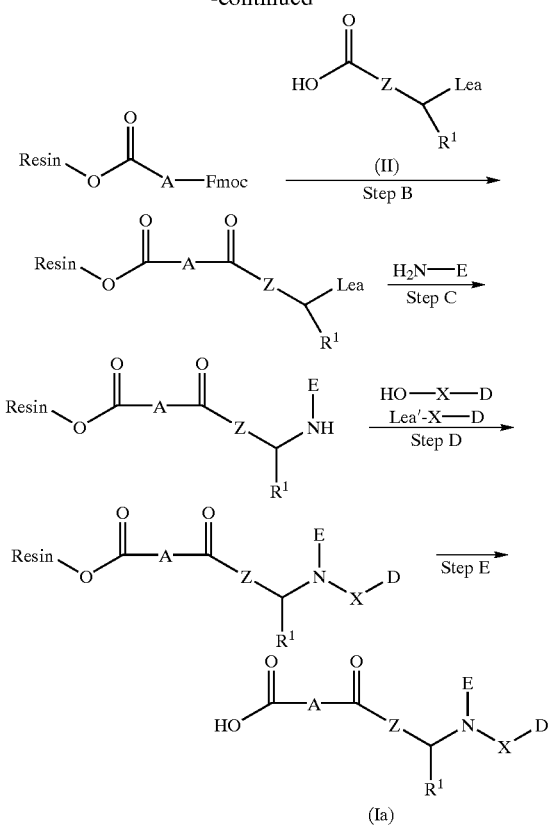

wherein

R¹, Z, E and D are as defined for formula (I),

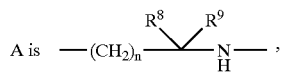

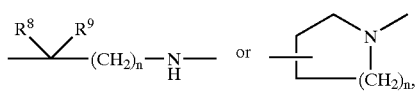

wherein R⁸ and R⁹ are as defined for formula (I),

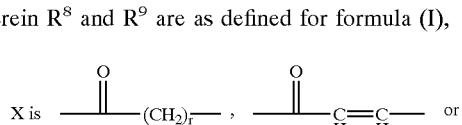

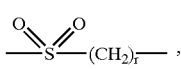

wherein r is as defined for formula (I),

Lea is a leaving group such as chloro, bromo, iodo, mesyl or tosyl,

Lea' is a leaving group such as —OSu, chloro, phenoxy or 4-nitrophenoxy, and

Resin denotes a polystyrene resin with a linker such as the Wang linker:

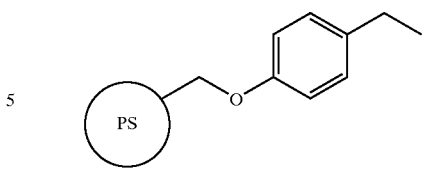

wherein PS denotes polystyrene.

Step A:

The reaction is known (Wang S. J., J. Am. Chem. Soc. 95, 1328, 1973) and is generally performed by stirring polystyrene resin loaded with a linker such as the Wang linker with a 4–10 molar excess of Fmoc-protected amino acid activated with a 2–5 molar excess of diisopropylcarbodiimide or dicyclohexylcarbodiimide in the presence of a catalyst such as N,N-4-dimethylaminopyridine. The esterification is carried out in a solvent such as THF, dioxane, toluene, dichloromethane, DMF, NMP or a mixture of two or more of these. The reactions are performed between 0° C. to 80° C., preferably between 20° C. to 40° C. When the esterification is complete excess of reagents is removed by filtration. The resin is successively washed with the solvent used in the reaction, followed by washings with methanol. The resin bound product can be further dried and analyzed.

Step B:

N-Fluorenylmethyloxycarbonyl protection group is removed by treating the resin bound derivative with a 20%–50% solution of a secondary amine such as piperidine in a polar solvent such as DMF or NMP (Carpino L., Han G., J. Org. Chem. 37, 3404, 1972). The reaction is performed between 20° C. and 180° C., preferably between 20° C. and 40° C. The deprotection can be quantitated by the absorbance of piperidine-dibenzofulvene adduct released from the resin (The combinatorial index, Ed. Bunin B. A., 1998, Academic press, p. 219). When the reaction is complete excess of reagents is removed by filtration. The resin is successively washed with solvent used in the reaction. The resulting resin bound intermediate is acylated with acid (II). The acylation is known (The combinatorial index, Ed. Bunin B. A., 1998, Academic press, p. 78) and is generally performed by stirring resin bound intermediate with a 2–5 molar excess of acid (II) activated with a 2–5 molar excess of diisopropylcarbodiimide or dicyclohexylcarbodiimide in the presence of a side reaction inhibitor such as N-hydroxybenzotriazole. The acylation is carried out in a solvent such as THF, dioxane, toluene, dichloromethane, DMF, NMP or a mixture of two or more of these. The reactions are performed between 0° C. and 80° C., preferably between 20° C. and 40° C. When the acylation is complete excess of reagents is removed by filtration. The resin is successively washed with the solvent used in the reaction, followed by washings with methanol. The resin bound product can be further dried and analyzed.

Step C:

The reaction is known (The combinatorial index, Ed. Bunin B. A., 1998, Academic press, p. 112) and is generally performed by stirring the resin bound intermediate obtained in step B with a 10–20 molar excess of amine. The nucleophilic displacement is carried out in a solvent such as DMSO, DMF, NMP or a mixture of two or more of these. The reaction is performed between 20° C. and 120° C., preferably between 60° C. and 80° C. When the reaction is complete excess of reagents is removed by filtration. The resin is successively washed with the solvent used in the reaction, followed by washings with methanol. The resin bound product can be further dried and analyzed.

Step D:

The reaction is known (The combinatorial index, Ed. Bunin B. A., 1998, Academic press, p. 78) and is generally performed by stirring the resin bound intermediate obtained in step C with a 4–10 molar excess of acid HO—X-D activated with a 2–5 molar excess of diisopropylcarbodiimide or dicyclohexylcarbodiimide in the presence of a catalyst such as pyridine and/or 4-dimethylaminopyridine. The reaction is carried out in a solvent such as THF, dioxane, toluene, dichloromethane, DMF, NMP or a mixture of two or more of these. The reactions are performed between 0° C. and 80° C., preferably between 20° C. and 40° C. When the reaction is complete excess of reagents is removed by filtration. Alternatively, a solution of Lea'-X-D in an appropriate solvent such as acetonitrile, toluene, DMF, NMP, THF, dichloromethane, 1,2-dichloroethane or DMSO or a mixture of two or more of these, is added and the mixture is vortexed in the presence of a base such as triethylamine, diisopropylethylamine, dicyclohexylmethylamine or any other tertiary amine or potassium carbonate under heating, if necessary. The resin is successively washed with solvent used in the reaction, followed by washings with dichloromethane.

Step E:

The reaction is known (The combinatorial index, Ed. Bunin B. A., 1998, Academic press, p. 21) and is generally performed by stirring resin bound intermediate obtained in step D with a 50–95% solution of TFA. The final cleavage is carried out in a solvent such as THF, dichloromethane, 1,2-dichloroethane, 1,3-dichloropropane, toluene or a mixture of two or more of these. The reaction is performed between 0° C. and 80° C., preferably between 20° C. and 40° C. When the reaction is complete the product is removed by filtration. The resin is successively washed with dichloromethane. The product and washings are collected. The solvent is removed and the product is dried in vacuo. The residue is dissolved in a 1:1 mixture of methanol and dichloromethane (1 mL) and concentrated in vacuo. The product (Ia) is dried in vacuo overnight.

General Procedure (B) for the Solid Phase Synthesis of Compounds of the General Formula (Ia)

Alternatively, steps B and C of procedure (A) can be modified so that step C is a reductive amination of a resin bound aldehyde or ketone:

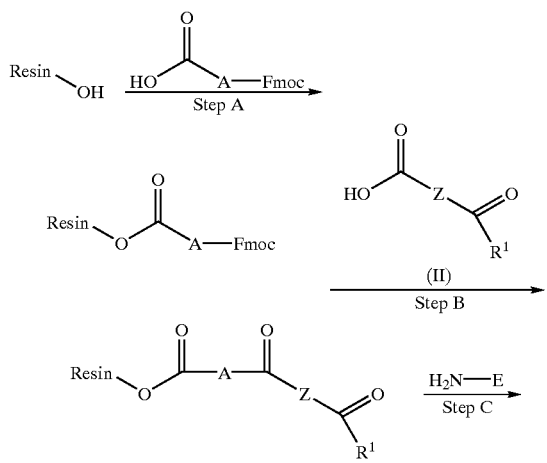

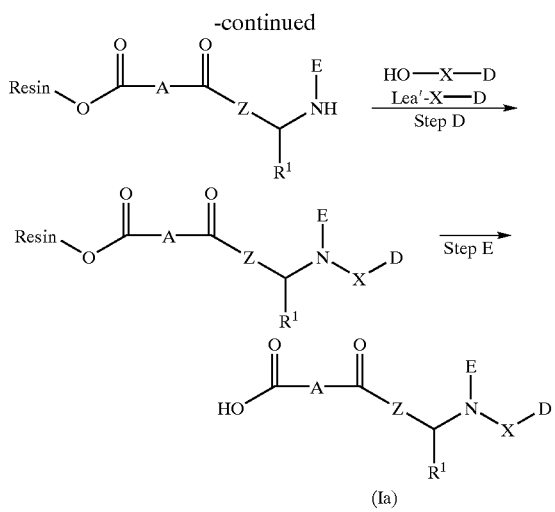

(Ia)

wherein
R$^1$, Z, E and D are as defined for formula (I),

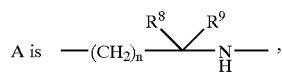

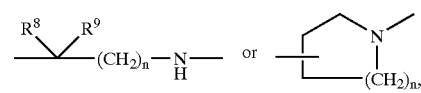

wherein R$^8$ and R$^9$ are as defined for formula (I),
X is

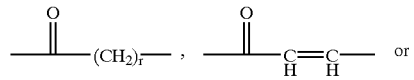

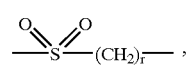

wherein r is as defined for formula (I),
Lea' is a leaving group such as —OSu, chloro, phenoxy or 4-nitrophenoxy, and
Resin denotes a polystyrene resin with a linker such as the Wang linker:

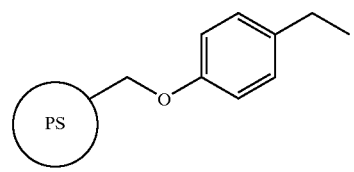

wherein PS denotes polystyrene.

Step B:
This step is identical to step B of general procedure (A) with the modification that acid (III) is used instead of acid (II).

Step C:
The reaction is generally known (The combinatorial index, Ed. Bunin, B. A. 1998, Academic Press, p. 133) and is generally performed by stirring resin bound aldehyde or ketone with an excess of amine at low pH (by addition of an acid, such as acetic acid or formic acid) in a solvent such as THF, DMF, NMP, methanol, ethanol, DMSO, dichloromethane, 1,2-dichloroethane, trimethyl orthoformate, triethyl orthoformate, or a mixture of two or more of these. A reducing agent such as sodium cyanoborohydride may be used. The reaction is performed between 20° C. and 120° C., preferably at 25° C.

The following examples 1 to 9 were prepared according to general procedure (A).

EXAMPLE 1

General Procedure (A)

3-(4-{[N-(5-Chlorobenzo[b]thiophen-3-carbonyl)-N-(2,2-diphenylethyl)amino]methyl}benzoylamino)propionic acid

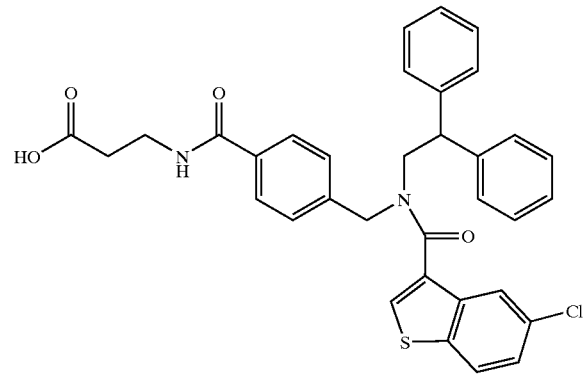

Step A: Resin bound Fmoc-3-aminopropionic acid

Polystyrene resin loaded with the Wang linker (1.07 mmol/g, 25.0 g, 26.75 mmol) was treated overnight at 25° C. with a solution of N-Fmoc-3-aminopropionic acid (33.3 g, 107 mmol) in 100 mL THF activated with diisopropylcarbodiimide (8.5 mL, 54 mmol) in the presence of 4-dimethylaminopyridine (0.2 g). Excess of reagents was removed by filtration. The resin bound intermediate was successively washed with 3×100 mL THF, 3×100 mL DMF and 3×100 mL methanol. The resin was dried overnight in vacuo at 50° C. for 16 hours to afford 31.54 g resin bound Fmoc-3-aminopropionic acid.

A small sample of resin bound intermediate (25 mg) was withdrawn and treated with 50% TFA in dichloromethane for 30 min. The resin was drained and washed with dichloromethane several times. The combined filtrates were concentrated in vacuo. The residue was diluted with 10 mL acetonitrile and analyzed by HPLC. The yield was calculated from HPLC trace at 214 nm compared to the solution of a standard.

Step B: Resin bound 3-[4-(bromomethyl)benzoyl]aminopropionic acid

The above resin bound Fmoc-3-aminopropionic acid (3.95 g, 2.4 mmol) was treated with 40 mL 50% piperidine in DMF for 15 min. The reagent was removed by filtration. The resin was successively washed with 3×20 mL DMF and 20 mL of a 1 M solution of N-hydroxybenzotriazole in DMF. The resulting resin bound intermediate was treated with a solution of 4-bromomethylbenzoic acid (2.15 g, 10 mmol) and N-hydroxybenzotriazole (1.52 g, 10 mmol) in 25 mL THF activated by diisopropylcarbodiimide (1.57 mL, 10 mmol). The reaction was performed at 25° C. for 12 hours. Excess of reagents was removed by filtration. The resin bound intermediate was successively washed with 3×20 mL THF, 3×20 mL DMF and 3×20 mL methanol. The resin was dried in vacuo at 50° C. for 16 hours to afford 3.77 g resin bound 3-[4-(bromomethyl)benzoyl]aminopropionic acid.

An analytical sample of resin bound intermediate (0.05 g) was withdrawn and treated with 1 mL 50% TFA in dichloromethane for 30 min. The resin was drained and washed with dichloromethane several times. The combined filtrates were concentrated in vacuo. The residue was diluted with 20 mL of acetonitrile and characterized by analytical RP-HPLC ($R_t$=8.25 min) and by HPLC-MS (Method A) (m/z=287 (M+1)).

Step C: Resin bound 3-(4-{[(N-2,2-diphenylethyl)methyl]benzoyl}amino)propionic acid The above resin bound 3-[4-(bromomethyl)benzoyl]aminopropionic acid (1.0 g, 0.64 mmol) was treated with 2,2-diphenylethylamine (1.26 g, 6.4 mmol) in 4 mL DMSO. The reaction was stirred at 80° C. for 12 hours. Excess of reagents was removed by filtration. The resin was successively washed with 3×10 mL DMSO and 3×10 mL methanol and dried in vacuo at 50° C. for 16 hours to afford 1.07 g resin bound 3-(4-{[(N-2,2-diphenylethyl)methyl]benzoyl}amino)propionic acid.

An analytical sample of resin bound intermediate (0.05 g) was withdrawn and treated with 1 mL 50% TFA in dichloromethane for 30 min. The resin was drained and washed with dichloromethane several times. The combined filtrates were concentrated in vacuo. The residue was dissolved in 20 mL of acetonitrile and characterized by analytical RP-HPLC ($R_t$=8.70 min) and by HPLC-MS (Method A) (m/z=417 (M+1)).

Step D: Resin bound 3-(4-{[N-(5-chlorobenzo[b]thiophen-3-carbonyl)-N-(2,2-diphenylethyl)amino]methyl}benzoylamino)propionic acid The above resin bound 3-(4-{[(N-2,2-diphenylethyl)methyl]benzoyl}amino)propionic acid (1.02 g, 0.61 mmol) was suspended in THF and successively washed with 2×10 mL THF, 2×10 mL 5% diisopropylethylamine in THF and 5×10 mL THF. The resin slurry was then treated with with 5-chlorobenzo[b]thiophen-3-carboxylic acid (0.51 g, 2.4 mmol) in 4 mL THF, 4 mL pyridine, diisopropylcarbodiimide (0.19 mL, 1.2 mmol) and 4-dimethylaminopyridine (24 mg, 0.12 mmol) The reaction mixture was stirred at 25° C. for 12 hours. The resin was drained and successively washed with 3×10 mL THF, 3×10 mL DMF and 5×10 mL dichloromethane and used in next step without any characterization.

Step E: 3-(4-{[N-(5-Chlorobenzo[b]thiophen-3-carbonyl)-N-(2,2-diphenylethyl)amino]methyl}benzoylamino)propionic acid The resin bound 3-(4-{[N-(5-chlorobenzo[b]thiophen-3-carbonyl)-N-(2,2-diphenylethyl)amino]methyl}benzoylamino)propionic acid was treated with a 50% solution of TFA in dichloromethane (10 mL). The cleavage mixture was stirred for 45 min at 25° C. The resin was drained and washed with dichloromethane several times. The combined filtrates were concentrated in vacuo. The residue was dissolved in a 1:1 mixture of methanol and dichloromethane (1 mL) and concentrated in vacuo to afford 0.359 g of the title compound. The product was characterized by analytical RP-HPLC ($R_t$=14.2 min) and by HPLC-MS (Method A) (m/z=597 (M+1)).

The crude product (50 mg) was purified by column chromatography on RP-C18 silica gel (Sep-Pak, Waters) eluting with a mixture of acetonitrile and water. Pure fractions were pooled and evaporated in vacuo to afford 16.7 mg of pure title compound.

EXAMPLE 2

General Procedure (A)

3-(4-{[N-(5-Chlorobenzo[b]thiophen-3-carbonyl)-N-(3,4-dichlorophenylethyl)amino]methyl}benzoylamino)propionic acid

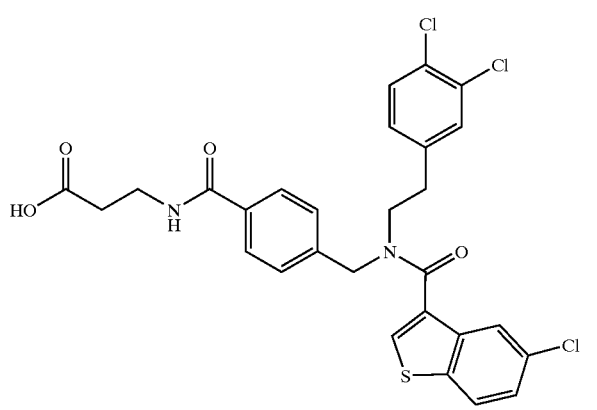

The product was characterized by analytical RP-HPLC ($R_t$=14.12 min) and by HPLC-MS (Method A) (m/z=589 (M+1)).

EXAMPLE 3

General Procedure (A)

3-(4-{[N-(2-Benzo[b]thiophen-3-yl-acetyl)-N-(4-tert-butylcyclohexyl)amino]methyl}benzoylamino)propionic acid

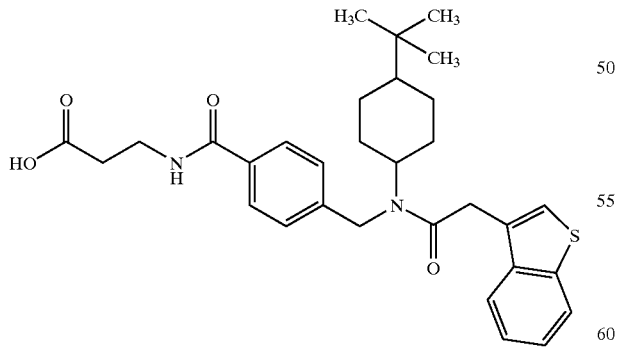

The product was characterized by analytical RP-HPLC ($R_t$=14.96 min) and by HPLC-MS (Method A) (m/z=535 (M+1)).

EXAMPLE 4

General Procedure (A)

3-(4-{[N-(Benzo[b]thiophen-2-carbonyl)-N-(4-tert-butylcyclohexyl)amino]methyl}benzoylamino)propionic acid

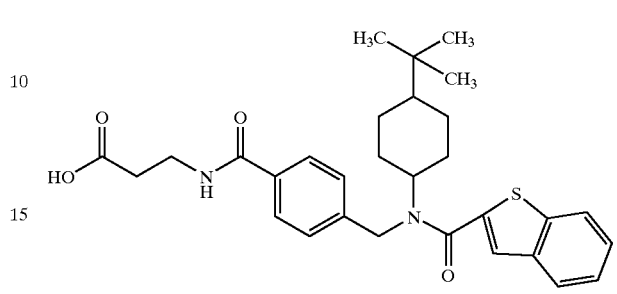

The product was characterized by analytical RP-HPLC ($R_t$=15.17 min) and by HPLC-MS (Method A) (m/z=521 (M+1)).

EXAMPLE 5

General Procedure (A)

3-(4-{[N-[3-(2,6-Dichlorophenyl)acryloyl]-N-(2-ethylhexyl)amino]methyl}benzoylamino)propionic acid

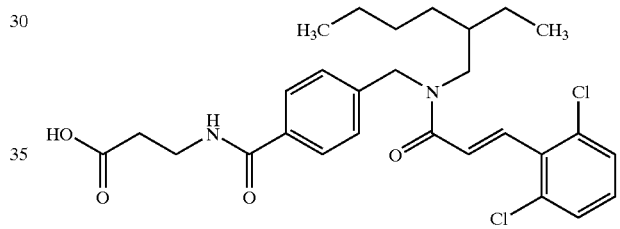

The product was characterized by analytical RP-HPLC ($R_t$=15.26 min) and by HPLC-MS (Method A) (m/z=533 (M+1)).

EXAMPLE 6

General Procedure (A)

3-(4-{[N-[3-(2,6-Dichlorophenyl)acryloyl]-N-(4-tert-butylbenzyl)amino]methyl}benzoylamino)propionic acid

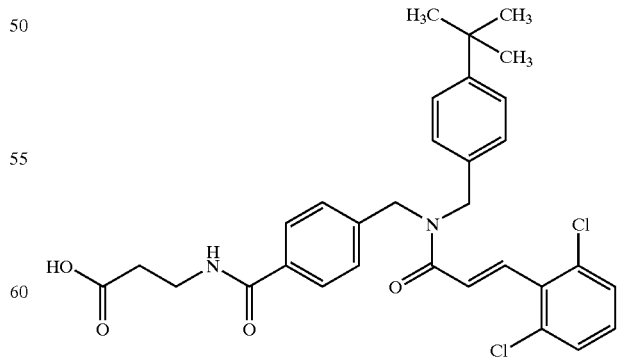

The product was characterized by analytical RP-HPLC ($R_t$=15.08 min) and by HPLC-MS (Method A) (m/z=567 (M+1)).

EXAMPLE 7

General Procedure (A)

3-(4-{[N-(Benzo[b]thiophen-2-carbonyl)-N-(4-tert-butylbenzyl)amino]methyl}benzoylamino)propionic acid

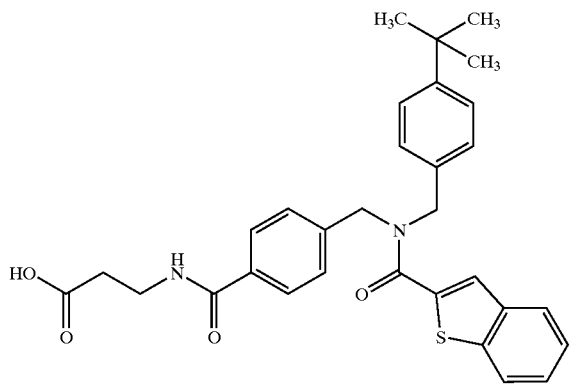

The product was characterized by analytical RP-HPLC ($R_t$=14.70 min) and by HPLC-MS (Method A) (m/z=529 (M+1)).

EXAMPLE 8

General Procedure (A)

3-(4-{[N-(4-Chlorobenzoyl)-N-(3,3-diphenylpropyl)amino]methyl}benzoylamino)propionic acid

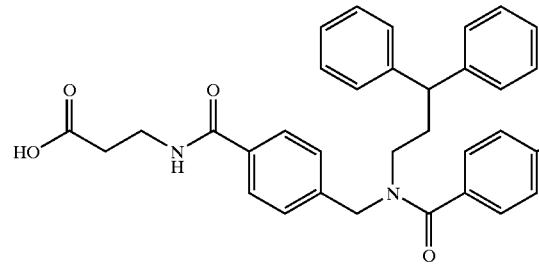

The product was characterized by analytical RP-HPLC ($R_t$=13.6 min) and by HPLC-MS (Method A) (m/z=555 (M+1)).

EXAMPLE 9

General Procedure (A)

3-(3-{[N-(5-Chlorobenzo[b]thiophene-3-carbonyl)-N-(2,2-diphenylethyl)amino]methyl}benzoylamino)propionic acid The product was characterized by analytical RP-HPLC ($R_t$=14.5 min) and by HPLC-MS (Method A) (m/z=597 (M+1)).

General Procedure (C) for the Solid Phase Synthesis of Compounds of the General Formula

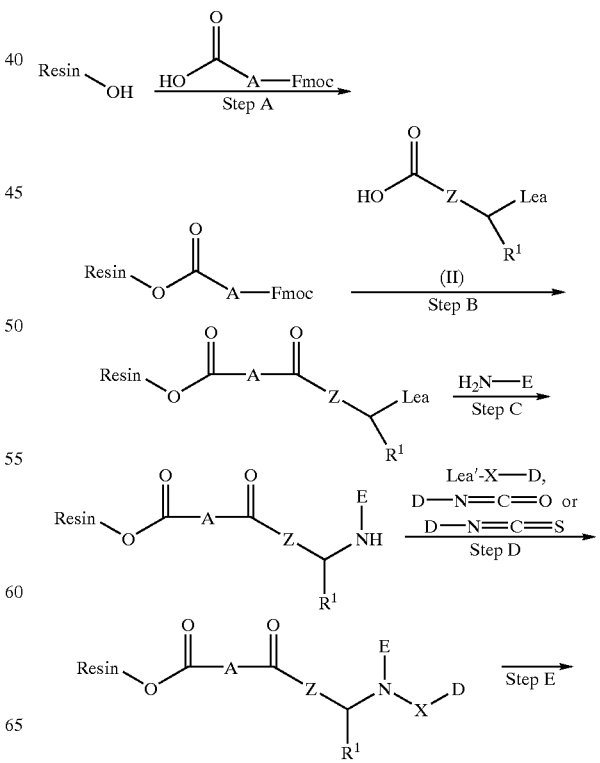

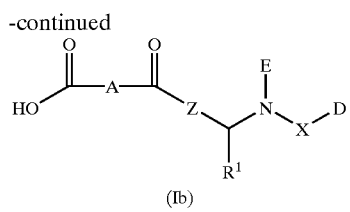

(Ib)

wherein
A, Z, R¹, E and D are as defined for formula (I),
X is —S(O)₂—(CH₂)ᵣ—, —C(O)NH— or —C(S)NH—, wherein r is as defined for formula (I),
Lea is a leaving group such as chloro, bromo, iodo, mesyl or tosyl,
Lea' is a leaving group such as —OSu, chloro, phenoxy or 4-nitrophenoxy, and
Resin denotes a polystyrene resin with a linker such as the Wang linker:

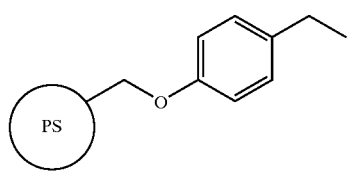

wherein PS denotes polystyrene.

Step A:

Wang resin (10.0 g, Bachem 1250, 0.96 mmol/g) is suspended in NMP (100 mL) and drained, resuspended in THF (100 mL) and drained again. A solution of a Fmoc-protected amino acid (eg Fmoc-p-alanine) (58 mmol), diisopropylcarbodiimide (4.2 g, 34 mmol) and 4-dimethylaminopyridine (0.07 g, 0.6 mmol) in THF (80 mL) is added to the resin and vortexed for 16 hours. The resin is drained and washed with THF (3×100 mL) and NMP (3×100 mL).

Step B:

All the resin synthesised in step A is used in this step. A solution of 20% piperidine in NMP (100 mL) is added to the resin and the mixture vortexed for 1 hour. After draining the resin is washed in NMP (3×100 mL) and THF (5×100 mL). A solution of intermediate (II), eg 4-(bromomethyl)benzoic acid (or a substituted analogue thereof) (29 mmol), hydroxybenzotriazole (4.4 g, 29 mmol) and diisopropylcarbodiimide (3.6 g, 29 mmol) in THF (70 mL) is added and the mixture is vortexed for 16 hours. The resin is drained and washed with THF (2×100 mL), NMP (2×100 mL), dichloromethane (2×100 mL) and methanol (5×100 mL), and dried in vacuo.

Step C:

6 g of the resin synthesised in step B is used in this step. A solution of a primary amine (eg 2-phenethylamine or 4-tert-butylcyclohexylamine) (48 mmol) in DMSO is added to the resin and vortexed at 80° C. for 16 hours. The resin is drained and washed with NMP (3×100 mL), dichloromethane (3×100 mL) and methanol (4×100 mL), and dried in vacuo.

Step D:

50 mg of the resin produced in step C is used in this step. The resin is suspended in NMP (1.5 mL) and drained. A solution of an isothiocyanate or an isocyanate (eg phenylisocyanate or 4-trifluoromethoxyphenylisocyanate) (0.24 mmol) in NMP (1 mL) is added and the mixture is vortexed for 16 hours. Alternatively, a solution of Lea'-X-D in an appropriate solvent such as acetonitrile, toluene, DMF, NMP, THF, dichloromethane, 1,2-dichloroethane or DMSO or a mixture of two or more of these, is added and the mixture is vortexed in the presence of a base such as triethylamine, diisopropylethylamine, dicyclohexylmethylamine or any other tertiary amine or potassium carbonate under heating, if necessary. The resin is drained and washed with DMF (3×1 mL), methanol (3×1 mL), 2-propanol (3×1 mL), tert-butylmethylether (3×1 mL) and dichloromethane (3×1 mL).

Step E:

All the resin synthesised in step D is used. A solution of TFA and dichloromethane (1:1, 2 mL) is added to the resin and vortexed for 45 min. The resin is drained and the eluent evaporated in vacuo to give a compound of general formula (Ib).

Optionally, the compound can be purified by chromatography eg HPLC.

The compounds of general formula (Ib) can be prepared either as single compounds or by parallel synthesis using the protocol mentioned above in a combinatorial approach. Thousands of compounds of formula (Ib) can thus be prepared by this combinatorial approach which can be semi-automated or fully automated. The automation of this protocol can be performed eg using a 96 well setup using an automated synthesizer device.

The following examples were prepared according to general procedure (C).

EXAMPLE 10

General Procedure (C)

3-{4-[3-Biphenyl-4-yl-1-(2-ethylhexyl)ureidomethyl]benzoylamino}propionic acid

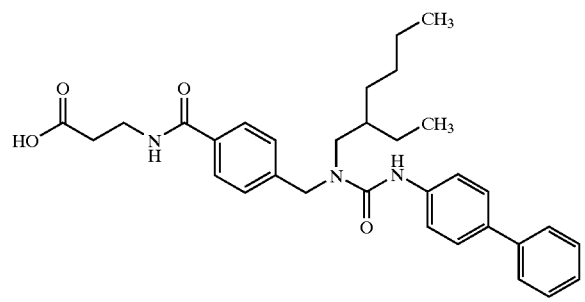

The product was characterized by HPLC-MS (Method C): $R_t$=4.30 min, m/z=530 (M+1).

EXAMPLE 11

General Procedure (C)

3-{4-[1-(4-tert-Butylcyclohexyl)-3-(4-trifluoromethoxyphenyl)ureidomethyl]benzoylamino}propionic acid

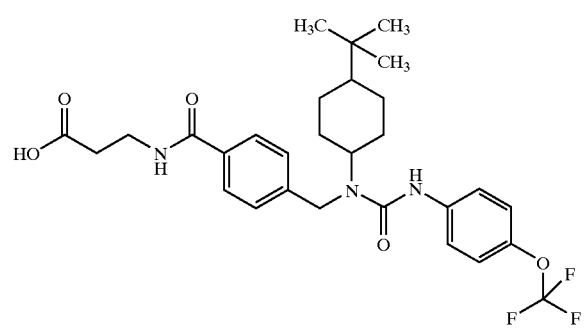

The product was characterized by HPLC-MS (Method C): $R_t$=4.33 min, m/z=564 (M+1).

EXAMPLE 12

General Procedure (C)

3-{4-[3-Biphenyl-4-yl-1-(4-tert-butylcyclohexyl)ureidomethyl]benzoylamino}propionic acid

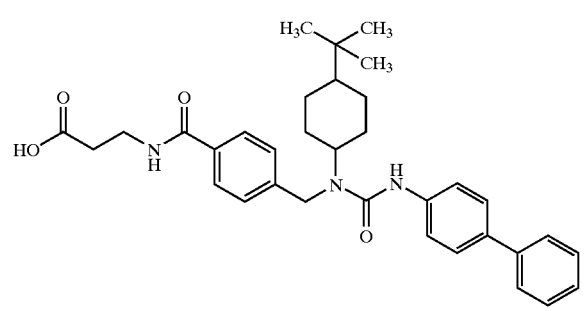

The product was characterized by HPLC-MS (Method C): $R_t$=4.40 min, m/z=556 (M+1).

EXAMPLE 13

General Procedure (C)

3-{4-[1-(4-tert-Butylcyclohexyl)-3-(3-trifluoromethylphenyl)ureidomethyl]benzoylamino}propionic acid

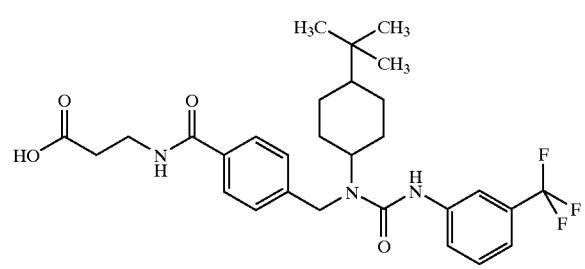

The product was characterized by HPLC-MS (Method C): $R_t$=4.31 min, m/z=548 (M+1).

EXAMPLE 14

General Procedure (C)

3-{4-[1-(2-Ethylhexyl)-3-(4-phenoxyphenyl)ureidomethyl]benzoylamino}propionic acid

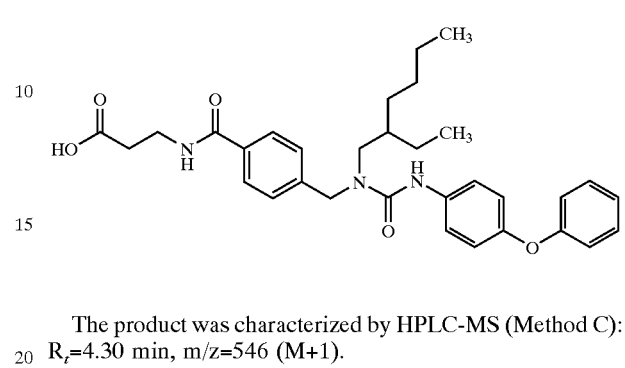

The product was characterized by HPLC-MS (Method C): $R_t$=4.30 min, m/z=546 (M+1).

EXAMPLE 15

General Procedure (C)

3-{4-[1-(4-Methylcyclohexyl)-3-(4-trifluoromethoxyphenyl)ureidomethyl]benzoylamino}propionic acid

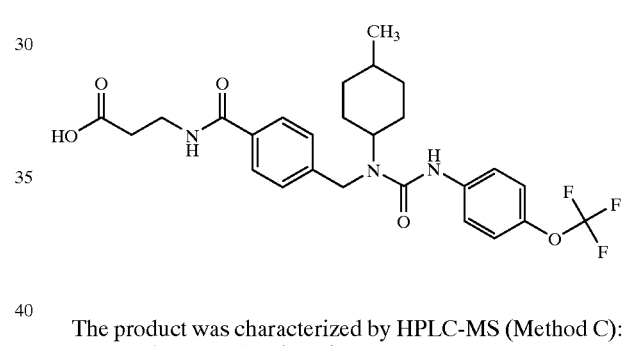

The product was characterized by HPLC-MS (Method C): $R_t$=3.78 min, m/z=522 (M+1).

EXAMPLE 16

General Procedure (C)

3-{4-[1-(4-tert-Butylcyclohexyl)-3-(3,4-dichlorophenyl)ureidomethyl]benzoylamino}propionic acid

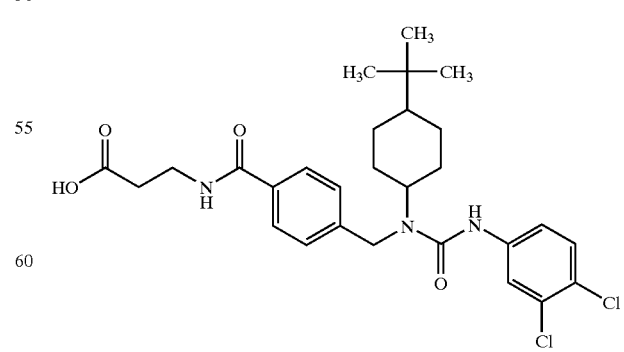

The product was characterized by HPLC-MS (Method C): $R_t$=4.62 min, m/z=548 (M+1).

EXAMPLE 17

General Procedure (C)

3-{4-[1-(4-tert-Butylcyclohexyl)-3-(4-phenoxyphenyl)ureidomethyl]benzoylamino}propionic acid

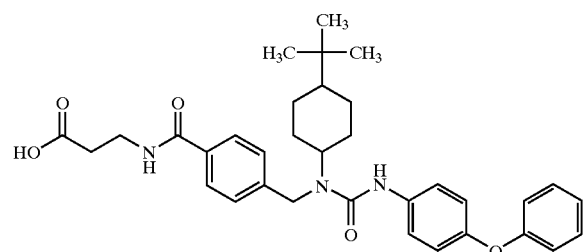

The product was characterized by HPLC-MS (Method C): $R_t$=4.30 min, m/z=572 (M+1).

EXAMPLE 18

General Procedure (C)

3-{4-[1-(3,3-Diphenylpropyl)-3-(4-trifluoromethoxyphenyl)ureidomethyl]benzoylamino}propionic acid

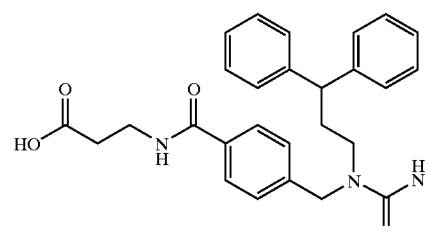

The product was characterized by HPLC-MS (Method C): $R_t$=4.13 min, m/z=620 (M+1).

EXAMPLE 19

General Procedure (C)

3-{4-[1-[2-(3,4-Dichlorophenyl)ethyl]-3-(4-trifluoromethoxyphenyl)ureidomethyl]benzoylamino}propionic acid

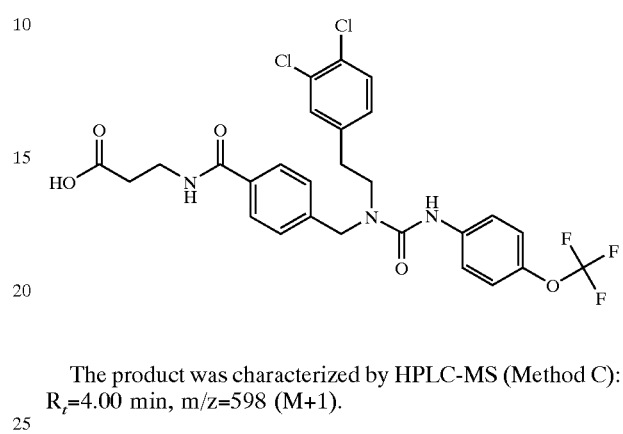

The product was characterized by HPLC-MS (Method C): $R_t$=4.00 min, m/z=598 (M+1).

EXAMPLE 20

General Procedure (C)

3-{4-[3-(3-Cyanophenyl)-1-(2-ethylhexyl)ureidomethyl]benzoylamino}propionic acid

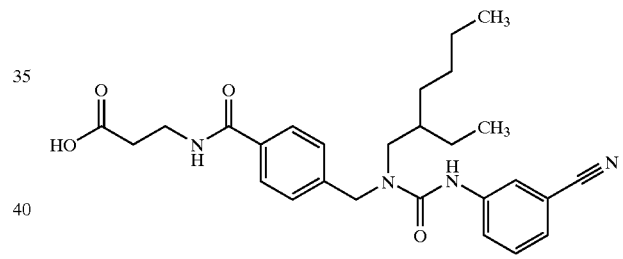

The product was characterized by HPLC-MS (Method B): $R_t$=5.50 min, m/z=479 (M+1).

EXAMPLE 21

General Procedure (C)

3-{4-[1-(2-Ethylhexyl)-3-(3-trifluoromethylphenyl)ureidomethyl]benzoylamino}propionic acid

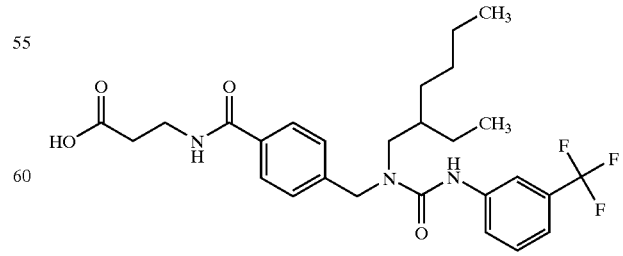

The product was characterized by HPLC-MS (Method B): $R_t$=6.17 min, m/z=552 (M+1).

EXAMPLE 22

General Procedure (C)

3-{4-[1-(4-Methylcyclohexyl)-3-(4-phenoxyphenyl)ureidomethyl]benzoylamino}propionic acid

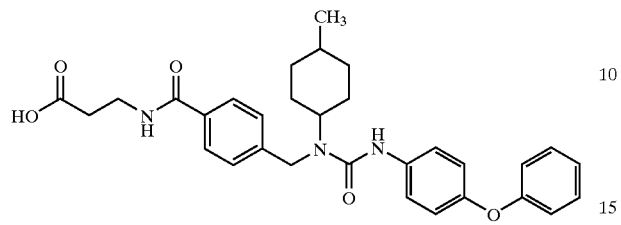

The product was characterized by HPLC-MS (Method B): $R_t$=5.73 min, m/z=530 (M+1).

EXAMPLE 23

General Procedure (C)

3-{4-[1-(4-tert-Butylcyclohexyl)-3-(2-thiophen-2-ylethyl)ureidomethyl]benzoylamino}propionic acid

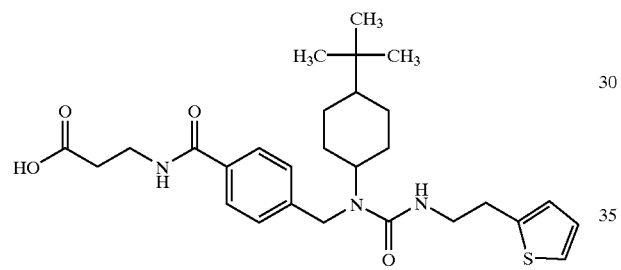

The product was characterized by HPLC-MS (Method B): $R_t$=5.60 min, m/z=514 (M+1).

EXAMPLE 24

General Procedure (C)

3-{4-[1-(4-tert-Butylcyclohexyl)-3-(5-chloro-2,4-dimethoxyphenyl)ureidomethyl]benzoylamino}propionic acid

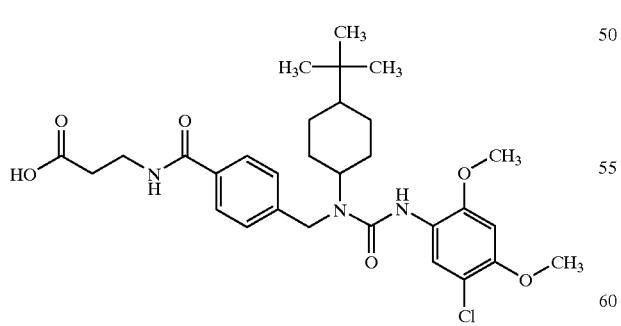

The product was characterized by HPLC-MS (Method B): $R_t$=6.30 min, m/z=574 (M+1).

EXAMPLE 25

General Procedure (C)

3-{4-[1-(4-tert-Butylcyclohexyl)-3-(2-trifluoromethylphenyl)ureidomethyl]benzoylamino}propionic acid

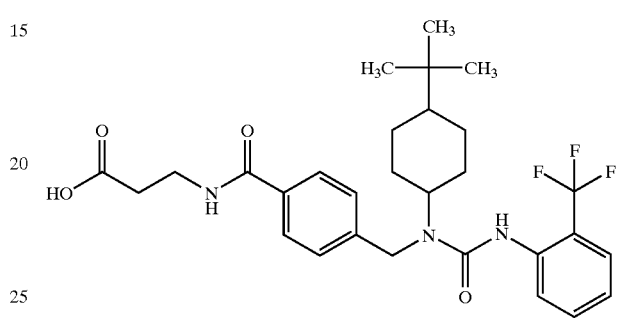

The product was characterized by HPLC-MS (Method B): $R_t$=6.10 min, m/z=548 (M+1).

EXAMPLE 26

General Procedure (C)

3-{4-[1-(4-tert-Butylcyclohexyl)-3-(3-methylsulfanylphenyl)ureidomethyl]benzoylamino}propionic acid

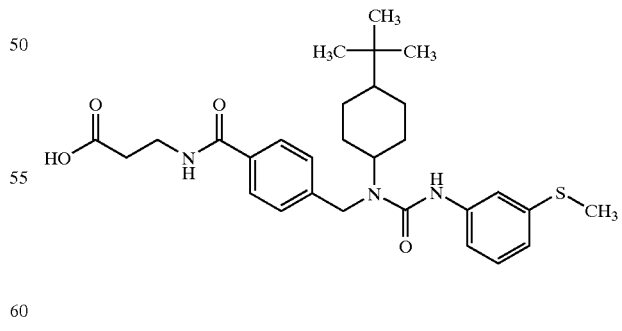

The product was characterized by HPLC-MS (Method B): $R_t$=6.03 min, m/z=526 (M+1).

EXAMPLE 27

General Procedure (C)

3-{4-[1-(4-tert-Butylcyclohexyl)-3-phenethylureidomethyl]benzoylamino}propionic acid

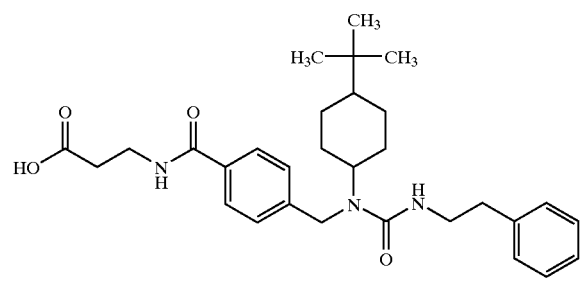

The product was characterized by HPLC-MS (Method B): $R_t$=5.53 min, m/z=508 (M+1).

EXAMPLE 28

General Procedure (C)

3-{4-[3-Biphenyl-2-yl-1-(4-tert-butylcyclohexyl)ureidomethyl]benzoylamino}propionic acid

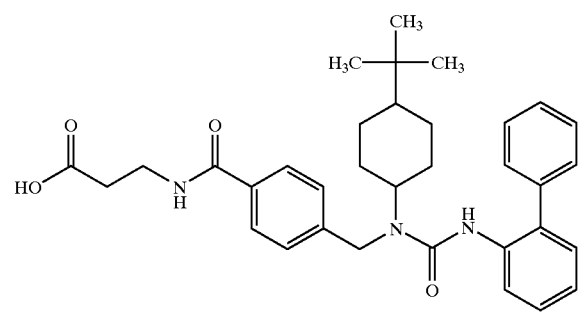

The product was characterized by HPLC-MS (Method B): $R_t$=6.14 min, m/z=556 (M+1).

EXAMPLE 29

General Procedure (C)

3-{4-[1-(4-tert-Butylcyclohexyl)-3-(4-isopropylphenyl)ureidomethyl]benzoyl}aminopropionic acid

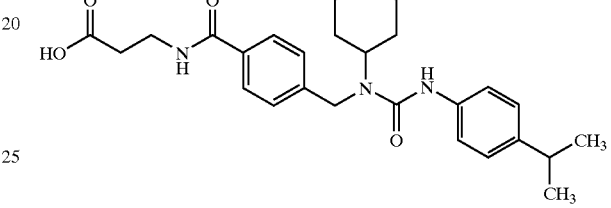

The product was characterized by HPLC-MS (Method B): $R_t$=7.98 min, m/z=522 (M+1).

EXAMPLE 30

General Procedure (C)

3-{4-[1-(4-tert-Butylcyclohexyl)-3-(4-methylsulfanylphenyl)ureidomethyl]benzoyl}aminopropionic acid

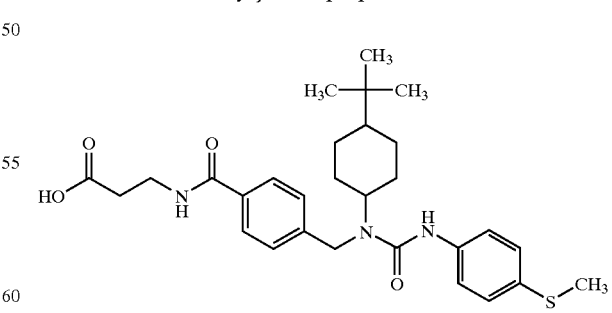

The product was characterized by HPLC-MS (Method B): $R_t$=7.58 min, m/z=526 (M+1).

EXAMPLE 31

General Procedure (C)

3-{4-[1-(4-tert-Butylcyclohexyl)-3-(4-methoxyphenyl)ureidomethyl]benzoyl}aminopropionic acid

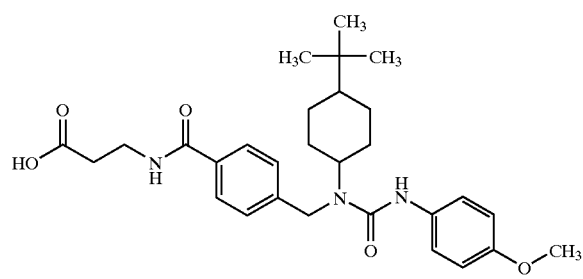

The product was characterized by HPLC-MS (Method B): $R_t$=6.93 min, m/z=510 (M+1).

EXAMPLE 32

General Procedure (C)

3-{4-[1-(4-tert-Butylcyclohexyl)-3-(4-acetylphenyl)ureidomethyl]benzoyl}aminopropionic acid

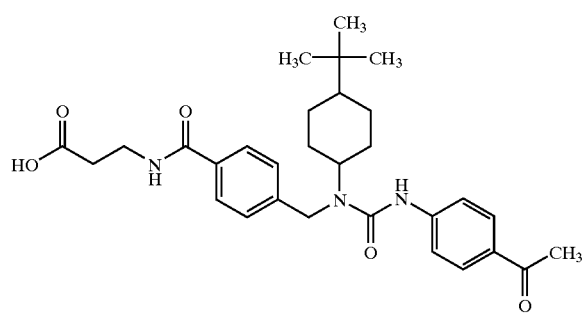

The product was characterized by HPLC-MS (Method B): $R_t$=7.03 min, m/z=522 (M+1).

EXAMPLE 33

General Procedure (C)

4-{3-(4-tert-Butylcyclohexyl)-3-[4-(2-carboxyethylcarbamoyl)benzyl]ureido}benzoic acid butyl ester

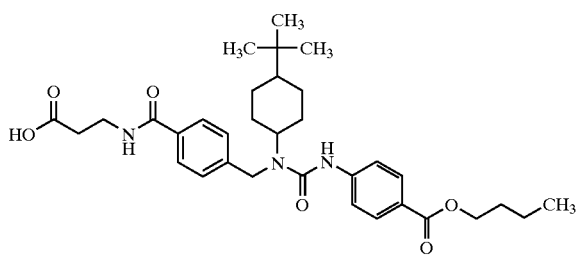

The product was characterized by HPLC-MS (Method B): $R_t$=8.33 min.

EXAMPLE 34

General Procedure (C)

3-{4-[1-(4-tert-Butylcyclohexyl)-3-(4-chlorophenyl)ureidomethyl]benzoyl}aminopropionic acid

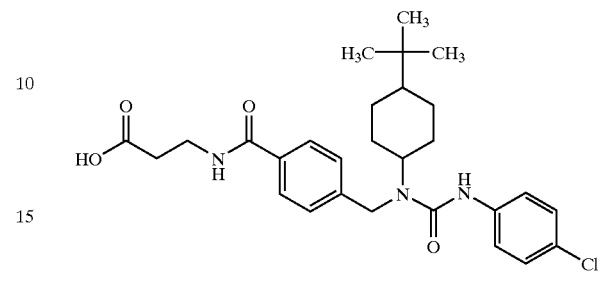

The product was characterized by HPLC-MS (Method B): $R_t$=7.68 min, m/z=514 (M+1).

EXAMPLE 35

General Procedure (C)

3-{4-[1-(4-trans-tert-Butylcyclohexyl)-3-(2,4-dichlorophenyl)ureidomethyl]benzoylamino}propionic acid

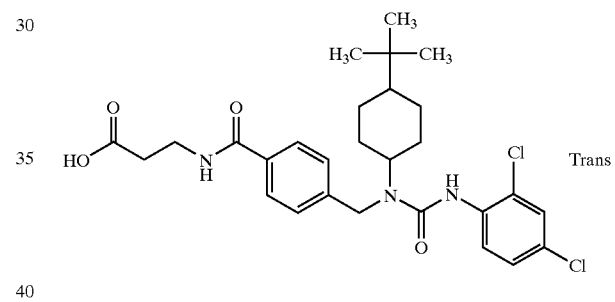

$^1$H NMR (DMSO-$d_6$): δ 0.82 (9H, s), 0.9–1.7 (9H, m), 4.04 (1H, t), 4.60 (2H, s), 7.38 (4H, m), 7.60 (2H, m), 7.78 (2H, d), 8.48 (1H, t).

HPLC-MS (Method B): $R_t$=8.25 min, m/z=548 (M+1).

EXAMPLE 36

General Procedure (C)

3-{4-[1-(2-Ethylhexyl)-3-(4-trifluoromethylphenyl)ureidomethyl]benzoylamino}propionic acid

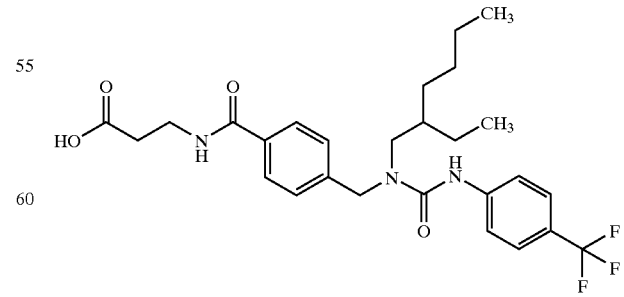

$^1$H NMR (DMSO-$d_6$): δ 7.33 (2H, d), 7.59 (2H, d), 7.68 (2H, d), 7.81 (2H, d), 8.50 (1H, t), 8.81 (1H, s).

EXAMPLE 37

General Procedure (C)

4-[3-[4-(2-Carboxyethylcarbamoyl)benzyl]-3-(2-ethylhexyl)ureido]benzoic acid butyl ester

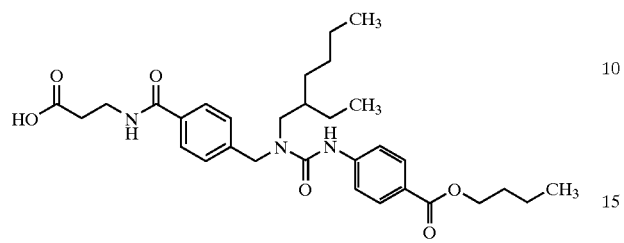

$^1$H NMR (DMSO-d$_6$): δ 4.23 (2H, t), 4.69 (2H, s), 7.33 (2H, d), 7.60 (2H, d), 7.80 (2H, d), 7.84 (2H, d), 8.49 (1H, bt), 8.81 (1H, s).

EXAMPLE 38

General Procedure (C)

3-{4-[3-(4-Chlorophenyl)-1-(2-ethylhexyl)ureidomethyl]benzoylamino}propionic acid

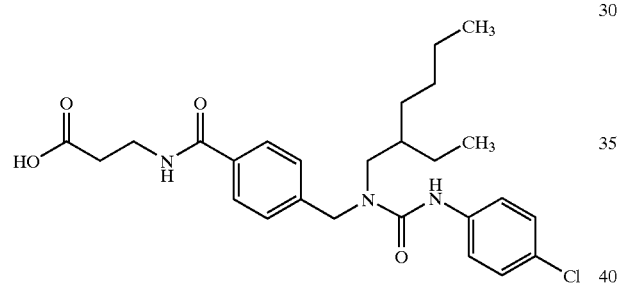

$^1$H NMR (DMSO-d$_6$): δ 4.64 (2H, s), 7.04 (2H, d), 7.3–7.35 (4H, m), 7.81 (2H, d), 8.28 (1H, s), 8.48 (1H, bt).

EXAMPLE 39

General Procedure (C)

3-{4-[1-(2-Ethylhexyl)-3-p-tolylureidomethyl]benzoylamino}propionic acid

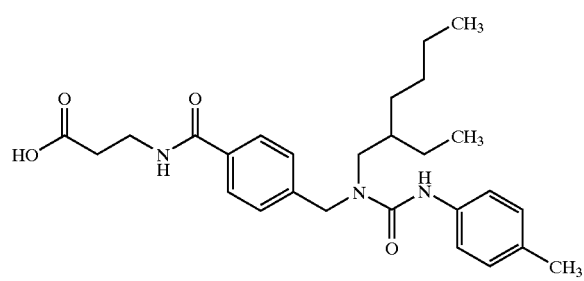

$^1$H NMR (DMSO-d$_6$): δ 4.65 (2H, s), 7.06 (2H, d), 7.31–7.33 (4H, m), 7.81 (2H, d), 8.29 (1H, s), 8.49 (1H, bt).

EXAMPLE 40

General Procedure (C)

3-[3-[4-(2-Carboxyethylcarbamoyl)benzyl]-3-(2-ethylhexyl)ureido]benzoic acid ethyl ester

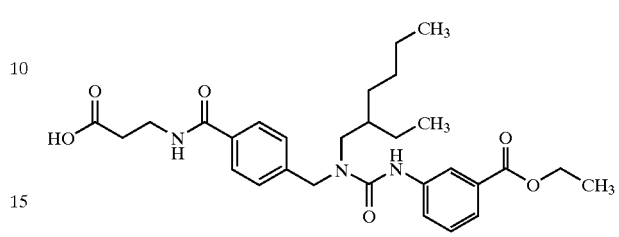

$^1$H NMR (DMSO-d$_6$): δ 4.30 (2H, q), 4.67 (2H, s), 7.33 (2H, d), 7.36 (1H, t), 7.53 (1H, t), 7.74 (1H, bd), 7.80 (2H, d), 8.07 (1H, s), 8.48 (1H, bt), 8.65 (1H, s).

EXAMPLE 41

General Procedure (C)

3-{4-[1-(2-Ethylhexyl)-3-(4-methylsulfanylphenyl)ureidomethyl]benzoylamino}propionic acid

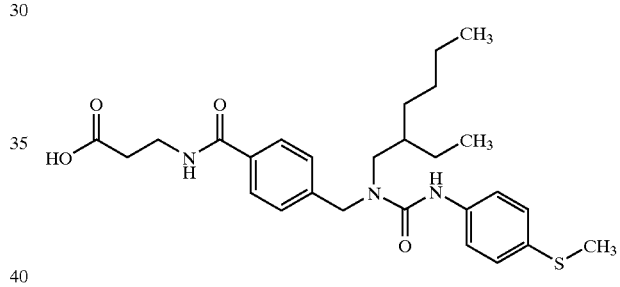

$^1$H NMR (DMSO-d$_6$): δ 4.66 (2H, s), 7.18 (2H, d), 7.31 (2H, d), 7.39 (2H, d), 7.78 (2H, d), 8.40 (1H, s), 8.50 (1H, bt).

EXAMPLE 42

General Procedure (C)

3-{4-[1-(2-Ethylhexyl)-3-(4-ethylphenyl)ureidomethyl]benzoylamino}propionic acid

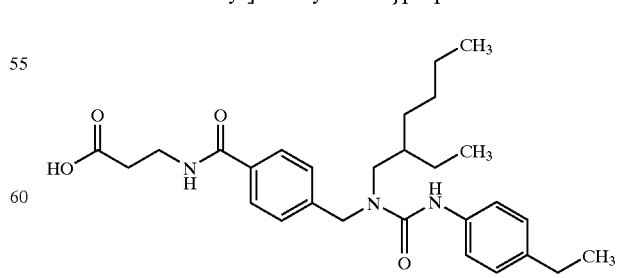

$^1$H NMR (DMSO-d$_6$): δ 4.51 (2H, s), 7.10 (2H, d), 7.32 (4H, m), 7.79 (2H, d), 8.28 (1H, s), 8.48 (1H, t).

EXAMPLE 43

General Procedure (C)

3-{4-[1-(2-Ethylhexyl)-3-(4-isopropylphenyl)ureidomethyl]benzoylamino}propionic acid

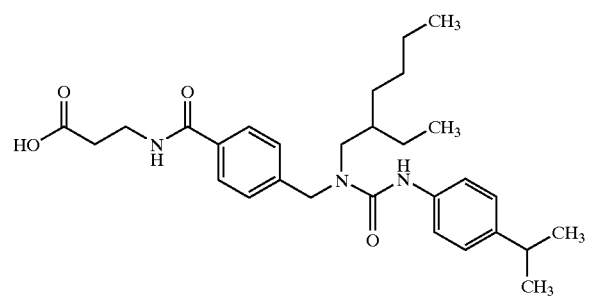

$^1$H NMR (DMSO-d$_6$): δ 4.70 (2H, s), 7.33 (2H, d), 7.58 (2H, d), 7.67 (2H, d), 7.78 (2H, d), 7.78 (2H, d), 8.46 (1H, t), 8.70 (1H, d).

EXAMPLE 44

General Procedure (C)

3-{4-[1-(3-Methylcyclohexyl)-3-(4-phenoxyphenyl)ureidomethyl]benzoylamino}propionic acid

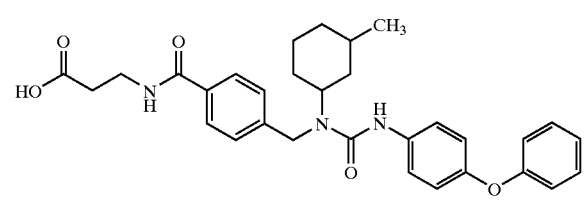

$^1$H NMR (DMSO-d$_6$): δ 4.61 (2H, s), 6.92 (4H, m), 7.07 (1H, t), 7.33 (4H, m), 7.41 (2H, m), 7.76 (2H, d), 8.29 (1H, d), 8.45 (1H, t).

EXAMPLE 45

General Procedure (C)

3-{4-[3-(4-Benzyloxyphenyl)-1-(4-methylcyclohexyl)ureidomethyl]benzoylamino}propionic acid

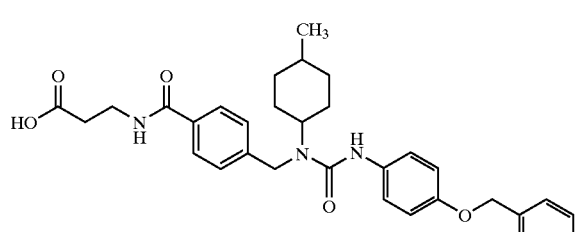

$^1$H NMR (DMSO-d$_6$): δ 5.01 (2H, s), 6.90 (2H, d), 7.1–7.3 (10H, m), 7.77 (2H, d), 8.15 (1H, s), 8.44 (1H, bt).

EXAMPLE 46

General Procedure (C)

3-{4-[1-[2-(3,4-Dichlorophenyl)ethyl]-3-(4-ethylphenyl)ureidomethyl]benzoylamino}propionic acid

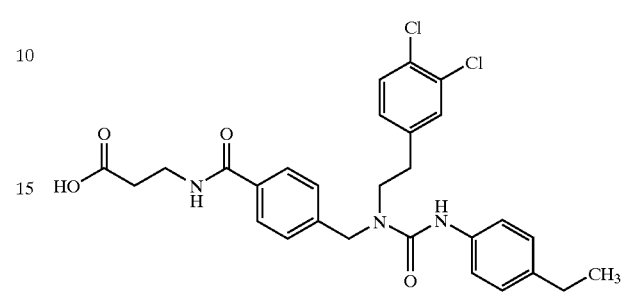

$^1$H NMR (DMSO-d$_6$): δ 4.67 (2H, s), 7.08 (2H, d), 7.25 (1H, d), 7.35 (4H, m), 7.53 (2H, m), 7.81 (2H, d), 8.31 (1H, s), 8.48 (1H, bt).

EXAMPLE 47

General Procedure (C)

3-{4-[3-(4-Benzyloxyphenyl)-1-[2-(3,4-dichlorophenyl)ethyl]ureidomethyl]benzoylamino}propionic acid

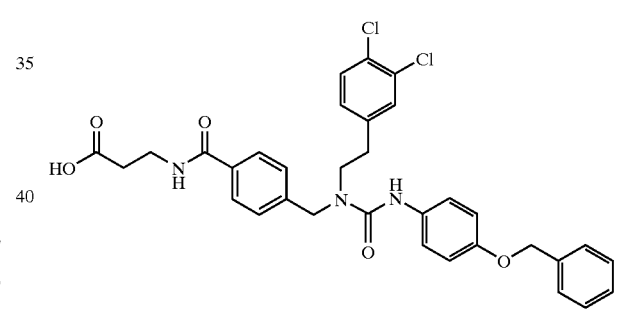

$^1$H NMR (DMSO-d$_6$): δ 4.60 (2H, s), 5.10 (2H, s), 6.92 (2H, d), 7.25–7.47 (10H, m), 7.55 (2H, m), 7.25 (1H, d), 7.81 (2H, d), 8.27 (1H, s), 8.45 (1H, t).

EXAMPLE 48

General Procedure (C)

3-{4-[1-(2-Methylcyclohexyl)-3-(4-phenoxyphenyl)ureidomethyl]benzoylamino}propionic acid

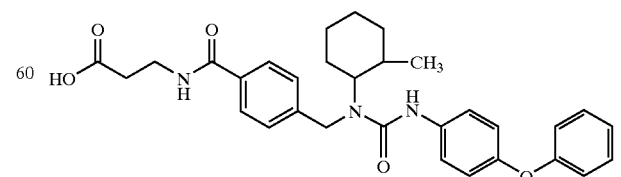

HPLC-MS (Method C): m/z: 530, R$_t$=6.96 min.

EXAMPLE 49

General Procedure (C)

4-[3-[4-(2-Carboxyethylcarbamoyl)benzyl]-3-(2-phenylpropyl)ureido]benzoic acid butyl ester

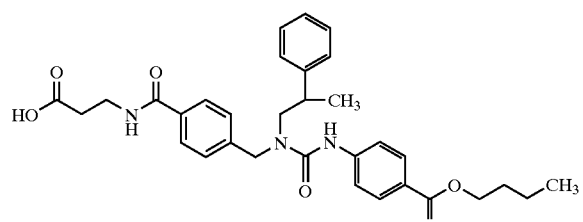

$^1$H NMR (DMSO-$d_6$): δ 7.20 (2H, t), 7.3 (6H, m), 7.55 (2H, d), 7.77 (2H, d), 7.83 (2H, d), 8.46 (1H, d), 8.69 (1H, s).

EXAMPLE 50

General Procedure (C)

3-{4-[3-(4-Isopropylphenyl)-1-(2-phenylpropyl)ureidomethyl]benzoylamino}propionic acid

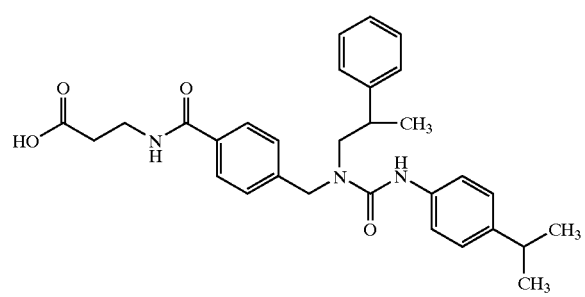

$^1$H NMR (DMSO-$d_6$): δ 7.11 (2H, d), 7.2–7.35 (9H, m), 7.78 (2H, d), 8.23 (1H, s), 8.49 (1H, t).

EXAMPLE 51

General Procedure (C)

4-{3-[4-(2-Carboxyethylcarbamoyl)benzyl]-3-[2-(4-chlorophenyl)ethyl]ureido}benzoic acid butyl ester

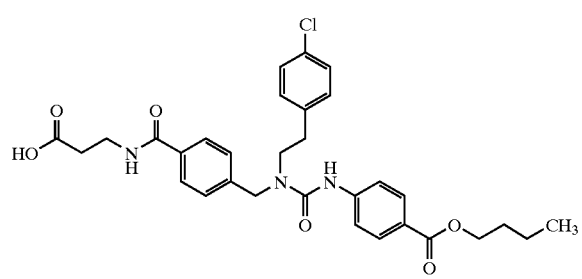

$^1$H NMR (DMSO-$d_6$): δ 7.27 (2H, d), 7.31–7.36 (4H, m), 7.60 (2H, d), 7.81 (2H, d), 7.86 (2H, d), 8.47 (1H, t), 8.77 (1H, s).

EXAMPLE 52

General Procedure (C)

3-{4-[1-[2-(4-Chlorophenyl)ethyl]-3-(4-isopropylphenyl)ureidomethyl]benzoylamino}propionic acid

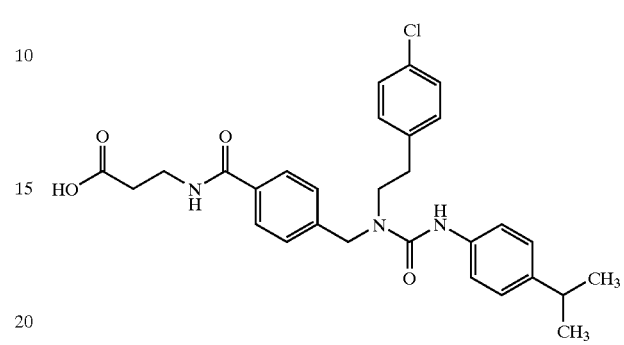

$^1$H NMR (DMSO-$d_6$): δ 7.10 (2H, d), 7.24 (2H, d), 7.30–7.34 (6H, m), 7.78 (2H, d), 8.29 (1H, s).

EXAMPLE 53

General Procedure (C)

3-{4-[1-(2,2-Diphenylethyl)-3-(4-phenoxyphenyl)ureidomethyl]benzoylamino}propionic acid

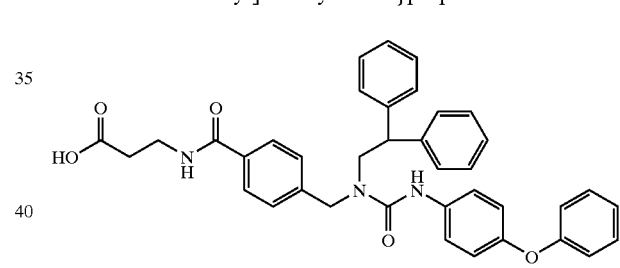

HPLC-MS (Method C): m/z 614, $R_t$=7.35 min.

EXAMPLE 54

General Procedure (C)

4-[3-[4-(2-Carboxyethylcarbamoyl)benzyl]-3-(2,2-diphenylethyl)ureido]benzoic acid butyl ester

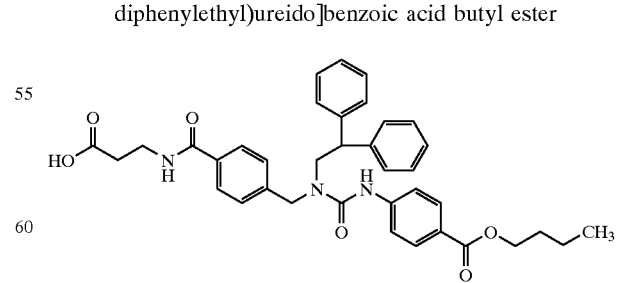

$^1$H NMR (DMSO-$d_6$): δ 7.18 (2H, t), 7.25–7.3 (6H, m), 7.34 (4H, m), 7.47 (2H, d), 7.75 (2H, d), 7.80 (2H, d), 8.52 (1H, b), 8.71 (1H, s).

EXAMPLE 55

General Procedure (C)

3-{4-[1-(2,2-Diphenylethyl)-3-(4-isopropylphenyl)ureidomethyl]benzoylamino}propionic acid

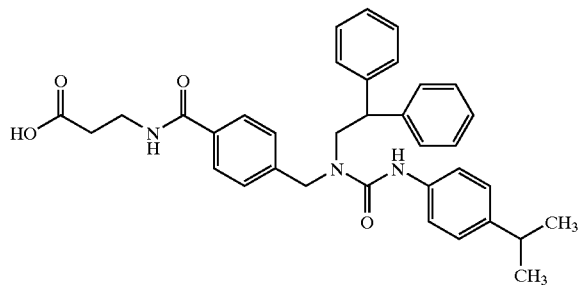

¹H NMR (DMSO-d₆): δ 7.06 (2H, d), 7.16–7.35 (14H, m), 7.75 (2H, d), 8.24 (1H, s).

EXAMPLE 56

General Procedure (C)

3-{4-[1-(4-tert-Butylcyclohexyl)-3-(4-isopropylphenyl)ureidomethyl]benzoylamino}propionic acid

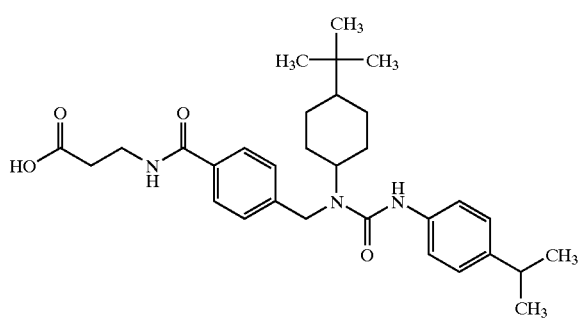

¹H NMR (DMSO-d₆): δ 8.41 (s, 1H); 8.20 (s, 1H); 7.75 (d, 2H); 7.34 (d, 2H); 7.32 (d, 2H); 7.08 (d, 2H); 4.08 (s, 2H); 1.19 (d, 6H); 0.83 (s, 9H).

EXAMPLE 57

General Procedure (C)

3-{4-[1-(4-tert-Butylcyclohexyl)-3-(4-phenoxyphenyl)ureidomethyl]benzoylamino}propionic acid

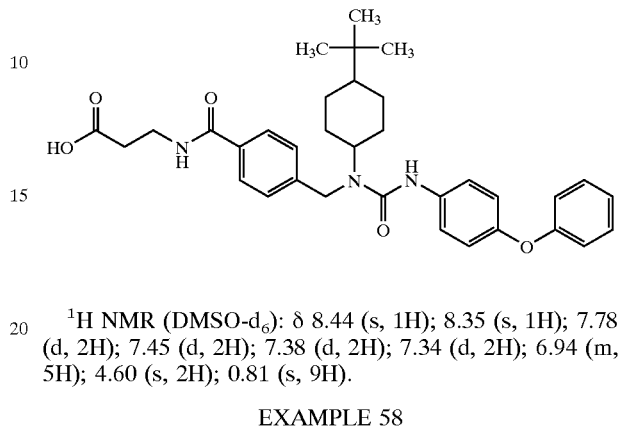

¹H NMR (DMSO-d₆): δ 8.44 (s, 1H); 8.35 (s, 1H); 7.78 (d, 2H); 7.45 (d, 2H); 7.38 (d, 2H); 7.34 (d, 2H); 6.94 (m, 5H); 4.60 (s, 2H); 0.81 (s, 9H).

EXAMPLE 58

General Procedure (C)

3-{4-[1-(4-tert-Butylcyclohexyl)-3-(4-trifluoromethylsulfanylphenyl)ureidomethyl]benzoylamino}propionic acid

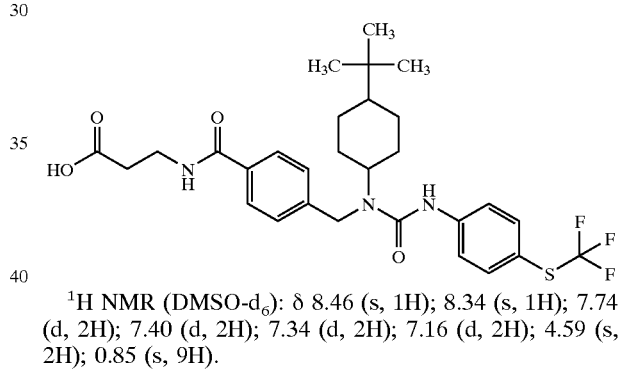

¹H NMR (DMSO-d₆): δ 8.46 (s, 1H); 8.34 (s, 1H); 7.74 (d, 2H); 7.40 (d, 2H); 7.34 (d, 2H); 7.16 (d, 2H); 4.59 (s, 2H); 0.85 (s, 9H).

EXAMPLE 59

General Procedure (C)

3-{4-[1-(4-tert-Butylcyclohexyl)-3-(4-methoxyphenyl)ureidomethyl]benzoylamino}propionic acid

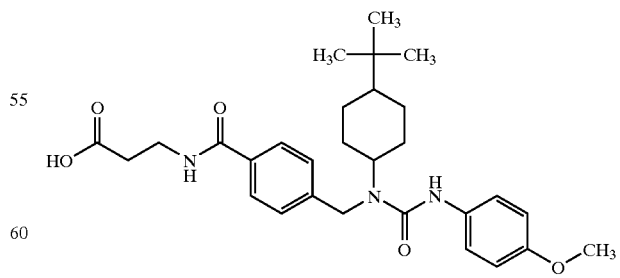

¹H NMR (DMSO-d₆): δ 8.46 (s, 1H); 8.18 (s, 1H); 7.76 (d, 2H); 7.30 (d, 2H); 7.28 (d, 2H); 6.8 (d, 2H); 4.58 (s, 2H); 3.73 (s, 3H); 0.80 (s, 9H).

EXAMPLE 60

General Procedure (C)

3-{4-[3-(4-Acetylphenyl)-1-(4-tert-butylcyclohexyl)ureidomethyl]benzoylamino}propionic acid

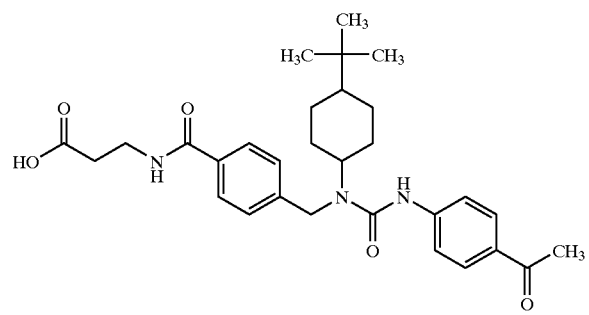

$^1$H NMR (DMSO-$d_6$): δ 8.70 (s, 1H); 8.42 (s, 1H); 7.86 (d, 2H); 7.76 (d, 2H); 7.62 (d, 2H); 7.30 (d, 2H); 4.62 (s, 2H); 0.81 (s, 9H).

EXAMPLE 61

General Procedure (C)

4-{3-(4-tert-Butylcyclohexyl)-3-[4-(2-carboxyethylcarbamoyl)benzyl]ureido}benzoic acid butyl ester

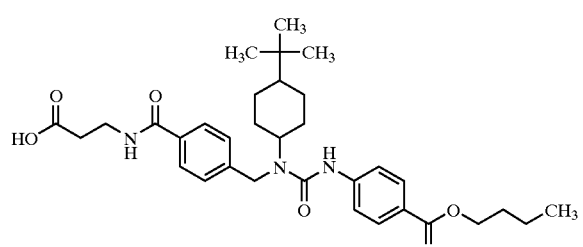

$^1$H NMR (DMSO-$d_6$): δ 8.71 (s, 1H); 8.42 (t, 2H); 7.83 (d, 2H); 7.76 (d, 2H); 7.61 (s, 2H); 7.32 (d, 2H); 4.64 (s, 2H); 4.26 (t, 2H); 0.94 (t, 3H); 0.83 (s, 9H).

EXAMPLE 62

General Procedure (C)

3-{4-[1-(4-tert-Butylcyclohexyl)-3-(4-isobutylphenyl)ureidomethyl]benzoylamino}propionic acid

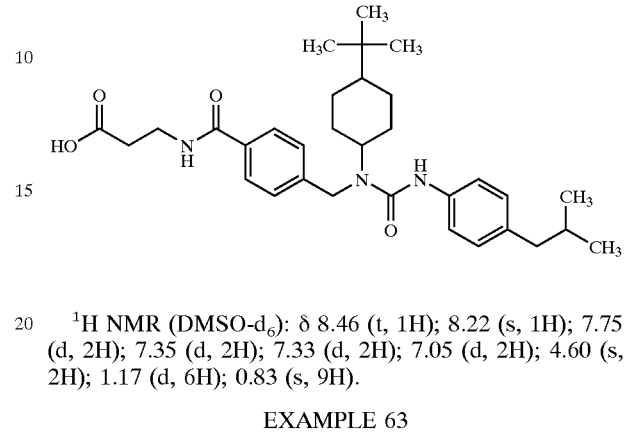

$^1$H NMR (DMSO-$d_6$): δ 8.46 (t, 1H); 8.22 (s, 1H); 7.75 (d, 2H); 7.35 (d, 2H); 7.33 (d, 2H); 7.05 (d, 2H); 4.60 (s, 2H); 1.17 (d, 6H); 0.83 (s, 9H).

EXAMPLE 63

General Procedure (C)

3-{4-[1-(4-tert-Butylcyclohexyl)-3-(4-trifluoromethylphenyl)ureidomethyl]benzoylamino}propionic acid

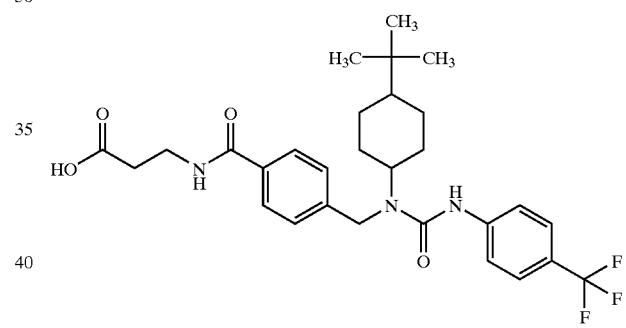

$^1$H NMR (DMSO-$d_6$): δ 8.72 (s, 1H); 8.45 (t, 1H); 7.78 (d, 2H); 7.72 (d, 2H); 7.60 (d, 2H); 7.35 (d, 2H); 4.65 (s, 2H); 4.10 (m, 1H); 0.85 (s, 9H).

EXAMPLE 64

General Procedure (C)

3-{4-[1-(2-Ethylhexyl)-3-(4-isobutylphenyl)ureidomethyl]benzoylamino}propionic acid

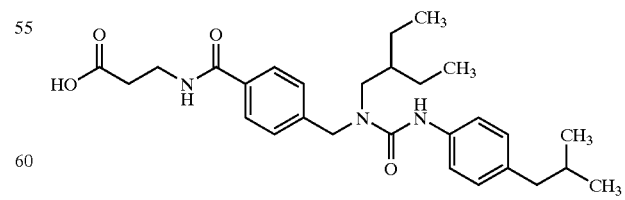

$^1$H NMR (DMSO-$d_6$): δ 8.47 (t, 1H); 8.30 (s, 1H); 7.82 (d, 2H); 7.36 (d, 2H); 7.32 (d, 2H); 7.05 (d, 2H); 4.65 (s, 2H), 1.12 (m, 9H); 0.85 (m, 12H).

EXAMPLE 65

General Procedure (C)

3-{4-[3-(4-Trifluoromethoxyphenyl)-1-(2,6,6-trimethylbicyclo[3.1.1]hept-3-yl)ureidomethyl]benzoylamino}propionic acid

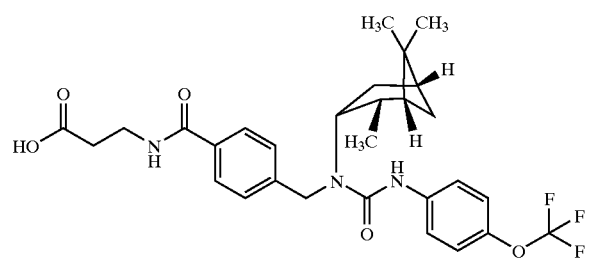

$^1$H NMR (DMSO-d$_6$): δ 8.52 (s, 1H); 8.44 (t, 1H); 7.81 (d, 2H); 7.52 (d, 2H); 7.35 (d, 2H); 7.22 (d, 2H); 4.91 (m, 1H); 4.76 (s, 2H); 1.22 (s, 3H); 1.13 (s, 3H); 0.98 (d, 3H).

EXAMPLE 66

General Procedure (C)

3-{4-[3-(4-Isopropylphenyl)-1-(2,6,6-trimethylbicyclo[3.1.1]hept-3-yl)ureidomethyl]benzoylamino}propionic acid

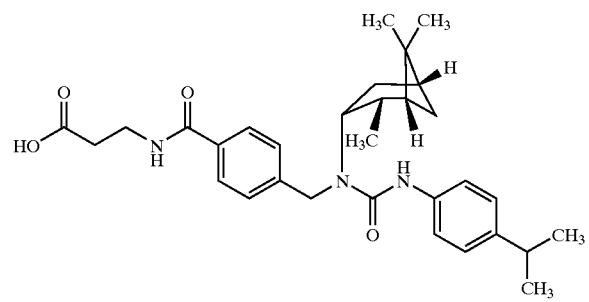

$^1$H NMR (DMSO-d$_6$): δ 8.44 (s, 1H); 8.17 (t, 1H); 7.78 (d, 2H); 7.34 (d, 2H); 7.26 (d, 2H); 7.08 (d, 2H); 4.93 (m, 1H); 4.72 (s, 2H); 1.22 (s, 3H); 1.18 (d, 6H); 1.13 (s, 3H); 0.98 (d, 3H).

EXAMPLE 67

General Procedure (C)

3-{4-[1-(4-tert-Butylcyclohexyl)-3-(4-nitrophenyl)ureidomethyl]benzoylamino}propionic acid

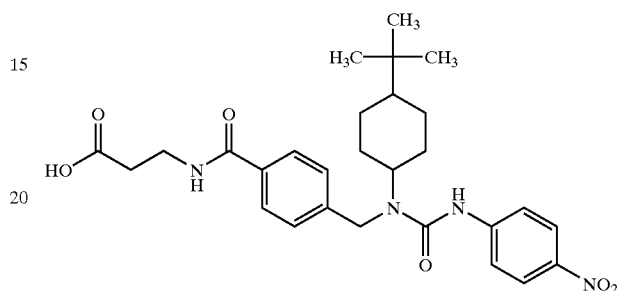

$^1$H NMR (DMSO-d$_6$): δ 9.03 (s, 1H); 8.45 (t, 1H); 8.16 (d, 2H); 7.77 (d, 2H); 7.73 (d, 2H); 7.33 (d, 2H); 4.67 (s, 2H); 4.10 (t, 1H); 0.86 (s, 9H).

EXAMPLE 68

General Procedure (C)

3-{4-[1-(4-tert-Butylcyclohexyl)-3-(4'-cyanobiphenyl-4-yl)ureidomethyl]benzoylamino}propionic acid

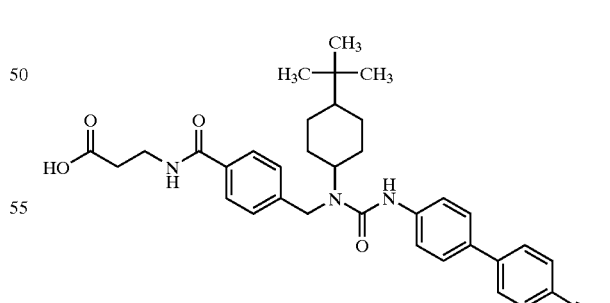

$^1$H NMR (DMSO-d$_6$): δ 8.52 (1H, s), 8.48 (1H, t), 7.88 (4H, dd), 7.79 (2H, d), 7.79 (2H, d), 7.62 (2H, d), 7.38 (2H, d).

EXAMPLE 69

General Procedure (C)

3-{4-[3-(4-Butoxyphenyl)-1-(4-tert-butyl-cyclohexyl)ureidomethyl]benzoylamino}propionic acid

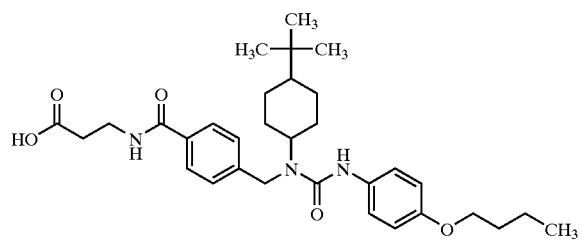

$^1$H NMR (DMSO-d$_6$): δ 8.45 (1H, m), 8.15 (1H, s), 7.78 (2H, d), 7.33 (4H, dd), 6.82 (2H, d).

EXAMPLE 70

General Procedure (C)

3-{4-[1-(4-tert-Butylcyclohexyl)-3-(4-cyano-3-trifluoromethylphenyl)ureidomethyl]benzoylamino}propionic acid

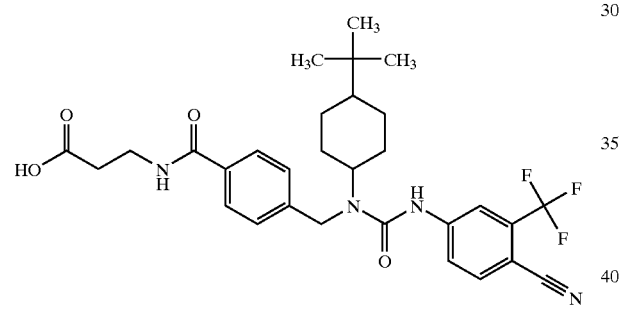

$^1$H NMR (DMSO-d$_6$): δ 8.43 (1H, m), 8.18 (1H, s), 7.98 (2H, s), 7.75 (2H, d), 7.43 (2H, d).

EXAMPLE 71

General Procedure (C)

3-{4-[1-(4-tert-Butylcyclohexyl)-3-(4-fluoro-3-trifluoromethylphenyl)ureidomethyl]benzoylamino}propionic acid

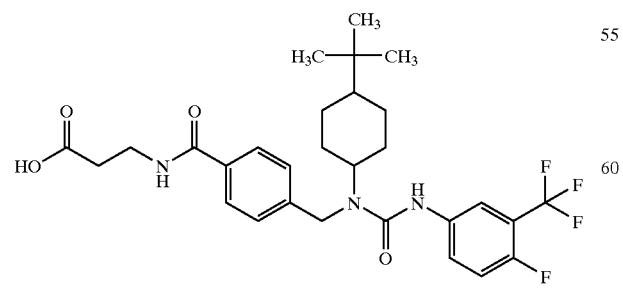

HPLC-MS (method B): m/z: 566, R$_t$=7.95 min.

EXAMPLE 72

General Procedure (C)

3-{4-[1-(4-tert-Butylcyclohexyl)-3-(3,4-difluorophenyl)ureidomethyl]benzoylamino}propionic acid

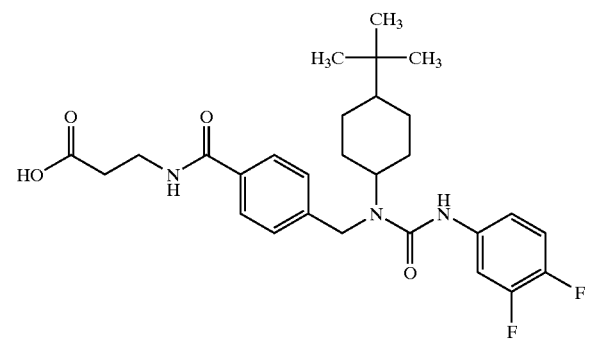

HPLC-MS (method B): m/z: 517, R$_t$=7.29 min.

EXAMPLE 73

General Procedure (C)

4-{3-(4-tert-Butylcyclohexyl)-3-[4-(2-carboxyethylcarbamoyl)benzyl]ureido}benzoic acid isopropyl ester

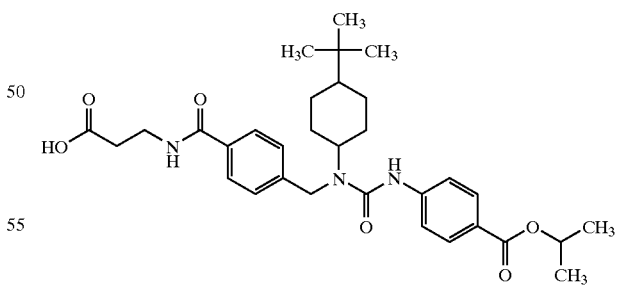

$^1$H NMR (DMSO-d$_6$): δ 8.70 (1H, s), 8.48 (1H, t), 7.83 (2H, d), 7.78 (2H, d), 7.63 (2H, d), 7.32 (2H, d).

HPLC-MS (method B): m/z: 566, R$_t$=7.69 min.

EXAMPLE 74

General Procedure (C)

3-{4-[1-(4-tert-Butylcyclohexyl)-3-(4-chloro-3-trifluoromethylphenyl)ureidomethyl]benzoylamino}propionic acid

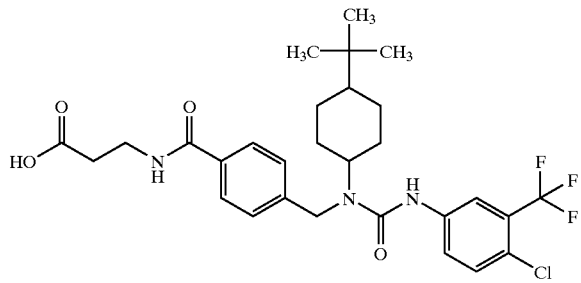

$^1$H NMR (DMSO-d$_6$): δ 8.80 (1H, s), 8.48 (1H, t), 8.05 (1H, s), 7.82 (1H, d), 7.77 (1H, d), 7.58 (1H, d), 7.32 (1H, s).

HPLC-MS (method B): m/z: 583, R$_t$=8.03 min.

General Procedure (D) for the Solid Phase Synthesis of Compounds of the General Formula (Ib):

The compounds of the general formula (Ib) may also be prepared by the use of the following method:

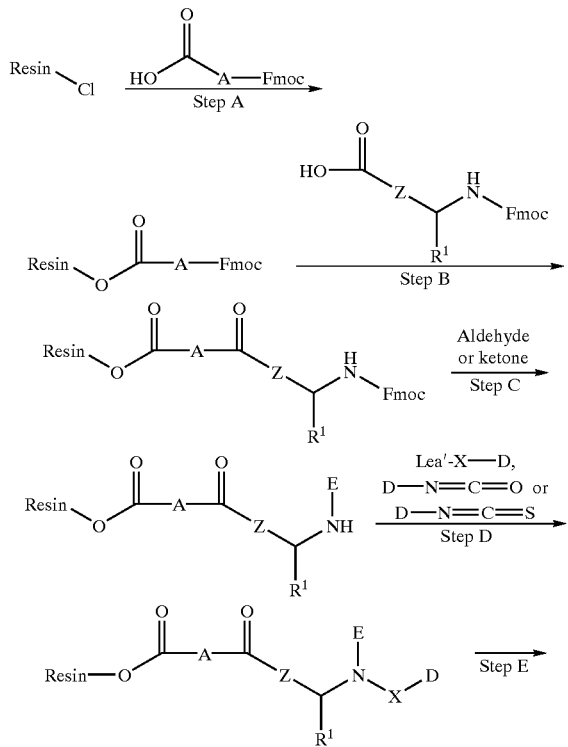

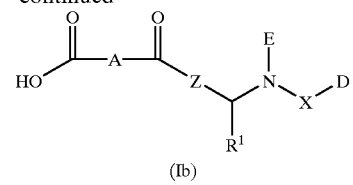

(Ib)

wherein
R$^1$, A, Z, E and D are as defined for formula (I),
X is —S(O)$_2$—(CH$_2$)$_r$—, —C(O)NH— or —C(S)NH—, wherein r is as defined for formula (I),
Lea' represents a leaving group such as —OSu, Cl—, PhO—, or 4-NO$_2$-PhO—, and

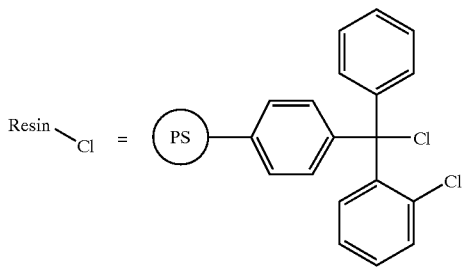

where PS is polystyene.

Step A:

The reaction is known (The combinatorial index, Ed. Bunin, B. A. 1998, Academic Press, p. 24) and is generally performed by shaking a suspension of the resin with a solution of an Fmoc amino acid in the presence of a base such as triethylamine, diisopropylethylamine, dicyclohexylmethylamine or any other tertiary amine. Typical solvents are pyridine, dichloromethane, 1,2-dichloroethane, DMF, NMP, THF, DMSO or mixtures of two or more of these. The reaction is performed between 20° C. and 120° C., preferably at 25° C. Excess reagents are filtered off and the resin is washed with any solvent mentioned above including mixtures hereof, containing a base as mentioned above and an alcohol, typically methanol, as a scavenger of unreacted resin bound 2-chlorotritylchloride.

Step B:

The Fmoc protecting group is removed using a solution of 20% piperidine in DMF, which is added to the resin and vortexed for 0.5 hours. After draining the resin is washed with DMF containing 1-hydroxybenzotriazole (50 mg/mL) and DMF.

The acylation (The combinatorial index, Ed. Bunin, B. A. 1998, Academic Press, p. 78) is performed by adding an excess of Fmoc amino-benzoic acid in a solvent such as DMF, NMP, THF, dichloromethane, 1,2-dichloroethane, acetonitrile, DMSO or a mixture of two or more of the these, optionally in the presence of a base such as N-methylmorpholine, triethylamine, diisopropylethylamine, dicyclohexylmethylamine or another tertiary amine, followed by a coupling reagent such as dicyclohexylcarbodiimide, diisopropylcarbodiimide, 1,1'-carbonyldiimidazole, 2-(1H-9-azabenzotriazole-1-yl)-1,1,3,3-tetramethyluronium hexafluorophosphate or bromo-trispyrrolidinophosphonium hexafluorophosphate in a solvent such as DMF, NMP, THF, dichloromethane, 1,2-dichloroethane, acetonitrile, DMSO or a mixture of two or more of these, optionally in the presence of a side reaction inhibitor such as 3-hydroxy-4-oxo-3,4-dihydro-1,2,3-benzotriazine, N-hydroxybenzotriazole or 1-hydroxy-7-azabenzotriazole. The reaction is performed between 20° C. and 40° C., preferably at 25° C. Excess reagents are filtered off and the resin is washed several times with the solvent used during the reaction.

Step C:

The Fmoc protecting group is removed eg using a solution of 20% piperidine in DMF. The reductive amination is generally known (The combinatorial index, Ed. Bunin, B. A. 1998, Academic Press, p. 167) and is performed by stirring resin bound amine with an excess of ketone or aldehyde at low pH (by addition of an acid, such as acetic acid or formic acid) in a solvent such as THF, DMF, NMP, methanol, ethanol, DMSO, dichloromethane, 1,2-dichloroethane, trimethyl orthoformate, triethyl orthoformate, or a mixture of two or more of the above. As reducing agent sodium trisacetoxy borohydride can be used. The reaction is performed between 20° C. and 120° C., preferably at 25° C. Excess reagents are filtered off and the resin is washed several times with the solvent used during the reaction optionally in combination with water.

Step D:

The reaction is generally known (Matthew, J.; Rivero, R. A. *J. Org. Chem.* 1997, 62, 6090–6092) and is usually performed by shaking resin bound amine with an excess of isocyanate or an equivalent such as a carbamate Lea'-X-D in a solvent such as DMF, NMP, THF, dichloromethane, 1,2-dichloroethane, DMSO or a mixture of two or more of the above and when using Lea'-X-D in the presence of a base such as triethylamine, diisopropylethylamine, dicyclohexylmethylamine or any other tertiary amine or potassium carbonate. The reaction is performed between 20° C. and 120° C., preferably between 20° C. and 40° C. Excess reagent is filtered off and the resin is washed several times with the solvent used during the reaction.

Step E:

The reaction is known (The combinatorial index, Ed. Bunin B. A., 1998, Academic press, p. 21) and is generally performed by stirring the resin bound intermediate with a 5–95% solution of TFA. The final cleavage is carried out in a solvent such as THF, dichloromethane, 1,2-dichloroethane, 1,3-dichloropropane, toluene or a mixture of two or more of the above. The reaction is performed between 0° C. and 80° C., preferably between 20° C. and 40° C. When the reaction is complete the product is removed by filtration. The resin is successively washed with the solvent used during the reaction, optionally containing TFA. The product and washings are collected and the solvent is removed in vacuo.

A specific example illustrating the preparation of compounds of the general formula (Ib) according to the invention is provided below.

EXAMPLE 75

General Procedure (D)

3-{4-[1-(4-Propylcyclohexyl)-3-(4-trifluoromethoxyphenyl)ureidomethyl]benzoylamino}propionic acid

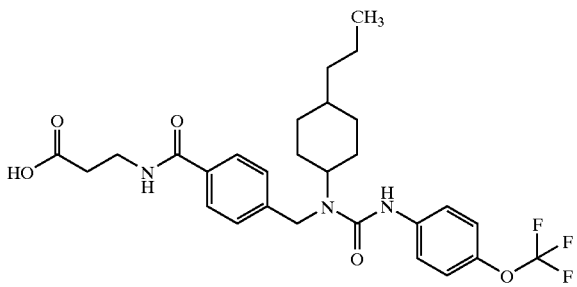

Step A: Resin bound Fmoc β-alanine

150 μmol Fmoc β-alanine was dissolved in a mixture of 250 μL dichloromethane, 250 μL DMF and 100 μL diisopropylethylamine and added to 50 mg polystyrene resin functionalized with a 2-chlorotrityl chloride linker. After shaking the suspension for 4 hours at 25° C., the resin was isolated by filtration and washed with 2×1 mL dichloromethane:methanol:diisopropylethylamine 17:2:1 and 2×1 mL DMF.

Step B: Resin bound 3-{4-[(9H-fluoren-9-ylmethoxycarbonylamino)methyl]benzoylamino}propionic acid To the above resin bound Fmoc β-alanine was added 500 μL of a 20% solution of piperidine in DMF. Upon shaking 30 min, the resin was drained and washed with 1 mL DMF containing 1-hydroxybenzotriazole (50 mg/mL) and DMF (2×1 mL). Then 200 μmol 4-[(9H-fluoren-9-ylmethoxycarbonylamino)methyl]benzoic acid (74.2 mg) dissolved in a mixture of 430 μL DMF and 70 μL diethylisopropylamine was added followed by 200 μmol bromo-tris-pyrrolidinophosphonium hexafluorophosphate (PyBrOP, 93 mg) dissolved in 500 μL DMF. The mixture was shaken for 4 hours at 25° C. followed by filtration and washing of the resin with 3×1 mL DMF.

Step C: Resin bound 3-{4-[(4-propylcyclohexylamino)methyl]benzoylamino}propionic acid The Fmoc protecting group was removed from the above resin bound 3-{4-[(9H-fluoren-9-ylmethoxycarbonylamino)methyl]benzoylamino}propionic acid using 500 μL of a 20% solution of piperidine in DMF. Upon shaking for 30 min, the resin was drained and washed with 1 mL DMF containing 1-hydroxybenzotriazole (50 mg/mL) and DMF (2×1 mL), 2×1 mL 1,2-dichloroethane and 20 μL acetic acid dissolved in 1 mL 1,2-dichloroethane.

The resulting resin bound 3-(4-aminomethylbenzoylamino)propionic acid was treated with 98 mg 4-propylcyclohexanone (700 μmol) dissolved in 500 μL 1,2-dichloroethane, 50 μL acetic acid and a slurry of 148 mg NaBH(OAc)₃ (700 μmol) in 1 mL 1,2-dichloroethane. Over night shaking at 25° C. followed by filtration and washing with 2×1 mL dichloromethane, 2×1 mL CH₃OH:DMF 1:1 and 3×1 mL DMF afforded resin bound 3-{4-[(4-propylcyclohexylamino)methyl]benzoylamino}propionic acid.

Step D: Resin bound 3-{4-[1-(4-propylcyclohexyl)-3-(4-trifluoromethoxyphenyl)ureidomethyl]benzoylamino}propionic acid 200 μmol 4-trifluoromethoxyphenylisocyanate dissolved in 500 μL 1,2-dichloroethane was added to the above resin bound 3-{4-[(4-propylcyclohexylamino)methyl] benzoylamino}propionic acid. Shaking the mixture for 5 hours at 25° C. followed by filtration and washing of the resin with 2×1 mL dichloromethane, 4×1 mL DMF, 2×1 mL H₂O, 3×1 mL THF, 3×1 mL dichloromethane afforded the resin bound 3-{4-[1-(4-propylcyclohexyl)-3-(4-trifluoromethoxyphenyl)ureidomethyl] benzoylamino}propionic acid.

Step E: 3-{4-[1-(4-Propylcyclohexyl)-3-(4-trifluoromethoxyphenyl)ureidomethyl] benzoylamino}propionic acid The above resin bound 3-{4-[1-(4-propylcyclohexyl)-3-(4-trifluoromethoxyphenyl)ureidomethyl] benzoylamino}propionic acid was treated with 1 mL 5% TFA in dichloromethane for 1 hour at 25° C. The product was filtered off and the resin was washed with 1 mL dichloromethane. The combined extracts were concentrated in vacuo. The residue was dissolved in 50 μL DMSO+500 μL CH₃CN and purified by preparative HPLC using a Supelcosil ABZ+25 cm×10 mm 5μ column. The starting eluent composition was 5% CH₃CN in H₂O changing over 30 minutes to 90% CH₃CN in H₂O which was then kept constant for 5 minutes before going back to the starting composition over 10 min. The flow rate was kept constant at 8 mL/min. collecting one fraction per minute. The process was monitored using an UV detector operating at 214 nm. The fractions containing the desired products were combined and evaporated in vacuo to afford the title compound.

HPLC-MS (method B) (m/z=550), (7.46, 7.58 min)

The HPLC purification allowed the separation of the cis and trans isomers of the title compound. The products were characterized by HPLC-MS and ¹H NMR.

EXAMPLE 76

General Procedure (D)

3-{4-[1-(4-trans-Propylcyclohexyl)-3-(4-trifluoromethoxyphenyl)ureidomethyl] benzoylamino}propionic acid

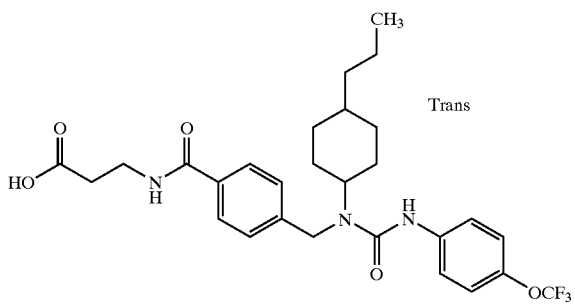

¹H NMR (400 MHz), (DMSO-d₆): δ 12.20 (s br, 1H); 8.55 (s, 1H); 8.50 (t, 1H); 7.75 (d, 2H); 7.55 (d, 2H); 7.30 (d, 2H); 7.20 (d, 2H), 4.60 (s, 2H); 4.10 (t, 1H); 3.40 (m, 2H); 2.45 (t, 2H); 0.70–1.80 ppm (m, 16H).

HPLC-MS (method B) (m/z=550), (R$_t$=7.46 min).

EXAMPLE 77

General Procedure (D)

3-{4-[1-(4-cis-Propylcyclohexyl)-3-(4-trifluoromethoxyphenyl)ureidomethyl] benzoylamino}propionic acid

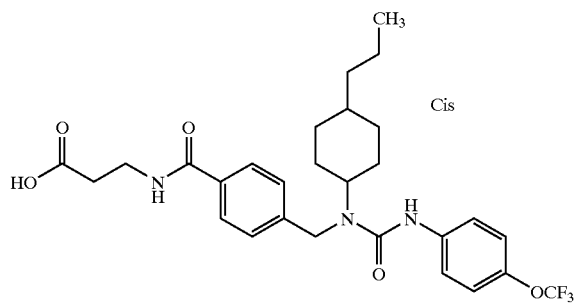

¹H NMR (400 MHz), (DMSO-d₆): δ 12.15 (s br, 1H); 8.55 (s, 1H); 8.50 (t, 1H); 7.80 (d, 2H); 7.55 (d, 2H); 7.35 (d, 2H); 7.25 (d, 2H), 4.65 (s, 2H); 4.10 (s br, 1H); 3.45 (m, 2H); 2.50 (2H); 1.15–1.65 ppm (m, 13H), 0.85 (t, 3H).

HPLC-MS (method B) (m/z=550), (7.58 min).

EXAMPLE 78

General Procedure (D)

3-{4-[1-[4-trans-(1,1-Dimethylpropyl)cyclohexyl]-3-(4-trifluoromethoxyphenyl)ureidomethyl] benzoylamino}propionic acid

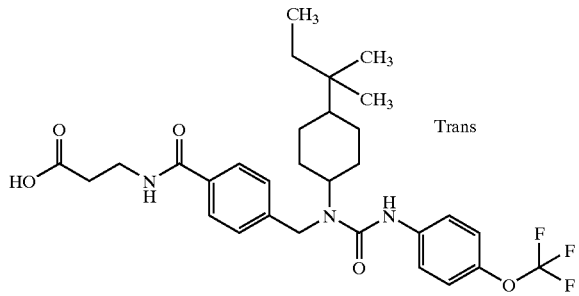

HPLC-MS (method B) (m/z=578) (7.84 min, 7.94 min).

EXAMPLE 79

General Procedure (D)

3-{4-[1-(Decahydronaphthalen-2-yl)-3-(4-trifluoromethoxyphenyl)ureidomethyl]benzoylamino}propionic acid

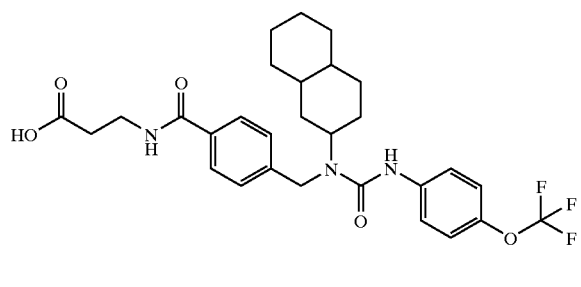

$^1$H NMR (400 MHz, DMSO-d$_6$): δ 8.50 (s, 1H); 8.47 (t, 1H); 7.76 (d, 2H); 7.55 (d, 2H); 7.30 (d, 2H); 7.22 (d, 2H); 4.60 (s, 2H); 4.30 (t, 1H), 3.45 (m, 2H); 2.50 (t, 2H); 1.85–0.70 (m).

HPLC-MS (method B) (m/z=562) (7.48 min, 7.49 min).

EXAMPLE 80

General Procedure (D)

3-{4-[1-(4-cis-Phenylcyclohexyl)-3-(4-trifluoromethoxyphenyl)ureidomethyl]benzoylamino}propionic acid

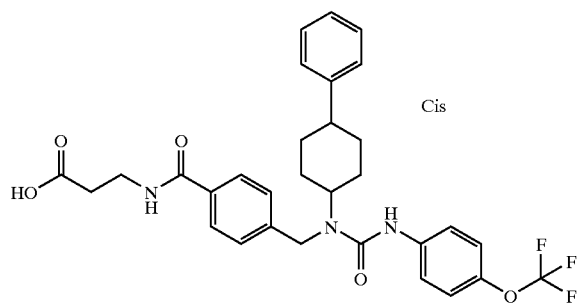

HPLC-MS (method B) (m/z=584), (7.22 min, 7.33 min).

EXAMPLE 81

General Procedure (D)

3-{4-[1-(4-trans-Phenylcyclohexane)-3-(4-trifluoromethoxyphenyl)ureidomethyl]benzoylamino}propionic acid

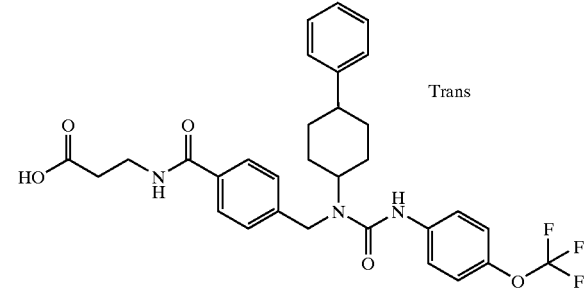

HPLC-MS (method B) (m/z=584), (7.22 min, 7.33 min).

EXAMPLE 82

General Procedure (D)

3-{4-[1-(4-Isopropylcyclohexyl)-3-(4-trifluoromethoxyphenyl)ureidomethyl]benzoylamino}propionic acid

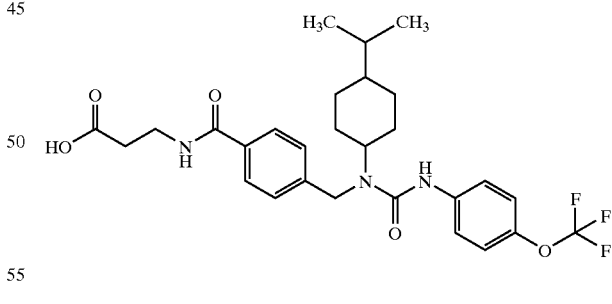

$^1$H NMR (200 MHz), (DMSO-d$_6$): δ 8.55 (s, 1H); 8.45 (t, 1H); 7.75 (d, 2H); 7.55 (d, 2); 7.35 (d, 2H); 7.20 (d, 2H); 4.60 (s, 2H); 4.05–4.15 (m br, 1H); 3.45 (m, 2H); 2.50 (t, 2H); 0.90–1.8 (m, 10H); 0.85 (d, 6H).

HPLC-MS (method B) (m/z=550), (R$_t$=7.38 min, 7.50 min).

EXAMPLE 83

General Procedure (D)

3-{4-[1-(4-Ethylcyclohexyl)-3-(4-trifluoromethoxyphenyl)ureidomethyl]benzoylamino}propionic acid

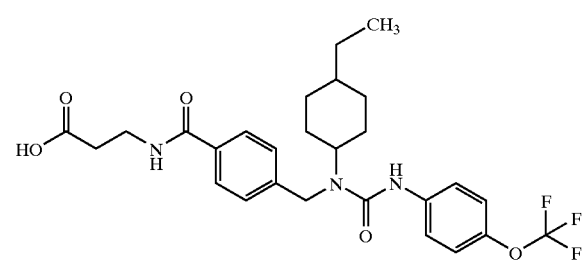

$^{1}$H NMR (300 MHz), (DMSO-d$_{6}$): δ 8.55 (s, 1H); 8.45 (t, 1H); 7.75 (d, 2H); 7.55 (d, 2H); 7.30 (d, 2H); 7.25 (d, 2H); 4.60 (s, 2H); 4.05–4.15 (m br, 1H); 3.45 (m, 2H); 2.50 (t, 2H); 0.75–1.8 (m, 14H).

HPLC-MS (method B) (m/z=536), (R$_{t}$=7.59 min).

EXAMPLE 84

General Procedure (D)

4-[3-[4-(2-Carboxyethylcarbamoyl)benzyl]-3-(4-isopropylcyclohexyl)ureido]benzoic acid butyl ester

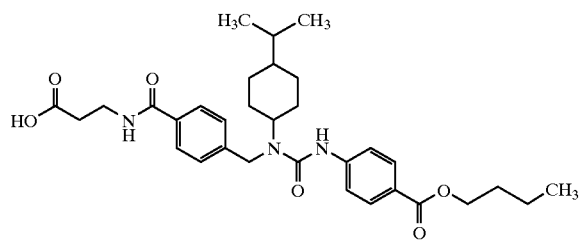

$^{1}$H NMR (DMSO-d$_{6}$): δ 8.70 (s, 1H); 8.45 (t, 1H); 7.83 (d, 2H); 7.78 (d, 2H); 7.60 (d, 2H); 7.34 (d, 2H); 4.67 (s, 2H); 4.24 (t, 2H); 4.14 (m, 1H); 0.96 (t, 3H); 0.85 (d, 6H).

EXAMPLE 85

General Procedure (D)

3-{4-[3-(3,5-Bis(trifluoromethyl)phenyl)-1-(3-ethylcyclopentyl)ureidomethyl]benzoylamino}propionic acid

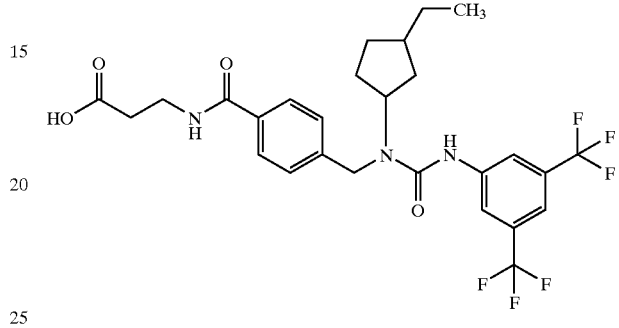

$^{1}$H NMR (DMSO-d$_{6}$): δ 9.04 (s, 1H); 8.48 (t, 1H); 8.28 (s, 2H); 7.71 (d, 2H); 7.62 (s, 1H); 7.84 (d, 2H); 4.65 (s, 2H).

EXAMPLE 86

General Procedure (D)

3-{4-[3-(3,5-Bis(trifluoromethyl)phenyl)-1-(1,2,3,4-tetrahydronaphthalen-2-yl)ureidomethyl]benzoylamino}propionic acid

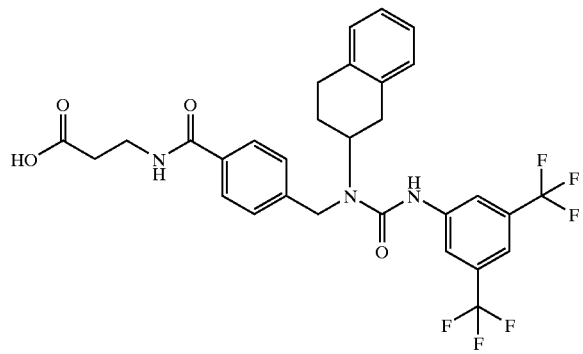

$^{1}$H NMR (DMSO-d$_{6}$): δ 9.20 (s, 1H); 8.50 (t, 1H); 8.82 (s, 2H); 7.81 (d, 2H); 7.62 (s, 1H); 7.42 (d, 2H); 7.10 (m, 4H); 4.75 (dd, 2H); 4.52 (m, 1H).

EXAMPLE 87

General Procedure (D)

3-{4-[1-[4-(1,1-Dimethylpropyl)cyclohexyl]-3-(4-trifluoromethoxyphenyl)ureidomethyl]benzoylamino}propionic acid

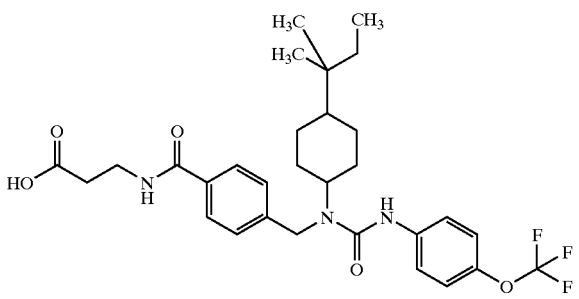

$^1$H NMR (400 MHz, DMSO-d$_6$): δ 12.05 (s br) 8.60 (s); 8.55 (s); 8.45 (t); 7.80 (d); 7.55 (d); 7.30 (d); 7.20 (d); 4.72 (s); 4.60 (s); 4.25 (t); 4.05 (t); 3.45 (q); 2.50 (t); 1.90–1.00 (m) 0.77 (s); 0.73 (s).

EXAMPLE 88

General Procedure (D)

3-{4-[1-(4,4-Dipropylcyclohexyl)-3-(4-trifluoromethoxyphenyl)ureidomethyl]benzoylamino}propionic acid

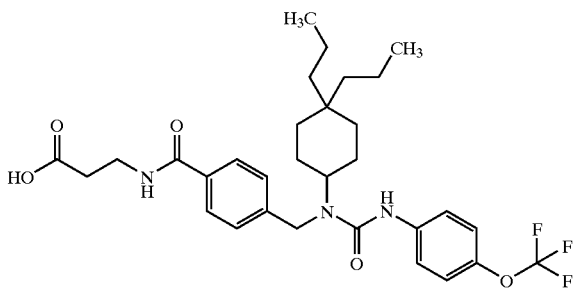

$^1$H NMR (300 MHz, DMSO-d$_6$): δ 8.55 (s, 1H); 8.45 (t, 1H); 7.75 (d, 2H); 7.52 (d, 2H); 7.30 (d, 2H); 7.20 (d, 2H); 4.62 (s, 2H); 4.05 (t, 1H); 3.45 (q, 2H); 2.45 (t, 2H); 1.70–0.70 (m, 22H).

HPLC-MS (method B): m/z=592, R$_t$=8.60 min.

The compounds of the invention can also be prepared by conventional solution phase synthesis methods as described below:

EXAMPLE 89

3-{4-[1-(1,4-Dioxaspiro[4.5]dec-8-yl)-3-(4-trifluoromethoxyphenyl)ureidomethyl]benzoylamino}propionic acid

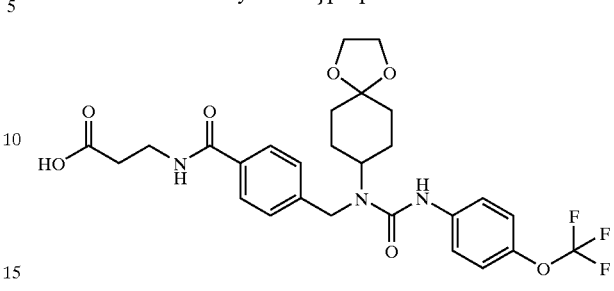

Ethyl 3-(4-aminomethylbenzoylamino)propanoate hydrochloride was prepared from β-alanine ethyl ester hydrochloride and 4-(tert-butoxycarbonylaminomethyl)benzoic acid by methods known to those skilled in the art.

3-{4-[(1,4-Dioxaspiro[4.5]dec-8-ylamino)methyl]benzoylamino}propionic acid ethyl ester 1.2 g Ethyl 3-(4-aminomethylbenzoylamino)propanoate hydrochloride (4.18 mmol) was mixed with 20 mL 1,2-dichloroethane and 6 mL saturated K$_2$CO$_3$ by vigorous stirring. The phases were separated and the aqueous phase was extracted with another 20 mL 1,2-dichloroethane. 240 μL HOAc was added to the combined 1,2-dichloroethane phase followed by 0.691 g 1,4-dioxaspiro[4.5]decan-8-one (4.42 mmol). 1.272 g NaBH(OAc)$_3$ (6 mmol) was added and the reaction was stirred for 16 hours at 25° C. The reaction volume was reduced on a rotary evaporator to about 20 mL and then poured into a mixture of 60 mL H$_2$O and 10 mL sat. K$_2$CO$_3$. The phases were separated and the aqueous phase was extracted twice with 40 mL 1,2-dichloroethane. The combined 1,2-dichloroethane fractions were dried over MgSO$_4$ and evaporated to afford the title compound. The crude product was used in the next step without further purification.

3-{4-[1-(1,4-Dioxaspiro[4.5]dec-8-yl)-3-(4-trifluoromethoxyphenyl)ureidomethyl]benzoylamino}propionic acid ethyl ester 0.312 g 4-Trifluoromethoxyphenylisocyanate dissolved in 1 mL acetonitrile was added to 0.5 g of the above 3-{4-[(1,4-dioxaspiro[4.5]dec-8-ylamino)methyl]benzoylamino}propionic acid ethyl ester dissolved in 5 mL acetonitrile and was allowed to react at 25° C. The product precipitated after 1 hour and was collected by filtration.

$^1$H NMR (400 MHz), (DMSO-d$_6$): δ 8.55 (s, 1H); 8.50 (t, 1H); 7.75 (d, 2H); 7.50 (d, 2H); 7.30 (d, 2H); 7.20 (d, 2H); 4.60 (s, 2H); 4.20 (s br, 1H); 4.05 (q, 2H); 3.75 (s, 4H); 3.30 (m, 2H); 2.60 (t, 2H); 1.60–1.70 (m, 8H); 1.15 (t, 3H)

3-{4-[1-(1,4-Dioxaspiro[4.5]dec-8-yl)-3-(4-trifluoromethoxyphenyl)ureidomethyl]benzoylamino}propionic acid 180 mg LiOH dissolved in 2.2 mL H$_2$O was added to the entire yield of the above 3-{4-[1-(1,4-dioxaspiro[4.5]dec-8-yl)-3-(4-trifluoromethoxyphenyl)ureidomethyl]benzoylamino}propionic acid ethyl ester dissolved in 22 mL abs. EtOH. After 1 hour at 25° C. the solvent was evaporated and 10 mL H$_2$O followed by 500 mg citric acid dissolved in 20 mL H$_2$O was added to the residue affording a pH of 4–5. The resulting product was a mixture of the acid and its lithium salt.

$^1$H NMR (400 MHz), (DMSO-d$_6$+TFA): δ 8.60 (s, 1H); 8.50 (t, 1H); 7.80 (d, 2H); 7.55 (d, 2H); 7.30 (d, 2H); 7.20 (d, 2H); 4.60 (s, 2H); 4.20 (s br, 1H); 3.80 (s, 4H); 3.45 (m, 2H); 2.50 (t, 2H); 1.55–1.75 (m, 8H).

HPLC-MS (method B) (m/z=566 M+1), (R$_t$=6.10 min).

General Procedure (E) for the Solid Phase Synthesis of Compounds of the General Formula (Ic)

Compounds of the general formula (Ic) according to the invention can be synthesized on solid support using a procedure comprising attachment of acrylic acid to a polystyrene 2-chlorotritylchloride resin followed by a Michael addition of R$^7$—NH$_2$. Acylation followed by reductive amination and urea formation as described above affords the desired compounds:

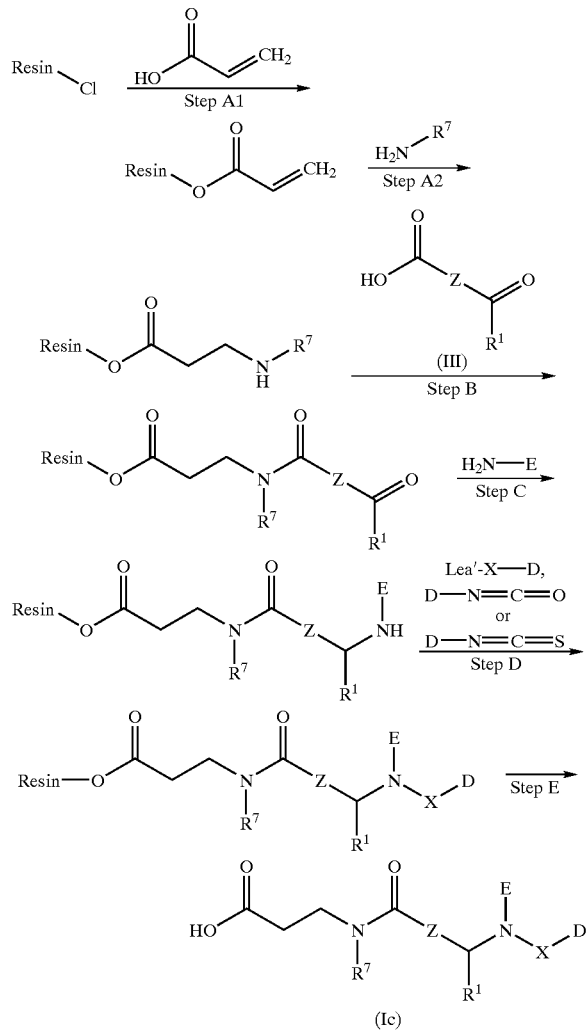

wherein

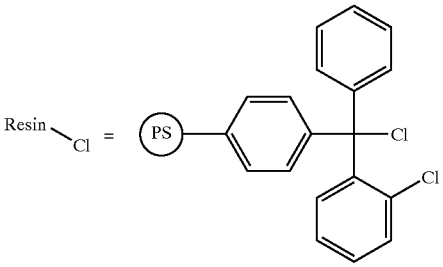

wherein PS is polystyrene

Lea' is a leaving group such as —OSu, chloro, phenoxy or 4-nitrophenoxy,

R$^1$, E and D are as defined for formula (I),

R$^7$ is C$_{1-6}$-alkyl or C$_{3-8}$-cycloalkyl-C$_{1-6}$-alkyl, and

X is —S(O)$_2$—(CH$_2$)$_r$—, —C(O)NH— or —C(S)NH—, wherein r is as defined for formula (I).

Step A1:

The reaction is known (The combinatorial index, Ed. Bunin, B. A. 1998, Academic Press, p. 24) and is generally performed by shaking a suspension of the resin with a solution of acrylic acid in the presence of a base such as triethylamine, diisopropylethylamine, dicyclohexylmethylamine or any other tertiary amine. Typical solvents are pyridine, dichloromethane, 1,2-dichloroethane, DMF, NMP, THF, DMSO or mixtures of two or more of these. The reaction is performed between 20° C. and 120° C., preferably at 25° C. Excess reagents are filtered off and the resin is washed with any solvent mentioned above including mixtures hereof, containing a base as mentioned above and an alcohol, typically methanol, as a scavenger of unreacted resin bound 2-chlorotritylchloride.

Step A2:

The reaction is known (Hamper, B. C.; Kolodziej, S. A.; Scates, A. M.; Smith, R. G.; Cortez, E. *J. Org. Chem.* 1998, 63, 703–718) and is performed by shaking the resin bound acrylic acid with an excess of a primary amine in a solvent such as DMSO, DMF, NMP, THF, methanol, ethanol, dichloromethane, 1,2-dichloroethane or a mixture of two or more of these. The reaction is carried out between 20° C. and 120° C., preferably at 25° C. Excess amine is filtered of and the resin is washed several times with the solvent used during the reaction.

Step B:

The reaction is known (The combinatorial index, Ed. Bunin, B. A. 1998, Academic Press, p. 78) and is performed by adding an excess of acid (III) in a solvent such as DMF, NMP, THF, dichloromethane, 1,2-dichloroethane, acetonitrile, DMSO or a mixture of the above, optionally in the presence of a base such as N-methylmorpholine, triethylamine, diisopropylethylamine, dicyclohexylmethylamine or another tertiary amine, followed by a coupling reagent such as dicyclohexylcarbodiimide, diisopropylcarbodiimide, 1,1'-carbonyldiimidazole, 2-(1H-9-azabenzotriazol-1-yl)-1,1,3,3-tetramethyluronium hexafluorophosphate or bromo-tris-pyrrolidinophosphonium hexafluorophosphate in a solvent such as DMF, NMP, THF, dichloromethane, 1,2-dichloroethane, acetonitrile, DMSO or a mixture of two or more of these optionally in the presence of a side reaction inhibitor such as 3-hydroxy-4-oxo-3,4-dihydro-1,2,3- benzotriazine, N-hydroxybenzotriazole or 1-hydroxy-7-azabenzotriazol. The reaction is performed between 20° C. and 40° C., preferably at 25° C. Excess of reagents is filtered off and the resin is washed several times with the solvent used in the reaction.

Step C:

The reaction is generally known (The combinatorial index, Ed. Bunin, B. A. 1998, Academic Press, p. 133) and is generally performed by stirring the resin bound aldehyde or ketone obtained in step B with an excess of amine at low pH (by addition of an acid, such as acetic acid or formic acid) in a solvent such as THF, DMF, NMP, methanol, ethanol, DMSO, dichloromethane, 1,2-dichloroethane, trimethyl orthoformate, triethyl orthoformate, or a mixture of two or more of these. A reducing agent such as sodium cyanoborohydride can be used. The reaction is performed between 20° C. and 120° C., preferably at 25° C. Excess of reagents is filtered off and the resin is washed several times with the solvent used in the reaction optionally in combination with water.

Step D:

The reaction is generally known (Matthews, J.; Rivero, R. A. *J. Org. Chem.* 1997, 62, 6090–6092) and is usually performed by shaking resin bound amine obtained in step C with an excess of an isocyanate or isothiocyanate or alternatively Lea'-X-D in a solvent such as DMF, NMP, THF, dichloromethane, 1,2-dichloroethane, DMSO or a mixture of two or more of the above and when using Lea'-X-D in the presence of a base such as triethylamine, diisopropylethylamine, dicyclohexylmethylamine or any other tertiary amine or potassium carbonate. The reaction is performed between 20° C. and 120° C., preferably between 20° C. and 40° C. Excess of reagent is filtered off and the resin is washed several times with the solvent used in the reaction.

Step E:

The reaction is known (The combinatorial index, Ed. Bunin B. A., 1998, Academic press, p. 21) and is generally performed by stirring the resin bound intermediate obtained in step D with a 5–95% solution of TFA. The final cleavage is carried out in a solvent such as THF, dichloromethane, 1,2-dichloroethane, 1,3-dichloropropanee, toluene or a mixture of two or more of these. The reaction is performed between 0° C. and 80° C., preferably between 20° C. and 40° C. When the reaction is complete the product is removed by filtration. The resin is successively washed with the solvent used in the reaction, optionally containing TFA. The product and washings are collected. The solvent is removed in vacuo.

The following examples were prepared according to general procedure (E).

EXAMPLE 90

General Procedure (E)

3-({4-[1-(4-tert-Butylcyclohexyl)-3-(4-trifluoromethoxyphenyl)ureidomethyl]benzoyl}cyclopropylmethyl)aminopropionic acid

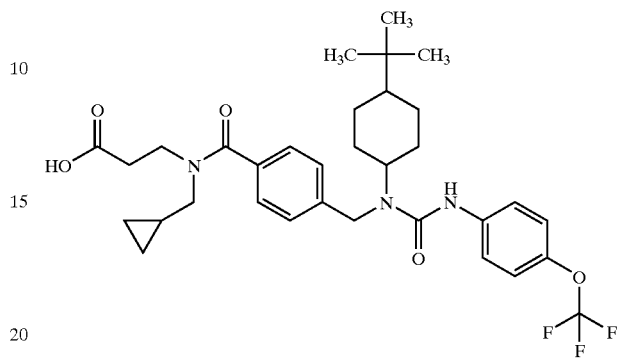

Step A1: Resin bound acrylic acid

150 μmol acrylic acid was dissolved in a mixture of 500 μL dichloromethane and 100 μL diisopropylethylamine and added to 50 mg polystyrene resin functionalized with a 2-chlorotrityl chloride linker. After shaking the suspension for 4 hours at 25° C., the resin was isolated by filtration and washed with 2×1 mL dichloromethane:methanol:diisopropylethylamine 17:2:1 and 2×1 mL DMSO.

Step A2: Resin bound N-(cyclopropylmethyl)-3-aminopropionic acid

The above resin bound acrylic acid (50 mg) was treated with 300 μmol cyclopropylmethyl amine (21.3 mg) in 300 μL DMSO for 72 hours at 25° C. The excess reagent was filtered off and the resin was washed with 3×1 mL DMSO and 3×1 mL DMF.

Step B: Resin bound 3-[cyclopropylmethyl-(4-formylbenzoyl)amino]propionic acid

To the above resin bound N-(cyclopropylmethyl)-3-aminopropionic acid (50 mg) was added 200 μmol 4-formylbenzoic acid (30 mg) dissolved in a mixture of 430 μL DMF and 70 μL diisopropylethylamine followed by 200 μmol bromo-tris-pyrrolidinophosphonium hexafluorophosphate (PyBrOP, 93 mg) dissolved in 500 μL DMF. The mixture was shaken at 25° C. for 4 hours followed by filtration and washing of the resin with 3×1 mL DMF and 1 mL trimethylorthoformate.

Step C: Resin bound 3-({4-[(4-tert-butylcyclohexylamino)methyl]benzoyl}cyclopropylmethylamino)propionic acid The above resin bound 3-[cyclopropylmethyl-(4-formylbenzoyl)amino]propionic acid (50 mg) was treated with 1 mL 0.5 M (0.5 mmol, 77.5 mg) 4-tert-butylcyclohexylamine solution in DMF:trimethylorthoformate 1:1, 100 μL glacial acetic acid and sodium cyanoborohydride (750 μmol, 48 mg) suspended in 0.5 mL DMF:trimethylorthoformate 1:1. Overnight shaking at 25° C. followed by filtration and washing with 2×1 mL 20% H₂O in DMF, 3×1 mL DMF and 2×1 mL dichloromethane afforded the desired product.

Step D: Resin bound 3-({4-[1-(4-tert-butylcyclohexyl)-3-(4-trifluoromethoxyphenyl)ureidomethyl]benzoyl}cyclopropylmethyl)aminopropionic acid 200 μmol 4-trifluoromethoxyphenylisocyanate dissolved in 500 μL dichloromethane was added to the above resin bound 3-({4-[(4-tert-butylcyclohexylamino)methyl]benzoyl}cyclopropylmethyl)aminopropionic acid (50 mg).

Shaking the mixture 5 hours at 25° C. followed by filtration and washing of the resin with 2×1 mL dichloromethane, 4×1 mL DMF, 2×1 mL H₂O, 3×1 mL THF and 3×1 mL dichloromethane afforded the resin bound title compound.

Step E: 3-({4-[1-(4-tert-butylcyclohexyl)-3-(4-trifluoromethoxyphenyl)ureidomethyl]benzoyl}cyclopropylmethyl)aminopropionic acid The above resin bound 3-({4-[1-(4-tert-butylcyclohexyl)-3-(4-trifluoromethoxyphenyl)ureidomethyl]benzoyl}cyclopropylmethyl)aminopropionic acid (50 mg) was treated with 1 mL 5% TFA in dichloromethane for 1 hour at 25° C. The product was filtered off and the resin was washed with 1 mL dichloromethane. The combined extracts were concentrated in vacuo. The residue was dissolved in 50 μL DMSO+500 μL acetonitrile and purified by preparative HPLC using a Supelcosil ABZ+25 cm×10 mm 5μ column. The starting eluent composition was 5% acetonitrile in water changing over 30 min to 90% acetonitrile in water which was then kept constant for 5 min before going back to the starting composition over 10 min. The flow rate was kept constant at 8 mL/min collecting one fraction per minute. The process was monitored using an UV detector operating at 214 nm. The fractions containing the desired product were combined and evaporated in vacuo to afford the title compound.

The product was characterized by HPLC-MS (Method B): $R_t$=7.91 min, m/z=618 (M+1).

EXAMPLE 91

General Procedure (E)

3-({4-[1-(4-tert-Butylcyclohexyl)-3-(4-trifluoromethoxyphenyl)ureidomethyl]benzoyl}ethylamino)propionic acid

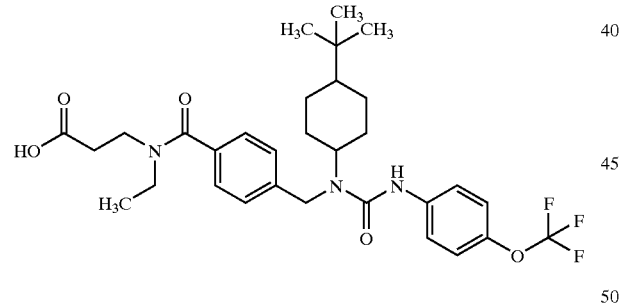

The product was characterized by HPLC-MS (Method B): $R_t$=7.94 min, m/z=592 (M+1).

The compounds of the invention can also be prepared by conventional solution phase synthesis methods as the following general method describes.

General Procedure (F) for the Solution Phase Synthesis of Compounds of General Formula (Id)

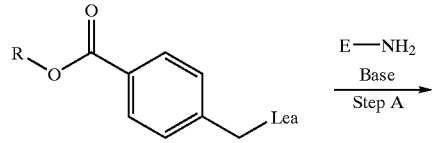

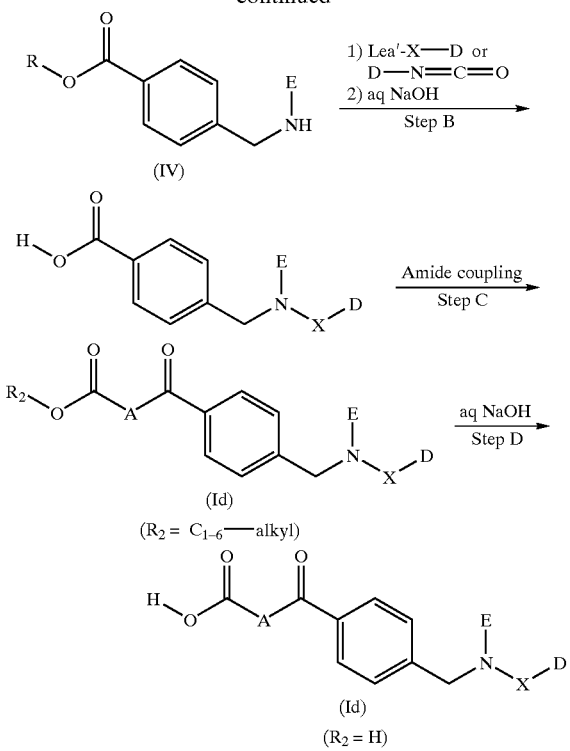

wherein R is $C_{1-6}$-alkyl,
A, X, D, and E are as defined in general formula (I),
Lea is a leaving group such as chloro, bromo, iodo, mesyl, or tosyl, and
Lea' is a leaving group such as —OSu, chloro, phenoxy, or 4-nitrophenoxy.

In case the intermediate of the formula (IV) is a mixture of isomers, separation of these may be performed eg by column chromatography of the intermediate of the formula (IV) or crystallisation of the intermediate imine.

The procedure is illustrated in example 92.

EXAMPLE 92

General Procedure (F)

3-{4-[1-(4-trans-tert-Butylcyclohexyl)-3-(4-trifluoromethoxyphenyl)ureidomethyl]benzoylamino}propionic acid

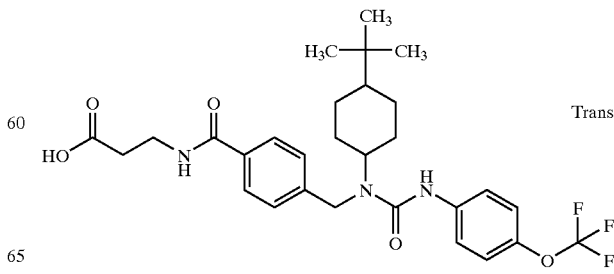

Step A: 4-[(4-tert-Butylcyclohexylamino)methyl]benzoic acid methyl ester

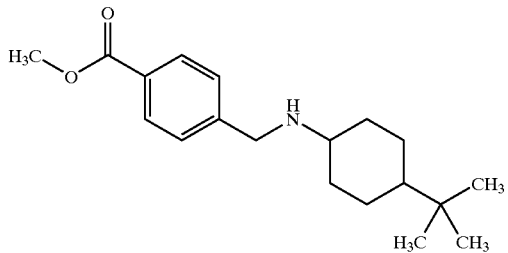

4-(Bromomethyl)benzoic acid methyl ester (5.0 g, 22 mmol) and 4-tert-butylcyclohexylamine (cis/trans mixture) (3.4 g, 22 mmol) were dissolved in DMF where after potassium carbonate (6.1 g, 44 mmol) was added. The reaction mixture was stirred at 100° C. for 7 hours and for 16 hours at 20° C. Water (100 mL) and ethyl acetate (200 mL) were added to the reaction mixture. The organic phase was isolated and washed with water (2×100 mL) and a saturated solution of sodium chloride (2×100 mL). The organic phase was dried (MgSO$_4$), filtered and concentrated in vacuo to give a cis/trans mixture of 4-[(4-tert-butylcyclohexylamino)methyl]benzoic acid methyl ester as a crude product. The two isomers were separated on silica (110 g) using a mixture of ethyl acetate and dichloromethane (7:3) as eluent.

trans isomer:
Micro analysis: Calculated for $C_{19}H_{29}NO_2$: C: 75.21, H: 9.63, N: 4.62%. Found: C: 75.02, H: 9.80, N: 4.64%.
HPLC-MS (Method B): $R_t$=5.23 min, m/z=304 (M+1).
$^1$H NMR (DMSO-d$_6$), 400 MHz: δ 7.90 (d, 2H), 7.48 (d, 2H), 3.82 (s, 3H), 3.78 (s, 2H), 2.30–2.20 (m, 1H), 2.05–1.90 (m, 3H), 1.73–1.65 (m, 2H), 1.10–0.90 (m, 4H), 0.8 (s, 9H).

cis isomer:
HPLC-MS (Method B): $R_t$=4.83 min, m/z=304 (M+1).
$^1$H NMR (DMSO-d$_6$), 400 MHz: δ 7.92 (d, 2H), 7.58 (d, 2H), 3.90 (dd, 1H), 3.85 (s, 3H), 3.80 (dd, 1H), 2.50–2.35 (m, 1H), 2.00–1.85 (m, 2H), 1.80–1.70 (m, 2H), 1.70–1.45 (m, 2H), 1.00–0.80 (m, 1H), 0.80 (s, 9H).

Step B: 4-[1-(trans-4-tert-Butylcyclohexyl)-3-(4-trifluoromethoxyphenyl)ureidomethyl]benzoic acid

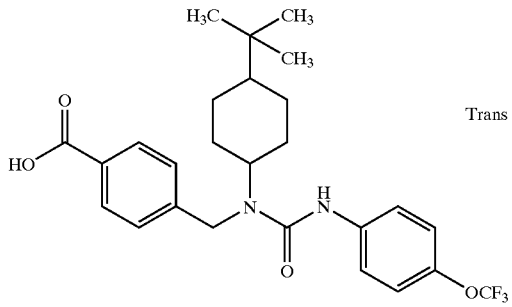

4-[(trans-4-tert-Butylcyclohexylamino)methyl]benzoic acid methyl ester (2.6 g, 8.6 mmol) and 4-(trifluoromethoxy)phenyl isocyanate (1.7 g, 8.6 mmol) were dissolved in acetonitrile (40 mL) and stirred at 20° C. for 16 hours. The reaction mixture was concentrated in vacuo and the crude product purified on silica (100 g) using heptane and ethyl acetate (3:1) as eluent to give 4-[1-(trans-4-tert-butylcyclohexyl)-3-(4-trifluoromethoxyphenyl)ureidomethyl]benzoic acid methyl ester. The product was suspended in ethanol (80 mL) and sodium hydroxide (4N, 17 mL) was added. The reaction mixture was stirred at 50° C. for 3 hours and then concentrated in vacuo until all ethanol was removed. The reaction mixture was diluted with water (100 mL) and adjusted to pH 2 with hydrochloric acid (4N). The aqueous phase was extracted with ethyl acetate (3×75 mL) and the combined organic phases were dried (MgSO$_4$) and concentrated in vacuo to give 4-[1-(trans-4-tert-butylcyclohexyl)-3-(4-trifluoromethoxyphenyl)ureidomethyl]benzoic acid.

$^1$H NMR (DMSO-d$_6$), 400 MHz: δ 12.80 (s, 1H), 8.55 (s, 1H), 7.90 (d, 2H), 7.55 (d, 2H), 7.35 (d, 2H), 7.21 (d, 2H), 4.62 (s, 2H), 4.10–4.00 (m, 1H), 2.00 (s, 2H), 1.80–1.60 (m, 4H), 1.48–1.38 (m, 2H), 1.20–1.00 (m, 2H), 1.00–0.88 (m, 1H), 0.80 (s, 9H).
HPLC-MS (Method B): $R_t$=8.37 min, m/z=493 (M+1).

Step C: 3-{4-[1-(trans-4-tert-Butylcyclohexyl)-3-(4-trifluoromethoxyphenyl)ureidomethyl]benzoylamino}propionic acid ethyl ester

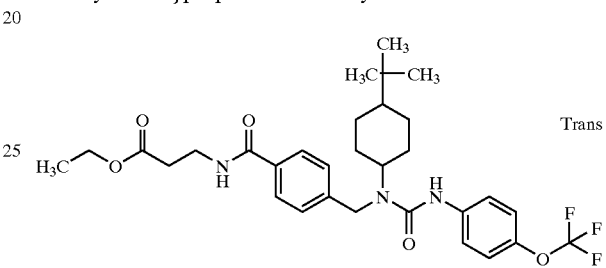

4-[1-(trans-4-tert-Butylcyclohexyl)-3-(4-trifluoromethoxyphenyl)ureidomethyl]benzonic acid (2.0 g, 4.1 mmol), 1-hydroxybenzotriazole (0.6 g, 4.3 mmol) and 1-(3-dimethylaminopropyl)-3-ethylcarbodiimide (0.8 g, 4.3 mmol) were dissolved in DMF (40 mL). A solution of diisopropylethylamine (0.5 g, 4.1 mmol) and 3-aminopropionic acid ethyl ester, hydrochloride (0.4 g, 4.3 mmol) in DMF (10 mL) was added and the reaction mixture was stirred for 16 hours at 20° C. Ethyl acetate (150 mL) and water (100 mL) were added and the organic phase isolated. The aqueous phase was extracted with ethyl acetate (50 mL) and the organic phases combined, dried (MgSO$_4$) and concentrated in vacuo. The crude product was purified on silica (80 g) using heptane and ethyl acetate (1:1) as eluent to give 3-{4-[1-(trans-4-tert-Butylcyclohexyl)-3-(4-trifluoromethoxyphenyl)ureidomethyl]benzoylamino}propionic acid ethyl ester.

M.p.=108–111° C.
$^1$H NMR (DMSO-d$_6$), 400 MHz: δ 8.55 (s, 1H), 8.50 (t, 1H), 7.75 (d, 2H), 7.55 (d, 2H), 7.31 (d, 2H), 7.22 (d, 2H), 4.60 (s, 2H), 4.10–4.00 (m, 1H), 3.60 (s, 3H), 3.45 (dd, 2H), 2.55 (t, 2H), 1.80–1.60 (m, 4H), 1.50–0.80 (m, 5H), 0.80 (s, 9H).
HPLC-MS (Method B): $R_t$=8.43 min, m/z=578 (M+1).

Step D:
3-{4-[1-(trans-4-tert-Butylcyclohexyl)-3-(4-trifluoromethoxyphenyl)ureidomethyl]benzoylamino}propionic acid ethyl ester (1.4 g, 2.4 mmol) was suspended in ethanol (50 mL) and sodium hydroxide (4 N, 6 mL) added. The reaction mixture was stirred for 2 hours at 50° C. and then concentrated in vacuo until all ethanol was removed. The reaction mixture was diluted with water (100 mL) and adjusted to pH 2 with hydrochloric acid (4N), and the title compound was isolated by filtration.

M.p.=152–154° C.
$^1$H NMR (DMSO-d$_6$), 400 MHz: δ 12.20 (s, 1H), 8.55 (s, 1H), 7.95 (t, 1H), 7.75 (d, 2H), 7.55 (d, 2H), 7.31 (d, 2H), 7.22 (d, 2H), 4.60 (s, 2H), 4.10–4.00 (m, 1H), 3.45 (dd, 2H), 2.50 (2H), 1.80–1.60 (m, 4H), 1.45–1.35 (m, 2H), 1.15–1.05 (m, 2H), 0.95–0.85 (m, 1H), 0.80 (s, 9H).

HPLC-MS (Method B): $R_t$=7.88 min, m/z=564 (M+1).

Micro analysis: Calculated for $C_{29}H_{36}F_3N_3O_5$, 0.75$H_2O$: C: 60.35, H: 6.55, N: 7.28%. Found: C: 60.47, H: 6.32, N: 7.32%.

Alternative Method for the Preparation of the Compound (General Procedure (K))

General procedure (K) is described in the following:
Step 6, Using Pure Isocyanate Prepared from (Substituted) Anilines and Diphosgene as Described Under the General Procedure (K):

Methyl trans-4-{(4-tert-butylcyclohexyl)aminomethyl}benzoylaminopropanoate, hydrochloride (10.0 g 24 mmol, prepared by using anhydrous hydrogen chloride in ethyl acetate in general procedure (K), step 5) was suspended in acetonitrile (300 mL) and diisopropylethylamine (4.14 mL, 24 mmol) was added. To this suspension 4-trifluoromethoxyphenylisocyanate (3.75 mL, 24 mmol) was added. Stirring at room temperature was continued for 4 hours and then the mixture was left at 5° C. for 16 hours. Filtration and washing with cold acetonitrile afforded 11.9 g (85%) of 3-{4-[1-(4-trans-tert-butylcyclohexyl)-3-(4-trifluoromethoxyphenyl)ureidomethyl]benzoylamino}propionic acid methyl ester.
Step 7:
Hydrolysis of this ester using the method described in example 46, step D afforded the title compound (11 g, 94%).

EXAMPLE 93

3-{4-[1-(cis-4-tert-Butylcyclohexyl)-3-(4-trifluoromethoxy-phenyl)ureidomethyl]benzoylamino}propionic acid

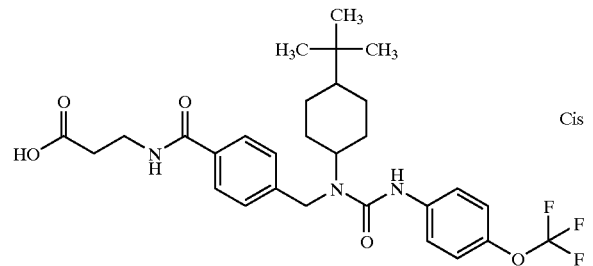

Step A: 4-[1-(cis-4-tert-Butylcyclohexyl)-3-(4-trifluoromethoxyphenyl)ureidomethyl]benzoic acid

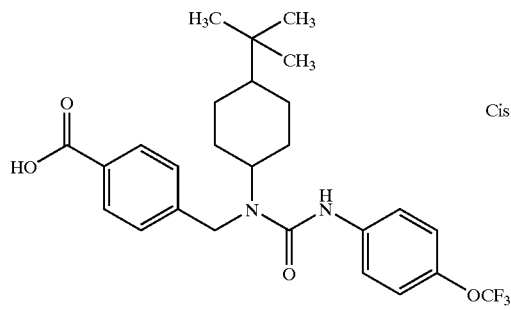

4-[(cis-4-tert-Butylcyclohexylamino)methyl]benzoic acid methyl ester (0.36 g, 1.2 mmol) and 4-(trifluoromethoxy)phenyl isocyanate (0.24 g, 1.2 mmol) were dissolved in acetonitrile (10 mL) and stirred at 20° C. for 16 hours. The reaction mixture was concentrated in vacuo and the crude product purified on silica (25 g) using heptane and ethyl acetate (9:1) as eluent to give 4-[1-(cis-4-tert-butylcyclohexyl)-3-(4-trifluoromethoxyphenyl)ureidomethyl]benzoic acid methyl ester. The product was suspended in ethanol (10 mL) and sodium hydroxide (4N, 1.1 mL) was added. The reaction mixture was stirred at 50° C. for 3 hours and then concentrated in vacuo until all ethanol was removed. The reaction mixture was diluted with water (50 mL) and adjusted to pH 2 with hydrochloric acid (4N). The aqueous phase was extracted with ethyl acetate (75 mL) and the organic phase was dried (MgSO$_4$) and concentrated in vacuo to give 4-[1-(cis-4-tert-butylcyclohexyl)-3-(4-trifluoromethoxyphenyl)ureidomethyl]benzoic acid.

Micro analysis: Calculated for $C_{26}H_{31}F_3N_2O_4$: C: 63.40, H: 6.34, N: 5.69%. Found: C: 63.29, H: 6.33, N: 5.65%.

$^1$H NMR (DMSO-d$_6$), 400 MHz: δ 12.80 (s, 1H), 8.61 (s, 1H), 7.90 (d, 2H), 7.55 (d, 2H), 7.35 (d, 2H), 7.22 (d, 2H), 4.72 (s, 2H), 4.32–4.22 (m, 1H), 1.85–1.70 (m, 2H), 1.65–1.45 (m, 4H), 1.40–1.10 (m, 3H), 0.80 (s, 9H).

HPLC-MS (Method B): $R_t$=7.85 min, m/z=493 (M+1).
Step B: 3-{4-[1-(cis-4-tert-Butylcyclohexyl)-3-(4-trifluoromethoxyphenyl)ureidomethyl]benzoylamino}propionic acid ethyl ester

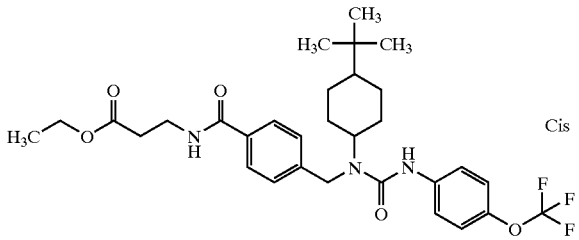

4-[1-(cis-4-tert-Butylcyclohexyl)-3-(4-trifluoromethoxyphenyl)ureidomethyl]benzoic acid (0.3 g, 0.6 mmol), 1-hydroxybenzotriazole (0.1 g, 0.7 mmol) and 1-(3-dimethylaminopropyl)-3-ethylcarbodiimide (0.13 g, 0.7 mmol) were dissolved in DMF (10 mL). Diisopropylethylamine (0.1 g, 0.7 mmol) and 3-aminopropionic acid ethyl ester, hydrochloride (0.07 g, 0.7 mmol) in DMF was added and the reaction mixture was stirred for 16 hours at 20° C. Ethyl acetate (80 mL) and water (50 mL) were added and the organic phase isolated. The aqueous phase was extracted with ethyl acetate (50 mL) and the organic phases combined, dried (MgSO$_4$) and concentrated in vacuo. The residue was crystallised from heptane and ethyl acetate (4:1) to give 3-{4-[1-(cis-4-tert-butylcyclohexyl)-3-(4-trifluoromethoxyphenyl)ureidomethyl]benzoylamino}propionic acid ethyl ester.

M.p.=87–90° C.

$^1$H NMR (DMSO-d$_6$), 400 MHz: δ 8.60 (s, 1H), 8.48 (t, 1H), 7.75 (d, 2H), 7.52 (d, 2H), 7.28 (d, 2H), 7.21 (d, 2H), 4.70 (s, 2H), 4.30–4.20 (m, 1H), 3.60 (s, 3H), 3.48 (dd, 2H), 2.55 (t, 2H), 1.82–1.70 (m, 2H), 1.60–1.45 (m, 4H), 1.40–1.10 (m, 3H), 0.80 (s, 9H).

HPLC-MS (Method B): $R_t$=7.80 min, m/z=578 (M+1).

Micro analysis: Calculated for $C_{30}H_{38}F_3N_3O_5$: C: 62.38, H: 6.63, N:7.27%. Found: C: 62.49, H: 6.75, N:7.20%.
Step C:
3-{4-[1-(cis-4-tert-Butylcyclohexyl)-3-(4-trifluoromethoxyphenyl)ureidomethyl]benzoylamino}propionic acid ethyl ester (0.2 g, 0.3 mmol) was suspended in ethanol (8 mL) and sodium hydroxide (4N, 0.6 mL) added. The reaction mixture was stirred for 16 hours at 20° C. and then concentrated in vacuo until all ethanol was removed. The reaction mixture was diluted with water (50 mL) and adjusted to pH 2 with hydrochloric acid (4N). The aqueous phase was extracted with ethyl acetate (80 mL) and the organic phase was dried (MgSO$_4$) and concentrated in vacuo to give the title compound.

$^1$H NMR (DMSO-d$_6$), 400 MHz: δ 12.20 (s, 1H), 8.60 (s, 1H), 8.45 (t, 1H), 7.77 (d, 2H), 7.53 (d, 2H), 7.28 (d, 2H), 7.20 (d, 2H), 4.70 (s, 2H), 4.30–4.20 (m, 1H), 3.45 (dd, 2H), 2.50 (2H), 1.82–1.70 (m, 2H), 1.60–1.45 (m, 4H), 1.40–1.30 (m, 2H), 1.20–1.10 (m, 1H), 0.80 (s, 9H).

HPLC-MS (Method B): R$_t$=7.32 min, m/z=564 (M+1).

Micro analysis: Calculated for C$_{29}$H$_{36}$F$_3$N$_3$O$_5$, 0.25H$_2$O: C: 61.53, H: 6.54, N: 7.18%. Found: C: 61.36, H: 6.80, N: 7.09%.

The following compounds were prepared using the general procedure (F) as described above.

EXAMPLE 94

General Procedure (F)

1-{4-[1-(trans-4-tert-Butylcyclohexyl)-3-(4-trifluoromethoxyphenyl)ureidomethyl]benzoyl}piperidine-3-carboxylic acid

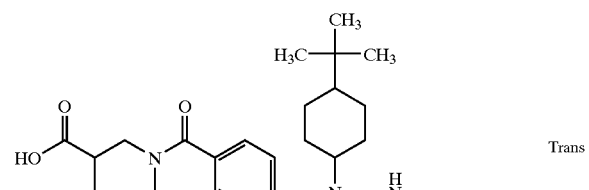

The compound was prepared using nipecotic acid methyl ester, hydrochloride instead of 3-aminopropionic acid methyl ester, hydrochloride in step C.

HPLC-MS (Method B): R$_t$=8.17 min, m/z=604 (M+1).

Micro analysis: Calculated for C$_{32}$H$_{40}$F$_3$N$_3$O$_5$: C: 63.67, H: 6.68, N: 6.96%. Found: C: 63.66, H: 6.75, N: 6.94%.

EXAMPLE 95

General Procedure (F)

3-{4-[1-(trans-4-tert-Butylcyclohexyl)-3-(4-trifluoromethoxyphenyl)ureidomethyl]benzoylamino}acetic acid

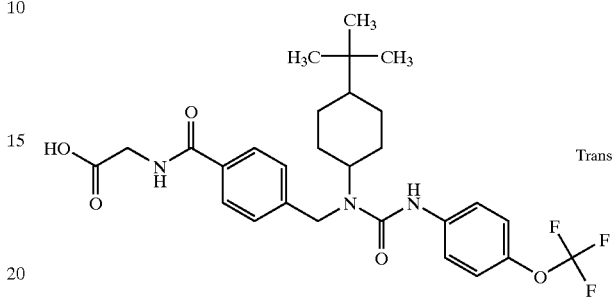

The compound was prepared using glycine methyl ester, hydrochloride instead of 3-aminopropionic acid methyl ester, hydrochloride in step C.

$^1$H NMR (DMSO-d$_6$), 400 MHz: δ 12.55 (s, 1H), 8.76 (t, 1H), 8.52 (s, 1H), 7.81 (d, 2H), 7.55 (d, 2H), 7.33 (d, 2H), 7.22 (d, 2H), 4.61 (s, 2H), 4.10–4.00 (m, 1H), 3.80 (d, 2H), 1.75–1.60 (m, 4H), 1.45–1.30 (m, 2H), 1.20–1.00 (m, 2H), 1.00–0.80 (m, 1H), 0.80 (s, 9H).

HPLC-MS (Method B): R$_t$=7.88 min, m/z=550 (M+1).

EXAMPLE 96

General Procedure (F)

3-{4-[1-(2-Ethylhexyl)-3-(4-trifluoromethoxyphenyl)ureidomethyl]benzoylamino}propionic acid

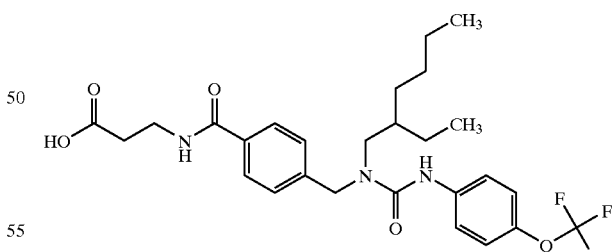

The compound was prepared using 2-ethylhexylamine instead of 4-tert-butylcyclohexylamine in step A.

$^1$H NMR (DMSO-d$_6$), 400 MHz: δ 12.20 (s, 1H), 8.63 (s, 1H), 8.49 (t, 1H), 7.82 (d, 2H), (d, 2H), 7.54 (d, 2H), 7.31 (d, 2H), 7.22 (d, 2H), 4.65 (s, 2H), 3.45 (dd, 2H), 3.25 (m, 2H), 2.50 (2H), 1.70–1.60 (m, 1H), 1.40–1.10 (m, 8H), 0.90–0.70 (m, 6H).

HPLC-MS (Method B): $R_t$=7.17 and 7.25 min, m/z=538 (M+1).

Micro analysis: Calculated for $C_{27}H_{34}F_3N_3O_5$: C: 60.33, H: 6.37, N: 7.82%. Found: C: 60.51, H: 6.60, N: 7.48%.

EXAMPLE 97

3-{4-[1-(trans-4-(4-Trifluoromethoxyphenylcarbamoyloxy)cyclohexyl)-3-(4-trifluoromethoxyphenyl)ureidomethyl]benzoylamino}propionic acid

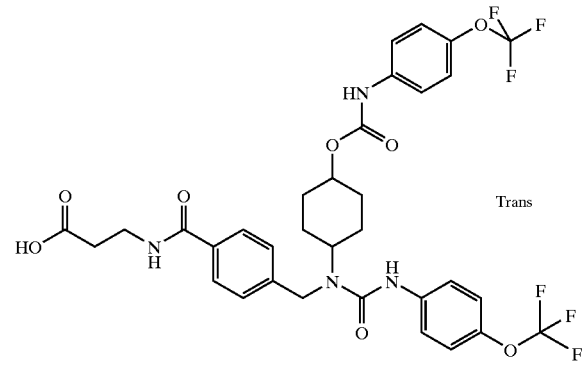

This compound was prepared on solid support using the same methodology as described in general procedure (F) using trans 4-hydroxycyclohexylamine instead of 4-tert-butylcyclohexylamine.

HPLC-MS (Method B): $R_t$=7.68 min, m/z=727 (M+1).

Micro analysis: Calculated for $C_{33}H_{32}F_3N_4O_8$: C: 54.55, H: 4.44, N: 7.71%. Found: C: 54.17, H: 4.53, N: 7.44%.

EXAMPLE 98

General Procedure (F)

3-{4-[1-(trans-4-tert-Butylcyclohexyl)-3-(4-trifluoromethoxyphenyl)ureidomethyl]benzoylamino}propionic acid methyl ester

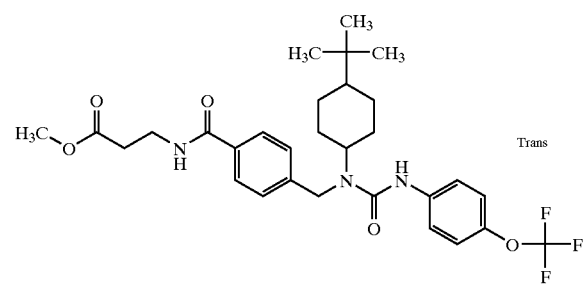

The compound was prepared according to procedure (F) but omitting step D.

Micro analysis: Calculated for $C_{29}H_{36}F_3N_3O_5 \cdot 0.1H_2O$: C, 61.87%; H, 6.44%; N, 7.46%. Found: C, 61.60%; H, 6.45%; N, 7.43%.

HPLC-MS (Method B): m/z: 564.

EXAMPLE 99

General Procedure (F)

3-{4-[1-(4-tert-Butylcyclohexyl)-3-(4-cyanophenyl)ureidomethyl]benzoylamino}propionic acid

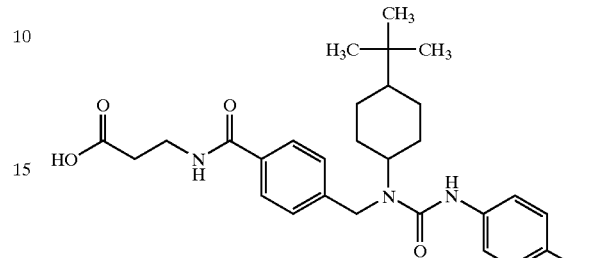

$^1$H NMR (DMSO-$d_6$): δ 12.2 (1H, broad), 8.82 (1H, s), 8.48 (1H, t), 7.78 (2H, d), 7.68 (4H, s), 7.32 (2H, d), 4.62 (2H, s), 4.05 (1H, m), 3.42 (2H, dd), 1.80–85 (9H, m), 0.80 (9H, s).

HPLC-MS (method B): m/z: 505, $R_t$=7.28 min.

EXAMPLE 100

General Procedure (F)

3-{4-[3-(3,5-Bis-trifluoromethylphenyl)-1-(trans-4-tert-butylcyclohexyl)ureidomethyl]benzoylamino}propionic acid

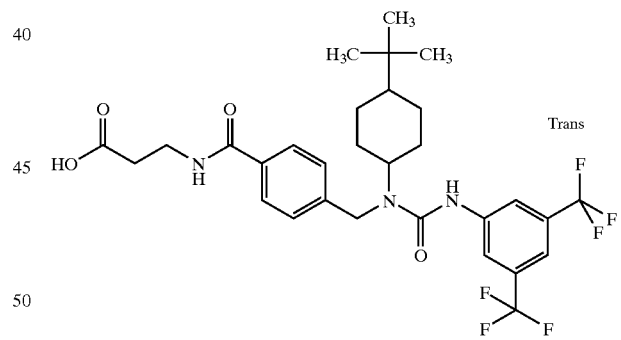

The starting material, 4-[(trans-4-tert-butylcyclohexylamino)methylbenzoic acid methyl ester, was prepared as described in step A of the general procedure (F).

$^1$H NMR (DMSO-$d_6$): δ 12.2 (s, 1H), 9.05 (s, 1H), 8.45 (t, 1H), 8.25 (s, 2H), 7.76 (d, 2H), 7.61 (s, 1H), 7.32 (d, 2H), 4.63 (s, 2H), 4.05 (m, 1H), 3.45 (m, 2H), 1.80–0.75 (m, 9H), 0.82 (s, 9H).

HPLC-MS (method B): m/z: 616, $R_t$=8.3 min.

MA: calculated for $C_{30}H_{35}F_6N_3O_4$: 58.53% C; 5.73% H; 6.83% N; Found 58.25% C; 5.75% H; 7.02% N.

General Procedure (G) for the Solution Phase Synthesis of Compounds of the General Formula (Ie)

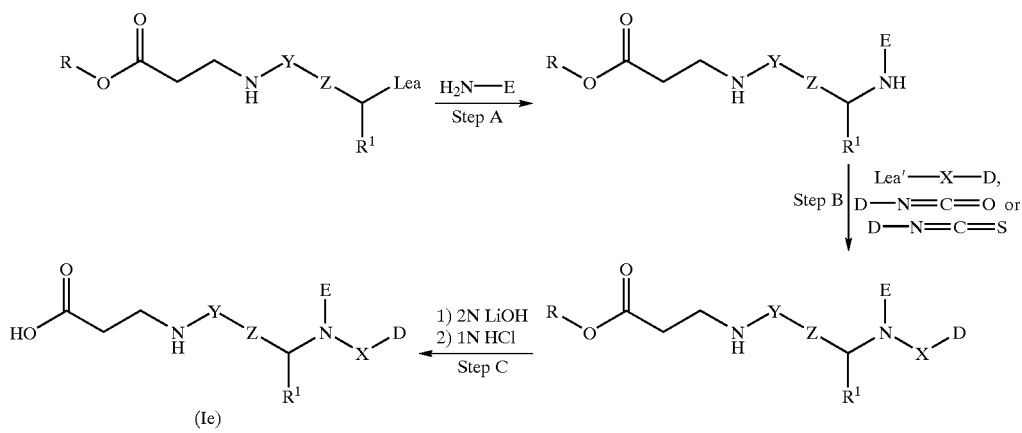

(Ie)

wherein
R¹, E, Z and D are as defined for formula (I),
X is —S(O)$_2$—(CH$_2$)$_r$—, —C(O)NH— or —C(S)NH—, wherein r is as defined for formula (I),
Y is —C(O)— or —S(O)$_2$—,
R is C$_{1-6}$-alkyl,
Lea is a leaving group such as chloro, bromo, iodo, mesyl or tosyl, and
Lea' is a leaving group such as —OSu, chloro, phenoxy, 4-nitrophenoxy.

Step A:

The appropriate alkylhalide (0.02 mmol) in DMF was dispensed into the wells of a deepwell plate containing solid potassium carbonate (3 equivalents) and the appropriate amine, NH$_2$-E, (0.02 mmol). The reactions were agitated at room temperature for four hours and at 50° C. for 12 hours. The solids were filtered off and the desired amines were used without further purification in the next step.

Step B:

To the amines in DMF was added the desired isocyanate or isothiocyanate or alternatively Lea'-X-D (0.02 mmol) in DMF. When using Lea'-X-D a base such as triethylamine, diisopropylethylamine, dicyclohexylmethylamine or any tertiary amine or potassium carbonate was also added. The reactions are shaken for 30 minutes to give the desired ureas or thioureas.

Step C:

To the crude products obtained in step B was added aqueous 2 N LiOH (10 equivalents). The samples were shaken overnight and filtered. Aqueous 1 N HCl was then added to give the desired carboxylic acids.

General Preparation of Halomethylarylcarboxamides as Starting Materials

The halomethylarylcarboxamides were prepared from the coupling of the corresponding halomethylarylcarboxylic acid and the methyl or ethyl-3-aminopropionate hydrochloride according to the procedure described below.

To a solution of the arylcarboxylic acid in a suitable solvent such as CH$_2$Cl$_2$, DMF or THF was added diisopropylethylamine (3 eq) and HBTU (1.1 eq). The reaction was allowed to stir for 30 minutes before ethyl or methyl-3-aminopropionate hydrochloride (1.1 eq) was added. The solution was stirred at room temperature for 4 hours. The solvents were evaporated under reduced pressure. The residue was taken up in ethyl acetate and 1N HCl. The organic layer was separated and washed with H$_2$O (2×), aqueous NaHCO$_3$ (3×), brine (2×), dried over MgSO$_4$ and concentrated to give the desired product.

Ethyl 3-{[4-(chloromethyl)benzoyl]amino}propionate

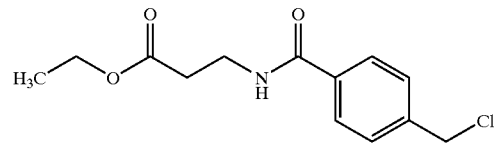

¹H NMR (DMSO-d$_6$): δ 1.2 (t, 3H), 2.6 (t, 2H), 3.5 (qt, 2H), 4.1 (qt, 2H), 4.8 (s, 2H), 7.6 (d, 2H), 7.8 (d, 2H), 8.6 (t, 1H).

Ethyl 3-{[3-(chloromethyl)benzoyl]amino}propionate

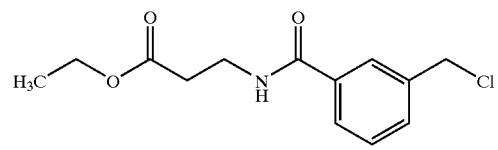

¹H NMR (DMSO-d$_6$): δ 2.61 (t, 2H), 3.50 (qt, 2H), 3.61 (s, 3H), 4.81 (s, 2H), 7.47 (t, 1H), 7.59 (d, 1H), 7.79 (d, 1H), 7.90 (s, 1H), 8.62 (brd t, 1H).

Ethyl 3-({[4-(bromomethyl)phenyl]sulfonyl}amino)propionate

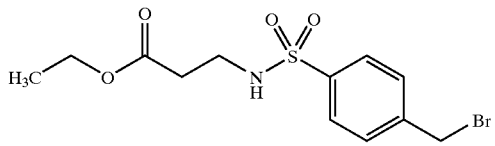

To a solution of the 4-bromomethylphenylsulfonylchloride (10 g, 37 mmol) in CH$_2$Cl$_2$ (200 mL) at 0° C. was added diisopropylethylamine (16 mL, 93 mmol) followed by ethyl-3-aminopropionate hydrochloride (5.1 g, 37 mmol)). The reaction was stirred for 10 minutes at 0° C. and the solvent was evaporated at room temperature under reduced pressure. The residue was dissolved in ethyl acetate and washed with 1N HCl (3×), H$_2$O, aqueous NaHCO$_3$ (3×), brine (3×) and dried over MgSO$_4$. The solvent was concentrated to give a syrup. Addition of ethyl ether induced crystallization of the product as a white solid (10 g, 30 mmol, 81%).

$^1$H NMR (CDCl$_3$): δ 1.24 (t, 3H), 2.55 (t, 2H), 3.22 (qt, 2H), 4.13 (qt, 2H), 4.50 (s, 2H), 5.28 (t, 1H), 7.53 (d, 2H), 7.85 (d, 2H).

Ethyl 3-({[5-(bromomethyl)-2-thienyl]carbonyl}amino)propionate

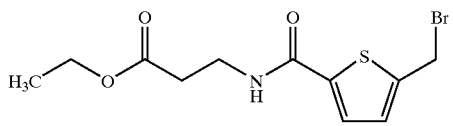

To a solution of methylthiophene carboxylic acid (20 g, 0.14 mol) in DMF (30 mL) was added at 0° C. carbonyldiimidazole (23 g, 0.14 mol) in portions of 10 g. After stirring at 0° C. for 1 hour, a solution of ethyl 3-aminopropionate hydrochloride (21 g, 0.14 mol) in DMF (30 mL) was added followed by triethylamine (20 mL, 0.14 mol). The mixture was stirred at ambient temperature for 16 hours, filtered by suction, and the filtrate was concentrated. The residue was dissolved in ethyl acetate (100 mL), washed with water (2×50 mL), 1N hydrochloric acid (2×50 mL), sodium bicarbonate solution (2×50 mL), brine (50 mL), dried (MgSO$_4$), and concentrated. Addition of hexane to the residue induced the crystallization of ethyl 3-({[(5-methyl-2-thienyl)carbonyl]amino}propionate (27 g, 80%).

$^1$H NMR (CDCl$_3$): δ 1.28 (t, 3H), 2.50 (s, 3H), 2.62 (t, 2H), 3.68 (q, 2H), 4.17 (q, 2H), 6.60 (brd s, 1H), 6.66 (d, 1H), 7.30 (d, 1H).

The above product (27 g, 0.11 mol) was dissolved in carbon tetrachloride (150 mL). N-bromosuccinimide (21 g, 0.12 mol) and AIBN (200 mg) was added. The mixture was refluxed for 5 hours, and filtered by suction. The solid was extracted with ethyl acetate until the filtrate appeared colourless. The combined ethyl acetate extracts (200 mL) were washed with water (2×50 mL), dried over MgSO$_4$ and concentrated. The residue was recrystallized from hexane, ethyl acetate 1:1 to give ethyl 3-({[5-(bromomethyl)-2-thienyl]carbonyl}amino)propionate as a white solid (15 g, 41%).

$^1$H NMR (CDCl$_3$): δ 1.28 (t, 3H), 2.63 (t, 2H), 3.69 (t, 2H), 4.18 (q, 2H), 4.68 (s, 2H), 7.06 (brd s, 1H), 7.07 (d, 1H), 7.32 (d, 1H).

MS (APCl, neg.): 320, 318.

The following examples were prepared according to the general procedure (G).

EXAMPLE 101

General Procedure (G)

3-{4-[1-(4-tert-Butylcyclohexyl)-3-(4-trifluoromethylsulfanylphenyl)ureidomethyl]benzoylamino)propionic acid

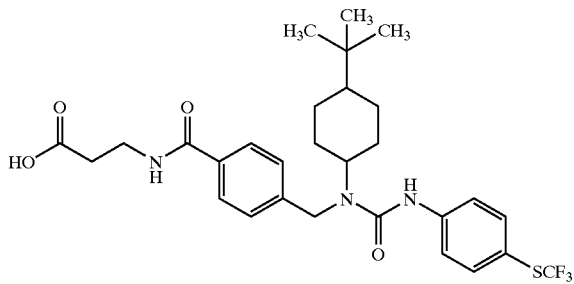

$^1$H NMR (Acetone-d$_6$): δ 0.83 (s, 9H), 0.98 (m, 1H), 1.13–1.20 (q, 2H), 1.50–1.57 (q, 2H), 2.05 (brd s, 4H), 2.52 (t, 2H), 3.15 (q, 2H), 4.17 (qt, 1H), 4.76 (s, 2H), 6.70 (brd s, 1H), 7.54 (d, 2H), 7.56 (d, 2H), 7.66 (d, 2H), 7.83 (d, 2H), 8.19 (s, 1H).

EXAMPLE 102

General Procedure (G)

3-{4-[1-(4-tert-Butylcyclohexyl)-3-naphthalen-2-ylureidomethyl]benzoylamino)propionic acid

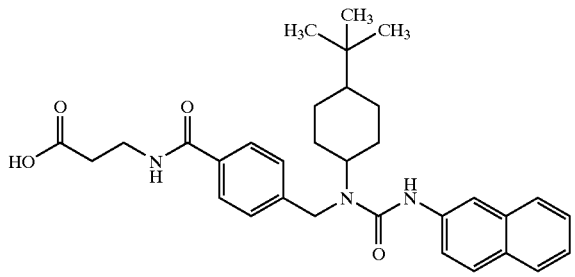

$^1$H NMR (DMSO-d$_6$): δ 0.83 (s, 9H), 0.91 (m, 1H), 1.11 (m, 2H), 1.40 (m, 2H), 1.67–1.76 (m, 4H), 2.44 (t, 2H), 3.44 (q, 2H), 4.10 (qt, 1H), 4.64 (s, 2H), 7.31–7.44 (m, 4H), 7.60 (dd, 1H), 7.72–7.83 (m, 5H), 7.99 (d, 1H), 8.47 (t, 1H), 8.57 (s, 1H), 12.10 (brd s, 1H).

MS (APCl, pos): 532.3, 531.2, 530.2, 362.3, 361.2.

EXAMPLE 103

General Procedure (G)

3-{4-[1-(4-tert-Butylcyclohexyl)-3-(2,6-dichloropyridin-4-yl)ureidomethyl]benzoylamino)propionic acid

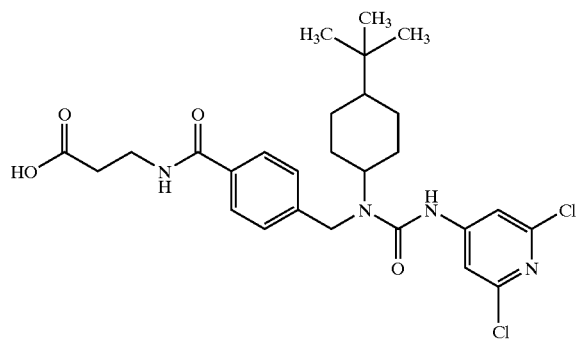

$^1$H NMR (DMSO-d$_6$): δ 0.81 (s, 9H), 0.91 (m, 1H), 1.07 (m, 2H), 1.39 (m, 2H), 1.63–1.74 (m, 4H), 2.49 (t, 2H), 3.44 (q, 2H), 4.10 (t, 1H), 4.61 (s, 2H), 7.29 (d, 2H), 7.66 (s, 2H), 7.76 (d, 2H), 8.47 (t, 1H), 9.21 (s, 1H), 12.10 (brd s, 1H).

MS (APCl, pos): 549.2, 362.2, 361.2.

EXAMPLE 104

General Procedure (G)

3-{4-[1-(4-tert-Butylcyclohexyl)-3-(3,5-dichlorophenyl)ureidomethyl]benzoylamino)propionic acid

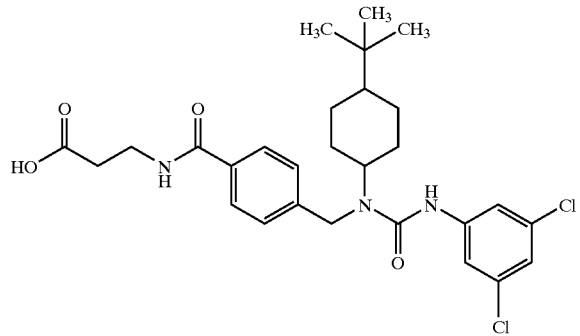

$^1$H NMR (DMSO-d$_6$): δ 0.82 (s, 9H), 0.90 (m, 1H), 1.05–1.15 (m, 2H), 1.40 (m, 2H), 1.65–1.75 (m, 4H), 2.51 (t, 2H), 3.44 (q, 2H), 4.00 (m, 1H), 4.59 (s, 2H), 7.12 (t, 1H), 7.30 (d, 2H), 7.62 (d, 2H), 7.75 (d, 2H), 8.45 (t, 1H), 8.69 (s, 1H), 12.50 (brd s, 1H).

MS (APCl, pos): 552.2, 550.2, 549.2, 548.2, 362.3, 361.2.

EXAMPLE 105

General Procedure (G)

3-{4-[1-(4-tert-Butylcyclohexyl)-3-(4-trifluoromethylsulfanylphenyl)ureidomethyl]benzenesulfonylamino)propionic acid

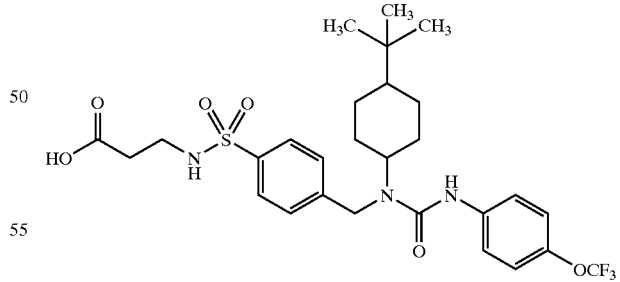

$^1$H NMR (Acetone-d$_6$): δ 0.83 (s, 9H), 0.97 (m, 1H), 1.17 (q, 2H), 1.54 (q, 2H), 1.81 (m, 4H), 2.50 (t, 2H), 3.15 (t, 2H), 4.17 (t, 1H), 4.76 (s, 2H), 6.60 (brd s, 1H), 7.56 (m, 4H), 7.67 (d, 2H), 7.83 (d, 2H), 8.19 (s, 1H).

MS (APCl, pos): 617.2, 616.2, 399.2, 398.1, 397.2.

EXAMPLE 106

General Procedure (G)

3-{4-[1-(4-tert-Butylcyclohexyl)-3-(4-trifluoromethoxyphenyl)ureidomethyl]benzenesulfonylamino)propionic acid $^1$H NMR (DMSO-d$_6$): δ 0.82 (s, 9H), 1.11–1.17 (m, 3H), 1.49 (q, 2H), 1.70 (t, 4H), 2.32 (t, 2H), 2.90 (t, 2H), 4.01 (m, 2H), 4.62 (s, 2H), 7.22 (d, 2H), 7.45 (d, 2H), 7.55 (d, 2H), 7.72 (d, 2H), 8.59 (s, 1H), 12.20 (brd s, 1H).

MS (APCl, pos): 601.3, 600.2, 399.2, 398.3, 397.2.

EXAMPLE 107

General Procedure (G)

3-{4-[1-(4-tert-Butylcyclohexyl)-3-(3-fluoro-4-methylphenyl)ureidomethyl]benzenesulfonylamino)propionic acid

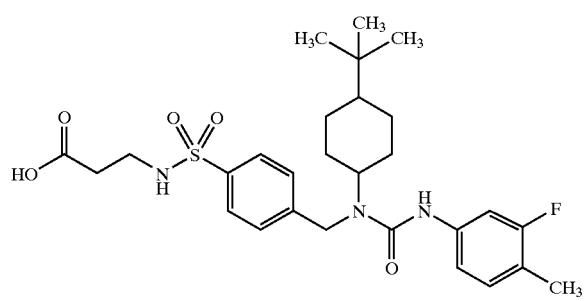

$^1$H NMR (Acetone-d$_6$): δ 0.82 (s, 6H), 0.84 (s, 3H), 1.21 (m, 1H), 1.43–1.59 (m, 5H), 1.79–1.92 (m, 3H), 2.16 (s, 3H), 2.52 (t, 2H), 3.14 (q, 2H), 4.36 (m, 1H), 4.85 (s, 2H), 6.51 (btd t, 1H), 7.07 (d, 2H), 7.49–7.57 (m, 3H), 7.83–7.90 (m, 3H), 11.50 (brd s, 1H).

MS (APCl, pos): 548.2, 399.1, 398.3, 397.2.

EXAMPLE 108

General Procedure (G)

3-{4-[1-(4-tert-Butylbenzyl)-3-(3,5-dichlorophenyl)ureidomethyl]benzoylamino)propionic acid

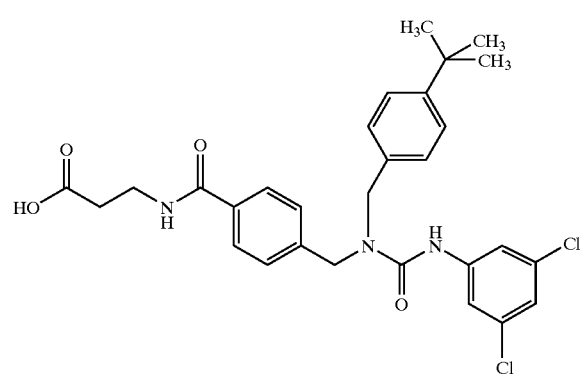

$^1$H NMR (DMSO-d$_6$): δ 1.25 (s, 9H), 3.33 (m, 2H), 3.43 (m, 2H), 4.51 (s, 2H), 4.63 (s, 2H), 7.14–7.17 (m, 3H), 7.30 (d, 2H), 7.36 (d, 2H), 7.66 (m, 2H), 7.79 (s, 1H), 8.50 (t, 1H), 8.97 (s, 1H), 12.25 (brd s, 1H).

MS (APCl, pos): 558.2, 557.2, 556.2, 370.1, 369.1.

EXAMPLE 109

General Procedure (G)

3-{4-[1-((1R)-1-Cyclohexylethyl)-3-naphthalene-2-ylureidomethyl]benzoylamino)propionic acid

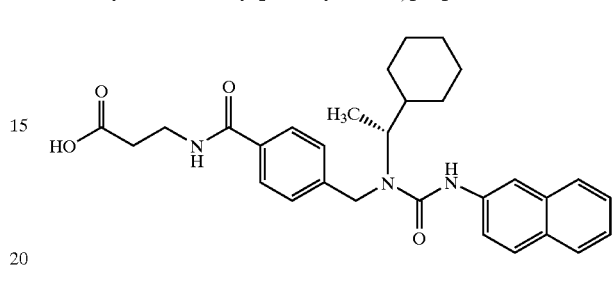

$^1$H NMR (CDCl$_3$): δ 0.92–1.10 (m, 8H), 1.36 (q, 1H), 1.59 (m, 2H), 1.67 (d, 3H), 2.51 (t, 2H), 3.54 (q, 2H), 4.05 (m, 1H), 4.30 (d, 2H), 4.50 (d, 2H), 6.32 (brd s, 2H), 6.47 (brd s, 1H), 7.00–7.07 (m, 2H), 7.23 (t, 1H), 7.27–7.30 (m, 3H), 7.5407.67 (m, 6H).

MS (APCl, pos): 503.3, 502.3, 333.3.

EXAMPLE 110

General Procedure (G)

3-{4-[1-((1S)-1-Cyclohexylethyl)-3-naphthalene-2-ylureidomethyl]benzoylamino)propionic acid

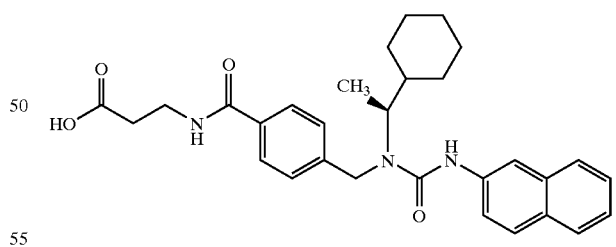

$^1$H NMR (DMSO-d$_6$): δ 0.91 (m, 3H), 1.09 (d, 3H), 1.11 (m, 3H), 1.15–1.88 (m, 6H), 2.44 (t, 2H), 3.34 (q, 2H), 4.09 (q, 1H), 4.36 (d, 1H), 4.80 (d, 1H), 7.32 (t, 1H), 7.38 (d, 2H), 7.42 (t, 1H), 7.55 (dd, 1H), 7.71–7.79 (m, 5H), 7.97 (dd, 1H), 8.52 (t, 1H).

MS (APCl, pos): 502.2, 353.0.

EXAMPLE 111

General Procedure (G)

3-{4-[1-(2,3-Dihydro-1H-inden-2-yl)-3-(4-trifluoromethoxyphenyl)ureidomethyl]benzoylamino)propionic acid

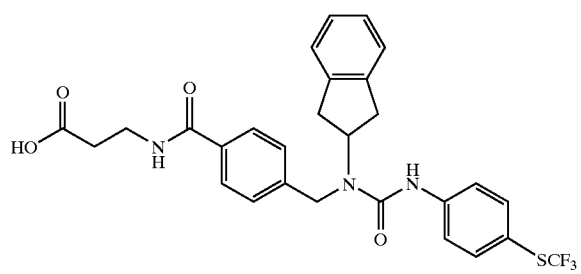

¹H NMR (DMSO-d₆): δ 2.44 (t, 2H), 2.90–3.06 (m, 4H), 3.40–3.46 (m, 2H), 4.67 (s, 2H), 5.09 (qt, 1H), 7.06–7.21 (m, 4H), 7.29 (d, 2H), 7.52 (d, 2H), 7.68 (d, 2H), 7.77 (d, 2H), 8.48 (t, 1H), 8.88 (s, 1H), 12.00 (brd s, 1H).

MS (APCl, pos): 558.2, 339.1.

EXAMPLE 112

General Procedure (G)

3-{4-[1-(2,3-Dihydro-1H-inden-2-yl)-3-(4-butylphenyl)ureidomethyl]benzoylamino)propionic acid

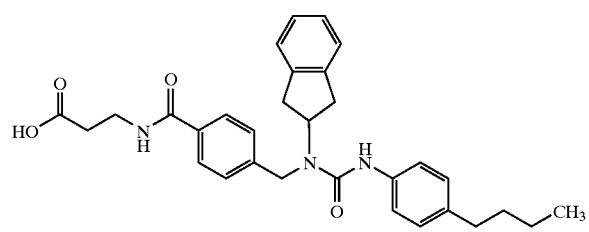

¹H NMR (DMSO-d₆): δ 0.87 (t, 3H), 1.28 (hex, 2H), 1.49 (qt, 2H), 2.51 (t, 2H), 2.69 (t, 2H), 2.95 (d, 1H), 3.01 (d, 1H), 3.25 (d, 1H), 3.30 (d, 1H), 3.70 (q, 2H), 4.59 (s, 2H), 5.21 (qt, 1H), 6.21 (s, 1H), 6.91 (t, 1H), 7.02 (s, 4H), 7.18 (s, 4H), 7.37 (d, 2H), 7.47 (d, 2H).

MS (APCl, pos): 514.2, 339.1.

EXAMPLE 113

General Procedure (G)

3-{5-[1-(4-tert-Butylcyclohexyl)-3-(4-trifluoromethoxyphenyl)ureidomethyl]thiophene-2-carbonylamino)propionic acid

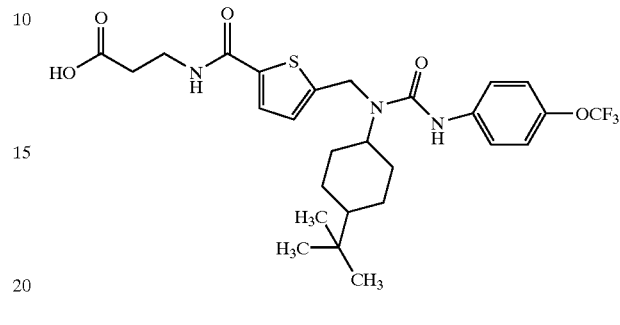

¹H NMR (DMSO-d₆): δ 0.61 (s, 9H), 0.73 (m, 1H), 0.87 (q, 2H), 1.24 (q, 2H), 1.51 (m, 4H), 2.21 (t, 2H), 3.16 (q, 2H), 3.73 (t, 1H), 4.42 (s, 2H), 6.77 (d, 1H), 7.02 (d, 2H), 7.29 (d, 2H), 7.33 (d, 1H), 8.21 (t, 1H), 8.37 (s, 1H), 11.99 (brd s, 1H).

MS (APCl, neg): 568.0, 569.0.

EXAMPLE 114

General Procedure (G)

3-{4-[1-((2R,3R)-2,6,6-Trimethylbicyclo[3.3.1]hept-3-yl)-3-(3,5-dichlorophenyl)ureidomethyl]benzoylamino)propionic acid

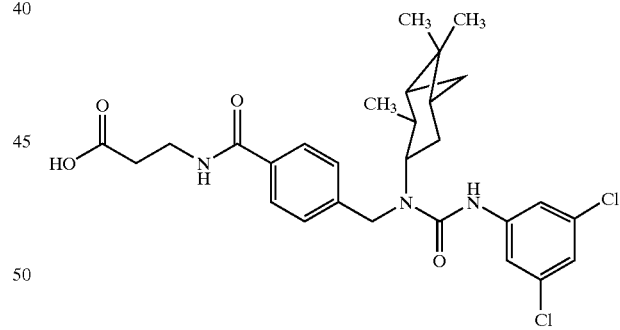

¹H NMR (DMSO-d₆): δ 0.96 (d, 3H), 1.07 (s, 3H), 1.18 (s, 3H), 1.65–1.71 (m, 2H), 1.89–1.94 (m, 2H), 2.20–2.28 (m, 2H), 2.44 (t, 2H), 3.49 (q, 2H), 4.66 (s, 2H), 4.85 (m, 1H), 7.10 (t, 1H), 7.30 (d, 2H), 7.53 (d, 2H), 7.80 (d, 2H), 8.47 (t, 1H), 8.69 (s, 1H).

MS (APCl, pos): 546.1, 359.2, 287.1.

The following examples 115 to 136 were all found to displace more than 50% of the glucagon tracer when screened at 1 μM concentration in the glucagon binding assay II. These compounds are all expected to be present in the library.

EXAMPLE 115

General Procedure (G)

3-{4-[1-(2-Trifluoromethoxybenzyl)-3-naphthalene-2-ylureidomethyl]benzoylamino)propionic acid

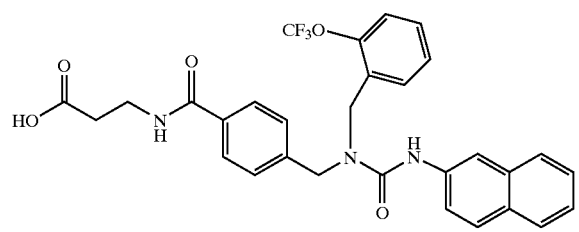

EXAMPLE 116

General Procedure (G)

3-{4-[1-(2-Trifluoromethoxybenzyl)-3-(4-butylphenyl)ureidomethyl]benzoylamino)propionic acid

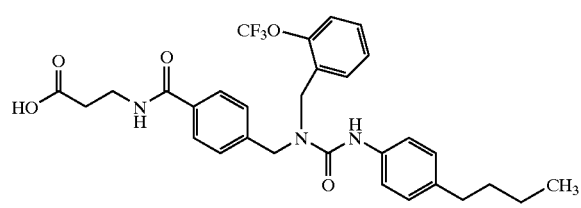

EXAMPLE 117

General Procedure (G)

3-{4-[1-(2-Trifluoromethoxybenzyl)-3-(4-trifluoromethylsulfanylphenyl)ureidomethyl]benzoylamino)propionic acid

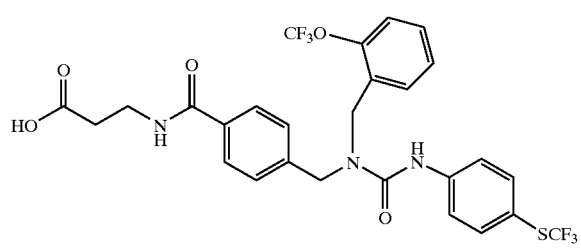

EXAMPLE 118

General Procedure (G)

3-{4-[1-(4-Trifluoromethylbenzyl)-3-(4-butylphenyl)ureidomethyl]benzoylamino)propionic acid

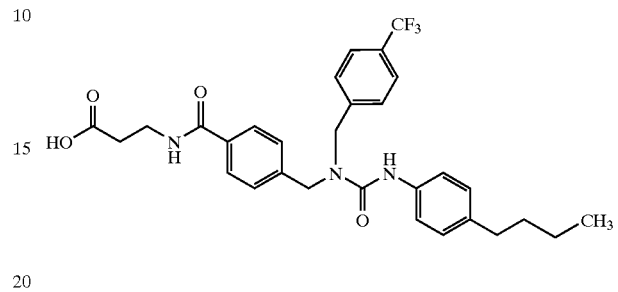

EXAMPLE 119

General Procedure (G)

3-{4-[1-(4-Trifluoromethylbenzyl)-3-(4-butoxyphenyl)ureidomethyl]benzoylamino)propionic acid

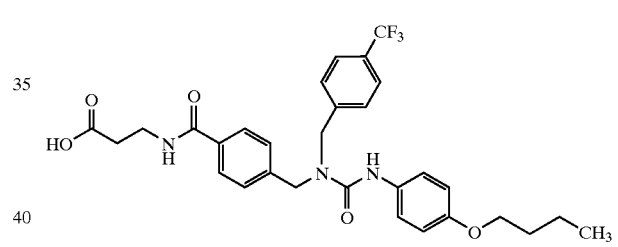

EXAMPLE 120

General Procedure (G)

3-{4-[1-(4-Trifluoromethylbenzyl)-3-(4-trifluoromethylsulfanylphenyl)ureidomethyl]benzoylamino)propionic acid

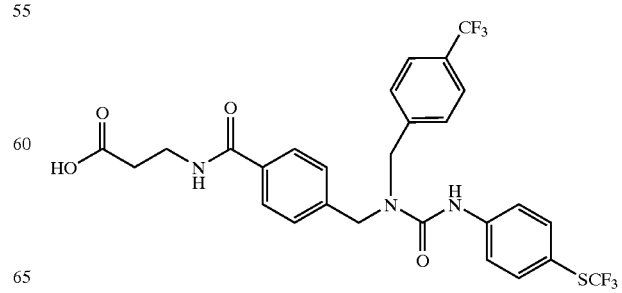

EXAMPLE 121

General Procedure (G)

3-{4-[1-(4-Hydroxy-3-methoxybenzyl)-3-(4-methylphenyl)ureidomethyl]benzoylamino)propionic acid

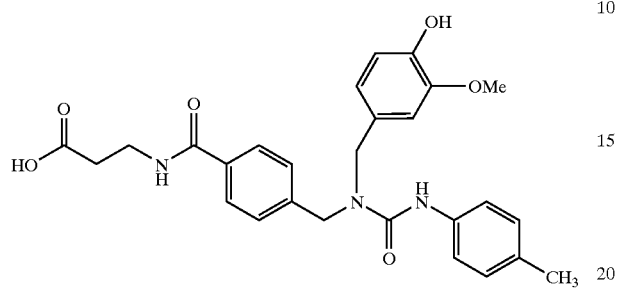

EXAMPLE 122

General Procedure (G)

3-{4-[1-(4-Hydroxy-3-methoxybenzyl)-3-(3,4-methylenedioxyphenyl)ureidomethyl]benzoylamino)propionic acid

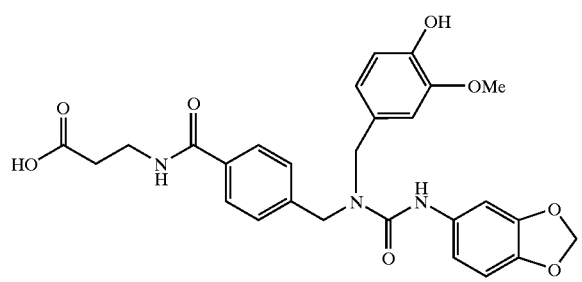

EXAMPLE 123

General Procedure (G)

3-{4-[1-(1-Hydroxycyclohexylmethyl)-3-(3,4-methylenedioxyphenyl)ureidomethyl]benzoylamino)propionic acid

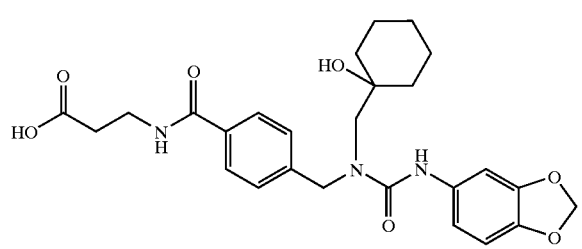

EXAMPLE 124

General Procedure (G)

3-{5-[1-(2-Trifluoromethoxybenzyl)-3-naphthalene-2-ylureidomethyl]thiophene-2-carbonylamino)propionic acid

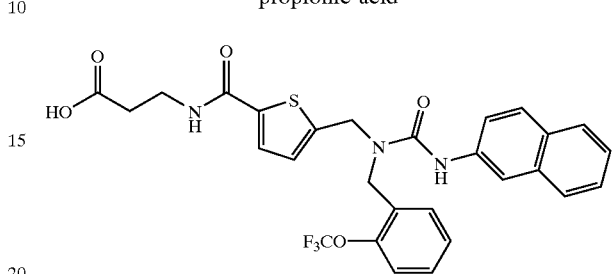

EXAMPLE 125

General Procedure (G)

3-{5-[1-(2-Trifluoromethoxybenzyl)-3-(4-butoxyphenyl)ureidomethyl]thiophene-2-carbonylamino)propionic acid

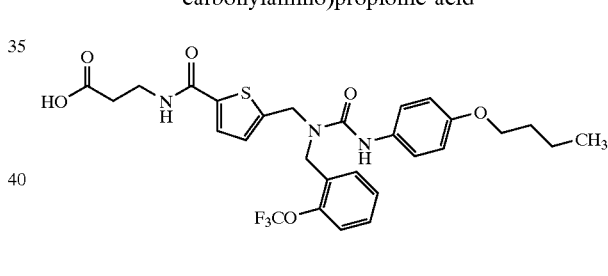

EXAMPLE 126

General Procedure (G)

3-{5-[1-(2-Trifluoromethoxybenzyl)-3-(4-trifluoromethylsulfanylphenyl)ureidomethyl]thiophene-2-carbonylamino)propionic acid

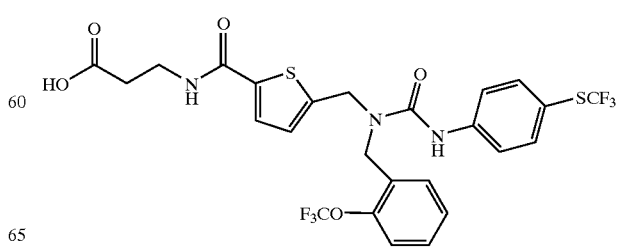

EXAMPLE 127

General Procedure (G)

3-{5-[1-(4-tert-Butylbenzyl)-3-naphthalene-2-ylureidomethyl]thiophene-2-carbonylamino)propionic acid

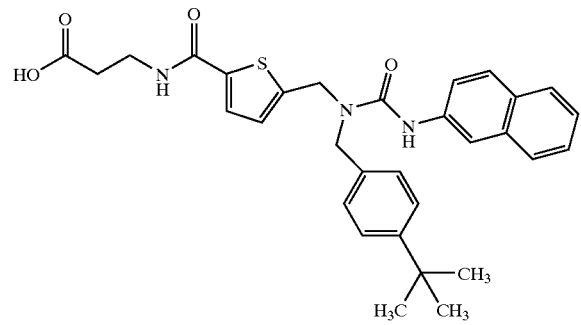

EXAMPLE 128

General Procedure (G)

3-{5-[1-(4-Trifluoromethylbenzyl)-3-naphthalene-2-ylureidomethyl]thiophene-2-carbonylamino)propionic acid

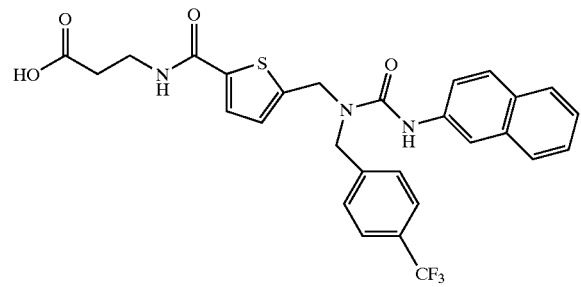

EXAMPLE 129

General Procedure (G)

3-{5-[1-(4-tert-Butylbenzyl)-3-(4-butoxyphenyl)ureidomethyl]thiophene-2-carbonylamino)propionic acid

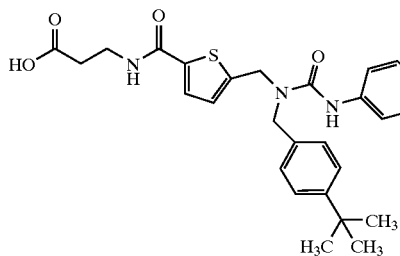

EXAMPLE 130

General Procedure (G)

3-{5-[1-(4-tert-Butylbenzyl)-3-(4-trifluoromethylsulfanylphenyl)ureidomethyl]thiophene-2-carbonylamino)propionic acid

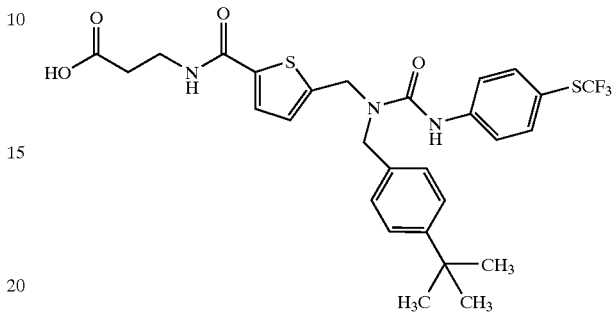

EXAMPLE 131

General Procedure (G)

3-{5-[1-(4-Trifluoromethylbenzyl)-3-(4-trifluoromethylsulfanylphenyl)ureidomethyl]thiophene-2-carbonylamino)propionic acid

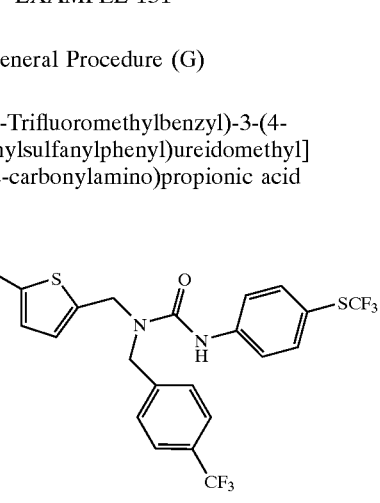

EXAMPLE 132

General Procedure (G)

3-{4-[1-(4-tert-Butylcyclohexyl)-3-(2-phenylcyclopropyl)ureidomethyl]benzoylamino)propionic acid

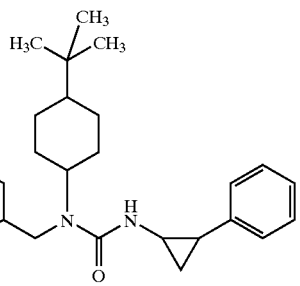

EXAMPLE 133

General Procedure (G)

3-{4-[3-(4-Bromophenyl)-1-(4-tert-butylcyclohexyl)ureidomethyl]benzoylamino)propionic acid

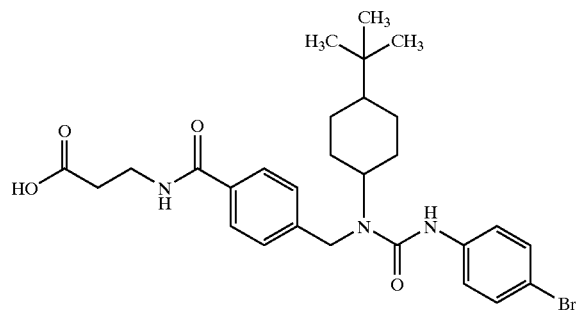

EXAMPLE 134

General Procedure (G)

3-{3-[1-(4-tert-Butylcyclohexyl)-3-(4-trifluoromethoxyphenyl)ureidomethyl]benzoylamino)propionic acid

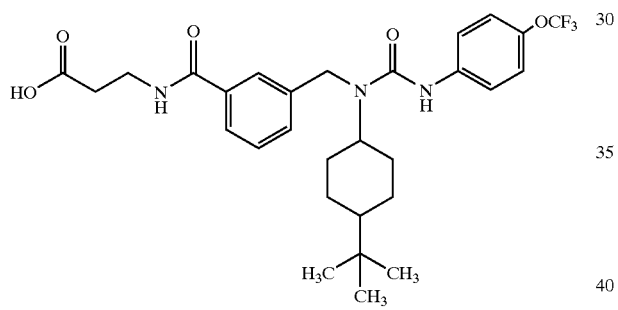

EXAMPLE 135

General Procedure (G)

3-{3-[1-(4-tert-Butylcyclohexyl)-3-(3,5-dichlorophenyl)ureidomethyl]benzoylamino)propionic acid

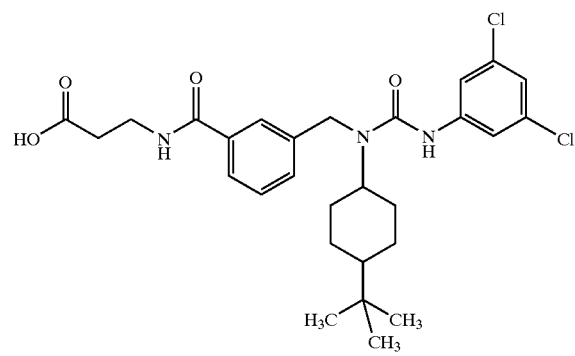

EXAMPLE 136

General Procedure (G)

3-{4-[3-(4-Butylphenyl)-1-(4-trifluoromethylbenzyl)ureidomethyl]benzoylamino)propionic acid

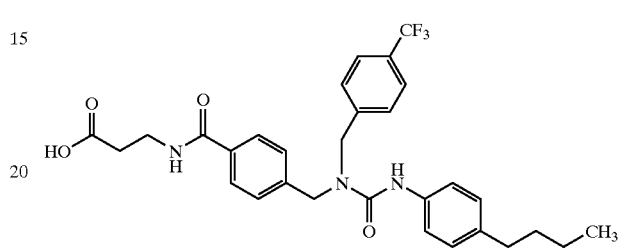

EXAMPLE 137

General Procedure (G)

3-{4-[1-(1-Indan-2-yl)-3-(4-trifluoromethoxyphenyl)ureidomethyl]benzoylamino)propionic acid

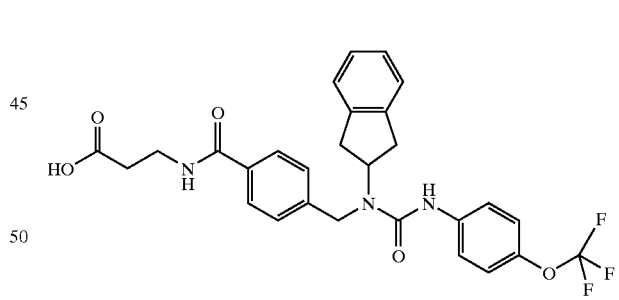

$^1$H NMR (DMSO-$d_6$): δ 2.52 (t, 2H), 2.97 (m, 4H), 3.47 (qt, 2H), 4.72 (s, 2H), 7.09–7.20 (m, 4H), 7.24 (d, 2H), 7.29 (d, 2H), 7.57 (d, 2H), 7.77 (d, 2H), 8.48 (brd t, 1H), 8.73 (brd s, 1H), 12.21 (brd s, 1H).

MS (APCl, pos): 542.2, 543.2, 339.1.

EXAMPLE 138

General Procedure (G)

3-{4-[1-Indan-2-yl-3-(3,5-dichlorophenyl)ureidomethyl]benzoylamino}propionic acid

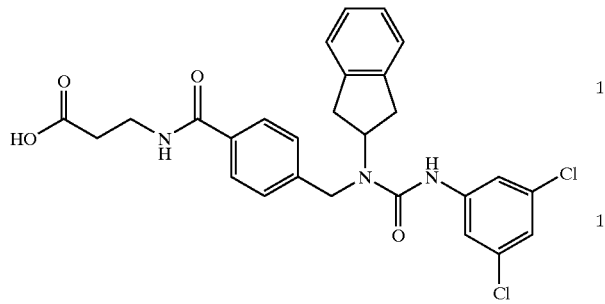

$^1$H NMR (DMSO-d$_6$): δ 2.51 (t, 2H), 2.95–2.99 (m, 4H), 3.45 (qt, 2H), 4.71 (s, 2H), 7.09–7.18 (m, 5H), 7.28 (d, 2H), 7.64 (s, 2H), 7.78 (d, 2H), 8.49 (t, 1H), 8.86 (s, 1H), 12.21 (brd s, 1H).

MS (APCl, pos): 526.1, 339.1.

EXAMPLE 139

General Procedure (G)

3-{4-[1-((1S)-1-Cyclohexylethyl)-3-(4-trifluoromethoxyphenyl)ureidomethyl]benzoylamino)propionic acid (S)

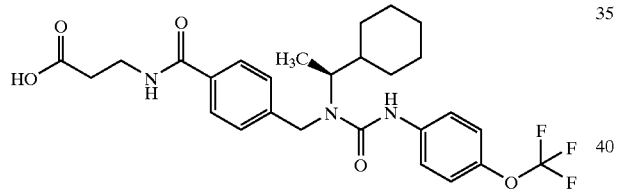

$^1$H NMR (DMSO-d$_6$): δ 0.84–1.19 (m, 8H), 1.47–1.70 (m, 6H), 1.88 (t, 2H), 3.16 (qt, 2H), 4.03 (quintet, 1H), 4.33 (d, 1H), 4.78 (d, 1H), 7.10 (d, 2H), 7.50 (d, 2H), 7.70 (d, 2H), 8.62 (brd s, 1H), 8.95 (brd t, 1H).

MS (APCl, pos): 536.2, 537.2, 538.2.

EXAMPLE 140

General Procedure (G)

3-{4-[1-((1S)-1-Cyclohexylethyl)-3-(3,5-dichlorophenyl)ureidomethyl]benzoylamino)propionic acid (S)

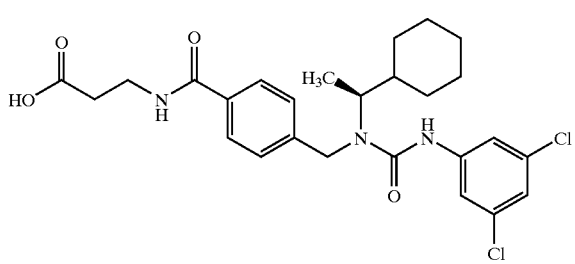

$^1$H NMR (CDCl$_3$): δ 1.16–1.27 (m, 8H), 1.40 (m, 1H), 1.69–1.80 (m, 5H), 2.68 (t, 2H), 3.70 (qt, 2H), 4.20 (m, 1H), 4.43 (dd, 2H), 6.44 (brd s, 1H), 6.94 (m, 2H), 7.17 (s, 2H), 7.36 (d, 2H), 7.74 (d, 2H).

MS (APCl, pos): 520.2, 522.1, 333.2.

General Procedure (H) for the Solution Phase Synthesis of Compounds of the General Formula (If)

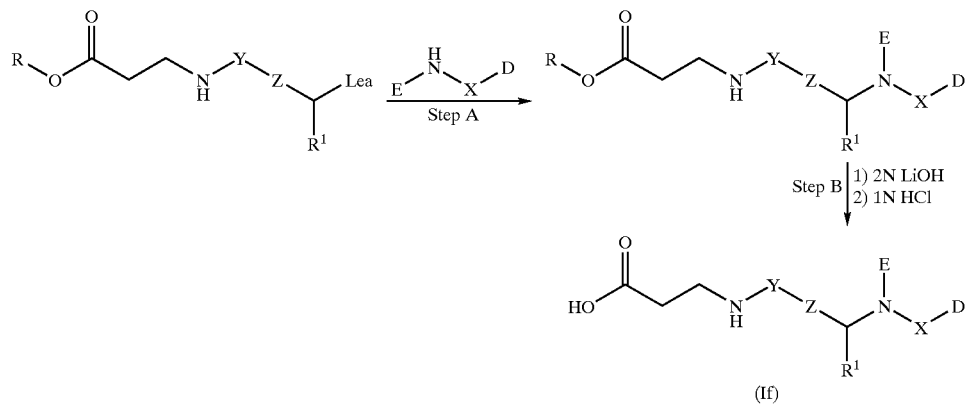

wherein $R^1$, E, Z and D are as defined for formula (I),
X is —$(CH_2)_q$—, wherein q is as defined for formula (I),
Y is —C(O)— or —$S(O)_2$—,
R is $C_{1-6}$-alkyl and
Lea is a leaving group such as chloro, bromo, iodo, mesyl or tosyl.

The preparation of starting materials are as described above in procedure (G).

Library solution phase synthesis (procedure (H)) of compounds of the general formula (If):

Step A:

The appropriate alkylhalide (0.02 mmol) in DMF was added into the wells of a deepwell plate containing the appropriate amine (E-NH—X-D) (0.02 mmol) and solid potassium carbonate (2 eq) in DMF. The mixtures were agitated at 55° C. for 16 hours to give the alkylated product.

Step B:

To the crude product from step A was added aqueous 2M LiOH (4 eq). The mixtures are agitated for at least four hours before they are filtered. Aqueous 1 N HCl was then added to give the desired carboxylic acids.

The following examples 141 to 152 were prepared according to the general procedure (H). They were all found to displace more than 50% of the glucagon tracer when screened at 1 μM concentration in the glucagon binding assay II. The compounds are all expected to be present in the library.

EXAMPLE 141

General Procedure (H)

3-(4-{[(3,3-Diphenylpropyl)-(4-trifluoromethylbenzyl)amino]methyl}benzoylamino)propionic acid

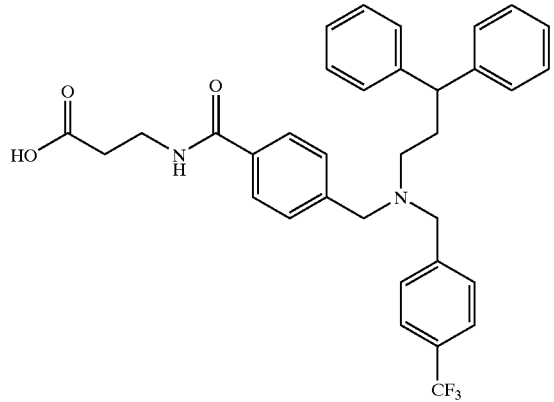

EXAMPLE 142

General Procedure (H)

3-(5-{[(3,3-Diphenylpropyl)-(4-trifluoromethylbenzyl)amino]methyl}thiophene-2-carbonylamino)propionic acid

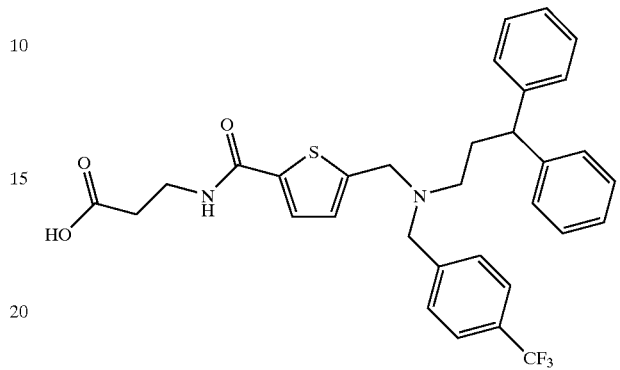

EXAMPLE 143

General Procedure (H)

3-(4-{[(2,2-Diphenylethyl)-(2-chlorobenzyl)amino]methyl}benzoylamino)propionic acid

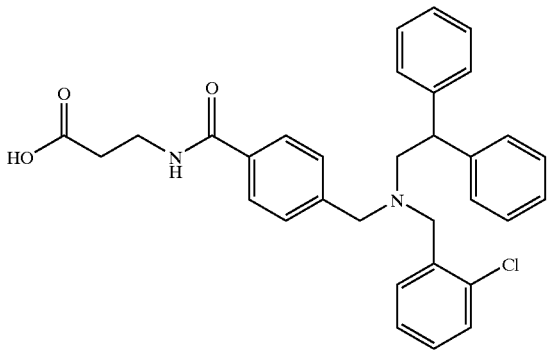

EXAMPLE 144

General Procedure (H)

3-(5-{[(2,2-Diphenylethyl)-(2-chlorobenzyl)amino]methyl}thiophene-2-carbonylamino)propionic acid

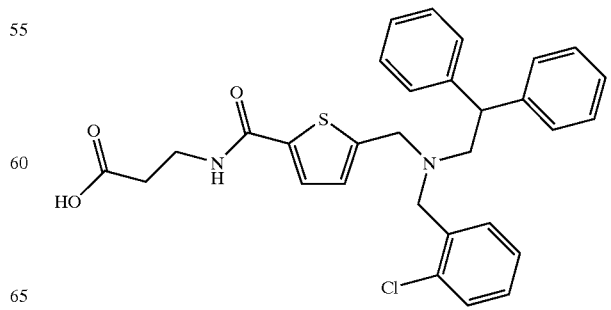

EXAMPLE 145

General Procedure (H)

3-(4-{[(2-Phenylethyl)-(4-phenoxybenzyl)amino]methyl}benzoylamino)propionic acid

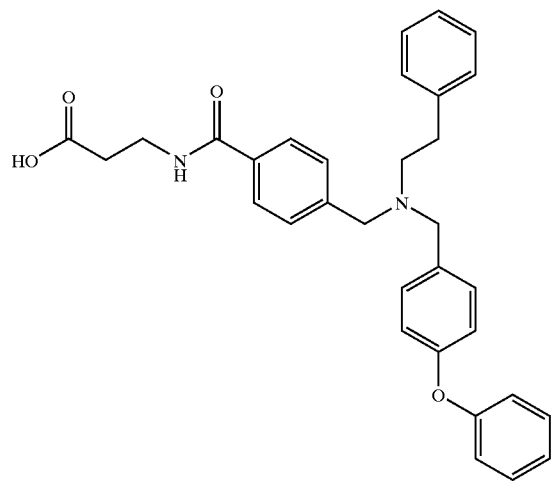

EXAMPLE 146

General Procedure (H)

3-(5-{[(2-Phenylethyl)-(4-phenoxybenzyl)amino]methyl}thiophene-2-carbonylamino)propionic acid

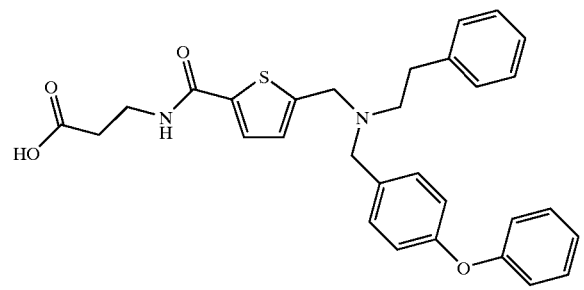

EXAMPLE 147

General Procedure (H)

3-(5-{[(2,4-Dichlorophenylethyl)-(4-methylbenzyl)amino]methyl}thiophene-2-carbonylamino)propionic acid

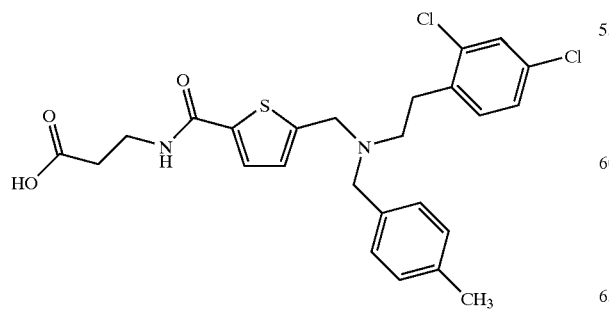

EXAMPLE 148

General Procedure (H)

3-(5-{[Bis-(4-chlorobenzyl)amino]methyl}thiophene-2-carbonylamino)propionic acid

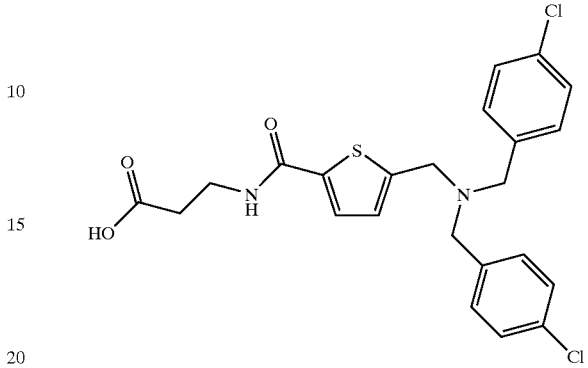

EXAMPLE 149

General Procedure (H)

3-(4-{[(3,4-Dimethoxybenzyl)-(4-isopropylbenzyl)amino]methyl}benzoylamino)propionic acid

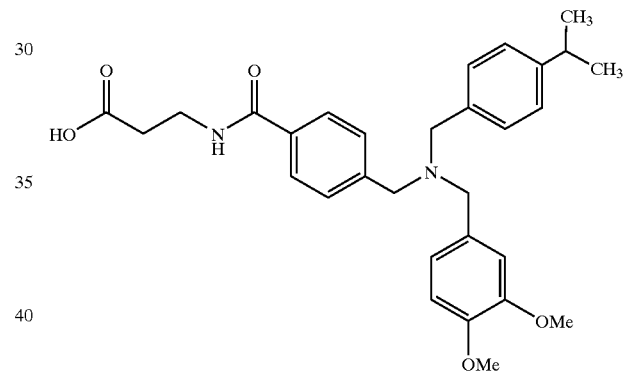

EXAMPLE 150

General Procedure (H)

3-(5-{[(3,4-Dimethoxybenzyl)-(4-isopropylbenzyl)amino]methyl}thiophene-2-carbonylamino)propionic acid

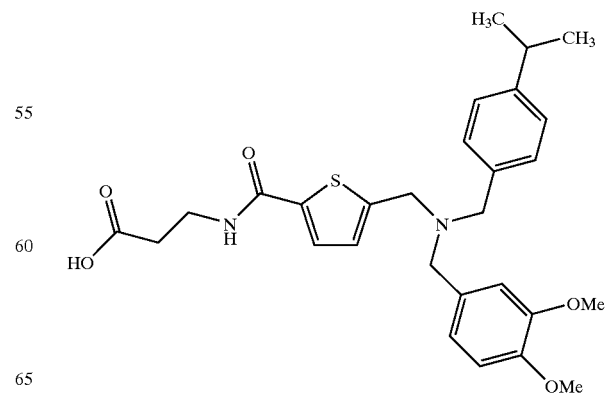

EXAMPLE 151

General Procedure (H)

3-(4-{[(3,4-Dimethoxybenzyl)-(3-[3-trifluoromethylphenoxy]benzyl)amino]methyl}benzoylamino)propionic acid

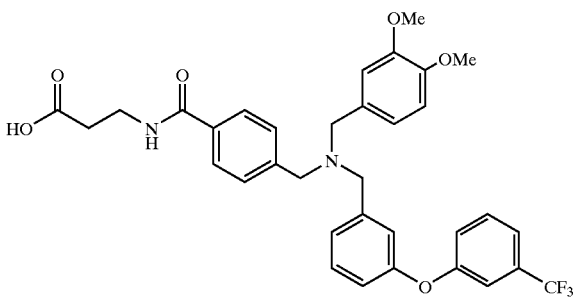

EXAMPLE 152

General Procedure (H)

3-(5-{[(3,4-Dimethoxybenzyl)-(3-[3-trifluoromethylphenoxy]benzyl)amino]methyl}thiophene-2-carbonylamino)propionic acid

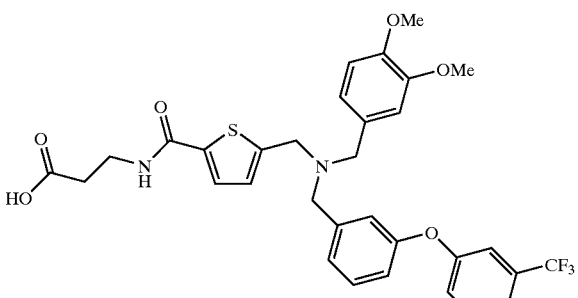

EXAMPLE 153

General Procedure (H)

3-(4-{[(2,4-Dichlorophenylethyl)-(4-methylbenzylamino]methyl}benzoylamino)propionic acid

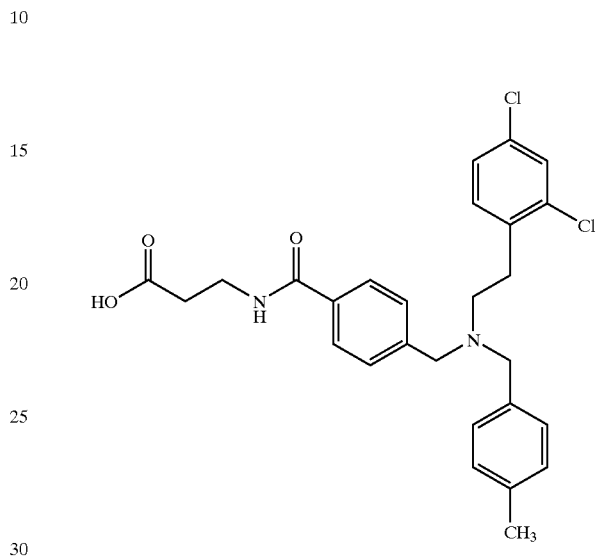

$^1$H NMR (MeOH-d$_4$): δ 2.38 (s, 3H), 2.64 (t, 2H), 3.10 (m, 4H), 3.50 (qt, 2H), 4.40 (s, 2H), 4.50 (s, 2H), 7.20 (m, 4H), 7.40 (m, 3H), 7.50 (d, 2H), 7.90 (d, 2H), 8.60 (t, 1H).

MS (APCl, pos): 499.1, 500.2, 501.2.

EXAMPLE 154

General Procedure (H)

3-(4-{[Bis-(3-chlorobenzyl)amino]methyl}benzoylamino)propionic acid

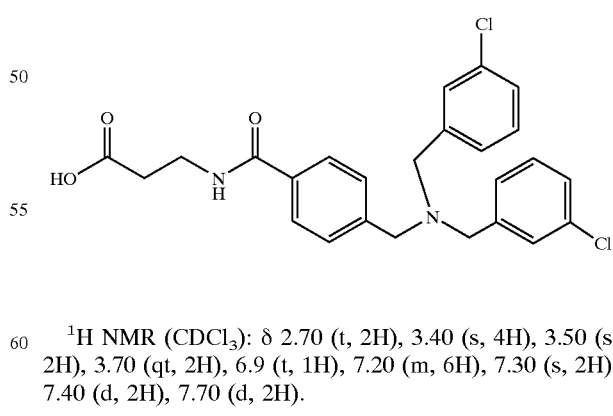

$^1$H NMR (CDCl$_3$): δ 2.70 (t, 2H), 3.40 (s, 4H), 3.50 (s, 2H), 3.70 (qt, 2H), 6.9 (t, 1H), 7.20 (m, 6H), 7.30 (s, 2H), 7.40 (d, 2H), 7.70 (d, 2H).

MS (APCl, pos): 471.0, 472.0, 473.0.

EXAMPLE 155

General Procedure (H)

3-(4-{[(3,3-Diphenylpropyl)-(3,4-methylenedioxybenzyl)amino]methyl}benzoylamino)propionic acid

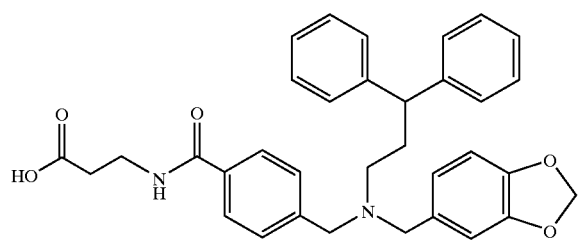

$^1$H NMR (CD$_3$CN): δ 2.46–2.54 (m, 2H), 2.63 (t, 2H), 2.82–2.88 (m, 2H), 3.61 (qt, 2H), 3.86 (t, 1H), 4.20–4.40 (m, 4H), 6.02 (s, 2H), 6.83 (d, 1H), 6.90 (d, 1H), 6.97 (s, 1H), 7.16–7.29 (m, 10H), 7.50 (d, 2H), 7.77 (d, 2H).

MS (APCl, pos): 551.2, 552.2, 553.2.

General Procedure (I) for the Solution Phase Synthesis of Compounds of the General Formula (Ig)

temperature for 5 hours. The reaction was diluted with ethyl acetate and washed with aqueous sodium bicarbonate (3×), brine (3×), dried over MgSO$_4$, and concentrated to a syrup. The desired secondary amine was purified by silica gel column chromatography using ethyl acetate.

$^1$H NMR (DMSO-d$_6$): δ 0.78 (s, 9H), 0.91 (brd m, 5H), 1.30 (t, 3H), 1.67 (brd m, 2H) 1.93 (brd m, 2H), 2.21 (1H), 3.77 (s, 2H), 4.30 (qt, 2H), 7.44 (d, 2H), 7.87 (d, 2H).

Step B:

To a solution of the above benzoate in THF/MeOH (3/1) was added aqueous 1M NaOH. After stirring the reaction at room temperature for 15 minutes, the solution was made acidic with 1N HCl. The product was extracted with ethyl acetate (3×) and washed with brine (3×), dried over MgSO$_4$, and concentrated to a solid. The carboxylic acid product was recrystallized from dichloromethane as the hydrochloride salt.

$^1$H NMR (DMSO-d$_6$): δ 0.82 (s, 9H), 0.97 (m, 3H), 1.44 (qt, 2H), 1.81 (m, 2H), 2.17 (m, 2H), 2.90 (brd m, 1H), 4.20 (t, 2H), 7.73 (d, 2H), 7.95 (d, 2H), 9.52 (s, 2H), 12.60 (brd s, 1H).

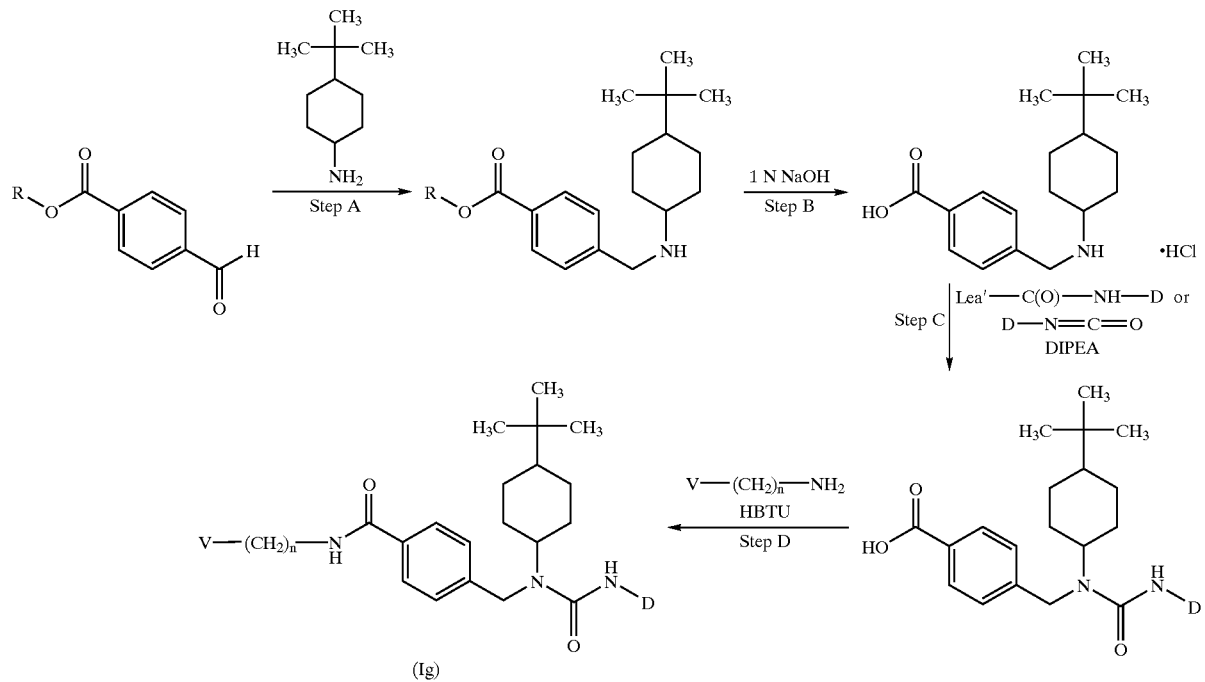

wherein
n, D and V are as defined for formula (I),
R is C$_{1-6}$-alkyl and
Lea' is a leaving group such as —OSu, chloro, phenoxy or 4-nitrophenoxy.

Step A:

To a solution of ethyl 4-formylbenzoate (6 g, 33.7 mmol) in DMF was added 4-tert-butylcyclohexylamine (5.8 g, 37.1 mmol), sodium cyanoborohydride (3.2 g, 50.6 mmol) and a catalytic amount of TFA. The solution was stirred at room Step C:

To a solution of the amine in DMF was added the desired isocyanate (1.1 eq) or alternatively Lea'-C(O)—NH-D, and the reaction was stirred at room temperature for 10 minutes. When using Lea'-C(O)—NH-D a base such as triethylamine, diisopropylethylamine, dicyclohexylmethylamine or any tertiary amine or potassium carbonate was also added. The solvent was concentrated to an oil. The residue was suspended in ethyl acetate and upon sitting in cold, the desired urea crystallized as a white solid.

Examples of products prepared in this fashion are shown below.

4-[1-(4-tert-Butylcyclohexyl)-3-(4-trifluoromethoxyphenyl)ureidomethyl]benzoic acid

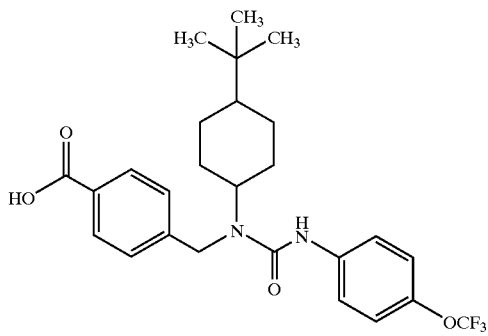

¹H NMR (DMSO-d₆): δ 0.81 (brd s, 9H), 1.12 (qt, 2H), 1.37 (qt, 2H), 1.69 (t, 4H), 4.06 (t, 1H), 4.62 (s, 2H), 7.21 (d, 2H), 7.35 (d, 2H), 7.54 (d, 2H), 7.87 (d, 2H), 8.57 (s, 1H), 12.84 (brd s, 1H).

4-[1-(4-tert-Butylcyclohexyl)-3-(4-chlorophenyl)ureidomethyl]benzoic acid

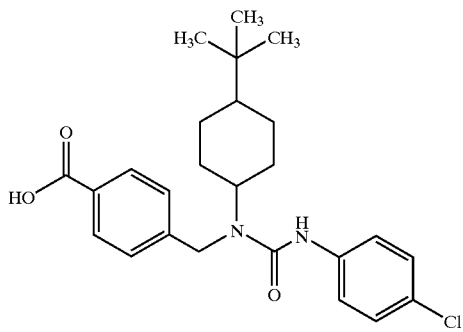

¹H NMR (DMSO-d₆): δ 0.82 (s, 9H), 0.91 (m, 1H), 1.15 (qt, 2H), 1.37 (qt, 2H), 1.69 (t, 4H), 4.04 (m, 1H), 4.61 (s, 2H), 7.26 (d, 2H), 7.35 (d, 2H), 7.47 (d, 2H), 7.86 (d, 2H), 8.49 (s, 1H), 12.83 (brd s, 1H).

4-[1-(4-tert-Butylcyclohexyl)-3-(3,5-dichlorophenyl)ureidomethyl]benzoic acid

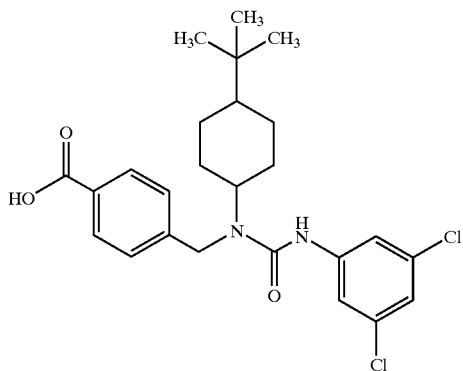

¹H NMR (DMSO-d₆): δ 0.81 (s, 9H), 0.92 (m, 1H), 1.14 (qt, 2H), 1.47 (qt, 2H), 1.69–1.72 (m, 4H), 4.04 (m, 1H), 4.61 (s, 2H), 7.12 t, 1H), 7.35 (d, 2H), 7.63 (d, 2H), 7.88 (d,2H), 8.87 (s, 1H), 12.95 (brd s, 1H).

Step D:

This step was carried out in a combinatorial fashion in solution.

To a solution of one of the above benzoic acids (0.02 mmol) in a suitable solvent such as CH₂Cl₂, DMF, or THF was added diisopropylethylamine (3 eq) and HBTU (1.1 eq). The reaction was allowed to stir for 30 minutes before the amine (1.1 eq) was added. The solution was stirred at room temperature for 4 hours. The solvents were evaporated under reduced pressure to afford the crude product.

The following examples were prepared according to the general procedure (I).

EXAMPLE 156

General Procedure (I)

4-[1-(4-tert-Butylcyclohexyl)-3-(4-trifluoromethoxyphenyl)ureidomethyl]-N-[2-(1H-tetrazol-5-yl)ethyl]benzamide

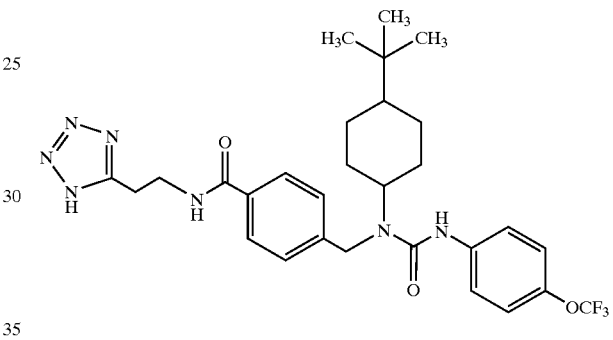

¹H NMR (DMSO-d₆): δ 0.81 (s, 9H), 0.90 (m, 1H), 1.11 (qt, 2H), 1.41 (qt, 2H), 1.70 (m, 4H), 3.13 (t, 2H), 3.60 (qt, 2H), 4.05 (quintet, 1H), 4.60 (s, 2H), 7.22 (d, 2H), 7.31 (d, 2H), 7.55 (d, 2H), 7.73 (d, 2H), 8.54 (s, 1H), 8.56 (t, 1H). MS (APCl, pos): 588.3.

EXAMPLE 157

General Procedure (I)

4-[1-(4-tert-Butylcyclohexyl)-3-(3,5-dichlorophenyl)ureidomethyl]-N-[2-(1H-tetrazol-5-yl)ethyl]benzamide

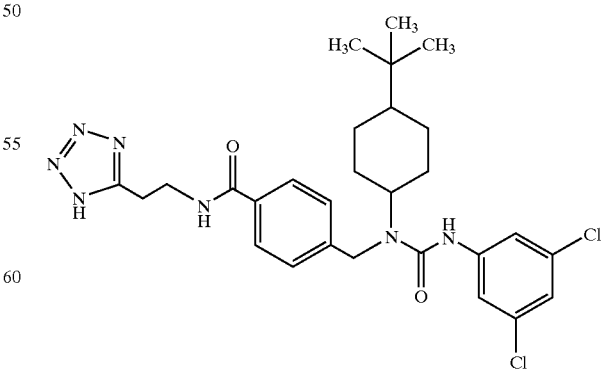

¹H NMR (MeOH-d₄): δ 0.87 (s, 9H), 1.01 (m, 1H), 1.25 (m, 2H), 1.46 (q, 2H), 1.83 (t, 4H), 3.27 (t, 2H), 3.78 (t, 2H), 4.10 (m, 1H), 4.67 (s, 2H), 7.04 (t, 1H), 7.38 (d, 2H), 7.43 (t, 2H), 7.75 (d, 2H), 8.44 (brd s, 1H).

MS (APCl, pos): 480.2, 478.2, 477.2, 435.1, 433.2, 290.1, 156.2.

EXAMPLE 158

General Procedure (I)

4-[1-(trans-4-tert-Butylcyclohexyl)-3-(4-trifluoromethoxyphenyl)ureidomethyl]-N-(2H-tetrazol-5-yl)benzamide

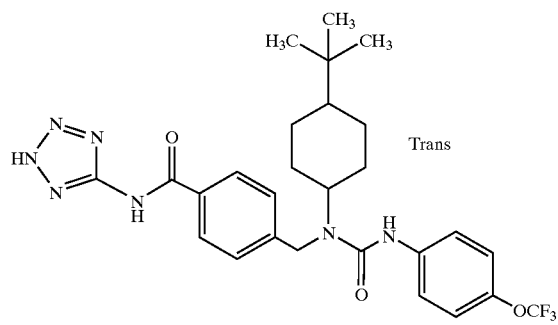

$^1$H NMR (MeOH-d$_4$): δ 0.86 (s, 9H), 1.01 (m, 1H), 1.22 (qt, 2H), 1.48 (qt, 2H), 1.85 (m, 4H), 4.11 (m, 1H), 4.70 (s, 2H), 7.16 (d, 2H), 7.42 (d, 2H), 7.46 (d, 2H), 7.99 (d, 2H).

MS (APCl, pos): 560.2, 561.2, 357.1, 358.2.

The following examples 159 to 171 were all found to displace more than 50% of the glucagon tracer when screened at 1 μM concentration in the glucagon binding assay II. The compounds are all expected to be present in the library.

EXAMPLE 159

General Procedure (I)

4-[1-(4-tert-Butylcyclohexyl)-3-(4-chlorophenyl)ureidomethyl]-N-(1H-tetrazol-5-yl)benzamide

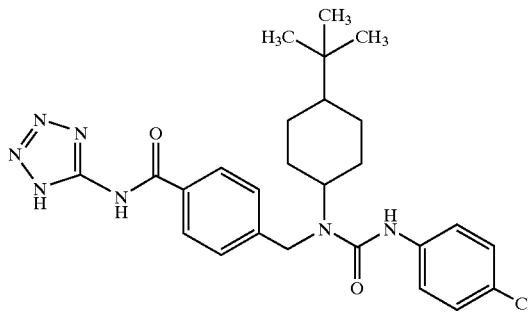

EXAMPLE 160

General Procedure (I)

4-[1-(4-tert-Butylcyclohexyl)-3-(4-chlorophenyl)ureidomethyl]-N-(2,3-dihydro-1,4-benzodioxin-6-yl)benzamide

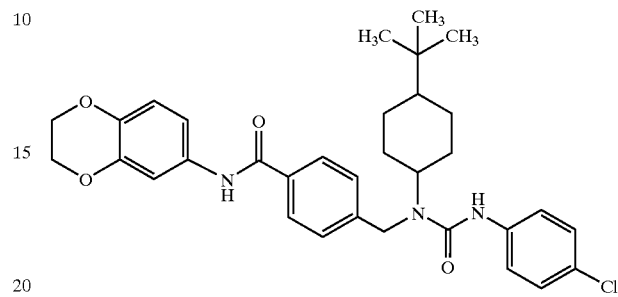

EXAMPLE 161

General Procedure (I)

4-[1-(4-tert-Butylcyclohexyl)-3-(4-trifluoromethoxyphenyl)ureidomethyl]-N-(2,3-dihydro-1,4-benzodioxin-6-yl)benzamide

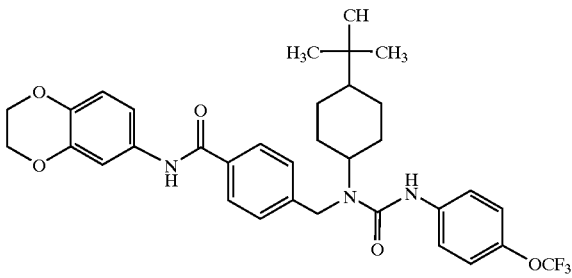

EXAMPLE 162

General Procedure (I)

4-[1-(4-tert-Butylcyclohexyl)-3-(4-chlorophenyl)ureidomethyl]-N-(4-hydroxy-3-nitrophenyl)benzamide

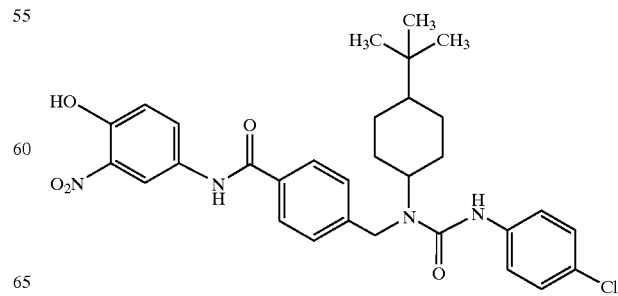

EXAMPLE 163

General Procedure (I)

4-[1-(4-tert-Butylcyclohexyl)-3-(4-trifluoromethoxyphenyl)ureidomethyl]-N-(4-hydroxy-3-nitrophenyl)benzamide

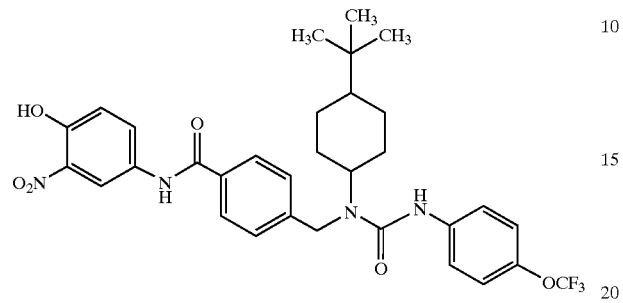

EXAMPLE 164

General Procedure (I)

4-[1-(4-tert-Butylcyclohexyl)-3-(4-chlorophenyl)ureidomethyl]-N-(1H-pyrazolo[3,4-d]pyrimidin-4-yl)benzamide

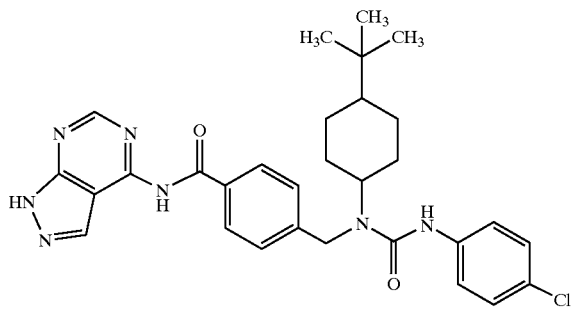

EXAMPLE 165

General Procedure (I)

4-[1-(4-tert-Butylcyclohexyl)-3-(4-trifluoromethoxyphenyl)ureidomethyl]-N-(1H-pyrazolo[3,4-d]pyrimidin-4-yl)benzamide

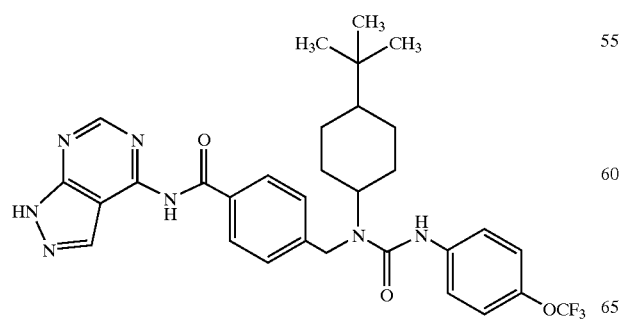

EXAMPLE 166

General Procedure (I)

4-[1-(4-tert-Butylcyclohexyl)-3-(4-chlorophenyl)ureidomethyl]-N-(1,3-dioxo-2,3-dihydro-1H-isoindol-5-yl)benzamide

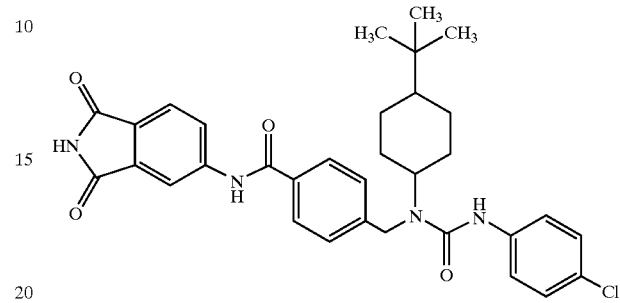

EXAMPLE 167

General Procedure (I)

4-[1-(4-tert-Butylcyclohexyl)-3-(4-trifluoromethoxyphenyl)ureidomethyl]-N-(2,3-dihydro-1,4-benzodioxin-6-yl)benzamide

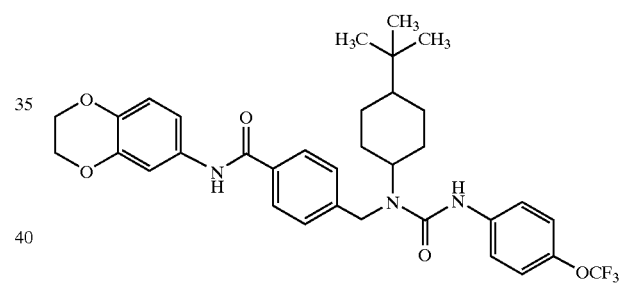

EXAMPLE 168

General Procedure (I)

4-[1-(4-tert-Butylcyclohexyl)-3-(3,5-dichlorophenyl)ureidomethyl]-N-(2,3-dihydro-1,4-benzodioxin-6-yl)benzamide

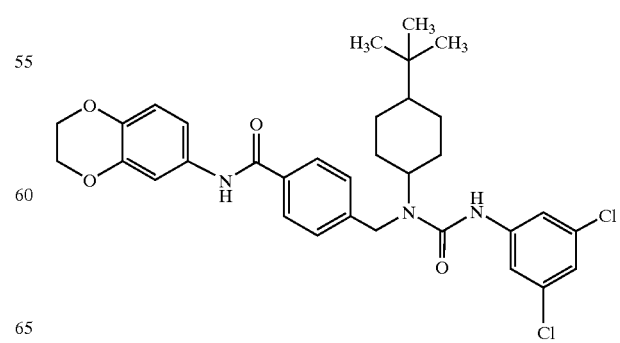

EXAMPLE 169

General Procedure (I)

4-[1-(4-tert-Butylcyclohexyl)-3-(3,5-dichlorophenyl)ureidomethyl]-N-(4-hydroxy-3-nitrophenyl)benzamide

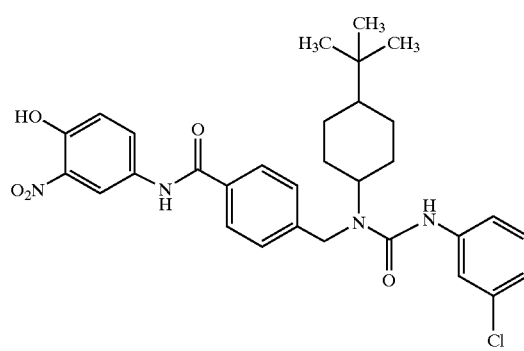

EXAMPLE 170

General Procedure (I)

4-[1-(4-tert-Butylcyclohexyl)-3-(3,5-dichlorophenyl)ureidomethyl]-N-(1H-pyrazolo[3,4-d]pyrimidin-4-yl)benzamide

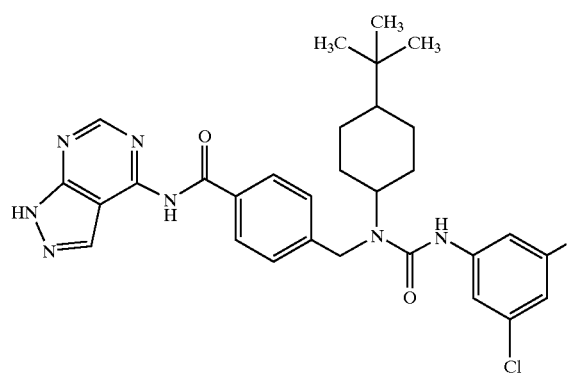

EXAMPLE 171

General Procedure (I)

4-[1-(4-tert-Butylcyclohexyl)-3-(3,5-dichlorophenyl)ureidomethyl]-N-(1,3-dioxo-2,3-dihydro-1H-isoindol-5-yl)benzamide

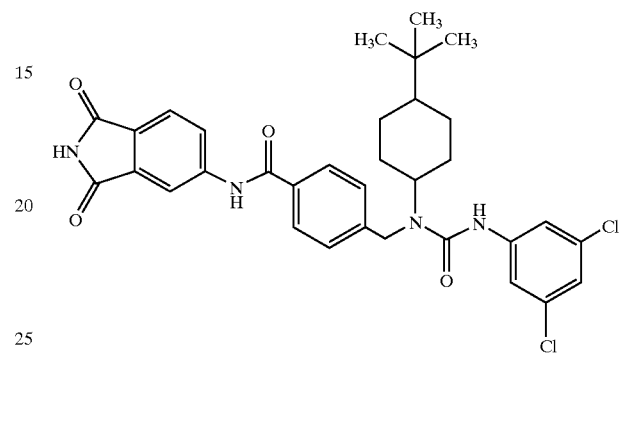

EXAMPLE 172

General Procedure (I)

4-[1-(4-tert-Butylcyclohexyl)-3-(3,5-dichlorophenyl)ureidomethyl]-N-(2H-tetrazol-5-yl)benzamide

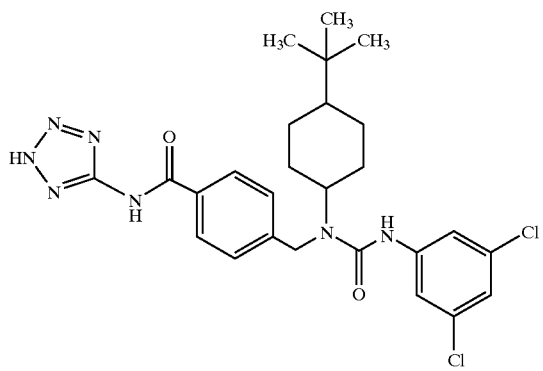

$^1$H NMR (MeOH-$d_4$): δ 0.92 (s, 9H), 1.01 (m, 1H), 1.18–1.31 (m, 2H), 1.44–1.52 (m, 2H), 1.80–1.87 (m, 4H), 4.12 (m, 1H), 4.72 (s, 2H), 7.05 (t, 1H), 7.46 (d, 2H), 7.49 (d, 2H), 8.02 (d, 2H).

MS (APCl, pos): 544.2, 357.2.

EXAMPLE 173

General Procedure (I)

4-[1-(4-tert-Butylcyclohexyl)-3-(3,5-dichlorophenyl)ureidomethyl]-N-(2H-tetrazol-5-ylmethyl)benzamide

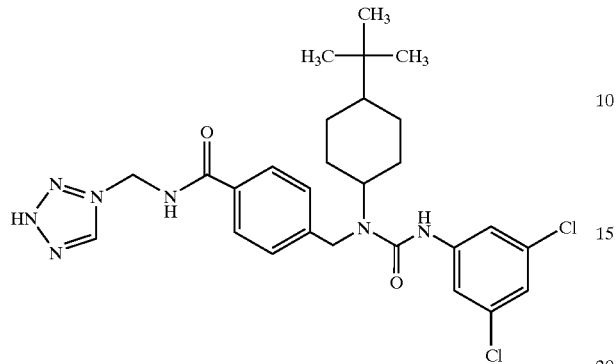

$^1$H NMR (DMSO-d$_6$): δ 0.82 (s, 9H), 0.92 (d, 1H), 1.04–1.20 (m, 2H), 1.42 (qt, 2H), 1.70 (m, 4H), 4.05 (qt, 1H), 4.61 (s, 2H), 4.73 (d, 2H), 7.12 (s, 1H), 7.34 (d, 2H), 7.62 (s, 2H), 7.83 (d, 2H), 8.70 (s, 1H), 9.18 (t, 1H).

MS (APCl, pos): 558.2, 560.2, 372.2, 343.2.

EXAMPLE 174

General Procedure (I)

4-[1-(trans-4-tert-Butylcyclohexyl)-3-(3,5-dichlorophenyl)ureidomethyl]-N-(2H-tetrazol-5-yl)benzamide

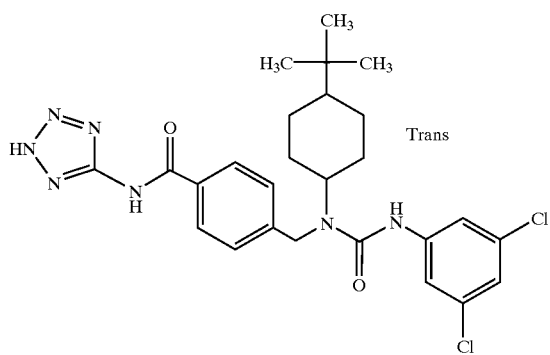

$^1$H NMR (DMSO-d$_6$): δ 0.82 (s, 9H), 1.01 (m, 1H), 1.10 (m, 2H), 1.42 (m, 2H), 1.74 (m, 4H), 4.40 (m, 1H), 4.63 (s, 2H), 7.13 (s, 1H), 7.39 (d, 2H), 7.63 (s, 2H), 8.01 (d, 2H), 8.73 (s, 1H).

MS (APCl, neg): 542.1, 544.1.

EXAMPLE 175

General Procedure (I)

4-[1-(trans-4-Cyclohexylcyclohexyl)-3-(3,5-dichlorophenyl)ureidomethyl]-N-(2H-tetrazol-5-yl)benzamide

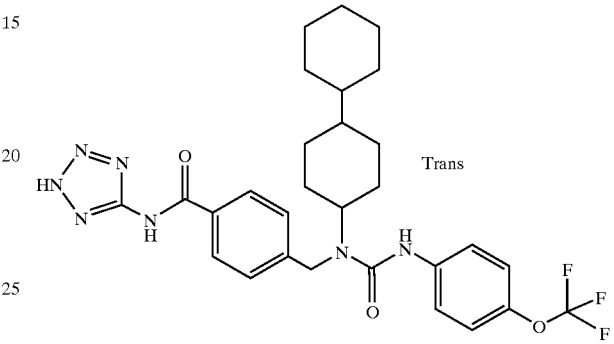

trans-4-Cyclohexylcyclohexylamine was prepared according to H. Booth, G. C. Gidley, P. R. Thornburrow, J. Chem. Soc. B, 1971, 1047–50.

The cis isomer may be prepared by reductive amination of cyclohexylcyclohexyl ketone with the appropriate amine followed by column chromatographic separation of the cis/trans isomers.

$^1$H NMR (DMSO-d$_6$): δ 0.82–1.10 (m, 10H), 1.60 (m, 2H), 1.64–1.80 (m, 8H), 4.03 (quintet, 1H), 4.64 (s, 2H), 7.22 (d, 2H), 7.41 (d, 2H), 7.54 (d, 2H), 8.03 (d, 2H), 8.56 (s, 1H), 12.32 (s, 1H), 15.90 (brd s, 1H).

MS (APCl, pos): 586.1, 587.2, 383.2, 384.2.

General Procedure (J) for the Solution Phase Synthesis of Compounds of the General Formula (Ih)

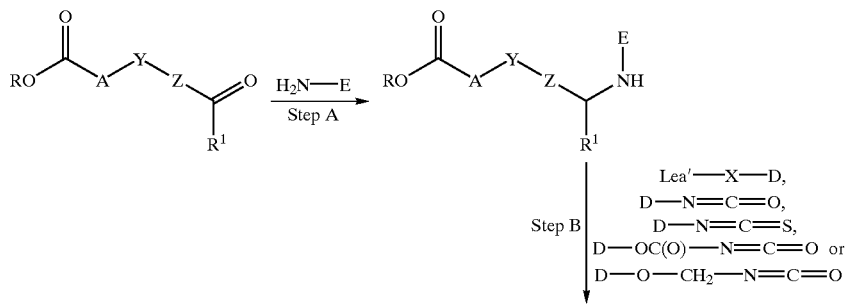

-continued

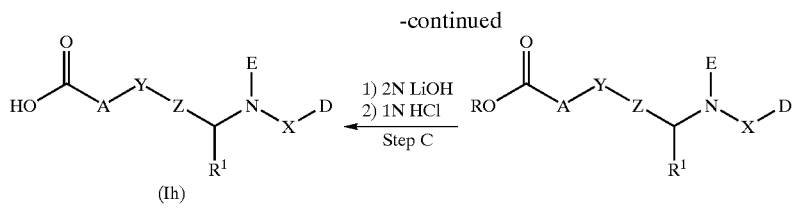

wherein
R¹, E and D are as defined for formula (I),
X is —C(O)NH—, —C(O)NH—CH₂—O—, —C(O)NH—C(O)O— or —C(S)NH—,
—A—Y— is —(CH)₂—NH—C(O)— or —(CH₂)ₙ—O—, wherein n is as defined for formula (I), and Z is as defined for formula (I),
or
—A—Y—Z— together is

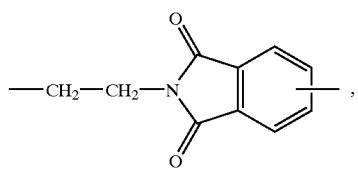

R is $C_{1-6}$-alkyl and
Lea' is a leaving group such as —OSu, chloro, phenoxy or 4-nitrophenoxy.

Step A:
The appropriate aldehyde (0.011 mmol) in $CH_2Cl_2$ was dispensed into the wells of a deepwell plate containing the desired amines in $CH_2Cl_2$. To this solution was added sodium triacetoxyborohydride (1.5 eq) followed by a catalytic amount of acetic acid. The reaction was left to proceed for 15 hours.

Step B:
To the resulting amines from step A was added the desired isocyanate or isothiocyanate or alternatively Lea'-X-D (0.011 mmol) in $CH_2Cl_2$. When using Lea'-X-D a base such as triethylamine, diisopropylethylamine, dicyclohexylmethylamine or any tertiary amine or potassium carbonate was also added. The reactions were agitated for three hours and the solvents were removed under reduced pressure to give the desired ureas or thioureas.

Step C:
The residue obtained in step B was dissolved in DMF and aqueous 2 M lithium hydroxide (10 eq.) was added into each reaction well. The samples were shaken overnight and filtered. Aqueous 1 N HCl was then added to give the desired carboxylic acids.

General Preparation of Formylarylcarboxamides as Starting Materials

The formylarylcarboxamides were prepared from the coupling of the corresponding oxoarylcarboxylic acid and the methyl or ethyl-3-aminopropionate hydrochloride according to the procedure described below.

To a solution of the formylarylcarboxylic acid in a suitable solvent such as $CH_2Cl_2$, DMF, or THF was added diisopropylethylamine (3 eq) and HBTU (1.1 eq). The reaction was allowed to stir for 30 minutes before ethyl or methyl-3-aminopropionate hydrochloride (1.1 eq) was added. The solution was stirred at room temperature for 4 hours. The solvents were evaporated under reduced pressure. The residue was taken up in ethyl acetate and 1N HCl. The organic layer was separated and washed with $H_2O$ (2×), aqueous $NaHCO_3$ (3×), brine (2×), dried over $MgSO_4$ and concentrated to give the desired product.

Methyl 3-[(4-formylbenzoyl)amino]propionate

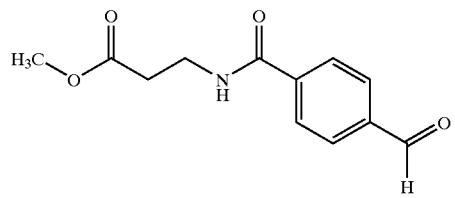

¹H NMR (DMSO-d₆): δ 2.62 (t, 2H), 3.52 (q, 2H), 3.60 (s, 3H), 8.00 (m, 4H), 8.98 (t, 1H), 10.06 (s, 1H).

MS (APCI, neg.): 234.0, 147.9

Ethyl 3-[(5-formyl-2-furoyl)aminopropionate

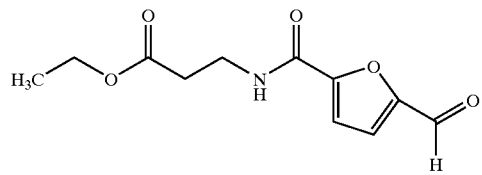

¹H NMR (DMSO-d₆): δ 1.67 (t, 3H), 2.57 (t, 2H), 3.48 (q, 2H), 4.08 (q, 2H), 7.29 (d, 1H), 7.59 (d, 1H), 8.83 (brd t, 1H), 9.69 (s, 1H).

MS (APCI, pos.): 240.1, 194.1, 152.0.

Ethyl 4-(4-formylphenoxy)butyrate

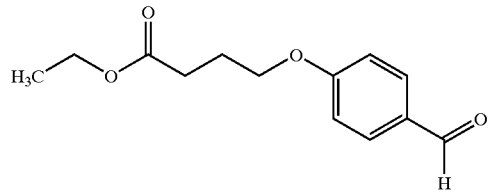

This compound was prepared according to D. R. Buckle, A. E. Fenwick, D. J. Outred, C. J. M. Rockwell, J. Chem. Res. Miniprint 12 (1987) 3144–3177.

Ethyl 3-[5-formyl-1,3-dioxo-1,3-dihydro-2H-isoindol-2-yl]propionate

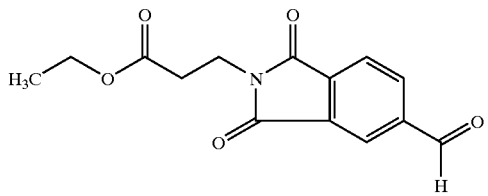

Step 1: Ethyl 3-[5-methyl-1,3-dioxo-1,3-dihydro-2H-isoindol-2-yl]propionate

A solution of 4-methylphthalic anhydride (21.3 g, 0.13 mol), ethyl 3-aminopropionate hydrochloride (20.2 g, 0.13 mol), and triethylamine (19 mL) in NMP was stirred at ambient temperature for 3 days, and heated to 130° C. for 3 hours. The mixture was diluted with water (300 mL), and extracted with ethyl acetate (3×100 mL). The combined organic extracts were washed with 1N hydrochloric acid (2×50 mL), sodium bicarbonate solution (2×50 mL), dried ($MgSO_4$), and concentrated to give 27.3 g yellow oil.

$^1$H NMR ($CDCl_3$): δ 1.21 (t, 3H), 2.50 (s, 3H), 2.70 (t, 2H), 3.97 (t, 2H), 4.17 (q, 2H). 7.51 (d, 1H), 7.64 (s, 1H), 7.71 (d, 1H).

MS (APCl, pos.): 262, 216.

Step 2: Ethyl 3-[5-bromomethyl-1,3-dioxo-1,3-dihydro-2H-isoindol-2-yl]propionate The material from step 1 (27.3 g, 0.10 mol) was dissolved in carbon tetrachloride (50 mL), and N-bromosuccinimide (19.5 g, 0.11 mol) and AIBN (200 mg) was added. The mixture was refluxed for 5 hours, filtered by suction, and the filtrate was concentrated to give 35.4 g yellow oil.

$^1$H NMR ($CDCl_3$): δ 1.23 (t, 3H), 2.50 (s, 3H), 2.72 (t, 2H), 4.00 (t, 2H), 4.13 (q, 2H), 4.55 (s, 2H), 7.71 (d, 1H), 7.82 (d, 1H), 7.87 (s, 1H).

MS (APCl, pos.): 340, 342.

Step 3: Ethyl 3-[5-formyl-1,3-dioxo-1,3-dihydro-2H-isoindol-2-yl]propionate

The crude material from step 2 was dissolved in DMSO (70 mL). Powdered $K_2HPO_4$ (18 g, 0.10 mol) and $KH_2PO_4$ (7 g, 0.05 mol) were added. The mixture was stirred at 80° C. for 5 hours, diluted with water (500 mL), and extracted with ethyl acetate (3×100 mL). The combined organic extracts were dried ($MgSO_4$), and concentrated. After column chromatography (hexane, ethyl acetate 3:1) 4.8 g of the title compound was obtained.

$^1$H NMR ($CDCl_3$): δ 1.23 (t, 3H), 2.75 (t, 2H), 4.04 (t, 2H), 4.13 (q, 2H), 8.03 (d, 1H), 8.26 (d, 1H), 8.35 (s, 1H), 10.17 (s, 1H).

MS (APCl, neg.): 275.

The following examples were prepared according to the general procedure (J).

EXAMPLE 176

General Procedure (J)

3-{4-[3-(3,5-Dichlorophenyl)-1-(3,3,5-trimethylcyclohexyl)ureidomethyl]benzoylamino)propionic acid

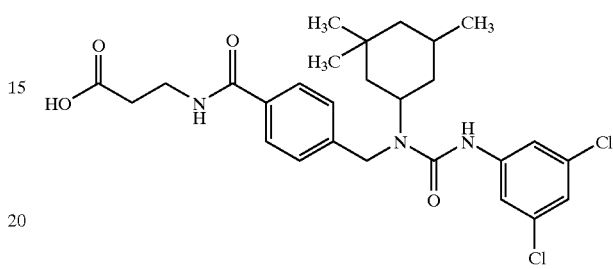

$^1$H NMR (DMSO-$d_6$): δ 1.14–1.29 (m, 5H), 1.33–1.37 (m, 1H), 1.98 (brd, 1H), 2.49 (t, 2H), 3.44 (q, 2H), 4.50 (m, 1H), 4.65 (d, 2H), 7.11 (t, 1H), 7.29 (d, 2H), 7.57 (s, 2H), 7.78 (d, 2H), 8.85 (t, 1H), 8.62 (s, 1H), 12.21 (s, 1H).

MS (APCl, pos.): 536.2, 535.2, 534.2.

EXAMPLE 177

General Procedure (J)

3-{4-[3-(3,5-Dichlorophenyl)-1-(3,5-dimethylcyclohexyl)ureidomethyl]benzoylamino)propionic acid

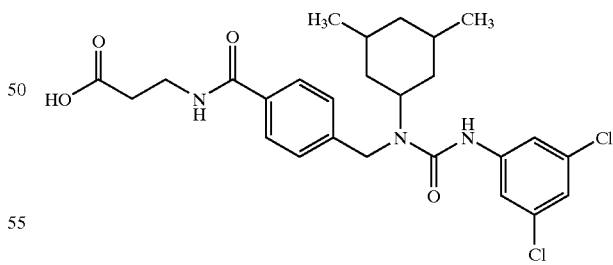

$^1$H NMR (DMSO-$d_6$): δ 0.62 (q, 1H), 0.83 (d, 6H), 1.15 (m, 2H), 1.63–1.80 (m, 5H), 2.50 (t, 2H), 3.37 (m, 2H), 4.45 (s, 1H), 4.78 (s, 2H), 7.11 (s, 1H), 7.26 (d, 2H), 7.59 (s, 2H), 7.77 (d, 2H), 8.47 (t, 1H), 8.72 (s, 1H), 12.15 (brd, 1H).

MS (APCl, pos.): 520.2

EXAMPLE 178

General Procedure (J)

3-{4-[1-(1,4-Dithiaspiro[4.5]dec-8-yl)-3-(4-trifluoromethoxyphenyl)ureidomethyl]benzoylamino)propionic acid

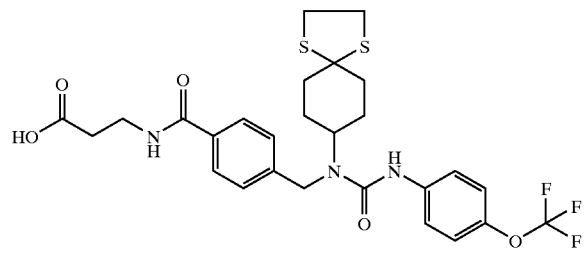

$^1$H NMR (DMSO-d$_6$): δ 1.62 (m, 4H), 2.03 (m, 4H), 3.24 (m, 4H), 3.40 (m, 2H), 4.13 (m, 1H), 4.57 (s, 2H), 7.23 (d, 2H), 7.32 (d, 2H), 7.54 (d, 2H), 7.76 (d, 2H), 8.46 (t, 1H), 8.57 (s, 1H), 12.20 (brd, 1H).

MS (APCl, pos.): 598.2.

EXAMPLE 179

General Procedure (J)

3-{4-[1-(4-Cyclohexylphenyl)-3-(4-trifluoromethoxyphenyl)ureidomethyl]benzoylamino}propionic acid

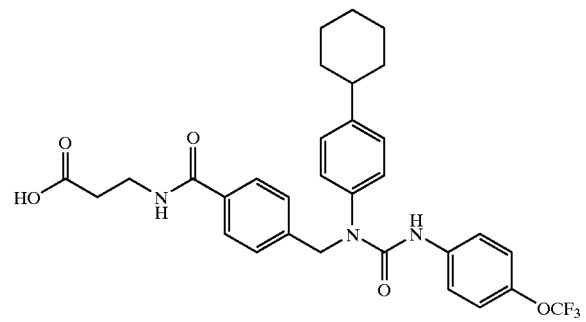

$^1$H NMR (MeOH-d$_4$): δ 1.28–1.48 (m, 5H), 1.75–1.87 (m, 5H), 2.54 (m, 1H), 2.66 (t, 2H), 3.62 (t, 2H), 4.98 (s, 2H), 7.10–7.16 (m, 4H), 7.26 (d, 2H), 7.39 (d, 2H), 7.43 (d, 2H), 7.75 (d, 2H).

MS (APCl, pos): 584.2, 585.2, 586.2.

The following examples 180 to 229 were all found to displace more than 50% of the glucagon tracer when screened at 1 μM concentration in the glucagon binding assay II. The compounds are all expected to be present in the library.

EXAMPLE 180

General Procedure (J)

3-{4-[1-[2-(3-Chlorophenyl)ethyl]-3-(4-trifluoromethoxyphenyl)ureidomethyl]benzoylamino}propionic acid

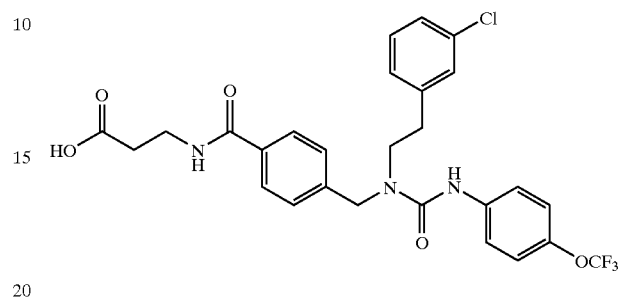

EXAMPLE 181

General Procedure (J)

3-{4-[1-[2-(3-Chlorophenyl)ethyl]-3-(4-chloro-3-trifluoromethylphenyl)ureidomethyl]benzoylamino}propionic acid

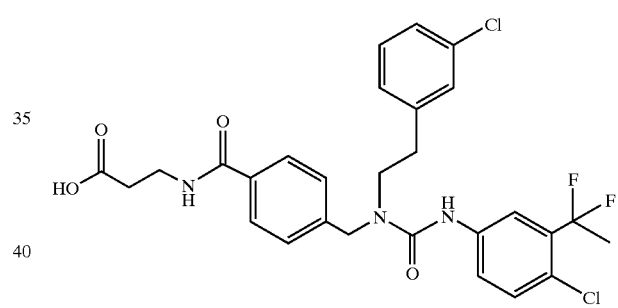

EXAMPLE 182

General Procedure (J)

3-{4-[1-(2-Mercaptobenzothiazol-6-yl)-3-(4-trifluoromethoxyphenyl)ureidomethyl]benzoylamino}propionic acid

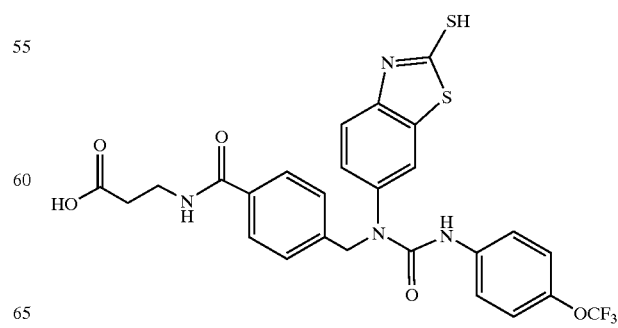

EXAMPLE 183

General Procedure (J)

3-{4-[3-(4-Chloro-3-trifluoromethylphenyl)-1-(2-mercaptobenzothiazol-6-yl)ureidomethyl]benzoylamino}propionic acid

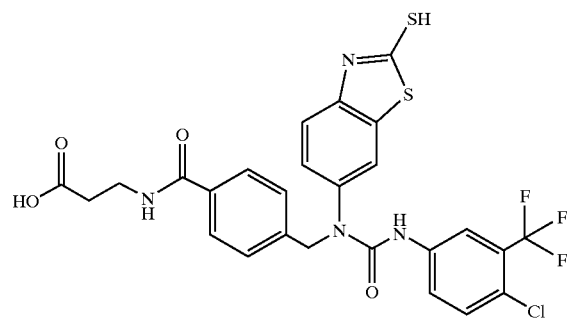

EXAMPLE 184

General Procedure (J)

4-{3-(Benzo[1,3]dioxo-5-yl)-3-[4-(2-carboxyethylcarbamoyl)benzyl]ureido}benzoic acid

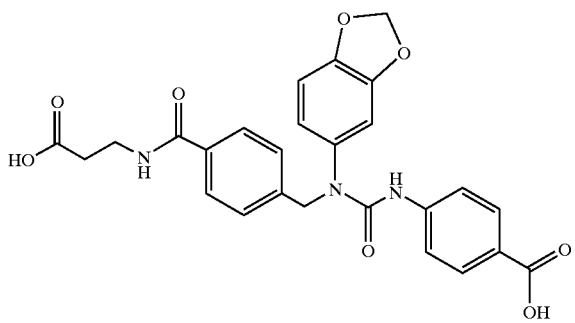

EXAMPLE 185

General Procedure (J)

3-{4-[3-(4-Chloro-3-trifluoromethylphenyl)-1-(4-cyclohexylphenyl)ureidomethyl]benzoylamino}propionic acid

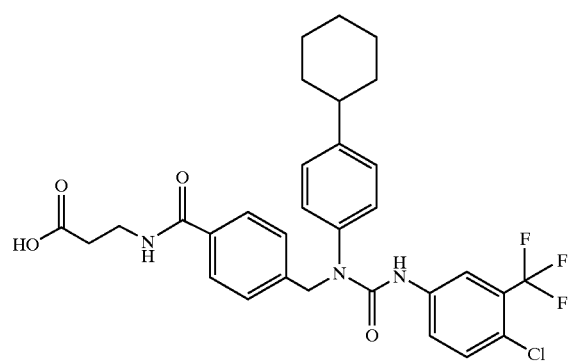

EXAMPLE 186

General Procedure (J)

3-{4-[1-(4-Cyclohexylphenyl)-3-(3,5-dimethylphenyl)ureidomethyl]benzoylamino}propionic acid

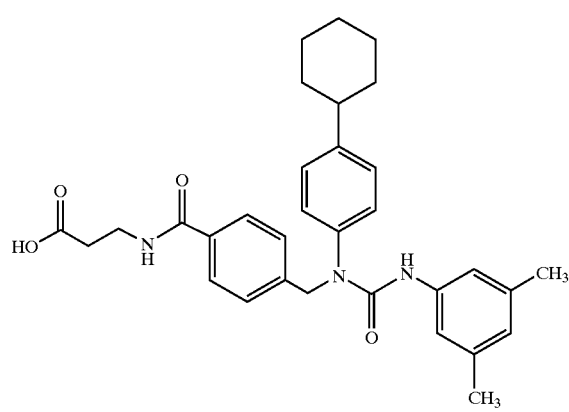

EXAMPLE 187

General Procedure (J)

3-{4-[1-(2-Phenylcyclopropyl)-3-(4-trifluoromethoxyphenyl)ureidomethyl]benzoylamino}propionic acid

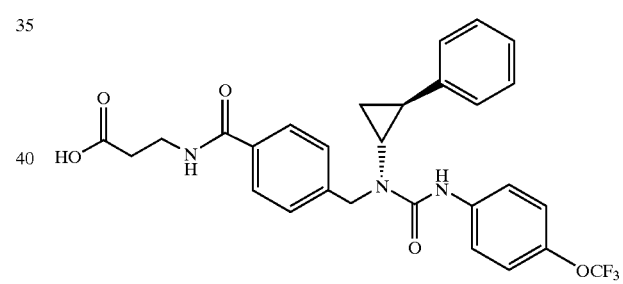

EXAMPLE 188

General Procedure (J)

3-{4-[3-(4-Chloro-3-trifluoromethylphenyl)-1-(2-phenylcyclopropyl)ureidomethyl]benzoylamino}propionic acid

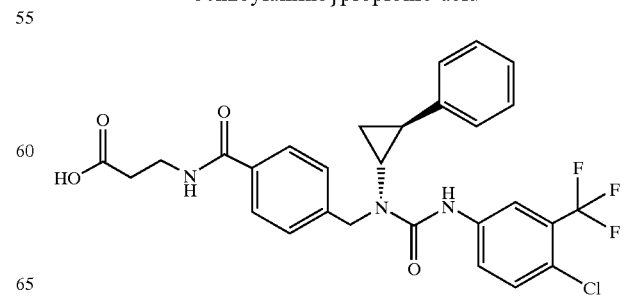

EXAMPLE 189

General Procedure (J)

3-{4-[3-(4-Chloro-3-trifluoromethylphenyl)-1-(2-cyclohexyl-1-hydroxymethylethyl)ureidomethyl]benzoylamino}propionic acid

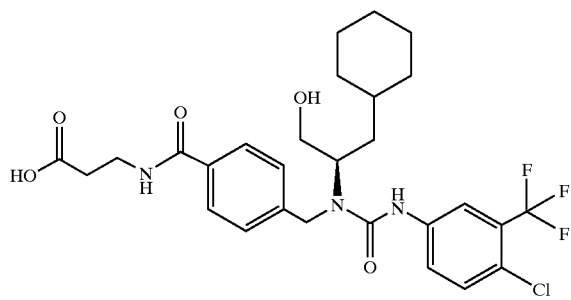

EXAMPLE 190

General Procedure (J)

3-{4-[1-(4-Bromobenzyl)-3-(4-chloro-3-trifluoromethylphenyl)ureidomethyl]benzoylamino}propionic acid

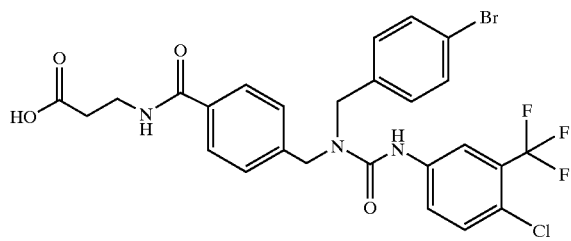

EXAMPLE 191

General Procedure (J)

3-{4-[3-(4-Chloro-3-trifluoromethyl-phenyl)-1-(2,2,3,3-tetrafluoro-2,3-dihydrobenzo[1,4]-dioxin-6-yl)ureidomethyl]benzoylamino}propionic acid

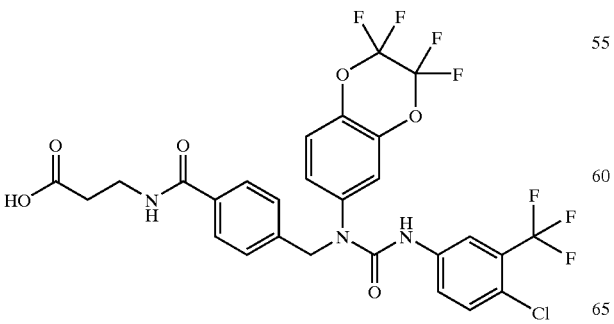

EXAMPLE 192

General Procedure (J)

3-(4-{3-(4-Chloro-3-trifluoromethylphenyl)-1-[4-(2,2,2-trifluoroacetylamino)cyclohexyl]ureidomethyl}benzoylamino)propionic acid

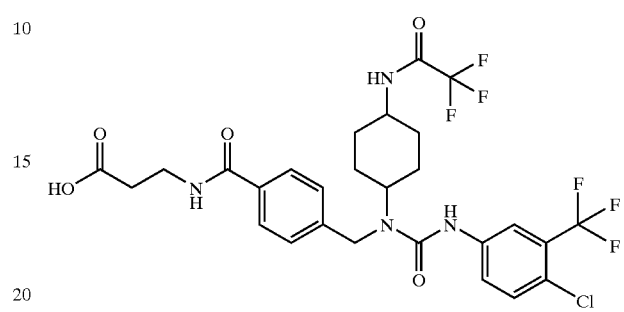

EXAMPLE 193

General Procedure (J)

3-(4-{3-(4-Chloro-3-trifluoromethylphenyl)-1-[3-(2-methylpiperidin-1-yl)propyl]ureidomethyl}benzoylamino)propionic acid

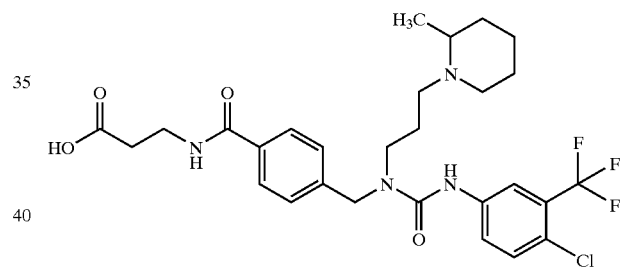

EXAMPLE 194

General Procedure (J)

3-{4-[1-(1-Acetyl-2,3-dihydro-1H-indol-5-yl)-3-(4-chloro-3-trifluoromethylphenyl)ureidomethyl]benzoylamino}propionic acid

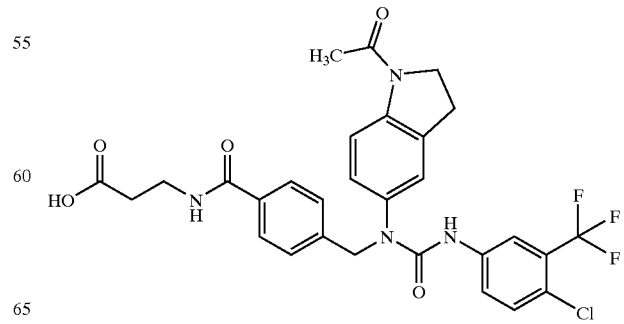

EXAMPLE 195

General Procedure (J)

3-{4-[3-(4-Chloro-3-trifluoromethylphenyl)-1-(5,6-dichloro-1H-benzimidazol-2-yl)ureidomethyl]benzoylamino}propionic acid

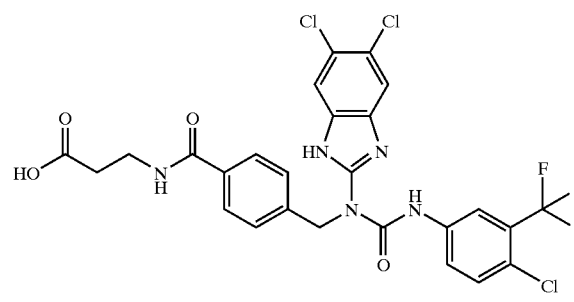

EXAMPLE 196

General Procedure (J)

4-{3-(4-tert-Butylcyclohexyl)-3-[4-(2-carboxyethylcarbamoyl)benzyl]ureido}benzoic acid

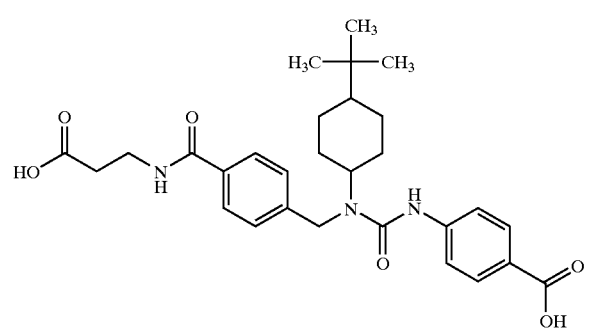

EXAMPLE 197

General Procedure (J)

3-{4-[1-(4-tert-Butylcyclohexyl)-3-(3,5-dimethylphenyl)ureidomethyl]benzoylamino}propionic acid

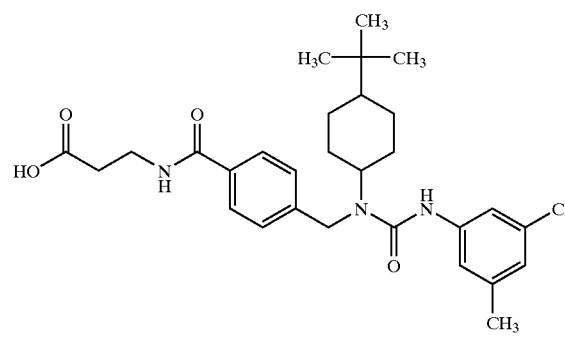

EXAMPLE 198

General Procedure (J)

4-{4-[1-(4-tert-Butylcyclohexyl)-3-(3-trifluoromethylsulfanylphenyl)ureidomethyl]phenoxy}butyric acid

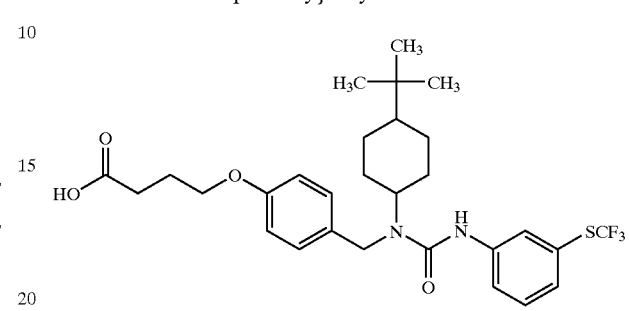

EXAMPLE 199

General Procedure (J)

3-{4-[1-(4-tert-Butylcyclohexyl)-3-(3-trifluoromethylsulfanylphenyl)ureidomethyl]benzoylamino}propionic acid

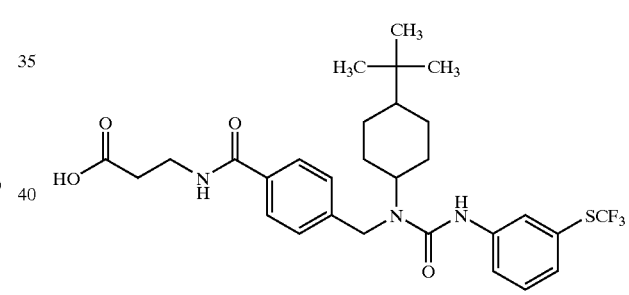

EXAMPLE 200

General Procedure (J)

3-{4-[1-(4-tert-Butylcyclohexyl)-3-(4-ethoxyphenyl)ureidomethyl]benzoylamino}propionic acid

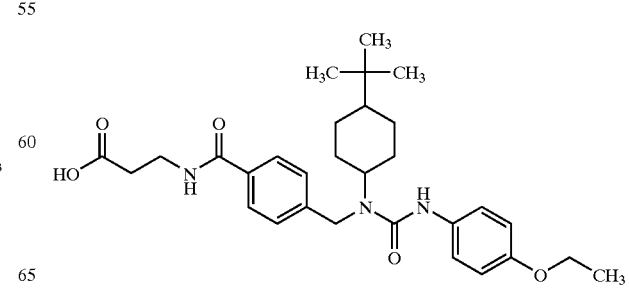

EXAMPLE 201

General Procedure (J)

3-{4-[1-[2-(3-Chlorophenyl)ethyl]-3-(3-trifluoromethylsulfanylphenyl)ureidomethyl]benzoylamino}propionic acid

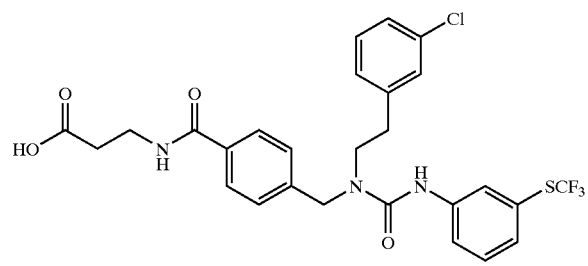

EXAMPLE 202

General Procedure (J)

3-{4-[1-(4-Cyclohexylphenyl)-3-(3-trifluoromethylsulfanylphenyl)ureidomethyl]benzoylamino}propionic acid

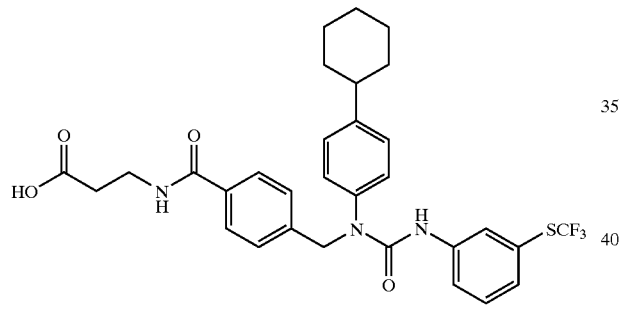

EXAMPLE 203

General Procedure (J)

3-{4-[1-(4-Cyclohexylphenyl)-3-(naphthalen-2-yloxymethyl)ureidomethyl]benzoylamino}propionic acid

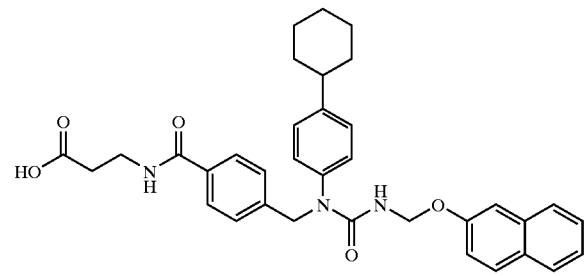

EXAMPLE 204

General Procedure (J)

3-{4-[1-(6,6-Dimethylbicyclo[3.1.1]hept-2-ylmethyl)-3-(3-trifluoromethylsulfanylphenyl)ureidomethyl]benzoylamino}propionic acid

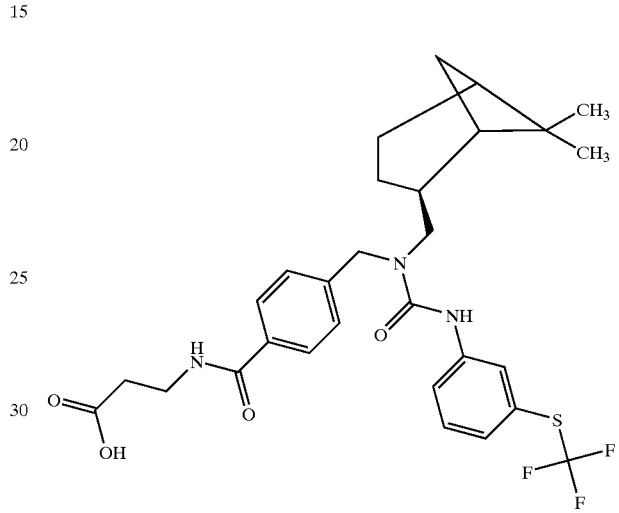

EXAMPLE 205

General Procedure (J)

3-{4-[3-(Naphthalen-2-yloxymethyl)-1-(2,2,3,3-tetrafluoro-2,3-dihydro-benzo[1,4]dioxin-6-yl)ureidomethyl]benzoylamino}propionic acid

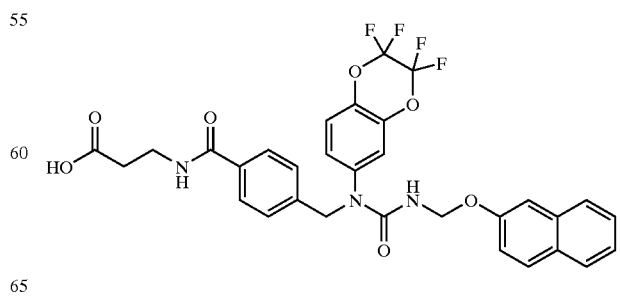

EXAMPLE 206

General Procedure (J)

3-{4-[1-(1-Acetyl-2,3-dihydro-1H-indol-5-yl)-3-(naphthalen-2-yloxymethyl)ureidomethyl]benzoylamino}propionic acid

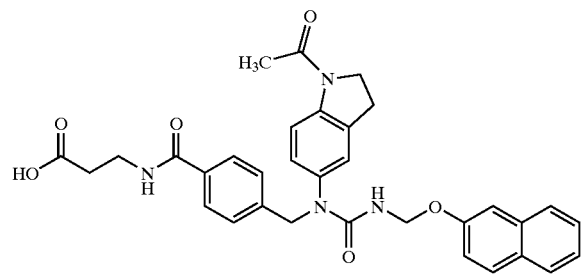

EXAMPLE 207

General Procedure (J)

3-{4-[1-[2-(N-tert-Butoxycarbonyl-N-methylamino)ethyl]-3-(3-trifluoromethylsulfanylphenyl)ureidomethyl]benzoylamino}propionic acid

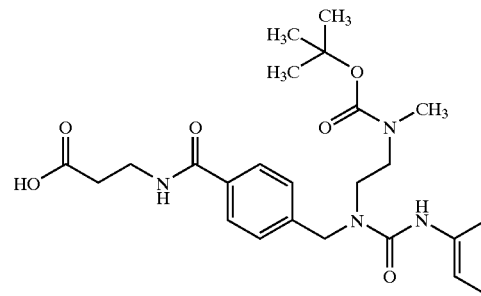

EXAMPLE 208

General Procedure (J)

3-{4-[1-(4-tert-Butylcyclohexyl)-3-(phenoxycarbonyl)ureidomethyl]benzoylamino}propionic acid

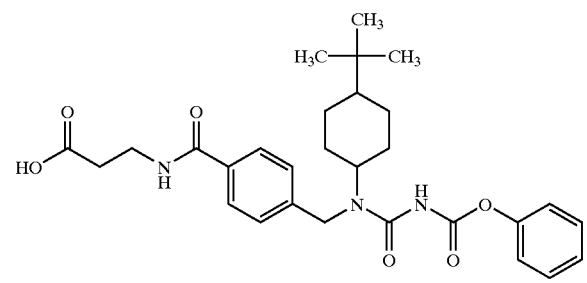

EXAMPLE 209

General Procedure (J)

3-{4-[1-(4-tert-Butylcyclohexyl)-3-(2-methyl-1,3-dioxo-2,3-dihydro-1H-isoindol-5-yl)ureidomethyl]benzoylamino}propionic acid

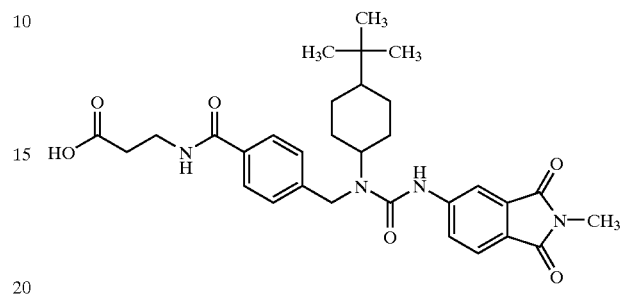

EXAMPLE 210

General Procedure (J)

3-({5-[1-(4-cyclohexylphenyl)-3-(3-trifluoromethylsulfanylphenyl)ureidomethyl]furan-2-carbonyl}amino)propionic acid

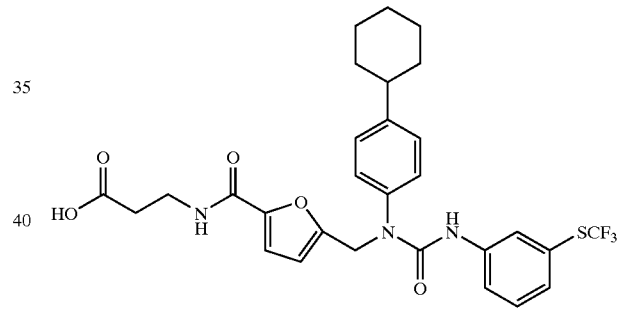

EXAMPLE 211

General Procedure (J)

3-({5-[1-(4-tert-Butylcyclohexyl)-3-(3-trifluoromethylsulfanylphenyl)ureidomethyl]furan-2-carbonyl}amino)propionic acid

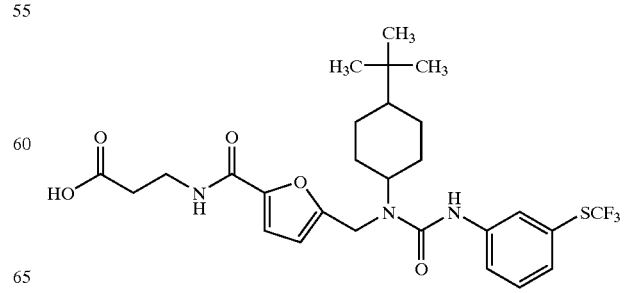

EXAMPLE 212

General Procedure (J)

3-({5-[3-(4-Chloro-3-trifluoromethylphenyl)-1-(4-cyclohexylphenyl)ureidomethyl]furan-2-carbonyl}amino)propionic acid

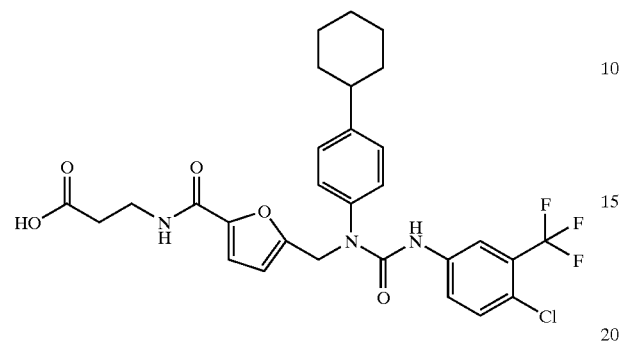

EXAMPLE 213

General Procedure (J)

3-({5-[1-(4-tert-Butylcyclohexyl)-3-(4-chloro-3-trifluoromethylphenyl)ureidomethyl]furan-2-carbonyl}amino)propionic acid

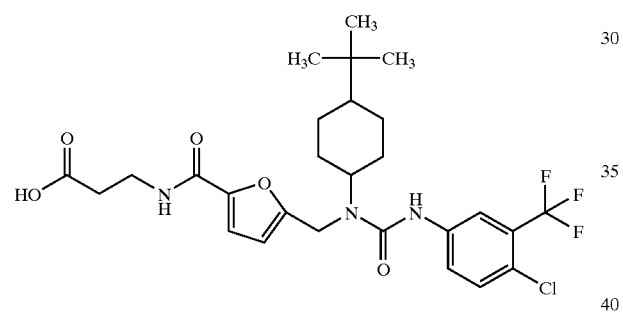

EXAMPLE 214

General Procedure (J)

4-{4-[1-(6,6-Dimethylbicyclo[3.1.1]hept-2-ylmethyl)-3-(4-trifluoromethoxyphenyl)ureidomethyl]phenoxy}butyric acid

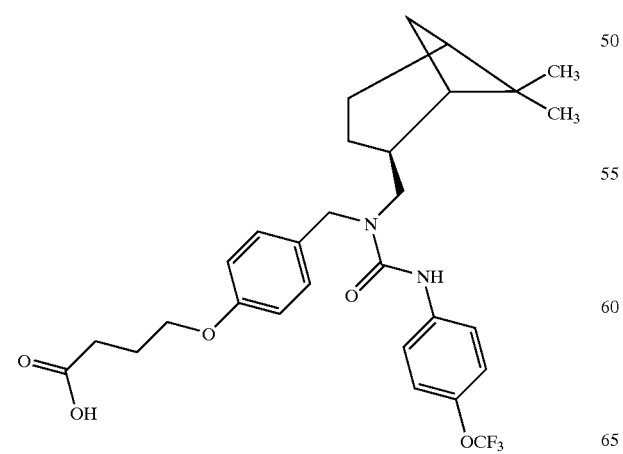

EXAMPLE 215

General Procedure (J)

4-{4-[3-(4-Chloro-3-trifluoromethylphenyl)-1-(6,6-dimethylbicyclo[3.1.1]hept-2-ylmethyl)ureidomethyl]phenoxy}butyric acid

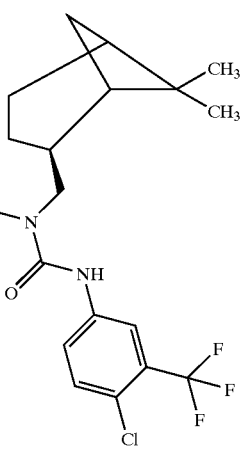

EXAMPLE 216

General Procedure (J)

4-{4-[1-(4-Cyclohexylphenyl)-3-(4-trifluoromethoxyphenyl)ureidomethyl]phenoxy}butyric acid

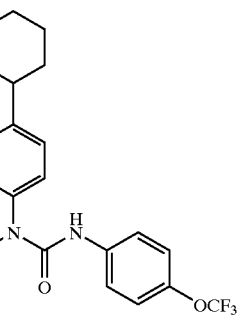

EXAMPLE 217

General Procedure (J)

4-{4-[3-(4-Chloro-3-trifluoromethylphenyl)-1-(4-cyclohexylphenyl)ureidomethyl]phenoxy}butyric acid

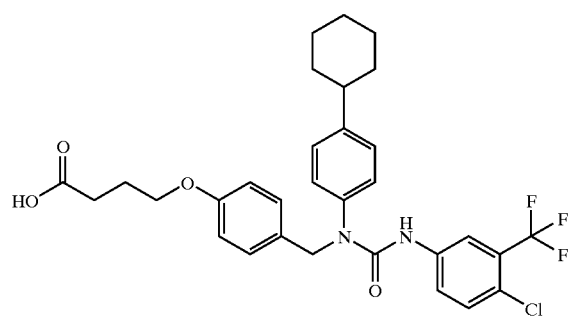

EXAMPLE 218

General Procedure (J)

4-[3-[4-(3-Carboxypropoxy)benzyl]-3-(4-cyclohexylphenyl)ureido]benzoic acid

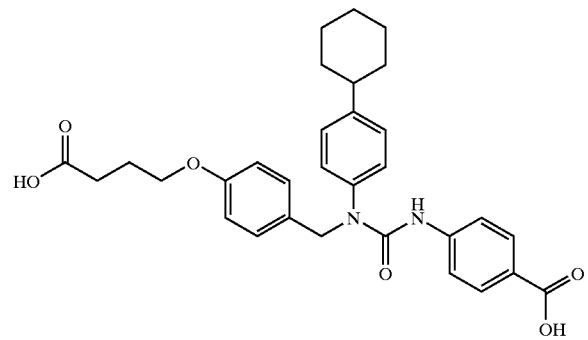

EXAMPLE 219

General Procedure (J)

4-{4-[1-(4-Cyclohexylphenyl)-3-(3,5-dimethylphenyl)ureidomethyl]phenoxy}butyric acid

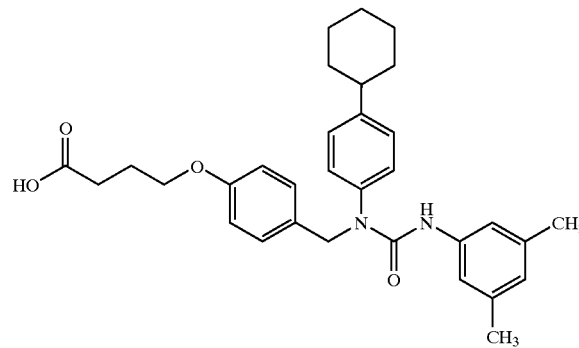

EXAMPLE 220

General Procedure (J)

5-[3-[4-(3-Carboxypropoxy)benzyl]-3-(4-cyclohexylphenyl)ureido]isophthalic acid

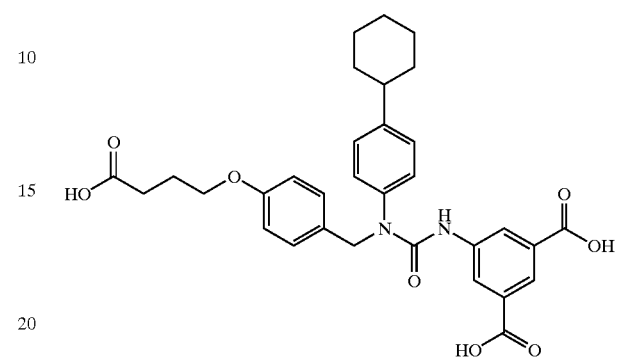

EXAMPLE 221

General Procedure (J)

4-{4-[3-(4-Chloro-3-trifluoromethylphenyl)-1-(5-methoxythiazolo[5,4-b]pyridin-2-yl)ureidomethyl]phenoxy}butyric acid

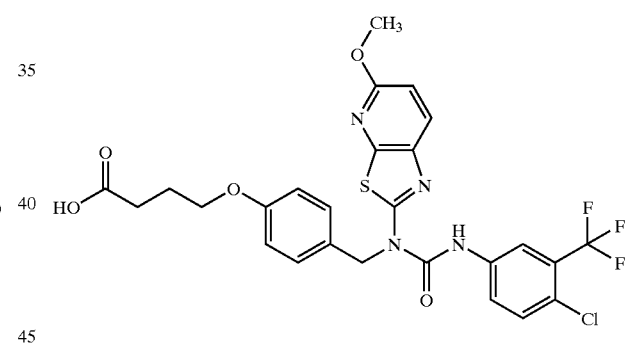

EXAMPLE 222

General Procedure (J)

4-{4-[1-(2-Phenylcyclopropyl)-3-(4-trifluoromethoxyphenyl)ureidomethyl]phenoxy}butyric acid

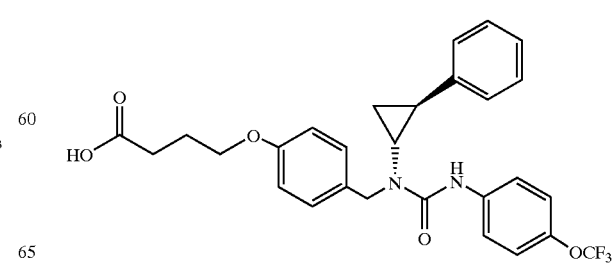

EXAMPLE 223

General Procedure (J)

4-{4-[3-(4-Chloro-3-trifluoromethylphenyl)-1-(2-phenylcyclopropyl)ureidomethyl]phenoxy}butyric acid

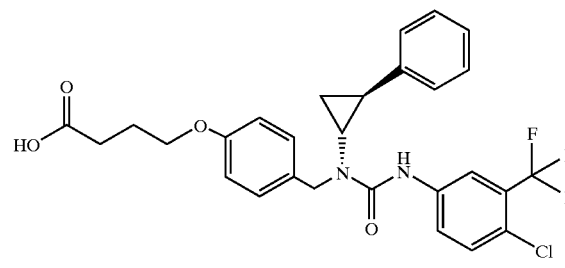

EXAMPLE 224

General Procedure (J)

4-{4-[1-(4-tert-Butylcyclohexyl)-3-(4-trifluoromethoxyphenyl)ureidomethyl]phenoxy}butyric acid

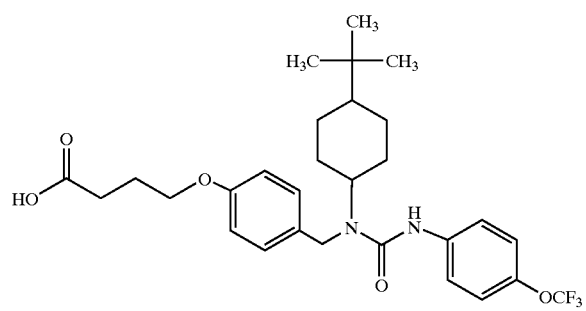

EXAMPLE 225

General Procedure (J)

4-{4-[1-(4-tert-Butylcyclohexyl)-3-(4-chloro-3-trifluoromethylphenyl)ureidomethyl]phenoxy}butyric acid

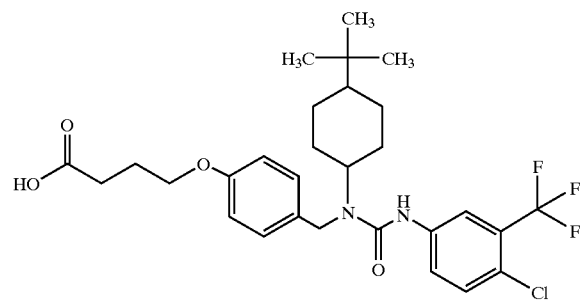

EXAMPLE 226

General Procedure (J)

4-{3-(4-tert-Butylcyclohexyl)-3-[4-(3-carboxypropoxy)benzyl]ureido}benzoic acid

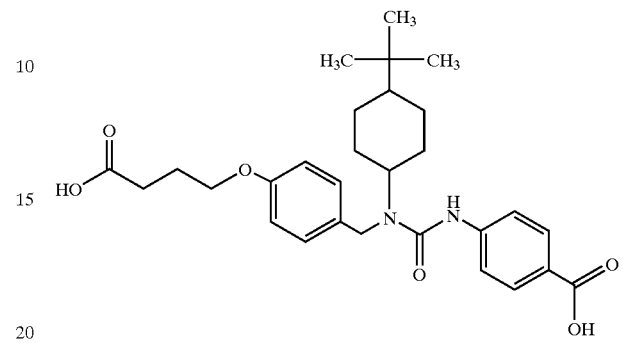

EXAMPLE 227

General Procedure (J)

4-{4-[1-(4-tert-Butylcyclohexyl)-3-(3,5-dimethylphenyl)ureidomethyl]phenoxy}butyric acid

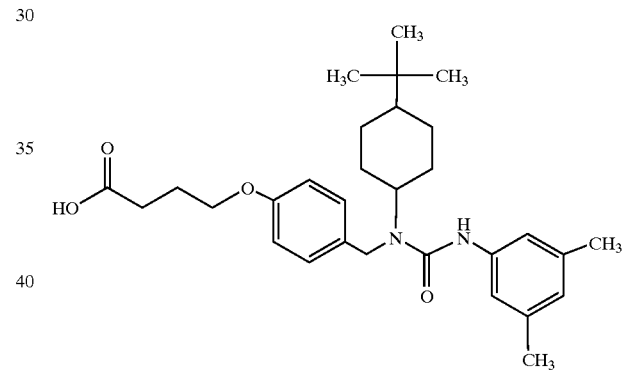

EXAMPLE 228

General Procedure (J)

3-{5-[1-(2-Mercaptobenzothiazol-6-yl)-3-(4-trifluoromethoxyphenyl)ureidomethyl]-1,3-dioxo-1,3-dihydro-isoindol-2-yl}propionic acid

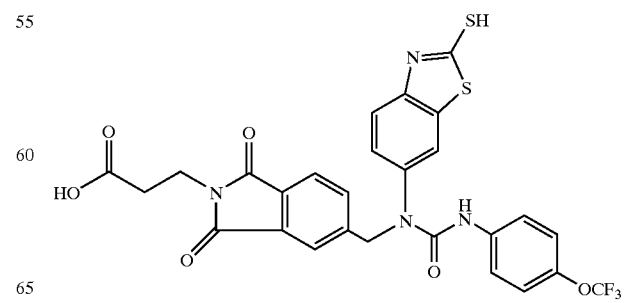

EXAMPLE 229

General Procedure (J)

3-{5-[3-(4-Chloro-3-trifluoromethylphenyl)-1-(2-mercaptobenzothiazol-6-yl)ureidomethyl]1,3-dioxo-1,3-dihydro-isoindol-2-yl}propionic acid

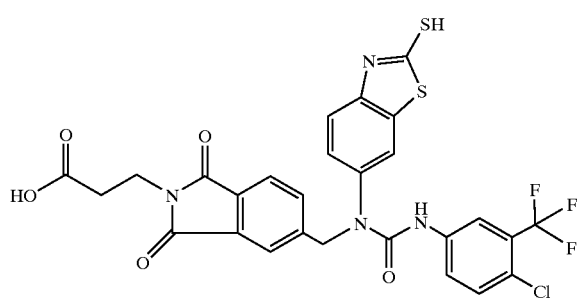

EXAMPLE 230

General Procedure (J)

3-{4-[1-(4-tert-Butylcyclohexyl)-3-(4-chlorophenyl)ureidomethyl]benzoylamino}propionic acid

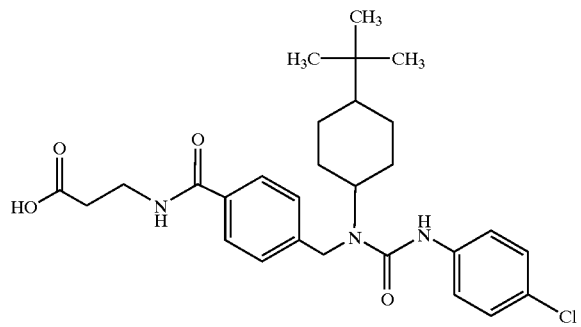

$^1$H NMR (DMSO-d$_6$): δ 0.80 (s, 9H), 0.94 (m, 1H), 1.11 (qt, 2H), 1.39 (qt, 2H), 1.69 (m, 4H), 2.45 (t, 2H), 3.44 (qt, 2H), 4.05 (m, 1H), 4.59 (s, 2H), 7.27 (d, 2H), 7.31 (d, 2H), 7.48 (d, 2H), 7.45 (d, 2H), 8.44 (t, 1H), 8.47 (s, 1H), 12.30 (brd s, 1H).

MS (APCl, pos): 516.2, 514.2, 361.2, 362.2, 289.2.

EXAMPLE 231

General Procedure (J)

3-{4-[1-(2-Phenylcyclopropyl)-3-(4-trifluoromethoxyphenyl)ureidomethyl]benzoylamino}propionic acid

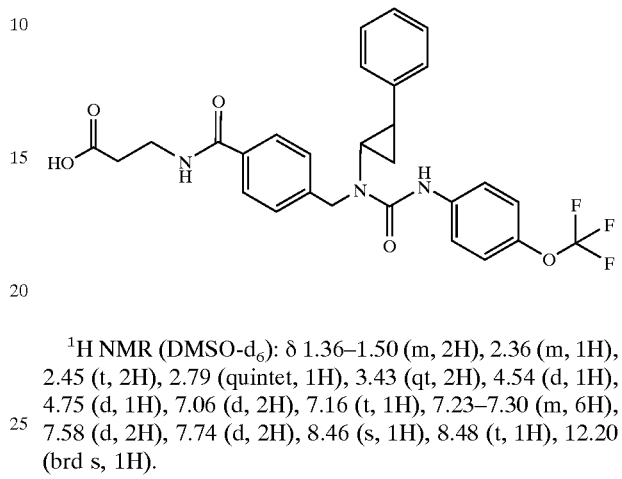

$^1$H NMR (DMSO-d$_6$): δ 1.36–1.50 (m, 2H), 2.36 (m, 1H), 2.45 (t, 2H), 2.79 (quintet, 1H), 3.43 (qt, 2H), 4.54 (d, 1H), 4.75 (d, 1H), 7.06 (d, 2H), 7.16 (t, 1H), 7.23–7.30 (m, 6H), 7.58 (d, 2H), 7.74 (d, 2H), 8.46 (s, 1H), 8.48 (t, 1H), 12.20 (brd s, 1H).

MS (APCl, pos): 542.2, 543.2, 544.2, 339.1.

EXAMPLE 232

General Procedure (J)

3-{4-[1-(4-Cyclohexylphenyl)-3-(3,5-dichlorophenyl)ureidomethyl]benzoylamino}propionic acid

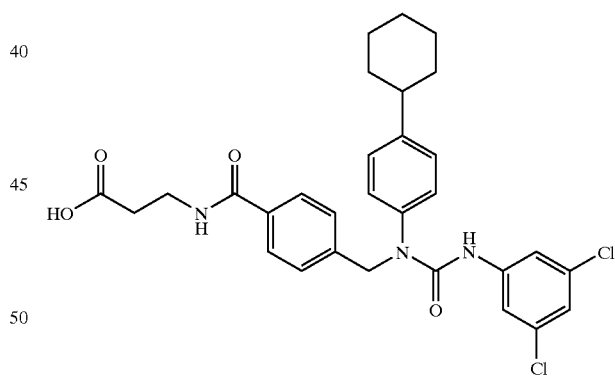

$^1$H NMR (DMSO-d$_6$): δ 1.10–1.42 (m, 5H), 1.60–1.80 (m, 5H), 2.45 (t, 2H), 3.43 (qt, 2H), 4.92 (s, 2H), 7.12–7.20 (M, 5H), 7.30 (d, 2H), 7.58 (s, 2H), 7.74 (d, 2H), 8.46 (t, 1H), 8.55 (s, 1H).

MS (APCl, pos): 568.2, 569.2, 570.2, 571.2.

Alternative Method for the Preparation of the Compound

To a solution of 4-formylbenzoic acid (27.4 g, 0.18 mol) in DMF (300 mL) was added N-ethyl-N'-3-dimethylaminopropylcarbodiimide (34.5 g, 0.18 mol) and N-hydroxybenzotriazole (29.9 g, 0.22 mol). The resulting mixture was stirred at room temperature for 1 hour, then β-alanine ethyl ester hydrochloride (65.4 g, 0.42 mol) and diisopropylethylamine (76 mL, 0.44 mol) was added. After 16 hours stirring at ambient temperature the reaction mixture was partitioned between water (600 mL) and ethyl acetate (600 mL). The organic phase was washed successively with hydrochloric acid (1N, 300 mL), saturated aqueous ammonium chloride (300 mL), water (2×300 mL) and brine (300 mL). The solvent was removed by rotary evaporation to leave an oil, which crystallised upon standing to afford 29.0 g (65%) of 3-(4-formylbenzoylamino)propionic acid ethyl ester.

$^1$H NMR (DMSO-d$_6$): δ 1.18 (t, 3H); 2.62 (t, 2H); 3.54 (q, 2H); 4.09 (q, 2H); 8.00 (s, 4H); 8.78 (t, 1H); 10.08 (s, 1H).

To a well stirred solution of 3-(4-formylbenzoylamino) propionic acid ethyl ester (13.8 g, 55.3 mmol) in ethanol (150 mL) was added a solution of 4-cyclohexylaniline (9.70 g, 55.3 mmol) in ethanol (75 mL). The mixture was heated to reflux for 30 minutes, and then acetic acid (50 mL) and sodium cyanoborohydride (3.50 g, 55.5 mmol) were added. After 10 minutes of additional heating, the mixture was cooled on an ice-bath. The solid precipitate was collected by filtration, washed several times with cold water and dried in a vacuum oven overnight to afford 18.16 g (80%) of 3-{4-[(4-cyclohexylphenylamino)methyl] benzoylamino}propionic acid ethyl ester.

$^1$H NMR (CDCl$_3$): δ 1.28 (t, 3H); 1.35 (m, 5H); 1.78 (m, 5H); 2.38 (m, 1H); 2.64 (t, 2H); 3.74 (q, 2H); 4.18 (q, 2H); 4.36 (s, 2H); 6.53 (d, 2H); 6.81 (bt, 1H); 7.00 (d, 2H); 7.43 (d, 2H); 7.72 (d, 2H).

3-{4-[(4-Cyclohexylphenylamino)methyl] benzoylamino}propionic acid ethyl ester (15.0 g, 0.37 mol) was dissolved in dichloromethane (250 mL), and 3,5-dichlorophenylisocyanate (6.9 g, 0.37 mol) was added. The mixture was stirred overnight at room temperature. The solvent was removed by rotary evaporation, and the crystalline residue was re-dissolved in ethanol (400 mL). Sodium hydroxide (100 mL, 4N) was added, and the reaction mixture was left at room temperature for 30 min. Water (600 mL) was added and the mixture was cooled on an ice bath. The clear solution was then acidified with hydrochloric acid (100 mL, 4N), and the resulting precipitate subsequently collected by filtration. Recrystallisation from acetonitrile/water afforded 15.5 g of the title compound as a white powder.

$^1$H NMR (DMSO-d$_6$): δ 1.36 (m, 5H); 1.78 (m, 6H); 2.50 (t, 2H); 3.44 (q, 2H); 4.92 (s, 2H); 7.12 (d, 1H); 7.16 (d, 2H); 7.21 (d, 2H); 7.32 (d, 2H); 7.60 (d, 2H); 7.75 (d, 2H); 8.45 (t, 1H); 8.53 (s, 1H); 12.20 (bs, 1H).

EXAMPLE 233

General Procedure (J)

3-{4-[1-(4-Cyclohexylphenyl)-3-(4-trifluoromethylsulfanylphenyl)ureidomethyl] benzoylamino}propionic acid

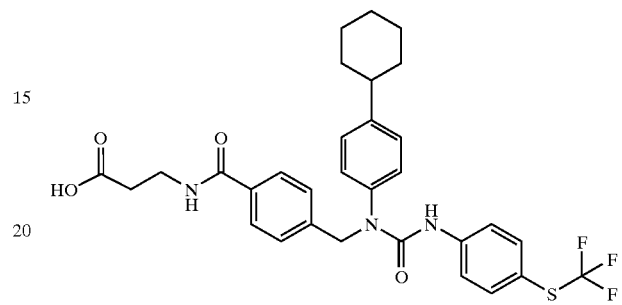

$^1$H NMR (DMSO-d$_6$): δ 1.10–1.35 (m, 5H), 1.50–1.75 (m, 5H), 2.40 (m, 1H), 2.47 (t, 2H), 3.45 (t, 2H), 4.81 (s, 2H), 6.98 (d, 2H), 7.10 (d, 2H), 7.21 (d, 2H), 7.33 (d, 2H), 7.36 (d, 2H), 7.57 (d, 2H).

MS (APCl, pos): 600.2, 601.2, 602.2.

EXAMPLE 234

General Procedure (J)

3-{4-[1-([(1S,2R,5R)-6,6-Dimethylbicyclo[3.1.1] hept-2-yl]methyl)-3-(4-trifluoromethoxyphenyl) ureidomethyl]benzoylamino}propionic acid

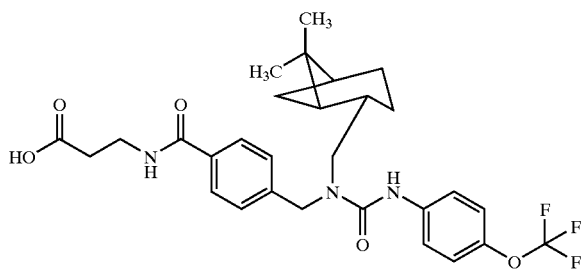

$^1$H NMR (MeOH-d$_4$): δ 0.90 (d, 1H), 1.05 (s, 3H), 1.15 (s, 3H), 1.49 (m, 1H), 1.80–1.95 (m, 5H), 2.36–2.47 (m, 2H), 2.62 (t, 2H), 3.40 (d, 2H), 3.61 (t, 2H), 4.70 (qt, 2H), 7.16 (d, 2H), 7.35 (d, 2H), 7.41 (d, 2H), 7.78 (d, 2H).

MS (APCl, pos): 562.2, 563.1.

EXAMPLE 235

General Procedure (J)

3-{4-[1-(trans-4-tert-Butylcyclohexyl)-3-(4-(trifluoromethoxysulfanylphenyl)ureidomethyl]benzoylamino}propionic acid

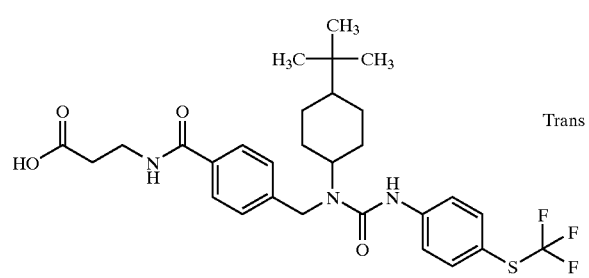

Trans $^1$H NMR (CDCl$_3$): δ 0.80 (s, 9H), 0.90 (d, 1H), 1.20 (qt, 2H), 1.40 (qt, 2H), 1.90 (t, 4H), 2.75 (t, 2H), 3.70 (qt, 2H), 4.10 (brd t, 1H), 4.50 (s, 2H), 6.50 (s, 1H), 6.90 (t, 1H), 7.20 (d, 2H), 7.40 (d, 2H), 7.50 (d, 2H), 7.70 (d, 2H).

MS (APCl, pos): 580.2, 581.2.

EXAMPLE 236

General Procedure (J)

3-{4-[1-tert-Butylcyclohexyl)-3-(4-chloro-3-trifluoromethylphenyl)ureidomethyl]benzoylamino}propionic acid

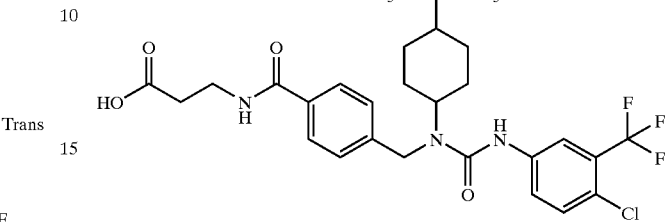

$^1$H NMR (DMSO-d$_6$): δ 0.78 (s, 9H), 1.10 (m, 1H), 1.33 (m, 2H), 1.50 (m, 4H), 1.75 (m, 2H), 2.40 (t, 2H), 3.43 (qt, 2H), 4.24 (quintet, 1H), 4.69 (s, 2H), 7.27 (d, 2H), 7.53 (d, 1H), 7.74–7.79 (m, 3H), 8.03 (s, 1H), 8.45 (t, 1H), 8.85 (s, 1H); 12.00 (brd s, 1H).

MS (APCl, pos): 582.2, 361.2.

General Procedure (K) for the Solution Phase Synthesis of Compounds of the General Formula (Ii)

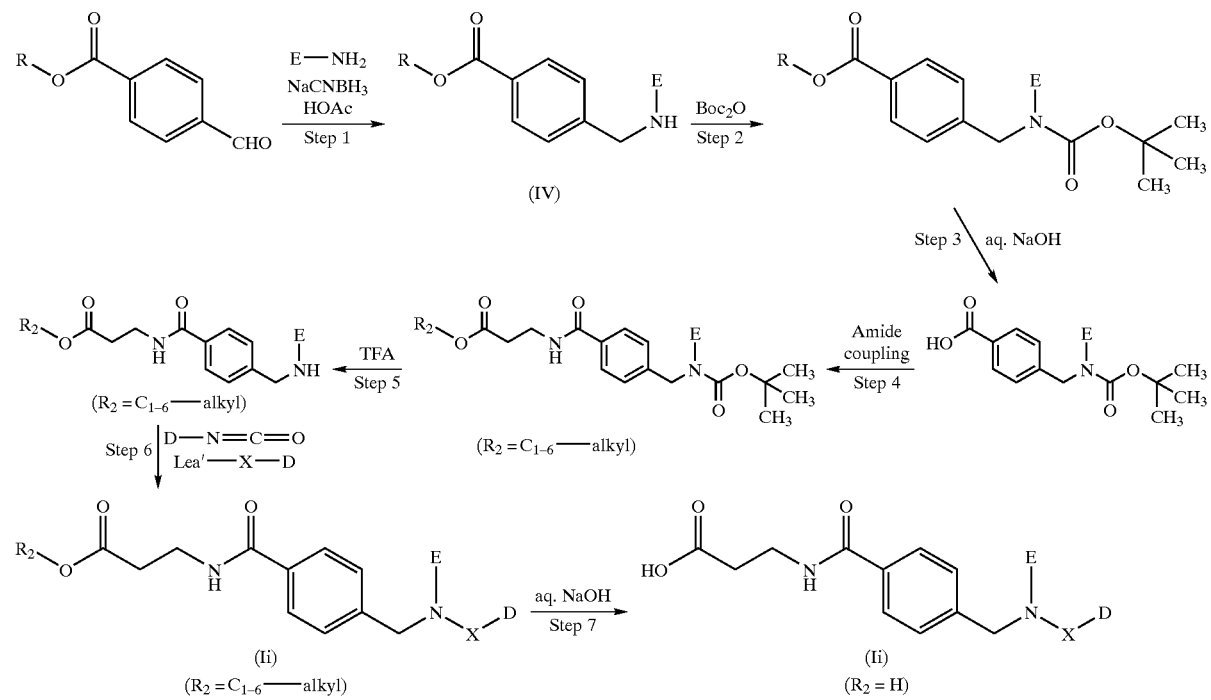

wherein R is C$_{1-6}$-alkyl,
V, X, D, and E are as defined in general formula (I), and
Lea' is a leaving group such as —OSu, chloro, phenoxy, or 4-nitrophenoxy.

In case the intermediate of the formula (IV) is a mixture of isomers, separation of these can either be performed by column chromatography of the intermediate of the formula (IV) or crystallisation of the intermediate imine.

Step 1: trans-4-[(4-tert-Butylcyclohexylamino)methyl]benzoic acid methyl ester

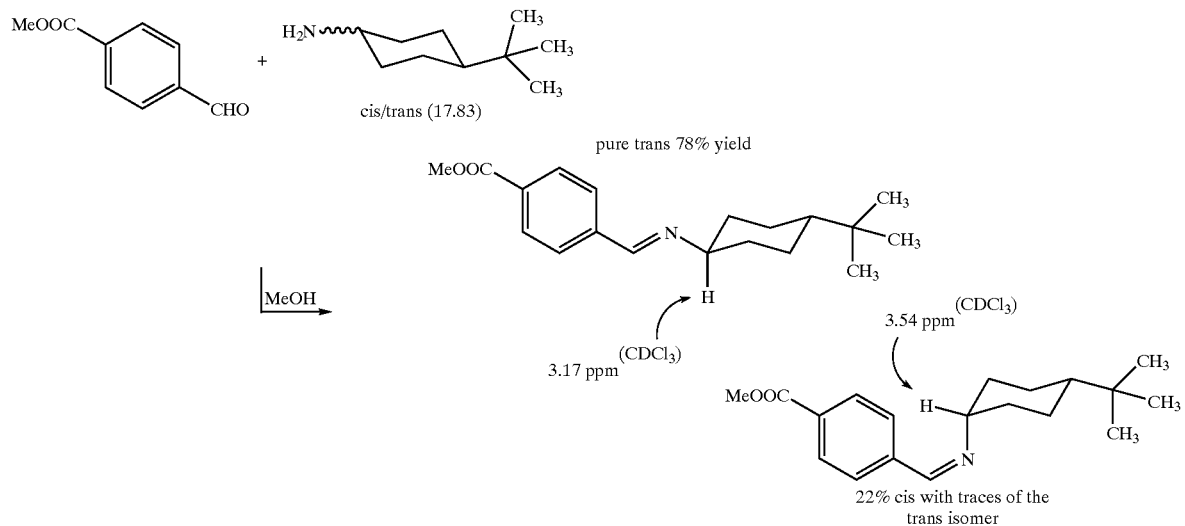

pure trans 78% yield

22% cis with traces of the trans isomer

4-Formylbenzoic acid methyl ester (10.6 g, 64.4 mmol) was dissolved in methanol (200 mL). A 17:83 cis/trans mixture of 4-tert-butylcyclohexylamine (10.0 g, 64.4 mmol, Aldrich) was added, leading to immediate precipitation of white crystals. The mixture was heated to reflux for 30 min to complete imine formation, then cooled to 0° C. on an ice bath. The crystalline pure trans-4-[(4-tert-butylcyclohexylimino)methyl]benzoic acid methyl ester was then collected by filtration, and dried overnight in vacuo. Yield: 15.3 g (78%).

$^1$H NMR (CDCl$_3$), 300 MHz: δ 8.37 ppm. (s, 1H); 8.06 (d, 2H); 7.77 (d, 2H); 3.92 (s, 3H); 3.17 (m, 1H); 1.83 (m, 4H); 1.60 (m, 2H), 1.09 (m, 3H); 0.87 (s, 9H).

Micro Analysis: Calculated for C$_{19}$H$_{27}$NO$_2$ C: 75.71%, H: 9.03%, N: 4.65%. Found: C: 75.60%, H: 9.37%, N: 4.68%.

The mother liquid was taken to dryness to leave 4.2 g (22%) white solid, which according to NMR consisted mainly of the imino cis isomer.

$^1$H NMR (CDCl$_3$), 300 MHz: δ 8.36 ppm. (s, 1H); 8.07 (d, 2H); 7.81 (d, 2H); 3.92 (s, 3H); 3.54 (m, 1H); 1.55–1.92 (m, 8H); 1.14 (m, 1H); 0.90 (s, 9H).

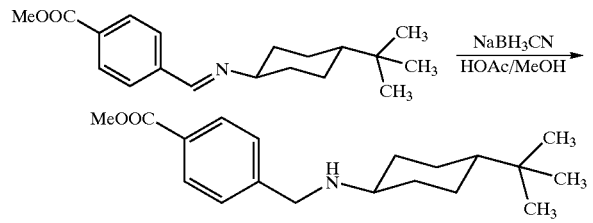

trans-4-[(4-tert-Butylcyclohexylimino)methyl]benzoic acid methyl ester (21.0 g, 69.2 mmol) was suspended in methanol (300 mL), and acetic acid (50 mL) was added. To the resulting clear solution was added sodium cyanoborohydride (3.5 g, 55.5 mmol), and the mixture was stirred at ambient temperature for 30 min. The reaction volume was then reduced to one third by rotary evaporation, and ethyl acetate (500 mL) was added. The organic phase was washed with sodium carbonate solution (5%, 500 mL), and dried with Na$_2$SO$_4$. The solvent was removed by rotary evaporation to leave the title material as a white crystalline solid sufficiently pure for further reactions. Yield: 21.1 g (100%).

$^1$H NMR (CDCl$_3$), 300 MHz: δ 7.98 ppm. (d, 2H); 7.38 (d, 2H); 3.90 (s, 3H); 3.86 (s, 2H); 2.39 (m, 1H); 2.01 (m, 2H); 1.77 (m, 2H); 1.51 (bs, 1H); 0.93–1.18 (m, 5H); 0.82 (s, 9H).

HPLC-MS (Method B: R$_t$=4.87 m/z=304 (M+1).

Alternatively, step 1 can be performed in the same way as step A of the general procedure (F).

Step 2: trans-4-{[N-(tert-Butoxycarbonyl)-N-(4-tert-butylcyclohexyl)amino]methyl}benzoic acid methyl ester trans-4-[(4-tert-Butylcyclohexylamino)methyl]benzoic acid methyl ester (20.0 g, 65.9 mmol) was dissolved in THF (300 mL). Di-tert-butylpyrocarbonate (16.0 g, 73.4 mmol) and diisopropylethylamine (12.0 g, 92.9 mmol) was added and the clear solution stirred overnight at ambient temperature. Solvent was removed by rotary evaporation.

Step 3: trans-4-{[N-(tert-Butoxycarbonyl)-N-(4-tert-butylcyclohexyl)amino]methyl}benzoic acid The crystalline residue from step 2 was re-dissolved in ethanol (200 mL) and aqueous sodium hydroxide solution (100 mL, 4N) was added whereafter the mixture was heated to 70° C. for 4 hours. After cooling, the reaction volume was reduced to one third by rotary evaporation, and water (300 mL) was added. The mixture was extracted with diethyl ether (2×200 mL) to remove traces of non-hydrolysed material. The aqueous phase was then acidified to pH 3.0 by addition of aqueous 4N HCl, whereupon the title material separated out of solution as compact crystals. The crystals were washed once with water and dried overnight in a vacuum oven (40° C.). Yield: 24.3 g (93%).

$^1$H NMR (CDCl$_3$), 300 MHz: δ 8.04 ppm. (d, 2H); 7.31 (d, 2H); 4.39 (bs, 2H); 4.05 (bs, 1H); 1.78 (bd, 4H); 0.95–1.65 (m, 14H); 0.83 (s, 9H). The signals were broad due to the presence of cis/trans carbamate isomers.

Micro analysis Calculated for C$_{23}$H$_{35}$NO$_4$: C, 70.92%; H, 9.06%; N, 3.60%. Found: C, 70.67%; H, 9.36%; N: 3.57%.

Step 4: Methyl trans-4-{[N-(tert-butoxycarbonyl)-N-(4-tert-butylcyclohexyl)amino]methyl}benzoylaminopropanoate Trans-4-{[N-(tert-butoxycarbonyl)-N-(4-tert-butylcyclohexyl)amino]methyl}benzoic acid (22.0 g, 56.5 mmol) and 1-hydroxybenzotriazole (8.6 g, 57.0 mmol, containing 12% w/w water) was dissolved in DMF (300 mL). N-Dimethylaminopropyl-N'-ethylcarbodiimide hydrochloride (10.9 g, 56.8 mmol), β-alanine methyl ester (8.4 g, 60 mmol) and diisopropylethylamine (25 mL, 142 mmol) were added and the clear solution stirred at 20° C. for 16 hours. Solvent was removed by rotary evaporation and the residual oil re-dissolved in ethyl acetate (500 mL). The organic phase was washed with 5% aqueous sodium hydrogen carbonate solution (2×500 mL), 0.5 M citric acid (2×250 mL) and brine before being dried with anhydrous Na$_2$SO$_4$. Solvent was removed and the residual oil evaporated twice from acetonitrile. The oil was used without further purification. Yield: 24.0 g (89%).

$^1$H NMR (CDCl$_3$), 300 MHz: δ 7.69 (d, 2H); 7.28 (d, 2H); 6.81 (t, 1H); 4.38 (bs, 2H); 3.23 (s, 3H); 3.21 (t, 2H); 2.66 (t, 2H); 1.75 (bd, 4H); 0.95–1.65 (m, 14H); 0.80 (s, 9H).

Step 5: Methyl trans-4-{N-(4-tert-butylcyclohexyl) aminomethyl}benzoylaminopropanoate trifluoroacetate Methyl trans-4-{[N-(tert-butoxycarbonyl)-N-(4-tert-butylcyclohexyl)amino]methyl}benzoylaminopropanoate (19.5 g, 41.1 mmol) was dissolved in a mixture of TFA (200 mL) and dichloromethane (200 mL), while cooling on an ice bath. The ice bath was removed and the mixture allowed to stir at room temperature for 30 min. Solvent was removed by rotary evaporation, and the crystalline residue recrystallized from ethyl acetate/heptane. Yield: 14.8 g (74%).

$^1$H NMR (CDCl$_3$), 300 MHz: δ 9.98 (trace of TFA); 8.06 (bs, 2H); 7.73 (d, 2H); 7.41 (d, 2H); 7.34 (t, 1H); 4.21 (t, 2H); 3.75 (s, 3H); 3.74 (t, 2H); 3.04 (m, 1H); 2.70 (t, 2H); 2.17 (bd, 2H); 1.95 (bd, 2H); 1.50 (m, 2H); 0.92–1.15 (m, 3H); 0.85 (s, 9H).

Micro analysis. Calculated for C$_{22}$H$_{34}$N$_2$O$_3$·C$_2$HF$_3$O$_2$: C, 59.00%; H, 7.22%; N, 5.73%. Found: C, 58.95%; H, 7.37%; N: 5.70%.

General Procedure for Forming Isocyanates from (Substituted) Anilines and Diphosgene to be Used in Step 6:

To a solution of the amine in anhydrous toluene was added 1 N HCl in diethyl ether (5 eq). A precipitate formed. The toluene was evaporated. To the solid was added more anhydrous toluene and the toluene was evaporated again to remove excess HCl. This procedure was repeated 2–3 times. To a mixture of the solid in toluene (about 10 g in 300 mL) was added diphosgene (trichloromethyl chloroformate) (10 eq or more) or phosgene. The mixture was refluxed under nitrogen overnight. A clear solution was obtained. If more solid was present, more diphosgene was added and reflux continued. When a clear solution was obtained, the reaction was concentrated in vacuo at 60–90° C. to remove the toluene and excess diphosgene until the theoretical weight was obtained. To the crude isocyanate was added more anhydrous toluene and concentrated again to remove excess HCl. The crude isocyanate was used without further purification.

This method gives the isocyanates in pure form, which may be used in step 6.

EXAMPLE 237

General Procedure (K)

3-{4-[3-(3,5-Bis-trifluoromethylphenyl)-1-(trans-4-tert-butylcyclohexyl)ureidomethyl]benzoylamino}propionic acid

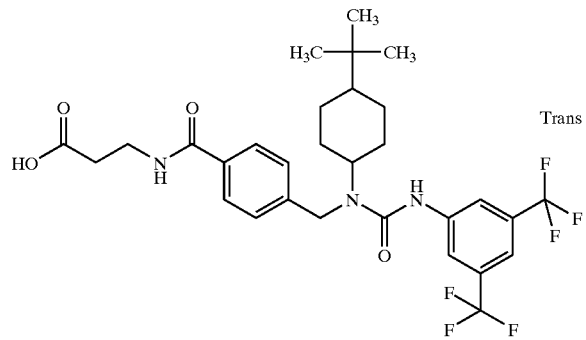

Step 6, Using a Phenyl Carbamate or Nitrophenyl Carbamate 3,5-Bis-(trifluoromethyl)aniline (2.0 g, 8.7 mmol) was dissolved in dichloromethane (80 mL) and N,N-diisopropylethylamine (1.6 mL, 9.6 mmol) was added followed by slow addition of phenyl chloroformate (1.1 mL, 8.7 mmol). The resulting mixture was stirred at room temperature for 16 hours. The mixture was successively washed with 1N hydrochloric acid (3×100 mL), water (3×100 mL), a mixture of water and saturated aqueous sodium hydrogen carbonate (1:1, 2×100 mL) and a mixture of water and saturated aqueous sodium chloride (1:1, 3×100 mL), dried (MgSO$_4$) and concentrated in vacuo. The residue was crystallised from heptane containing a little diethyl ether to afford 1.3 g (43%) of (3,5-bis-trifluoromethylphenyl)carbamic acid phenyl ester as a solid.

Calculated for C$_{15}$H$_9$F$_6$NO$_2$: C, 51.59%; H, 2.60%; N, 4.01%. Found: C, 51.27%; H, 2.56%; N, 4.01%; C, 51.40%; H, 2.57%; N, 3.92%.

The above carbamic acid phenyl ester (1.0 g, 2.9 mmol) was mixed with 3-{4-[(4-tert-butyl-cyclohexylamino) methyl]benzoylamino}propionic acid methyl ester, trifluoroacetate (1.07 g, 2.9 mmol), prepared as described above and triethylamine (1.2 mL, 8.6 mmol) in dichloromethane (55 mL) and the resulting mixture was refluxed for 4 hours. The cooled reaction mixture was diluted with toluene (50 mL) and washed with water (3×50 mL) and a mixture of water and saturated aqueous sodium chloride (1:1, 3×100 mL), dried (MgSO$_4$) and concentrated in vacuo to afford 1.2 g (67%) of 3-{4-[3-(3,5-bis-trifluoromethylphenyl)-1-(4-tert-butylcyclohexyl)ureidomethyl]benzoylamino}propionic acid methyl ester as a solid.

$^1$H NMR (CDCl$_3$): δ 0.83 (9H, s), 0.9–1.5 (5H, m), 1.88 (4H, bt), 7.62 (H, t), 3.72 (5H, m), 4.18 (1H, bt), 4.57 (2H, s), 6.80 (1H, s), 6.90 (1H, t), 7.38 (2H, d), 7.46 (1H, s), 7.77 (2H, d), 7.80 (2H, s).

HPLC-MS (Method B): R$_t$=9.07 min, m/z=630 (M+1).

Step 7:

The above propionic acid methyl ester (1.0 g, 1.6 mmol) was dissolved in warm ethanol (50 mL), and after cooling to room temperature 4N aqueous sodium hydroxide (6 mL) was added. The reaction mixture was stirred at room temperature for 1 hour. Glacial acetic acid (10 mL) was added and the mixture was concentrated in vacuo. The residue was partitioned between water (50 mL) and ethyl acetate (2×50 mL). The combined organic phases were dried (MgSO$_4$) and concentrated in vacuo to afford 0.88 g (93%) of the title compound as a solid.

$^1$H NMR (DMSO-d$_6$): δ 0.83 (9H, s), 0.9–1.5 (5H, m), 1.70 (4H, bt), 2.50 (2H, t, below DMSO), 3.45 (2H, q, below water), 4.05 (1H, bt), 4.62 (2H, s), 7.32 (2H, d), 7.60 (2H, d), 8.24 (2H), 8.45 (1H, t), 9.00 (1H, s), 12 (1H, bs).

HPLC-MS (Method B): R$_t$=8.60 min, m/z=616 (M+1).

Calculated for C$_{30}$H$_{35}$F$_6$N$_3$O$_4$×0.25H$_2$O: C, 57.47%; H, 5.57%; N, 6.93%. Found: C, 57.60%; H, 5.81%; N, 6.47%; C, 57.63%; H, 5.76%; N, 6.45%.

EXAMPLE 238

General Procedure (K)

3-{4-[1-(trans-4-tert-Butylcyclohexyl)-3-(3,4,5-trichlorophenyl)ureidomethyl]benzoylamino}propionic acid

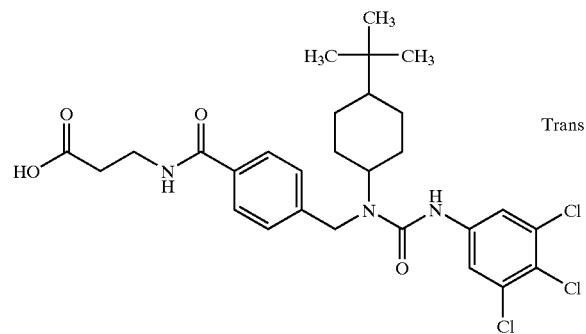

Step 6, Using Isocyanate Formed in situ from (Substituted) Anilines and Triphosgene:

Triphosgene (bis-trichloromethylcarbonate) (152 mg, 0.51 mmol) was dissolved in dichloromethane (4 mL) and cooled to 0° C. To this solution a solution of 3,4,5-trichloroaniline (303 mg, 1.54 mmol) and diisopropylethylamine (540 μL, 3.1 mmol) in dichloromethane (3 mL) was added at 0° C. over 1 hour. The mixture was then allowed to reach room temperature. To this mixture a solution of methyl trans-4-{(4-tert-butylcyclohexyl)aminomethyl}benzoylaminopropanoate trifluoroacetate (576 mg, 1.54 mmol) and diisopropylethylamine (800 μL) in dichloromethane (10 mL) was added and stirring at room temperature was continued for 30 minutes. The mixture was diluted with more dichloromethane (10 mL) and washed with saturated aqueous citric acid (2×20 mL). The organic phase was dried (Na$_2$SO$_4$) and concentrated in vacuo to afford 653 mg (71%) of 3-{4-[1-(4-trans-tert-butylcyclohexyl)-3-(3,4,5-trichlorophenyl)ureidomethyl]benzoylamino}propionic acid methyl ester as a solid.

$^1$H NMR (DMSO-d$_6$): δ 0.81 (s, 9H), 0.92 (m, 1H), 1.12 (m, 2H), 1.44 (m, 2H), 1.68 (m, 4H), 2.56 (t, 2H), 3.45 (q, 2H), 3.59 (s, 3H), 4.05 (b t, 1H), 4.58 (s, 2H), 7.30 (d, 2H), 7.78 (d, 2H), 7.83 (s, 2H), 8.44 (t, 1H), 8.75 (s, 1H).

Step 7:

Hydrolysis of this ester using the method described in example 92, step D afforded the title compound (495 mg, 78%).

$^1$H NMR (DMSO-d$_6$): δ 0.82 (s, 9H), 0.91 (m, 1H), 1.10 (m, 2H), 1.39 (m, 2H), 1.71 (m, 4H), 2.51 (t, 2H), 3.35 (q, 2H), 4.01 (t, 1H), 4.59 (s, 2H), 7.30 (d, 2H), 7.78 (d, 2H), 7.85 (s, 2H), 8.46 (t, 1H), 8.76 (s, 1H), 12.21 (b s, 1H).

EXAMPLE 239

General Procedure (K)

3-{4-[1-(trans-4-tert-Butylcyclohexyl)-3-(4-butylsulfamoylphenyl)ureidomethyl]benzoylamino}propionic acid

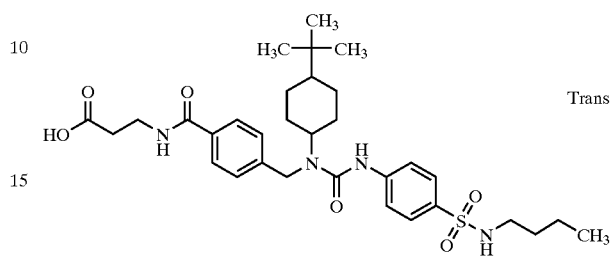

4-Nitrophenylsulfonyl chloride (3.0 g, 13.5 mmol) was dissolved in THF and a catalytic amount of 4-dimethylaminopyridine and 1-butylamine (4.0 mL, 41 mmol) was added and the mixture was refluxed for 16 hours. The mixture was concentrated in vacuo and the residue was dissolved in ethyl acetate (100 mL) and washed with water (50 mL) and a 10% aqueous solution of sodium hydrogen carbonate (50 mL). The organic phase was dried (MgSO$_4$) and concentrated in vacuo to afford 3.01 g (86%) of N-butyl-4-nitrobenzenesulfonamide as a solid.

$^1$H NMR (CDCl$_3$): δ 0.89 (3H, t), 1.30 (2H, m), 1.48 (2H, m), 3.03 (2H, t), 4.9 (1H, b), 8.06 (2H, d), 8.37 (2H, d).

Sodium dithionite (11.4 g, 65 mmol) and sodium carbonate (5.6 g, 53 mmol) were dissolved in water (65 mL) and heated to 70° C. A suspension of the above 4-nitrophenylsulfonamide (2.64 g, 10.2 mmol) in methanol (65 mL) was added and the resulting mixture was stirred at 70° C. for 1.5 hour. The cooled mixture was filtered and the volume of the filtrate was reduced by 50% in vacuo. The aqueous mixture was extracted with ethyl acetate (3×60 mL), and the combined organic extracts were dried (MgSO$_4$) and concentrated in vacuo to afford 0.14 g (6%) of 4-amino-N-butylbenzenesulfonamide as a solid.

$^1$H NMR (DMSO-d$_6$): δ 0.80 (3H, t), 1.2–1.4 (4H, m), 2.65 (2H, q), 5.90 (2H, s), 6.60 (2H, d), 7.04 (1H, t), 7.40 (2H, d).

HPLC-MS (Method B): R$_t$=5.15 min, m/z=229 (M+1).

The above 4-aminophenylsulfonamide (0.14 g) was dissolved in dichloromethane (6 mL), N,N-diisopropylethylamine (172 μL, 1 mmol) and phenyl chloroformate (122 μL, 0.92 mmol) and the resulting mixture was stirred at room temperature for 16 hours. The reaction mixture was diluted with dichloromethane (50 mL) and was washed with 1N hydrochloric acid (3×20 mL), water (3×20 mL), a mixture of water and a saturated solution of sodium hydrogen carbonate (1:1, 2×20 mL) and a mixture of water and a saturated solution of sodium chloride (1:1, 2×20 mL). Drying (MgSO$_4$) and concentration in vacuo afforded crude (4-butylsulfamoylphenyl)carbamic acid phenyl ester.

From the above crude carbamic acid phenyl ester and 3-{4-[(4-trans-tert-butylcyclohexylamino)methyl]benzoylamino}propionic acid methyl ester trifluoroacetate the title compound was obtained similarly as described above.

HPLC-MS (Method B): R$_t$=7.37 min, m/z=615 (M+1).

EXAMPLE 240

General Procedure (K)

3-{4-[1-(trans-4-tert-Butylcyclohexyl)-3-(4-diethylcarbamoylphenyl)ureidomethyl]benzoylamino}propionic acid

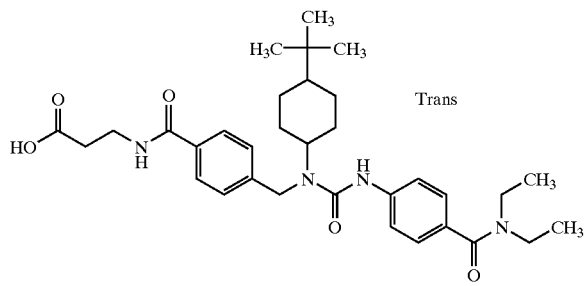

The title compound was prepared similarly as described above starting from 4-nitrobenzoyl chloride, diethylamine and 3-{4-[(4-trans-tert-butylcyclohexylamino)methyl]benzoylamino}propionic acid methyl ester trifluoroacetate.

HPLC-MS (Method B): $R_t$=6.76 min, m/z=579 (M+1).

EXAMPLE 241

General Procedure (K)

3-{4-[1-(trans-4-tert-Butylcyclohexyl)-3-(4-cyclopropylmethoxyphenyl)ureidomethyl]benzoylamino}propionic acid

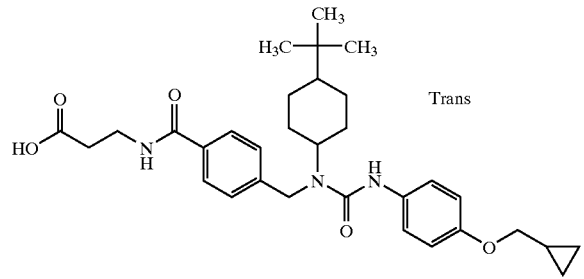

4-Nitrophenol (2.0 g, 14.4 mmol) was dissolved in DMF (50 mL) and potassium carbonate (6.0 g, 43 mmol) and bromomethylcyclopropane (1.51 mL, 16 mmol) were added and the resulting mixture was stirred at room temperature for 16 hours. The mixture was diluted with ethyl acetate (50 mL) and washed with a saturated aqueous solution of sodium chloride (2×50 mL). Drying (MgSO$_4$) and concentration afforded 2.23 g (75%) of 1-cyclopropylmethoxy-4-nitrobenzene as an oil.

$^1$H NMR (CDCl$_3$): δ 0.40 (2H, m), 0.58 (2H, m), 1.30 (1H, m), 3.89 (2H, d), 6.94 (2H, d), 8.12 (2H, d).

The above 4-nitrobenzene (2.0 g, 9.5 mmol) was dissolved in ethanol (50 mL) and tin(II) chloride dihydrate (10.7 g, 48 mmol) was added and the mixture was refluxed for 24 hours. After cooling, the mixture was concentrated in vacuo. The residue was dissolved in ethyl acetate (40 mL) and 1N aqueous sodium hydroxide (180 mL). This mixture was filtered through celite. The aqueous phase was extracted with ethyl acetate (2×50 mL) and the combined organic extracts were dried (MgSO$_4$) and concentrated in vacuo to afford 0.88 g (52%) of 4-cyclopropylmethoxyaniline.

$^1$H NMR (DMSO-d$_6$): δ 0.25 (2H, m), 0.53 (2H, m), 1.15 (1H, m), 3.63 (2H, d), 4.55 (2H, s), 6.4–6.5 (3H, m), 6.62 (2H, d).

From the above aniline and 3-{4-[(4-trans-tert-butylcyclohexylamino)methyl]benzoylamino}propionic acid methyl ester trifluoroacetate the title compound was prepared similarly as described in example 238.

$^1$H NMR (DMSO-d$_6$): δ 0.42 (2H, m), 0.62 (2H, m), 0.85 (9H, s), 0.92 (1H, m), 1.1–1.4 (5H, m), 1.9 (4H, bt), 2.70 (4H, m), 4.14 (1H, t), 4.52 (2H, s), 6.08 (1H, s), 6.77 (2H, d), 6.88 (1H, t), 7.10 (2H, d), 7.40 (2H, d), 7.76 (2H, d).

HPLC-MS (Method B): $R_t$=7.73 min, m/z=550 (M+1).

EXAMPLE 242

General Procedure (K)

3-{4-[3-(2-Bromo-4-trifluoromethoxyphenyl)-1-(trans-4-tert-butylcyclohexyl)ureidomethyl]benzoylamino}propionic acid

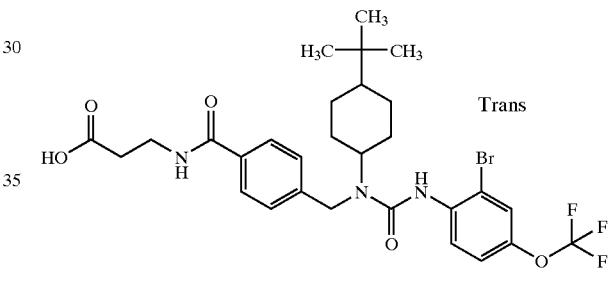

4-Trifluoromethoxyaniline (1.0 g, 5.6 mmol) was dissolved in glacial acetic acid (10 mL). Bromine (585 µL, 11 mmol) dissolved in glacial acetic acid (2 mL) was added with stirring during 10 minutes at room temperature. The resulting mixture was stirred at room temperature for 2 hours and then poured into water (100 mL). The solid formed (2,5-dibromo-4-trifluoromethoxyaniline) was filtered off. The filtrate was made alkaline with solid sodium hydroxide and extracted with dichloromethane (100 mL), dried (MgSO$_4$) and concentrated (30° C.; 200 mBar) to afford 0.57 g (40%) of 2-bromo-4-trifluoromethoxyaniline.

$^1$H NMR (DMSO-d$_6$): δ 5.55 (2H, bs), 6.85 (1H, d), 7.10 (1H, dd), 7.37 (1H, d), 7.37 (1H, d).

From the above 2-bromoaniline and 3-{4-[(4-trans-tert-butylcyclohexylamino)methyl]benzoylamino}propionic acid methyl ester trifluoroacetate the title compound was prepared similarly as described in example 238.

$^1$H NMR (DMSO-d$_6$): δ 0.86 (9H, s), 0.95 (1H, m), 1.2 (2H, m), 1.4 (2H, m), 1.9 (4H, m), 2.74 (2H, t), 3.75 (2H, q), 4.16 (1H, t), 4.60 (2H, s), 6.85 (1H, t), 6.88 (1H, s), 7.16 (1H, dd), 7.31 (1H, d), 7.43 (2H, d), 7.76 (2H, d), 8.26 (2H, d).

EXAMPLE 243

General Procedure (K)

3-{4-[1-(trans-4-tert-Butylcyclohexyl)-3-phenylureidomethyl]benzoylamino}propionic acid

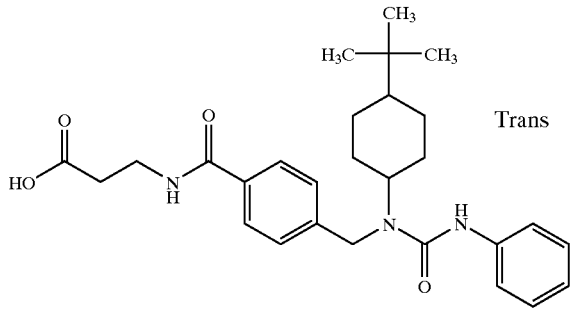

From 3-{4-[(4-trans-tert-butylcyclohexylamino)methyl]benzoylamino}propionic acid methyl ester trifluoroacetate and phenylisocyanate the title compound was prepared similarly as described in the alternative method for preparing example 92 according to the general procedure (K).

$^1$H NMR (DMSO-$d_6$): δ 0.84 (9H, s), 0.93 (1H, m), 1.2 (2H, m), 1.4 (2H, m), 1.85 (4H, m), 2.63 (2H, t), 3.70 (2H, q), 4.19 (1H, t), 4.58 (2H, s), 6.75 (1H, s), 6.97 (1H, t), 7.2–7.3 (4H, m), 7.4 (3H, m), 7.80 (2H, d).

HPLC-MS (Method B): $R_t$=7.28 min, m/z=480 (M+1).

EXAMPLE 244

General Procedure (K)

3-{4-[1-(4-Phenoxycyclohexyl)-3-(4-trifluoromethoxyphenyl)ureidomethyl]benzoylamino}propionic acid

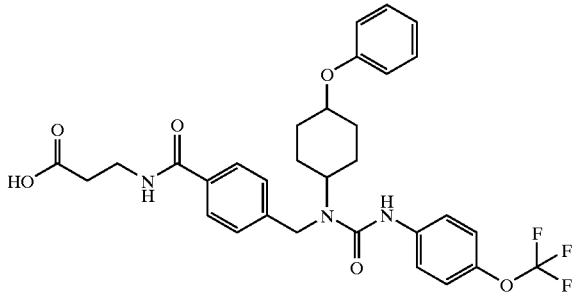

Synthesis of intermediate 4-{[tert-butoxycarbonyl-(4-phenoxycyclohexyl)amino]methyl}benzoic acid:

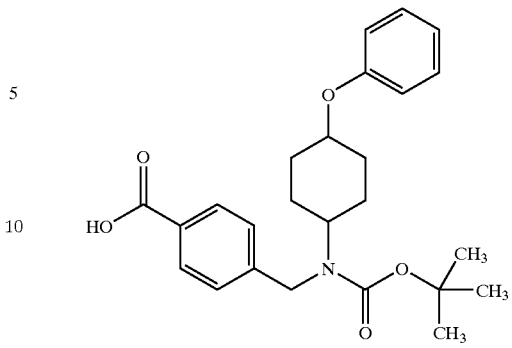

Methyl 4-(bromomethyl)benzoate (5.0 g, 22 mmol) was dissolved in DMF (50 mL) and trans-4-aminocyclohexanol (3.04 g, 26 mmol) was added followed by addition of potassium carbonate (6.08 g, 44 mmol). The reaction mixture was heated to 80° C. for 16 hours. The reaction mixture was diluted with ethyl acetate (300 mL) and water (200 m) was added. The aqueous phase was extracted with ethyl acetate (100 mL), and the combined organic phases were washed with water (2×100 mL) and dried (MgSO$_4$). The organic phase was concentrated in vacuo to give 2.5 g of trans-4-[(4-hydroxycyclohexylamino)methyl]benzoic acid methyl ester.

HPLC-MS (method B): m/z: 264, $R_t$=3.48 min.

trans-4-[(4-Hydroxycyclohexylamino)methyl]benzoic acid methyl ester (2.46 g, 9.3 mmol) was suspended in sodium hydroxide (1N, 9 mL). Di-tert-butylpyrocarbonate (2.44 g, 11.2 mmol) dissolved in THF (11 mL) was added during 15 minutes. Additional THF (8 mL) was added and the reaction mixture was stirred for 16 hours. The reaction mixture was evaporated in vacuo until THF was removed. Water (25 mL), sodium hydroxide (1N, 1.5 mL), and diethyl ether (50 mL) was added. The water phase was extracted with diethyl ether (25 mL) and the combined organic phases were washed with an aqueous solution of sodium hydrogensulphate (10%, 30 mL), water (3×20 mL), and dried (MgSO$_4$). The organic phase was concentrated in vacuo to give 3.60 g of trans-4-{[tert-butoxycarbonyl-(4-hydroxycyclohexyl)amino]methyl}benzoic acid methyl ester.

HPLC-MS (method B): m/z: 364, $R_t$=5.75 min.

trans-4-{[tert-Butoxycarbonyl-(4-hydroxycyclohexyl)amino]methyl}benzoic acid methyl ester (1.0 g, 2.75 mmol) was dissolved in THF (4 mL) and triphenylphosphine (1.12 g, 4.1 mmol) was added followed by addition of phenol (0.26 g, 2.75 mmol). Diethylazodicarboxylate (0.72 g, 4.1 mmol) dissolved in THF (2 mL) was added drop wise, and the reaction mixture was stirred for 16 hours. The reaction mixture was concentrated in vacuo. The residue was purified by flash chromatography (100 g silica) using ethyl acetate and heptane (1:9) as eluent to give 0.27 g of trans-4-{[tert-butoxycarbonyl-(4-phenoxycyclohexyl)amino]methyl}benzoic acid methyl ester. The ester was dissolved in ethanol (5 mL) and sodium hydroxide (4N, 1 mL) was added. After 5 hours the reaction mixture was concentrated in vacuo, the residue was dissolved in ethyl acetate (25 mL), and hydrochloric acid (4N, 1.3 mL) was added. The organic phase was washed with water (3×10 mL), dried (MgSO$_4$) and concentrated in vacuo to give 0.25 g of trans-4-{[tert-butoxycarbonyl-(4-phenoxycyclohexyl)amino]methyl}benzoic acid.

$^1$H NMR (DMSO-$d_6$): δ 12.85 (1H, broad), 7.90 (2H, d), 7.36 (2H, d), 7.22 (2H, t), 6.88 (3H, m), 4.53 (1H, m), 4.43 (2H, m), 2.0–1.2 (18H, m).

This intermediate was used for the synthesis the title compound.

¹H NMR (DMSO-d₆): δ 12.2 (1H, broad), 8.58 (2H, s), 8.48 (1H, t), 7.79 (2H, s), 7.55 (2H, s), 7.37 (2H, s), 7.25 (4H, m), 6.91 (3H, m), 4.67 (2H, s), 4.58 (1H, s), 4.24 (1H, m). 3.42 (2H, dd), 2.52–2.48 (2H, m), 2.00–1.90 (2H, m), 1.80–1.55 (4H, m), 1.50–1.40 (2H, m).

EXAMPLE 245

General Procedure (K)

4-{3-(trans-4-tert-Butylcyclohexyl)-3-[4-(2-carboxyethylcarbamoyl)benzyl]ureido}piperidine-1-carboxylic acid ethyl ester

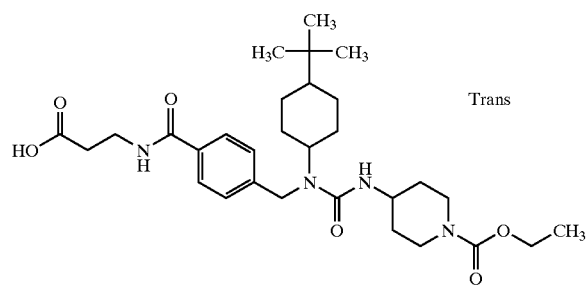

¹H NMR (DMSO-d₆): δ 12.2 (1H, broad), 8.42 (1H, t), 7.72 (2H, d), 7.25 (2H, d), 6.02 (1H, d), 4.42 (2H, broad), 4.02 (2H, q), 3.92–3.60 (3H, m), 3.50–3.40 (2H, m), 2.90–2.70 (2H, m), 1.80–0.80 (10H, m), 0.80 (13H, s).

EXAMPLE 246

General Procedure (K)

3-{4-[1-(4-tert-Butylcyclohexyl)-3-(6-phenoxypyridin-3-yl)ureidomethyl]benzoylamino}propionic acid

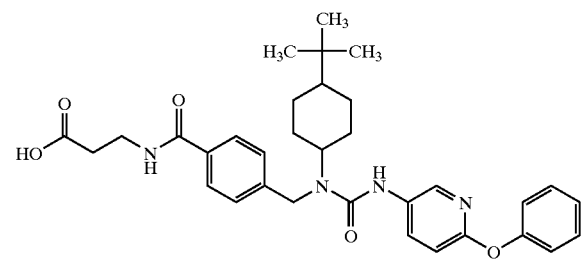

HPLC-MS (method B): m/z: 573, R_t=7.23 min.
Synthesis of intermediate 5-amino-2-phenoxypyridine:

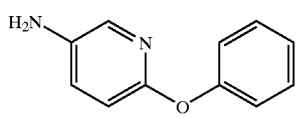

Phenol (0.9 g, 9.5 mmol) was dissolved in sodium hydroxide (50% solution, 12 mL). 5-Nitro-2-chloropyridine (1.5 g, 9.5 mmol) in toluene (15 mL) was added followed by addition of tetrabutylammonium bromide (0.3 g, 0.95 mmol). The reaction mixture was stirred for 16 hours at 20° C. and 5 hours at 80° C. where after it was cooled to room temperature and diethyl ether (100 mL) added. The organic phase was washed with water (5×50 mL), dried (MgSO₄), and concentrated in vacuo to give 1.0 g of 5-nitro-2-phenoxypyridine.

M.p. 85–87° C.

5-Nitro-2-phenoxypyridine (0.5 g, 2.3 mmol) was added portion wise to a solution of stannous chloride (2.6 g, 12 mmol) dissolved in concentrated hydrochloric acid (10 mL) at a temperature of 0–5° C. The reaction mixture was then stirred at 20° C. for 16 hours. Sodium carbonate (5 g) and aqueous ammonia (50 mL) was added. The mixture was extracted with ethyl acetate (2×50 mL) and the combined organic phases were washed with water (2×40 mL), dried (MgSO₄), and concentrated in vacuo to give 0.3 g of 5-amino-2-phenoxypyridine.

¹H NMR (DMSO-d₆): δ 7.55 (1H, s), 7.33 (2H, dd), 7.08 (2H, dd), 6.93 (2H, d), 6.75 (1H, d), 5.12 (2H, broad).

This compound was transformed into the corresponding phenylcarbamate (as described for in example 237 and used in the synthesis of the title compound.

¹H NMR (DMSO-d₆): δ 8.51 (1H, s), 8.45 (1H, broad), 8.20 (1H, d), 7.90 (1H, dd), 7.75 (2H, d), 7.35 (4H, m), 7.15 (1H, t), 7.05 (2H, d), 6.92 (1H, d), 4.57 (2H, broad), 4.02 (1H, broad), 3.40 (m), 3.38 (2H, m), 1.80–0.80 (10H, m), 0.80 (13H, s).

EXAMPLE 247

General Procedure (K)

3-{4-[1-(trans-4-tert-Butylcyclohexyl)-3-(4-cyano-2-trifluoromethoxyphenyl)ureidomethyl]benzoylamino}propionic acid

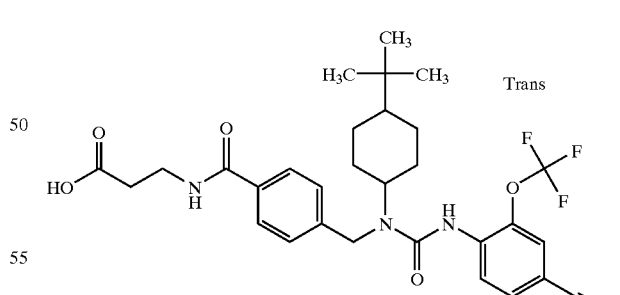

¹H NMR (DMSO-d₆): δ 12.2 (1H, broad), 8.48 (1H, t), 8.32 (1H, broad), 7.92 (1H, s), 7.90 (1H, d), 7.75 (3H, m), 7.34 (2H, d), 4.60 (2H, broad), 4.03 (1H, m), 3.45 (2H, m), 1.80–0.85 (9H, m), 0.80 (9H, s).

HPLC-MS (method B): m/z: 589, R_t=8.07 min.

EXAMPLE 248

General Procedure (K)

3-{4-[1-(4-Cyclopropylidenecyclohexyl)-3-(4-trifluoromethoxyphenyl)ureidomethyl]benzoylamino}propionic acid

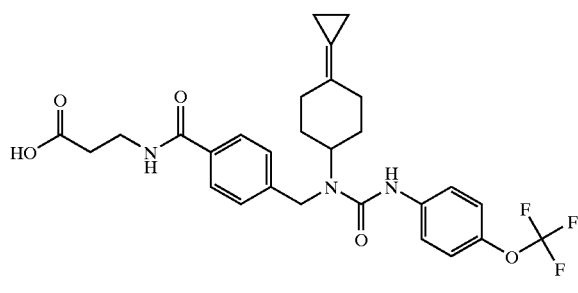

Synthesis of intermediate 4-[(4-cyclopropylidenecyclohexylamino)methyl]benzoic acid methyl ester:

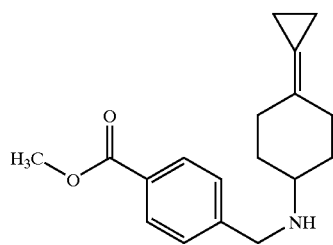

Cyclopropyltriphenylphosphonium bromide (10.8 g, 28 mmol) was suspended in dry THF (30 mL) and cooled to −60° C. N-Butyllithium (1.6M in THF, 17 mL, 27 mmol) was added dropwise at −40 to −60° C. The temperature was raised to 20° C. and after 3 hours at this temperature, the reaction mixture was cooled to −60° C. 1,4-Cyclohexane dione mono ethylene ketal (4.0 g, 26 mmol) dissolved in THF (30 mL) was added at −60° C. whereafter the temperature was raised to 20° C. After 16 hours the reaction mixture was diluted with THF (75 mL) filtered through hyflo and concentrated in vacuo. The residue was purified by flash chromatography (4×15 cm column of silica) using heptane and ethyl acetate (4:1) as eluent to give 2.5 g of 8-cyclopropylidene-1,4-dioxa-spiro[4.5]decane (cf Synthetic Communications 21(20), 2015–2023, 1991).

Silica gel 60 (6.0 g) was suspended in dichloromethane (12 mL) and oxalic acid (10% in water, 0.6 g) was added. After 20 minutes 8-cyclopropylidene-1,4-dioxa-spiro[4.5]decane (1.6 g, 8.9 mmol) dissolved in dichloromethane (5 mL) was added and the reaction mixture was stirred for 48 hours at 20° C. Sodium hydrogen carbonate (200 mg) was added and after 1 hour the reaction mixture was filtered. The filtrate was concentrated in vacuo and the crude product of 4-cyclopropylidenecyclohexanone was used for the next step without further purification.

4-Aminomethylbenzoic acid methyl ester, hydrochloride salt (2.2 g, 11 mmol) was suspended in 1,2 dichloropropane (30 mL) and an aqueous saturated solution of potassium carbonate (15 mL) was added. The next day the organic phase was isolated and dried (MgSO$_4$). 4-Cyclopropylidenecyclohexanone (1.5 g, 11 mmol) dissolved in dichloromethane (15 mL) was added followed by addition of acetic acid (400 μL) and sodium triacetoxyborohydride (3.3 g, 16.5 mmol). After 72 hours at 20° C. the reaction mixture was diluted with dichloromethane (50 mL) and washed with aqueous saturated sodium hydrogen carbonate (2×30 mL) and water (5×30 mL). The organic phase was dried (MgSO$_4$) and concentrated in vacuo. The residue was purified by flash chromatography (50 g silica) using ethyl acetate and methanol (97:3) as eluent to give 1.1 g of 4-[(4-cyclopropylidenecyclohexylamino)methyl]benzoic acid methyl ester.

$^1$H NMR (DMSO-d$_6$): δ 7.90 (2H, d), 7.48 (2H, d), 3.84 (3H, s), 3.80 (2H), 3.63 (1H, m), 2.60–0.90 (12H, m).

HPLC-MS (method B): m/z: 286, R$_t$=4.45 min.

This intermediate product was used for the synthesis of the title compound.

$^1$H NMR (DMSO-d$_6$): δ 2.2 (1H, broad), 8.60 (1H, s), 8.43 (1H, t), 7.75 (2H, d), 7.55 (2H, d), 7.30 (2H, d), 7.22 (2H, d), 4.65 (2H, broad), 4.32 (1H, m), 3.45 (2H, m), 2.60–0.90 (1H, m).

HPLC-MS (method B): m/z: 546, R$_t$=7.38 min.

EXAMPLE 249

General Procedure (K)

3-{4-[1-(4-Cyclopropylcyclohexyl)-3-(4-trifluoromethoxyphenyl)ureidomethyl]benzoylamino}propionic acid

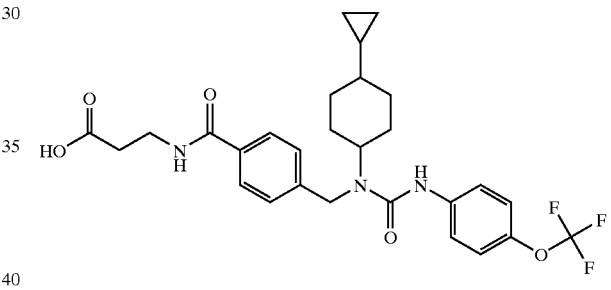

Synthesis of intermediate 4-[(4-cyclopropylcyclohexylamino)methyl]benzoic acid methyl ester:

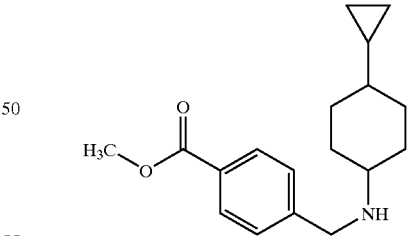

4-[(4-Cyclopropylidenecyclohexylamino)methyl]benzoic acid methyl ester (1.1 g, 3.9 mmol) was dissolved in DMF (40 mL) and p-toluenesulfonic acid hydrazide (2.8 g, 15.4 mmol) was added. The reaction was heated to 100° C. for 16 hours. After cooling to room temperature the reaction mixture was diluted with ethyl acetate (75 mL) and water (40 mL) was added. The aqueous phase was extracted with ethyl acetate (25 mL) and the combined organic phases washed with aqueous saturated sodium hydrogen carbonate (2×30 mL) and water (5×30 mL). The organic phase was dried (MgSO$_4$) and concentrated in vacuo. The residue was purified by flash chromatography (25 g silica) using heptane and ethyl acetate (1:1) as eluent to give 4-[(4-cyclopropylcyclohexylamino)methyl]benzoic acid methyl ester.

This intermediate product was used for the synthesis of the title compound.

$^1$H NMR (DMSO-d$_6$): δ 12.2 (1H, broad), 8.51 (1H, s), 8.43 (1H, t), 7.75 (2H, dd), 7.55 (2H, d), 7.32 (2H, dd), 7.22 (2H, d), 4.68 (1H, s), 4.60 (1H, s), 4.10 (1H, m), 3.45 (2H, dd), 1.80–0.25 (13H, m).

HPLC-MS (method B): m/z: 548, R$_t$=7.38 min.

EXAMPLE 250

General Procedure (K)

3-{4-[1-(trans-4-tert-Butylcyclohexyl)-3-(4-cyclopropylmethoxy-2-trifluoromethylphenyl)ureidomethyl]benzoylamino}propionic acid

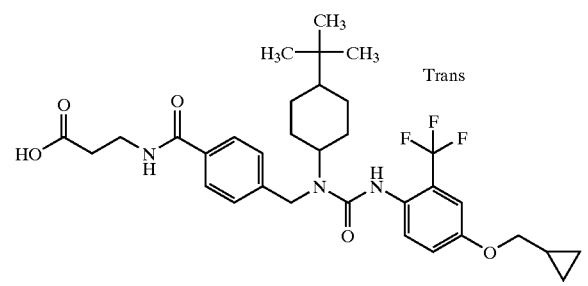

The intermediate, 4-cyclopropylmethoxy-2-trifluoromethylaniline, was prepared analogously to the aniline intermediate used in example 241.

$^1$H NMR (DMSO-d$_6$): δ 12.1 (1H, broad), 8.45 (1H, t), 7.98 (1H, broad), 7.75 (2H, d), 7.32 (2H, d), 7.29 (1H, s), 7.15 (2H, m), 4.52 (2H, broad), 3.88 (2H, d), 3.45 (1H, m), 1.80–0.85 (10H, m), 0.80 (9H, s), 0.60 (2H, m), 0.33 (2H, m).

HPLC-MS (method B): m/z: 618, R$_t$=6.65 min.

EXAMPLE 251

General Procedure (K)

3-{4-[1-(trans-4-tert-Butylcyclohexyl)-3-(3-cyano-4-trifluoromethoxyphenyl)ureidomethyl]benzoylamino}propionic acid

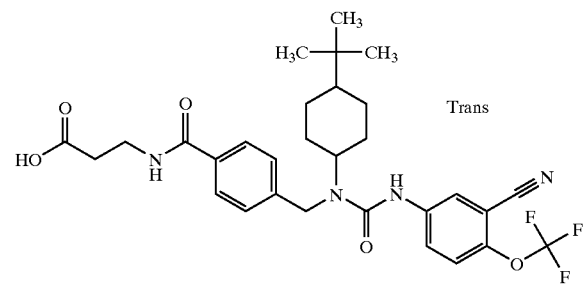

$^1$H NMR (DMSO-d$_6$): δ 12.2 (s, broad), 8.90 (1H, s), 8.43 (1H, t), 8.10 (1H, s), 7.90 (2H, dd), 7.75 (2H, d), 7.55 (1H, d), 7.32 (2H, d), 4.61 (2H, broad), 4.04 (2H, m), 3.45 (2H, m), 1.80–0.85 (10H, m), 0.80 (9H, s).

EXAMPLE 252

General Procedure (K)

3-{4-[1-(4-tert-Butylcyclohexyl)-3-(3-methylsulfonylphenyl)ureidomethyl]benzoylamino}propionic acid

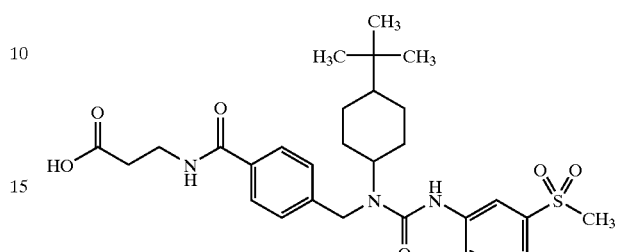

The title compound was prepared form the corresponding 3-methylsulfanyl compound (general procedure (K)) followed by oxidation of the sulfanyl group and hydrolysis of the propionic acid ester.

$^1$H NMR (DMSO-d$_6$): δ 12.2 (s, broad), 8.76 (1H, s), 8.45 (1H, t), 8.07 (1H, s), 7.83 (1H, d), 7.74 (2H, d), 7.50 (2H, m), 7.30 (2H, d), 4.60 (2H, broad), 4.08 (2H, d), 3.45 (2H, t), 3.18 (3H, s), 2.50 (2H, t), 1.80–0.85 (9H, m), 0.80 (9H, s).

HPLC-MS (method B): m/z: 558, R$_t$=6.52 min.

EXAMPLE 253

General Procedure (K)

3-{4-[1-(4-trans-tert-Butylcyclohexyl)-3-(5-Phenyl-2H-pyrazol-3-yl)ureidomethyl]benzoylamino}propionic acid

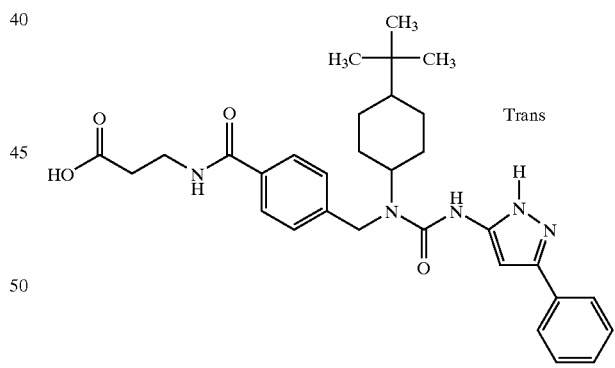

Using isocyanate formed in situ from 5-amino-3-phenylpyrrole and triphosgene:

To a suspension of 5-amino-3-phenylpyrazole (183 mg, 8.7 mmol) in 1,2-dichloroethane (5 mL) was added N,N-diisopropylethylamine (0.2 mL, 1.2 mmol) followed by addition of triphosgene (115 mg, 0.38 mmol). The solution was heated to reflux for two hours. To this mixture a solution of 3-{4-[(4-trans-tert-butylcyclohexylamino)methyl]benzoylamino}propionic acid methyl ester trifluoroacetate (350 mg, 0.70 mmol) and N,N-diisopropylethylamine (0.2 mL, 1.2 mmol) in DMF (4 mL) was added and stirring at 80° C. was continued for 2 hours. The mixture was allowed to cool to room temperature, poured into water (50 mL) and the water phase was washed ethyl acetate (2×50 mL). The combined organic phases were concentrated in vacuo and purification on silica column with dichloromethane/methanol (95:5) afforded the 3-{4-[1-(4-trans-tert-butylcyclohexyl)-3-(5-phenyl-2H-pyrazol-3-yl)ureidomethyl]benzoylamino}propionic acid methyl ester as a solid which was redissolved in ethanol (4 mL). Sodium hydroxide (1 mL, 4 N) was added and the reaction mixture was left at room temperature for 30 min. Hydrochloric acid (4 mL, 1 N) was added, and the resulting precipitate was subsequently collected by filtration. Recrystallisation from acetonitrile afforded the title compound.

$^1$H NMR (CDCl$_3$): δ 0.82 (9H, s), 0.9–1.5 (5H, m), 1.69 (4H, bt), 4.09 (1H, bt), 4.58 (2H, s), 6.64 (1H, s), 7.25–7.50 (5H, m), 7.60–7.80 (4H, m), 8.50 (1H, t), 9.0 (1H, s).

HPLC-MS (Method B): R$_t$=6.52 min, m/z=546 (M+1).

EXAMPLE 254

General Procedure (K)

2-{3-(4-trans-tert-Butylcyclohexyl)-3-[4-(2-carboxyethylcarbamoyl)benzyl]ureido}benzothiazole-6-carboxylic acid ethyl ester

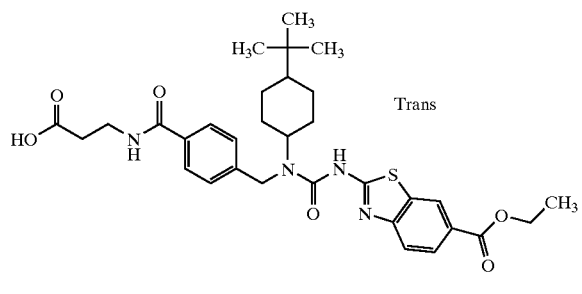

Using isocyanate formed in situ from (substituted) 2-aminobenzothiazole and diphosgene in pyridine:

Ethyl-2-aminobenzothiazole-6-carboxylate (262 mg, 1.2 mmol) was suspended in pyridine (4 ml). Diphosgene (80 μL, 0.66 mmol) was added and the solution was stirred for two hours at room temperature. To this mixture a solution of 3-{4-[(4-trans-tert-butylcyclohexylamino)methyl]benzoylamino}propionic acid methyl ester trifluoroacetate (300 mg, 0.61 mmol) and N,N-diisopropylethylamine (0.4 mL, 2.4 mmol) in DMF (4 mL) was added and stirring at 80° C. was continued for 2 hours. The mixture was allowed to cool to room temperature and poured into acetonitrile (50 mL), the resulting precipitate was filtered off and the filtrate was then partitioned between ethyl acetate (50 mL) and hydrochloric acid (2×50 mL, 1 N). The organic phase was concentrated in vacuo to give an oil which was redissolved in ethanol (4 mL). Sodium hydroxide (1 mL, 4 N) was added and the reaction mixture was left at room temperature for 30 min. Hydrochloric acid (4 mL, 1 N) was added, and the resulting precipitate was subsequently collected by filtration to afford the title compound.

HPLC-MS (Method B): R$_t$=7.65 min, m/z=609 (M+).

EXAMPLE 255

General Procedure (K)

3-{4-[1-(trans-4-tert-Butylcyclohexyl)-3-(3,5-dichlorophenyl)ureidomethyl]benzoylamino}propionic acid

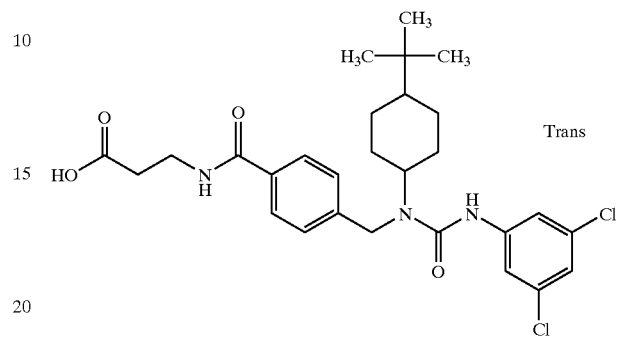

$^1$H NMR (DMSO-d$_6$): δ 12.2 (s, 1H), 8.68 (s, 1H), 8.45 (t, 1H), 7.74 (d, 2H), 7.61 (s, 2H), 7.30 (d, 2H), 7.11 (s, 1H), 4.57 (s, 2H), 4.02 (m, 1H), 3.43 (m, 2H), 2.50 (m, 2H), 1.8–0.75 (m, 9H), 0.80 (s, 9H).

HPLC-MS (method B): m/z: 548, R$_t$=8.35 min

MA: Calc for C$_{28}$H$_{35}$Cl$_2$N$_3$O$_4$: 61.31% C, 6.43% H, 7.66% N; Found 61.20% C, 6.59% H, 7.34% N.

General Procedure (L) for the Solid Phase Synthesis of Compounds of the General Formula (Ij)

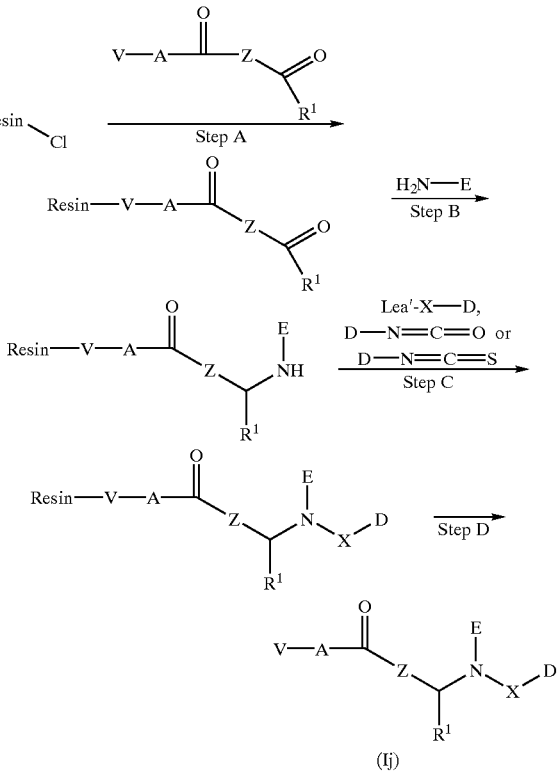

wherein

A, V, Z, R¹, E and D are as defined for formula (I),

X is

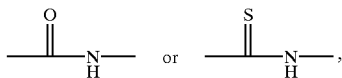

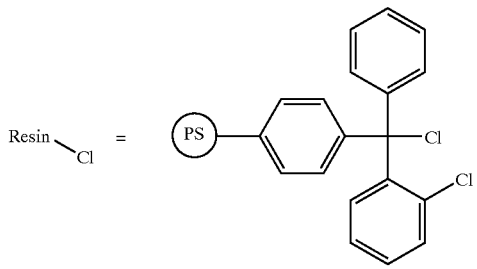

wherein PS is polystyrene, and

Lea' is a leaving group such as —OSu, chloro, phenoxy, or 4-nitrophenoxy.

Step A:

The reaction is known (The combinatorial index, Ed. Bunin, B. A. 1998, Academic Press, p. 24) and is generally performed by shaking a suspension of the resin with a solution of V-A-Z-C(O)R¹ in the presence of a base such as triethylamine, diisopropylethylamine, dicyclohexylmethylamine or any other tertiary amine. Typical solvents are pyridine, dichloromethane, 1,2-dichloroethane, DMF, NMP, THF, DMSO or mixtures of two or more of these. The reaction is performed between 20° C. and 120° C., preferably at 25° C. Excess reagents are filtered off and the resin is washed with any solvent mentioned above including mixtures hereof, containing a base as mentioned above and an alcohol, typically methanol, as a scavenger of unreacted resin bound 2-chlorotritylchloride.

Step B:

Step B is identical to step C of general procedure (T).

Step C:

Step C is identical to step D of general procedure (T).

Step D:

Step D is identical to step E of general procedure (T).

Preparation of starting materials D-N=C=O

N,N-Dimethyl-3-nitro-benzenesulfonamide

3-Nitrobenzenesulfonyl chloride (22.8 mmol, 5.05 g) was dissolved in dry THF (50 mL). Dimethylamine in THF (2M, 34 mL) was added and the mixture was refluxed for 2 hours. Upon cooling, the mixture was filtered and the filtrate was evaporated in vacuo. The residue was dissolved in ethyl acetate (250 mL), washed with water (3×50 mL) and dried over MgSO₄. Evaporation of the solvent afforded the title compound.

1-(3-Nitrobenzenesulfonyl)piperidine was prepared as described above using piperidine instead of dimethylamine.

3-Amino-N,N-dimethylbenzenesulfonamide

To a solution of the above N,N-dimethyl-3-nitro-benzenesulfonamide (20.4 mmol, 4.7 g) in ethanol (50 mL) was added SnCl₂ (105 mmol, 19.9 g) and the mixture was refluxed for 1 hour. Upon cooling, the solvent was removed in vacuo. Ethyl acetate (200 mL) and NaHCO₃ (sat, 100 mL) were added to the residue followed by another 200 mL ethyl acetate and 500 mL water. The phases were separated and the organic phase was washed twice with water. The organic phase was filtered, washed with water (2×100 mL) dried over MgSO₄ and evaporated to leave the title compound.

3-(Piperidine-1-sulfonyl)phenylamine was prepared as described above from 1-(3-nitro-benzenesulfonyl)piperidine.

3-Isocyanato-N,N-dimethylbenzenesulfonamide

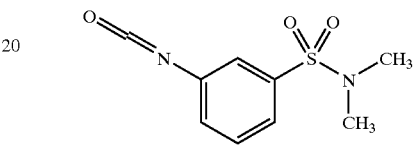

To a slurry of the above 3-amino-N,N-dimethylbenzenesulfonamide (3.26 g, 16 mmol) in toluene (200 mL) was added triphosgene (1.67 g) and the mixture was refluxed 16 h and evaporated. The residue was used without further purification.

1-(3-Isocyanatobenzenesulfonyl)piperidine was prepared as described above from 3-piperidine-1-sulfonyl)phenylamine.

1-Ethylsulfanyl-3-isocyanatobenzene

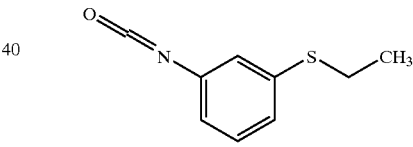

To a solution of 3-aminothiophenol (40 mmol, 5 g) in DMF (50 mL) was added K₂CO₃ (4.8 mmol, 6.63 g) and 2.98 mL bromoethane. The mixture was stirred over night at 25° C. and poured into 200 mL ice water. 200 mL ethylacetate was added and the phases were separated. The aqueous phase was extracted with 100 mL ethylacetate and the combined organic extracts were dried over MgSO₄. Evaporation of the solvent and re-dissolving the residue in ethyl acetate (100 mL) and HCl in ethyl acetate (2M, 20 mL) afforded 3-ethyl-sulfanylphenylamine hydrochloride, which was collected by filtration.

To a slurry of the above 3-ethylsulfanylphenylamine hydrochloride (31.6 mmol, 6 g) in toluene (100 mL) was added diphosgene (trichloromethyl chloroformate, 158 mmol, 31.3 g) and the mixture was refluxed for 2 hours affording a clear solution. The solvent was removed in vacuo and the residue was used without further purification.

The other starting materials used in the following examples were prepared in a similar way.

EXAMPLE 256

General Procedure (L)

4-[3-(3-Cyanophenyl)-1-(4-cyclohexylphenyl)ureidomethyl]-N-(2H-tetrazol-5-yl)benzamide

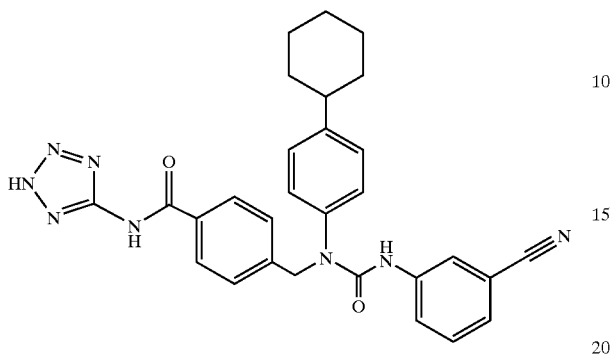

Step A: Resin bound 4-formyl-N-(2H-tetrazol-5-yl)benzamide

150 μmol 4-Formyl-N-(2H-tetrazol-5-yl)benzamide was dissolved in a mixture of 250 μL dichloromethane, 250 μL DMF and 100 μL diisopropylethylamine and added to 50 mg polystyrene resin functionalized with a 2-chlorotrityl chloride linker. After shaking the suspension for 4 hours at 25° C., the resin was isolated by filtration and washed with 2×1 mL dichloromethane:methanol:diisopropylethylamine 17:2:1 and 2×1 mL DMF.

Step B: Resin bound 4-[(4-cyclohexylphenylamino)methyl]-N-(2H-tetrazol-5-yl)benzamide The above resin bound 4-formyl-N-(2H-tetrazol-5-yl)benzamide (50 mg) was treated with a 0.5 M solution of 4-cyclohexylaniline (0.25 mmol, 41.25 mg) in a mixture of DMF and trimethylorthoformate (1:1, 0.5 mL) and glacial acetic acid (50 μL) for 1 hour at 25° C. followed by sodium cyanoborohydride (250 μmol, 16 mg) dissolved in a mixture of DMF and methanol (1:1, 0.25 mL). Shaking at 25° C. for 4 hours followed by filtration and washing with a mixture of DMF and methanol (1:1, 2×1 mL), 3×1 mL DMF and 2×1 mL dichloromethane afforded the desired product.

Step C: Resin bound 4-[3-(3-cyanophenyl)-1-(4-cyclohexylphenyl)ureidomethyl]-N-(2H-tetrazol-5-yl)benzamide 200 μmol 3-cyanophenylisocyanate dissolved in 500 μL dichloroethane was added to the above resin bound 4-[(4-cyclohexylphenylamino)methyl]-N-(2H-tetrazol-5-yl)benzamide (50 mg). Shaking the mixture for 5 hours at 25° C. followed by filtration and washing of the resin with 2×1 mL dichloromethane, 4×1 mL DMF, 2×1 mL H$_2$O, 3×mL THF and 3×1 mL dichloromethane afforded the resin bound title compound.

Step D: 4-[3-(3-Cyanophenyl)-1-(4-cyclohexylphenyl)ureidomethyl]-N-(2H-tetrazol-5-yl)benzamide The above resin bound 4-[3-(3-cyanophenyl)-1-(4-cyclohexylphenyl)ureidomethyl]-N-(2H-tetrazol-5-yl)benzamide (50 mg) was treated with 1 mL 5% TFA in dichloromethane for 1 hour at 25° C. The product was filtered off and the resin was washed with 1 mL dichloromethane. The combined extracts were concentrated in vacuo. The residue was dissolved in 50 μL DMSO+500 μL acetonitrile and purified by preparative HPLC using a Supelcosil ABZ+25 cm×10 mm 5μ column. The starting eluent composition was 5% acetonitrile in water changing over 30 min to 90% acetonitrile in water which was then kept constant for 5 min before going back to the starting composition over 10 min. The flow rate was kept constant at 8 mL/min collecting one fraction per minute. The process was monitored using a UV detector operating at 214 nm. The fractions containing the desired product were combined and evaporated in vacuo to afford the title compound.

Optionally, the compound can be purified by recrystallisation from eg acetonitrile.

$^1$H NMR (300 MHz, DMSO-d$_6$): δ 12.35 (s br, 1H); 8.58 (s, 1H); 8.05 (d, 2H); 7.95 (s, 1H); 7.73 (d, 1H); 7.50–7.38 (m, 4H); 7.20 (s, 4H); 5.00 (s, 2H); 1.85–1.60 (m, 5H); 1.45–1.10 (m, 6H).

HPLC-MS (method B): m/z=521, R$_t$=7.60 min.

EXAMPLE 257

General Procedure (L)

4-[3-Benzothiazol-6-yl-1-(4-tert-butylphenyl)ureidomethyl]-N-(2H-tetrazol-5-yl)benzamide

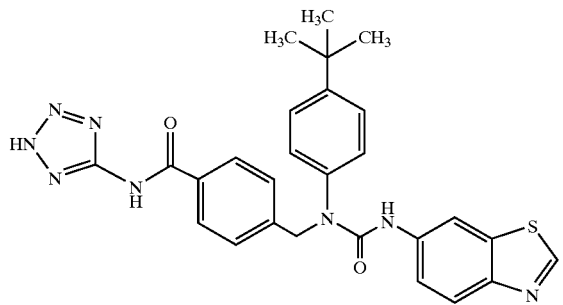

$^1$H NMR (DMSO-d$_6$): δ 8.5 (s, 1H); 8.28 (s, 1H); 8.05 (d, 2H); 7.93 (d, 2H); 7.55 (d, 1H); 7.48 (d, 2H); 7.43 (d, 2H); 7.22 (d, 2H); 5.03 (s, 2H); 1.28 (s, 9H).

HPLC-MS (Method B): m/z=527 (M+1). R$_t$=6.47 min.

EXAMPLE 258

General Procedure (L)

4-[1-(4-Cyclohexylphenyl)-3-(1,1-dioxo-2,3-dihydro-1H-1-benzo[b]thiophen-6-yl)ureidomethyl]-N-(2H-tetrazol-5-yl)benzamide

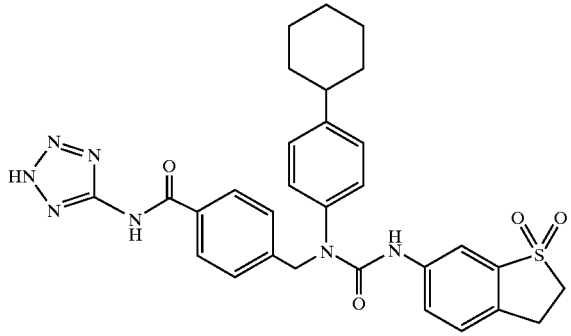

The benzothiophene moiety was synthesized from commercially available 6-amino-1,1-dioxo-1H-1-benzo[b]thiophene using Pd/C and H$_2$ employing methods known by those skilled in the art. The aniline was converted to an isocyanate by methods mentioned previously.

$^1$H NMR (DMSO-d$_6$): δ 12.40 (s, 1H); 8.60 (s, 1H); 8.05 (s, 2H); 7.88 (s, 1H); 7.68 (d, 1H); 7.45 (d, 2H); 7.39 (d, 1H);

7.20 (s, 4H); 5.00 (s, 2H).3.58 (t, 2H); 3.30 (t, 2H); 1.85–1.65 (m, 5H); 1.50–1.15 (m, 5H).

HPLC-MS (Method B): m/z=586 (M+1). $R_t$=7.88 min.

EXAMPLE 259

General Procedure (L)

4-[1-(4-tert-Butylphenyl)-3-(1,1-dioxo-2,3-dihydro-1H-benzo[b]thiophen-6-yl)ureidomethyl]-N-(2H-tetrazol-5-yl)benzamide

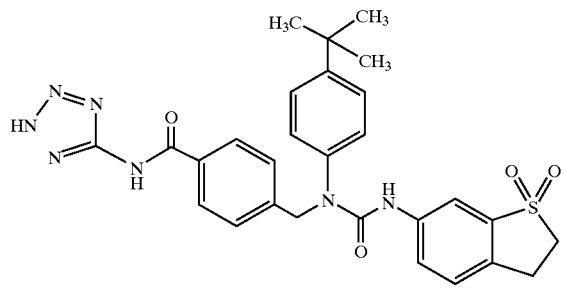

$^1$H NMR (DMSO-$d_6$): δ 12.40 (s, 1H); 8.65 (s, 1H); 8.05 (s, 2H); 7.88 (s, 1H); 7.60 (d, 1H); 7.48 (d, 2H); 7.45–7.38 (m, 3H); 7.22 (d, 2H); 5.00 (s, 2H); 3.58 (t, 2H); 3.34 (t, 2H), 1.32 (s, 9H).

HPLC-MS (Method B): m/z=560 (M+1). $R_t$=7.58 min.

EXAMPLE 260

General Procedure (L)

4-[1-(4-Cyclohexylphenyl)-3-(2-fluoro-5-methylsulfonylphenyl)ureidomethyl]-N-(2H-tetrazol-5-yl)benzamide

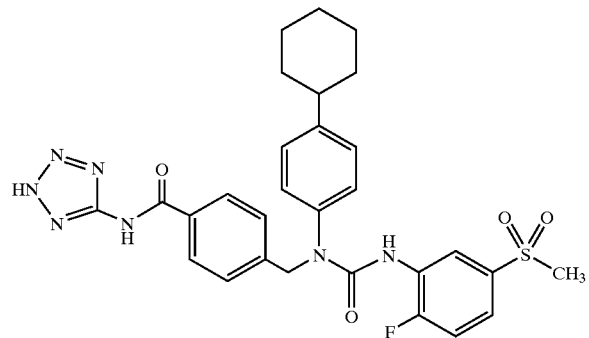

2-Fluoro-5-methylsulfonylphenyl isocyanate was prepared from the corresponding 2-fluoro-5-methylsulfonyl-1-nitrobenzene via reduction to the corresponding aniline as described previously.

$^1$H NMR (DMSO-$d_6$): δ 11.50 (s br, 1H); 8.30 (d, 1H); 8.00 (d, 2H); 7.90 (s, 1H); 7.65 (m, 1H); 7.50–7.40 (m, 3H); 7.25 (s, 4H); 5.05 (s, 2H); 3.18 (s, 3H); 1.85–1.65 (m, 5H); 1.50–1.15 (m, 5H).

HPLC-MS (Method B): m/z=592 (M+1). $R_t$=7.04 min.

EXAMPLE 261

General Procedure (L)

4-[1-(4-Cyclohexylphenyl)-3-(5-methylsulfonyl-2-methylphenyl)ureidomethyl]-N-(2H-tetrazol-5-yl)benzamide

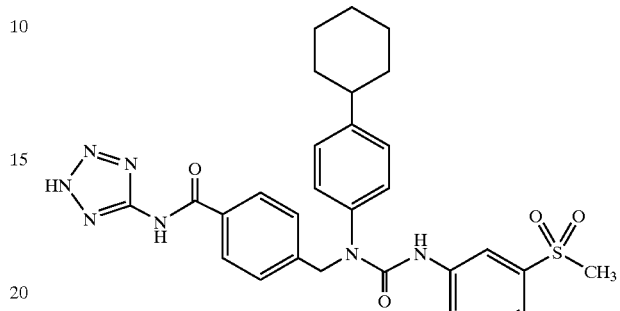

5-Methylsulfonyl-2-methylphenyl isocyanate was prepared from the corresponding 5-methylsulfonyl-2-methyl-1-nitrobenzene via reduction to the corresponding aniline followed by conversion to the isocyanate as described previously.

$^1$H NMR (DMSO-$d_6$): δ 12.10 (s br, 1H); 8.15 (s, 1H); 8.05 (d, 2H); 7.62 (m, 6H); 7.28 (dd, 4H); 5.03 (s, 2H); 3.15 (s, 3H); 2.10 (s, 3H); 1.85–1.65 (m, 5H); 1.50–1.15 (m, 5H).

HPLC-MS (Method B): m/z=588 (M+1). $R_t$=7.10 min.

EXAMPLE 262

General Procedure (L)

4-[1-(4-Cyclohexylphenyl)-3-(3-fluoro-5-trifluoromethylphenyl)ureidomethyl]-N-(2H-tetrazol-5-yl)benzamide

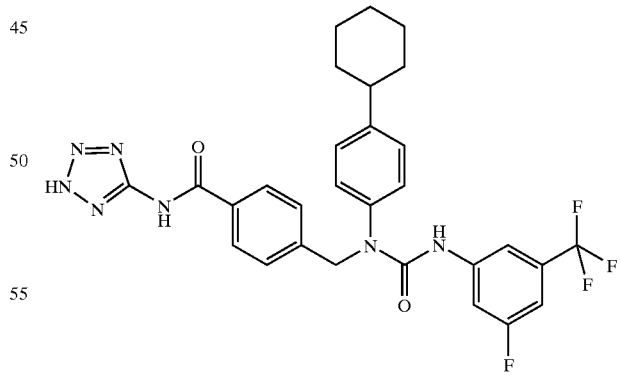

$^1$H NMR (DMSO-$d_6$): δ 12.40 (s, 1H); 8.82 (s, 1H); 8.08 (d, 2H); 7.75 (m, 2H); 7.45 (d, 2H); 7.25–7.15 (m, 5H); 5.02 (s, 2H); 1.85–1.65 (m, 5H); 1.50–1.15 (m, 5H).

HPLC-MS (Method B): m/z=582 (M+1). $R_t$=8.05 min.

Alternative method for the preparation of the title compound:

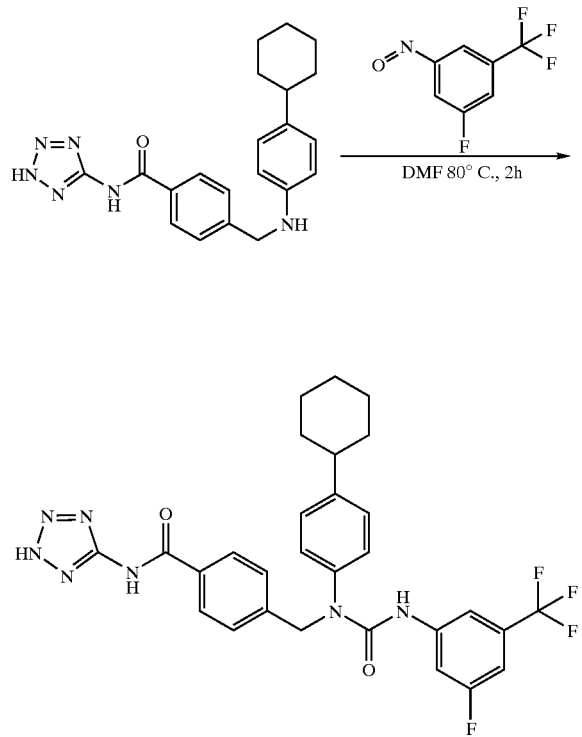

Preparation of 3-fluoro-5-trifluoromethylphenylisocyanate:

3-Fluoro-5-trifluoromethylaniline (2 g, 11.2 mmol) was dissolved in 20 mL diethylether and added concentrated hydrochloric acid (37%, 1.5 mL, 18 mmol). Upon stirring for 1 hour at 25° C. the solvent was removed in vacuo and the white solid was stripped with toluene (3×20 mL). Diphosgene (20 mL) was added to the hydrochloride salt and the mixture was refluxed over night. Excess diphosgene was removed in vacuo and the clear oil was stripped with toluene (3×20 mL). The obtained isocyanate was used without further purification.

Preparation of 4-[1-(4-Cyclohexylphenyl)-3-(3-fluoro-5-trifluoromethylphenyl)ureidomethyl]-N-(2H-tetrazol-5-yl)benzamide:

A slurry of 4-[(4-cyclohexylphenylamino)methyl]-N-(2H-tetrazol-5-yl)benzamide (3 g, 7.96 mmol) in DMF (50 mL) was added to the above 3-fluoro-5-trifluoromethylphenylisocyanate and the mixture was heated to 80° C. After 2 hours the reaction was allowed to cool to 25° C. and acetonitrile (500 mL) was added. The mixture was filtered, the precipitate was discarded and the filtrate evaporated. The residue was refluxed in acetonitrile (75 mL) and allowed to cool to 25° C. After filtration, a new precipitate was formed affording the title compound (850 mg).

EXAMPLE 263

General Procedure (L)

4-[3-(3-Bromo-5-trifluoromethylphenyl)-1-(4-tert-butylphenyl)ureidomethyl]-N-(2H-tetrazol-5-yl)benzamide

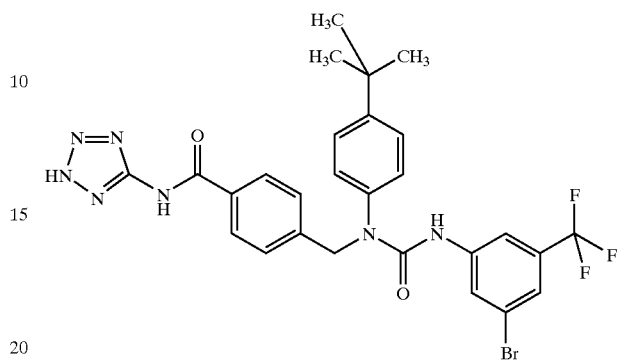

HPLC-MS (Method B): m/z=617 (M+1). $R_f$=7.95 min.
$^1$H NMR (DMSO): δ 12.40 (s, 1H); 8.80 (s, 1H); 8.10 (s, 1H); 8.04 (d, 2H); 7.92 (s, 1H); 7.50 (s, 1H); 7.49 (d, 2H); 7.42 (d, 2H); 7.23 (d, 2H); 5.02 (s, 2H); 1.32 (s, 9H).

EXAMPLE 264

General Procedure (L)

4-[3-(3-Bromo-5-trifluoromethylphenyl)-1-(4-cyclohexylphenyl)ureidomethyl]-N-(2H-tetrazol-5-yl)benzamide

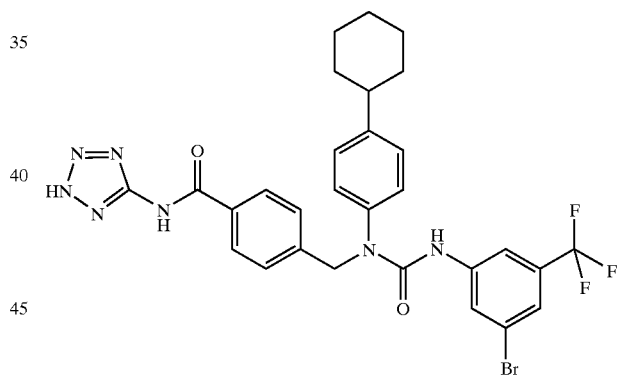

HPLC-MS (Method B): m/z=642 (M+1). $R_f$=8.45 min.

Alternative method for the preparation of the title compound:

Preparation of 3-bromo-5-trifluoromethylphenylisocyanate:

3-Bromo-5-trifluoromethylaniline (2.16 g, 9 mmol) was dissolved in 20 mL diethylether and added concentrated hydrochloric acid (37%, 1.5 mL, 18 mmol). Upon stirring for 1 hour at 25° C. the solvent was removed in vacuo and the white solid was stripped with toluene (3×20 mL). Diphosgene (13 mL) was added to the ammonium chloride salt and the mixture was refluxed for 3.5 hours until no solid material precipitated on cooling. Excess diphosgene was removed in vacuo and the clear oil was stripped with toluene (3×20 mL). The obtained isocyanate was used without further purification.

Preparation of 4-[3-(3-bromo-5-trifluoromethylphenyl)-1-(4-cyclohexylphenyl)ureidomethyl]-N-(2H-tetrazol-5-yl)benzamide:

The above isocyanate was dissolved in DMF (20 mL) and added 4-[(4-cyclohexylphenylamino)methyl]-N-(2H-tetrazol-5-yl)benzamide (1.88 g, 5 mmol) and the mixture was heated at 80° C. After 1 hour the reaction was allowed to cool to 25° C. and the solvent was evaporated. The residue was refluxed in acetonitrile (10 mL) and allowed to cool to 25° C. The desired product was isolated by filtration and dried in vacuo (2.5 g).

$^1$H NMR (DMSO): δ 12.35 (s, 1H); 8.75 (s, 1H); 8.10 (s, 1H); 8.04 (d, 2H); 7.92 (s, 1H); 7.50 (s, 1H); 7.48 (d, 2H); 7.23 (s, 4H); 5.00 (s, 2H); 1.85–1.65 (m, 5H); 1.45–1.15 (m, 5H).

HPLC-MS (Method F): m/z=642 (M+1). $R_t$=5.67 min.

EXAMPLE 265

General Procedure (L)

3-(4-{1-(4-Cyclohexylphenyl)-3-[3-(ethylphenylsulfamoyl)phenyl]ureidomethyl}benzoylamino)propionic acid

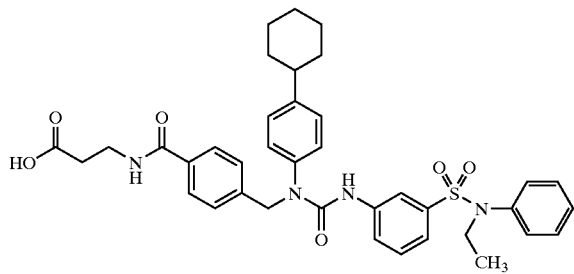

HPLC-MS (Method B): m/z=683 (M+1). $R_t$=7.60 min.

EXAMPLE 266

General Procedure (L)

4-{1-(4-Cyclohexylphenyl)-3-[3-(methylphenylsulfamoyl)phenyl]ureidomethyl}-N-(2H-tetrazol-5-yl)benzamide

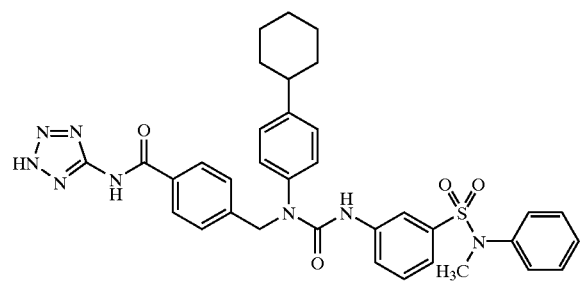

HPLC-MS (Method B): m/z=665 (M+1). $R_t$=7.67 min.

EXAMPLE 267

General Procedure (L)

4-{1-(4-Cyclohexylphenyl)-3-[3-(2,3-dihydroindole-1-sulfonyl)phenyl]ureidomethyl}-N-(2H-tetrazol-5-yl)benzamide

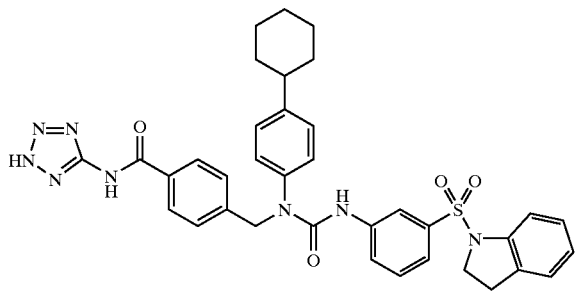

HPLC-MS (Method B): m/z 677 (M+1). $R_t$=7.75 min.

EXAMPLE 268

General Procedure (L)

4-[3-(3,5-Bis-trifluoromethylphenyl)-1-(4-cyclohex-1-enylphenyl)ureidomethyl]-N-(2H-tetrazol-5-yl)benzamide

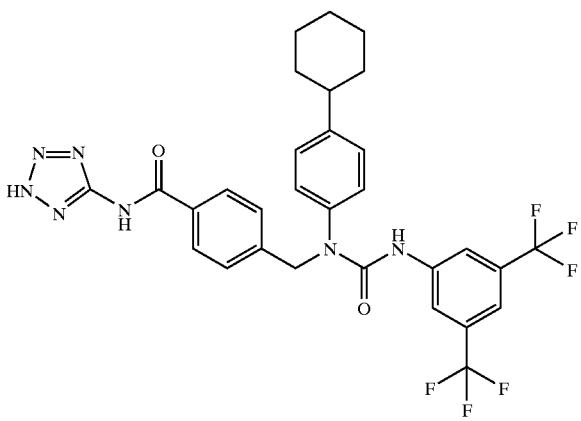

The starting material 4-(cyclohex-1-enyl)phenylamine was prepared in the following way:

Step 1: 1-(1-Bromocyclohexyl)-4-nitrobenzene

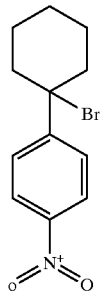

4-Cyclohexylnitrobenzene (22.6 g, 0.11 mol) and N-bromosuccinimide (21.6 g, 0.12 mol) were suspended in tetrachloromethane (200 mL) and a catalytic amount of dibenzoylperoxide was added. The reaction mixture was stirred at 80° C. for 4.5 hours. The reaction mixture was concentrated in vacuo and the residue dissolved in ethyl acetate (400 mL) and washed with water (100 mL). The aqueous phase was extracted with ethyl acetate (200 mL) and the combined organic phases were washed with water (3×150 mL), dried over MgSO$_4$ and concentrated in vacuo. The residue was crystallised from ethyl acetate and heptane to give 18.4 g of 1-(bromocyclohexyl)-4-nitrobenzene.

$^1$H NMR (DMSO-d$_6$): δ 1.29–1.40 (1H, m), 1.60–1.71 (3H, d), 1.73–1.85 (2H, m), 2.06–2.18 (2H, m), 2.55 (2H, m), 7.92 (2H, d), 8.34 (2H, d).

M.p.: 83.5–85.5° C.

MA: calc 50.72% C, 4.97% H, 4.93% N; Found 50.65% C, 5.10% H, 4.91% N.

Step 2: 1-Cyclohex-1-enyl-4-nitrobenzene

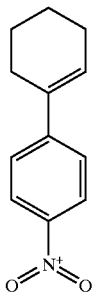

1-(Bromocyclohexyl)-4-nitrobenzene (18.4 g, 64.8 mmol), lithium carbonate (5.3 g, 71.2 mmol), and lithium bromide (6.2 g, 71.2 mmol) were reacted together in DMF (100 mL) for 2 hours at 160° C. The reaction mixture was cooled to 20° C., diluted with ethyl acetate (500 mL), and washed with water (300 mL). The aqueous phase was extracted with ethyl acetate (200 mL) and the combined organic phases were washed with water (3×150 mL), dried over MgSO$_4$ and concentrated in vacuo. The residue was purified on silica (350 g) using ethyl acetate and heptane (1:9) as eluent to give 11.7 g of 1-cyclohex-1-enyl-4-nitrobenzene.

$^1$H NMR (DMSO-d$_6$): δ 1.57–1.69 (2H, m), 1.60–1.70 (2H, m), 2.18–2.29 (2H, m), 2.38–2.46 (2H, m), 6.46 (1H, t), 7.67 (2H, d), 8.17 (2H, d).

Step 3: 4-(Cyclohex-1-enyl)phenylamine

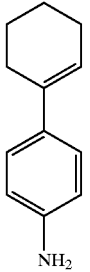

1-Cyclohex-1-enyl-4-nitrobenzene (11.7 g, 57.6 mmol) was dissolved in hot absolute ethanol (170 mL). Stannous chloride (65 g, 288 mmol) was added and the reaction mixture was stirred at reflux temperature for 1.5 hours. The reaction mixture was concentrated in vacuo and the residue was added ethyl acetate (700 mL) and water (700 mL), and neutralised to pH 7 with sodium hydroxide (4 N). Ethyl acetate (150 mL) was added and the mixture was filtered through celite. The organic phase of the filtrate was washed with water and a saturated solution of sodium chloride, dried over MgSO$_4$, and concentrated in vacuo. The residue was purified on silica (200 g) using ethyl acetate and heptane (1:4) as eluent to give 7.4 g of 4-(cyclohex-1-enyl) phenylamine.

HPLC-MS (method B): m/z: 174, R$_t$=4.05 min.

$^1$H NMR (DMSO-d$_6$): δ 1.52–1.60 (2H, m), 1.63–1.72 (2H, m), 2.13 (2H, m), 2.28 (2H, m), 5.0 (2H, s), 5.90 (1H, t), 6.50 (2H, d), 7.08 (2H, d).

The title compound was prepared using 4-(cyclohex-1-enyl)phenylamine in step B.

$^1$H NMR (DMSO-d$_6$): δ 12.40 (s, 1H); 8.92 (s, 1H); 8.28 (s, 2H); 8.04 (d, 2H); 7.61 (s, 1H); 7.48 (d, 2H); 7.46 (d, 2H); 7.25 (d, 2H); 6.20 (s br, 1H); 5.03 (s, 2H); 2.38 (m br, 2H); 2.18 (m br, 2H); 1.71 (m br, 2H); 1.60 (m br, 2H).

HPLC-MS (Method B): m/z=630 (M+1). R$_t$=8.25 min.

EXAMPLE 269

General Procedure (L)

4-[3-(3-Bromo-5-trifluoromethylphenyl)-1-(4-cyclohex-1-enylphenyl)ureidomethyl]-N-(2H-tetrazol-5-yl)benzamide

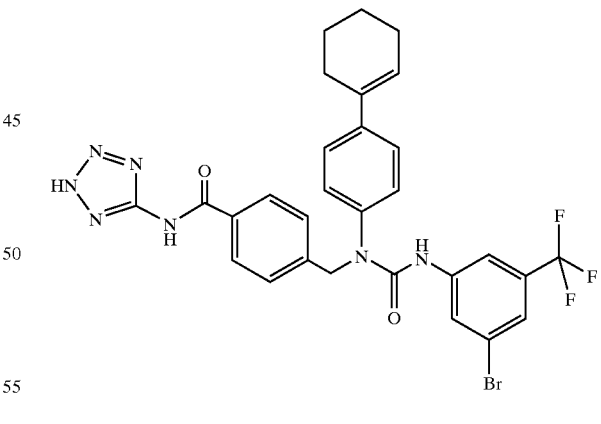

$^1$H NMR (DMSO-d$_6$): δ 12.40 (s, 1H); 8.75 (s, 1H); 8.10 (s, 1H); 8.04 (d, 2H); 7.92 (s, 1H); 7.50–7.35 (m, 5H); 7.25 (d, 2H); 6.20 (s br, 1H); 5.03 (s, 2H); 2.35 (m br, 2H); 2.15 (m br, 2H); 1.72 (m br, 2H); 1.60 (m br, 2H).

HPLC-MS (Method B): m/z=641 (M+1). R$_t$=8.27 min.

EXAMPLE 270

General Procedure (L)

4-[1-(4-Cyclohexylphenyl)-3-(3-fluoro-5-trifluoromethylbenzyl)ureidomethyl]-N-(2H-tetrazol-5-yl)benzamide

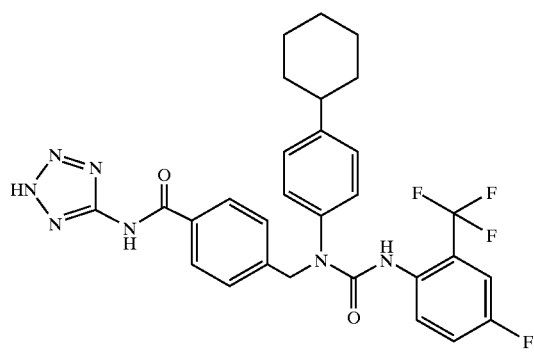

$^1$H NMR (DMSO-d$_6$): δ 12.40 (s, 1H); 8.04 (d, 2H); 7.53 (d, 1H); 7.45 (s, 1H); 7.38 (d, 2H); 7.24 (d, 2H); 7.12 (d, 2H); 6.69 (t, 1H); 4.90 (s, 2H); 4.30 (d, 2H); 1.80–1.65 (m, 5H); 1.50–1.15 (m, 5H).

HPLC-MS (Method B): m/z=596 (M+1). R$_t$=7.70 min.

EXAMPLE 271

General Procedure (L)

4-[3-(3,5-Bis-trifluoromethylphenyl)-1-(4-cyclohexylphenyl)ureidomethyl]-N-(2H-tetrazol-5-yl)benzamide

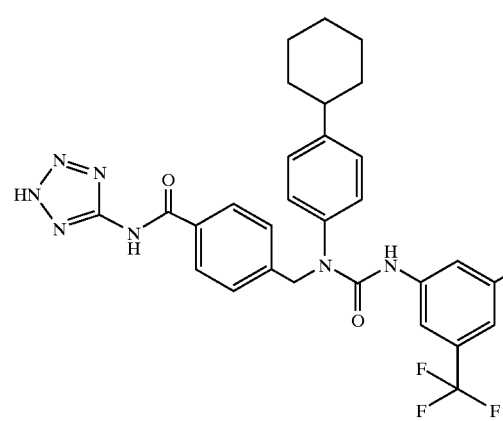

$^1$H NMR (DMSO-d$_6$): δ 12.40 (s br, 1H); 8.95 (s, 1H); 8.25 (s, 2H); 8.05 (d, 2H); 7.62 (s, 1H); 7.45 (d, 2H); 7.24 (s, 4H); 5.02 (s, 2H); 1.82–1.65 (m, 5H); 1.50–1.15 (m, 5H).

HPLC-MS (Method B): m/z=632 (M+1). R$_t$=8.37 min.

EXAMPLE 272

General Procedure (L)

4-[3-(4-Acetylphenyl)-1-(4-cyclohexylphenyl)ureidomethyl]-N-(2H-tetrazol-5-yl)benzamide

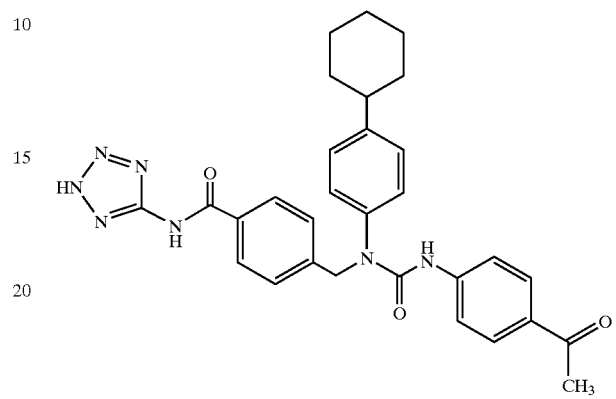

$^1$H NMR (300 MHz, DMSO-d$_6$): δ 12.35 (s br, 1H); 8.62 (s, 1H); 8.05 (d, 2H); 7.85 (d, 2H); 7.60 (d, 2H); 7.45 (d, 2H); 7.20 (s, 4H); 5.00 (s, 2H); 1.85–1.60 (m, 5H); 1.45–1.10 (m, 6H).

HPLC-MS (method B): m/z=538, R$_t$=7.42 min.

EXAMPLE 273

General Procedure (L)

4-[3-(4-Acetylphenyl)-1-(4-tert-butylcyclohexyl)ureidomethyl]-N-(2H-tetrazol-5-yl)benzamide

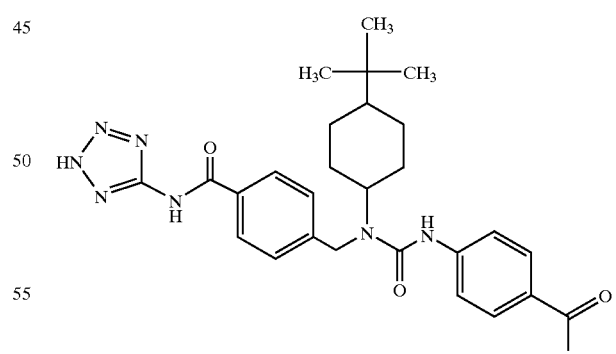

$^1$H NMR (300 MHz, DMSO-d$_6$): δ 12.35 (s br, 1H); 8.85 (s, 1H); 8.05 (d, 2H); 7.85 (d, 2H); 7.62 (d, 2H); 7.43 (d, 2H); 4.70 (s, 2H); 4.10 (t br, 1H); 1.85–0.90 (m, 9H); 0.85 (s, 9H).

HPLC-MS (method B): m/z=518, R$_t$=7.35 min.

EXAMPLE 274

General Procedure (L)

4-[1-(4-tert-Butylcyclohexyl)-3-(3-cyanophenyl)ureidomethyl]-N-(2H-tetrazol-5-yl)benzamide

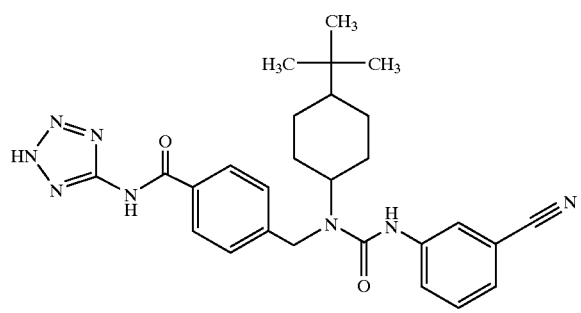

$^1$H NMR (300 MHz, DMSO-$d_6$): δ 12.30 (s br, 1H); 8.73 (s, 1H); 8.05 (d, 2H); 7.93 (s, 1H); 7.75 (d, 1H); 7.50–7.30 (m, 4H); 4.65 (s, 2H); 4.08 (t br, 1H); 1.83–0.90 (m, 9H); 0.85 (s, 9H).

HPLC-MS (method B): m/z=501, $R_t$=7.62 min.

EXAMPLE 275

General Procedure (L)

4-[1-(4-Cyclohexylphenyl)-3-(3-dimethylsulfamoylphenyl)ureidomethyl]-N-(2H-tetrazol-5-yl)benzamide

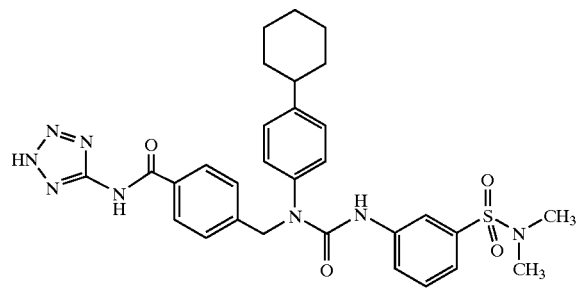

$^1$H NMR (300 MHz, DMSO-$d_6$): δ 12.40 (s br, 1H); 8.70 (s, 1H); 8.05 (d, 2H); 7.90 (s, 1H); 7.73 (d, 1H); 7.50–7.40 (m, 3H); 7.30 (d, 1H); 7.20 (s, 4H); 5.00 (s, 2H); 2.60 (s, 6H); 1.85–1.60 (m, 5H); 1.45–1.10 (m, 6H).

HPLC-MS (method B): m/z=603, $R_t$=7.08 min.

EXAMPLE 276

General Procedure (L)

4-[1-(4-tert-Butylphenyl)-3-(3-dimethylsulfamoylphenyl)ureidomethyl]-N-(2H-tetrazol-5-yl)benzamide

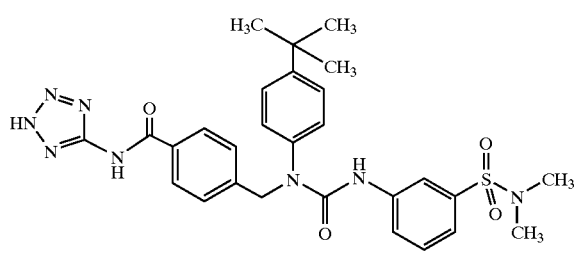

$^1$H NMR (200 MHz, DMSO-$d_6$): δ 12.40 (s br, 1H); 8.70 (s, 1H); 8.05 (d, 2H); 7.90 (t, 1H); 7.70 (d, 1H); 7.55–7.35 (m, 5H); 7.30 (d, 1H); 7.23 (d, 2H); 5.00 (s, 2H); 2.60 (s, 6H) 1.28 (s, 9H).

HPLC-MS (method B): m/z=577, $R_t$=6.48 min.

EXAMPLE 277

General Procedure (L)

4-{1-(4-Cyclohexylphenyl)-3-[3-(piperidine-1-sulfonyl)phenyl]ureidomethyl}-N-(2H-tetrazol-5-yl)benzamide

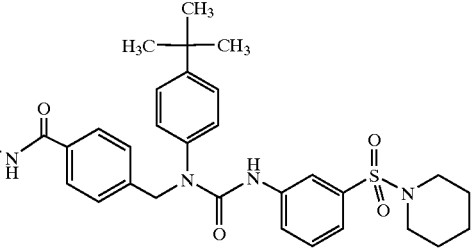

$^1$H NMR (300 MHz), (DMSO-$d_6$): δ 12.40 (s br, 1H); 8.70 (s, 1H); 8.05 (d, 2H); 7.90 (s, 1H); 7.70 (d, 1H); 7.52–7.18 (m, 8H); 5.00 (s, 2H); 2.90 (t, 4H) 1.65–1.35 (m, 6H); 1.28 (s, 9H).

HPLC-MS (method B): m/z=617, $R_t$=7.22 min.

EXAMPLE 278

General Procedure (L)

4-[1-(4-Cyclohexylphenyl)-3-(3-trifluoromethylsulfanylphenyl)ureidomethyl]-N-(2H-tetrazol-5-yl)benzamide

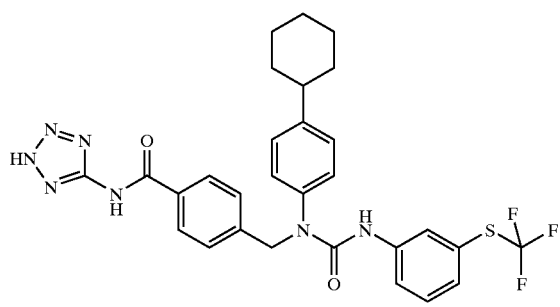

$^1$H NMR (300 MHz, DMSO-$d_6$): δ 12.40 (s br, 1H); 8.58 (s, 1H); 8.05 (d, 2H); 7.90 (s, 1H); 7.70 (d, 1H); 7.45 (d, 2H); 7.40 (t, 1H); 7.30–7.15 (m, 5H); 5.00 (s, 2H); 1.85–1.10 (m, 11H).

HPLC-MS (method B): m/z=596, $R_t$=8.30 min.

EXAMPLE 279

General Procedure (L)

4-[1-(4-Cyclohexylphenyl)-3-phenylureidomethyl]-N-(2H-tetrazol-5-yl)benzamide

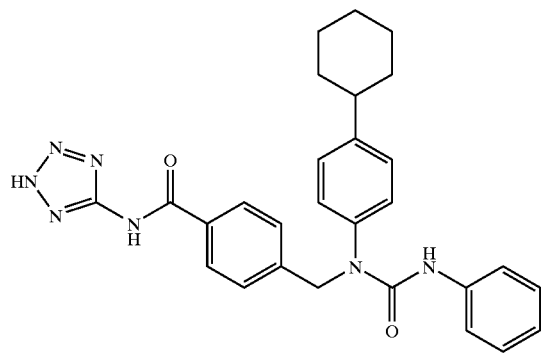

$^1$H NMR (300 MHz, DMSO-$d_6$): δ 12.35 (s br, 1H); 8.12 (s, 1H); 8.05 (d, 2H); 7.48 (d, 2H); 7.42 (t, 1H); 7.20 (m, 6H); 6.95 (t, 1H); 5.00 (s, 2H); 1.85–1.10 (m, 11H).

HPLC-MS (method B): m/z=496, $R_t$=7.72 min.

EXAMPLE 280

General Procedure (L)

4-[1-(4-Butylphenyl)-3-phenylureidomethyl]-N-(2H-tetrazol-5-yl)benzamide

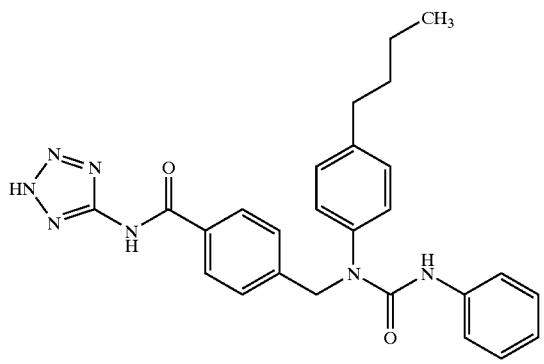

$^1$H NMR (300 MHz, DMSO-$d_6$): δ 12.35 (s br, 1H); 8.10 (s, 1H); 8.04 (d, 2H); 7.46 (d, 2H); 7.42 (d, 2H); 7.30–7.10 (m, 6H); 6.95 (t, 1H); 5.00 (s, 2H); 2.55 (t, 2H); 1.55 (k, 2H); 1.32 (sx, 2H); 0.90 (t, 3H).

HPLC-MS (method B): m/z=470, $R_t$=7.38 min.

EXAMPLE 281

General Procedure (L)

4-[1-(4-Butylphenyl)-3-(3-cyanophenyl)ureidomethyl]-N-(2H-tetrazol-5-yl)benzamide

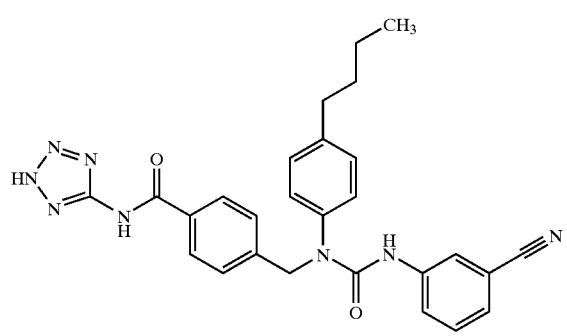

$^1$H NMR (300 MHz, DMSO-$d_6$): δ 12.35 (s br, 1H); 8.50 (s, 1H); 8.05 (d, 2H); 7.95 (s, 1H); 7.75 (d, 1H); 7.46–7.38 (m, 4H); 7.20 (s, 4H); 5.00 (s, 2H); 2.55 (t, 2H); 1.55 (k, 2H); 1.32 (sx, 2H); 0.90 (t, 3H).

HPLC-MS (method B): m/z=495, $R_t$=7.28 min.

EXAMPLE 282

General Procedure (L)

4-[3-(4-Chloro-3-trifluoromethylphenyl)-1-(4-cyclohexylphenyl)ureidomethyl]-N-(2H-tetrazol-5-yl)benzamide

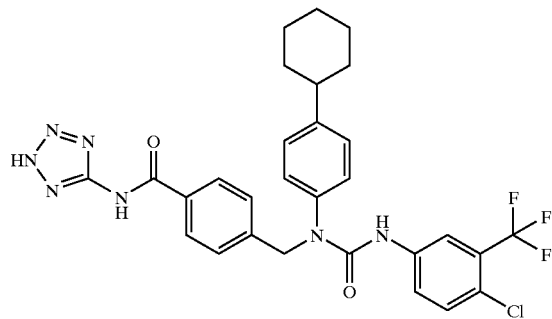

$^1$H NMR (300 MHz, DMSO-d$_6$): δ 12.40 (s br, 1H); 8.70 (s, 1H); 8.05 (d+s, 3H); 7.80 (d, 1H); 7.55 (d, 1H); 7.45 (d, 2H); 7.22 (s, 4H); 5.00 (s, 2H); 1.85–1.10 (m, 11H).

HPLC-MS (method B): m/z=598, R$_t$=8.55 min.

$^1$H NMR (MeOH-d$_4$): δ 1.20–1.50 (m, 5H), 1.75–1.90 (m, 5H), 2.55 (m, 1H), 5.02 (s, 2H), 7.19 (d, 2H), 7.30 (d, 2H), 7.44–7.50 (m, 3H), 7.60 (d, 1H), 7.90 (s, 1H), 7.99 (d, 2H).

MS (APCl, neg): 596.2, 597.2, 598.2, 375.2, 376.2.

EXAMPLE 283

General Procedure (L)

4-[3-(3-Acetylphenyl)-1-(4-cyclohexylphenyl)ureidomethyl]-N-(2H-tetrazol-5-yl)benzamide

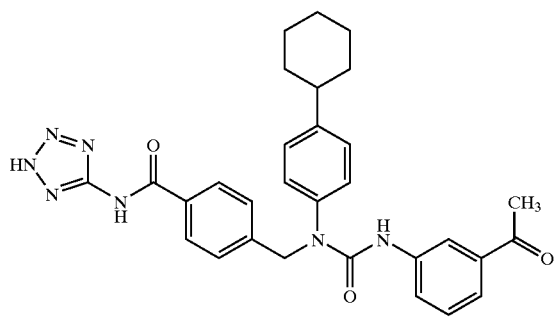

$^1$H NMR (300 MHz, DMSO-d$_6$): δ 12.40 (s br, 1H); 8.48 (s, 1H); 8.05 (d+s, 3H); 7.68 (d, 1H); 7.58 (d, 1H); 7.45 (d, 2H); 7.38 (t, 1H); 7.20 (s, 4H); 5.00 (s, 2H); 2.10 (s, 3H); 1.85–1.10 (m, 11H).

HPLC-MS (method B): m/z=538, R$_t$=7.38 min.

EXAMPLE 284

General Procedure (L)

4-[3-(4-Chloro-3-trifluoromethylphenyl)-1-(4-trifluoromethoxyphenyl)ureidomethyl]-N-(2H-tetrazol-5-yl)benzamide

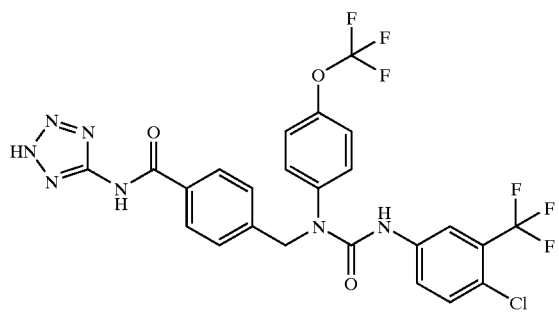

$^1$H NMR (300 MHz, DMSO-d$_6$): δ 12.40 (s br, 1H); 8.90 (s, 1H); 8.05 (d+s, 3H); 7.83 (d, 1H); 7.60 (d, 1H); 7.50–7.30 (m, 6H); 5.05 (s, 2H).

HPLC-MS (method B): m/z=600, R$_t$=7.75 min.

EXAMPLE 285

General Procedure (L)

4-[3-(3-Nitrophenyl)-1-(4-trifluoromethoxyphenyl)ureidomethyl]ureidomethyl]-N-(2H-tetrazol-5-yl)benzamide

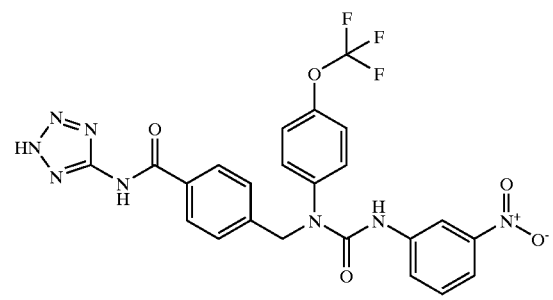

$^1$H NMR (300 MHz, DMSO-d$_6$): δ 12.40 (s br, 1H); 9.00 (s, 1H); 8.48 (t, 1H); 8.05 (d, 2H); 7.92 (d, 1H); 7.82 (d, 1H); 7.60–7.30 (m, 7H); 5.05 (s, 2H).

HPLC-MS (method B): m/z=543, R$_t$=326.62 min.

EXAMPLE 286

General Procedure (L)

4-[1-(4-Cyclohexylphenyl)-3-(3-nitrophenyl)ureidomethyl]-N-(2H-tetrazol-5-yl)benzamide

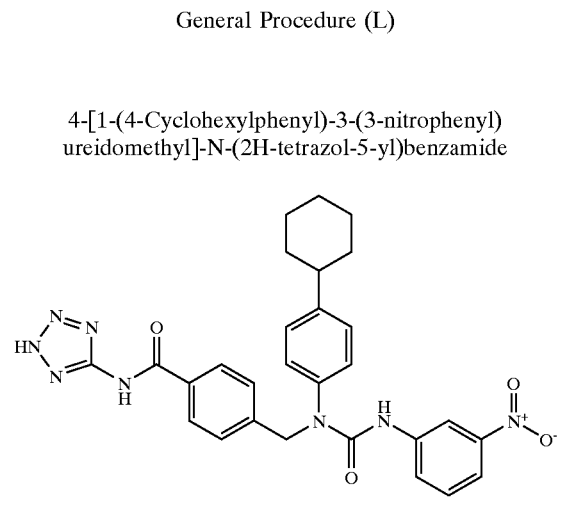

$^1$H NMR (200 MHz, DMSO-d$_6$): δ 12.40 (s br, 1H); 8.78 (s, 1H); 8.48 (t, 1H); 8.05 (d+s, 3H); 7.90 (d, 1H); 7.78 (d, 1H); 7.55–7.42 (m, 3H); 7.22 (s, 4H); 5.05 (s, 2H); 1.85–1.10 (m, 11H).

HPLC-MS (method B): m/z=541, R$_t$=7.67 min.

EXAMPLE 287

General Procedure (L)

4-[1-(4-tert-Butylphenyl)-3-(3-nitrophenyl)ureidomethyl]-N-(2H-tetrazol-5-yl)benzamide

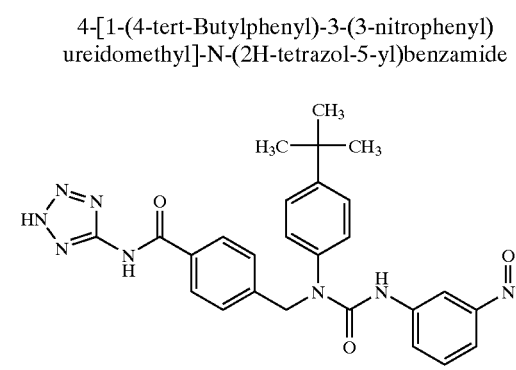

$^1$H NMR (200 MHz, DMSO-d$_6$): δ 12.40 (s br, 1H); 8.82 (s, 1H); 8.48 (t, 1H); 8.05 (d, 2H); 7.93 (d, 1H); 7.81 (d, 1H); 7.60–7.35 (m, 5H); 7.25 (d, 2H); 5.05 (s, 2H); 1.30 (s, 9H).

HPLC-MS (method B): m/z=515, R$_t$=7.13 min.

EXAMPLE 288

General Procedure (L)

4-[1-(4-Butylphenyl)-3-(3-nitrophenyl)ureidomethyl]-N-(2H-tetrazol-5-yl)benzamide

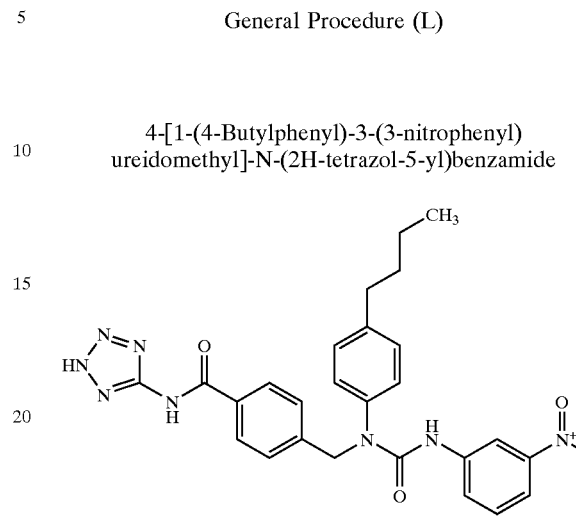

$^1$H NMR (200 MHz, DMSO-d$_6$): δ 12.40 (s br, 1H); 8.82 (s, 1H); 8.50 (t, 1H); 8.05 (d, 2H); 7.93 (d, 1H); 7.81 (d, 1H); 7.60–7.45 (m, 3H); 7.20 (s, 4H); 5.03 (s, 2H); 2.60 (t, 2); 1.55 (k, 2H); 1.35 (sx, 2H); 0.90 (t, 3H).

HPLC-MS (method B): m/z=515, R$_t$=7.33 min.

EXAMPLE 289

General Procedure (L)

4-[1-(4-Cyclohexylphenyl)-3-(3-ethylsulfanylphenyl)ureidomethyl]-N-(2H-tetrazol-5-yl)benzamide

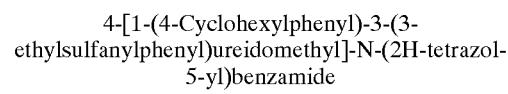
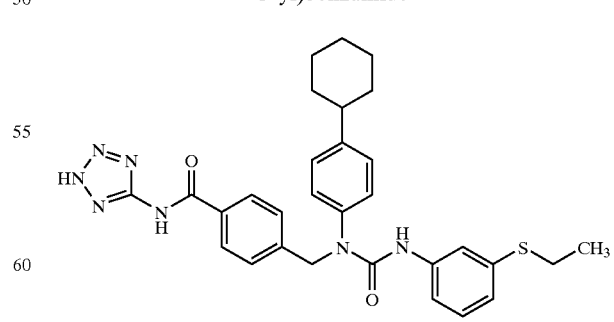

HPLC-MS (method B): m/z=556, R$_t$=8.07 min.

EXAMPLE 290

General Procedure (L)

5-{3-(4-sec-Butylphenyl)-3-[4-(2H-tetrazol-5-ylcarbamoyl)benzyl]ureidoisophtalic acid dimethyl ester

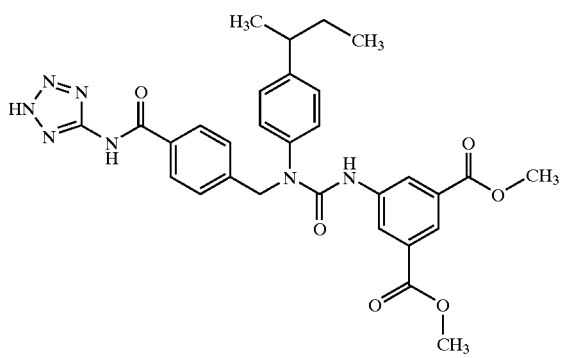

HPLC-MS (method B): m/z=586, $R_t$=7.23 min.

EXAMPLE 291

General Procedure (L)

4-[1-(4-Cyclohexylphenyl)-3-(4-trifluoromethoxyphenyl)ureidomethyl]-N-(2H-tetrazol-5-yl)benzamide

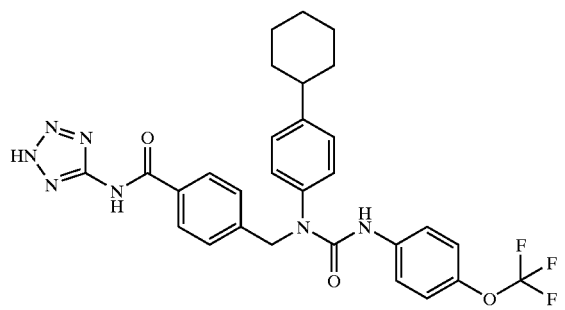

$^1$H NMR (DMSO-d$_6$): δ 1.1–1.4 (5H, m), 1.65–1.85 (5H, m), 5.00 (2H, s), 7.2 (6H, m), 7.46 (2H, d), 7.55 (2H, d), 8.04 (2H, d), 8.43 (1H, s), 12.4 (1H, bs).

HPLC-MS (Method B): $R_t$=8.22 min, m/z=580 (M+1).
Alternative Method for the Preparation of the Title Compound To a solution of 4-carboxybenzaldehyde (40.2 g, 0.27 mol) in DMF (400 mL) was added N-ethyl-N'-3-dimethylaminopropylcarbodiimide (65.5 g, 0.33 mol) followed by 5-aminotetrazol monohydrate (36.6 g, 0.35 mol). The mixture was stirred for 24 hours at ambient temperature. The reaction volume was then reduced to one half by rotary evaporation, and water (800 mL) was added. The precipitate was collected by filtration, washed with cold acetonitrile and dried overnight in a vacuum oven to afford 46.0 g (80%) of 4-formyl-N-(2H-tetrazol-5-yl)benzamide.

$^1$H NMR (DMSO-d$_6$): δ 8.08 (d, 2H); 8.26 (d, 2H); 10.15 (s, 1H); 12.68 (bs, 1H).

4-Formyl-N-(2H-tetrazol-5-yl)benzamide (8.94 g, 41.2 mmol) was dissolved in DMF (50 mL) by gentle heating. A solution of 4-cyclohexylaniline (7.20 g, 41.2 mmol) in methanol (100 mL) was added and a turbid suspension was formed. The suspension was heated to 70° C. for 1 hour. Acetic acid (50 mL) and sodium cyanoborohydride (2.0 g, 31.7 mmol) was then added. The turbid suspension was heated to 70° C. for an additional hour, before being cooled to 0° C. on an ice bath. The insoluble material was collected by filtration and washed twice with water, before being dried overnight in a vacuum oven to afford 12.94 g (83.5%) of 4-[(4-cyclohexylphenylamino)methyl]-N-(2H-tetrazol-5-yl)benzamide.

$^1$H NMR (DMSO-d$_6$): δ 1.28 (m, 5H); 1.68 (m, 5H); 2.28 (m, 1H); 4.32 (s, 2H); 6.17 (bs, 1H); 6.48 (d, 2H); 6.88 (d, 2H); 7.52 (d, 2H); 8.03 (d, 2H); 12.30 (s, 1H).

To a suspension of 4-[(4-cyclohexylphenylamino)methyl]-N-(2H-tetrazol-5-yl)benzamide (12.5 g, 33.2 mmol) in DMF (120 mL) was added 4-trifluoromethoxyphenyl isocyanate (6.8 g, 33.2 mmol). A clear solution was obtained upon heating to 80° C. After 30 minutes heating at 80° C., the solution was allowed to cool to room temperature. Solvent was removed by rotary evaporation, and the residual oil taken up into hot acetonitrile (500 mL). The title material, which separated out upon cooling, was collected by filtration and washed twice with cold acetonitrile to afford 15.32 g (80.0%) of the title compound.

$^1$H NMR (DMSO-d$_6$): δ 1.35 (m, 5H); 1.78 (m, 5H); 2.42 (m, 1H); 4.96 (s, 2H); 7.20 (s, 4H); 7.24 (d, 2H); 7.47 (d, 2H); 7.55 (d, 2H); 8.02 (d, 2H); 8.44 (s, 1H); 12.35 (s, 1H).

EXAMPLE 292

General Procedure (L)

4-[1-(4-Butylphenyl)-3-(4-trifluoromethoxyphenyl)ureidomethyl]-N-(2H-tetrazol-5-yl)benzamide

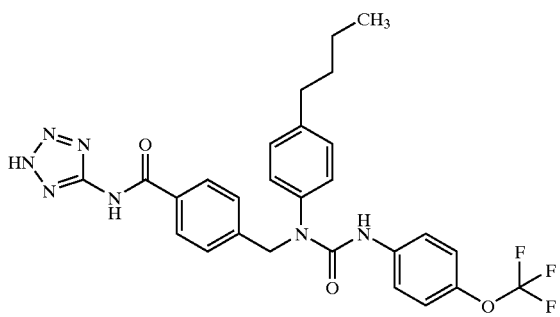

$^1$H NMR (DMSO-d$_6$): δ 0.90 (3H, t), 1.33 (2H, sixtet), 1.56 (2H, pentet), 2.55 (2H, partly hidden by DMSO), 5.00 (2H, s), 7.20 (4H, s), 7.23 (2H, d), 7.45 (2H, d), 7.57 (2H, 8.02 (2H, d), 8.36 (1H, s), 12.4 (1H, bs).

HPLC-MS (Method B): $R_t$=7.85 min, m/z=554 (M+1).

EXAMPLE 293

General Procedure (L)

4-[1-(4-tert-Butylphenyl)-3-(3-methylsulfanylphenyl)ureidomethyl]-N-(2H-tetrazol-5-yl)benzamide

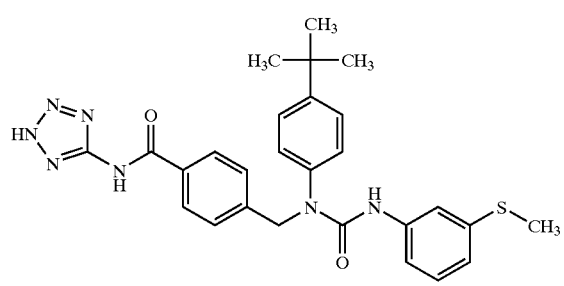

$^1$H NMR (DMSO-d$_6$): δ 1.28 (9H, s), 2.43 (3H, s), 5.01 (2H, s), 6.36 (1H, d), 7.15–7.25 (4H, m), 7.40 (3H, m), 7.48 (2H, d), 8.04 (2H, d), 8.25 (1H, s), 12.4 (1H, bs).

HPLC-MS (Method B): R$_t$=7.42 min, m/z=516 (M+1).

EXAMPLE 294

General Procedure (L)

4-[1-(4-tert-Butylphenyl)-3-(3-trifluoromethylphenyl)ureidomethyl]-N-(2H-tetrazol-5-yl)benzamide

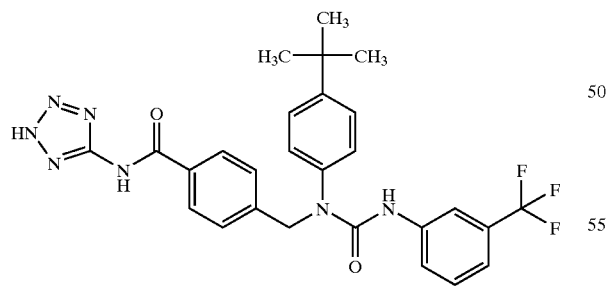

$^1$H NMR (DMSO-d$_6$): δ 1.30 (9H, s), 5.01 (2H, s), 7.25 (2H, d), 7.30 (1H, d), 7.4–7.5 (5H, m), 7.75 (1H, m), 7.93 (1H, s), 8.05 (2H, d), 8.62 (1H, s), 12.4 (1H, bs).

HPLC-MS (Method B): R$_t$=7.58 min, m/z=538 (M+1).

EXAMPLE 295

General Procedure (L)

4-[1-(4-tert-Butylphenyl)-3-(3-cyanophenyl)ureidomethyl]-N-(2H-tetrazol-5-yl)benzamide

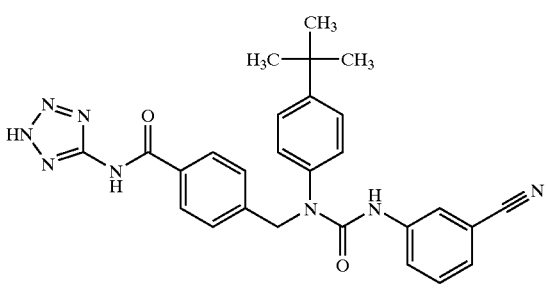

$^1$H NMR (DMSO-d$_6$): δ 1.28 (9H, s), 5.00 (2H, s), 7.24 (2H, d), 7.4–7.5 (6H, m), 7.77 (1H, dt), 7.94 (1H, s), 7.93 (1H, s), 8.04 (2H, d), 8.60 (1H, s), 12.3 (1H, bs).

HPLC-MS (Method B): R$_t$=6.83 min, m/z=495 (M+1).

EXAMPLE 296

General Procedure (L)

4-[1-(4-tert-Butylphenyl)-3-(3-chlorophenyl)ureidomethyl]-N-(2H-tetrazol-5-yl)benzamide

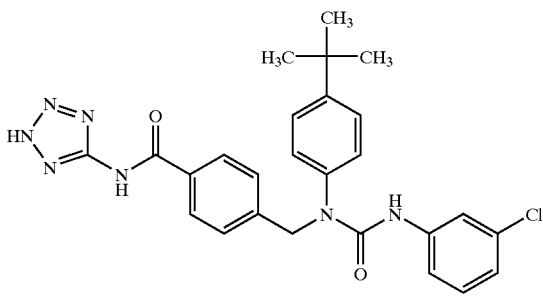

$^1$H NMR (DMSO-d$_6$): δ 1.28 (9H, s), 5.01 (2H, s), 7.00 (1H, d), 7.2–7.25 (3H, m), 7.35–7.4 (3H, m), 7.47 (2H, d), 7.64 (1H, t), 8.05 (2H, d), 8.43 (1H, s), 12.4 (1H, bs).

HPLC-MS (Method C): R$_t$=5.38 min, m/z=504 (M+1).

EXAMPLE 297

General Procedure (L)

4-[3-(3-Acetylphenyl)-1-(4-tert-butylphenyl)ureidomethyl]-N-(2H-tetrazol-5-yl)benzamide

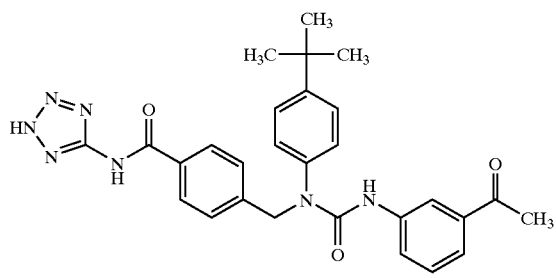

$^1$H NMR (DMSO-$d_6$): δ 1.28 (9H, s), 2.53 (3H, s), 5.03 (2H, s), 7.24 (2H, d), 7.4 (3H, m) 7.48 (2H, d), 7.57 (1H, d), 7.78 (1H, d), 8.0–8.05 (3H, m), 8.49 (1H, s), 12.4 (1H, bs).

HPLC-MS (Method C): $R_t$=4.75 min, m/z=512 (M+1).

EXAMPLE 298

General Procedure (L)

4-[1-(4-Cyclohexylphenyl)-3-(4-methylsulfanylphenyl)ureidomethyl]-N-(2H-tetrazol-5-yl)benzamide

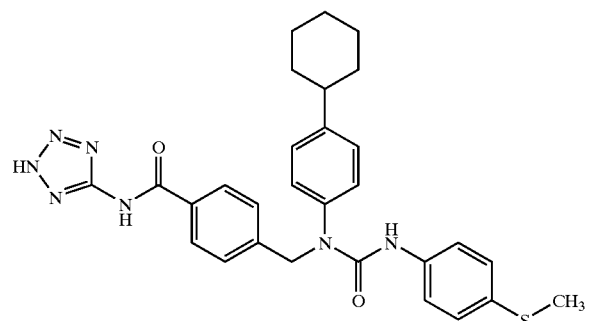

$^1$H NMR (DMSO-$d_6$): δ 1.1–1.4 (5H, m), 1.6–1.8 (5H, m), 2.40 (3H, s), 5.00 (2H, s), 7.2 (6H, m), 7.40 (2H, d), 7.46 (2H, d), 8.04 (2H, d), 8.20 (1H, s), 8.0–8.05 (3H, m), 8.49 (1H, s), 12.3 (1H, bs).

HPLC-MS (Method C): $R_t$=5.73 min, m/z=542 (M+1).

EXAMPLE 299

General Procedure (L)

4-[1-(4-Cyclohexylphenyl)-3-(3-cyclopropylmethylsulfanylphenyl)ureidomethyl]-N-(2H-tetrazol-5-yl)benzamide

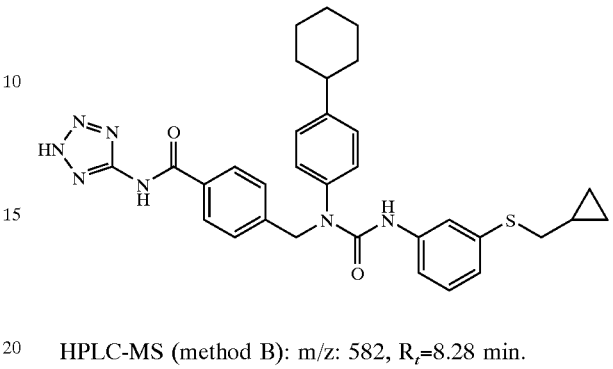

HPLC-MS (method B): m/z: 582, $R_t$=8.28 min.

EXAMPLE 300

General Procedure (L)

4-[1-(4-Cyclohexylphenyl)-3-(3-cyclopentylsulfanylphenyl)ureidomethyl]-N-(2H-tetrazol-5-yl)benzamide

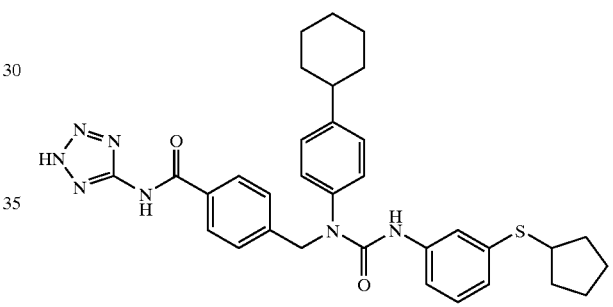

HPLC-MS (method B): m/z: 596, $R_t$=8.70 min.

EXAMPLE 301

General Procedure (L)

4-[1-(4-Cyclohexylphenyl)-3-(4-trifluoromethylsulfanylphenyl)ureidomethyl]-N-(2H-tetrazol-5-yl)benzamide

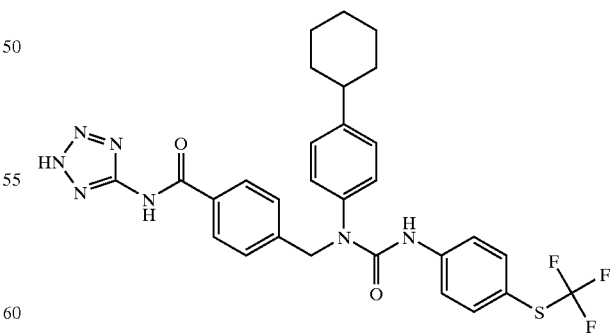

$^1$H NMR (300 MHz, DMSO-$d_6$): δ 8.63 (s, 1H); 8.04 (d, 2H); 7.64 (d, 2H); 7.56 (d, 2H); 7.23 (d, 2H); 7.18 (d, 2H); 4.49 (s 2H); 1.80 (m, 4H); 1.69 (m, 1H); 1.38 (m, 4H); 1.27 (m, 1H).

HPLC-MS (method B) m/z=596, $R_t$=8.58 min.

EXAMPLE 302

General Procedure (L)

4-[1-(4-Cyclohexylphenyl)-3-(3-methylsulfanylphenyl)ureidomethyl]-N-(2H-tetrazol-5-yl)benzamide

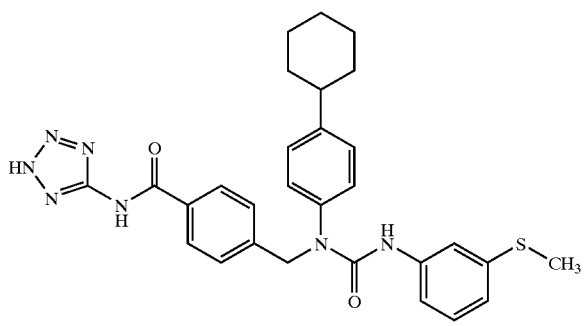

$^1$H NMR (DMSO-d$_6$): δ 8.22 (s, 1H), 7.95 (d, 2H), 7.40 (d, 3H), 7.25–7.10 (m, 6H), 6.83 (d, 1H), 4.97 (s, 2H), 4.02 (m, 1H), 2.42 (s, 3H), 1.85–1.15 (m, 10H).

HPLC-MS (method B): m/z: 542, R$_t$=7.92 min.

EXAMPLE 303

General Procedure (L)

4-[1-(4-Cyclohexylphenyl)-3-(3-trifluoromethylsulfonylphenyl)ureidomethyl]-N-(2H-tetrazol-5-yl)benzamide

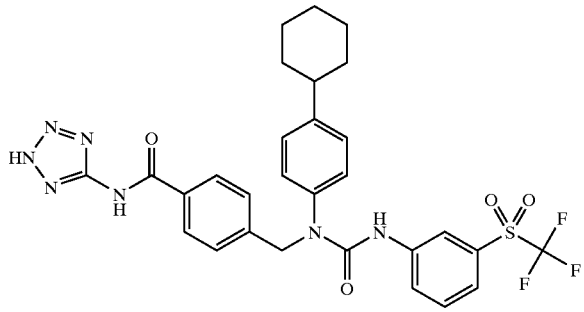

$^1$H NMR (DMSO-d$_6$): δ 12.4 (s, 1H), 8.90 (s, 1H), 8.32 (s, 1H), 8.11 (d, 1H), 8.03 (d, 2H), 7.70 (m, 2H), 7.45 (d, 2H), 7.23 (s, 4H), 5.00 (s, 2H), 1.85–1.15 (m, 10H).

HPLC-MS (method B): m/z: 628, R$_t$=8.05 min.

EXAMPLE 304

General Procedure (L)

4-[1-(4-Cyclohexylphenyl)-3-(3,5-dichlorophenyl)ureidomethyl]-N-(2H-tetrazol-5-yl)benzamide

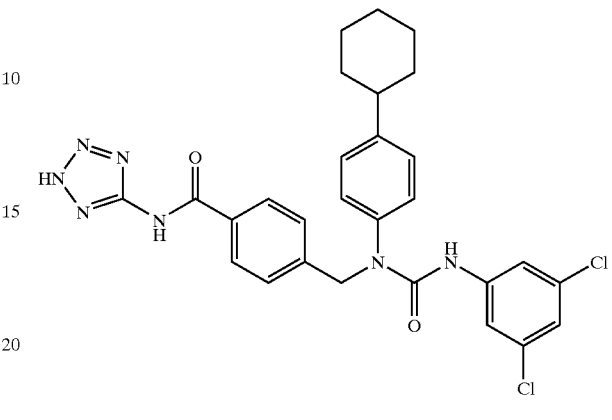

$^1$H NMR (DMSO-d$_6$): δ 12.25 (s, 1H), 8.61 (s, 1H), 8.02 (d, 2H), 7.60 (s, 2H), 7.45 (d, 2H), 7.21 (dd, 4H), 7.15 (s, 1H), 4.97 (s, 2H), 1.85–1.15 (m, 10H).

HPLC-MS (method B): m/z: 564, R$_t$=8.62 min.

EXAMPLE 305

General Procedure (L)

4-[1-(4-Cyclohexylphenyl)-3-(3-methylsulfonyl-4-methylphenyl)ureidomethyl]-N-(2H-tetrazol-5-yl)benzamide

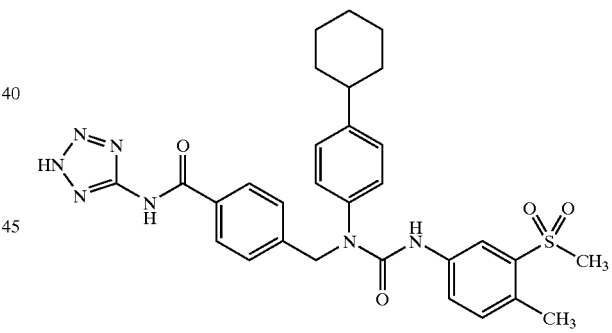

Preparation of intermediary 3-methylsulfonyl-4-methylaniline

Under a nitrogen atmosphere, thionylchloride (4 ml, 58 mmol) and methanesulphonic acid (9 mL, 146 mmol) were refluxed for 90 min. 4-Nitrotoluene (4 g, 29 mmol) and triflouromethanesulphonic acid (200 uL, 3 mmol) were added and the mixture was allowed to stand for 48 hours at 120° C. The mixture was cooled to 0° C. and water (50 mL) was carefully added, followed by addition of ethyl acetate (150 mL). The organic phase was separated and extracted with a saturated solution of sodium hydrogencarbonate (2×50 mL) and water (2×50 mL). The organic phase was dried (MgSO$_4$) and concentrated in vacuo. The residue was purified by flash chromatography (heptane/ethylacetate, 1:1) to give 0.75 g of 2-methylsulfonyl-1-methyl-4-nitrobenzene.

$^1$H NMR (400 MHz, DMSO-d$_6$): δ 2.78 (3H, s); 3.35 (3H, s); 7.78 (1H, d); 8.47 (1H, dd); 8.63 (1H, s).

2-Methylsulfonyl-1-methyl-4-nitrobenzene (500 mg, 2.3 mmol) was dissolved in absolute ethanol (15 mL). Stannous chloride (2.6 g, 11.6 mmol) was added and the reaction mixture was stirred at 75° C. for 4 hours. The mixture was poured into water (50 mL), pH was adjusted with a saturated solution of sodium carbonate to basic reaction, followed by addition of ethyl acetate (150 mL). The organic phase was extracted with water (2×50 mL), dried (MgSO$_4$) and concentrated in vacuo to give 0.36 g of 3-methylsulfonyl-4-methylaniline as an oil.

$^1$H NMR (300 MHz, DMSO-d$_6$): δ 2.42 (3H, s); 3.11 (3H, s); 5.42 (2H, s); 6.75 (1H, dd); 7.06 (1H, d); 7.16 (1H, d).

From 3-methylsulfonyl-4-methylaniline the corresponding isocyanato compound was prepared as described above. The isocyanato compound was used in step D of the general procedure (L) for the preparation of the title compound.

$^1$H NMR (DMSO-d$_6$): δ 12.35 (s, 1H), 8.05 (d, 2H), 7.52 (d, 2H), 7.39 (d, 2H), 6.49 (d, 1H), 4.35 (s, 2H), 2.30 (m, 1H), 2.09 (s, 3H), 1.85–1.15 (m, 10H).

HPLC-MS (method B): m/z: 589, R$_t$=7.0 min.

EXAMPLE 306

General Procedure (L)

4-{1-(4-Cyclohexylphenyl)-3-[3-(1-hydroxyethyl) phenyl]ureidomethyl}-N-(2H-tetrazol-5-yl) benzamide

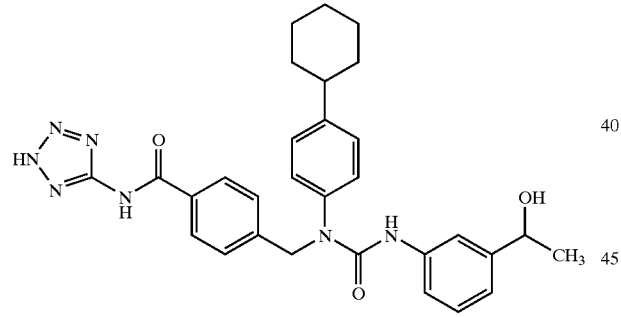

The title compound was prepared using 3-acetylphenylisocyante to give 4-{1-(4-cyclohexylphenyl)-3-[3-acetylphenyl]ureidomethyl}-N-(2H-tetrazol-5-yl)benzamide followed by solution phase reduction of the 3-acetyl group using sodium borohydride in methanol as reducing agent.

$^1$H NMR (DMSO-d$_6$): δ 12.35 (s, 1H), 8.15 (s, 1H), 8.03 (d, 1H), 7.46 (d, 2H), 7.39 (s, 1H), 7.32 (d, 1H), 7.20 (m, 5H), 6.90 (d, 1H), 5.10 (d, 1H), 5.00 (s, 2H), 4.63 (m, 1H), 1.85–1.15 (m, 13H).

HPLC-MS (method B): m/z: 540, R$_t$=6.9 min.

MA: calculated for C$_{30}$H$_{33}$N$_7$O$_3$: 66.77% C, 6.16% H, 18.17% N; Found: 66.52% C, 6.21% H, 17.93% N.

EXAMPLE 307

General Procedure (L)

4-[1-(4-Cyclohex-1-enylphenyl)-3-(4-trifluoromethoxyphenyl)ureidomethyl]-N-(2H-tetrazol-5-yl)benzamide

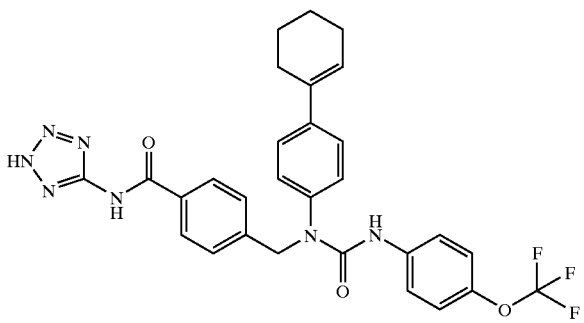

$^1$H NMR (DMSO-d$_6$): δ 8.45 (s, 1H), 7.95 (d, 2H), 7.55 (d, 2H), 7.40 (dd, 4H), 7.20 (dd, 4H), 6.18 (t, 1H), 5.00 (s, 2H), 2.35 (m, 2H), 2.18 (m, 2H), 1.72 (m, 2H), 1.60 (m, 2H).

HPLC-MS (method B): m/z: 578, R$_t$=7.83 min.

EXAMPLE 308

General Procedure (L)

4-[1-(4-Cyclohex-1-enylphenyl)-3-(3-nitrophenyl) ureidomethyl]-N-(2H-tetrazol-5-yl)benzamide

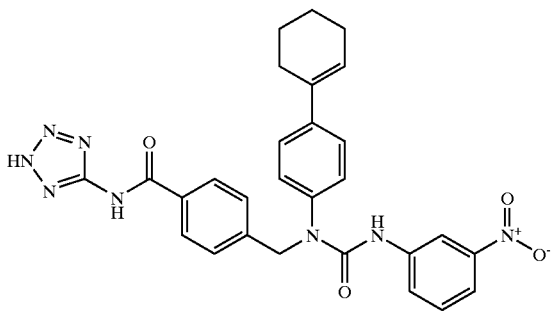

$^1$H NMR (DMSO-d$_6$): δ 8.79 (s, 1H), 8.48 (s, 1H), 7.95 (m, 3H), 7.80 (d, 1H), 7.51 (t, 1H), 7.42 (dd, 4H), 7.22 (d, 2H), 6.19 (t, 1H), 5.00 (s, 2H), 2.35 (m, 2H), 2.18 (m, 2H), 1.72 (m, 2H), 1.60 (m, 2H).

HPLC-MS (method B): m/z: 539, R$_t$=7.3 min.

EXAMPLE 309

General Procedure (L)

4-{1-(4-tert-Butylphenyl)-3-[3-(1-hydroxyethyl)phenyl]ureidomethyl}-N-(2H-tetrazol-5-yl)benzamide

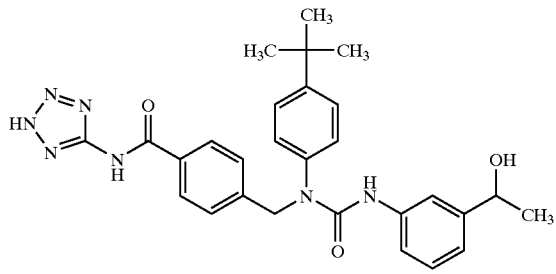

The title compound was prepared using 3-acetylphenylisocyante to give 4-{1-(4-tert-butylphenyl)-3-[3-acetylphenyl]ureidomethyl}-N-(2H-tetrazol-5-yl)benzamide followed by solution phase reduction of the 3-acetyl group using sodium borohydride in methanol as reducing agent, before cleavage from the support.

$^1$H NMR (DMSO-d$_6$): δ 8.18 (s, 1H), 8.03 (d, 2H), 7.48 (d, 2H), 7.39 (d, 2H), 7.32 (d, 1H), 7.20 (d, 2H), 7.15 (t, 1H), 6.90 (d, 1H), 5.10 (d, 1H), 5.00 (s, 2H), 4.63 (m, 1H), 1.30 (s, 9H).

HPLC-MS (method B): m/z: 514, R$_t$=6.2 min.

EXAMPLE 310

General Procedure (L)

4-[1-(4-Cyclohex-1-enylphenyl)-3-(3-methylsulfonylphenyl)ureidomethyl]-N-(2H-tetrazol-5-yl)benzamide

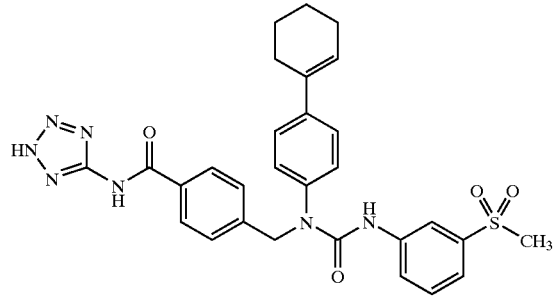

HPLC-MS (method B): m/z: 572, R$_t$=6.4 min.

$^1$H NMR (DMSO-d$_6$): δ 12.3 (s, 1H), 9.08 (s, 1H), 8.25 (s, 2H), 8.03 (d, 2H), 7.61 (s, 1H), 7.42 (d, 2H), 7.11 (s, 1H), 4.65 (s, 2H), 4.08 (m, 1H), 1.80–0.75 (m, 9H), 0.81 (s, 9H).

HPLC-MS (method B): m/z: 612, R$_t$=8.5 min.

MA: calculated for C$_{28}$H$_{31}$F$_6$N$_7$O$_2$: 54.99% C; 5.11% H; 16.03% N; Found: 54.62% C; 5.15% H; 15.85% N.

EXAMPLE 311

General Procedure (L)

4-[3-[3-(tert-Butyldimethylsilanyloxymethyl)-4-trifluoromethoxyphenyl]-1-(4-cyclohexylphenyl)ureidomethyl]-N-(2H-tetrazol-5-yl)benzamide

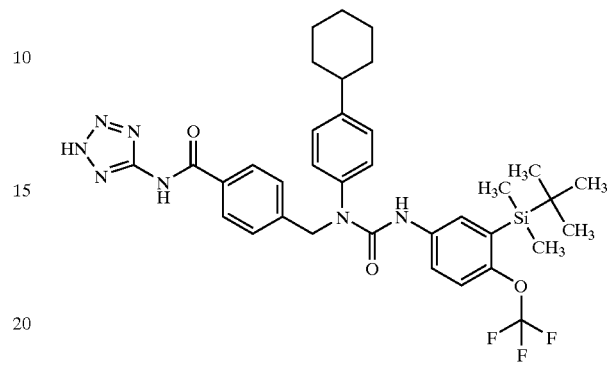

Fuming nitric acid (5 mL) was cooled on an ice bath. Methyl 2-(trifluoromethoxy)benzoate (5 g, 22.7 mmol) was slowly added within 30 minutes keeping the temperature below 15° C. The reaction was then stirred at 60° C. for 1 hour and 2 hours at room temperature. The mixture was poured on ice water whereupon an oil separated. The aqueous supernatant was decanted and additional water (50 mL) was added to the oil. After neutralisation with sodium hydrogen carbonate, the mixture was extracted with ethyl acetate (25 mL). The aqueous phase was extracted with ethyl acetate (15 mL) once more. The combined organic phases were washed with saturated sodium chloride (2×15 mL), dried (MgSO$_4$), and concentrated in vacuo to give 5.69 g of 5-nitro-2-trifluoromethoxybenzoic acid methyl ester.

$^1$H NMR (DMSO-d$_6$): δ 3.93 (3H, s), 7.82 (1H, d), 8.58 (1H, d), 8.67 (1H, s).

HPLC-MS (method B): m/z: 266; Rt=6.0 min.

5-Nitro-2-trifluoromethoxybenzoic acid methyl ester (5.69 g, 21.5 mmol) was dissolved in ethanol 99.9% (80 mL) and stannous (II) chloride dihydrate (24.2 g, 107 mmol) was added. The suspension was stirred on an oil-bath at 75° C. for 2 hours and concentrated in vacuo. Ethyl acetate (100 mL) and water (50 mL) was added and pH was adjusted to pH 8 with 4N sodium hydroxide (50 mL). The liquid was decanted from the precipitation. The precipitate was washed twice with ethyl acetate. The aqueous phase was extracted twice with ethyl acetate (60 mL). The combined organic phases were washed with a saturated sodium chloride solution (2×100 mL), dried (MgSO$_4$) and concentrated in vacuo. Purification by column chromatography (120 g silica) using ethyl acetate and heptane (1:1) as eluent afforded 3.8 g of 5-amino-2-trifluoromethoxybenzoic acid methyl ester.

$^1$H NMR (DMSO-d$_6$): δ 3.82 (3H, s), 5.63 (2H, s), 6.79 (1H, d), 7.07 (1H, s), 7.11 (1H, d).

HPLC-MS (method B): m/z: 236, Rt=4.6 min.

5-Amino-2-trifluoromethoxybenzoic acid methyl ester (3.0 g, 12.8 mmol) was dissolved in THF (20 mL) in a three-necked flask equipped with a thermometer and an addition funnel under nitrogen. Under stirring and ice-cooling lithium aluminum hydride (1M in THF, 15 mL) was added dropwise within 10 minutes. Stirring was continued at room temperature for 1 hr, and the reaction was concentrated in vacuo. The residue was suspended in dichloromethane (150 mL) and water (50 mL), then filtered through celite, washed with dichloromethane and water. The filtrate was separated, and the water phase was extracted once more with dichloromethane (30 mL). The combined organic phases were washed with water (2×20 mL), dried (MgSO$_4$) and concentrated in vacuo to give 2.47 g of (5-amino-2-trifluoromethoxy-phenyl)methanol.

$^1$H NMR (DMSO-d$_6$): δ 3.92 (2H, d), 5.18 (1H, t), 5.28 (2H, s), 6.45 (1H, d), 6.91 (1H, d).

HPLC-MS (method B): m/z: 208, Rt=7.2 min.

5-Amino-2-trifluoromethoxyphenyl)methanol (1.2 g, 5.8 mmol) was dissolved in DMF (5 mL) and imidazole (0.48 g, 7.1 mmol) and tert-butyldimethylsilyl chloride (0.99 g, 6.6 mmol) were added. The reaction mixture was stirred for 16 hours and water (20 mL) was added. The mixture was extracted with ethyl acetate (2×50 mL) and the combined organic phases were washed with water (10 mL), citric acid (10 mL, 10%) and water (2×10 mL), dried (MgSO$_4$) and concentrated in vacuo. The residue was purified by column chromatography (110 g, silica) using ethyl acetate and heptane (1:3) as eluent to give 1.2 g of 3-(tert-butyldimethylsilanyloxymethyl)-4-trifluoromethoxyaniline $^1$H NMR (DMSO-d$_6$): δ 0.82 (9H, s), 3.25 (6H, s), 4.52 (2H, s), 5.23 (2H, s), 6.41 (1H, d), 6.61 (1H, s), 6.86 (1H, d).

HPLC-MS (method B): m/z: 322; Rt=7.17 min.

Triphosgene (0.09 g, 0.31 mmol) was dissolved in dichloromethane (2 mL) under nitrogen and cooled on ice. 3-(tert-Butyldimethylsilanyloxymethyl)-4-trifluoromethoxyphenyl amine (0.3 g, 0.93 mmol) was evaporated twice with toluene and dissolved in dichloromethane (2 mL) and diisopropylethylamine (0.32 mL, 1.86 mmol) was added. This solution was then added to the solution of triphosgene, and after 2 hours at room temperature a slurry of 4-[(4-cyclohexylphenylamino)methyl]-N-(2H-tetrazol-5-yl) benzamide (0.35 g, 0.93 mmol) in DMF (6 mL) was added. Before adding 4-[(4-cyclohexylphenylamino)methyl]-N-(2H-tetrazol-5-yl)benzamide this was concentrated twice from toluene to remove any content of water. The mixture was stirred under nitrogen at 80° C. for 2 hours and concentrated in vacuo, and the residue was extracted with dichloromethane (80 mL) and citric acid (25 mL, 10%). The aqueous phase was extracted with dichloromethane (30 mL) and the combined organic phases were washed with citrus acid (3×25 mL, 10%), dried and concentrated in vacuo. The residue was purified by column chromatography (35 g silica) using dichloromethane and 10% ammonia in ethanol 85:15 as eluent to give 97 mg of 4-[3-[3-(tert-butyldimethylsilanyloxymethyl)-4-trifluoromethoxyphenyl]-1-(4-cyclohexylphenyl)ureidomethyl]-N-(2H-tetrazol-5-yl)benzamide.

$^1$H NMR (DMSO-d$_6$): δ 0.08 (6H, s), 0.89 (9H, s), 1.17–1.45 (5H, m), 1.67–1.82 (5H, m), 4.67 (2H, s), 5.00 (2H, s), 7.16–7.25 (5H, m), 7.45 (3H, d), 7.63 (1H, s), 8.02 (2H, d), 8.44 (1H, s), 11.97 (1H, broad).

HPLC-MS (method B): m/z: 610 (without dimethyl-tert-butylsilyl).

EXAMPLE 312

General Procedure (L)

4-[1-(4-tert-Butylphenyl)-3-(3-methylsulfonyl-4-trifluoromethoxyphenyl)ureidomethyl]-N-(2H-tetrazol-5-yl)benzamide

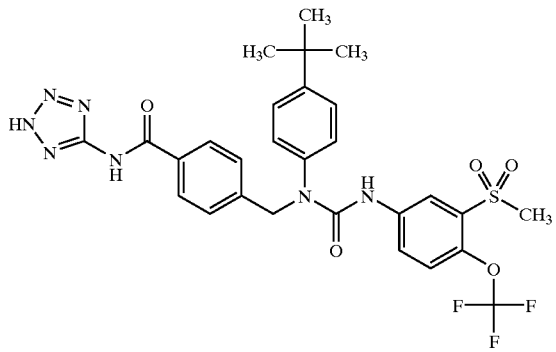

Synthesis of 3-methylsulfonyl-4-trifluoromethoxyphenyl isocyanate

To a solution of methyl iodide (59.0 g, 0.41 mol) in DMF (150 mL) was added potassium carbonate (23.0 g, 0.16 mol). 2-(Trifluoromethoxy)thiophenol (16.0 g, 0.08 mol) was added in portions during 30 minutes. The reaction mixture was then stirred vigorously overnight. Water (250 mL) was added. The reaction mixture was extracted with ethyl acetate (2×150 mL). The combined organic phases were extracted with a 50% saturated aqueous solution of sodium chloride (4×100 mL), dried (MgSO$_4$), and concentrated in vacuo to give 15.0 g of 1-methylsulfanyl-2-trifluoromethoxybenzene.

1-Methylsulfanyl-2-trifluoromethoxybenzene (15.0 g, 72 mmol) was dissolved in dichloromethane (200 mL) and m-chloroperoxybenzoic acid (39.0 g, 216 mmol) was added in small portions during 30 minutes. The reaction mixture was then allowed to stand overnight. Dichloromethane (200 mL) was added followed by slow addition of sodium hydroxide (2N, 200 mL). The organic phase was separated and extracted with sodium hydroxide (2N, 3×150 mL), dried (MgSO$_4$) and concentrated in vacuo to give 15.8 g of 1-methylsulfonyl-2-trifluoromethoxybenzene.

$^1$H NMR (400 MHz, CDCl$_3$): δ 8.11 (d, 1H); 7.71 (t, 1H); 7.48 (m, 2H); 3.23 (s 1H).

MA: Calculated for C$_8$H$_7$F$_3$O$_3$S: 40.00% C, 2.94% H; Found 40.22% C, 2.92% H.

m.p. 44–46° C.

1-Methylsulfonyl-2-trifluoromethoxybenzene (15.7 g, 65 mmol) was dissolved in concentrated sulfuric acid (27 mL) and the solution was heated to 40 OC. Nitric acid (100%, 27 mL) was added dropwise over 45 minutes. The reaction mixture was allowed to stand overnight at 60° C., cooled, and then poured on crushed ice (300 mL). The precipitated product was isolated by filtration, washed with water (10×50 mL) and dried (MgSO$_4$), affording 17.5 g of 3-methylsulfonyl-4-trifluoromethoxynitrobenzene.

$^1$H NMR (400 MHz, DMSO-d$_6$): δ 8.69 (d, 1H); 8.64 (d, 1H); 7.95 (d, 1H); 3.45 (s 3H).

MA: calculated for C$_8$H$_6$F$_3$NO$_5$S: 33.69% C, 2.12% H, 4.91% N; Found 33.91% C, 2.08% H, 4.92% N.

m.p. 102–104° C.

3-Methylsulfonyl-4-trifluoromethoxynitrobenzene (17.5 g) was dissolved in methanol (400 mL) followed by addition of palladium on carbon (10%, 50% water, 3.2 g). The reaction mixture was hydrogenated for 17 hours at 1 atm of hydrogen, filtered and concentrated in vacuo to give 14.3 g of 3-methylsulfonyl-4-trifluoromethoxyaniline.

$^1$H NMR (400 MHz, DMSO-$d_6$): δ 7.26 (d, 1H); 7.14 (d, 1H); 6.85 (dd, 1H); 5.89 (s, 2H); 3.21 (s, 3H).

MA: calculated for $C_8H_8F_3NO_3S$: 37.65% C, 3.16% H, 5.49% N; Found, 37.65% C, 3.14% H, 5.45% N.

m.p. 106–109° C.

To 3-methylsulfonyl-4-trifluoromethoxyaniline (2.0 mmol, 500 mg) dissolved in ethyl acetate (6 ml) was added 3N HCl in ethyl acetate (5 ml) followed by concentration in vacuo. The residue was treated with toluene (3×5 mL) and each time concentrated in vacuo. To the residue was added toluene (10 mL) and trichloromethyl chloroformate (6 mmol, 0.73 mL), and under a $N_2$-atmosphere the suspension was gently refluxed for 2 hours at 120° C. Additional trichloromethyl chloroformate (6 mmol, 0.73 mL) was added and refluxing was continued overnight. The reaction mixture was concentrated in vacuo to afford 3-methylsulfonyl-4-trifluoromethoxyphenyl isocyanate.

Synthesis of 4-[1-(4-tert-butylphenyl)-3-(3-methylsulfonyl-4-trifluoromethoxyphenyl)ureidomethyl]-N-(2H-tetrazol-5-yl)benzamide 3-methylsulfonyl-4-trifluoromethoxyphenyl isocyanate was used without further characterisation for the preparation of the title compound.

$^1$H NMR (300 MHz, DMSO-$d_6$): δ 10.72 (s, 1H); 10.38 (s, 1H); 8.51 (d, 1H); 8.28 (dd, 1H); 7.93 (d, 2H); 7.67 (dd 1H), 7.46 (d, 2H), 7.42 (d, 2H), 7.23 (d, 2H); 5.08 (s, 2H); 1.28 (s, 9H).

HPLC-MS (method B) m/z=632, $R_t$=6.98 min.

The following examples were made similarly as described in example 312.

EXAMPLE 313

General Procedure (L)

4-[1-(4-tert-Butylcyclohexyl)-3-(3-methylsulfonyl-4-trifluoromethoxyphenyl)ureidomethyl]-N-(2H-tetrazol-5-yl)benzamide

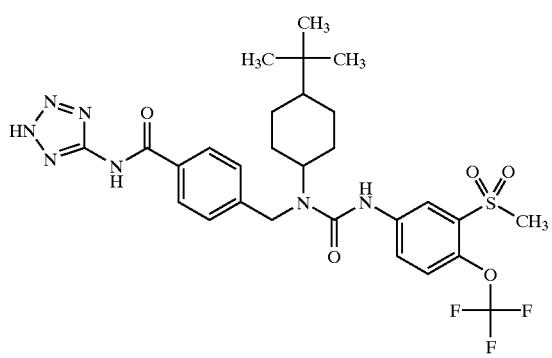

$^1$H NMR (300 MHz, DMSO-$d_6$): δ 12.25 (s, br, 1H); 8.95 (s, 1H); 8.19 (d, 1H), 8.04 (d, 2H), 7.42 (d, 2H), 4.68 (s, 2H), 4.09 (t, br, 1H); 3.28 (s, 3H); 0.82 (s, 9H).

HPLC-MS (method B) m/z=638, $R_t$=7.37 min.

EXAMPLE 314

General Procedure (L)

4-[1-(4-Cyclohexylphenyl)-3-(3-methylsulfonyl-4-trifluoromethoxyphenyl)ureidomethyl]-N-(2H-tetrazol-5-yl)benzamide

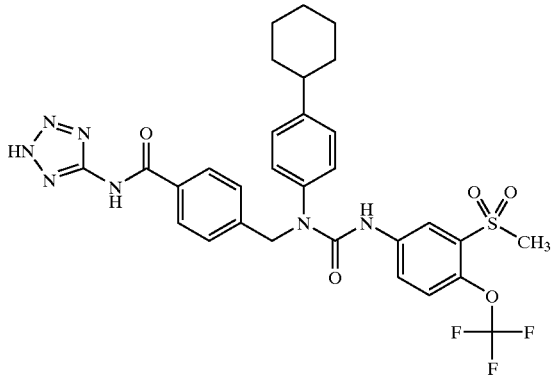

$^1$H NMR (300 MHz, DMSO-$d_6$): δ 10.72 (s, 1H); 10.38 (s, 1H); 8.51 (d, 1H), 8.28 (dd, 1H), 7.93 (d, 2H), 7.67 (dd, 1H), 7.46 (d, 2H) 7.23 (s, 4H); 5.06 (s, 2H).

HPLC-MS (method B) m/z=658, $R_t$=7.47 min.

EXAMPLE 315

General Procedure (L)

4-[1-(4-Cyclohex-1-enylphenyl)-3-(3-methylsulfonyl-4-trifluoromethoxyphenyl)ureidomethyl]-N-(2H-tetrazol-5-yl)benzamide NNC 25-0805, 22 nM, Glu bd assay III

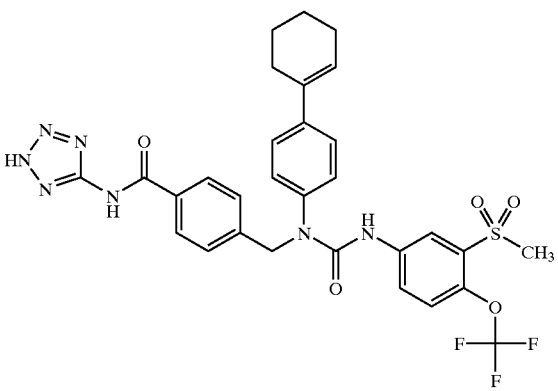

$^1$H NMR (400 MHz, DMSO-$d_6$): δ 10.72 (s, 1H);10.46 (s, 1H), 8.52 (d, 1H); 8.28 (dd, 1H), 7,93 (d, 2H), 7.46 (d, 2H), 7.41 (d, 2H), 7.23 (d, 2H), 6.18 (s, 1H), 3.27 (m, 2H), 2.18 (m, 2H), 1.71 (m, 2H), 1.6 (m, 2H).

HPLC-MS (method B) m/z=656, $R_t$=7.23 min.

EXAMPLE 316

General Procedure (L)

4-[3-(3,5-Dichlorophenyl)-1-(4-piperidin-1-ylphenyl)ureidomethyl]-N-(2H-tetrazol-5-yl)benzamide

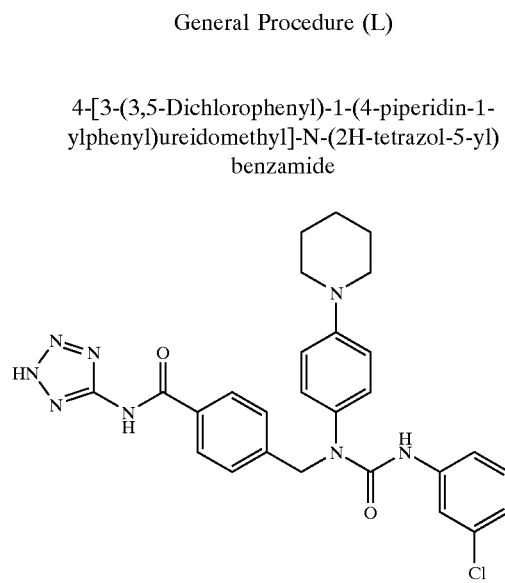

$^1$H NMR (DMSO-d$_6$): δ 4.90 (2H, s), 6.91 (2H, d), 7.07 (2H, d), 7.13 (1H, t), 7.44 (2H, d), 7.65 (2H, d), 8.02 (2H, d), 8.28 (1H, s).

HPLC-MS (Method B): m/z=565 (M+1), R$_t$=4.37 min.

EXAMPLE 317

General Procedure (L)

4-[3-(3-Methylsulfanylphenyl)-1-(4-piperidin-1-ylphenyl)ureidomethyl]-N-(2H-tetrazol-5-yl)benzamide

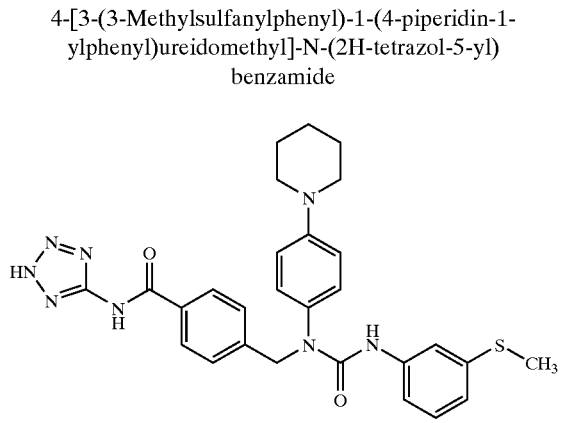

$^1$H NMR (DMSO-d$_6$): δ 4.97 (2H, s), 6.83 (1H, d), 6.95–7.25 (6H, m), 7.4–7.5 (3H, m), 7.95 (1H, s), 8.00 (2H, d), 12.4 (1H, s).

HPLC-MS (Method B): m/z=543 (M+1), R$_t$=4.72 min.

EXAMPLE 318

General Procedure (L)

4-[1-(4-Piperidin-1-ylphenyl)-3-(4-trifluoromethoxyphenyl)ureidomethyl]-N-(2H-tetrazol-5-yl)benzamide

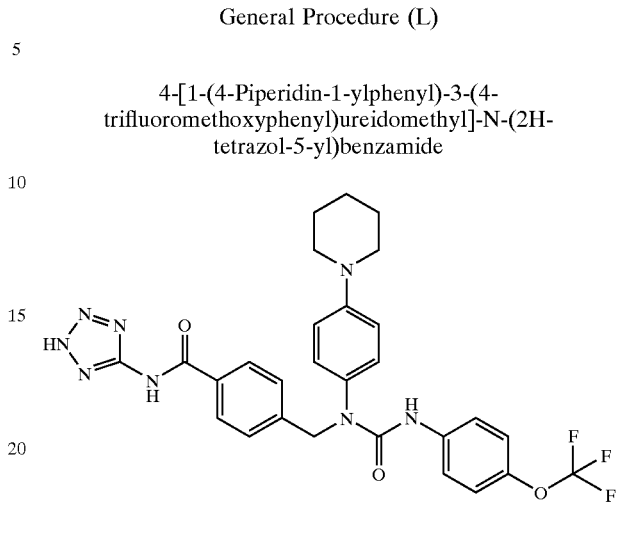

$^1$H NMR (DMSO-d$_6$): δ 1.5–1.6 (6H, m), 3.15 (4H, bs), 4.93 (2H, s), 6.94 (2H, d), 7.10 (2H, d), 7.22 (2H, d), 7.45 (2H, d), 7.55 (2H, d), 8.03 (2H, d), 8.10 (1H, s), 12.4 (1H, s).

HPLC-MS (Method B): m/z=581 (M+1), R$_t$=5.02 min.

EXAMPLE 319

General Procedure (L)

4-[1-(4-Cyclohexylphenyl)-3-(3-methoxy-5-trifluoromethylphenyl)ureidomethyl]-N-(2H-tetrazol-5-yl)benzamide

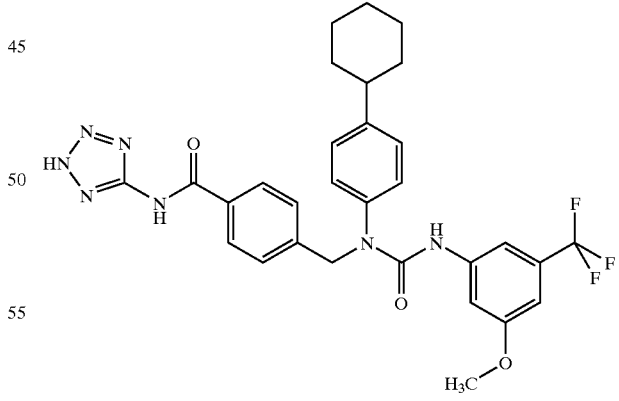

$^1$H NMR (DMSO-d$_6$): δ 12.40 (br s, 1H); 8.60 (s, 1H); 8.05 (d, 2H); 7.52 (s, 1H); 7.48 (1H); 7.46 (d, 2H); 7.20 (dd, 4H); 6.80 (s, 1H); 5.03 (s, 2H); 3.78 (s, 3H); 1.85–1.60 (m, 5H); 1.50–1.15 (m, 5H).

HPLC-MS (Method B): m/z=594 (M+1). R$_t$=7.92 min.

EXAMPLE 320

General Procedure (L)

4-[1-(4-Cyclohexylphenyl)-3-(5-methylsulfonylthiophen-2-yl)ureidomethyl]-N-(2H-tetrazol-5-yl)benzamide

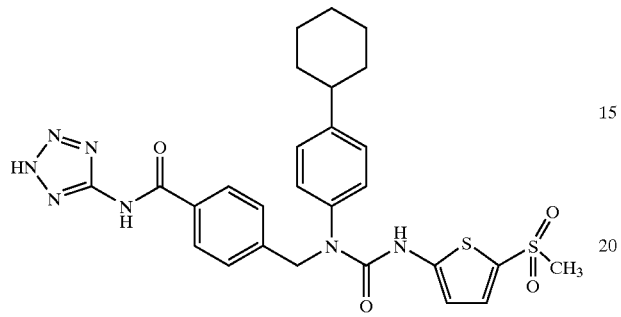

$^1$H NMR (DMSO-d$_6$): δ 12.40 (s, 1H); 10.10 (s, 1H); 8.06 (d, 2H); 7.42 (m, 3H); 7.28 (d, 2H); 7.19 (d, 2H); 6.70 (d, 1H); 3.20 (s, 3H); 1.75–1.60 (m, 5H); 1.50–1.10 (m, 5H).

HPLC-MS (Method B): m/z=580 (M+1). R$_t$=6.45 min.

EXAMPLE 321

General Procedure (L)

4-[3-(3,5-Bis(methylsulfonyl)phenyl)-1-(4-cyclohexylphenyl)ureidomethyl]-N-(2H-tetrazol-5-yl)benzamide

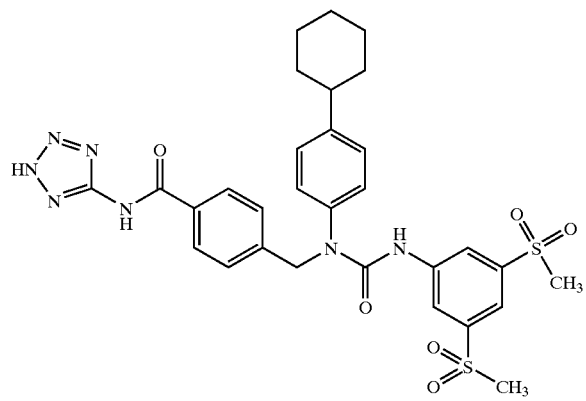

$^1$H NMR (DMSO-d$_6$): δ 8.45 (s, 2H); 8.05–7.95 (m, 3H); 7.50–7.42 (m, 2H); 7.22 (dd, 4H); 5.00 (s, 2H); 1.90–1.70 (m, 5H); 1.45–1.30 (m, 5H).

HPLC-MS (Method B): m/z=652 (M+1). R$_t$=6.33 min.

Preparation of 3,5-bis(methylsulfonyl)phenylamine:

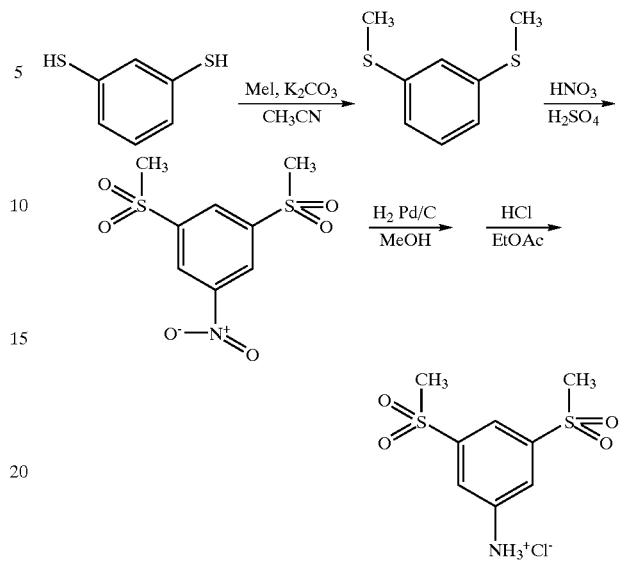

1,3-Bis-benzenethiol (5 g, 35.2 mmol) was dissolved in acetonitrile (50 mL) and added iodo-methane (4.62 mL, 73.9 mmol) and potassium carbonate (10.7 g, 77.4 mmol). Upon stirring overnight at 25° C., the mixture was filtered and the solvent removed in vacuo. The residue was partitioned between water (100 mL) and ethyl acetate (100 mL). The aqueous layer was extracted with ethyl acetate (2×50 mL) and the combined organic extracts were dried with MgSO$_4$ and evaporated. The residue was distilled at 17 torr, 138° C. affording 1,3-bis(methylsulfanyl)benzene (3.20 g).

The above 1,3-bis(methylsulfanyl)benzene (3.20 g) was dissolved in H$_2$SO$_4$ (8 mL) and cooled on an ice bath. A mixture of H$_2$SO$_4$ and HNO$_3$ (1:1, 10 mL) was added dropwise. Upon stirring 30 min at 25° C., the temperature was raised to 100° C. and kept there for 3 hours. Pouring the reaction mixture onto ice (100 mL) afforded a precipitate that still contained starting material (2.90 g). This material was dissolved in H$_2$SO$_4$ (5.2 mL) and added a mixture of H$_2$SO$_4$ and HNO$_3$ (1:1, 10.4 mL). The mixture was heated at 110° C. overnight and poured onto ice (100 mL). The formed precipitate was collected by filtration (1.01 g). Chromatography on silica gel using a mixture of heptane and ethyl acetate (4:1) as eluent afforded the desired 1,3-bis(methylsulfonyl)-5-nitrobenzene (0.7 g).

To a slurry of 1,3-bis(methylsulfonyl)-5-nitrobenzene (0.7 g) in methanol (10 mL) was added palladium on charcoal (0.1 g) and the mixture was hydrogenated at atmospheric pressure and 25° C. for 1 hour. The reaction mixture was filtered and evaporated. The residue was suspended in ethyl acetate (25 mL) and HCl in ethyl acetate (5 mL, appr. 2M) was added. Filtration afforded the desired aniline as its hydrochloride salt, which was converted into an isocyanate using diphosgene as described previously.

EXAMPLE 322

General Procedure (L)

3-(4-{1-(4-cyclohexylphenyl)-3-[3-(methylphenylsulfamoyl)phenyl]ureidomethyl}benzoylamino)propionic acid

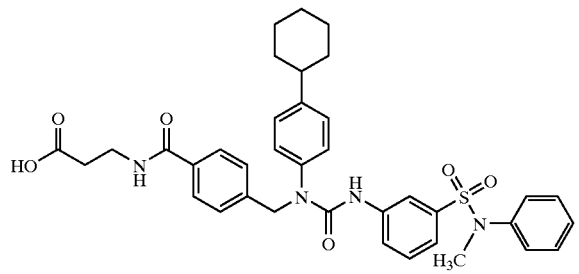

HPLC-MS (Method B): m/z=669 (M+1). R$_t$=7.38 min.

EXAMPLE 323

General Procedure (L)

4-[1-(4-Cyclohexylphenyl)-3-phenethylureidomethyl]-N-(2H-tetrazol-5-yl)benzamide

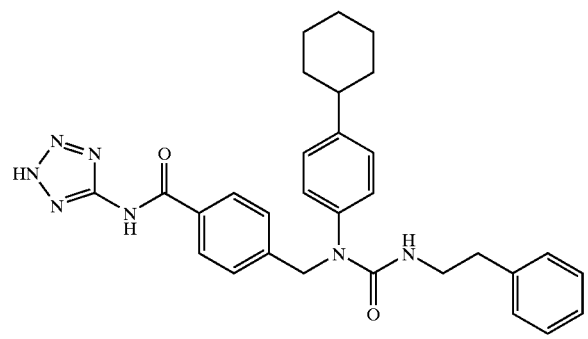

$^1$H NMR (DMSO): δ 12.40 (s, 1H); 8.00 (d, 2H); 7.40–7.08 (m, 8H); 7.02 (d, 2H); 5.70 (t, 1H); 4.90 (s, 2H); 3.27 (q, 2H); 2.72 (t, 2H); 1.75–1.62 (m, 5H): 1.45–1.10 (m, 5H).

HPLC-MS (Method B): m/z=524 (M+1). R$_t$=7.35 min.

EXAMPLE 324

General Procedure (L)

4-[1-(4-tert-Butylcyclohexyl)-3-phenethylureidomethyl]-N-(2H-tetrazol-5-yl)benzamide

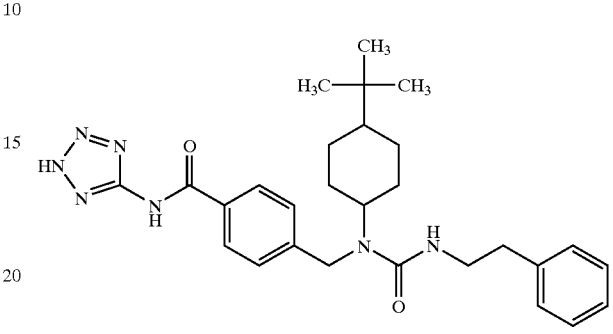

$^1$H NMR (DMSO): δ 12.35 (s, 1H); 8.00 (d, 2H); 7.45–7.10 (m, 7H); 6.45 (s br, 1H); 4.50 (d br, 2H); 4.10+ 3.85 (s br, 1H); 3.30 (s br, 2H); 2.80 (s br, 2H); 1.80–1.00 (m, 9H); 0.80 (s, 9H).

HPLC-MS (Method B): m/z=504 (M+1). R$_t$=7.05 min.

EXAMPLE 325

General Procedure (L)

4-[1-(4-Cyclohex-1-enylphenyl)-3-(3,4-dichlorophenyl)ureidomethyl]-N-(2H-tetrazol-5-yl)benzamide

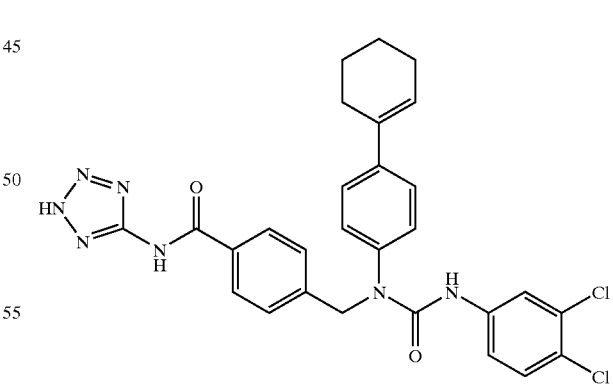

$^1$H NMR (DMSO): δ 12.30 (s, 1H); 8.52 (s, 1H); 8.05 (d, 2H); 7.70 (s, 1H); 7.50–7.38 (m, 6H); 7.20 (d, 2H); 6.18 (s br, 1H); 5.00 (s, 2H); 2.38 (m, 2H); 2.15 (m, 2H); 1.71 (m, 2H); 1.58 (m, 2H).

HPLC-MS (Method B): m/z=562 (M+1). R$_t$=7.90 min.

EXAMPLE 326

General Procedure (L)

4-[1-(4-Cyclohex-1-enylphenyl)-3-(3-trifluoromethylphenyl)ureidomethyl]-N-(2H-tetrazol-5-yl)benzamide

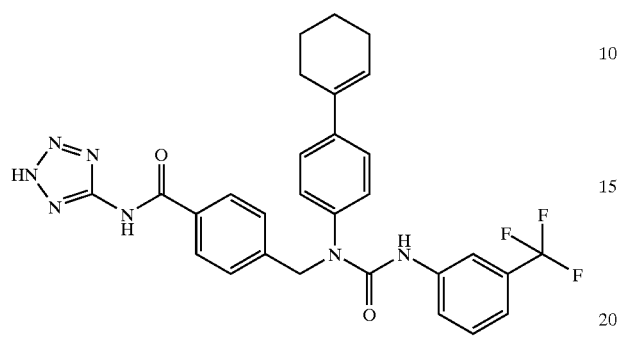

$^1$H NMR (DMSO): δ 12.35 (s, 1H); 8.60 (s, 1H); 8.05 (2H); 7.91 (s, 1H); 7.78 (d, 1H); 7.48–7.40 (m, 5H); 7.30 (d, 1H); 7.23 (d, 2H); 6.20 (t, 1H); 5.00 (s, 1H); 2.38 (m, 2H); 2.15 (m, 2H); 1.72 (m, 2H); 1.60 (m, 2H).

HPLC-MS (Method B): m/z=562 (M+1). $R_t$=7.73 min.

EXAMPLE 327

General Procedure (L)

4-[3-(3-Chloro-4-methylphenyl)-1-(4-cyclohexylphenyl)ureidomethyl]-N-(2H-tetrazol-5-yl)benzamide

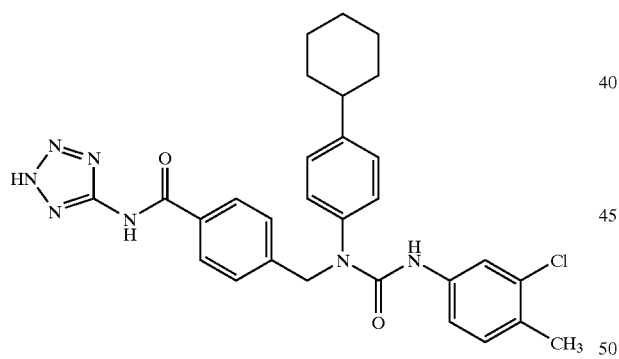

HPLC-MS (method B): m/z: 544, $R_t$=7.88 min.

$^1$H NMR (DMSO$_6$): δ 1.18–1.48 (5H, m), 1.66–1.87 (5H, m), 2.26 (3H, s), 5.00 (2H, s), 7.22 (4H, dd), 7.3 (2H, d), 7.47 (2H, d), 7.62 (1H, s), 8.02 (2H, d), 8.30 (1H, s), 12.2 (1H, broad).

EXAMPLE 328

General Procedure (L)

4-[1-(4-Cyclohex-1-enylphenyl)-3-(4-fluoro-3-trifluoromethylphenyl)ureidomethyl]-N-(2H-tetrazol-5-yl)benzamide

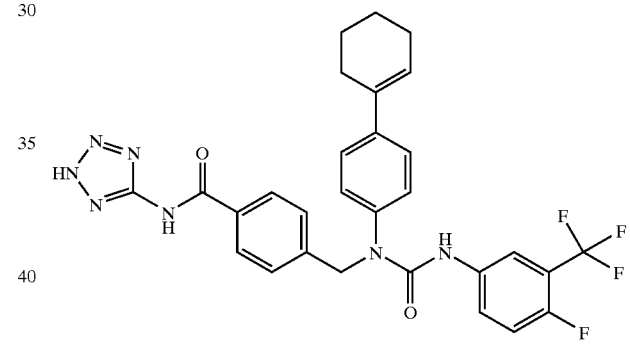

HPLC-MS (method B): m/z: 580, $R_t$=7.67 min.

General Procedure (M) for the Solution Phase Synthesis of Compounds of General Formula (Ik)

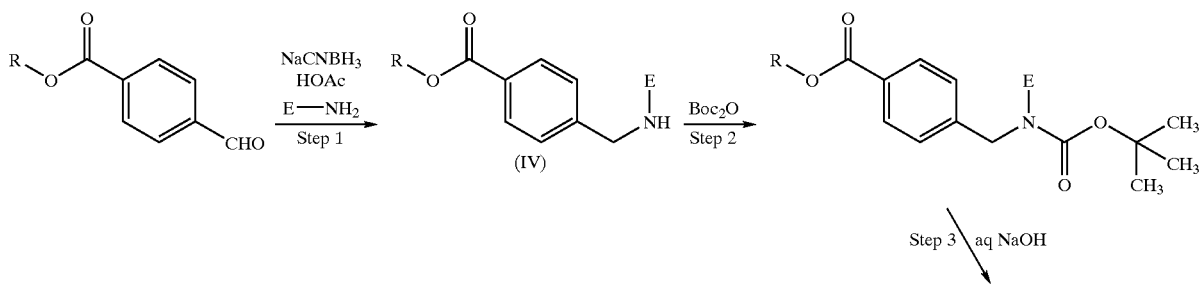

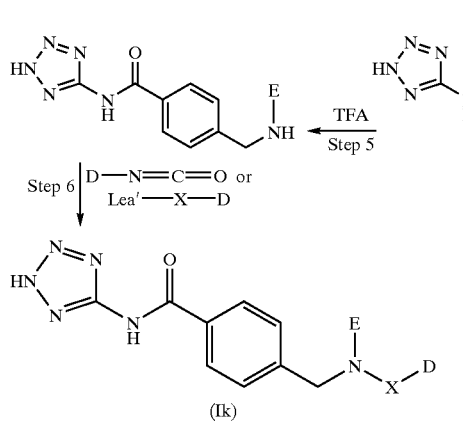
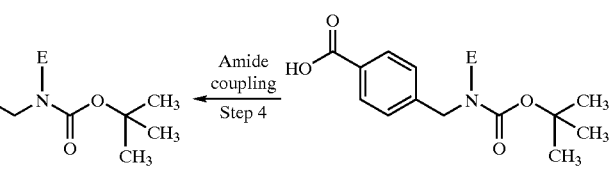

wherein R is $C_{1-6}$-alkyl,
X, D, and E are as defined in general formula (I), and
Lea' is a leaving group such as —OSu, chloro, phenoxy, or 4-nitrophenoxy.

In case the intermediate of the formula (IV) is a mixture of isomers, separation of these can either be performed by column chromatography of the intermediate of the formula (IV) or crystallisation of the intermediate imine.

EXAMPLE 329

General Procedure (M)

4-[1-(4-tert-Butylphenyl)-3-phenylureidomethyl]-N-(2H-tetrazol-5-yl))benzamide

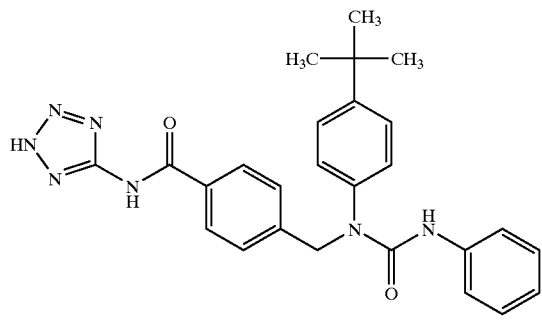

Step 1:
Step 1 is the same as described in general procedure (K). Alternatively, it can be performed as described for step A of the general procedure (F).

Step 2:
4-[(4-tert-Butylphenylamino)methyl]benzoic acid methyl ester (18.3 g, 61 mmol, prepared as described above) was dissolved in THF (300 mL) and N,N-diisopropylethylamine (15 mL, 3.13 mmol), a catalytic amount of 4-dimethylaminopyridine, and di-tert-butyldicarbonate (14.8 g, 68 mmol) was added. The resulting mixture was refluxed for 16 hours, cooled and concentrated in vacuo.

Step 3:
The residue was dissolved in ethanol (450 mL) and added 4N aqueous sodium hydroxide (135 mL) and the mixture was stirred at room temperature for 3 days. 4N Hydrochloric acid (140 mL) was added with occasional cooling by addition of crushed ice. The mixture was filtered and the solid was washed with water and dried in vacuo at 30° C. to afford 14.5 g (62%) of 4-{[tert-butoxycarbonyl-(4-tert-butylphenyl)amino]methyl}benzoic acid as a solid.

$^1$H NMR (CDCl$_3$): δ 1.29 (9H, s), 1.42 (9H, s), 4.89 (2H, s), 7.10 (2H, bd), 7.28 (2H, d), 7.37 (2H, d), 8.05 (2H, d).
HPLC-MS (Method B): R$_t$=8:10 min, m/z=328 ((M−$^t$Bu)+1) (trace: 384 (M+1)).

Step 4:
The above benzoic acid (2.80 g, 7.3 mmol) was dissolved in DMF (20 mL) and 1-hydroxybenzotriazol (1.18 g, 8.8 mmol) and N-(3-dimethylaminopropyl)-N'-ethylcarbodiimide hydrochloride (1.54 g, 8.0 mmol) were added and the resulting mixture was stirred at room temperature for 1 hour. 5-Aminotetrazole hydrate (0.90 g, 8.8 mmol) was added and the mixture was stirred at room temperature for 16 hours. Water (75 mL) was added and the mixture was extracted with ethyl acetate (2×75 mL). The combined organic phases were washed with a mixture of water and saturated aqueous sodium chloride (1:1, 2×100 mL) and water (100 mL), dried (MgSO$_4$) and concentrated in vacuo. The residue was crystallised from diethyl ether (30 mL) to afford 1.89 g (57%) of (4-tert-butylphenyl)-[4-(2H-tetrazol-5-ylcarbamoyl)benzyl]carbamic acid tert-butyl ester as a solid.

$^1$H NMR (CDCl$_3$): δ 1.29 (9H, s), 1.43 (9H, s), 4.93 (2H, s), 7.13 (2H, bd), 7.30 (2H, d), 8.28 (2H, d), 12.5 (1H, s).
HPLC-MS (Method B): R$_t$=7.63 min, m/z=395 ((M−$^t$Bu)+1) (trace: 451 (M+1)).

Step 5:
The above carbamic acid tert-butyl ester (1.7 g, 3.77 mmol) was suspended in ethyl acetate (12 mL) and a 3.4 M dry HCl solution in ethyl acetate (12 mL) was added and the suspension was stirred at room temperature for 16 hours. The mixture was concentrated in vacuo and re-suspended in ethyl acetate. Concentration in vacuo afforded 1.49 g (100%) of 4-[(4-tert-butylphenylamino)methyl]-N-(2H-tetrazol-5-yl)benzamide hydrochloride as a solid.

$^1$H NMR (DMSO-d$_6$): δ 1.37 (9H, s), 4.56 (2H, s), 7.18 (2H, bd), 7.38 (2H, d), 7.68 (2H, d), 8.19 (2H, d), 12.4 (1H, s).
HPLC-MS (Method B): R$_t$=5.22 min, m/z=351 (M+1).

Step 6:
The above benzamide hydrochloride (242 mg, 0.63 mmol) was mixed with dichloromethane (10 mL), N,N-diisopropylethylamine (330 μL, 1.89 mmol), and phenylisocyanate (68 μL, 0.63 mmol) and the resulting mixture was stirred at 25° C. for 16 hours. Alternatively, Lea'-X-D can be used in which case a base such as triethylamine, diisopropylethylamine, dicyclohexylmethylamine or any tertiary amine or potassium carbonate has to be added. The mixture was diluted with dichloromethane (20 mL) and the mixture was washed with saturated aqueous citric acid (20 mL), the organic phase was dried (MgSO$_4$) and concentrated in vacuo. The residue was crystallised from diethyl ether to afford 141 mg (48%) of the title compound as a solid.

$^1$H NMR (DMSO-d$_6$): δ 1.29 (9H, s), 5.00 (2H, s), 6.95 (1H, t), 7.2–7.3 (4H, m), 7.3–7.5 (7H, m), 8.04 (2H, d), 8.18 (1H, s), 12.3 (1H, s).

HPLC-MS (Method B): R$_t$=7.22 min, m/z=470 (M+1).

Similarly, the following compounds were made.

EXAMPLE 330

General Procedure (M)

4-[3-(3,5-Bis(trifluoromethyl)phenyl)-1-(4-tert-butylphenyl)ureidomethyl]-N-(2H-tetrazol-5-yl)benzamide

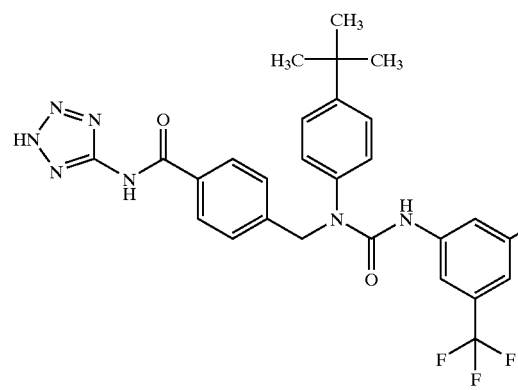

$^1$H NMR (DMSO-d$_6$): δ 1.29 (9H, s), 5.01 (2H, s), 7.30 (1H, t), 7.43 (2H, d), 7.47 (2H, d), 7.64 (1H, s), 8.05 (2H, d), 8.25 (2H, s), 9.00 (1H, s), 12.3 (1H, s).

HPLC-MS (Method B): R$_t$=8.43 min, m/z=606 (M+1).

EXAMPLE 331

General Procedure (M)

4-[1-(4-tert-Butylphenyl)-3-(4-chloro-3-trifluoromethylphenyl)ureidomethyl]-N-(2H-tetrazol-5-yl)benzamide

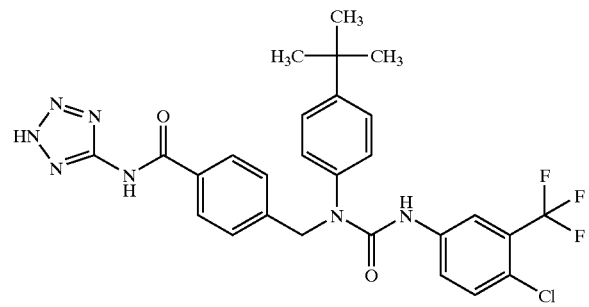

$^1$H NMR (DMSO-d$_6$): δ 1.28 (9H, s), 5.01 (2H, s), 7.23 (2H, d), 7.40 (2H, d), 7.45 (2H, d), 7.56 (1H, d), 7.80 (1H, dd), 8.05 (3H, m), 8.73 (1H, s), 12.3 (1H, s).

HPLC-MS (Method B): R$_t$=8.18 min, m/z=572 (M+1).

EXAMPLE 332

General Procedure (M)

4-[1-(4-tert-Butylphenyl)-3-(4-trifluoromethylsulfanylphenyl)ureidomethyl]-N-(2H-tetrazol-5-yl)benzamide

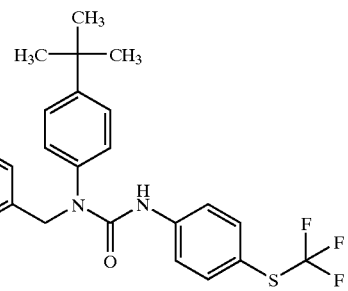

$^1$H NMR (DMSO-d$_6$): δ 1.28 (9H, s), 5.02 (2H, s), 7.21 (2H, d), 7.38 (2H, d), 7.46 (2H, d), 7.56 (2H, d), 7.63 (2H, d), 8.04 (2H, d), 8.64 (1H, s), 12.3 (1H, s).

HPLC-MS (Method B): R$_t$=8.20 min, m/z=570 (M+1).

EXAMPLE 333

General Procedure (M)

4-[1-(4-tert-Butylphenyl)-3-(3,5-dichlorophenyl)ureidomethyl]-N-(2H-tetrazol-5-yl)benzamide

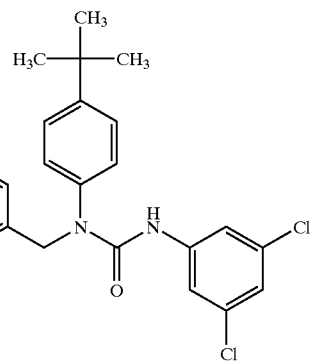

$^1$H NMR (DMSO-d$_6$): δ 1.35 (9H, s), 4.95 (2H, s), 6.88 (1H, s), 6.96 (1H, t), 7.10 (2H, d), 7.38 (2H, d), 7.43 (4H, m), 8.13 (2H, d), 8.64 (1H, s), 12.3 (1H, s).

HPLC-MS (Method B): R$_t$=7.98 min, m/z=538 (M+1).

EXAMPLE 334

General Procedure (M)

4-[1-(trans-4-tert-Butylcyclohexyl)-3-(4-cyclopropylmethoxy-2-trifluoromethylphenyl)ureidomethyl]-N-(2H-tetrazol-5-yl)benzamide

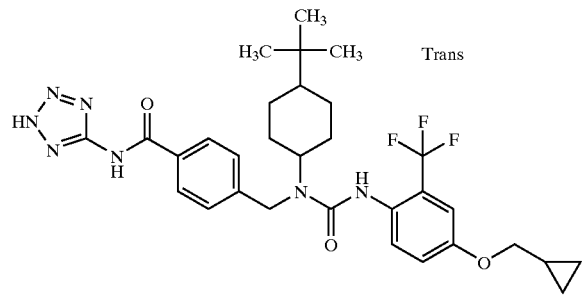

$^1$H NMR (DMSO-d$_6$): δ 7.98 (3H, m), 7.42 (2H, d), 7.32 (1H, d), 7.18 (1H, d), 7.13 (1H, s), 4.55 (2H, broad), 3.88 (2H, d), 1.80–0.85 (10H, m), 0.80 (9H, s), 0.60 (2H, m).

HPLC-MS (method B): m/z: 614, R$_t$=8.32 min.

Synthesis of intermediate 4-cyclopropylmethoxy-2-trifluoromethylphenylamine:

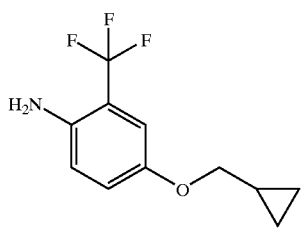

1-Nitro-4-hydroxy-2-trifluromethylbenzene (5.0 g, 14 mmol) and cyclopropylcarbinol (1.75 g, 24 mmol) were dissolved in THF (20 mL) under nitrogen. Triphenylphosphine (9.5 g, 36 mmol) was added and diethyl azodicarboxylate (5.7 mL, 36 mmol) dissolved in THF (10 mL) was added over 30 minutes. The reaction mixture was stirred at 20° C. for 16 hours and then concentrated in vacuo. The residue was dissolved in ethyl acetate (25 mL) and heptane (40 mL). The mixture was filtered and the filtrate was concentrated in vacuo. The residue was purified by flash chromatography (350 g silica) using heptane and ethyl acetate (9:1) as eluent to give 1.4 g of 4-cyclopropylmethoxy-1-nitro-2-trifluoromethylbenzene.

HPLC-MS (method B): m/z: 262, R$_t$=7.6 min.

Stannous chloride (4.75 g, 21 mmol) was added to a solution of 4-cyclopropylmethoxy-1-nitro-2-trifluoromethylbenzene (1.1 g, 4.2 mmol) in ethanol (12 mL). The reaction temperature was raised to 70° C. for 1.5 hour. The reaction mixture was concentrated in vacuo and the residue dissolved in ethyl acetate (20 mL). Water (15 mL) was added and sodium hydrogen carbonate was added until pH 7. The mixture was filtered and the organic phase collected. The aqueous phase was extracted with ethyl acetate (20 mL). The combined organic phases were dried (MgSO$_4$) and concentrated in vacuo. The residue was purified by flash chromatography (38 g) using heptane and ethyl acetate (9:1) as eluent to give 0.49 g of 4-cyclopropylmethoxy-2-trifluoromethylphenylamine.

$^1$H NMR (DMSO-d$_6$): δ 6.98 (1H, d), 6.85 (1H, s), 6.79 (1H, d), 5.10 (2H, broad), 3.72 (2H, d), 1.15 (1H, m), 0.53 (2H, m), 0.31 (2H, m).

HPLC-MS (method B): m/z: 232, R$_t$=5.9 min.

This intermediate product was transformed to the corresponding phenylcarbamate using the same methodology as described in example 239 and used for the synthesis of the title compound.

EXAMPLE 335

General Procedure (M)

4-[1-(4-Cyclohexylphenyl)-3-(2,5-dichlorothiophen-3-yl)ureidomethyl]-N-(2H-tetrazol-5-yl)benzamide

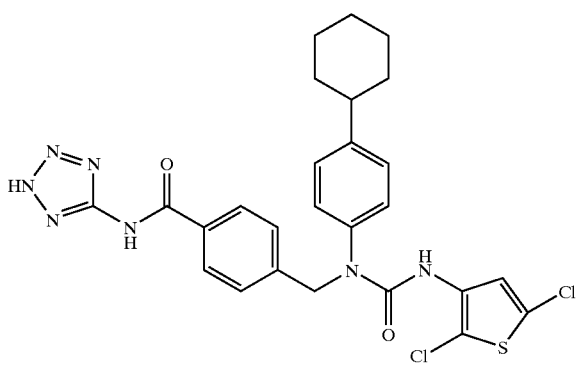

The intermediate 2,5-dichloro-3-thienylisocyanate was prepared by a Curtius reaction on 2,5-dichloro-3-thienylcarboxylic acid.

$^1$H NMR (DMSO-d$_6$): δ 7.63 (s, 1H), 7.49 (d, 2H), 7.33 (d, 2H), 7.27 (s, 1H), 7.22 (dd, 4H), 4.88 (s, 2H), 1.8–1.6 (m, 5H), 1.4–1.2 (m, 6H).

HPLC-MS (method B): m/z: 567, R$_t$=8.5 min.

EXAMPLE 336

General Procedure (M)

4-[3-[1-(4-Chlorophenyl)ethyl]-1-(4-cyclohexylphenyl)ureidomethyl]-N-(2H-tetrazol-5-yl)benzamide

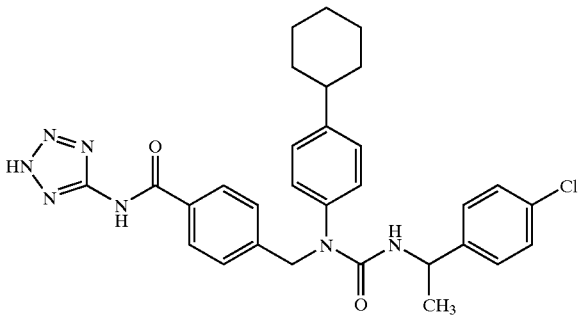

HPLC-MS (Method B): m/z=558 (M+1), R$_t$=7.83 min. $^1$H NMR (DMSO-d$_6$): δ 1.2–1.4 (8H, m), 1.7–1.8 (5H, m), 4.90 (3H, m), 7.1–7.2 (4H, m), 7.35 (5H, m), 7.52 (1H, m), 8.02 (2H, d).

EXAMPLE 337

General Procedure (M)

4-[3-[1-(4-Chlorophenyl)ethyl]-1-(4-Cyclohexylphenyl)ureidomethyl]-N-(2H-tetrazol-5-yl)benzamide, enantiomer A, first eluted

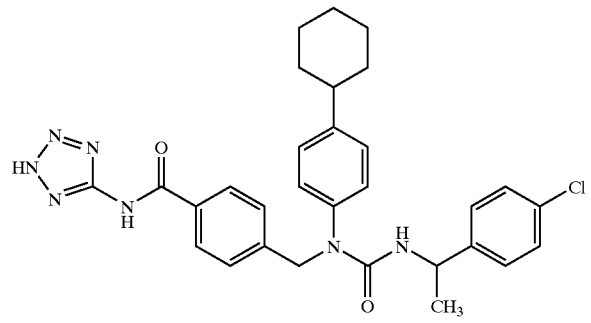

The compound of example 336 was separated into pure enantiomers using a (R,R)-Whelk-O 1 column (250-21.1 mm, Regis) eluted with n-heptane:ethanol, 1:1 at a flow rate of 15 mL/min. The compound was dissolved in ethyl acetate:ethanol:acetic acid:n-heptane (0.9:1.1:0.09:1.1), 5 mg/ml, injected in portions of 10 mg (2 ml) and detected at 225 and 254 nm. The two enantiomers A and B eluted at $T_R$ 9–12 min (A) and $T_R$ 37–42 min (B), respectively, and the fractions were collected (10 mL/fraction) and pooled. The purity of the enantiomers was determined using a Chiralcel OD (250-4.6 mm, Daicel) column eluted with ethanol:(n-heptane+0.1% TFA), 40:60 at a flow rate of 0.6 mL/min, $T_R$(A): 14.6 min and $T_R$(B): 12.0 min.

Used Instruments

HP1090 (analytical runs), Gilson HPLC system (preparative runs).

EXAMPLE 338

General Procedure (M)

4-[3-[1-(4-Chlorophenyl)ethyl]-1-(4-cyclohexylphenyl)ureidomethyl]-N-(2H-tetrazol-5-yl)benzamide, enantiomer B, second eluted

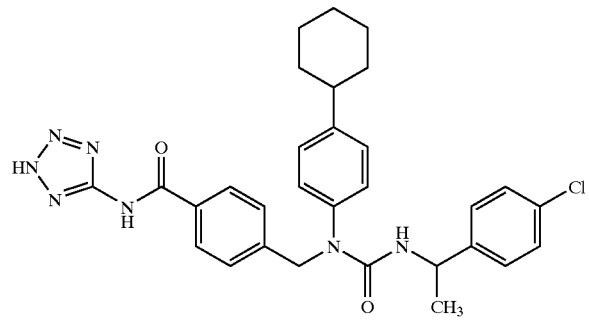

This compound was obtained as the second eluting enantiomer (enantiomer B) of example 337. For HPLC-data, see example 337.

EXAMPLE 339

General Procedure (M)

4-[1-(4-tert-Butylphenyl)-3-(3-methylsulfonyl-4-methoxyphenyl)ureidomethyl]-N-(2H-tetrazol-5-yl)benzamide

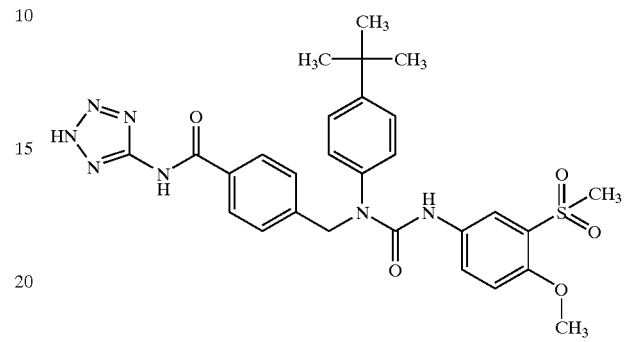

4-Methoxy-3-methylsulfonylaniline was prepared as described in Holmes, Ingold & Ingold, J. Chem. Soc., 1927, 1684–90, and the corresponding isocyanate was prepared using the triphosgene method described in example 240.

$^1$H NMR (DMSO-d$_6$): δ 1.30 (9H, s), 3.22 (3H, s), 3.90 (3H, s), 5.00 (2H, s), 7.2 (3H, m), 7.40 (2H, d), 7.45 (2H, d), 7.80 (1H, dd), 7.94 (1H, d), 8.03 (2, d), 8.48 (1H, s), 12.2 (H, s).

HPLC-MS (Method B): m/z=578 (M+1), R$_t$=5.63 min.

EXAMPLE 340

General Procedure (M)

4-[1-(4-Cyclohexylphenyl)-3-(3-methylsulfonyl-4-methoxyphenyl)ureidomethyl]-N-(2H-tetrazol-5-yl)benzamide

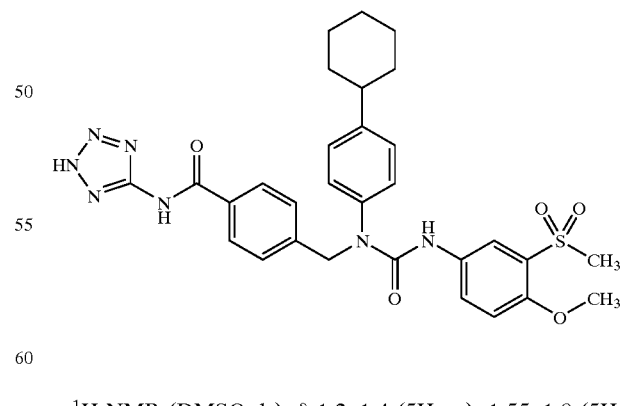

$^1$H NMR (DMSO-d$_6$): δ 1.2–1.4 (5H, m), 1.55–1.8 (5H, m), 3.22 (3H, s), 3.90 (3H, s), 4.99 (2H, s), 7.2 (5H, m), 7.44 (2H, d), 7.79 (1H, dd), 7.92 (1H, d), 8.02 (2H, d), 8.47 (1H, s), 11.9 (1H, s), 12.3 (1H, s).

HPLC-MS (Method B): m/z=604 (M+1), R$_t$=6.40 min.

EXAMPLE 341

General Procedure (M)

4-[1-(4-Cyclohexylphenyl)-3-(6-trifluoromethoxybenzothiazol-2-yl)ureidomethyl]-N-(2H-tetrazol-5-yl)benzamide

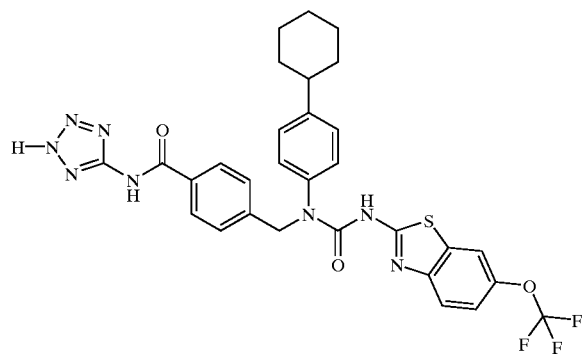

Using Isocyanate Formed in situ from (Substituted) 2-aminobenzothiazole and Diphosgene in Pyridine 2-Amino-6-(trifluoromethoxy)benzothiazole (334 mg, 1.43 mmol) was dissolved in pyridine (5 mL). Diphosgene (0.1 mL, 0.83 mmol) was added and the reaction mixture was stirred for 2 hours at room temperature. 4-[(4-cyclohexylphenylamino)methyl]-N-(2H-tetrazol-5-yl)benzamide (400 mg, 1.06 mmol) was added and the reaction mixture was heated to 80° C. for two hours. The reaction mixture was poured into acetonitrile (50 mL) and stored at −20° C. overnight and the resulting precipitate was subsequently collected by filtration to afford the title compound.

HPLC-MS (Method D): $R_t$=6.20 min, m/z=637 (M+1).

EXAMPLE 342

General Procedure (M)

4-[1-(4-Cyclohexylphenyl)-3-(6-nitrobenzothiazol-2-yl)ureidomethyl]-N-(2H-tetrazol-5-yl)benzamide

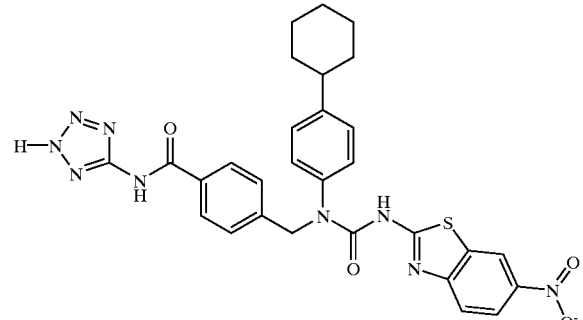

HPLC-MS (Method D): $R_t$=5.67 min, m/z=598 (M+1).

EXAMPLE 343

General Procedure (M)

2-{3-(4-Cyclohexylphenyl)-3-[4-(2H-tetrazol-5-ylcarbamoyl)benzyl]ureido}benzothiazole-6-carboxylic acid ethyl ester HPLC-MS (Method D): $R_t$=5.83 min, m/z=625 (M+1).

EXAMPLE 344

General Procedure (M)

4-[1-(4-Cyclohexylphenyl)-3-(3-trifluoromethoxyphenyl)ureidomethyl]-N-(2H-tetrazol-5-yl)benzamide $^1$H NMR (DMSO-d$_6$): δ 1.2–1.4 (m, 5H), 1.7–1.8 (m, 5H), 5.00 (s, 2H), 6.93 (d, 1H), 7.22 (m, 4H), 7.34 (t, 1H), 7.45 (m, 3H), 7.60 (s, 1H), 8.05 (d, 2H), 8.53 (s, 1H), 12.4 (bs, 1H).

HPLC-MS (method B): $R_t$=7.93 min, m/z=580 (M+1).

EXAMPLE 345

General Procedure (M)

4-[3-(2-Bromobenzyl)-1-(4-cyclohexylphenyl)ureidomethyl]-N-(2H-tetrazol-5-yl)benzamide

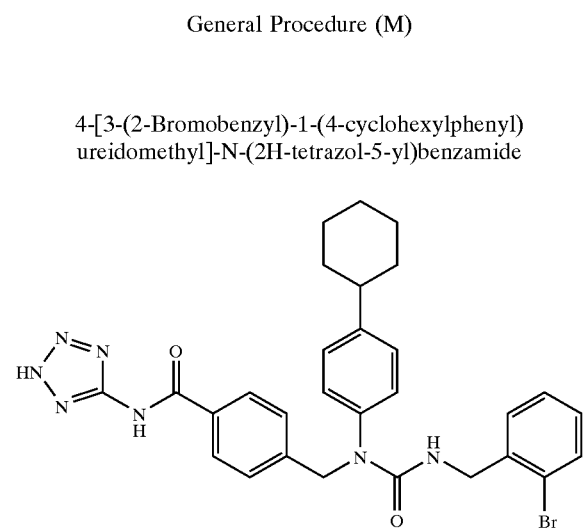

$^1$H NMR (DMSO-$d_6$): δ 1.2–1.5 (m, 5H), 1.7–1.8 (m, 5H), 4.25 (d, 2H), 4.92 (s, 2H), 6.46 (m, 1H), 7.15–7.30 (m, 6H), 7.45 (m, 3H), 7.56 (d, 1H), 8.07 (d, 2H), 12.4 (s, 1H).

EXAMPLE 346

General Procedure (M)

4-[1-(4-Cyclohexylphenyl)-3-(3,4-dichlorophenyl)ureidomethyl]-N-(2H-tetrazol-5-yl)benzamide

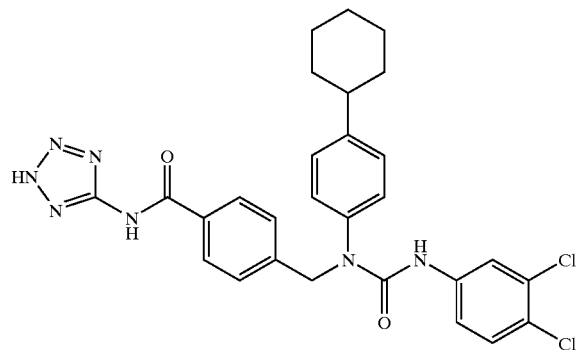

$^1$H NMR (DMSO-$d_6$): δ 1.3–1.4 (m, 5H), 1.7–1.8 (m, 5H), 5.00 (s, 2H), 7.22 (m, 4H), 7.45 (m, 3H), 7.83 (s, 1H), 8.04 (d, 2H), 8.53 (s, 1H), 12.4 (s, 1H).

HPLC-MS (method B): $R_t$=8.07 min, m/z=564 (M+1).

EXAMPLE 347

General Procedure (M)

4-[1-(4-Cyclohexylphenyl)-3-(4-trifluoromethoxybenzyl)ureidomethyl]-N-(2H-tetrazol-5-yl)benzamide

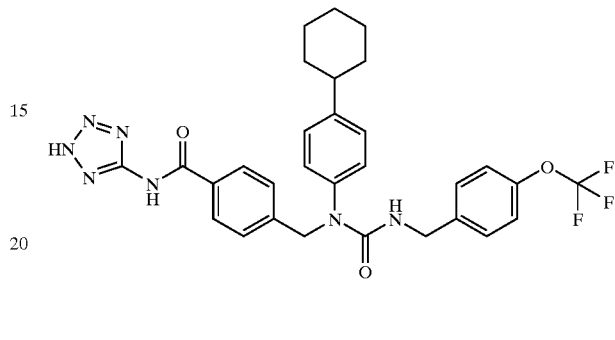

$^1$H NMR (DMSO-$d_6$): δ 1.2–1.4 (m, 5H), 1.7–1.8 (m, 5H), 2.57 (s, 1H), 4.28 (d, 2H), 4.91 (s, 2H), 6.57 (t, 1H), 7.14 (d, 2H), 7.22 (d, 2H), 7.29–7.40 (m, 6H), 8.02 (d, 2H), 12.3 (s, 1H).

HPLC-MS (method B): $R_t$=7.68 min, m/z=594 (M+1).

EXAMPLE 348

General Procedure (M)

4-[1-(4-Cyclohexylphenyl)-3-(2-trifluoromethoxybenzyl)ureidomethyl]-N-(2H-tetrazol-5-yl)benzamide

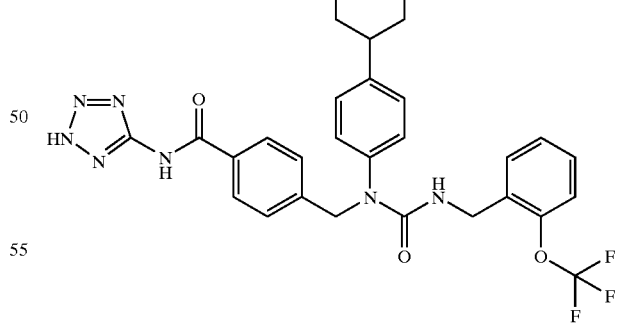

$^1$H NMR (DMSO-$d_6$): δ 1.2–1.4 (m, 5H), 1.7–1.8 (m, 5H), 2.55 (s, 1H), 4.34 (d, 2H), 4.91 (s, 2H), 6.44 (t, 1H), 7.17 (d, 2H), 7.22 (d, 2H), 7.29–7.42 (m, 6H), 8.02 (d, 2H), 12.3 (s, 1H).

HPLC-MS (method B): $R_t$=7.72 min, m/z=594 (M+1).

EXAMPLE 349

General Procedure (M)

4-[3-(3-Bromophenyl)-1-(4-cyclohex-1-enylphenyl)ureidomethyl]-N-(2H-tetrazol-5-yl)benzamide

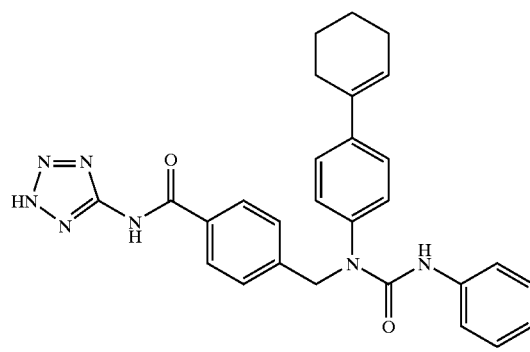

$^1$H NMR (DMSO-d$_6$): δ 1.59 (m, 2H), 1.72 (m, 2H), 2.17 (m, 2H), 2.35 (m, 2H), 5.01 (s, 2H), 6.19 (t, 1H), 7.1–7.25 (m, 4H), 7.5–7.5 (m, 5H), 7.79 (s, 1H), 8.04 (d, 2H), 8.42 (s, 1H), 12.4 (s, 1H).

HPLC-MS (method C): R$_t$=5.73 min, m/z=574 (M+1).

EXAMPLE 350

General Procedure (M)

4-[1-(4-Cyclohexylphenyl)-3-(2-trifluoromethoxyphenyl)ureidomethyl]-N-(2H-tetrazol-5-yl)benzamide

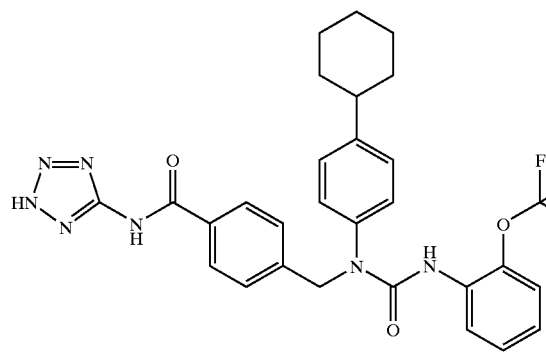

$^1$H NMR (DMSO-d$_6$): δ 1.2–1.4 (m, 5H), 1.7–1.8 (m, 5H), 4.99 (s, 2H), 6.44 (t, 1H), 7.12 (t, 1H), 7.20 (s, 1H), 7.25–7.35 (m, 6H), 7.49 (d, 2H), 8.05 (d, 2H), 8.11 (d, 1H), 12.4 (s, 1H).

HPLC-MS (method B): R$_t$=8.20 min, m/z=580 (M+1).

EXAMPLE 351

General Procedure (M)

4-[1-(4-Cyclohex-1-enylphenyl)-3-(2-trifluoromethoxyphenyl)ureidomethyl]-N-(2H-tetrazol-5-yl)benzamide

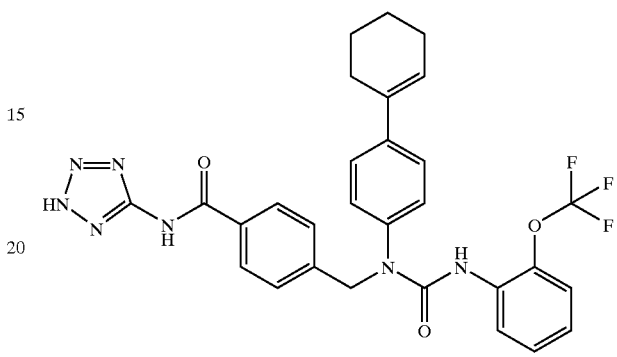

$^1$H NMR (DMSO-d$_6$): δ 1.60 (m, 2H), 1.71 (m, 2H), 2.17 (m, 2H), 2.33 (m, 2H), 5.01 (s, 2H), 6.19 (m, 1H), 7.15 (t, 1H), 7.30–7.50 (m, 9H), 7.99 (d, 1H), 8.05 (d, 2H), 12.4 (s, 1H).

HPLC-MS (method B): R$_t$=7.90 min, m/z=578 (M+1).

EXAMPLE 352

General Procedure (M)

4-[1-(4-Cyclohex-1-enylphenyl)-3-(3-trifluoromethoxyphenyl)ureidomethyl]-N-(2H-tetrazol-5-yl)benzamide

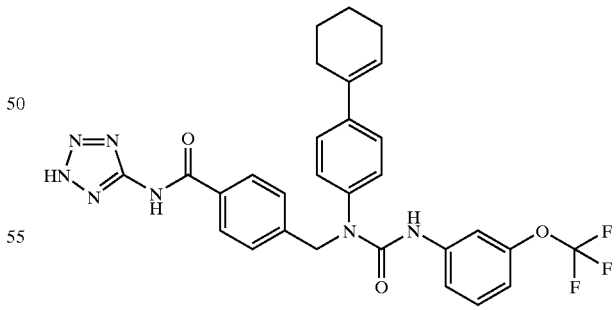

$^1$H NMR (DMSO-d$_6$): δ 1.60 (m, 2H), 1.70 (m, 2H), 2.18 (m, 2H), 2.34 (m, 2H), 5.00 (s, 2H), 6.19 (t, 1H), 6.93 (d, 1H), 7.22 (d, 2H), 7.35 (t, 1H), 7.4–7.5 (m, 5H), 7.60 (s, 1H), 8.03 (d, 2H), 8.53 (s, 1H), 12.4 (s, 1H).

HPLC-MS (method B): m/z=578 (M+1), R$_t$=7.77 min.

EXAMPLE 353

General Procedure (M)

4-[3-Biphenyl-2-ylmethyl-1-(4-cyclohex-1-enylphenyl)ureidomethyl]-N-(2H-tetrazol-5-yl)benzamide

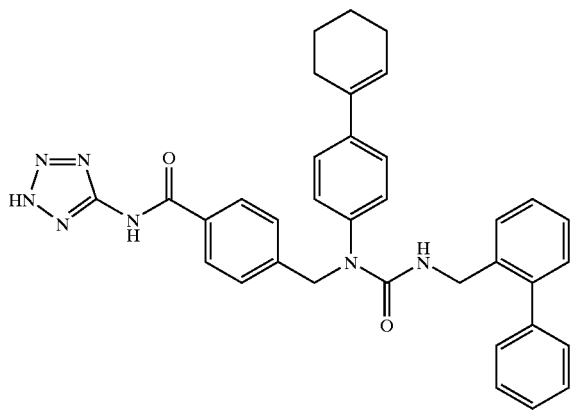

$^1$H NMR (DMSO-d$_6$): δ 1.59 (m, 2H), 1.70 (m, 2H), 2.15 (m, 2H), 2.33 (m, 2H), 4.21 (d, 2H), 4.90 (s, 2H), 6.15 (t, 1H), 6.28 (t, 1H), 7.10 (d, 2H), 7.18 (d, 1H), 7.3–7.5 (m, 15H), 7.95 (s, 1H), 8.00 (d, 2H), 12.3 (s, 1H).

HPLC-MS (method B): R$_t$=7.78 min, m/z=584 (M+1).

EXAMPLE 354

General Procedure (M)

4-[3-Biphenyl-2-ylmethyl-1-(4-cyclohexylphenyl)ureidomethyl]-N-(2H-tetrazol-5-yl)benzamide

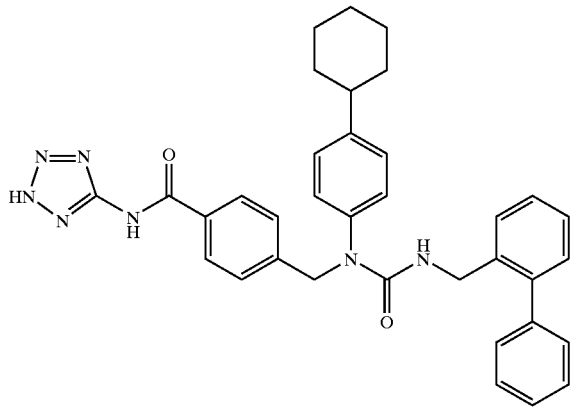

$^1$H NMR (DMSO-d$_6$): δ 1.15–1.4 (m, 5H), 1.6–1.8 (m, 5H), 4.20 (d, 2H), 4.88 (s, 2H), 6.16 (t, 1H), 7.08 (d, 2H), 7.11 (m, 3H), 7.3–7.45 (m, 11H), 8.00 (d, 2H), 12.4 (s, 1H).

EXAMPLE 355

General Procedure (M)

(R)-4-[3-[1-(4-Bromophenyl)ethyl]-1-(cyclohex-1-enylphenyl)ureidomethyl]-N-(2H-tetrazol-5-yl)benzamide

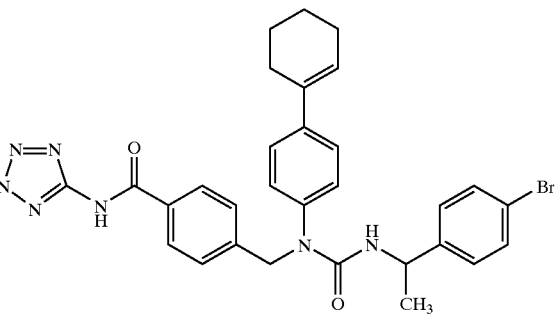

HPLC-MS (method B): R$_t$=7.72 min, m/z=601 (M+1).

EXAMPLE 356

General Procedure (M)

4-[3-(3-Bromophenyl)-1-(4-cyclohexylphenyl)ureidomethyl]-N-(2H-tetrazol-5-yl)benzamide

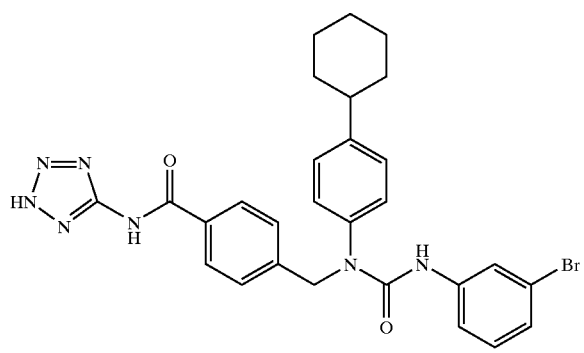

$^1$H NMR (DMSO-d$_6$): δ 1.3–1.5 (m, 5H), 1.7–1.8 (m, 5H), 4.99 (s, 2H), 7.1–7.2 (m, 7H), 7.4–7.5 (m, 3H), 7.78 (s, 1H), 8.02 (d, 2H), 8.40 (s, 1H), 12.4 (s, 1H).

HPLC-MS (method B): m/z=576 (M+1), R$_t$=7.88 min.

EXAMPLE 357

General Procedure (M)

4-[1-(4-Cyclohexylphenyl)-3-(3-tert-butylphenyl)ureidomethyl]-N-(2H-tetrazol-5-yl)benzamide

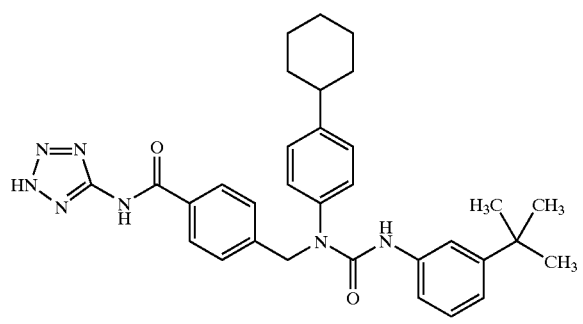

$^1$H NMR (DMSO-d$_6$): δ 1.25 (s, 9H), 1.3–1.5 (m, 5H), 1.7–1.8 (m, 5H), 4.99 (s, 2H), 6.99 (d, 1H), 7.1–7.3 (m, 6H), 7.4–7.5 (m, 3H), 8.05 (d, 2H), 8.13 (s, 1H), 12.4 (s, 1H).

HPLC-MS (method C): m/z=552 (M+1), R$_t$=6.27 min.

EXAMPLE 358

General Procedure (M)

4-[1-(4-Cyclohex-1-enylphenyl)-3-(2,2,4,4-tetrafluoro-4H-benzo[1,3]dioxin-6-yl)ureidomethyl]-N-(2H-tetrazol-5-yl)benzamide

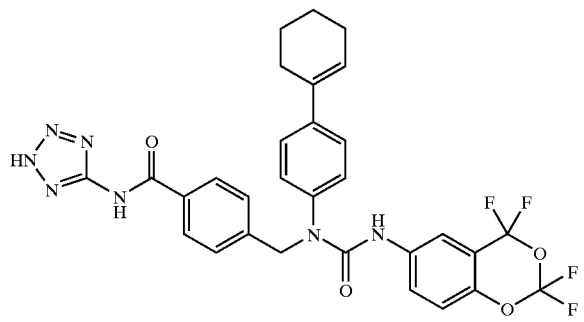

$^1$H NMR (DMSO-d$_6$): δ 1.60 (2H, m), 1.70 (2H, m), 2.17 (2H, br s), 2.35 (2H, br s), 5.03 (2H, s), 6.20 (1H, s), 7.20–7.30 (2H, m), 7.35–7.50 (6H, m), 7.85, (1H, d), 8.04 (3H, m), 8.65 (1H, s), 12.40 (1H, s).

EXAMPLE 359

General Procedure (M)

4-[3-(3-Cyano-5-trifluoromethylphenyl)-1-(4-cyclohexylphenyl)ureidomethyl]-N-(2H-tetrazol-5-yl)benzamide

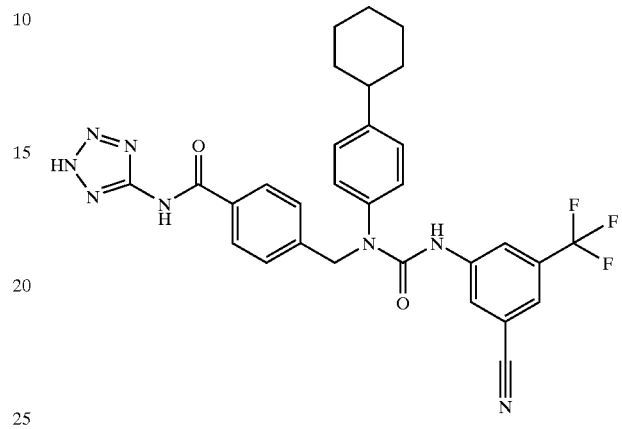

$^1$H NMR (DMSO): δ 12.40 (s, 1H); 8.90 (s, 1H); 8.25 (s, 1H); 8.20 (s, 1H); 8.02 (d, 2H); 7.86 (s, 1H); 7.48 (d, 2H); 7.22 (s, 4H); 5.00 (s, 2H); 1.85–1.65 (m, 5H); 1.45–1.20 (m, 5H).

HPLC-MS (Method B): m/z=589 (M+1). R$_t$=5.83 min.

Preparation of 3-Amino-5-trifluoromethylbenzonitrile

Commercially available 3-nitro-5-trifluoromethylbenzoic acid (10 g, 42.5 mmol) was dissolved in toluene (50 mL) and DMF (0.5 mL) and added thionyl chloride (5 mL). The mixture was refluxed for 4 hours. After cooling to 20° C., the volatiles were removed in vacuo. The residue was re-dissolved in toluene (50 mL) and stripped. Toluene (50 mL) was added to the residue, and the solution was cooled on ice and added concentrated aqueous ammonia (10 mL). The mixture was stirred overnight and allowed to reach 20° C. 3-Nitro-5-trifluoromethylbenzamide was collected by filtration.

The above 3-nitro-5-trifluoromethylbenzamide (7.25 g) was dissolved in DMF (25 mL) and added to an ice-cooled solution of POCl$_3$ (10 mL) in DMF (20 mL). The mixture was stirred 30 min at 0° C. and then heated to 40° C. for 4 hours. The reaction mixture was added to ice (300 mL), stirred for 1 hour and 3-nitro-5-trifluoromethylbenzonitrile was collected by filtration.

3-Nitro-5-trifluoromethylbenzonitrile (1 g, 4.63 mmol) was dissolved in methanol (8 mL) and added activated charcoal (0.1 g), FeCl$_3$.6H$_2$O (17 mg, 0.06 mmol) and N,N-dimethylhydrazine (3.7 mL, 48.6 mmol). The mixture was refluxed overnight. The mixture was filtered and the volatiles removed in vacuo. The residue was purified by chromatography on silica using a mixture of heptane and ethyl acetate (4:1) as eluent affording 3-amino-5-trifluoromethylbenzonitrile.

The aniline was converted into the corresponding isocyanate by methods already described.

EXAMPLE 360

General Procedure (M)

4-[3-(3-Benzoxazol-2-yl-4-trifluoromethoxyphenyl)-1-(4-cyclohexylphenyl)ureidomethyl]-N-(2H-tetrazol-5-yl)benzamide

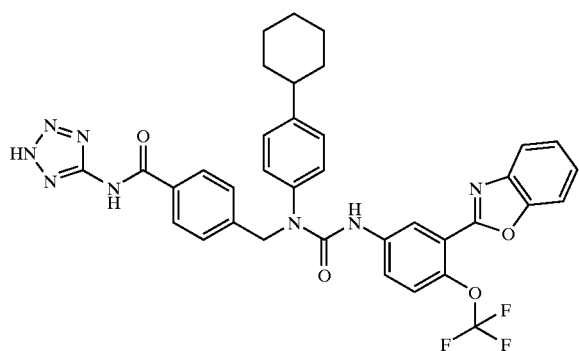

$^{1}$H NMR (DMSO-d$_{6}$): δ 1.32–1.50 (m, 5H); 1.63–1.86 (m, 5H); 5.04 (s, 2H); 7.26 (s, 5H); 7.43–7.55 (m, 5H); 7.76–7.92 (m, 3H); 8.05 (d, 2H); 8.51 (d, 1H); 8.84 (s, 1H); 12.17 (s, 1H).

Preparation of 2-(5-isocyanato-2-trifluoromethoxyphenyl)benzoxazole:

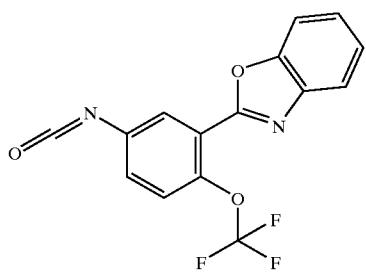

Concentrated sulphuric acid (26 mL) was added dropwise to a flask containing 26 mL of 100% nitric acid while the temperature was kept at 2–6° C. Stirring was continued at this temperature while 2-(trifluoromethoxy)benzonitrile (26.16 g, 0.1398 mol) was added dropwise. When the addition was complete, the mixture was heated at 60° C. for 1 hour and poured into ice water. The precipitate was filtered off and treated with aqueous sodium hydrogen carbonate until neutral reaction. The crystals were collected and dried to afford 28.53 g (82%) of 5-nitro-2-trifluoromethoxybenzoic acid.

Mp 134–135° C.

$^{1}$H NMR (DMSO-d$_{6}$): δ 7.79 (dd, 1H), 8.53 (dd, 1H), 8.64 (d, 1H), 14.13 (br s, 1H).

A mixture of 5-nitro-2-trifluoromethoxybenzoic acid (6.43 g, 25.6 mmol) and 128 mg of 10% Pd/C in 10 mL of absolute ethanol was stirred in a hydrogen atmosphere overnight at room temperature. The catalyst was filtered off and the filtrate was evaporated to dryness. The residue was triturated with diethyl ether and the crystals were filtered off and dried to afford 1.644 g (29%) of 5-amino-2-trifluoromethoxybenzoic acid.

Mp 196–197° C.

$^{1}$H NMR (DMSO-d$_{6}$): δ 5.83 (br s, 2H), 6.74 (dd, 1H), 7.06 (m, 2H), 12.52 (br s, 1H).

A mixture 750 mg of 5-amino-2-trifluoromethoxybenzoic acid (750 mg, 3.39 mmol) and 2-aminophenol (370 mg, 3.39 mmol) in 10 mL of polyphosphoric acid was heated and stirred at 250° C. for 3.5 hours. The mixture was poured into ice water under stirring, followed by addition of NaHCO$_{3}$ until pH 8. The mixture was extracted with ethyl acetate. The organic phase was washed with water twice, brine, rinsed with activated charcoal, dried over MgSO$_{4}$ and evaporated to give an oil, which contained two compounds, according to TLC. This mixture was dissolved in DMF and separated on semi preparative HPLC (Gilson 215 Liquid Handler), stationary phase: RP18, mobile phase: Water/MeCN gradient 95%/5%–5%/95% to afford 216 mg (22%) of 3-benzoxazol-2-yl-4-trifluoromethoxyphenylamine as crystals.

Mp 133–135° C.

$^{1}$H NMR (DMSO-d$_{6}$): δ 5.73 (br s, 2H), 6.82 (dd, 1H), 7.23 (dd, 1H), 7.44 (m, 3H), 7.82 (m, 2H).

A solution of 3-benzoxazol-2-yl-4-trifluoromethoxyphenylamine (210 mg, 0.71 mmol) in 5 mL of dry toluene was stirred while 1.15 mL of 3.1N hydrochloric acid in ethyl acetate was added. The precipitate was concentrated by evaporation. Another 5 mL of toluene was added followed by evaporation. This procedure was repeated 3 times to remove excess of hydrochloric acid. The amine hydrochloride was dissolved in 5 mL of toluene and trichloromethyl chloroformate (0.853 mL, 7.1 mmol) was added. The mixture was refluxed overnight under a nitrogen atmosphere, evaporated at 70° C. followed by stripping with dry toluene. 2-(5-Isocyanato-2-trifluoromethoxyphenyl)benzoxazole (160 mg, 70%) was obtained as crystals and used immediately to synthesize the title compound.

EXAMPLE 361

General Procedure (M)

4-[3-(2,5-Bis(trifluoromethyl)phenyl)-1-(4-cyclohex-1-enylphenyl)ureidomethyl]-N-(2H-tetrazol-5-yl)benzamide

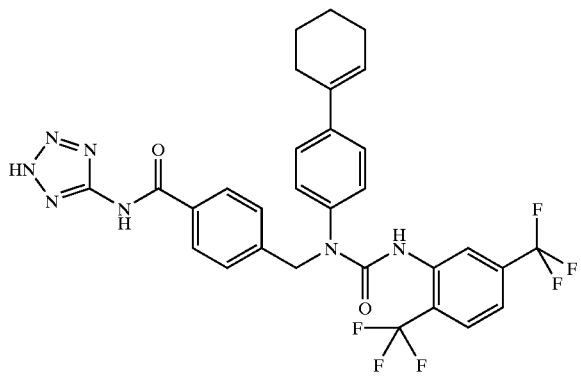

HPLC-MS (method B): m/z: 630, R$_{t}$=8.48 min.

$^{1}$H NMR (DMSO-d$_{6}$): δ 1.54–1.62 (2H, m), 1.68–1.78 (2H, m), 2.18 (2H, broad), 2.34 (2H, broad), 5.02 (2H, s), 6.21 (1H, broad), 7.32 (2H, d), 7.48 (4H, dd), 7.65 (1H, d), 7.90 (1H, d), 8.02 (2H, d), 8.40 (1H, s), 11.95 (1H, broad).

EXAMPLE 362

General Procedure (M)

4-[1-(4-Cyclohex-1-enylphenyl)-3-(3-methyl-5-trifluoromethylphenyl)ureidomethyl]-N-(2H-tetrazol-5-yl)benzamide

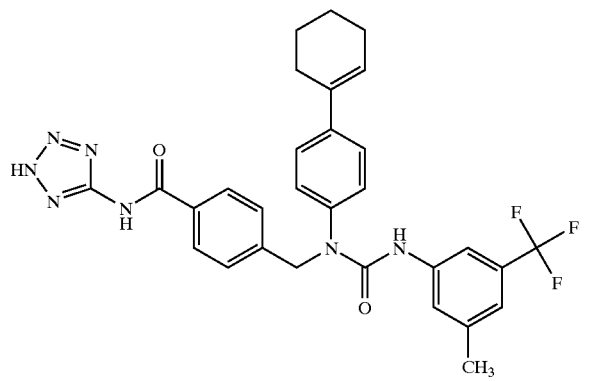

HPLC-MS (method B): m/z: 576, $R_t$=8.02 min.

$^1$H NMR (DMSO-d$_6$): δ 1.60 (2H, m), 1.70 (2H, m), 2.17 (2H, m), 2.32 (3H, s), 2.35 (2H, m), 5.02 (2H, s), 6.20 (s, 1H), 7.12 (1H, s), 7.24 (2H, d), 7.42 (2H, d), 7.46 (2H, d), 7.60 (1H, s), 7.74 (1H, s), 8.03 (2H, d), 8.49 (1H, s), 12.39 (1H, s).

Microanalysis: calculated for $C_{30}H_{28}F_3N_7O_2$: 62.60% C; 4.90% H; 17.03% N. Found: 62.57% C; 4.95% H; 17.07% N.

EXAMPLE 363

General Procedure (M)

4-[1-(4-tert-Butylcyclohexyl)-3-(3-methyl-5-trifluoromethylphenyl)ureidomethyl]-N-(2H-tetrazol-5-yl)benzamide

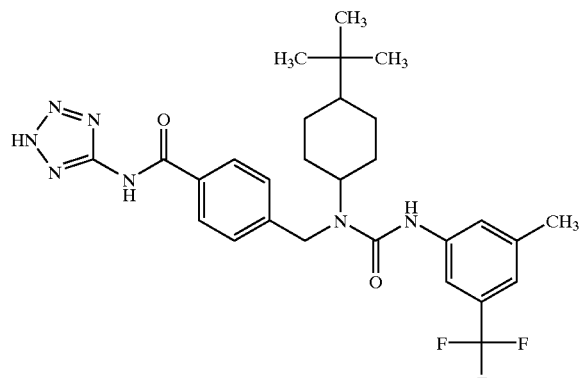

HPLC-MS (method D): m/z: 558, $R_t$=5.44 min.

$^1$H NMR (DMSO-d$_6$): δ 0.83 (9H, s), 0.96 (1H, m), 1.14 (2H, m), 1.44 (2H, m), 1.73 (4H, m), 2.25 (3H, s), 4.04 (1H, m), 4.64 (2H, s), 7.10 (1H, s), 7.40 (2H, d), 7.59 (1H, s), 7.75 (1H, s), 8.03 (2H, d), 8.66 (1H, s), 12.49 (1H, s).

EXAMPLE 364

2-{3-(4-Cyclohexylphenyl)-3-[4-(2H-tetrazol-5-ylcarbamoyl)benzyl]ureido}benzothiazole-6-carboxylic acid

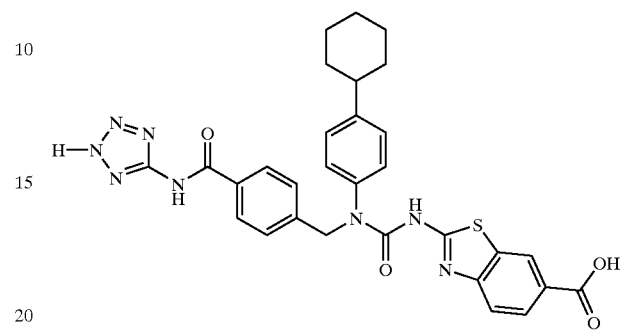

2-{3-(4-Cyclohexylphenyl)-3-[4-(2H-tetrazol-5-ylcarbamoyl)benzyl]ureido}benzothiazole-6-carboxylic acid ethyl ester (16 mg, 0.025 mmol) was dissolved in ethanol (4 mL). Sodium hydroxide (1 mL, 4 N) was added and the reaction mixture was left at room temperature for 16 hours. Hydrochloric acid (4 mL, 1 N) was added, and the resulting precipitate was subsequently collected by filtration to afford the title compound.

HPLC-MS (Method B): $R_t$=6.68 min, m/z=597 (M+1).

EXAMPLE 365

General Procedure (M)

4-[1-(4-Cyclohexylphenyl)-3-(6-methoxybenzothiazol-2-yl)ureidomethyl]-N-(2H-tetrazol-5-yl)benzamide

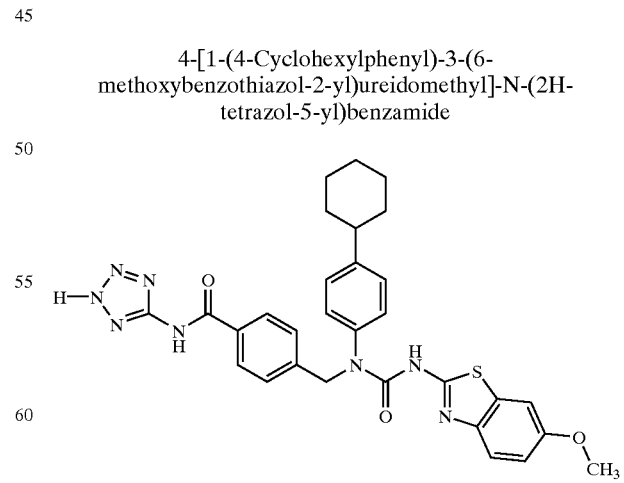

HPLC-MS (Method D): $R_t$=5.53 min., m/z=583 (M+1).

EXAMPLE 366

General Procedure (M)

4-[1-(4-Cyclohexylphenyl)-3-(2,2,4,4-tetrafluoro-4H-benzo[1,3]dioxin-6-yl)ureidomethyl]-N-(2H-tetrazol-5-yl)benzamide

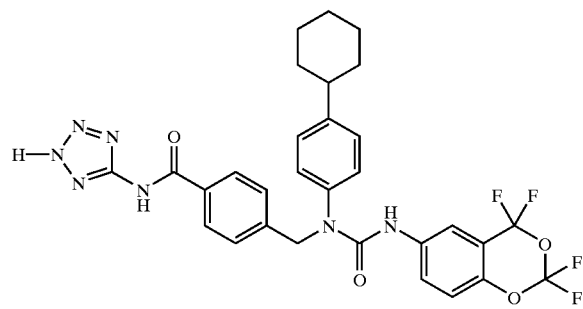

HPLC-MS (Method D): $R_t$=6.17 min, m/z=626 (M+1).

EXAMPLE 367

General Procedure (M)

4-[3-(4-Butoxy-3-methylsulfonylphenyl)-1-(4-tert-butylphenyl)ureidomethyl]-N-(2H-tetrazol-5-yl)benzamide

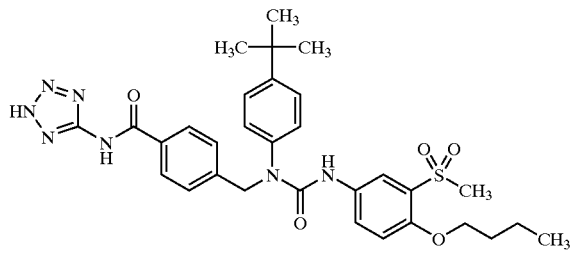

4-Butoxy-3-methylsulfonylaniline was prepared from 4-methoxy-3-methylsulfonylaniline as described in Gitis, Malinovskii, Prokhoda & Sribnaya J. Gen. Chem.USSR (Engl. Transl.) 1960 (30), 3045–7, and the corresponding isocyanate was prepared using the triphosgene method described in example 240.

$^1$H NMR (DMSO-d$_6$): δ 4.11 (2H, t), 4.96 (2H, s), 7.18 (3H, m), 7.37 (5H, m), 7.9 (3H, m), 8.45 (1H, s).

HPLC-MS (Method B): m/z=620 (M+1), $R_t$=6.97 min.

EXAMPLE 368

General Procedure (M)

4-[3-(4-Butoxy-3-methylsulfonylphenyl)-1-(4-cyclohexylphenyl)ureidomethyl]-N-(2H-tetrazol-5-yl)benzamide

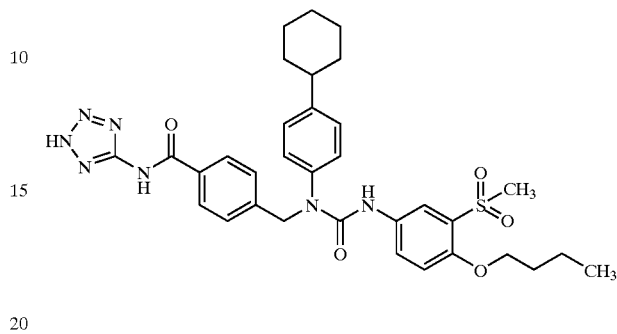

$^1$H NMR (DMSO-d$_6$): δ 0.94 (3H, t), 1.3–1.55 (8H, m), 1.7–1.8 (8H, m), 3.22 (3H, s), 4.10 (2H, t), 4.98 (2H, s), 7.2–7.3 (5H, m), 7.46 (2H, d), 7.78 (1H, dd), 7.93 (1H, d), 8.05 (2H, d), 8.45 (1H, s), 12.4 (1H, s).

HPLC-MS (Method B): m/z=646 (M+1), $R_t$=7.70 min.

EXAMPLE 369

General Procedure (M)

4-[1-(4-Cyclohexylphenyl)-3-(3-methylsulfonylmethylphenyl)ureidomethyl]-N-(2H-tetrazol-5-yl)benzamide

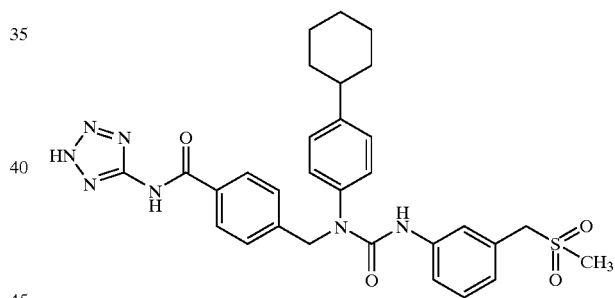

3-Methylsulfonylmethylphenyl isocyanate was prepared as follows:

m-Nitrobenzyl chloride (4.21 g, 24.5 mmol) was dissolved in DMF (40 mL) and added sodium methanesulfinate (3.00 g, 29.4 mmol) and the resulting mixture was stirred at room temperature for 16 hours. After evaporation of the solvent in vacuo the residue was partitioned between water (100 mL) and ethyl acetate (100 mL). The aqueous phase was extracted with ethyl acetate (100 mL) and the combined organic phases were dried (MgSO$_4$) and evaporated in vacuo to afford 4.45 g (84%) 1-methylsulfonylmethyl-3-nitrobenzene.

$^1$H NMR (CDCl$_3$): δ 2.92 (3H, s), 4.39 (2H), 7.65 (1H, t), 7.80 (1H, d), 8.29 (2H, m).

1-Methylsulfonylmethyl-3-nitrobenzene (4.70 g, 21.8 mmol) was added ethanol (70 mL) and the mixture was heated to reflux. At reflux the mixture was added SnCl$_2$ dihydrate (24.6 g, 109 mmol) and heating at reflux was continued for 1 hour. After cooling, the mixture was poured into ice/water (200 mL) and neutralised (to pH 7) with 1 N sodium hydroxide. The mixture was filtered through celite, and the filter cake was washed with ethyl acetate. The phases from the combined filtrate and washings were separated, and the aqueous phase was extracted with ethyl acetate (2×150 mL). The combined organic phases were dried (MgSO$_4$) and evaporated in vacuo to afford 2.23 g (55%) 3-(methylsulfonylmethyl)aniline.

$^1$H NMR (DMSO-d$_6$): δ 2.77 (3H, s), 3.76 (2H, bs), 4.15 (2H, s), 6.75 (3H, m), 7.18 (1H, t).

The corresponding isocyanate was prepared using the triphosgene method described in example 240.

$^1$H NMR (DMSO-d$_6$): δ 1.2–1.4 (6H, m, 1.7–1.8 (5H, m), 2.91 (3H, s), 4.40 (2H, s), 5.00 (2H, s), 6.99 (1H, d), 7.2–7.3 (5H, m), 7.46 (4H, m), 8.03 (2H, d), 8.32 (1H, s), 12.4 (1H, s).

HPLC-MS (Method B): m/z=588 (M+1), R$_t$=7.48 min.

EXAMPLE 370

General Procedure (M)

4-{1-(4-tert-Butylphenyl)-3-[3-(2-methyl-2H-tetrazol-5-yl)phenyl]ureidomethyl}-N-(2H-5-yl)benzamide

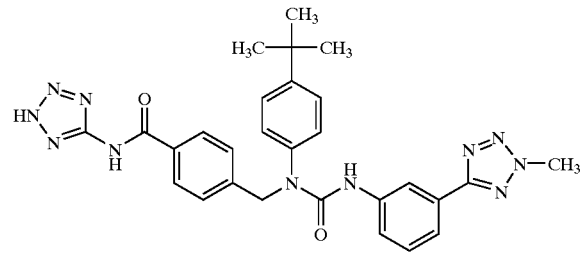

3-(2-Methyl-2H-tetrazol-5-yl)phenyl isocyanate was prepared as follows:

m-Nitrocyanobenzene (10 g, 67.5 mmol) was dissolved in DMF and ammonium chloride (7.2 g, 135 mmol) and sodium azide (8.8 g, 135 mmol) were added and the resulting mixture was stirred at 125° C. for 16 hours. After cooling to room temperature, the mixture was poured into water (1 L), acidified with 1 N hydrochloric acid and filtered immediately. The mother liquor was left for 1 hour and filtered and the solid was washed with water and dried by suction to afford 9.3 g (72%) 5-(3-nitrophenyl)-2H-tetrazole.

$^1$H NMR (DMSO-d$_6$): δ 7.94 (1H, t), 8.43 (1H, ddd), 8.48 (1H, dt), 8.85 (1H, t).

The above 5-(3-nitrophenyl)-2H-tetrazole (6.52 g, 34 mmol) was dissolved in DMF (75 mL) and potassium carbonate (14 g) and iodomethane (2.23 mL, 36 mmol) were added and the resulting mixture was stirred at room temperature for 16 hours. After evaporation in vacuo, the mixture was partitioned between water (150 mL) and ethyl acetate (100 mL). The aqueous phase was extracted with ethyl acetate (100 mL), and the combined organic phases were dried (MgSO$_4$) and evaporated in vacuo. The residue was washed with a mixture of heptane and diethyl ether to afford 7 g (100%) of a mixture of 1- and 2-methyl-5-(3-nitrophenyl)tetrazole. These isomers were separated using column chromatography.

2-Methyl-5-(3-nitrophenyl)-2H-tetrazole (2.12 g, 10 mmol) was added ethanol (50 mL) and heated to reflux. At reflux, the mixture was added SnCl$_2$ dihydrate (11.6 g, 52 mmol) and the mixture was heated at reflux for 2 hours. After cooling, the mixture was poured into ice/water (200 mL) and neutralised (to pH 7) with 1 N sodium hydroxide. The mixture was filtered through celite, and the filter cake was washed with ethyl acetate. For the combined filtrate and washings the phases were separated and the aqueous phase was extracted with ethyl acetate (2×250 mL). The combined organic phases were dried (MgSO$_4$) and evaporated in vacuo to afford 3-(2-methyl-2H-tetrazol-5-yl)aniline.

$^1$H NMR (CDCl$_3$): δ 3.80 (2H, bs), 4.40 (3H, s), 6.79 (1H, ddd), 7.28 (1H, dd), 7.47 (1H, m), 7.51 (1H, dt).

The corresponding isocyanate was prepared using the triphosgene method described in example 240.

HPLC-MS (Method B): m/z=552 (M+1), R$_t$=6.58 min.

EXAMPLE 371

General Procedure (M)

4-{1-(4-Cyclohexylphenyl)-3-[3-(2-methyl-2H-tetrazol-5-yl)phenyl]ureidomethyl}-N-(2H-tetrazol-5-yl))benzamide

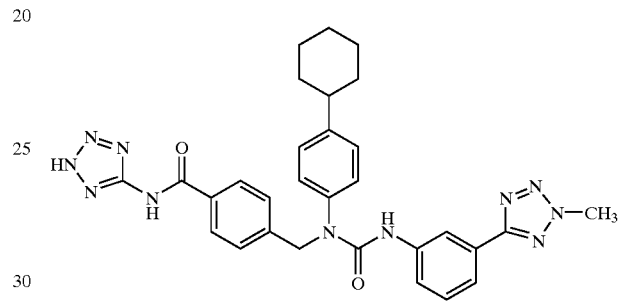

$^1$H NMR (DMSO-d$_6$): δ 1.2–1.4 (6H, m), 1.6–1.8 (5H, m), 4.40 (3H, s), 5.01 (2H, s), 7.22 (4H, m), 7.40 (1H, t), 7.45 (3H, m), 7.65 (2H, d), 8.01 (2H, d), 8.23 (1H, s), 8.52 (1H, s), 12.0 (1H), bs).

HPLC-MS (Method B): m/z=578 (M+1), R$_t$=5.37 min.

EXAMPLE 372

3-{4-[1-(4-Butylphenyl)-3-(4-trifluoromethoxyphenyl)ureidomethyl]benzoylamino}propionic acid

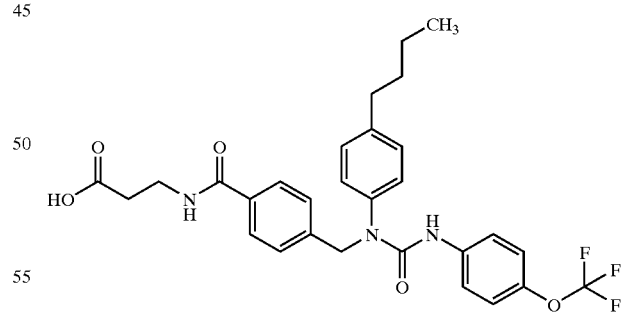

4-Formylbenzoic acid (15 g, 100 mmol) was dissolved in DMF (250 mL) and 1-hydroxybenzotriazole (14.9 g, 110 mmol) and N-(3-dimethylaminopropyl)-N'-ethylcarbodiimide hydrochloride (21.1 g, 110 mmol) were added and the resulting mixture was stirred at room temperature for 30 minutes. Triethylamine (34.8 mL, 250 mmol) and β-alanine methyl ester hydrochloride (15.4 g, 110 mmol) were added and the resulting mixture was stirred at room temperature for 1 hour. More triethylamine (17.4 mL)

and β-alanine methyl ester hydrochloride (7.7 g) were added and the mixture was stirred at room temperature for 16 hours. The mixture was concentrated in vacuo and the residue was partitioned between ethyl acetate (200 mL) and water (200 mL). The organic phase was dried (MgSO$_4$) and concentrated to afford 16.2 g (70%) of 3-(4-formylbenzoylamino)propionic acid methyl ester as an oil.

$^1$H NMR (CDCl$_3$): δ 2.70 (2H, t), 3.69 (3H, s), 3.70 (2H, q), 7.68 (1H, bt), 7.9–8.0 (4H, m), 10.1 (1H, s).

The above propionic acid methyl ester (2.0 g, 8.5 mmol) was dissolved in DMF (20 mL) and triethyl orthoformate (10 mL), glacial acetic acid (1 mL), sodium cyanoborohydride (0.81 g, 12.8 mmol) and 4-butylaniline 1.27 g, 8.5 mmol) were added and the resulting mixture was stirred at room temperature for 16 hours. The mixture was concentrated in vacuo and the residue was dissolved in ethyl acetate (100 mL) and washed with saturated aqueous sodium chloride (3×100 mL). The organic phase was dried (MgSO$_4$) and concentrated in vacuo. The residue was purified by column chromatography on silica gel eluting with a mixture of ethyl acetate and heptane (3:1) to afford 1.54 g (49%) of 3-{4-[(4-butylphenylamino)methyl]-benzoylamino}propionic acid methyl ester as an oil.

$^1$H NMR (CDCl$_3$): δ 0.92 (3H, t), 1.33 (2H, m), 1.54 (2H, pentet), 2.50 (2H, t), 2.67 (2H, t), 3.72 (5H, m), 4.38 (2H, s), 6.83 (1H, bt), 6.98 (2H, d), 7.43 (2H, d), 7.74 (2H, d).

The above propionic acid methyl ester (0.5 g, 1.4 mmol) was dissolved in acetonitrile (10 mL) and added N,N-diisopropylethylamine (232 μL, 1.4 mmol) and 4-(trifluoromethoxy)phenylisocyanate (308 μL, 2.0 mmol) and the resulting mixture was stirred at room temperature for 16 hours. More 4-(trifluoromethoxy)phenylisocyanate (308 μL, 2.0 mmol) was added and the mixture was stirred at room temperature for 16 hours. The reaction mixture was concentrated in vacuo. The residue was dissolved in ethyl acetate (50 mL) and washed with water (3×50 mL), dried (MgSO$_4$) and concentrated in vacuo. The residue was purified by column chromatography on silica gel eluting with a mixture of ethyl acetate and heptane (1:1) containing 1% glacial acetic acid. This afforded 0.53 g (69%) of 3-{4-[1-(4-butylphenyl)-3-(4-trifluoromethoxyphenyl)ureidomethyl]benzoylamino}propionic acid methyl ester as an oil.

$^1$H NMR (DMSO-d$_6$): δ 0.98 (3H, t), 1.30 (2H, m), 1.55 (2H, quintet), 2.60 (4H, m), 3.48 (2H, q), 3.61 (3H, s), 4.95 (2H, s), 7.15 (4H, m), 7.22 (2H, d), 7.33 (2H, d), 7.54 (2H, d), 7.75 (2H, d), 8.30 (1H, s), 8.49 (1H, t).

HPLC-MS (Method B): R$_t$=8.00 min, m/z=572 (M+1).

The above propionic acid methyl ester (0.53 g, 0.93 mmol) was dissolved in 1,4-dioxane (50 mL). 4N aqueous sodium hydroxide (6 mL) was added and the resulting mixture was stirred at room temperature for 4 hours. Glacial acetic acid (10 mL) was added and the mixture was concentrated in vacuo. The residue was dissolved in ethyl acetate (30 mL) and washed with water (30 mL). The aqueous phase was extracted with ethyl acetate (2×30 mL), and the combined organic extracts were dried (MgSO$_4$) and concentrated to afford 0.49 g (95%) of the title compound as an oil.

$^1$H NMR (CDCl$_3$): δ 0.94 (3H, t), 1.37 (2H, m), 1.62 (2H, quintet), 2.64 (2H, t), 2.71 (2H, t), 3.73 (5H, m), 4.94 (2H, s), 6.29 (1H, s), 6.87 (1H, t), 7.04 (2H, d), 7.09 (2H, d), 7.21 (2H, d), 7.29 (2H, d), 7.34 (2H, d), 7.68 (2H, d).

EXAMPLE 373

3-{4-[1-(4-tert-Butylphenyl)-3-(4-trifluoromethoxyphenyl)ureidomethyl]benzoylamino}propionic acid

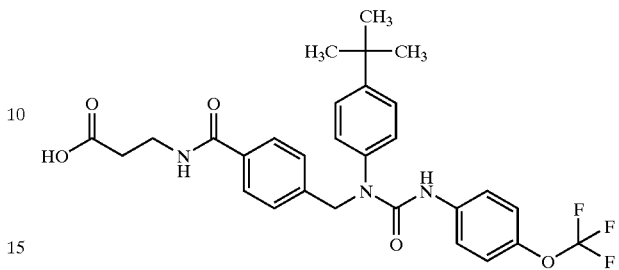

The above 3-(4-formylbenzoylamino)propionic acid methyl ester (2.0 g, 8.5 mmol) was dissolved in DMF (20 mL). Triethyl orthoformate (10 mL), glacial acetic acid (1 mL), sodium cyanoborohydride (0.81 g, 12.8 mmol) and 4-tert-butylaniline 1.27 g, 8.5 mmol) were added and the resulting mixture was stirred at room temperature for 16 hours. The mixture was added saturated aqueous sodium chloride (100 mL) and the mixture was extracted with ethyl acetate (3×100 mL). The combined organic extracts were washed with saturated aqueous sodium chloride (3×100 mL). The organic phase was dried (MgSO$_4$) and concentrated in vacuo. The residue was purified by column chromatography on silica gel eluting with a mixture of ethyl acetate and heptane (1:1) to afford 0.87 g (30%) of 3-{4-[(4-tert-butylphenylamino)methyl]benzoylamino}propionic acid methyl ester as an oil.

$^1$H NMR (CDCl$_3$): δ 1.28 (9H, s), 2.67 (2H, t), 3.73 (5H, m), 4.04 (1H, s), 4.38 (2H, s), 6.57 (2H, d, 6.83 (2H, d), 7.19 (2H, d), 7.44 (2H, d), 7.73 (2H, d).

HPLC-MS (Method B): R$_t$=6.63 min, m/z=369 (M+1).

The above propionic acid methyl ester (0.82 g, 2.2 mmol) was dissolved in acetonitrile (15 mL) and added N,N-diisopropylethylamine (378 μL, 2.2 mmol) and 4-(trifluoromethoxy)-phenylisocyanate (500 μL, 3.3 mmol). The resulting mixture was stirred at room temperature for 5 hours and at reflux for 16 hours. The cooled reaction mixture was concentrated in vacuo and the residue was dissolved in ethyl acetate (50 mL) and washed with water (2×50 mL), dried (MgSO$_4$) and concentrated in vacuo. The residue was crystallised from a mixture of ethyl acetate and heptane (1:1) containing 1% glacial acetic acid to afford 0.40 g (32%) of 3-{4-[1-(4-tert-butylphenyl)-3-(4-trifluoromethoxyphenyl)ureidomethyl]benzoylamino}propionic acid methyl ester as a solid.

$^1$H NMR (CDCl$_3$): δ 1.34 (9H, s), 2.67 (2H, t), 3.72 (5H, m), 4.94 (2H, s), 6.30 (1H, s), 6.80 (1H, t), 7.1 (4H, m), 7.3–7.4 (4H, m), 7.43 (2H, d), 7.70 (2H, d).

The above propionic acid methyl ester (0.25 g, 0.44 mmol) was dissolved in 1,4-dioxane (25 mL). 4N aqueous sodium hydroxide (6 mL) was added and the mixture was stirred at room temperature for 16 hours. 36% aqueous hydrochloric acid (10 mL) was added and the mixture was extracted with ethyl acetate (3×50 mL). The combined organic extracts were dried (MgSO$_4$) and concentrated in vacuo. The residue was crystallised from a mixture of diethyl ether and heptane to afford 0.10 g (42%) of the title compound as a solid.

$^1$H NMR (CDCl$_3$): δ 1.33 (9H, s), 2.70 (2H, t), 3.71 (2H, q), 4.95 (2H, s), 6.32 (1H, s), 6.88 (1H, t), 7.1 (4H, m), 7.28 (2H, d), 7.35 (2H, d), 7.43 (2H, d), 7.68 (2H, d).

EXAMPLE 374

4-[1-(4-tert-Butylphenyl)-3-(4-trifluoromethoxyphenyl)ureidomethyl]-N-(2H-tetrazol-5-yl)benzamide

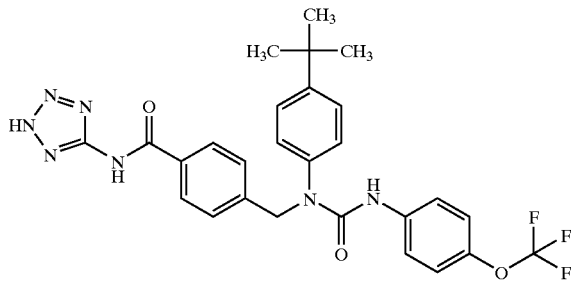

4-Formylbenzoic acid methyl ester (10.6 g, 64 mmol) was dissolved in methanol (200 mL). 4-tert-Butylaniline (9.61 g, 64 mmol) was added and the resulting suspension was refluxed for 15 minutes. After cooling to room temperature, TFA (5.18 mL, 68 mmol) was added followed by portion wise addition of sodium cyanoborohydride (3.26 g, 52 mmol). The resulting mixture was stirred at room temperature for 2 hours and concentrated in vacuo. The residue was partitioned between ethyl acetate (200 mL) and 1N aqueous sodium hydroxide (150 and 100 mL). The organic phase was dried (MgSO$_4$) and evaporated in vacuo to afford 19.0 g (99%) of 4-[(4-tert-butylphenylamino)methyl]benzoic acid methyl ester as a solid.

$^1$H NMR (CDCl$_3$): δ 1.28 (9H, s), 3.92 (3H, s), 4.39 (2H, s), 6.57 (2H, d), 7.20 (2H, d), 7.44 (2H, d), 8.00 (2H, d).

The above benzoic acid methyl ester (0.73 g, 2.44 mmol) was dissolved in acetonitrile (7 mL) and 4-trifluoromethoxyphenylisocyanate (405 μL, 2.68 mmol) was added. The resulting mixture was stirred at room temperature for 3 hours and then refluxed for 1.5 hour. After cooling and concentration in vacuo, the residue was purified by column chromatography on silica gel, eluting first with a mixture of ethyl acetate and heptane (1:6), then with a mixture of ethyl acetate and heptane (1:3) to afford 1.14 g (94%) of 4-[1-(4-tert-butylphenyl)-3-(4-trifluoromethoxyphenyl)ureidomethyl]benzoic acid methyl ester as an oil.

$^1$H NMR (CDCl$_3$): δ 1.35 (9H, s), 3.91 (3H, s), 4.97 (2H, s), 6.30 (1H, s), 7.1 (4H, m), 7.32–7.43 (6H, m), 7.96 (2H, d).

TLC: Rf=0.11 (SiO$_2$; ethyl acetate/heptane (1:6)).

HPLC-MS (Method B): R$_t$=9.05 min, m/z=501 (M+1).

The above ureidomethyl-benzoic acid methyl ester (1.14 g, 2.28 mmol) was dissolved in 1,4-dioxane (25 mL) and added 1N aqueous sodium hydroxide (5 mL). The resulting mixture was stirred at room temperature for 1 hour. Ethanol (15 mL) and 1N aqueous sodium hydroxide (5 mL) were added and the resulting mixture was stirred at room temperature for 16 hours. The mixture was concentrated in vacuo and partitioned between 1N hydrochloric acid (100 mL) and ethyl acetate (2×50 mL). The combined organic phases were dried (MgSO$_4$) and concentrated in vacuo to afford 847 mg (76%) of 4-[1-(4-tert-butylphenyl)-3-(4-trifluoromethoxyphenyl)ureidomethyl]benzoic acid as a solid.

$^1$H NMR (CDCl$_3$): δ 1.33 (9H, s), 3.91 (3H, s), 4.97 (2H, s), 6.30 (1H, s), 7.1 (4H, m), 7.33 (2H, d), 7.43 (4H, m), 8.03 (2H, d).

HPLC-MS (Method B): R$_t$=8.25 min, m/z=487 (M+1).

The above ureidomethyl-benzoic acid (508 mg, 1.04 mmol) was dissolved in dichloromethane (20 mL) and N,N-diisopropylethylamine (546 μL, 3.13 mmol) and 2-(1H-benzotriazole-1-yl)-1,1,3,3-tetramethyluronium hexafluorophosphate (321 mg, 1.15 mmol) were added. The resulting mixture was stirred at room temperature for 30 minutes. 5-Aminotetrazole hydrate (118 mg, 1.15 mmol) was added and the resulting mixture was stirred at room temperature for 16 hours. The mixture was partitioned between water (200 mL) and ethyl acetate (2×100 mL). The combined organic phases were dried and concentrated in vacuo. The residue was purified by column chromatography on silica gel eluting with a mixture of ethyl acetate and heptane (1:1), containing 1% acetic acid. This afforded 194 mg (34%) of the title compound as a solid.

$^1$H NMR (CDCl$_3$): δ 1.33 (9H, s), 3.91 (3H, s), 5.01 (2H, s), 6.35 (1H, s), 7.10 (2H, d), 7.14 (2H, d), 7.36 (2H, d), 7.45 (2H, d), 7.58 (2H, d), 8.22 (2H, d), 12.3 (1H, s).

HPLC-MS (Method B): R$_t$=7.95 min, m/z=554 (M+1).

EXAMPLE 375

4-[3-(3,5-Bis(trifluoromethyl)phenyl)-1-(trans-4-tert-butylcyclohexyl)ureidomethyl]-N-(2H-tetrazol-5-yl)benzamide

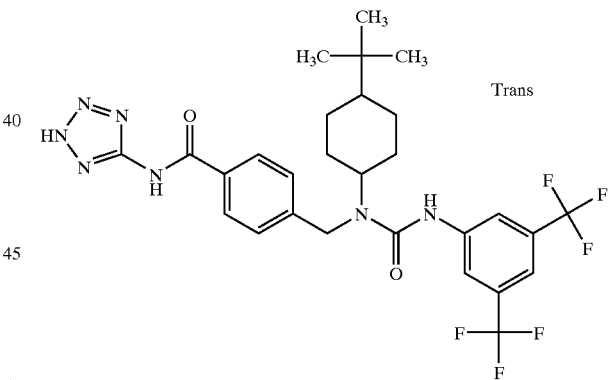

This compound was prepared similarly as described in example 374 starting from trans-4-[(4-tert-butylcyclohexylamino)methylbenzoic acid methyl ester (prepared as described in general procedure (K), step 1) followed by reaction with 3,5-bis(trifluoromethyl)phenyl isocyanate, hydrolysis and coupling with 5-aminotetrazole.

HPLC-MS (method B): m/z: 612. R$_t$=8.38 min.

$^1$H NMR (DMSO$_6$): δ 0.83 (9H, s), 0.96 (1H, m), 1.14 (2H, m), 1.44 (2H, m), 1.73 (4H, m), 4.09 (1H, m), 4.68 (2H, s), 7.45 (2H, d), 7.63 (1H, s), 8.07 (2H, d), 8.29 (2H, s), 9.08 (1H, s), 12.49 (1H, s).

EXAMPLE 376

4-[1-(trans-4-tert-Butylcyclohexyl)-3-(4-trifluoromethoxyphenyl)ureidomethyl]-N-(2-hydroxycarbamoylethyl)benzamide

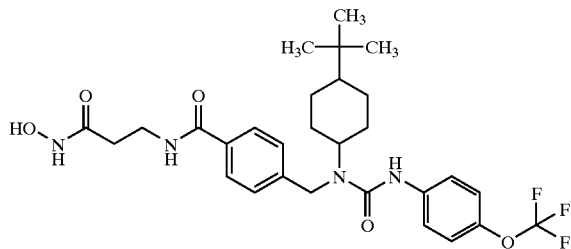

3-{4-[1-(4-tert-Butylcyclohexyl)-3-(4-trifluoromethoxyphenyl)ureidomethyl]benzoylamino}propionic acid (prepared as described in example 92; 0.2 g, 0.36 mmol) was dissolved in DMF (5 mL.) and 1-hydroxybenzotriazole (53 mg, 0.39 mmol) and N-(3-dimethylaminopropyl)-N'-ethylcarbodiimide hydrochloride (75 mg, 0.39 mmol) were added and the resulting mixture was stirred at room temperature for 30 minutes. The mixture was cooled to 0° C. and N,N-diisopropylethylamine (85 μL, 0.50 mmol) and O-(trimethylsilyl)hydroxylamine (60 μL, 0.50 mmol) were added and the mixture was stirred at room temperature for 16 hours. The mixture was concentrated in vacuo and the residue was dissolved in ethyl acetate (50 mL) and was washed with a saturated aqueous solution of sodium chloride (50 mL). The aqueous phase was extracted with ethyl acetate (2×50 mL) and the combined organic extracts were dried (MgSO$_4$) and concentrated in vacuo. The residue was purified by column chromatography on silica gel eluting with a mixture of ethyl acetate and glacial acetic acid (9:1) This afforded 95 mg (46%) of the title compound as a solid.

HPLC-MS (Method B): R$_t$=7.32 min, m/z=579 (M+1).

EXAMPLE 377

4-[1-(trans-4-tert-Butylcyclohexyl)-3-(4-trifluoromethoxyphenyl)ureidomethyl]-N-hydroxycarbamomethyl-benzamide

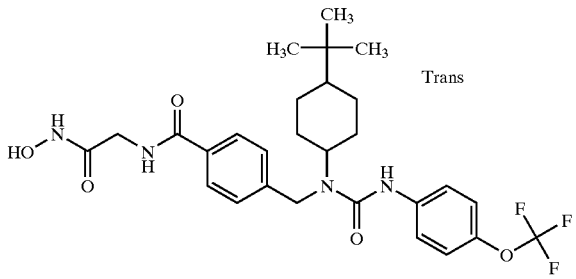

This compound was prepared from 3-{4-[1-(trans-4-tert-butylcyclohexyl)-3-(4-trifluoromethoxyphenyl)ureidomethyl]benzoylamino}acetic acid (example 95), by coupling this compound with O-trimethylsilylhydroxylamine using standard peptide coupling conditions as described in the art.

$^1$H NMR (DMSO-d$_6$): δ 10.60 (1H, s), 8.78 (1H, s), 8.65 (1H, t), 8.52 (1H, s), 7.80 (2H, d), 7.55 82H, d), 7.34 (2H, d), 7.23 (2H, d), 4.60 (2H, broad), 4.05 (1H, m), 3.75 (2H, d), 1.80–0.85 (10H, m), 0.80 (9H, s).

Micro analysis. Calculated for C$_{28}$H$_{35}$F$_3$N$_4$O$_5$, 0.75H$_2$O: C, 58.17%; H, 6.36%; N, 9.69%. Found: C, 58.29%; H, 6.28%; N, 9.97%.

EXAMPLE 378

4-[3-(2-Butyl-1,3-dioxo-2,3-dihydro-1H-isoindol-5-yl)-1-(4-tert-butylphenyl)ureidomethyl]-N-(2H-tetrazol-5-yl)benzamide

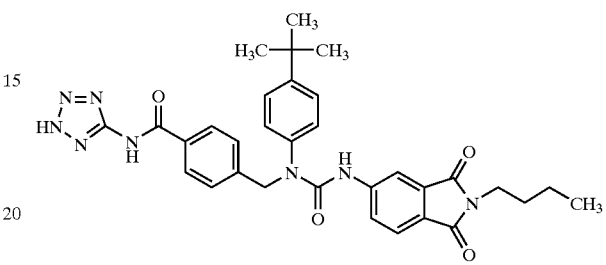

To a solution of 4-nitrophthalimide (7.20 g, 37.5 mmol) and n-bromobutane (25.5 g; 186 mmol) in DMF (50 mL) was added potassium carbonate (10.0 g; 72.5 mmol) and the resulting mixture was heated to 100° C. for 16 hours. The reaction mixture was cooled to room temperature and partitioned between water (200 mL) and ethyl acetate (200 mL). The organic layer was separated, washed once with brine and dried with anhydrous Na$_2$SO$_4$. The solvent was removed in vacuo by rotary evaporation to leave N-butyl-4-nitrophthalimide as an oil, which crystallised upon standing. Yield: 9.37 g (100%).

$^1$H NMR (DMSO-d$_6$): δ 0.91 (t, 3H); 1.31 (m, 2H); 1.60 (m, 2H); 3.62 (t, 2H); 8.11 (d, 1H); 8.47 (d, 1H); 8.61 (dd, 1H).

A solution of N-butyl-4-nitrophthalimide (1.45 g, 5.8 mmol) in methanol (30 mL) was added drop wise to a well stirred solution of sodium dithionite (6.50 g, 37.1 mmol) and sodium carbonate (3.22 g, 30.5 mmol) in water (40 mL), while the temperature was maintained at 70° C. After addition, heating at 70° C. was continued for a further 30 minutes, then the reaction mixture was allowed to cool to room temperature. The reaction volume was reduced to one third by rotary evaporation, and the residual water solution was extracted with diethyl ether (2×50 mL). The combined organic phases were dried with anhydrous Na$_2$SO$_4$, and then taken to dryness. The residual oil was recrystallised from ethanol/water to give 750 mg (59%) of N-butyl-4-aminophthalimide.

$^1$H NMR (DMSO-d$_6$): δ 0.89 (t, 3H); 1.26 (m, 2H); 1.53 (m, 2H); 3.48 (t, 2H); 6.44 (bs, 2H); 6.78 (dd, 1H); 6.92 (d, 1H); 7.46 (d, 1H).

N-Butyl-4-aminophthalimide (100 mg, 0.46 mmol) was suspended in toluene (2 mL), and bis(trichloromethyl) carbonate (50 mg, 0.17 mmol) was added. The mixture was heated to reflux for 1 hour, then cooled and taken to dryness by rotary evaporation. The solid residue was re-dissolved in DMF (2 mL). 4-[(4-tert-Butylphenylamino)methyl]-N-2H-tetrazol-5-yl)benzamide (161 mg, 0.46 mmol) was added and the mixture heated to 100° C. for 2 hours. After cooling to room temperature, water (3 mL) was added and the precipitated gum collected by filtration. Recrystallisation from acetonitrile afforded the title compound as a white powder. Yield: 20 mg (30%).

¹H NMR (DMSO-d₆): δ 0.88 (t, 3H); 1.25 (m, 2H); 1.28 (s, 9H); 1.55 (m, 2H); 3.54 (t, 2H); 5.03 (s, 2H); 7.25 (d, 2H); 7.42 (d, 2H); 7.48 (d, 2H); 7.72 (d, 1H); 7.80 (d, 1H); 8.02 (s, 1H); 8.04 (d, 2H); 8.95 (s, 1H); 12.26 (bs, 1H).

HPLC-MS (method B): 595.4 (M+1). $R_t$=7.68 min.

EXAMPLE 379

4-{1-(4-Cyclohexylphenyl)-3-[1-(5-methoxynaphthalen-2-yl)ethyl]ureidomethyl}-N-(2H-tetrazol-5-yl)benzamide

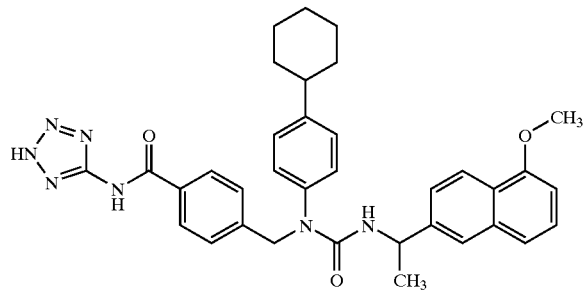

The isocyanate was prepared in situ via a Curtius rearrangement of the corresponding carboxylic acid:

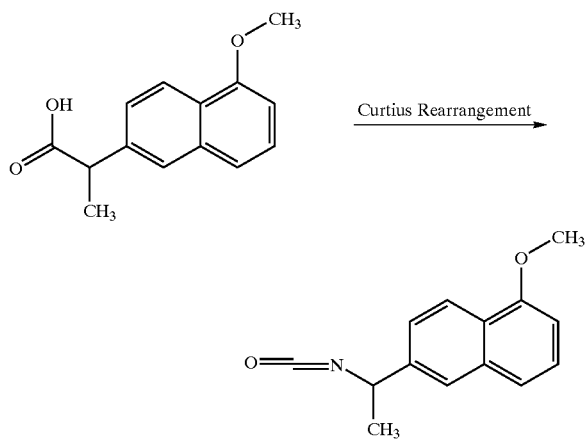

2-(5-Methoxynaphthalen-2-yl)propionic acid (0.26 g, 1.12 mmol) was dissolved in toluene (10 mL). Triethylamine (0.52 mL) was added followed by diphenylphosphoryl azide (0.40 mL, 1.86 mmol). The mixture was stirred for 2 hours at 25° C. and 4-[(4-cyclohexylphenylamino)methyl]-N-(2H-tetrazol-5-yl)benzamide (0.14 g, 0.37 mmol) was added. Stirring was continued at 25° C. for 16 hours then at 100° C. overnight. The solvent was removed in vacuo and the residue was purified by column chromatography on silica gel using a mixture of heptane and ethylacetate (1:1) as eluent to afford the title compound.

¹H NMR (DMSO-d₆): δ 12.40 (s, 1H); 8.05 (d, 2H); 7.72 (d, 2H); 7.62 (s, 1H); 7.45–7.35 (m, 3H); 7.28 (s, 1H); 7.25–7.10 (m, 5H); 5.05 (m, 1H); 4.93 (d, 2H); 3.86 (s, 3H); 1.75–1.65 (m, 4H); 1.50–1.15 (m, 9H).

HPLC-MS (Method B): m/z=604 (M+1). $R_t$=8.08 min.

EXAMPLE 380

4-[N-(trans-4-tert-Butylcyclohexyl)-N'-(4-trifluoromethoxybenzoyl)hydrazinomethyl]-N-(2H-tetrazol-5-yl)benzamide

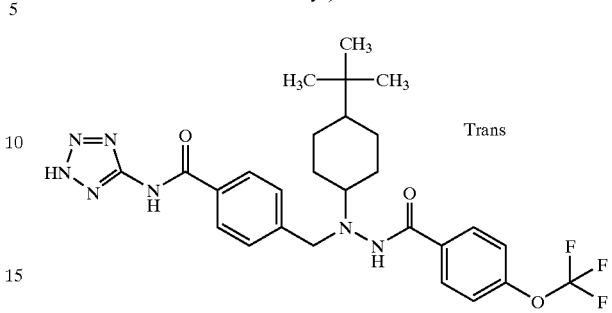

Trans-4-trifluoromethoxybenzoic acid N'-(4-tert-butylcyclohexyl)hydrazide (350 mg, 1.0 mmol) and methyl 4-(bromomethyl)benzoate (220 mg, 1.0 mmol) were dissolved in DMF (5.0 mL). Sodium hydrogen carbonate (300 mg) was added, and the mixture was stirred for 16 hours under a nitrogen atmosphere at ambient temperature. Water (30 mL) was added and the mixture was extracted with diethyl ether (2×25 mL). The combined organic phases were dried with Na₂SO₄ and evaporated in vacuo to afford methyl 4-[N-(4-tert-butylcyclohexyl)-N'-(4-trifluoromethoxybenzoyl)hydrazinomethylbenzoate as white crystals. Yield: 430 mg (85%).

¹H NMR (DMSO-d₆): δ 0.82 (s, 9H); 0.95 (m, 3H); 1.23 (m, 2H); 1.78 (m, 2H); 2.06 (m, 2H); 3.82 (s, 3H); 4.14 (s, 2H); 7.38 (d, 2H); 7.54 (d, 2H); 7.71 (d, 2H); 7.85 (d, 2H); 9.24 (s, 1H).

Methyl 4-[N-(4-tert-butylcyclohexyl)-N'-(4-trifluoromethoxybenzoyl)hydrazinomethylbenzoate (400 mg, 0.78 mmol) was dissolved in methanol (40 mL) by gentle heating. After cooling to room temperature, aqueous sodium hydroxide (4 mL; 4N) was added. The mixture was heated to reflux for 2 hours, then allowed to cool to ambient temperature. Acetic acid (3.0 mL) was added before the solvent was removed in vacuo. Water (30 mL) was added to the residue, and insoluble material was collected by filtration. Recrystallisation from acetonitrile afforded 4-[N-(4-tert-butylcyclohexyl)-N'-(4-trifluoromethoxy-benzoyl)hydrazinomethylbenzoic acid. Yield: 320 mg (83%).

¹H NMR (DMSO-d₆): δ 0.82 (s, 9H); 0.96 (m, 3H); 1.24 (m, 2H); 1.78 (m, 2H); 2.05 (m, 2H); 2.85 (t, 1H); 4.13 (s, 2H); 7.38 (d, 2H); 7.50 (d, 2H); 7.72 (d, 2H); 7.82 (d, 2H); 9.26 (s, 1H).

HPLC-MS (method B): 493.2 (M+1). $R_t$=7.92 min.

4-[N-(4-tert-Butylcyclohexyl)-N'-(4-trifluoromethoxybenzoyl)hydrazinomethylbenzoic acid (264 mg; 0.54 mmol), N-hydroxybenzotriazole monohydrate (82 mg, 0.54 mmol) and N-ethyl-N'-3-dimethylaminopropylcarbodiimide hydrochloride (105 mg, 0.54 mmol) were dissolved in DMF (4.0 mL). The mixture was stirred at room temperature for 30 minutes, and then 5-aminotetrazole monohydrate (100 mg; 0.96 mmol) was added. The reaction mixture was then left stirring at ambient temperature for 48 hours. The mixture was poured in water (40 mL), and the precipitated material collected by filtration. After several washes with water, the material was dried in vacuo to afford the title compound as a white powder. Yield: 257.2 mg; (86%).

¹H NMR (DMSO-d₆): δ 0.82 (s, 9H); 0.98 (m, 3H); 1.25 (m, 2H); 1.80 (m, 2H); 2.07 (m, 2H); 4.16 (s, 2H); 7.38 (d,

2H); 7.59 (d, 2H); 7.73 (d, 2H); 8.02 (d, 2H); 9.26 (s, 1H); 12.27 (bs, 1H).

HPLC-MS (method B): 560.4 (M+1). $R_t$=7.77 min.

EXAMPLE 381

3-{4-[1-(1-Cyclopropanecarbonylpiperidin-4-yl)-3-(4-trifluoromethoxyphenyl)ureidomethyl]benzoylamino}propionic acid

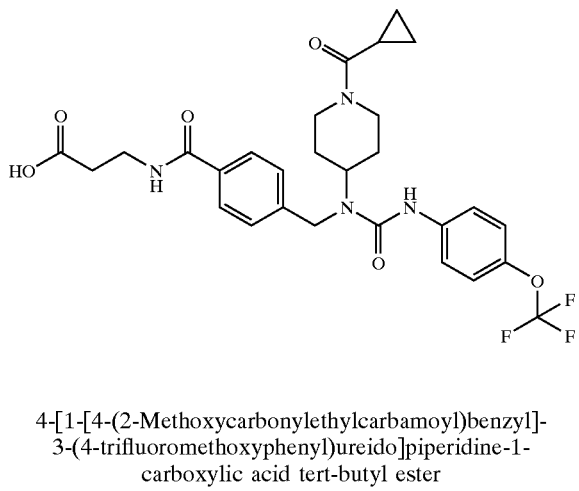

4-[1-[4-(2-Methoxycarbonylethylcarbamoyl)benzyl]-3-(4-trifluoromethoxyphenyl)ureido]piperidine-1-carboxylic acid tert-butyl ester 4-[1-[4-(2-Methoxycarbonylethylcarbamoyl)benzyl]-3-(4-trifluoromethoxyphenyl)ureido]piperidine-1-carboxylic acid tert-butyl ester was prepared in analogy with previously described methods (reductive amination using 4-aminopiperidine-1-carboxylic acid tert-butyl ester).

3-{4-[1-Piperidin-4-yl-3-(4-trifluoromethoxyphenyl)ureidomethyl]benzoylamino}propionic acid methyl ester hydrochloride The Boc-protecting group was removed by adding 20 mL HCl in ethyl acetate (2M) to a suspension of 4-[1-[4-(2-methoxycarbonylethylcarbamoyl)benzyl]-3-(4-trifluoromethoxyphenyl)ureido]piperidine-1-carboxylic acid tert-butyl ester (2.60 g) in 25 mL ethyl acetate. Stirring overnight at 25° C. followed by evaporation of the solvent afforded the desired compound.

3-{4-[1-(1-Cyclopropanecarbonylpiperidin-4-yl)-3-(4-trifluoromethoxyphenyl)ureidomethyl]benzoylamino}propionic acid methyl ester To a solution of 3-{4-[1-piperidin-4-yl-3-(4-trifluoromethoxyphenyl)ureidomethyl]benzoylamino}propionic acid methyl ester hydrochloride (0.20 g) in DMF (5 mL) was added diisopropylethylamine (0.30 mL) and cyclopropylcarboxylic acid chloride (0.16 mL). The mixture was stirred at 25° C. overnight. Water (100 mL) and ethyl acetate (100 mL) were added, the phases separated and the organic phase was washed with a solution of NH$_4$Cl (sat., 2×50 mL) and water (50 mL). Upon drying with MgSO$_4$ the solvent was evaporated and the residue purified by column chromatography.

3-{4-[1-(1-Cyclopropanecarbonylpiperidin-4-yl)-3-(4-trifluoromethoxyphenyl)ureidomethyl]benzoylamino}propionic acid The above 3-{4-[1-(1-cyclopropanecarbonylpiperidin-4-yl)-3-(4-trifluoromethoxyphenyl)ureidomethyl]benzoylamino}propionic acid methyl ester (0.17 g, 0.28 mmol) was dissolved in 10 mL ethanol and hydrolysed by adding lithium hydroxide (14 mg, 0.56 mmol) dissolved in water (1 mL). The mixture was stirred at 50° C. for 2 hours. The solvent was evaporated and water (25 mL) was added to the mixture followed by HCl (1 N) adjusting pH to 3–4 allowing the title compound to be isolated as a precipitate.

$^1$H NMR (300 MHz, DMSO-d$_6$): δ 12.22 (s br, 1H); 8.60 (s, 1H); 8.45 (t, 1H); 7.75 (d, 2H); 7.55 (d, 2H); 7.32 (d, 2H); 7.22 (d, 2H); 4.62 (s, 2H); 4.50–4.30 (m, 3H); 3.45 (q, 2H); 3.05 (t br, 1H); 2.50 (t, 2H); 1.95 (m, 1H); 1.70–1.40 (m, 4H); 0.70 (m, 4H).

HPLC-MS (method B): m/z=577, $R_t$=5.40 min.

EXAMPLE 382

3-{4-[1-(4-Diethylcarbamoylcyclohexyl)-3-(4-trifluoromethoxyphenyl)ureidomethyl]benzoylamino}propionic acid

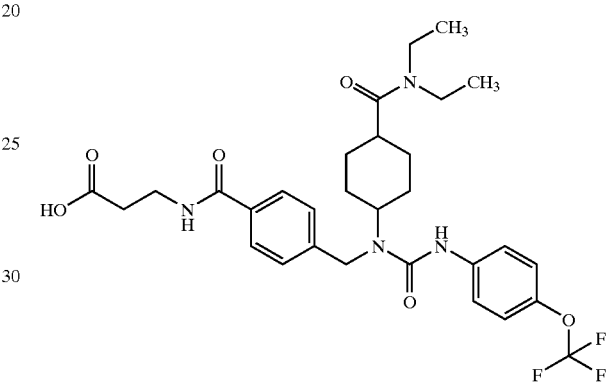

4-[(4-Carboxycyclohexylamino)methyl]benzoic acid methyl ester

Methyl 4-formylbenzoate (5 g, 30 mmol) was dissolved in DMF (60 mL) and 4-aminocyclohexylcarboxylic acid (4.36 g, 30 mmol) and NaBH$_4$ (1.1 g, 30 mmol) were added. The mixture was stirred at 70° C. overnight. Trimethylorthoformate (10 mL) was added and the mixture was stirred at 100° C. overnight. Toluene was added and the mixture was heated to 135° C. and stirred overnight. The solvent was evaporated leaving a DMF solution to which HCl (1N, 30 mL) was added causing precipitation. The desired product was collected by filtration.

4-[1-(4-Carboxycyclohexyl)-3-(4-trifluoromethoxyphenyl)ureidomethyl]benzoic acid methyl ester The above 4-[(4-carboxycyclohexylamino)methyl]benzoic acid methyl ester (1 g, 3.4 mmol) was dissolved in acetonitrile (25 mL) and 4-trifluoromethoxyphenylisocyanate (0.73 g, 3.4 mmol) was added. Stirring overnight at 50° C. followed by cooling to 25° C. formed a precipitate, which was removed by filtration. The filtrate was concentrated in vacuo and the product purified by chromatography using silica as stationary phase and a mixture of ethyl acetate, methanol and acetic acid as eluent (15:1:0.1).

4-[1-(4-Diethylcarbamoylcyclohexyl)-3-(4-trifluoromethoxylphenyl)ureidomethyl]benzoic acid methyl ester To the above 4-[1-(4-carboxylcyclohexyl)-3-(4-trifluoromethoxyphenyl)ureidomethyl]benzoic acid methyl ester (0.30 g, 0.6 mmol) dissolved in DMF (10 mL) was added 1-ethyl-3-(3-dimethylaminopropyl)carbodiimide hydrochloride (EDAC, 0.12 g, 0.6 mmol) and 1-hydroxybenzotriazole (HOBt, 0.098 g, 0.65 mmol). After stirring the mixture 30 min at 25° C., diethylamine (76 µL) was added. The mixture was allowed to react overnight at 25° C. Water (100 mL) and ethyl acetate (100 mL) were added, the phases separated and the aqueous phase was extracted with ethyl acetate (2×100 mL). The combined organic phase was dried with $MgSO_4$ and evaporated to give the desired product.

3-{4-[1-(4-Diethylcarbamoylcyclohexyl)-3-(4-trifluoromethoxyphenyl)ureidomethyl]benzoylamino}propionic acid The above 4-[1-(4-diethylcarbamoylcyclohexyl)-3-(4-trifluoromethoxyphenyl)ureidomethyl]benzoic acid methyl ester was converted into the title compound by methods already described.

$^1$H NMR (300 MHz, DMSO-$d_6$): δ 12.22 (s br, 1H); 8.55 (s, 1H); 8.45 (t, 1H); 7.75 (d, 2H); 7.55 (d, 2H); 7.30 (d, 2H); 7.20 (d, 2H); 4.55 (s, 2H); 4.10 (t br, 1H); 3.45 (q, 2H); 3.20 (m, 2H): 2.70 (s br, 1H); 2.10–1.40 (m, 8H); 1.10 (t, 3H); 0.95 (t, 3H).

HPLC-MS (method B): m/z=607, $R_t$=6.50 min.

EXAMPLE 383

3-{4-[1,5-Bis(4-trifluoromethoxyphenyl)-3-biuretmethyl]benzoylamino}propionic acid

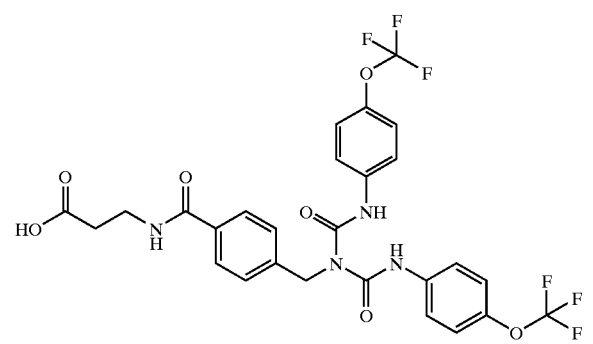

Ethyl 3-(4-aminomethylbenzoylamino)propanoate hydrochloride was prepared from β-alanine ethyl ester hydrochloride and 4-(tert-butoxycarbonylaminomethyl)benzoic acid by methods known to those skilled in the art.

3-{4-[3-(4-Trifluoromethoxyphenyl)ureidomethyl]benzoylamino}propionic acid ethyl ester

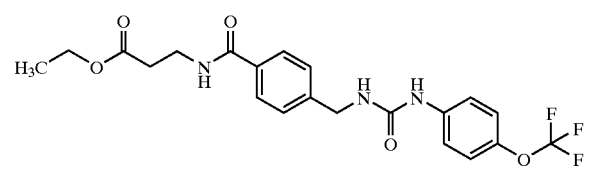

Ethyl 3-(4-Aminomethylbenzoylamino)propanoate hydrochloride (0.25 g, 0.87 mmol) in acetonitrile (5 mL) and diisopropylethylamine (0.15 mL) was allowed to react with 4-trifluoromethoxyphenylisocyanate (0.37 g, 1.74 mmol) at 50° C. overnight. Upon cooling to 25° C. the product precipitated and was collected by filtration.

3-{4-[1,5-Bis(4-trifluoromethoxyphenyl)-3-biuretmethyl]benzoylamino}propionic acid ethyl ester To a solution of the above 3-{4-[3-(4-trifluoromethoxyphenyl)ureidomethyl]benzoylamino}propionic acid ethyl ester (0.32 g, 0.71 mmol) in DMF (5 mL) was added sodium hydride (17 mg, 0.71 mmol). The mixture was stirred at 25° C. for 1 hr. Then 4-trifluoromethoxyphenylisocyanate (0.22 g, 1.06 mmol) was added and the mixture was stirred 5 hours at 25° C. The product was isolated by filtration.

3-{4-[1,5-Bis(4-trifluoromethoxyphenyl)-3-biuretmethyl]-benzoylamino}propionic acid The above 3-{4-[1,5-bis(4-trifluoromethoxyphenyl)-3-biuretmethyl]benzoylamino}propionic acid ethyl ester was hydrolysed into the title compound by methods already described.

$^1$H NMR (300 MHz, DMSO-$d_6$): δ 12.22 (s br, 1H); 10.20 (s, 2H); 7.75 (d, 2H); 7.55 (d, 4H); 7.42 (d, 1H); 7.32 (d, 4H); 5.10 (s, 2H); 3.45 (q, 2H).

HPLC-MS (method B): m/z=629, $R_t$=7.61 min.

EXAMPLE 384

3-(4-{[Bis(4-trifluoromethylbenzyl)amino]methyl}benzoylamino)propionic acid

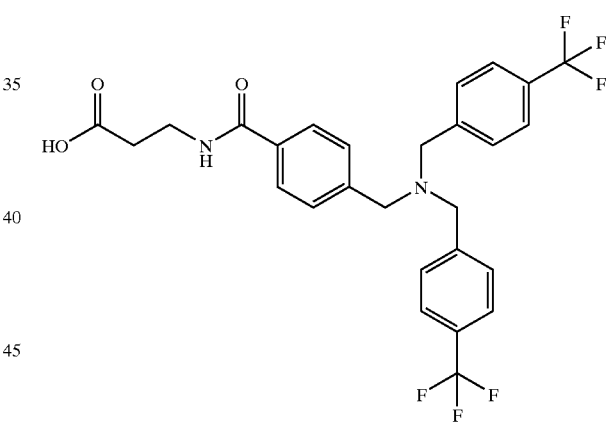

Resin bound Fmoc β-alanine

150 µmol Fmoc β-alanine was dissolved in a mixture of 250 µL dichloromethane, 250 µL DMF and 100 µL diisopropylethylamine and added to 50 mg polystyrene resin functionalized with a 2-chlorotrityl chloride linker. After shaking the suspension for 4 hours at 25° C., the resin was isolated by filtration and washed with 2×1 mL dichloromethane: methanol:diisopropylethylamine (17:2:1) and 2×1 mL DMF.

Resin bound 3-{4-[(9H-fluoren-9-ylmethoxycarbonylamino)methyl]benzoylamino}propionic acid To the above resin bound Fmoc β-alanine was added 500 µL of a 20% solution of piperidine in DMF. Upon shaking for 30 min, the resin was drained and washed with 1 mL DMF containing 1-hydroxybenzotriazole (50 mg/mL) and DMF (2×1 mL). Then 200 μmol 4-[(9H-fluoren-9-ylmethoxycarbonylamino)methyl]benzoic acid (74.2 mg) dissolved in a mixture of 430 μL DMF and 70 μL diethyl-isopropylamine was added followed by 200 μmol bromo-tris-pyrrolidinophosphonium hexafluorophosphate (PyBrOP, 93 mg) dissolved in 500 μL DMF. The mixture was shaken for 4 hours at 25° C. followed by filtration and washing of the resin with 3×1 mL DMF.

Resin bound 3-(4-{[bis(4-trifluoromethylbenzyl)amino]methyl}benzoylamino)propionic acid The Fmoc protecting group was removed from the above resin bound 3-{4-[(9H-fluoren-9-ylmethoxycarbonylamino)methyl]benzoylamino}propionic acid using 500 μL of a 20% solution of piperidine in DMF. Upon shaking for 30 min, the resin was drained and washed with 1 mL DMF containing 1-hydroxybenzotriazole (50 mg/mL) and DMF (2×1 mL), 2×1 mL 1,2-dichloroethane and 20 μL acetic acid dissolved in 1 mL 1,2-dichloroethane.

The resulting resin bound 3-(4-aminomethylbenzoylamino)propionic acid was treated with 98 mg 4-trifluoromethylbenzaldehyde (700 μmol) dissolved in 500 μL 1,2-dichloroethane, 50 μL acetic acid and a slurry of 148 mg NaBH(OAc)$_3$ (700 μmol) in 1 mL 1,2-dichloroethane. Overnight shaking at 25° C. followed by filtration and washing with 2×1 mL dichloromethane, 2×1 mL CH$_3$OH:DMF (1:1) and 3×1 mL DMF afforded resin bound 3-(4-{[bis(4-trifluoromethylbenzyl)amino]methyl}benzoylamino)propionic acid.

3-(4-{[Bis(4-trifluoromethylbenzyl)amino]methyl}benzoylamino)propionic acid

The above resin bound 3-(4-{[bis(4-trifluoromethylbenzyl)amino]methyl}benzoylamino)propionic acid was treated with 1 mL 5% TFA in dichloromethane for 1 hour at 25° C. The product was filtered off and the resin was washed with 1 mL dichloromethane. The combined extracts were concentrated in vacuo. The residue was dissolved in 50 μL DMSO+500 μL CH$_3$CN and purified by preparative HPLC using a Supelcosil ABZ+ 25 cm×10 mm 5μ column. The starting eluent composition was 5% CH$_3$CN in H$_2$O changing over 30 minutes to 90% CH$_3$CN in H$_2$O which was then kept constant for 5 minutes before going back to the starting composition over 10 min. The flow rate was kept constant at 8 mL/min collecting one fraction per min. The process was monitored using a UV detector operating at 214 nm. The fractions containing the desired products were combined and evaporated in vacuo to afford the title compound.

$^1$H NMR (300 MHz, DMSO-d$_6$): δ 8.48 (t, 1H); 7.82 (d, 2H); 7.72 (d, 2H); 7.62 (d, 2H); 7.45 (d, 2H); 3.85 (br, 6H).

HPLC-MS (method B): m/z=539, 5.90 min.

General Procedure (N) for the Solution Phase Synthesis of Compounds of the General Formula (Im)

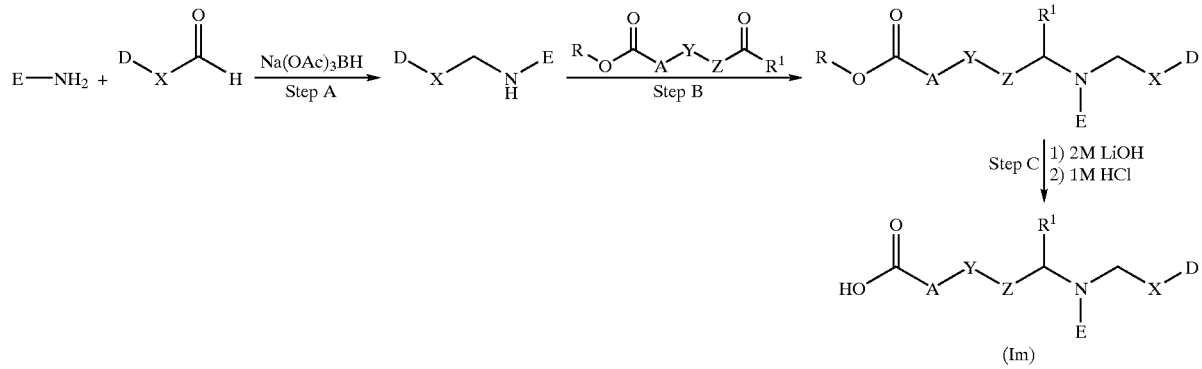

wherein
A, Y, Z, E, X, D and R$^1$ are as defined for formula (I) and R is C$_{1-6}$-alkyl.

Step A:

The appropriate carbonyl in dichloromethane was reacted with the desired amines (1.1 eq) in dichloromethane. To this solution was added sodium triacetoxyborohydride (1.5 eq.) followed by a catalytic amount of acetic acid or TFA. The reaction was left to proceed for 15 hours. The reactions were diluted with ethyl acetate and washed with saturated sodium bicarbonate (2×), water (2×), brine, and dried over MgSO$_4$. Evaporation of the solvent afforded the crude desired amine.

Step B:

To the amine from step A in dichloromethane was added R—OC(O)-A-Y-Z-C(O)—R$^1$, eg ethyl 3-[(4-formylbenzoyl)amino)]propionate, (0.9 eq) in dichloromethane. R—O(CO)-A-Y-Z-C(O)—R$^1$ may be prepared in a similar way as described in the general procedure (J) under the general preparation of formylarylcarboxamides. To this solution was added sodium triacetoxyborohydride (1.5 eq.) followed by a catalytic amount of acetic acid or TFA. The reaction was left to proceed for 15 hours. The reactions were diluted with ethyl acetate and washed with saturated sodium bicarbonate (2×), water (2×), brine, and dried over MgSO$_4$. Evaporation of the solvent afforded the crude desired amine.

Step C:

The residue obtained in step B was dissolved in DMF and aqueous 2M lithium hydroxide (10 eq) was added. The reactions were shaken overnight and filtered.

The following examples were prepared according to the general procedure (N).

EXAMPLE 385

General Procedure (N)

3-(4-{[(4-tert-Butylcyclohexyl)-(4-trifluoromethoxybenzyl)amino]methyl}benzoylamino)propionic acid

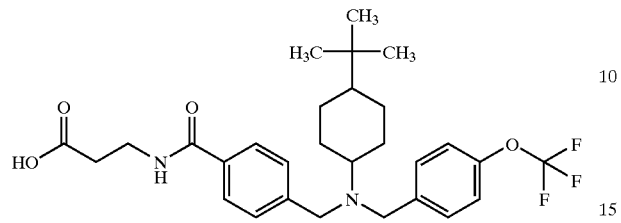

$^1$H NMR (DMSO-d$_6$): δ 0.79 (s, 9H), 0.86–1.05 (m, 3H), 1.60 (qt, 2H), 1.82 (d, 2H), 2.27 (d, 2H), 2.50 (t, 2H), 3.02 (t, 1H), 3.45 (qt, 2H), 4.18 (m, 2H), 4.50 (m, 2H), 7.36 (d, 2H), 7.62 (d, 2H), 7.34 (d, 2H), 7.81 (d, 2H), 8.63 (t, 1H), 10.80 (brd s, 1H), 12.00 (brd s, 1H).

MS (APCl, pos): 535.2, 536.2, 537.2.

EXAMPLE 386

General Procedure (N)

3-(4-{[(4-Cyclohexylphenyl)-(4-trifluoromethoxybenzyl)amino]methyl}benzoylamino)propionic acid

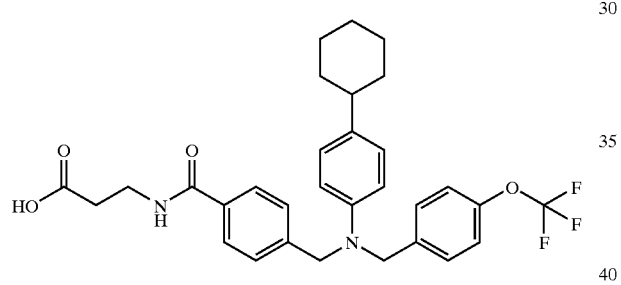

$^1$H NMR (MeOH-d$_4$): δ 0.95–1.15 (m, 5H), 1.40–1.52 (m, 5H), 2.12 (m, 1H), 2.39 (t, 2H), 3.39 (qt, 2H), 4.47–4.49 (m, 4H), 6.51 (d, 2H), 6.77 (d, 2H), 6.91 (d, 2H), 7.06 (m, 4H), 7.50 (d, 2H).

MS (APCl, pos): 552.2

EXAMPLE 387

General Procedure (N)

3-(4-{[(trans-4-cyclohexylcyclohexyl)-(4-trifluoromethoxybenzyl)amino]methyl}benzoylamino)propionic acid

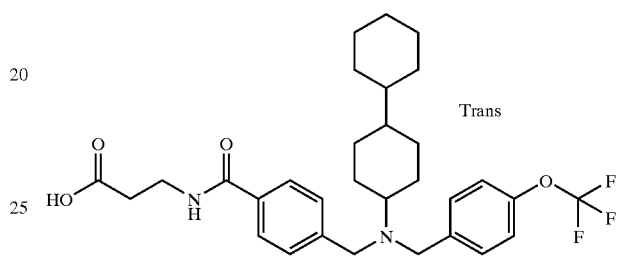

$^1$H NMR (DMSO-d$_6$): δ 0.80–1.06 (m, 10H), 1.20 (qt, 2H), 1.51–1.90 (m, 9H), 2.14 (t, 2H), 2.20 (m, 1H), 3.33 (t, 2H), 3.57 (brd m, 4H), 7.22 (d, 2H), 7.37 (d, 2H), 7.42 (d, 2H), 7.68 (d, 2H).

MS (APCl, pos): 561.2, 562.2, 489.2.

General Procedure (O) for the Solution Phase Synthesis of Compounds of the General Formula (In)

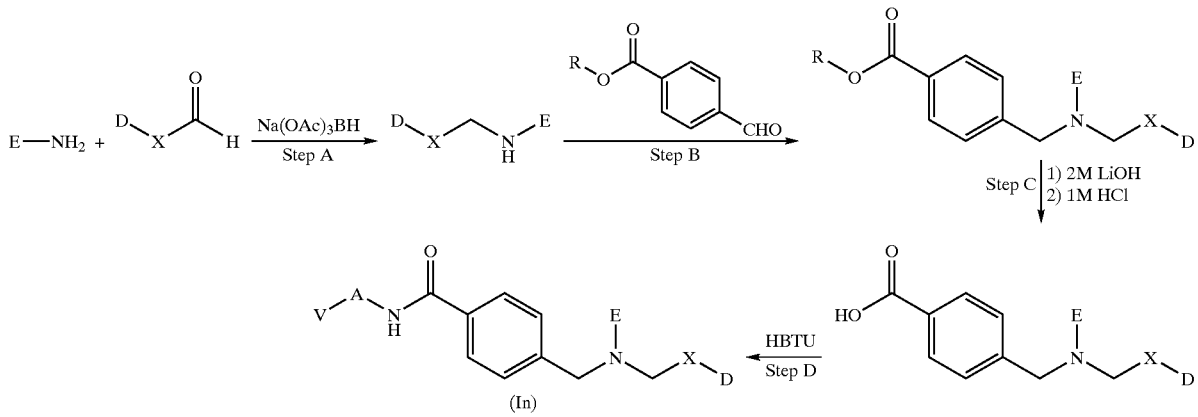

wherein

E, X, D, A, and V are as defined in formula (I), and

R is $C_{1-6}$-alkyl.

Step A:

The appropriate carbonyl compound, D—X—CHO, in dichloromethane was reacted with the desired amines (1.1 eq) in dichloromethane. To this solution was added sodium triacetoxyborohydride (1.5 eq.) followed by a catalytic amount of acetic acid or TFA. The reaction was left to proceed for 15 hours. The reactions were diluted with ethyl acetate and washed with saturated sodium bicarbonate (2×), water (2×), brine, and dried over $MgSO_4$. Evaporation of the solvent afforded the crude desired amine.

Step B:

To the amine from step A in dichloromethane was added $C_{1-6}$-alkyl 4-formylbenzoate (0.9 eq) in dichloromethane. To this solution was added sodium triacetoxyborohydride (1.5 eq.) followed by a catalytic amount of acetic acid or TFA. The reaction was left to proceed for 15 hours. The reactions were diluted with ethyl acetate and washed with saturated sodium bicarbonate (2×), water (2×), brine, and dried over $MgSO_4$. Evaporation of the solvent afforded the crude desired amine.

Step C:

The residue obtained in step B was dissolved in DMF and aqueous 2M lithium hydroxide (10 eq) were added. The reactions were shaken overnight, diluted with ethyl acetate and washed with water (3×), brine, dried over $MgSO_4$, filtered, and concentrated.

Step D:

To a solution of the acid from step C in a suitable solvent such as dichloromethane, DMF, or THF was added diisopropylethylamine (5 eq) and 2-(1H-benzotriazol-1-yl)-1,1,3,3-tetramethyluronium hexafluorophosphate (HBTU) (1.1 eq). The reaction was allowed to stir for 30 minutes before 5-aminotetrazole hydrochloride (3 eq) was added. The solution was stirred at room temperature for 4 hours. The solvents were evaporated under reduced pressure. The residue was taken up in ethyl acetate and 1 N HCl. The organic layer was separated and washed with $H_2O$ (2×), aqueous $NaHCO_3$ (3×), brine (2×), dried over $MgSO_4$, and concentrated to give the desired product.

The following examples were prepared according to the general procedure (O).

EXAMPLE 388

General Procedure (O)

4-{[(4-Cyclohexylphenyl)-(4-trifluoromethoxybenzyl)amino]methyl}-N-(2H-tetrazol-5-yl)benzamide

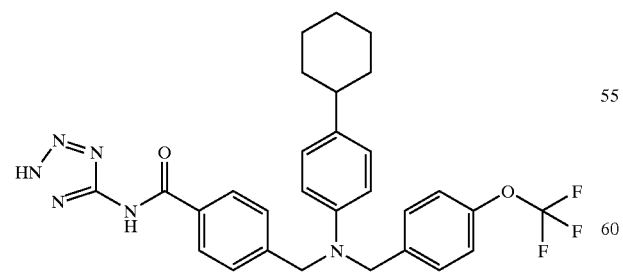

$^1$H NMR (DMSO-$d_6$): δ 1.28 (m, 5H), 1.70 (m, 5H), 2.30 (m, 1H), 4.74 (s, 2H), 4.77 (s, 2H), 6.57 (d, 2H), 6.95 (d, 2H), 7.32–7.44 (m, 6H), 8.07 (d, 2H), 12.40 (brd s, 1), 15.90 (bsd, s, 1H).

MS (APCl, Neg): 549.2, 550.2, 551.2.

General Procedure (P) for Solution Phase Synthesis of Compounds of the General Formula (Io)

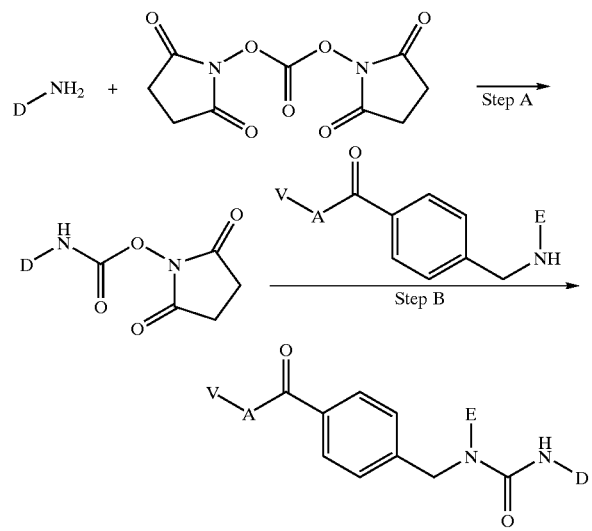

wherein

E and D are as defined in formula (I),

A is —$CH_2$—$CH_2$—NH— or —NH— and

V is tetrazol-5-yl or $C(O)OR^2$, wherein $R^2$ is hydrogen or $C_{1-6}$-alkyl.

Step A:

The appropriate primary amine (0.011 mmol) in acetonitrile was dispensed into reactor tubes containing N,N'-disuccinimidyl carbonate (0.011 mmol) in acetonitrile. The solutions were stirred at room temperature for 4 hours to give the corresponding carbamates in quantitative yields.

Step B:

To the resulting carbamates from step A was added the corresponding amine (0.011 mmol) in acetonitrile. The reactions were stirred at 80° C. overnight. Evaporation of the solvent under reduced pressure gave the desired urea.

In case V is $C(O)OC_{1-6}$-alkyl, a third synthesis step C may be added where $C(O)OC_{1-6}$-alkyl is hydrolysed to C(O)OH.

Step C:

The residue obtained in step B was dissolved in DMF and aqueous 2 M lithium hydroxide (10 eq.) were added into each reaction vessel. The samples were shaken overnight and filtered. Aqueous 1 N HCl was then added to give the desired carboxylic acids.

The following examples were prepared according to the general procedure (P).

EXAMPLE 389

General Procedure (P)

4-{1-(4-Cyclohexylphenyl)-3-[3-(propane-2-sulfonylmethyl)phenyl]ureidomethyl}-N-(2H-tetrazol-5-yl)benzamide

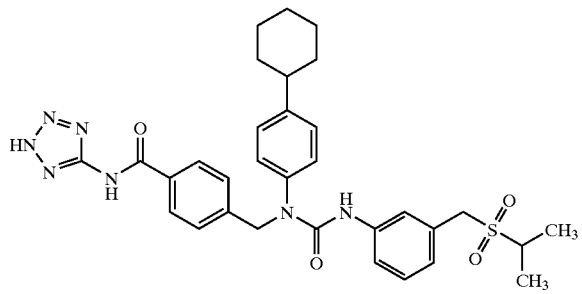

To a solution of 3-nitrobenzyl bromide (3 g, 13.9 mmol) and 2-propanethiol (1.16 g, 15.3 mmol) in THF (100 mL) was added CsCO₃ (6.5 g, 20 mmol). The mixture was refluxed for 16 hours, and filtered. To the filtrate was added excess 3-chloroperoxybenzoic acid. The mixture was stirred at room temperature for 16 hours, concentrated to one-third volume, diluted with water (100 mL), and extracted with ether. The organic extracts were washed with 10% sodium carbonate, dried (Na₂SO₄), and concentrated to provide a mixture containing desired product and starting material. After column chromatography on silicagel, eluting with a mixture of hexane and ethyl acetate (2:1) pure isopropyl 3-nitrobenzyl sulfone (2.7 g, 80%) was isolated.

¹H NMR (CDCl₃): δ 1.42 (d, 6H), 3.09 (m, 1H), 4.29 (s, 2H), 7.59 (t, 1H), 7.79 (d, 1H), 8.2–8.3 (s overlap with d, 2H).

To a solution of the above isopropyl 3-nitrobenzyl sulfone (1.4 g, 5.8 mmol) in ethanol (50 mL) was added 100 mg Pd/C(10%). The mixture was stirred under a hydrogen atmosphere at room temperature for 30 min. The catalyst was filtered off, and the filtrate was concentrated to give the isopropyl 3-aminobenzylsulfone.

¹H NMR (CDCl₃): δ 1.32 (d, 6H), 3.02 (m, 1H), 4.15 (s, 2H), 6.65–6.82 (m, 3H), 7.14 (t, 1H).

This title compound was prepared from isopropyl 3-aminobenzylsulfone and 4-[(4-cyclohexylanilino)methyl]-N-(2H-tetrazol-5-yl)benzamide following the general procedure for formation of ureas with di-(N-succinimidyl)carbonate.

¹H NMR (DMSO-d₆) δ: 1.27 (d, 6H), 1.28–1.45 (m, 6H), 1.62–1.88 (m, 5H), 3.20 (m, 1H), 4.36 (s, 2H), 4.99 (s, 2H), 7.00 (d, 1H), 7.15–7.30 (m, 3H), 7.47–7.55 (m, 4H), 7.98 (d, 2H), 8.28 (s, 1H), 11.3 (br, 1H).

LC-MS (APCl, pos.): 616 (M+1).

EXAMPLE 390

General Procedure (P)

3-(4-{1-(trans-4-Cyclohexylcyclohexyl)-3-[3-(N-ethyl-N-phenylsulfamoyl)-4-methylphenyl]ureidomethyl}benzoylamino)propionic acid

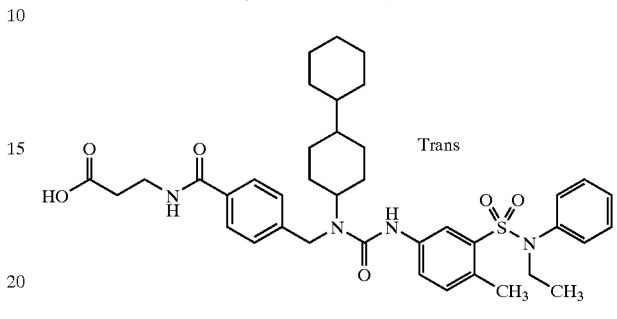

¹H NMR (DMSO-d₆): δ 0.90–1.30 (m, 13H), 1.39 (q, 2H), 1.65 (m, 8H), 2.14 (s, 3H), 2.48 (m, 2H), 3.59 (m, 2H), 3.32 (q, 2H), 4.03 (m, 1H), 4.59 (s, 2H), 7.18 (m, 3H), 7.33 (m, 5H), 7.67 (d, 1H), 7.73 (d, 2H), 7.96 (s, 1H), 8.43 (m, 1H), 8.58 (s, 1H).

MS (APCl, pos.): 703.3 (M+1).

EXAMPLE 391

General Procedure (P)

3-(4-{1-(trans-4-Cyclohexylcyclohexyl)-3-biphenyl-2-ylmethyl}ureidomethyl}benzoylamino)propionic acid

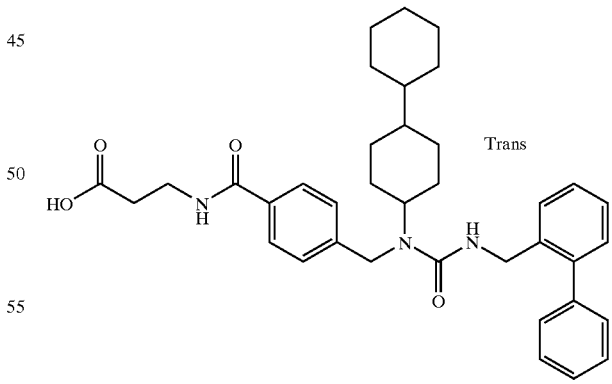

¹H NMR (DMSO-d₆): δ 0.62–1.25 (m, 10H), 1.39 (q, 2H), 1.60 (m, 8H), 2.46 (m, 2H), 3.43 (q, 2H), 3.85 (m, 1H), 3.97 (d, 2H), 4.44 (s, 2H), 6.50 (s, 1H), 6.94 (d, 1H), 7.02–7.23 (m, 10H), 7.52 (d, 2H), 7.75 (d, 2H, 8.23 (t, 1H).

MS (APCl, pos.): 596.4 (M+1).

EXAMPLE 392

General Procedure (P)

5-(3-{3-(trans-4-Cyclohexylcyclohexyl)-3-[4-(2-carboxyethylcarbamoyl)benzyl]ureido}phenyl)-2-methylfuran-3-carboxylic acid methyl ester

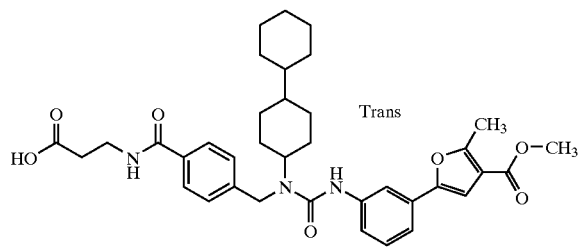

$^1$H NMR (DMSO-$d_6$): δ 0.70–1.25 (m, 10H), 1.41 (q, 2H), 1.66 (m, 8H), 2.47 (m, 2H), 3.78 (s, 3H), 4.08 (m, 1H), 4.62 (s, 2H), 7.02 (s, 1H), 7.21–7.38 (m, 4H), 7.43 (d, 2H), 7.75 (d, 2H), 7.81 (s, 1H), 8.45 (s, 1H).

MS (APCl, pos.): 644.3 (M+1).

EXAMPLE 393

General Procedure (P)

3-{4-[1-(trans-4-Cyclohexylcyclohexyl)-3-(3-bromo-5-trifluoromethylphenyl)ureidomethyl]benzoylamino}propionic acid

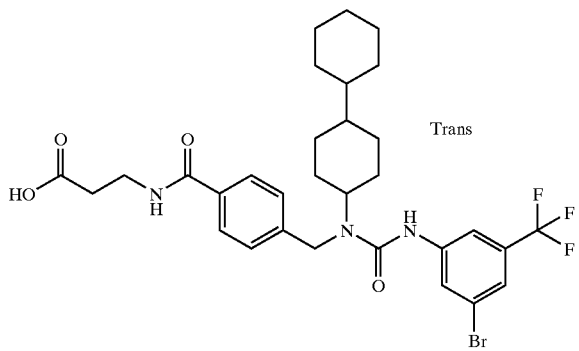

$^1$H NMR (DMSO-$d_6$): δ 0.62–1.25 (m, 10H), 1.39 (q, 2H), 1.65 (m, 8H), 2.40 (m, 2H), 3.32 (q, 2H), 4.04 (m, 1H), 4.60 (s, 2H), 7.31 (d, 2H), 7.46 (s, 1H), 7.75 (d, 2H), 7.93 (s, 1H), 8.08 (s, 1H), 8.45 (s, 1H), 8.83 (s, 1H).

MS (APCl, pos.): 652.2, 654.1 (M+1).

EXAMPLE 394

General Procedure (P)

3-{4-[1-(4-Cyclohexylphenyl)-3-(3-bromo-5-trifluoromethylphenyl)ureidomethyl]benzoylamino}propionic acid

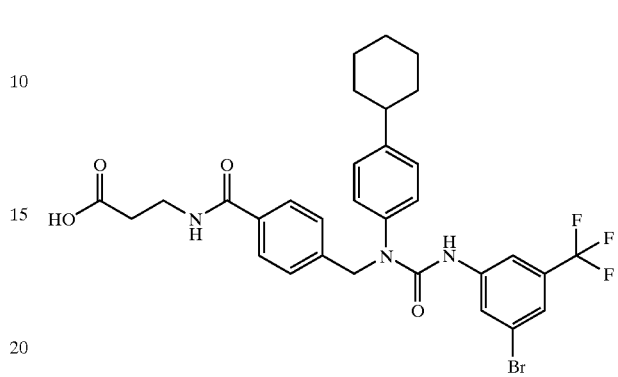

$^1$H NMR (DMSO-$d_6$): δ 1.38 (m, 6H), 1.79 (m, 5H), 2.48 (m, 2H) 4.96 (s, 2H), 7.22 (m, 4H), 7.36 (d, 2H), 7.50 (s, 1H), 7.77 (d, 2H), 7.94 (s, 1H), 8.09 (s, 1H), 8.50 (s, 1H), 8.71 (s, 1H),

MS (APCl, pos.): 646.2, 648.2 (M+1).

EXAMPLE 395

General Procedure (P)

3-{4-[1-(4-Cyclohexylphenyl)-3-(3,5-dichlorobenzyl)ureidomethyl]benzoylamino}propionic acid

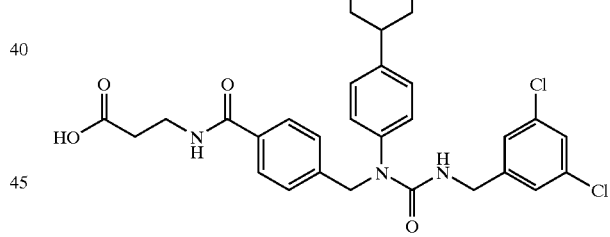

Step A:
To a solution of D-NH$_2$ (eg. 3,5-dichlorobenzylamine) (1.13 mmol) in acetonitrile (10 mL) was added N,N'-disuccinimidylcarbonate (360 mg, 1.13 mmol). The reaction mixture was stirred at room temperature for 4 hours.

Step B:
The intermediate 3-{4-[(4-cyclohexylphenylamino)methyl]benzoylamino}propionic acid ethyl ester (1.13 mmol) and diisopropylethylamine (440 mg, 3.42 mmol) were added to the reaction mixture and the reaction mixture was heated at 75° C. overnight and concentrated under reduced pressure. The residue was taken up in ethyl acetate and washed with 1N HCl (2×), brine (3×), dried over MgSO$_4$, filtered and concentrated. The material was introduced into a silica gel column and eluted with ethyl acetate/hexane (20/80).

Step C:
The product from step B (150 mg, 0.250 mmol) was dissolved in methanol (20 mL) and 2 M LiOH (20 mL) was added. The reaction was stirred for 30 minutes and concentrated. The residue was introduced into a silica gel column and eluted with ethyl acetate. Recrystallisation from ethyl ether/dichloromethane afforded the title compound as a beige solid (35 mg, 25% yield).

$^1$H NMR (DMSO-d$_6$): δ 1.10–1.34 (m, 6H), 1.70–1.78 (m, 5H), 2.45 (t, 2H), 3.44 (qt, 2H), 4.21 (d, 2H), 4.84 (s, 2H), 6.55 (t, 1H), 7.08 (d, 2H), 7.19–7.21 (m, 6H), 7.44 (s, 1H), 7.74 (d, 2H), 8.45 (t, 1H), 12.10 (brd s, 1H).

MS (APCl, pos): 582.1, 584.2.

EXAMPLE 396

General Procedure (P)

4-[1-(4-Cyclohexylphenyl)-3-(2,2,3,3-tetrafluoro-2,3-dihydrobenzo[1,4]dioxin-6-yl)ureidomethyl]-N-(2H-tetrazol-5-yl)benzamide

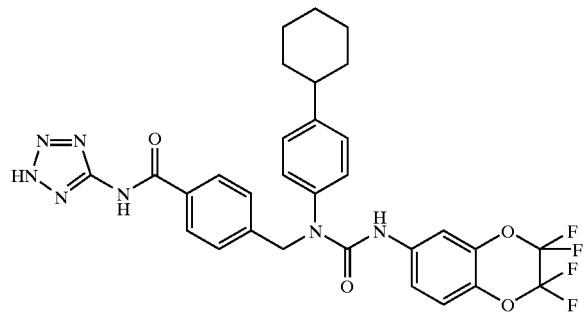

To a solution of 2,2,3,3-tetrafluoro-6-amino-2,3-dihydrobenzo[1,4]dioxine (120 mg, 0.53 mmol) in acetonitrile (10 mL) was added N,N'-disuccinimidylcarbonate (130 mg, 0.53 mmol). After stirring the solution for 4 hours at room temperature, 4-[(4-cyclohexylphenylamino)methyl]-N-(1H-tetrazol-5-yl)benzamide (200 mg, 0.53 mmol) and diisopropylethylamine (210 mg, 1.59 mmol) were added. The reaction mixture was heated at 75° C. overnight and concentrated under reduced pressure. The residue was taken up in ethyl acetate and washed with 1N HCl (2×), brine (3×), dried over MgSO4, filtered and concentrated. The material was introduced into a silica gel column and eluted with MeOH/ethyl acetate (5/95). The crude product was then recrystallized from ethyl acetate/hexane to afford the title compound as a white-beige powder (12 mg, 0.019 mmol).

$^1$H NMR (DMSO-d$_6$): δ 1.36 (m, 6H), 1.78 (m, 5H), 4.99 (s, 2H), 7.21 (m, 4H), 7.33 (s, 2H), 7.45 (d, 2H), 7.63 (s, 1H), 8.01 (s, 2H), 8.57 (s, 1H), 12.20 (brd s, 1H), 16.00 (brd s, 1H).

MS (APCl, pos): 626.2, 627.2.

EXAMPLE 397

General Procedure (P)

4-[1-(4-Cyclohexylphenyl)-3-(3,5-dichlorobenzyl)ureidomethyl]-N-(2H-tetrazol-5-yl)benzamide

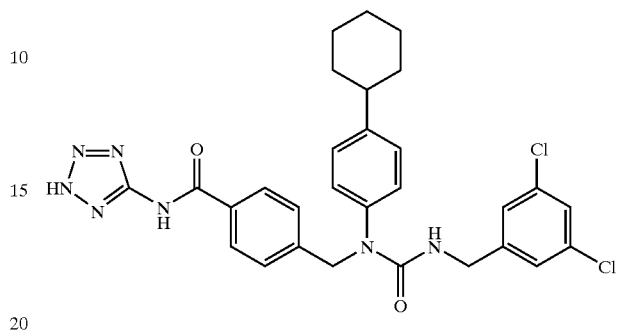

To a solution of 3,5-dichlorobenzylamine (200 mg, 1.14 mmol) was added N,N'-disuccinimidylcarbonate (360 mg, 1.13 mmol). After stirring the solution for 4 hours at room temperature, tetrazolylaminoamidobenzylaniline (420 mg, 1.13 mmol) and diisopropylethylamine (440 mg, 3.42 mmol) were added. The reaction was heated at 75° C. overnight and concentrated under reduced pressure. The residue was taken up in ethyl acetate and washed with 1N HCl (2×), brine (3×), dried over MgSO$_4$, filtered and concentrated. The title compound was purified by preparatory HPLC.

$^1$H NMR (DMSO-d$_6$): δ 11.22 (m, 6H), 1.71 (m, 5H), 4.24 (s, 2H), 4.90 (s, 2H), 6.64 (t, 1H), 7.13 (d, 2H), 7.23 (d, 2H), 7.27 (s, 2H), 7.39 (d, 2H), 7.45 (s, 1H), 8.04 (d, 2H), 12.29 (brd s, 1H), 16.00 (brd s, 1H).

MS (APCl, pos): 580.0.

General Procedure (Q) for the Solid Phase Synthesis of Compounds of the General Formula (Ip)

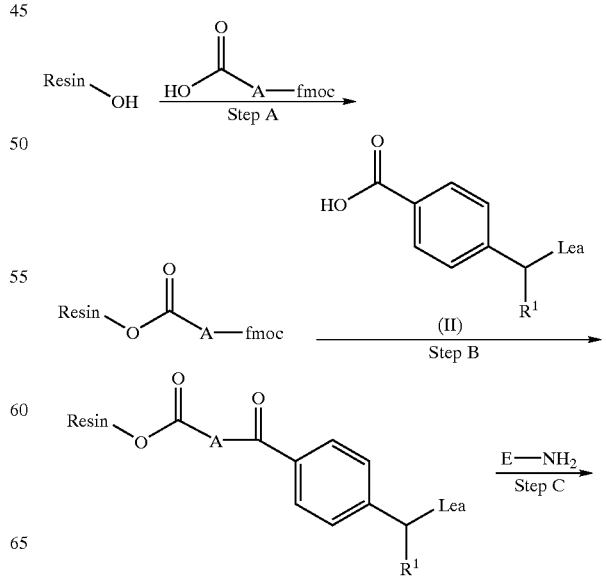

-continued

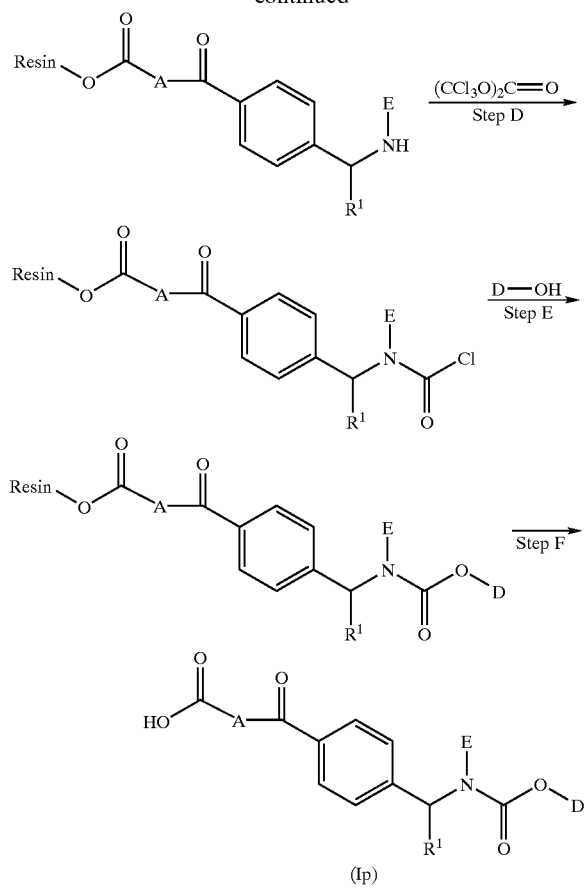

(Ip)

wherein
A, $R_1$, E and D are as defined for formula (Ia),
Lea is a leaving group such as chloro, bromo, iodo, mesyl or tosyl, and
Resin denotes a polystyrene resin with a linker such as the Wang linker:

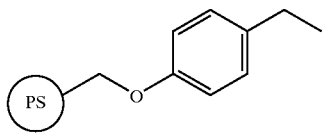

wherein PS denotes polystyrene.

Step A, Step B and Step C are performed as described under general procedure (A).

Alternatively, the resin can be a polystyrene resin with a 2-chlorotrityl linker. In this case, step A is performed as described in eg general procedure (L) or general procedure (V).

Step D:

The reaction is performed by stirring resin bound intermediate obtained as described in step C with bistrichloromethyl carbonate (3.3 equivalents). The reaction is carried out in solvents such as dichloromethane, 1,2-dichloroethane or toluene, containing 10 equivalents of a base such as diisopropylethylamine, triethylamine, dicyclohexylamine and the like. The reaction is performed between 0° C. and 40° C., preferably between 0° C. and 20° C. When the reaction is complete (1–3 h), excess of reagent is removed by filtration. The resin is then washed with dichloromethane and dried in vacuo to leave the resin bound chlorocarbamoyl derivatized intermediate.

Step E:

The reaction is performed by stirring resin bound chlorocarbamoyl derivatized intermediate as obtained in step D, with a 10–20 molar excess of alcohols of the type D-OH in the presence of an equal molar excess of base such as diisopropylethylamine, triethylamine, dicyclohexylamine, diazabicycloundecene, or preferably [2.2.2]-diazabicyclooctane. The reaction is carried out in solvents such as DMF, N-methyl-2-pyrrolidone, dichloromethane, 1,2-dichloroethane, THF, toluene or mixtures of one or more of these. The reaction is performed between 0° C. and 120° C., preferably at 25° C. When the reaction is completed (12–16 hours) excess of reagent is removed by filtration. The resin is then washed with the solvent used during the reaction followed by several washes with dichloromethane. The resin is dried in vacuo to leave the resin bound carbamate.

Step F:

The reaction is known (The combinatorial Index, Ed. Bunin, B. A. 1998, Academic Press, p. 21) and is generally performed by stirring resin bound intermediate with a 5–95% solution of TFA in dichloromethane. The reaction is performed between 0° C. and 40° C., preferably at 25° C. When the reaction is complete, the product is removed by filtration. The resin is successively washed with the solvent used during the reaction, optionally containing TFA. The product and the washings are collected, and the solvent is removed in vacuo.

Specific examples illustrating the preparation of compounds of the general formula (Ip) according to the invention are provided below.

EXAMPLE 398

General Procedure (Q)

3-(4-{[(Biphenyl-4-yloxycarbonyl)-(4-tert-butylcyclohexyl)amino]methyl}benzoylamino)propionic acid

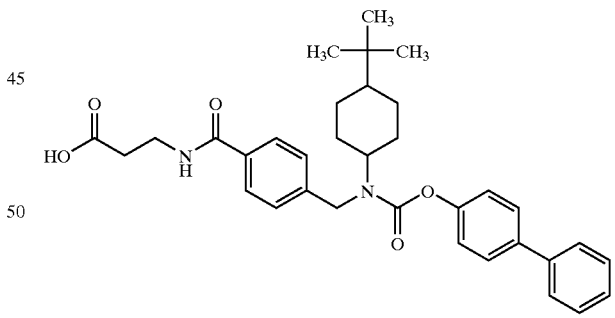

Step D: Resin bound 3-{4-[1-(4-tert-butylcyclohexyl)-N-(chlorocarbamoyl)aminomethyl]benzoylamino}propionic acid Resin bound 3-{4-[1-(4-tert-butylcyclohexyl)aminomethyl]benzoylamino}propionic acid (100 mg, 0.1 mmol) as prepared according to step C under general procedure A was suspended in dichloromethane for 1 hour. Solvent was removed by filtration, and a mixture of bis-trichloromethyl carbonate (89 mg, 0.3 mmol) and diisopropylethylamine (175 ul, 1.0 mmol) in dichloromethane (1,0 mL) was added. The mixture was stirred for 90 min. at room temperature. Excess of reagents were removed by filtration, and the resin was subsequently washed with dichloromethane (4×). The resin was dried in vacuo to leave 105 mg of resin bound 3-{4-[1-(4-tert-butylcyclohexyl)-N-(chlorocarbamoyl)aminomethyl]benzoylamino}propionic acid.

Step E: Resin bound 3-(4-{[(biphenyl-4-yloxycarbonyl)-(4-tert-butylcyclohexyl)amino]methyl}benzoylamino)propionic acid To the resin (50 mg, 0.05 mmol) prepared in step D was added a solution of (85 mg; 0.5 mmol) biphenyl-4-ol, and (2.2.2)-diazabicyclooctane (56 mg; 0.5 mmol) in DMF (1.0 mL). The mixture was stirred at room temperature overnight. Solvent was removed, and the resin was washed with DMF (3×) followed by dichloromethane (10×). The resin was dried in vacuo to leave 65 mg of resin bound 3-(4-{[(biphenyl-4-yloxycarbonyl)-(4-tert-butylcyclohexyl)amino]methyl}benzoylamino)propionic acid Step F: 3-(4-{[(Biphenyl-4-yloxycarbonyl)-(4-tert-butylcyclohexyl)amino]methyl}benzoylamino)propionic acid To the resin obtained above was added 2 mL of 50% of TFA in dichloromethane. After stirring for 30 min. at 25° C., the solvent was removed by filtration. The resin was washed twice with 50% of TFA in dichloromethane, and the combined filtrate and washings were evaporated to dryness by speed vacuum centrifugation, to leave the title material as a light coloured oil. The product was characterised by analytical HPLC-MS and NMR.

$^1$H NMR (DMSO): δ 8.44 (s, 1H); 8.35 (s, 1H); 7.78 (d, 2H); 7.45 (d, 2H); 7.38 (d, 2H); 7.34 (d, 2H); 6.94 (m, 5H); 4.60 (s, 2H); 0.81 (s, 9H).

EXAMPLE 399

General Procedure (Q)

3-(4-{[(4-tert-Butylcyclohexyl)-(4-nitrophenoxycarbonyl)amino]methyl}benzoylamino)propionic acid

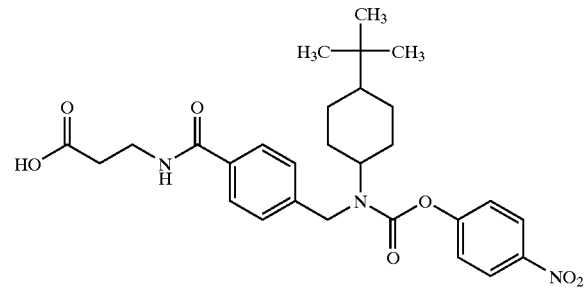

$^1$H NMR (DMSO): δ 8.40 (t, 1H); 8.25 (d, 2H); 7.82 (d, 2H); 7.78 (d, 2H); 7.44 (d, 2H); 4.61 (s, 2H); 0.85 (s, 9H).

EXAMPLE 400

General Procedure (Q)

3-(4-{[(4-Cyclohexylphenyl)-(3,5-dichlorophenoxycarbonyl)amino]methyl}benzoylamino)propionic acid

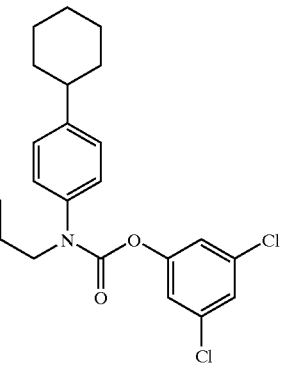

$^1$H NMR (DMSO); δ 8.57 (t, 1H); 7.88 (d, 2H); 7.60 (s, 1H); 7.50 (m, 4H); 7.40 (d, 2H); 7.29 (d, 2H).

EXAMPLE 401

General Procedure (Q)

3-(4-{[(4-tert-Butylcyclohexyl)-(3,4-dichlorophenoxycarbonyl)amino]methyl}benzoylamino)propionic acid

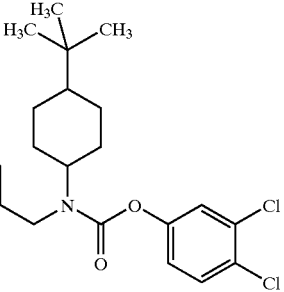

$^1$H NMR (DMSO): δ 8.58 (t, 1H); 7.91 (d, 2H); 7.73 (d, 1H); 7.58 (d, 1H); 7.48 (d, 2H); 7.22 (d, 1H).

EXAMPLE 402

General Procedure (Q)

3-(4-{[(4-tert-Butylcyclohexyl)-(3,5-dichlorophenoxycarbonyl)amino]methyl}benzoylamino)propionic acid

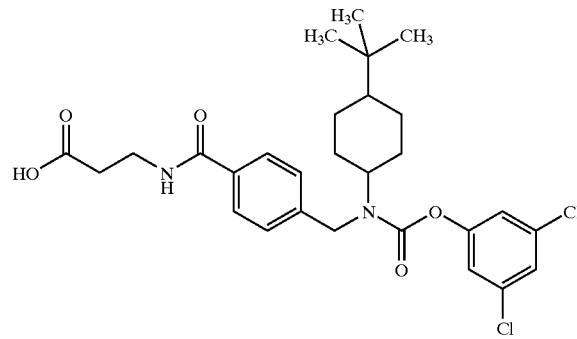

¹H NMR (DMSO): δ 8.59 (t, 1H); 7.90 (d, 2H); 7.55 (m, 4H); 7.35 (s, 1H).

EXAMPLE 403

General Procedure (Q)

3-(4-{[(3,5-Bis(trifluoromethyl)phenoxycarbonyl)-(4-tert-butylcyclohexyl)amino]methyl}benzoylamino)propionic acid

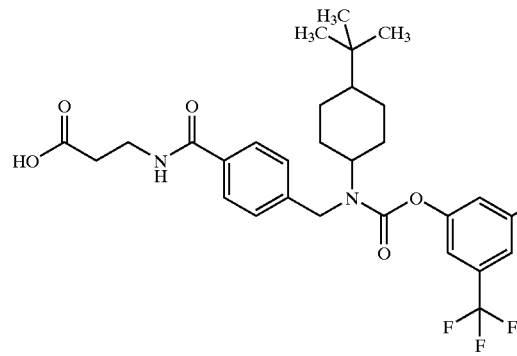

¹H NMR (DMSO): δ 8.58 (t, 1H); 8.12 ((d, 1H); 8.05 (d, 2H); 7.90 (m, 2H); 7.55 (m, 2H).

EXAMPLE 404

General Procedure (Q)

3-(4-{[(4-tert-Butylcyclohexyl)-(2,4-dibromophenoxycarbonyl)amino]methyl}benzoylamino)propionic acid

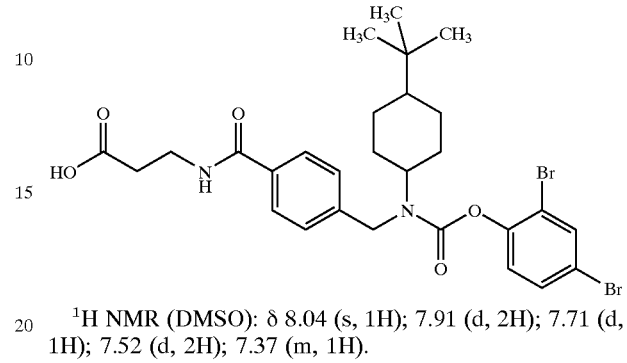

¹H NMR (DMSO): δ 8.04 (s, 1H); 7.91 (d, 2H); 7.71 (d, 1H); 7.52 (d, 2H); 7.37 (m, 1H).

EXAMPLE 405

General Procedure (Q)

3-(4-{[(4-tert-Butylcyclohexyl)-(4-trifluoromethoxyphenoxecarbonyl)amino]methyl}benzoylamino)propionic acid

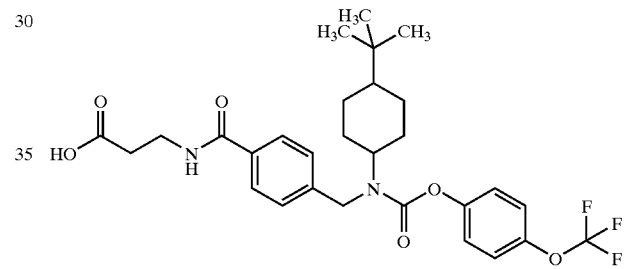

¹H NMR (DMSO): δ 8.59 (t, 1H); 7.91 (d, 2H); 7.47 (dd, 4H); 7.30 (d, 2H).

EXAMPLE 406

General Procedure (Q)

4-tert-Butylphenyl)-[4-(2H-tetrazol-5-ylcarbamoyl)benzyl]carbamic acid 3,5-bis(trifluoromethyl)phenyl ester

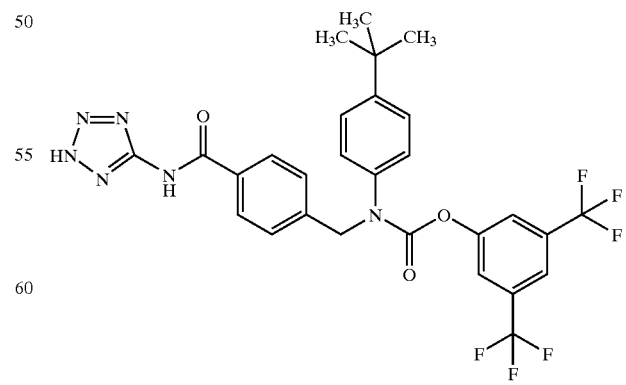

¹H NMR (DMSO): δ 8.17 (s, 2H); 8.11 (s, 1H); 7.67 (d, 2H); 7.51 (m, 4H); 5.18 (s, 2H).

EXAMPLE 407

General Procedure (Q)

3-(4-{[(4-tert-Butylphenyl)-(2,4-dichlorophenoxycarbonyl)amino]methyl}benzoylamino)propionic acid

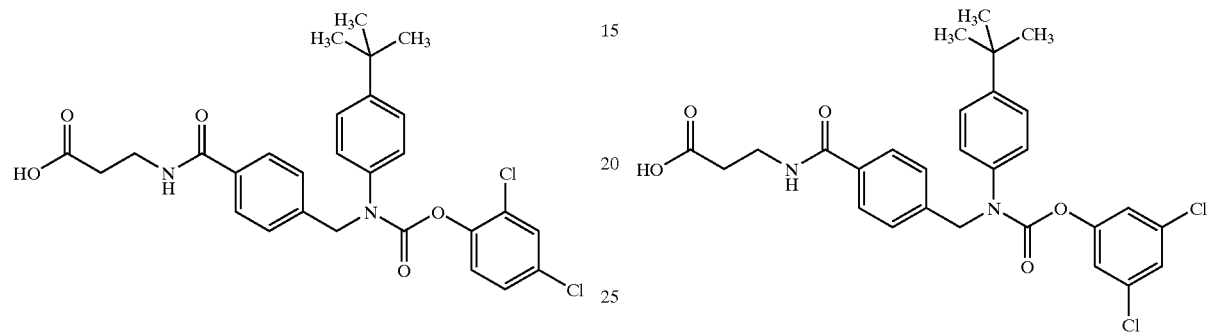

$^1$H NMR (DMSO): δ 8.58 (t, 1H); 7.89 (d, 2H); 7.84 (s, 1H); 7.56 (dd, 1H); 7.48 (m, 5H; 7.39 (d, 2H); 5.06 (s, 2H).

EXAMPLE 408

General Procedure (Q)

3-(4-{[(4-tert-Butylcyclohexyl)-(3-trifluoromethoxyphenoxycarbonyl)amino]methyl}benzoylamino)propionic acid

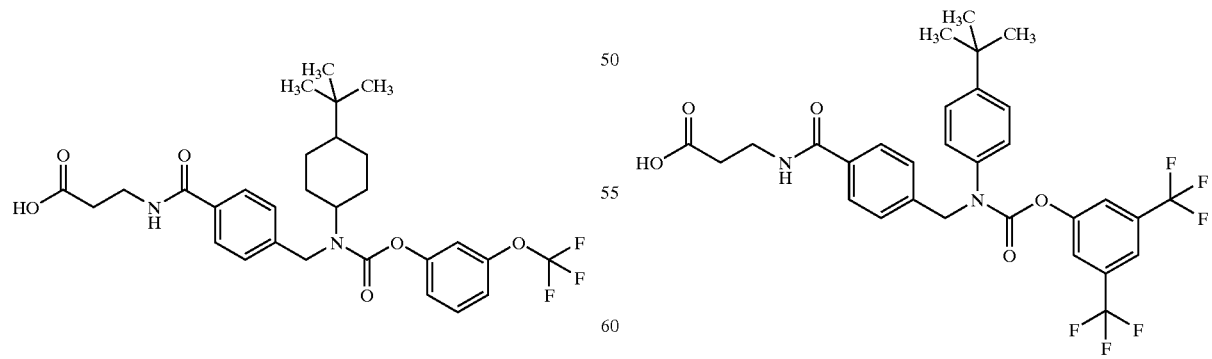

$^1$H NMR (DMSO): δ 8.59 (t, 1H); 7.91 (d, 2H); 7.69 (t, 1H); 7.47 (dd, 4H); 7.32 (m, 1H); 7.27 (m, 1H); 7.20 (m, 1H).

EXAMPLE 409

General Procedure (Q)

3-(4-{[(4-tert-Butylphenyl)-(3,5-dichlorophenoxycarbonyl)amino]methyl}benzoylamino)propionic acid $^1$H NMR (DMSO): δ 8.60 (t, 1H); 7.88 (d, 2H); 7.60 (s, 1H); 7.50 (m, 4H); 7.46 (d, 2H); 7.43 (d, 2H); 5.08 (s, 2H).

EXAMPLE 410

General Procedure (Q)

3-(4-{[(3,5-Bis(trifluoromethyl)phenoxycarbonyl)-(4-tert-butylphenyl)amino]methyl}benzoylamino)propionic acid $^1$H NMR (DMSO): δ 8.60 (t, 1H); 8.15 (s, 2H); 8.10 (s, 1H); 7.89 (d, 2H); 7.55 (d, 2H); 7.49 (s, 4H); 5.11 (s, 1H).

EXAMPLE 411

General Procedure (Q)

3-(4-{[(4-tert-Butylphenyl)-(4-trifluoromethoxyphenoxycarbonyl)amino]methyl}benzoylamino)propionic acid

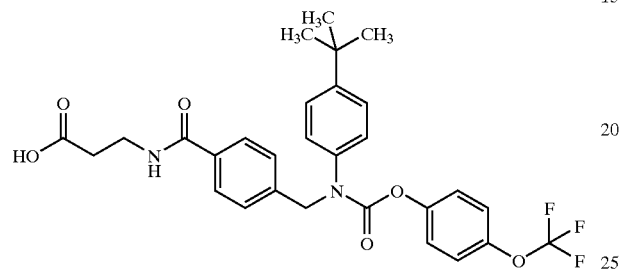

¹H NMR (DMSO): δ 8.59 (t, 1H); 7.88 (d, 2H); 7.48 (m, 6H); 7.39 (m, 4H); 5.09 (s, 2H).

EXAMPLE 412

General Procedure (Q)

3-(4-{[(4-tert-Butylphenyl)-(3-trifluoromethoxyphenoxycarbonyl)amino]methyl}benzoylamino)propionic acid

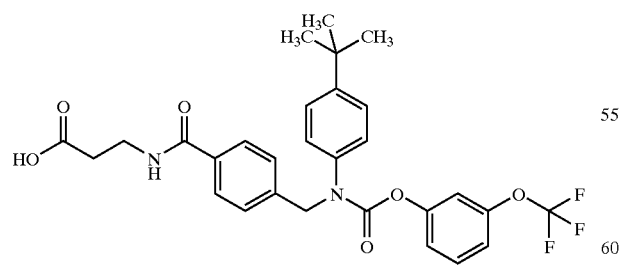

¹H NMR (DMSO): δ 8.59 (t, 1H); 7.88 (d, 2H); 7.61 (t, 1H); 7.48 (m, 4H); 7.39 (m, 5H); 5.09 (s, 2H).

EXAMPLE 413

General Procedure (Q)

3-(4-{[(4-Cyclohexylphenyl)-(4-nitrophenoxycarbonyl)amino]methyl}benzoylamino)propionic acid

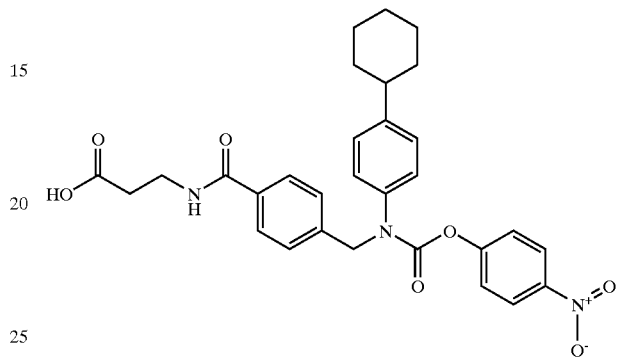

¹H NMR (DMSO): δ 8.57 (t, 1H); 8.36 (d, 2H); 7.88 (d, 2H); 7.55 (d, 2H); 7.49 (d, 2H); 7.40 (d, 2H); 7.31 (d, 2H); 5.09 (s, 2H).

EXAMPLE 414

General Procedure (Q)

3-(4-{[(4-Cyclohexylphenyl)-(3-nitrophenoxycarbonyl)amino]methyl}benzoylamino)propionic acid

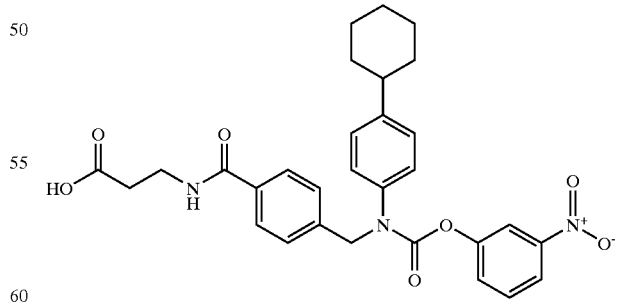

¹H NMR (DMSO): δ 8.57 (t, 1H); 8.19 (m, 2H); 7.88 (d, 2H); 7.76 (dd, 2H) 7.51 (d, 2H); 7.41 (d, 2H); 7.31 (d, 2H); 5.10 (s, 2H).

EXAMPLE 415

General Procedure (Q)

3-(4-{[(4-Cyclohexylphenyl)-(2-nitrophenoxycarbonyl)amino]methyl}benzoylamino)propionic acid

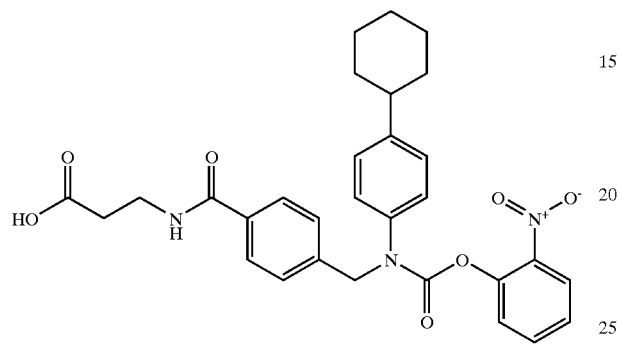

¹H NMR (DMSO): δ 8.59 (t, 1H); 8.21 (d, 1H); 7.89 (m, 3H); 7.63–7.31 (m, 7H); 5,05 (s, 2H).

EXAMPLE 416

General Procedure (Q)

3-(4-{[(4-Cyclohexylphenyl)-(2,4-dichlorophenoxycarbonyl)amino]methyl}benzoylamino)propionic acid

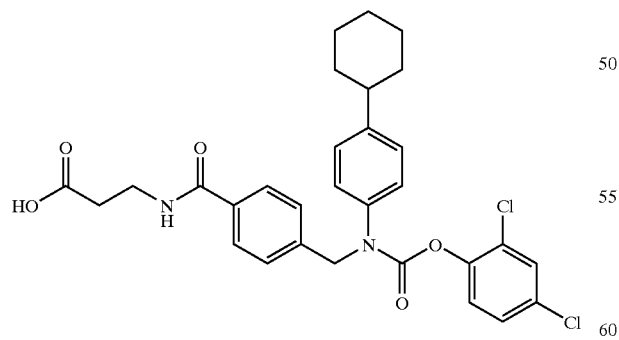

¹H NMR (DMSO): δ 8.58 (t, 1H); 7.88 (d, 2H); 7.83 (s, 1H); 7.57–7.45 (m, 5H); 7.38 (d, 2H; 7.31 (d, 2H); 5.06 (s, 2H).

EXAMPLE 417

General Procedure (Q)

3-(4-{[(4-Cyclohexylphenyl)-(3,4-difluorophenoxycarbonyl)amino]methyl}benzoylamino)propionic acid

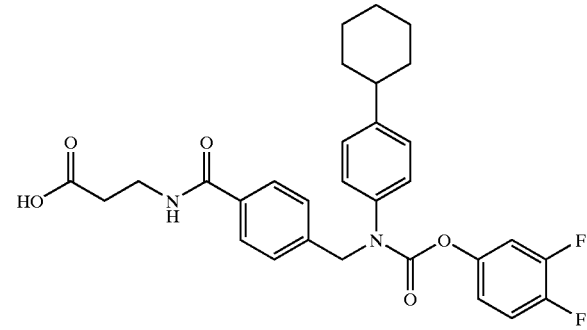

¹H NMR (DMSO): δ 8.58 (t, 1H); 7.87 (d, 2H); 7.55–7.45 (m, 4H); 7.38 (d, 2H); 7.29 (d, 2H); 7.13 (m, 1H); 5.07 (s, 2H).

EXAMPLE 418

General Procedure (Q)

3-(4-{[(4-Cyclohexylphenyl)-(4-methylsulfanylphenoxycarbonyl)amino]methyl}benzoylamino)propionic acid

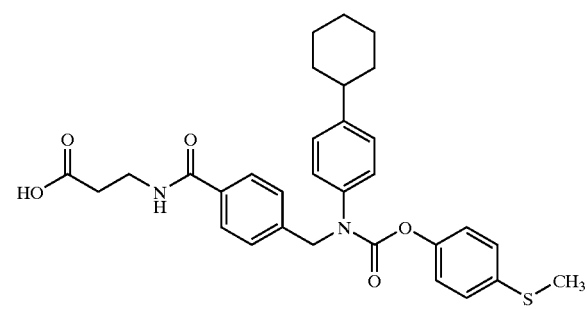

¹H NMR (DMSO): δ 8.58 (t, 1H); 7.87 (d, 2H); 7.46 (d, 2H); 7.35 (m, 4H); 7.29 (d, 2H); 7.18 (d, 2H); 5.07 (s, 2H).

EXAMPLE 419

General Procedure (Q)

3-(-4-{[(3,5-Bis(trifluoromethyl)phenoxycarbonyl)-(4-cyclohexylphenyl)amino]methyl}benzoylamino)propionic acid

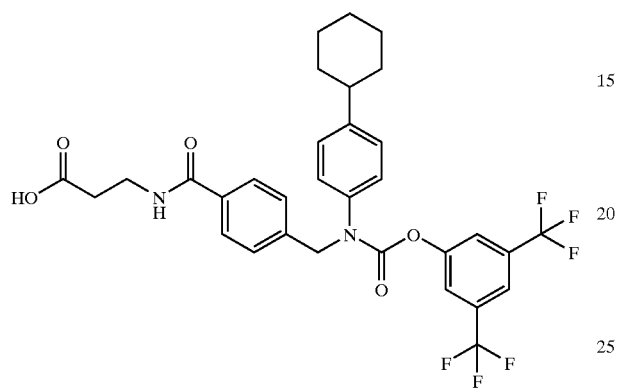

$^1$H NMR (DMSO): δ 8.58 (t, 1H); 8.14 (s, 2H); 8.10 (s, 1H); 7.88 (d, 2H); 7.53 (d, 2H); 7.47 (d, 2H); 7.31 (d, 2H); 5.10 (s, 2H).

EXAMPLE 420

General Procedure (Q)

3-(4-{[(4-Cyclohexylphenyl)-(2,4-dibromompheoxycarbonyl)amino]methyl}benzoylamino)propionic acid

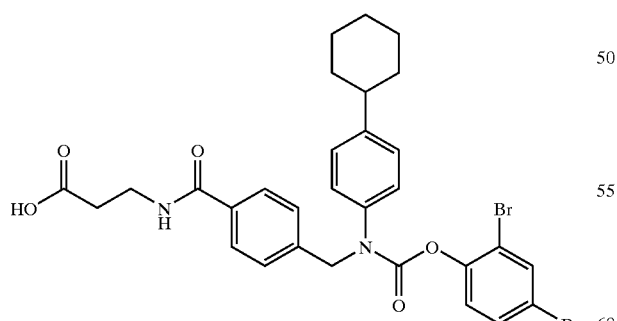

$^1$H NMR (DMSO): δ 8.57 (t, 1H); 8.04 (s, 1H); 7.88 (d, 2H); 7.72 (d, 1H); 7.50 (bd, 2H); 7.42 (m, 3H); 7.38 (d, 2H); 5.05 (s, 2H).

EXAMPLE 421

General Procedure (Q)

3-(4-{[(4-Cyclohexylphenyl)-(3-trifluoromethoxyphenoxycarbonyl)amino]methyl}benzoylamino)propionic acid

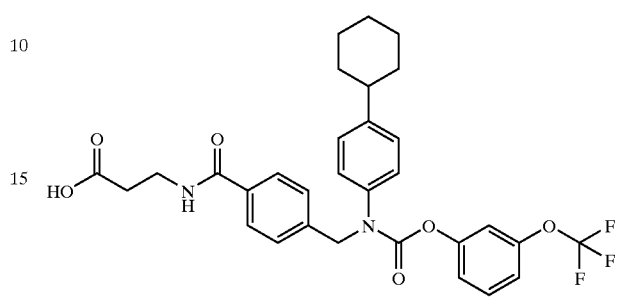

$^1$H NMR (DMSO): δ 8.59 (t, 1H); 7.88 (d, 2H); 7.62 (t, 1H); 7.49 (d, 2H); 7.41–7.30 (m, 7H); 5.09 (s, 2H).

General Procedure (R) for the Solid Phase Synthesis of Compounds of the General Formula (Iq)

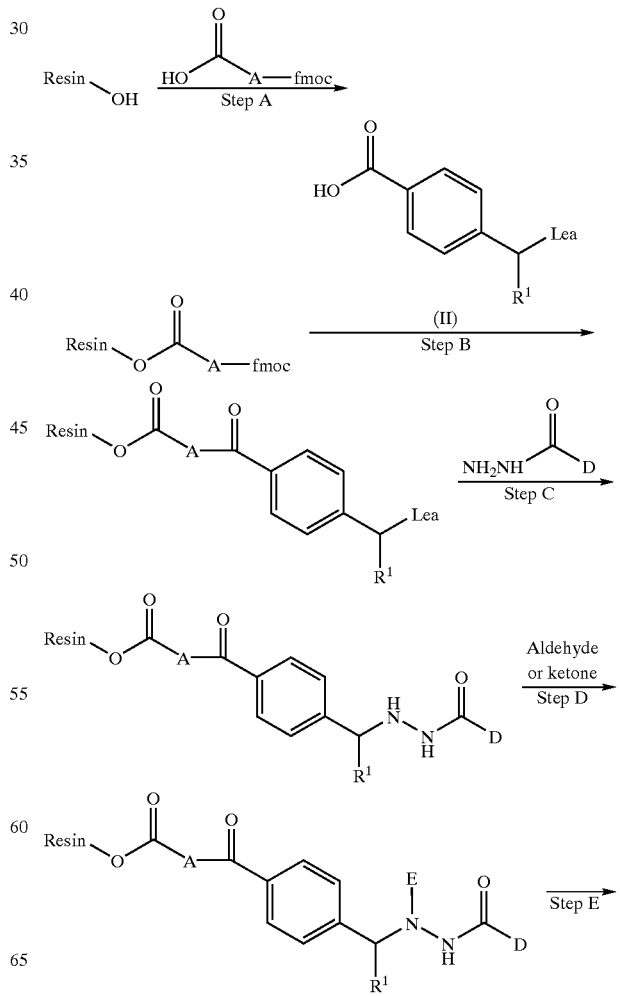

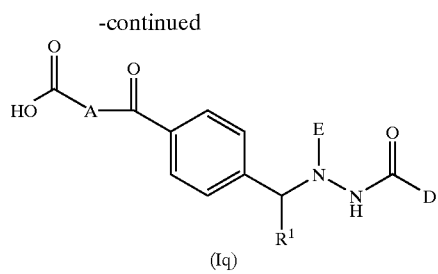

(Iq)

wherein
A, R¹, E and D are as defined for formula (Ia),
Lea is a leaving group such as chloro, bromo, iodo, mesyl or tosyl, and
Resin denotes a polystyrene resin with a linker such as the Wang linker:

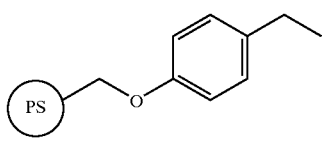

wherein PS denotes polystyrene.

Step A and Step B are performed as described under general procedure A.

Step C:

The reaction is performed by stirring the resin bound intermediate obtained in step B with 10–20 molar excess of hydrazide. The nucleophilic displacement is carried out in solvents such as DMSO, DMF, N-methyl-2-pyrollidone or mixtures of two or more of these. The reaction is performed between 20° C. and 120° C., preferably between 60° C. and 80° C. When the reaction is complete, excess of reagent is removed by filtration. The resin is successively washed with the solvent used in the reaction, followed by washings with methanol. The resin bound product can be further dried and analyzed.

Step D:

The reductive amination is generally known (The combinatorial Index, Ed. Bunin, B. A. 1998, Academic Press, p. 167) and is performed by stirring the resin bound hydrazide intermediate obtained in step C with an excess of aldehyde or ketone at low pH (by addition of an acid, such as acetic or formic acid). The reaction is carried out in solvents such as THF, DMF, N-methyl-2-pyrrolidone, ethanol, methanol, dichloromethane, 1,2-dichloroethane, trimethyl orthoformate, triethyl orthoformate, or mixtures of two or more of these. As reducing reagent sodium cyanoborohydride can be used. The reaction is performed between 20° C. and 120° C., preferably at 25° C. When the reaction is complete, excess of reagents are removed by filtration and the resin is washed several times with the solvent used during the reaction. The resin bound product can be further dried and analyzed.

Step E:

The cleavage reaction is known (The combinatorial Index, Ed. Bunin, B. A. 1998, Academic Press, p. 21) and is generally performed by stirring resin bound intermediate with a 5–95% solution of TFA in dichloromethane. The reaction is performed between 0° C. and 40° C., preferably at 25° C. When the reaction is complete, the product is removed by filtration. The resin is successively washed with the solvent used during the reaction, optionally containing TFA. The product and the washings are collected, and solvent removed in vacuo.

Specific examples illustrating the preparation of compounds of the general formula (Iq) according to the invention are provided below.

EXAMPLE 422

General Procedure (R)

3-{4-[N-(3,5-Dichlorobenzyl)-N'-(4-trifluoromethoxybenzoyl)hydrazinomethyl]benzoylamino}propionic acid

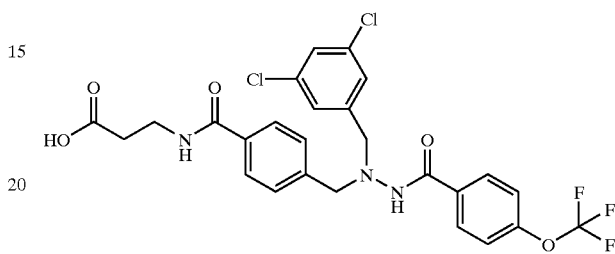

Step C: Resin bound 3-{4-[N'-(4-trifluoromethoxybenzoyl)hydrazinomethyl]benzoylamino}propionic acid Resin bound 3-[4-(bromomethyl)benzoylamino]propionic acid (50 mg; 0.05 mmol) prepared as described under general procedure (A), was suspended in DMSO for an hour. Solvent was removed by filtration, and a solution of 4-trifluoromethoxybenzoylhydrazide (110 mg; 0.5 mmol) in DMSO (1 mL) was added. The reaction mixture was stirred at 80° C. for 16 hours, before removing excess of reagent by filtration. The resin was then washed with DMF (3×1 mL) followed by dichloromethane (3×1 mL) to afford 50 mg of resin bounded 3-{4-[N'-(4-trifluoromethoxybenzoyl)hydrazinomethyl]benzoylamino}propionic acid.

Step D: Resin bound 3-{4-[N-(3,5-Dichlorobenzyl)-N'-(4-trifluoromethoxybenzoyl)hydrazinomethyl]benzoylamino}propionic acid To resin bound intermediate obtained as above was added a mixture of 3,5-dichloro-benzaldehyde (175 mg, 1.0 mmol) and acetic acid (0.1 mL) in trimethyl orthoformate (1.0 mL). The resin was stirred for 2 h at ambient temperature. Sodium cyanoborohydride (63 mg, 1.0 mmol) dissolved in DMF (1.0 mL) was then added and the mixture was left stirred at room temperature for 16 h. Excess of reagent was removed by filtration, and the resin was washed with DMF (3×1 mL) followed by dichloromethane (8×).

Step E: 3-{4-[N-(3,5-Dichlorobenzyl)-N'(4-trifluoromethoxybenzoyl)hydrazinomethyl]benzoylamino}propionic acid To the resin obtained above was added 2 mL of 50% of TFA in dichloromethane. After stirring for 30 min. at 25° C., the solvent was removed by filtration. The resin was washed twice with 50% of TFA in dichloromethane, and the combined filtrate and washings were taken to dryness by speed vacuum centrifugation, to leave the title compound as a light coloured oil. The product was characterised by analytical LC-MS and NMR.

¹H NMR (DMSO): δ 9.62 (s, 1H); 8.47 (t, 1H); 7.80 (d, 2H); 7.70 (d, 2H); 7.52 (s, 2H); 7.49 (d, 2H); 7.42 (d, 2H); 4.22 (s, 2H); 4.16 (s, 2H).

HPLC-MS (Method B): m/z=584.2 (M+1). $R_t$=7.11 min.

EXAMPLE 423

General Procedure (R)

3-{4-[N-[4-(1,1-Dimethylpropyl)cyclohexyl]-N'-(4-trifluoromethoxybenzoyl)hydrazinomethyl]benzoylamino}propionic acid

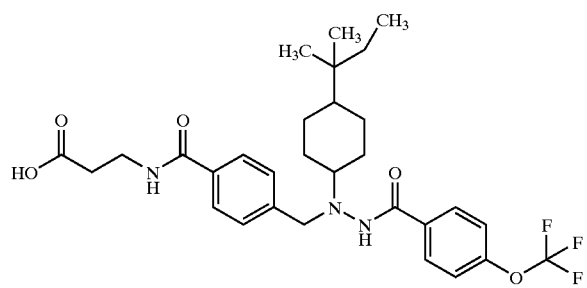

$^1$H NMR (DMSO): δ 9.21 (s, 1H); 8.42 (s, 1H); 7.73 (dd, 4H); 7.49 (d, 2H); 7.40 (d, 2H); 4.11 (s, 2H); 1.20 (t, 3H); 1.04 (q, 2H); 0,74 (s, 6H).

HPLC-MS (Method B): m/z=578.2 (M+1). R$_t$=7.74 min.

EXAMPLE 424

General Procedure (R)

3-{4-[N-(4-tert-Butylcyclohexyl)-N'-(4-trifluoromethoxybenzoyl)hydrazinomethyl]benzoylamino}propionic acid

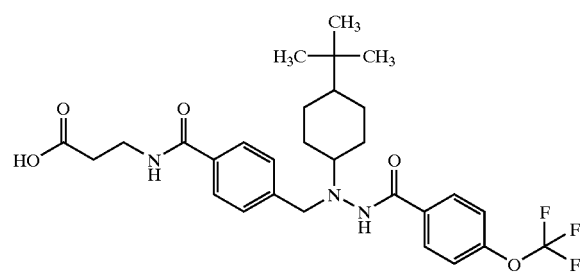

$^1$H NMR (DMSO): δ 9.20 (s, 1H); 8.42 (t, 1H); 7.72 (dd, 4H); 7.50 (d, 2H); 7.40 (d, 2H); 4.14 (s, 2H); 0.84 (s, 9H).

HPLC-MS (Method B): m/z=564.4 (M+1). R$_t$=7.47 min.

EXAMPLE 425

General Procedure (R)

3-{4-[N-(Octahydro-4,7-methanoinden-5-yl)-N'-(4-trifluoromethoxybenzoyl)hydrazinomethyl]benzoylamino}propionic acid

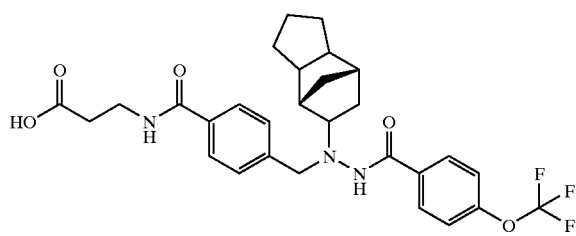

$^1$H NMR (DMSO): δ 9.29 (s, 1H); 8.46 (t, 1H); 7.75 (d, 2H); 7.70 (d, 2H); 7.47 (d, 2H); 7.40 (d, 2H).

HPLC-MS (Method B): m/z=560.4 (M+1). R$_t$=7.51 min.

EXAMPLE 426

General Procedure (R)

3-{4-[N-(4-Phenylcyclohexyl)-N'-(4-trifluoromethoxybenzoyl)hydrazinomethyl]benzoylamino}propionic acid

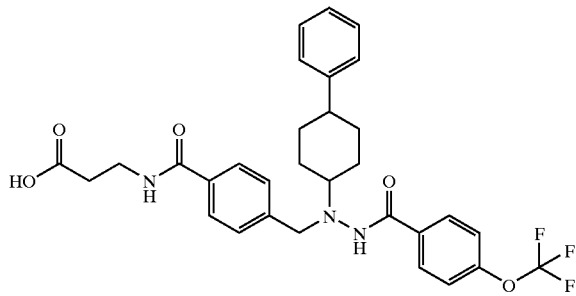

$^1$H NMR (DMSO): δ 9.38 (s, 1H); 8.46 (t, 1H); 7.76 (d, 2H); 7.71 (d, 2H); 7.53 (d, 2H); 7.40 (d, 2H); 7.18–7.43 (m, 5H); 4.18 (s, 2H).

HPLC-MS (Method B): m/z=584.4 (M+1). R$_t$=7.01 min.

EXAMPLE 427

General Procedure (R)

3-{4-[N-(Decahydronaphthalen-2-yl)-N'-(4-trifluoromethoxybenzoyl)hydrazinomethyl]benzoylamino}propionic acid

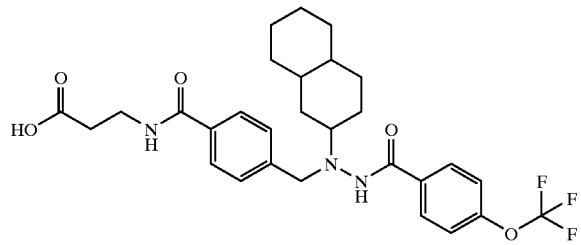

$^1$H NMR (DMSO): δ 9.23 (s, 1H); 8.42 (t, 1H); 7.72 (dd, 4H); 7.50 (d, 2H); 7.42 (d, 2H); 4.15 (s, 2H).

HPLC-MS (Method B): m/z=562.4 (M+1). R$_t$=7.24 min.

EXAMPLE 428

General Procedure (R)

3-{4-[N'-(3,5-Bis(trifluoromethyl)benzoyl)-N-(4-tert-butylcyclohexyl)hydrazinomethyl]benzoylamino}propionic acid

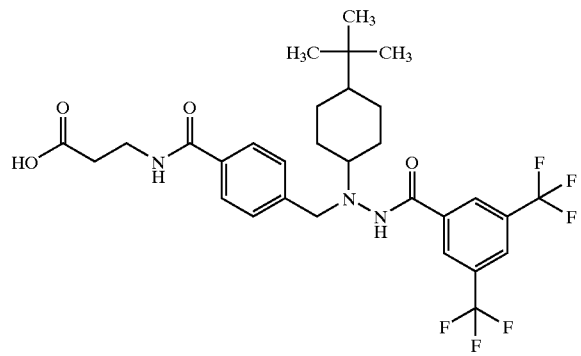

$^1$H NMR (DMSO): δ 9.55 (s, 1H); 8.46 (t, 1H); 8.26 (s, 2H); 7.75 (d, 2H); 7.50 (d, 2H); 4.18 (s, 2H); 0.85 (s, 9H).

HPLC-MS (Method B): m/z=616.4 (M+1). R$_t$=8.11 min.

EXAMPLE 429

3-{4-[N-(trans-4-tert-Butylcyclohexyl)-N'-(4-trifluoromethoxybenzoyl)hydrazinomethyl]benzoylamino}propionic acid

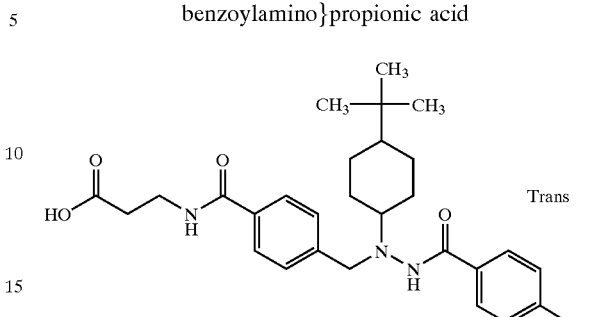

To an ice-cooled solution of hydrazine hydrate (16 mL, 25% (w/w), 125 mmol) in THF (100 mL) was added a solution of 4-trifluoromethoxybenzoyl chloride (4.3 g, 19.2 mmol) in THF (50 mL) over 30 min. The solution was stirred for a further 30 min and then diluted with ether (200 mL). The turbid organic solution was then washed with water (3×200 mL) and brine (200 mL). After drying (Na$_2$SO$_4$), solvent was removed by rotary evaporation. The solid residue was dissolved in ethanol/water (1:1, 200 mL), insoluble material was filtered off, and the filtrate taken to dryness to leave 3.63 g (86%) of pure 4-trifluoromethoxybenzoic acid hydrazide.

$^1$H NMR (DMSO-d$_6$), 300 MHz: δ 9.90 (s, 1H); 7.92 (d, 2H); 7.45 (d, 2H), 4.52 (bs, 2H).

HPLC-MS (Method B): R$_t$=4.04 min, m/z=221 (M+1).

The above 4-trifluoromethoxybenzoic acid hydrazide (3.60 g, 16.3 mmol) and 4-tert-butyl-cyclohexanone (2.52 g, 16.3 mmol) was dissolved in ethanol (150 mL) and the solution was heated to reflux. After 30 min, powdered sodium borohydride (0.96 g, 25.2 mmol) was carefully added, and the mixture stirred for an additional 30 min at reflux. The reaction was cooled to 25° C., and remains of sodium borohydride were quenched by addition of acetic acid (10 mL). The volume of the reaction mixture was reduced to one third by rotary evaporation before adding water (100 mL) and diethyl ether (200 mL). The organic phase was then collected, washed once with brine and dried over anhydrous Na$_2$SO$_4$. The organic phase was taken to dryness, and the residual oil purified by column chromatography (silica gel G 60, ethyl acetate/heptane (1:4)) to afford the pure trans and cis isomers of 4-trifluoromethoxybenzoic acid N'-(4-tert-butylcyclohexyl)hydrazide.

trans isomer: TLC: R$_f$=0.10 ethyl acetate/heptane (1:4).

$^1$H NMR (DMSO-d$_6$), 300 MHz: δ 10.04 (s, 1H); 7.94 (d, 2H); 7.45 (d, 2H); 4.98 (bs, 1H); 2.65 (m, 1H); 1.06–1.95 (m, 4H); 0.86–1.12 (m, 5H); 0.80 (s, 9H).

cis isomer: TLC: R$_f$=0.25 ethyl acetate/heptane (1:4).

$^1$H NMR (DMSO-d$_6$), 300 MHz: δ 10.02 (s, 1H); 7.96 (d, 2H); 7.45 (d, 2H); 4.89 (bs, 1H); 3.08 (s, 1H); 1.85 (m, 2H); 1.31–1.52 (m, 6H); 0.95 (m, 1H); 0.85 (s, 9H).

trans-3-{4-[N-(4-tert-Butylcyclohexyl)-N'-(4-trifluoromethoxybenzoyl)hydrazinomethyl]benzoylamino}propionic acid trans-4-Trifluoromethoxybenzoic acid N'-(4-tert-butylcyclohexyl)hydrazide (715 mg, 2 mmol) was dissolved in DMSO (8 mL), and added to 3-[4-(bromomethyl)

benzoyl]aminopropionic acid derivatized Wang resin (2.0 g, loading app. 0.5 mmol/g) prepared as described in example 1. The mixture was heated to 80° C. for 24 hours, and then cooled. After draining, the resin was washed with DMSO (3×), DMF (3×) and dichloromethane (10×). A 50% TFA/ dichloromethane solution (8 mL) was then added, and the mixture was left for 30 min at 25° C. The supernatant was collected, and the resin subsequently washed once with a 50% TFA/dichloromethane solution (8 mL). The combined supernatant and washing were taken to dryness by rotary evaporation, to leave a brown oil. Further purification by column chromatography (silica G60, 400 mesh, 48% ethyl acetate, 48% heptane, 4% acetic acid), and crystallization (ethanol/water) gave the title compound as fine needles.

$R_f$=0.15 ethyl acetate/heptane (1:1).

$^1$H NMR (DMSO-$d_6$), 300 MHz: δ 12.18 (s, 1H); 9.20 (s, 1H); 8.42 (t, 1H); 7.74 (d, 2H); 7.72 (d, 2H); 4.47 (d, 2H); 7.38 (d, 2H); 4.12 (s, 2H); 3.42 (dt, 2H); 2.82 (m, 1H); 2.50 (t, 2H); 2.04 (bd, 2H); 1.77 (bd, 2H); 1.24 (m, 2H); 0.96 (m, 3H); 0.82 (s, 9H).

HPLC-MS (Method B): $R_t$=7.57 min, m/z=564 (M+1).

General Procedure (S) for the Solid Phase Synthesis of Compounds of the General Formula (Ib)

Steps B and C are modified compared to general procedure (C) so that step C is a reductive amination of a resin bound aldehyde or ketone:

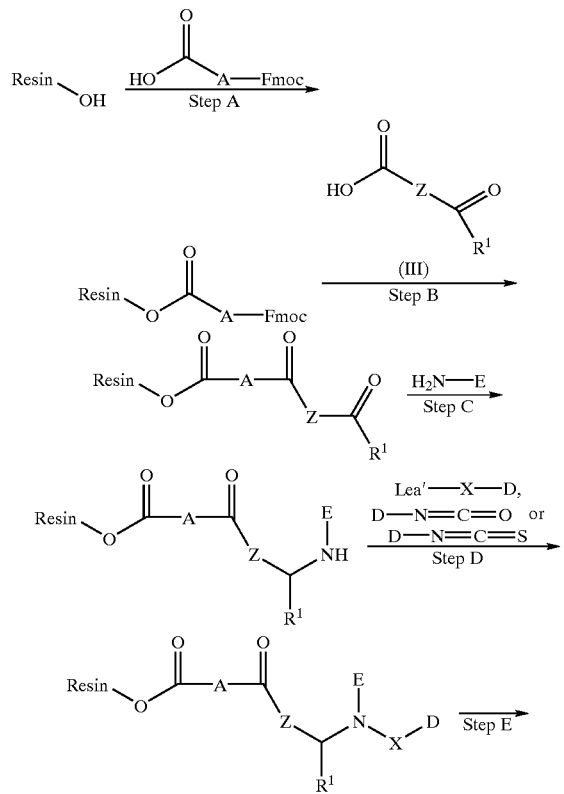

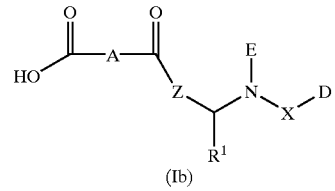

(Ib)

wherein
A, Z, $R^1$, E and D are as defined for formula (I),
X is —S(O)$_2$—(CH$_2$)$_r$—, —C(O)NH— or —C(S)NH—, wherein r is as defined for formula (I),
Lea' is a leaving group such as —OSu, chloro, phenoxy or 4-nitrophenoxy, and
Resin denotes a polystyrene resin with a linker such as the Wang linker:

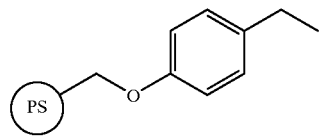

wherein PS denotes polystyrene.

Step B:

The Fmoc protecting group is removed using a solution of 20% piperidine in DMF which is added to the resin and vortexed for 0.5 hours. After draining the resin is washed with DMF containing 1-hydroxybenzotriazole (50 mg/mL) and DMF.

The acylation (The combinatorial index, Ed. Bunin, B. A. 1998, Academic Press, p. 78) is performed by adding an excess of acid (III) in a solvent such as DMF, N-methylpyrrolidinone, THF, dichloromethane, 1,2-dichloroethane, acetonitrile, DMSO or a mixture of two or more of these, optionally in the presence of a base such as N-methylmorpholine, triethylamine, diisopropylethylamine, dicyclohexylmethylamine or another tertiary amine, followed by a coupling reagent such as dicyclohexylcarbodiimide, diisopropylcarbodiimide, 1,1'-carbonyldiimidazole, 2-(1H-9-azabenzotriazole-1-yl)-1,1,3,3-tetramethyluronium hexafluorophosphate or bromo-tris-pyrrolidinophosphonium hexafluorophosphate in a solvent such as DMF, N-methylpyrrolidinone, THF, dichloromethane, 1,2-dichloroethane, acetonitrile, DMSO or a mixture of two or more of these, optionally in the presence of a side reaction inhibitor such as 3-hydroxy-4-oxo-3,4-dihydro-1,2,3-benzotriazine, N-hydroxybenzotriazole or 1-hydroxy-7-azabenzotriazole. The reaction is performed between 20° C. and 40° C., preferably at 25° C. Excess reagents are filtered off and the resin is washed several times with the solvent used during the reaction.

Step C:

The reaction is generally known (The combinatorial index, Ed. Bunin, B. A. 1998, Academic Press, p. 133) and is generally performed by stirring resin bound aldehyde or ketone with an excess of amine at low pH (by addition of an acid, such as acetic acid or formic acid) in a solvent such as THF, DMF, N-methylpyrrolidinone, methanol, ethanol, DMSO, dichloromethane, 1,2-dichloroethane, trimethyl orthoformate, triethyl orthoformate, or a mixture of two or more of these. As reducing agent sodium cyanoborohydride may be used. The reaction is performed between 20° C. and 120° C., preferably at 25° C.

EXAMPLE 430

General Procedure (S)

3-{4-[1-(4-Bromophenyl)-3-(4-trifluoromethoxyphenyl)ureidomethyl]benzoylamino}propionic acid

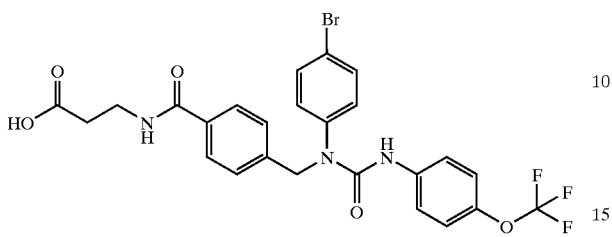

$^1$H NMR (DMSO): δ 6.52 (2H, d), 7.20 (2H, d), 7.43 (2H, d), 7.77 (2H, d), 8.47 (1H, t).

Step A: Resin bound Fmoc β-alanine

150 μmol Fmoc β-alanine was dissolved in 500 μL of a mixture of DMF and diisopropylethylamine (430:70) and added to 50 mg polystyrene resin functionalised with a Wang linker. 200 μmol PyBrOP dissolved in DMF (500 μL) was added. After shaking the suspension for 4 hours at 25° C., the resin was isolated by filtration and washed with 3×1 mL DMF.

Step B: Resin bound 3-(4-formylbenzoylamino)propionic acid

To the above resin bound Fmoc β-alanine was added 1000 μL of a 20% solution of piperidine in DMF. Upon shaking for 30 min, the resin was drained and washed with 1 mL DMF containing 1-hydroxybenzotriazole (50 mg/mL) and DMF (2×1 mL). Then 200 μmol 4-formylbenzoic acid (30 mg) and diisopropylethylamine (70 μL) were dissolved in DMF (430 μL) and added to the resin followed by 200 μmol PyBrOP dissolved in DMF (500 μL). The mixture was shaken for 4 hours at 25° C. followed by filtration and washing of the resin with DMF (3×1 mL) and trimethylorthoformate (1×1 mL).

Step C: Resin bound 3-{4-[(4-bromophenylamino)methyl]benzoylamino}propionic acid The above resin bound 3-(4-formylbenzoylamino)propionic acid (50 mg) was treated with a solution of 4-bromoaniline (500 μmol) in a mixture of DMF (500 μL) and trimethylorthoformate (500 μL). Glacial acetic acid (100 μL) was added and the mixture was shaked for 1 hour at 25° C. Sodium cyanoborohydride (750 μmol) suspended in a mixture of DMF and trimethylorthoformate (1:1, 1 mL) was added and the mixture was vortexed at 25° C. for 16 hours followed by filtration and washing with a mixture of DMF and water (4:1, 2×1 mL) followed by 3×1 mL DMF and 2×1 mL dichloromethane to afford the desired product.

Step D: Resin bound 3-{4-[1-(4-bromophenyl)-3-(4-trifluoromethoxyphenyl)ureidomethyl]benzoylamino}propionic acid 200 μmol 4-trifluoromethoxyphenylisocyanate dissolved in 500 μL dichloromethane was added to the above resin bound 3-{4-[(4-bromophenylamino)methyl]benzoylamino}propionic acid (50 mg). Shaking the mixture for 16 hours at 25° C. followed by filtration and washing of the resin with 4×1 mL DMF, 2×1 mL water, 3×1 mL THF and 5×1 mL dichloromethane afforded the resin bound title compound.

Step E: 3-{4-[1-(4-Bromophenyl)-3-(4-trifluoromethoxyphenyl)ureidomethyl]benzoylamino}propionic acid The above resin bound 3-{4-[1-(4-bromophenyl)-3-(4-trifluoromethoxyphenyl)ureidomethyl]benzoylamino}propionic acid (50 mg) was treated with 1 mL 50% TFA in dichloromethane for 1 hour at 25° C. The product was filtered off and the resin was washed with 1 mL dichloromethane. The combined extracts were concentrated in vacuo. The residue was purified by preparative HPLC to afford the title compound.

The following compounds were made according to the general procedure (S):

EXAMPLE 431

General Procedure (S)

3-{4-[1-(2-Chlorobenzyl)-3-(4-trifluoromethoxyphenyl)ureidomethyl]benzoylamino}propionic acid

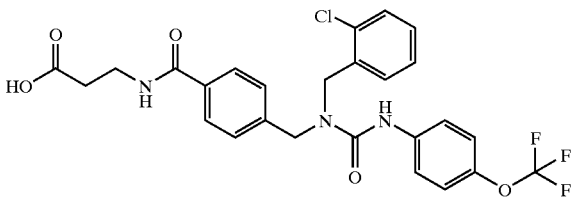

$^1$H NMR (DMSO): δ 4.63 (2H, s), 4.65 (2H, s), 7.2–7.4 (7H, m), 7.47 (1H, d), 7.61 (2H, d), 7.81 (2H, d), 8.49 (1H, t), 8.90 (1H, s).

EXAMPLE 432

General Procedure (S)

3-{4-[1-(3,4-Dichlorobenzyl)-3-(4-trifluoromethoxyphenyl)ureidomethyl]benzoylamino}propionic acid

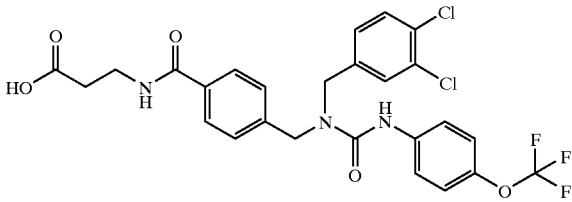

$^1$H NMR (DMSO): δ 8.85 (s, 1H); 8.46 (t, 1H); 7.80 (d, 2H); 7.61 (d, 2H); 7.59 (s, 1H); 7.50 (s, 1H); 7.35 (d, 2H); 7.25 (d, 2H); 7.23 (s, 1H); 4.65 (s, 2H); 4.52 (s, 2H); 3.46 (q, 2H); 2.50 (t, 2H).

EXAMPLE 433

General Procedure (S)

3-{4-[1-(4-Isopropylbenzyl)-3-(4-trifluoromethoxyphenyl)ureidomethyl]benzoylamino}propionic acid

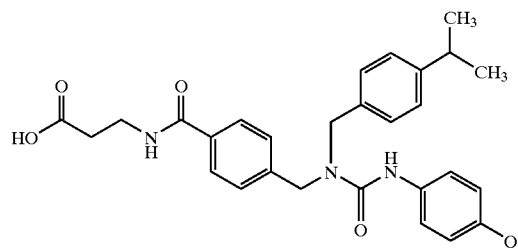

$^1$H NMR (DMSO): δ 8.80 (s, 1H); 8.51 (t, 1H); 7.82 (d, 2H); 7.60 (d, 2H); 7.30 d, 2H); 7.25 (d, 2H); 7.21 (d, 2H); 7.18 (d, 2H); 4.61 (s, 2H); 4.55 (s, 1H); 3.46 (q, 2H); 1.20 (d, 6H).

EXAMPLE 434

General Procedure (S)

3-{4-[1-(4-Piperidin-1-ylphenyl)-3-(4-trifluoromethoxyphenyl)ureidomethyl]benzoylamino}propionic acid

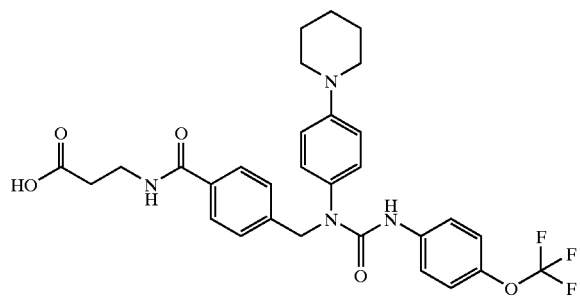

$^1$H NMR (DMSO): δ 8.46 (t, 1H); 8.10 (s, 1H); 7.78 (d, 2H); 7.55 (d, 2H); 7.35 (d, 2H); 7.25 (d, 2H); 7.12 (d, 2H); 7.05 (d, 2H); 4.90 (s, 2H).

General Procedure (T) for the Solid Phase Synthesis of Compounds of the General Formula (Ij)

Alternatively, the solid support used in general procedure (S) can be a 2-chlorotrityl polystyrene resin.

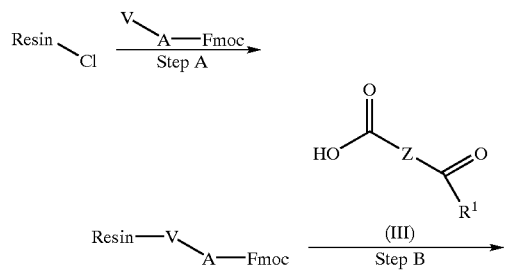

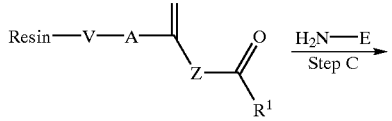

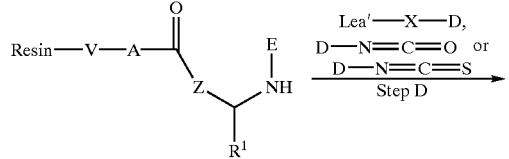

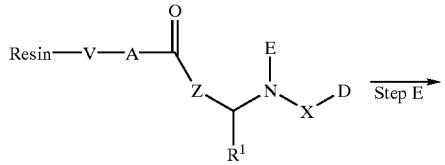

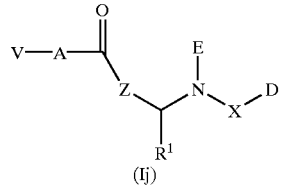

(Ij)

wherein

V, A, Z, R$^1$, E and D are as defined for formula (I),

X is —C(O)NH— or —C(S)NH— and

Lea' is a leaving group such as —OSu, chloro, phenoxy or 4-nitrophenoxy.

Step A:

The reaction is known (The combinatorial index, Ed. Bunin, B. A. 1998, Academic Press, p. 24) and is generally performed by shaking a suspension of the resin with a solution of a nucleophilic Fmoc protected amine (V-A-Fmoc) in the presence of a base such as triethylamine, diisopropylethylamine, dicyclohexylmethylamine or any other tertiary amine. Typical solvents are pyridine, dichloromethane, 1,2-dichloroethane, DMF, N-methylpyrrolidinone, THF, DMSO or mixtures of two or more of these. The reaction is performed between 20° C. and 120° C., preferably at 25° C. Excess reagents are filtered off and the resin is washed with any solvent mentioned above including mixtures hereof, containing a base as mentioned above and an alcohol, typically methanol, as a scavenger of unreacted resin bound 2-chlorotritylchloride.

Step B:

Step B is identical to step B of general procedure (S).

Step C:

Step C is identical to step C of general procedure (S).

Step D:

Step D is identical to step D of general procedure (S).

Step E:

Step E is identical to step E of general procedure (S).

EXAMPLE 435

General Procedure (T)

3-{4-[1-(4-Butoxyphenyl)-3-(4-trifluoromethoxyphenyl)ureidomethyl]benzoylamino}propionic acid

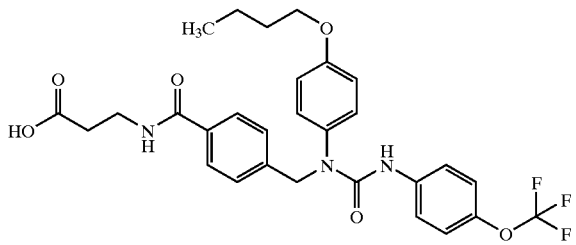

Step A: Resin bound Fmoc β-alanine

150 μmol Fmoc β-alanine was dissolved in a mixture of 250 μL dichloromethane, 250 μL DMF and 100 μL diisopropylethylamine and added to 50 mg polystyrene resin functionalized with a 2-chlorotrityl linker. After shaking the suspension for 4 hours at 25° C., the resin was isolated by filtration and washed with 2×1 mL dichloromethane: methanol:diisopropylethylamine 17:2:1 and 2×1 mL DMF.

Step B: Resin bound 3-(4-formylbenzoylamino)propionic acid

To the above resin bound Fmoc β-alanine was added 500 μL of a 20% solution of piperidine in DMF. After 30 min of shaking, the resin was drained and washed with 1 mL DMF containing 1-hydroxybenzotriazole (50 mg/mL) and DMF (2×1 mL). Then 200 μmol 4-formylbenzoic acid (30 mg) and 200 μmol HOBt (31 mg) dissolved in DMF (500 μL) were added to the resin followed by 200 μmol diisopropyl carbodiimide (DIC, 25.2 mg) dissolved in acetonitrile (500 μL). The mixture was shaken for 4 hours at 25° C. followed by filtration and washing of the resin with DMF (3×1 mL).

Step C: Resin bound 3-{4-[(4-Butoxyphenylamino)methyl]benzoylamino}propionic acid The above resin bound 3-(4-formylbenzoylamino)propionic acid (50 mg) was treated with a 0.5 M solution of 4-butoxyaniline (0.25 mmol, 41.25 mg) in a mixture of DMF and trimethyl-orthoformate (1:1, 0.5 mL) and glacial acetic acid (50 μL) for 1 hour at 25° C. Sodium cyanoborohydride (250 μmol, 16 mg) dissolved in a mixture of DMF and methanol (1:1, 0.25 mL) was added, and the mixture was vortexed at 25° C. for 4 hours followed by filtration and washing with a mixture of DMF and methanol (1:1, 2×1 mL) 3×1 mL DMF and 2×1 mL dichloromethane to afford the desired product.

Step D: Resin bound 3-{4-[1-(4-Butoxyphenyl)-3-(4-trifluoromethoxyphenyl)ureidomethyl]benzoylamino}propionic acid 200 μmol 4-trifluoromethoxyphenylisocyanate dissolved in 500 μL dichloroethane was added to the above resin bound 3-{4-[(4-butoxyphenylamino)methyl]benzoylamino}propionic acid (50 mg). Shaking the mixture 5 hours at 25° C. followed by filtration and washing of the resin with 2×1 mL dichloromethane, 4×1 mL DMF, 2×1 mL H₂O, 3×1 mL THF and 3×1 ml dichloromethane afforded the resin bound title compound.

Step E: 3-{4-[1-(4-Butoxyphenyl)-3-(4-trifluoromethoxyphenyl)ureidomethyl]benzoylamino}propionic acid The above resin bound 3-{4-[1-(4-butoxyphenyl)-3-(4-trifluoromethoxyphenyl)ureidomethyl]benzoylamino}propionic acid (50 mg) was treated with 1 mL 5% TFA in dichloromethane for 1 hour at 25° C. The product was filtered off and the resin was washed with 1 mL dichloromethane. The combined extracts were concentrated in vacuo. The residue was dissolved in 50 μL DMSO+500 μL acetonitrile and purified by preparative HPLC using a Supelcosil ABZ+ 25 cm×10 mm 5μ column. The starting eluent composition was 5% acetonitrile in water changing over 30 min to 90% acetonitrile in water which was then kept constant for 5 min before going back to the starting composition over 10 min. The flow rate was kept constant at 8 mL/min collecting one fraction pr. minute. The process was monitored using an UV detector operating at 214 nm. The fractions containing the desired product were combined and evaporated in vacuo to afford the title compound.

$^1$H NMR (400 MHz, DMSO-d$_6$): δ 12.20 (s br, 1H); 8.50 (t, 1H); 8.09 (s, 1H); 7.73 (d, 2H); 7.55 (d, 2H); 7.30 (d, 2H); 7.20 (d, 2H); 7.10 (d, 2H); 6.90 (d, 2H); 4.90 (s, 2H); 3.95 (t, 2H); 3.45 (m, 2H); 2.50 (t, 2H); 1.60 (k, 2H) 1.42 (sx, 2H); 0.95 (t, 3H).

The following examples can be made as described above.

EXAMPLE 436

General Procedure (T)

3-{4-[1-Quinolin-3-yl-3-(4-trifluoromethoxyphenyl)ureidomethyl]benzoylamino}propionic acid

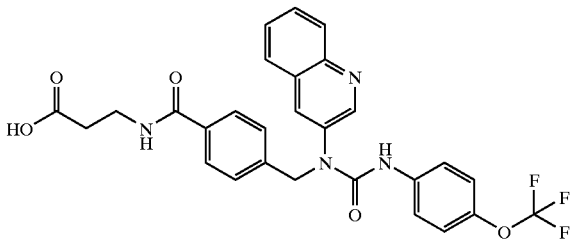

$^1$H NMR (400 MHz, DMSO-d$_6$): δ 12.20 (s br, 1H); 8.80 (m, 2H); 8.45 (t, 1H); 8.25 (s, 1H); 8.00 (d, 2H); 7.95 (d, 2H); 7.78 (m, 3H); 7.60 (t, 1H); 7.55 (d, 2H); 7.38 (d, 2H); 7.24 (d, 2H); 5.12 (s, 2H); 3.45 (m, 2H); 2.50 (t, 2H).

EXAMPLE 437

General Procedure (T)

3-{4-[3-(4-Trifluoromethoxyphenyl)-1-(4-trifluoromethylphenyl)ureidomethyl]benzoylamino}propionic acid

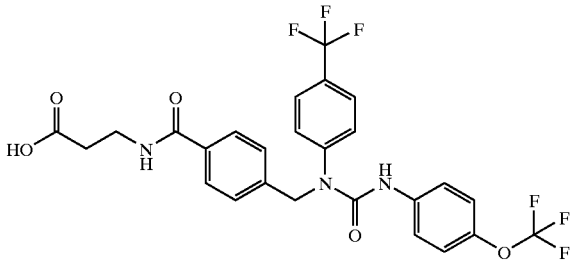

$^1$H NMR (400 MHz, DMSO-d$_6$): δ 12.15 (s br, 1H); 8.95 (s, 1H); 8.48 (t, 1H); 7.75 (d, 2H); 7.68 (d, 2H); 7.58 (d, 2H); 7.50 (d, 2H); 7.35 (d, 2H); 7.25 (d, 2H); 5.10 (s, 2H); 3.45 (m, 2H); 2.50 (t, 2H).

EXAMPLE 438

General Procedure (T)

3-{4-[1,3-Bis(4-trifluoromethoxyphenyl)ureidomethyl]benzoylamino}propionic acid

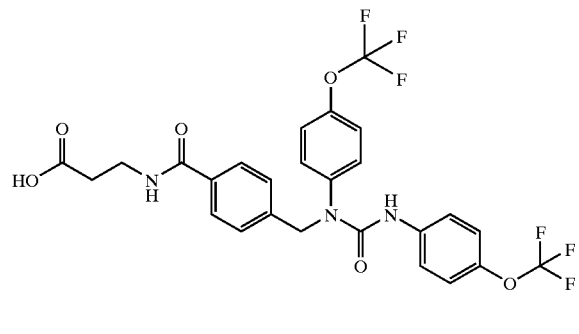

$^1$H NMR (400 MHz, DMSO-d$_6$): δ 12.25 (s br, 1H); 8.65 (s, 1H); 8.48 (t, 1H); 7.75 (d, 2H); 7.55 (d, 2H); 7.35 (m, 6H); 7.22 (d, 2H); 5.00 (s, 2H); 3.40 (m, 2H); 2.50 (t, 2H).

EXAMPLE 439

General Procedure (T)

3-{4-[1-(4-Propylphenyl)-3-(4-trifluoromethoxyphenyl)ureidomethyl]benzoylamino}propionic acid

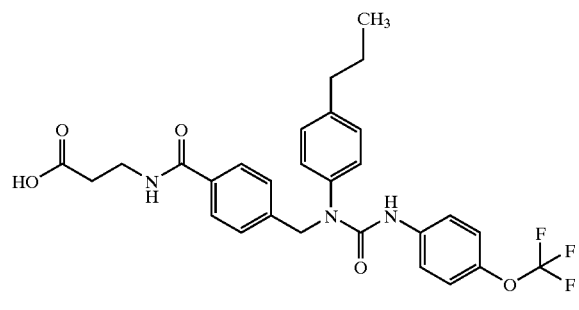

$^1$H NMR (300 MHz, DMSO-d$_6$): δ 12.20 (s, 1H); 8.45 (t, 1H); 8.30 (s, 1H); 7.73 (d, 2H); 7.52 (d, 2H); 7.32 (d, 2H); 7.20–7.10 (m, 6H); 4.95 (s, 2H); 3.45 (m, 2H); 2.50 (m, 4H); 1.60 (sx, 2H); 0.90 (t, 3H).

EXAMPLE 440

General Procedure (T)

3-{4-[1-(4-Butyl-2-methylphenyl)-3-(4-trifluoromethoxyphenyl)ureidomethyl]benzoylamino}propionic acid

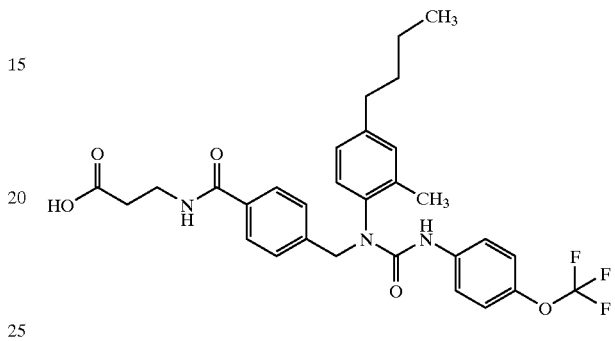

$^1$H NMR (300 MHz, DMSO-d$_6$): δ 12.20 (s br, 1H); 8.45 (t, 1H); 7.87 (s, 1H); 7.75 (d, 2H); 7.52 (d, 2H); 7.30 (d, 2H); 7.22 (d, 2H); 7.10 (s, 1H) 7.05 (d, 1H); 6.95 (d, 1H); 5.15–4.85 (d br, 2H); 3.45 (m, 2H); 2.55–2.50 (m, 4H); 1.60 (k, 2H); 1.32 (sx, 2H); 0.90 (t, 3H).

EXAMPLE 441

General Procedure (T)

3-{4-[1-(4-Isopropylphenyl)-3-(4-trifluoromethoxyphenyl)ureidomethyl]benzoylamino}propionic acid

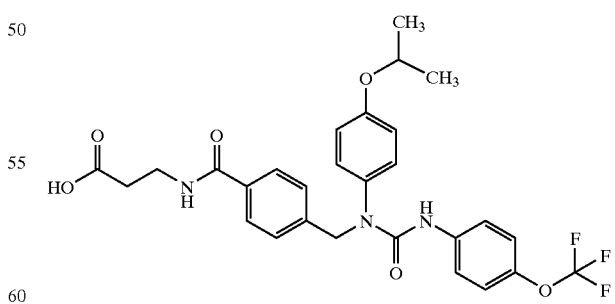

$^1$H NMR (DMSO-d$_6$): δ 8.47 (t, 1H); 8.10 (s, 1H); 7.75 (d, 2H); 7.56 (d, 2H); 7.36 (d, 2H); 7.23 (d, 2H); 7.12 (d, 2H); 6.90 (d, 2H); 4,92 (s, 2H); 4.60 (q, 1H); 1.25 (d, 6H).

EXAMPLE 442

General Procedure (T)

3-{4-[1-(4-Ethoxyphenyl)-3-(4-trifluoromethoxyphenyl)ureidomethyl]benzoylamino}propionic acid

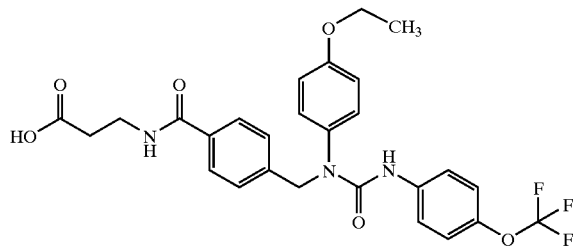

$^1$H NMR (DMSO-d$_6$): δ 8.46 (t, 1H); 8.06 (s, 1H); 7.78 (d, 2H); 7.56 (d, 2H); 7.34 (d, 2H); 7.22 (d, 2H); 7.14 (d, 2H); 6.92 (d, 2H); 4.91 (s, 2H); 4.01 (q, 2H); 1.32 (t, 3H).

EXAMPLE 443

General Procedure (T)

3-{4-[1-(4-Cyclohexylphenyl)-3-(3-nitrophenyl)ureidomethyl]benzoylamino}propionic acid

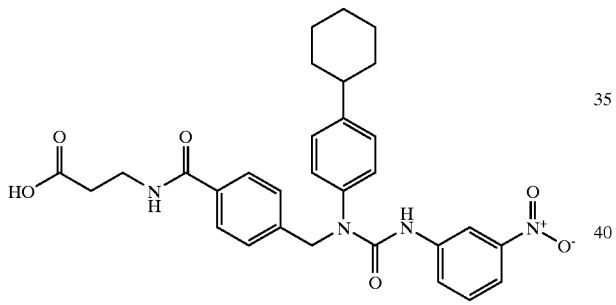

$^1$H NMR (DMSO-d$_6$): δ 12.20 (s br, 1H); 8.78 (s, 1H); 8.45 (s+t, 2H); 7.92 (d, 1H); 7.80 (d, 1H); 7.75 (d, 2H); 7.50 (t, 1H) 7.30 (d, 2H); 7.20 (d, 2H); 7.15 (d, 2H); 4.95 (s, 2H); 3.45 (m, 2H); 2.50 (t, 2H); 1.90–1.10 (m, 11H).

HPLC-MS (Method B): m/z=545 (M+1). R$_t$=7.47 min.

General Procedure (U) for the Solid Phase Synthesis of Compounds of the General Formula (Ir)

Alternatively, molecules of general formula (Ii) obtained by the previously described general method (T) may be modified after step D. This applies to all general procedures comprising a step similar to step D of procedure (T):

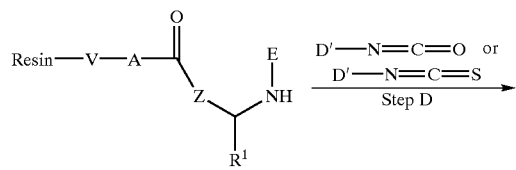

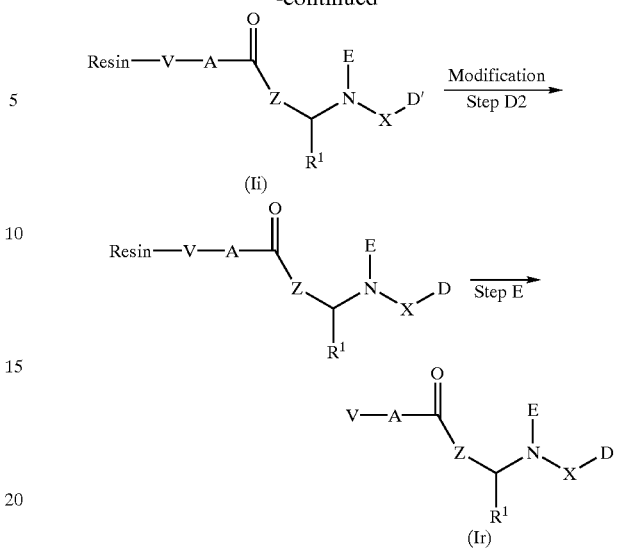

wherein
A, V, Z, R$^1$, E and D are as defined for formula (I),
D' is a subgroup of D containing functionalities that may be further derivatized like sulfides, sulfoxides, or esters,
X is

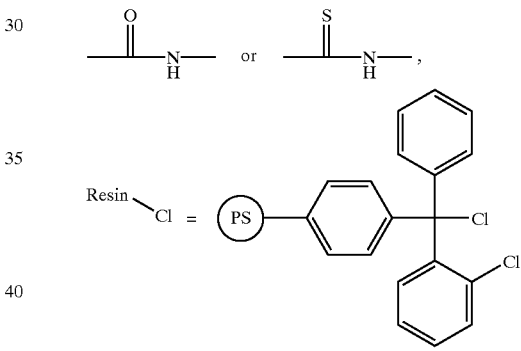

Step D2: Oxidation of Sulfides or Sulfoxides

The reaction is known (The combinatorial index, Ed. Bunin, B. A. 1998, Academic Press, p. 132) and is performed by treating the resin bound intermediate with an oxidizing agent like 3-chloroperoxybenzoic acid or peracetic acid in a solvent like dichloromethane, 1,2-dichloroethane, THF or a mixture thereof. The reaction is performed between 20° C. and 120° C., preferably at 25° C. Excess reagents are filtered off and the resin is washed with dichloromethane, 1,2-dichloroethane, DMF, N-methylpyrrolidinone, THF, DMSO or mixtures of two or more of these.

Step D2: Derivatization of Esters

Ester hydrolysis. The reaction is known (Hoekstra et al, Bioorg. Med. Chem. Lett. 1996, 6, 2371–2376) and is performed by treating the resin bound intermediate with a solution of potassium trimethylsilanolate in a solvent like THF or dioxan. The reaction is performed between 20° C. and 120° C., preferably at 25° C. Excess reagents are filtered off and the resin is washed with dichloromethane, 1,2-dichloroethane, dioxan, DMF, N-methylpyrrolidinone, THF, DMSO or mixtures of two or more of these in combination with an acid like acetic acid to afford the corresponding resin bound carboxylic acid.

The above resin bound carboxylic acid is converted into an active ester by the use of pentafluorophenyl trifluoroacetate or 4-nitrophenyl trifluoroacetate in the presence of pyridine in a solvent such as DMF, N-methylpyrrolidinone, THF, dichloromethane, 1,2-dichloroethane, acetonitrile, DMSO or a mixture of two or more of these. The reaction is performed between 20° C. and 40° C., preferably at 25° C. Excess reagents are filtered off and the resin is washed several times with the solvent used during the reaction.

The above resin bound active ester is allowed to react with nucleophiles like ammonia, primary or secondary amines, N-hydroxyamidines or hydrazides to afford resin bound carboxylic acid derivatives.

EXAMPLE 444

General Procedure (U))

4-[1-(4-Cyclohexylphenyl)-3-(3-methylsulfonylphenyl)ureidomethyl]-N-(2H-tetrazol-5-yl)benzamide

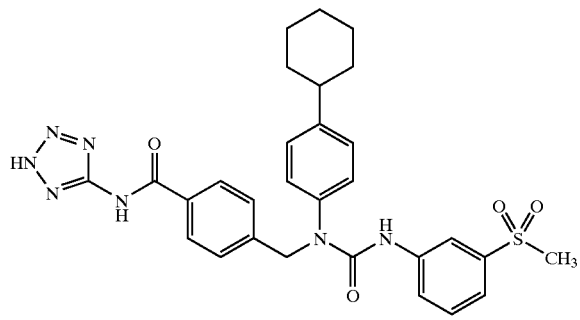

Step A: Resin bound 4-formyl-N-(2H-tetrazol-5-yl)benzamide

150 μmol 4-formyl-N-(2H-tetrazol-5-yl)benzamide was dissolved in a mixture of 250 μL dichloromethane, 250 μL DMF and 100 μL diisopropylethylamine and added to 50 mg polystyrene resin functionalized with 2-chlorotrityl chloride. After shaking the suspension for 4 hours at 25° C., the resin was isolated by filtration and washed with 2×1 mL dichloromethane:methanol:diisopropylethylamine 17:2:1 and 2×1 mL DMF.

Step C: Resin bound 4-[(4-cyclohexylphenylamino)methyl]-N-(2H-tetrazol-5-yl)benzamide The above resin bound 4-formyl-N-(2H-tetrazol-5-yl)benzamide (50 mg) was treated with a 0.5 M solution of 4-cyclohexylaniline (0.25 mmol, 41.25 mg) in a mixture of DMF and trimethylorthoformate (1:1, 0.5 mL) and glacial acetic acid (50 μL) for 1 hour at 25° C. followed sodium cyanoborohydride (250 μmol, 16 mg) dissolved in a mixture of DMF and methanol (1:1, 0.25 mL). Shaking at 25° C. for 4 hours followed by filtration and washing with a mixture of DMF and methanol (1:1, 2×1 mL), 3×1 mL DMF and 2×1 mL dichloromethane afforded the desired product.

Step D: Resin bound 4-[1-(4-cyclohexylphenyl)-3-(3-methylsulfanylphenyl)ureidomethyl]-N-(2H-tetrazol-5-yl)benzamide 200 μmol 3-Thiomethylphenylisocyanate dissolved in 500 μL dichloroethane was added to the above resin bound 4-[(4-cyclohexylphenylamino)methyl]-N-(2H-tetrazol-5-yl)benzamide (50 mg). Shaking the mixture 5 hours at 25° C. followed by filtration and washing with 2×1 mL dichloromethane, 4×1 mL DMF, 2×1 mL H$_2$O, 3×1 mL THF and 3×1 mL dichloromethane afforded the resin bound title compound.

Step D2: Resin bound 4-[1-(4-Cyclohexylphenyl)-3-(3-methylsulfonylphenyl)ureidomethyl]-N-(2H-tetrazol-5-yl)benzamide To the above resin bound 4-[1-(4-cyclohexylphenyl)-3-(3-methylsulfanylphenyl)ureidomethyl]-N-(2H-tetrazol-5-yl)benzamide was added a solution of 3-chloroperbenzoic acid (2.0–2.8 mmol) in 1,2-dichloroethane (500 μL). The mixture was shaken overnight at 25° C. Filtration followed by washing of the resin with dichloromethane (2×1 mL) afforded the resin bound title compound.

Step E: 4-[1-(4-Cyclohexylphenyl)-3-(3-methylsulfonylphenyl)ureidomethyl]-N-(2H-tetrazol-5-yl)benzamide The above resin bound 4-[1-(4-cyclohexylphenyl)-3-(3-methylsulfonylphenyl)ureidomethyl]-N-(2H-tetrazol-5-yl)benzamide (50 mg) was washed with DMF (4×1 mL), H$_2$O (2×1 mL), THF (3×1 mL) and dichloromethane (3×1 mL) and treated with 1 mL 5% TFA in dichloromethane for 1 hour at 25° C. The product was filtered off and the resin was washed with 1 mL dichloromethane. The combined extracts were concentrated in vacuo. The residue was dissolved in 50 μL DMSO+500 μL acetonitrile and purified by preparative HPLC using a Supelcosil ABZ+ 25 cm×10 mm 5μ column. The starting eluent composition was 5% acetonitrile in water changing over 30 min to 90% acetonitrile in water which was then kept constant for 5 min before going back to the starting composition over 10 min. The flow rate was kept constant at 8 mL/min collecting one fraction pr. minute. The process was monitored using an UV detector operating at 214 nm. The fractions containing the desired product were combined and evaporated in vacuo to afford the title compound.

$^1$H NMR (300 MHz, DMSO-d$_6$): δ 12.30 (s br, 1H); 8.70 (s, 1H); 8.05 (d, 2H); 7.75 (m, 1H); 7.52–7.42 (m, 4H); 7.20 (s, 4H); 5.00 (s, 2H); 3.15 (s, 3H); 1.85–1.60 (m, 5H); 1.50–1.15 (m, 6H).

HPLC-MS (method B) m/z=574, R$_t$=7.18 min.

The following examples can be made as described above.

EXAMPLE 445

General Procedure (U)

4-[1-(4-tert-Butylcyclohexyl)-3-(3-methylsulfonylphenyl)ureidomethyl]-N-(2H-tetrazol-5-yl)benzamide

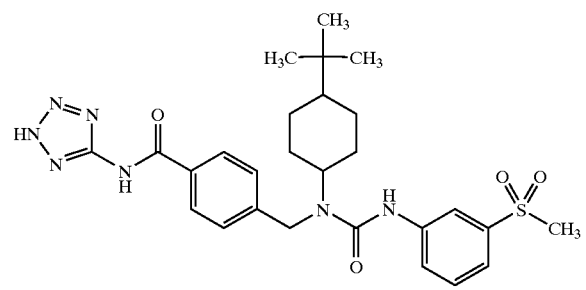

$^1$H NMR (300 MHz, DMSO-d$_6$): δ 12.30 (s br, 1H); 8.82 (s, 1H); 8.05 (d, 2H); 8.15–8.00 (m, 3H); 7.78 (d, 1H); 7.55–7.45 (m, 4H); 4.65 (s, 2H); 4.10 (t br, 1H); 3.13 (s, 3H); 1.83–0.90 (m, 9H); 0.85 (s, 9H).

HPLC-MS (method B) m/z=554, R$_t$=7.12 min.

EXAMPLE 446

General Procedure (U)

4-[1-(4-sec-Butylphenyl)-3-(3-methylsulfonylphenyl)ureidomethyl]-N-(2H-tetrazol-5-yl)benzamide

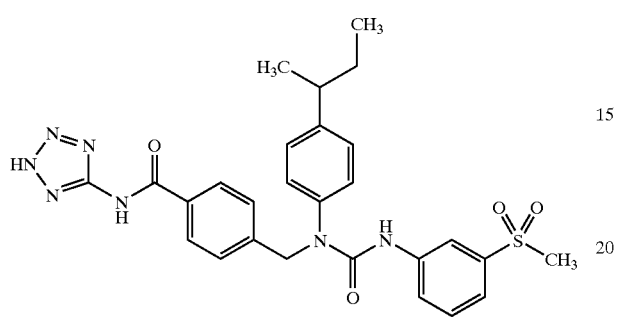

$^1$H NMR (300 MHz, DMSO-d$_6$): δ 12.35 (s br, 1H); 8.65 (s, 1H); 8.10–8.00 (m, 4H); 7.75 (m, 1H); 7.52–7.42 (m, 4H); 7.20 (s, 4H); 5.00 (s, 2H); 3.15 (s, 3H); 2.55 (q, 1H); 1.55 (k, 2H); 1.20 (d, 3H); 0.75 (t, 3H).

HPLC-MS (method B) m/z=548, R$_t$=6.03 min.

EXAMPLE 447

General Procedure (U)

4-[1-(4-Butylphenyl)-3-(3-methylsulfonylphenyl)ureidomethyl]-N-(2H-tetrazol-5-yl)benzamide

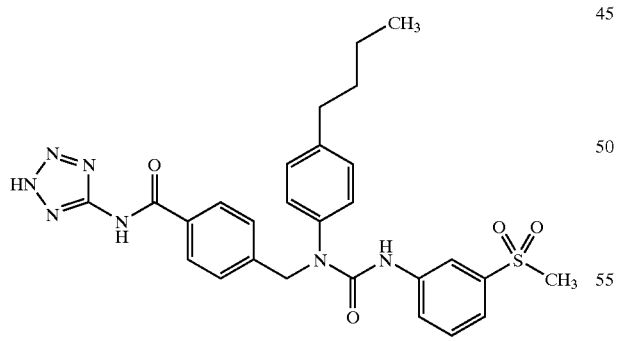

$^1$H NMR (DMSO-d$_6$): δ 0.90 (3H, t), 1.42 (2H, sixtet), 1.57 (2H, pentet), 2.58 (2H, partly hidden by DMSO), 3.15 (3H, s), 5.02 (2H, s), 7.21 (4H, s), 7.45–7.52 (4H, m), 7.85 (1H, m), 8.0–8.1 (3H, m), 8.61 (1H, s), 12.4 (1H, bs).

HPLC-MS (Method B): R$_t$=6.37 min, m/z=548 (M+1).

EXAMPLE 448

General Procedure (U)

4-[1-(4-sec-Butylphenyl)-3-(4-methylsulfonylphenyl)ureidomethyl]-N-(2H-tetrazol-5-yl)benzamide

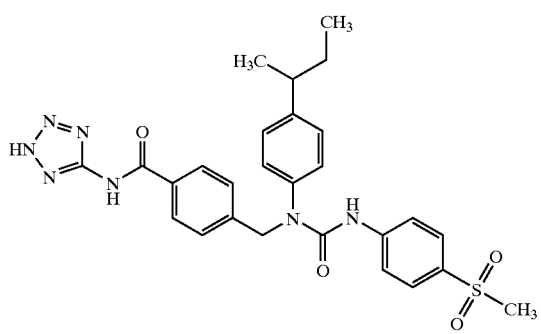

$^1$H NMR (300 MHz, DMSO-d$_6$): δ 12.30 (s br, 1H); 8.72 (s, 1H); 8.05 (d, 2H); 7.75 (d, 2H); 7.70 (d, 2H); 7.45 (d, 2H); 7.20 (s, 4H); 5.00 (s, 2H); 3.11 (s, 3H); 2.60 (q, 1H); 1.55 (k, 2H); 1.20 (d. 3H); 0.75 (t, 3H).

HPLC-MS (method B) m/z=548, R$_t$=6.03 min.

EXAMPLE 449

General Procedure (U) 4-[1-(4-tert-Butylphenyl)-3-(3-methylsulfonylphenyl)ureidomethyl]-N-(2H-tetrazol-5-yl)benzamide

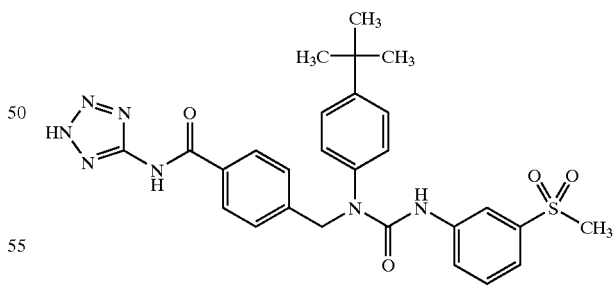

$^1$H NMR (DMSO-d$_6$): δ 1.30 (9H, s), 3.18 (3H, s), 5.03 (2H, s), 7.24 (2H, d), 7.41 (2H, d), 7.45–7.55 (8H, m), 7.85 (1H, m), 8.05 (2H, d), 8.08 (1H, s), 8.70 (1H, s), 12.4 (1H, bs).

HPLC-MS (Method B): R$_t$=5.97 min, m/z=548 (M+1).

EXAMPLE 450

General Procedure (U)

4-[3-(3-Methylsulfonylphenyl)-1-(4-trifluoromethoxyphenyl)ureidomethyl]-N-(2H-tetrazol-5-yl)benzamide

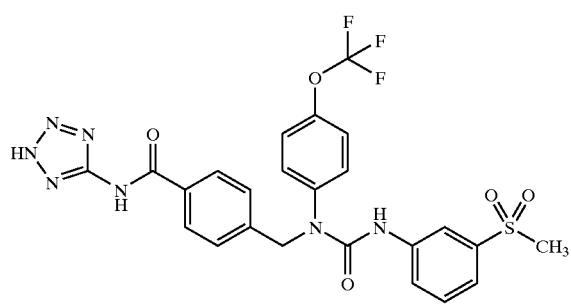

$^1$H NMR (300 MHz, DMSO-d$_6$): δ 12.35 (s, 1H); 8.85 (s, 1H); 8.05 (d, 2H); 7.75 (m, 1H); 7.55–7.35 (m, 9H); 7.20 (s, 4H); 5.05 (s, 2H); 3.15 (s, 3H).

HPLC-MS (method B) m/z=576, R$_t$=5.42 min.

EXAMPLE 451

General Procedure (U)

4-[3-(4-Methylsulfonylphenyl)-1-(4-trifluoromethoxyphenyl)ureidomethyl]-N-(2H-tetrazol-5-yl)benzamide

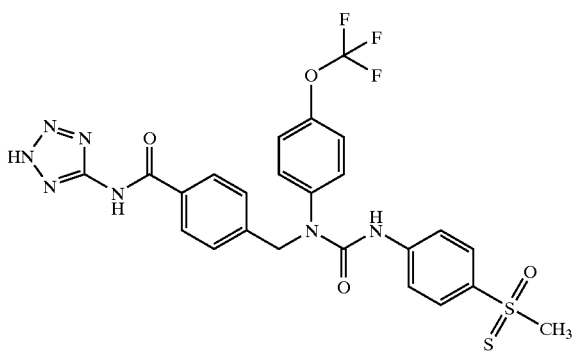

$^1$H NMR (300 MHz, DMSO-d$_6$): δ 12.35 (s, 1H); 8.95 (s, 1H); 8.05 (d, 2H); 7.70 (d, 2H); 7.65 (d, 2H); 7.49 (d, 2H); 7.43 (d, 2H), 7.45 (d, 2H); 5.05 (s, 2H); 3.12 (s, 3H).

HPLC-MS (method B) m/z=576, R$_t$=5.42 min.

EXAMPLE 452

General Procedure (U)

4-[3-(3-Ethylsulfonylphenyl)-1-(4-trifluoromethoxyphenyl)ureidomethyl]-N-(2H-tetrazol-5-yl)benzamide

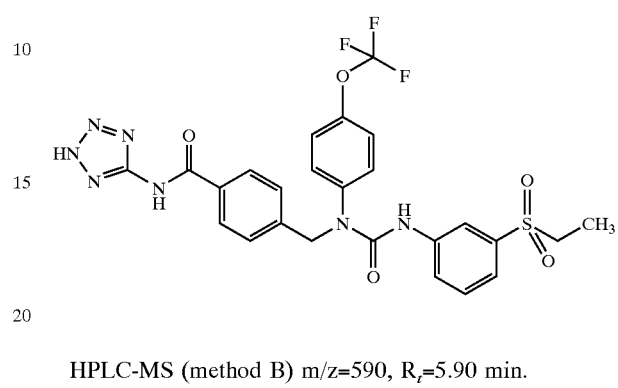

HPLC-MS (method B) m/z=590, R$_t$=5.90 min.

EXAMPLE 453

General Procedure (U)

4-[1-(4-Cyclohexylphenyl)-3-(3-ethylsulfonylphenyl)ureidomethyl]-N-(2H-tetrazol-5-yl)benzamide

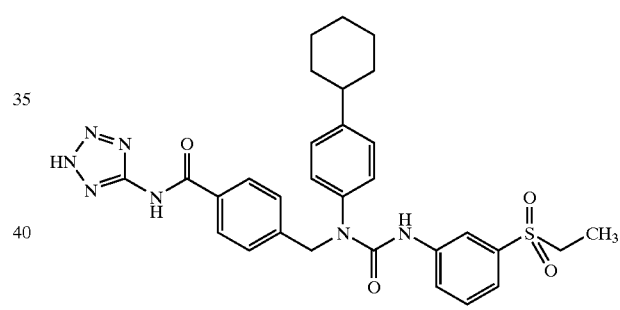

HPLC-MS (method B) m/z=588, R$_t$=7.10 min.

EXAMPLE 454

General Procedure (U)

4-[1-(4-tert-Butylphenyl)-3-(3-ethylsulfonylphenyl)ureidomethyl]-N-(2H-tetrazol-5-yl)benzamide

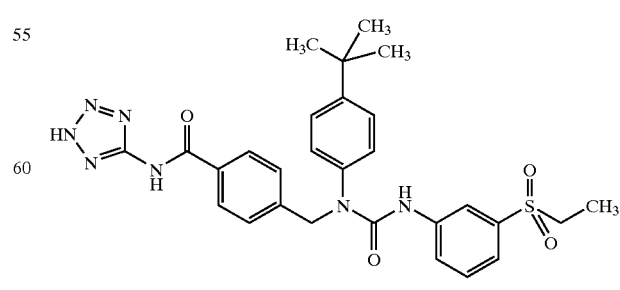

HPLC-MS (method B) m/z=561, R$_t$=6.40 min.

EXAMPLE 455

General Procedure (U)

4-[1-(4-Cyclohexylphenyl)-3-(4-trifluoromethylsulfonylphenyl)ureidomethyl]-N-(2H-tetrazol-5-yl)benzamide

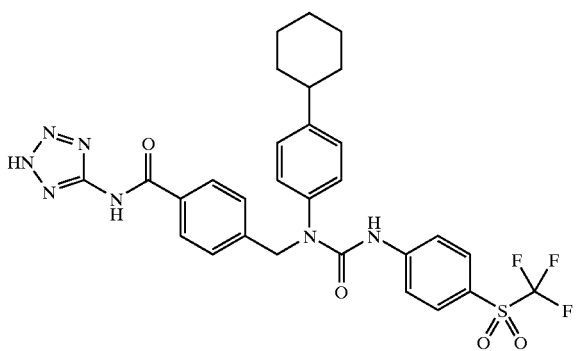

$^1$H NMR (DMSO-d$_6$): δ 9.20 (1H, broad), 7.90 (5H, m), 7.79 (1H, dd), 7.44 (2H, d), 7.21 (4H, s), 5.00 (2H, broad), 1.90–1.00 (10H, m).

HPLC-MS (method B): m/z: 628, R$_t$=8.05 min.

EXAMPLE 456

General Procedure (U)

3-{3-(4-tert-Butylphenyl)-3-[4-(2H-tetrazol-5-ylcarbamoyl)benzyl]ureido}benzoic acid

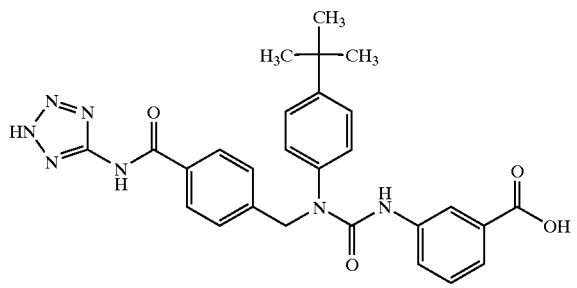

Step A: Resin bound 4-formyl-N-(2H-tetrazol-5-yl)benzamide

1500 μmol 4-formyl-N-(2H-tetrazol-5-yl)benzamide was dissolved in a mixture of 2500 μL dichloromethane, 2500 μL DMF and 1000 μL diisopropylethylamine and added to 500 mg polystyrene resin functionalized with 2-chlorotrityl chloride. After shaking the suspension for 4 hours at 25° C., the resin was isolated by filtration and washed with 2×10 mL dichloromethane:methanol:diisopropylethylamine 17:2:1 and 2×10 mL DMF.

Step C: Resin bound 4-[(4-tert-butylphenylamino)methyl]-N-(2H-tetrazol-5-yl)benzamide The above resin bound 4-formyl-N-(2H-tetrazol-5-yl)benzamide (500 mg) was treated with a 0.5 M solution of 4-tert-butylaniline (2.5 mmol, 412.5 mg) in a mixture of DMF and trimethyl-orthoformate (1:1, 5 mL) and glacial acetic acid (500 μL) for 1 hour at 25° C. followed by sodium cyanoborohydride (2.5 mmol, 160 mg) dissolved in a mixture of DMF and methanol (1:1, 2.5 mL). Shaking at 25° C. for 4 hours followed by filtration and washing with a mixture of methanol and DMF (1:1, 2×10 mL), DMF(3×10 mL) and dichloromethane (2×10 mL) afforded the desired product.

Step D: Resin bound 3-{3-(4-tert-butylphenyl)-3-[4-(2H-tetrazol-5-ylcarbamoyl)benzyl]ureido}benzoic acid methyl ester 2.50 mmol 3-isocyanatobenzoic acid methyl ester dissolved in 5 mL dichloroethane was added to the above resin 4-[(4-tert-butylphenylamino)methyl]-N-(2H-tetrazol-5-yl)benzamide (500 mg). Shaking the mixture 5 hours at 25° C. followed by filtration and washing of the resin with dichloromethane (2×10 mL), DMF (2× mL) and THF (3×10 mL) afforded the resin bound title compound.

Step D2: Derivatization of Esters

Resin bound 3-{3-(4-tert-butylphenyl)-3-[4-(2H-tetrazol-5-ylcarbamoyl)benzyl]ureido}benzoic acid To the above resin bound 3-{3-(4-tert-butylphenyl)-3-[4-(2H-tetrazol-5-ylcarbamoyl)benzyl]ureido}benzoic acid methyl ester was added a solution of potassium trimethylsilanolate in THF (1M, 5 mL). The mixture was shaken 4 hours at 25° C., filtered and allowed to react with a solution of acetic acid in THF (20%, 5 mL) at 25° C. overnight. Filtration followed by washing of the resin with dichloromethane (2×10 mL) afforded the resin bound title compound.

Step E: 3-{3-(4-tert-Butylphenyl-3-[4-(2H-tetrazol-5-ylcarbamoyl)benzyl]ureido}benzoic acid The above resin bound 3-{3-(4-tert-butylphenyl)-3-[4-(2H-tetrazol-5-ylcarbamoyl)benzyl]ureido}benzoic acid (500 mg) was washed with DMF (4×10 mL), H$_2$O (2×10 mL), THF (3×10 mL), dichloromethane (3×10 mL) and treated with 10 mL 5% TFA in dichloromethane for 1 hour at 25° C. The product was filtered off and the resin was washed with 10 mL dichloromethane. The combined extracts were concentrated in vacuo. The residue was recrystallised in acetonitrile to afford the title compound.

$^1$H NMR (200 MHz, DMSO-d$_6$): δ 12.90 (s br, 1H); 12.35 (s br, 1H); 8.50 (s, 1H); 8.05 (d, 2H); 7.75 (d, 1H) 7.60–7.15 (m, 8H); 5.00 (s, 2H); 1.22 (s, 9H).

HPLC-MS (method B) m/z=514, R$_t$=5.98 min.

EXAMPLE 457

General Procedure (U)

3-{3-(4-tert-Butylphenyl)-3-[4-(2H-tetrazol-5-ylcarbamoyl)benzyl]ureido}benzoic acid pentafluorophenyl ester

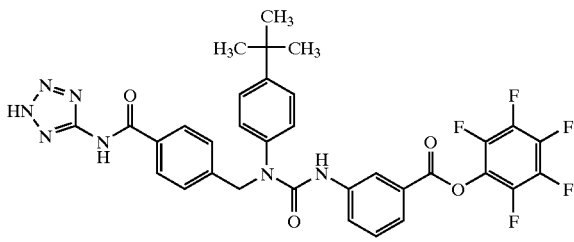

Step D2: Derivatisation of Esters

Resin bound 3-{3-(4-tert-butylphenyl)-3-[4-(2H-tetrazol-5-ylcarbamoyl)benzyl]ureido}benzoic acid pentafluorophenyl ester To the above resin bound 3-{3-(4-tert-butylphenyl)-3-[4-(2H-tetrazol-5-ylcarbamoyl)benzyl]ureido}benzoic acid was added a solution of pyridine (500 μL) in DMF (5 mL) followed by pentafluorophenyl trifluoroacetate (850 μL). The mixture was shaken for 4 hours at 25° C., filtered and washed with DMF (2×10 mL), affording the resin bound title compound.

Step E: 3-{3-(4-tert-Butylphenyl)-3-[4-(2H-tetrazol-5-ylcarbamoyl)benzyl]ureido}benzoic acid pentafluorophenyl ester The above resin bound 3-{3-(4-tert-butylphenyl)-3-[4-(2H-tetrazol-5-ylcarbamoyl)benzyl]ureido}benzoic acid pentafluorophenyl ester (500 mg) was washed with DMF (4×10 mL), H₂O (2×10 mL), THF (3×10 mL), dichloromethane (3×10 mL) and treated with 10 mL 5% TFA in dichloromethane for 1 hour at 25° C. The product was filtered off and the resin was washed with 10 mL dichloromethane. The combined extracts were concentrated in vacuo. The residue was recrystallised in CH₃CN to afford the title compound.

¹H NMR (300 MHz, DMSO-d₆): δ 12.30 (s br, 1H); 8.05 (d, 2H); 8.00–7.60 (m, 2H) 7.55–7.15 (m, 8H); 5.00 (s, 2H); 1.22 (s, 9H).

HPLC-MS (method B) m/z=680, R$_t$=8.27 min.

EXAMPLE 458

General Procedure (U)

N-Methyl-3-{3-(4-tert-butylphenyl)-3-[4-(2H-tetrazol-5-ylcarbamoyl)benzyl]ureido}benzamide

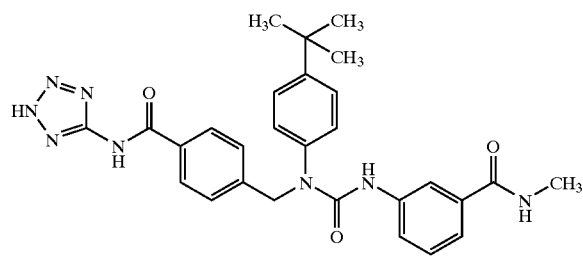

Step D2: Derivatisation of Esters

Resin bound N-methyl-3-{3-(4-tert-butylphenyl)-3-[4-(2H-tetrazol-5-ylcarbamoyl)benzyl]ureido}benzamide To the above resin bound 3-{3-(4-tert-butylphenyl)-3-[4-(2H-tetrazol-5-ylcarbamoyl)benzyl]ureido}benzoic acid pentafluorophenyl ester was added a solution of methylamine in THF (2M, 5 mL). The mixture was shaken at 25° C. overnight, filtered and washed with THF (2×10 mL), affording the resin bound title compound.

Step E: N-Methyl-3-{3-(4-tert-butylphenyl)-3-[4-(2H-tetrazol-5-ylcarbamoyl)benzyl]ureido}benzamide The above resin bound N-methyl-3-{3-(4-tert-butylphenyl)-3-[4-(2H-tetrazol-5-ylcarbamoyl)benzyl]ureido}benzamide (500 mg) was washed with DMF (4×10 mL), H₂O (2×10 mL), THF (3×10 mL), dichloromethane (3×10 mL) and treated with 10 mL 5% TFA in dichloromethane for 1 hour at 25° C. The product was filtered off and the resin was washed with 10 mL dichloromethane. The combined extracts were concentrated in vacuo. The residue was recrystallized from CH₃CN to afford the title compound.

¹H NMR (200 MHz, DMSO-d₆): δ 12.35 (s br, 1H); 8.40 (s, 1H); 8.43 (q, 1H); 8.05 (d, 2H); 7.85 (s, 1H); 7.63 (d, 1H); 7.50–7.15 (m, 8H); 5.03 (s, 2H); 2.80 (d, 3H); 1.25 (s, 9H).

HPLC-MS (method B): m/z=527, R$_t$=5.55 min.

The following examples were made as described above.

EXAMPLE 459

General Procedure (U)

3-{3-(4-tert-Butylphenyl)-3-[4-(2H-tetrazol-5-ylcarbamoyl)benzyl]ureido}benzamide

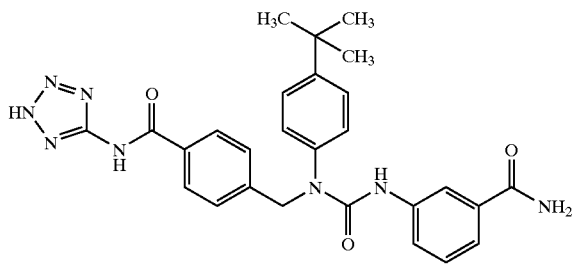

HPLC-MS (method B): m/z=513, R$_t$=5.52 min.

EXAMPLE 460

General Procedure (U)

N-Ethyl-3-{3-(4-tert-butylphenyl)-3-[4-(2H-tetrazol-5-ylcarbamoyl)benzyl]ureido}benzamide

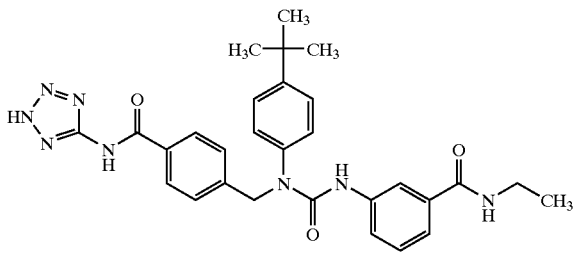

¹H NMR (200 MHz, DMSO-d₆): δ 12.35 (s br, 1H); 8.40 (m, 2H); 8.05 (d, 2H); 7.80 (s, 1H); 7.63 (d, 1H); 7.55–7.15 (m, 8H); 5.03 (s, 2H); 3.30 (dq, 2H); 1.30 (s, 9H); 1.12 (t, 3H).

HPLC-MS (method B): m/z=541, R$_t$=5.83 min.

EXAMPLE 461

General Procedure (U)

N,N-Dimethyl-3-{3-(4-tert-butylphenyl)-3-[4-(2H-tetrazol-5-ylcarbamoyl)benzyl]ureido}benzamide

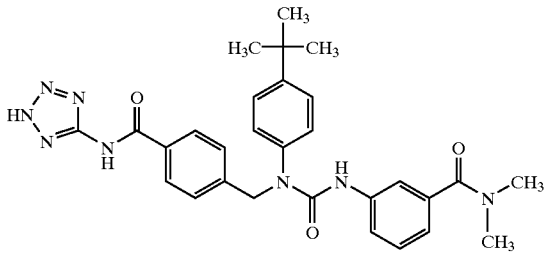

¹H NMR (200 MHz, DMSO-d₆): δ 12.35 (s br, 1H); 8.40 (s, 1H); 8.05 (d, 2H); 7.55–7.15 (m, 9H); 6.98 (d, 1H); 5.03 (s, 2H); 2.95 (d, br, 6H); 1.30 (s, 9H).

EXAMPLE 462

General Procedure (U)

N,N-Diethyl-3-{3-(4-tert-butylphenyl)-3-[4-(2H-tetrazol-5-ylcarbamoyl)benzyl]ureido}benzamide

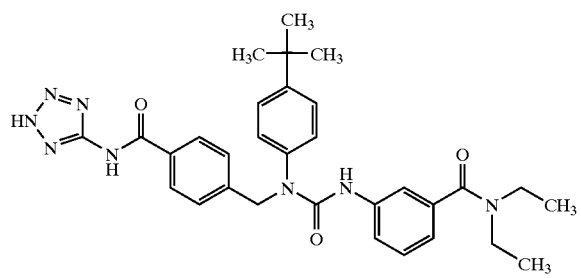

$^1$H NMR (200 MHz, DMSO-d$_6$): δ 12.35 (s br, 1H); 8.40 (s, 1H); 8.05 (d, 2H); 7.50–7.18 (m, 9H); 6.95 (d, 1H); 5.01 (s, 2H); 3.24 (s, br, 4H); 1.30 (s, 9H); 1.10 (s, br, 6H).

HPLC-MS (method B) m/z=569, R$_t$=6.77 min.

EXAMPLE 463

General Procedure (U)

N,N-Dimethyl-3-{3-(4-cyclohexylphenyl)-3-[4-(2H-tetrazol-5-ylcarbamoyl)benzyl]ureido}benzamide

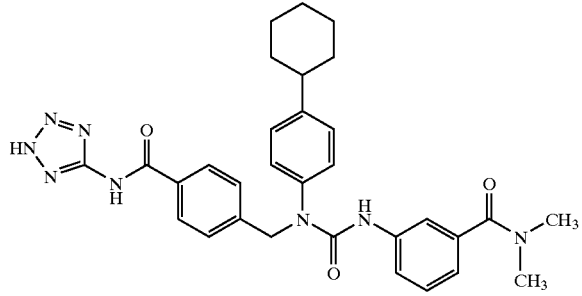

$^1$H NMR (300 MHz, DMSO-d$_6$): δ 12.30 (s br, 1H); 8.35 (s, 1H); 8.05 (d, 2H); 7.50 (m, 4H); 7.20 (m, 5H); 6.95 (d, 1H); 5.00 (s, 2H); 3.15 (s, 3H); 2.94 (d br, 6H); 1.85–1.15 (m, 11H).

HPLC-MS (method B): m/z=567, R$_t$=6.47 min.

EXAMPLE 464

General Procedure (U)

N-Butyl-N-methyl-3-{3-(4-cyclohexylphenyl)-3-[4-(2H-tetrazol-5-ylcarbamoyl)benzyl]ureido}benzamide

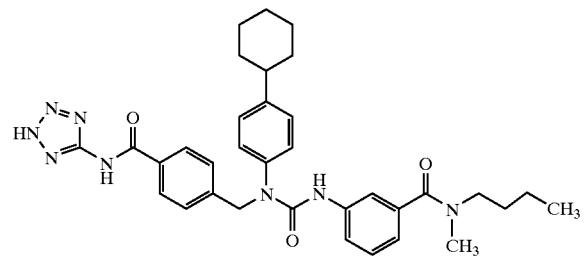

$^1$H NMR (300 MHz, DMSO-d$_6$): δ 12.30 (s br, 1H); 8.35 (s, 1H); 8.05 (d, 2H); 7.48 (m, 4H); 7.35–7.20 (m, 5H); 6.95 (d, 1H); 5.00 (s, 2H); 2.92 (d br, 3H); 1.85–0.70 (m, 18H).

HPLC-MS (method B): m/z=609, R$_t$=7.51 min.

EXAMPLE 465

General Procedure (U)

N-Butyl-3-{3-(4-cyclohexylphenyl)-3-[4-(2H-tetrazol-5-ylcarbamoyl)benzyl]ureido}benzamide

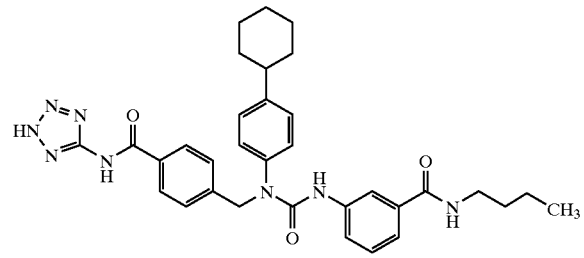

$^1$H NMR (300 MHz, DMSO-d$_6$): δ 11.35 (s br, 1H); 8.55 (m, 2H); 8.05 (d, 2H); 7.70 (s, 1H); 7.62 (d, 1H); 7.42 (m, 3H); 7.35–7.10 (m, 5H); 5.00 (s, 2H); 1.85–1.10 (m, 15H); 0.90 (t, 3H).

HPLC-MS (method B): m/z=595, R$_t$=7.48 min.

EXAMPLE 466

General Procedure (U)

4-[1-(4-Cyclohexylphenyl)-3-(2-methylsulfonylphenyl)ureidomethyl]-N-(2H-tetrazol-5-yl)benzamide

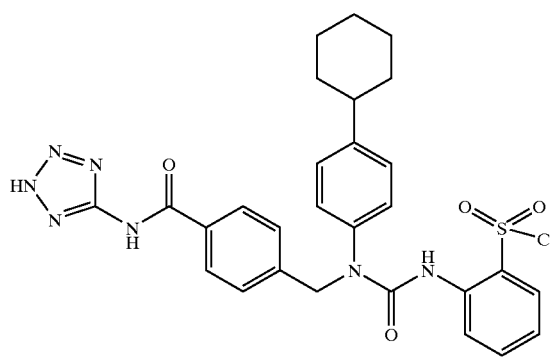

$^1$H NMR (DMSO-d$_6$): δ 12.40 (s, 1H); 8.50–8.45 (s+d, 2H); 8.05 (d, 2H); 7.68 (d, 1H); 7.65 (t, 1H); 7.52 (d, 2H); 7.22 (s, 4H); 7.18 (t, 1H); 5.00 (s, 2H); 3.00 (s, 3H); 1.85–1.65 (m, 5H); 1.50–1.15 (m, 5H)

HPLC-MS (Method B): m/z=574 (M+1). R$_t$=7.38 min

EXAMPLE 467

General Procedure (U)

4-[3-(2-Chloro-5-methylsulfamoylphenyl)-1-(4-cyclohexylphenyl)ureidomethyl]-N-(2H-tetrazol-5-yl)benzamide

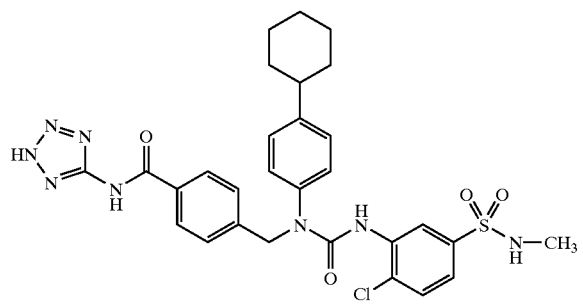

$^1$H NMR (DMSO-d$_6$): δ 8.5 (d, 1H); 7.76 (d br, 2H); 7.60–7.35 (m, 5H); 7.32 (s, 4H); 5.00 (s, 2H); 2.43 (d, 3H); 1.85–1.65 (m, 5H); 1.50–1.15 (m, 5H).

HPLC-MS (Method B): m/z=623 (M+1). R$_t$=7.82 min.

EXAMPLE 468

General Procedure (U)

4-{1-(4-Cyclohexylphenyl)-3-[3-(3-isopropyl-[1,2,4]oxadiazol-5-yl)phenyl]ureidomethyl}-N-(2H-tetrazol-5-yl)benzamide

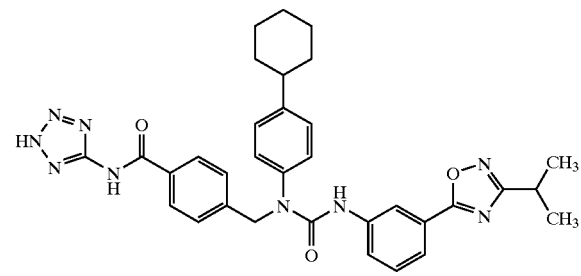

The oxadiazole was prepared by using N-hydroxy-isobutyramidine as nucleophile instead of an amine as described in example 458. After cleavage from the resin, ring closure to the oxadiazole was conducted in refluxing toluene.

$^1$H NMR (DMSO-d$_6$): δ 12.05 (s br, 1H); 8.68 (s, 1H); 8.28 (s, 1H); 8.05 (d, 2H); 7.80 (d, 1H); 7.63 (d, 1H); 7.55–7.45 (m, 3H); 7.20 (s, 4H); 5.04 (s, 2H); 3.12 (h, 1H); 1.85–1.65 (m, 5H); 1.50–1.15 (m+d, 11H).

HPLC-MS (Method B): m/z=624 (M+1). R$_t$=8.07 min.

EXAMPLE 469

General Procedure (U)

3-{4-[1-(4-Cyclohexylphenyl)-3-(3-methylsulfonylphenyl)ureidomethyl]benzoylamino}propionic acid

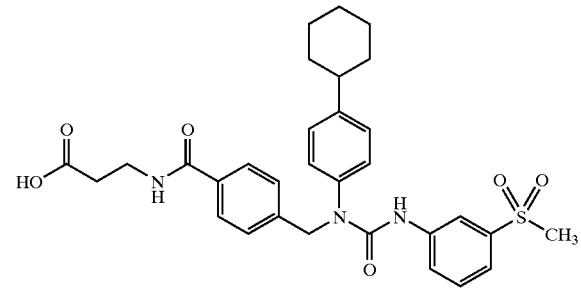

¹H NMR (DMSO-d₆): δ 8.65 (s, 1H); 8.51 (t, 1H); 8.05 (s, 1H); 8.78 (m, 1H); 7.75 (d, 2H); 7.45 (m, 2H); 7.30 (d, 2H); 7.22 (d, 2H); 7.12 (d, 2H); 4.95 (s, 2H); 3.40 (m); 3.15 (s, 3H); 2.43 (t, 2H); 1.90–1.15 (m).

HPLC-MS (Method B): m/z=578 (M+1). $R_t$=6.32 min.

EXAMPLE 470

General Procedure (U)

4-[1-Cyclohexylphenyl)-3-(3-cyclopropylmethylsulfanylphenyl)ureidomethyl]-N-(2H-tetrazol-5-yl)benzamide

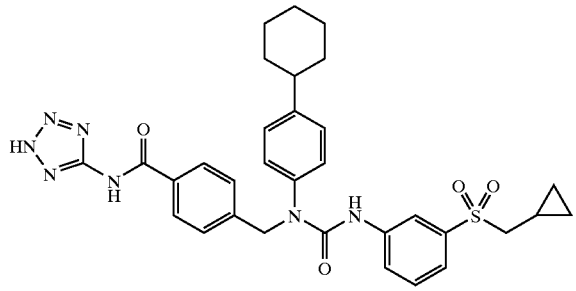

HPLC-MS (method B): m/z: 614, $R_t$=7.35 min.

EXAMPLE 471

General Procedure (U)

4-[1-(4-Cyclohexylphenyl)-3-(3-cyclopentylsulfanylphenyl)ureidomethyl]-N-(2H-tetrazol-5-yl)benzamide

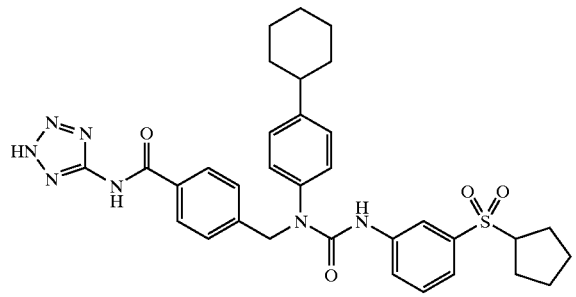

HPLC-MS (method B): m/z: 628, $R_t$=7.55 min.

EXAMPLE 472

General Procedure (U)

4-[1-(4-Cyclohexylphenyl)-3-(3-methylsulfinylphenyl)ureidomethyl]-N-(2H-tetrazol-5-yl)benzamide

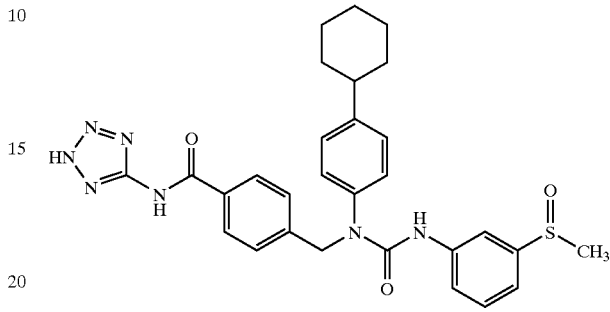

¹H NMR (DMSO-d₆): δ 8.58 (s, 1H), 7.99 (d, 2H), 7.80 (s, 1H), 7.63 (d, 1H), 7.42 (d, 2H), 7.40 (d, 1H), 7.20 (dd, 4H), 5.00 (s, 2H), 2.70 (s, 3H), 1.85–1.15 (m, 10H).

HPLC-MS (method B): m/z: 558, $R_t$=6.22 min.

General Procedure (V) for the Solid Phase Synthesis of Compounds of the General Formula (Ij)

Alternatively, the solid support used in general procedure (B) can be a 2-chlorotrityl polystyrene resin.

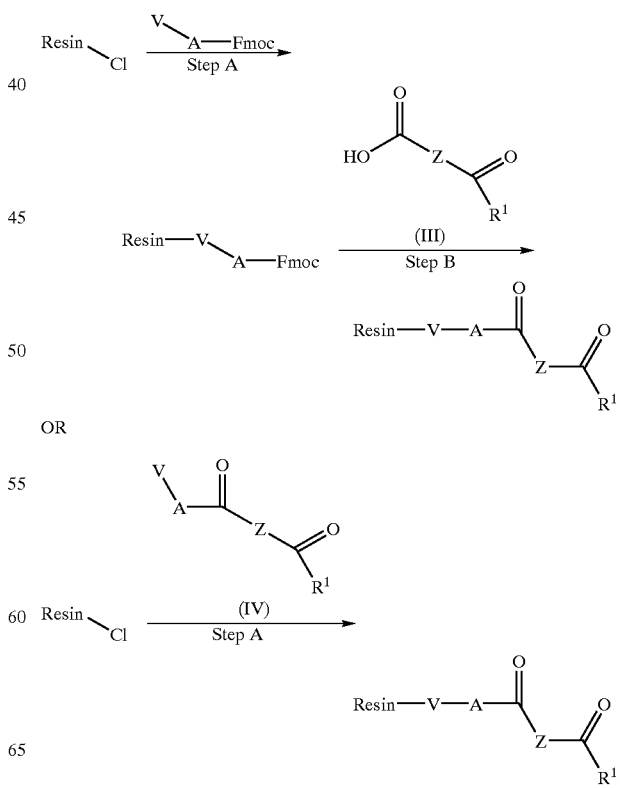

343

-continued

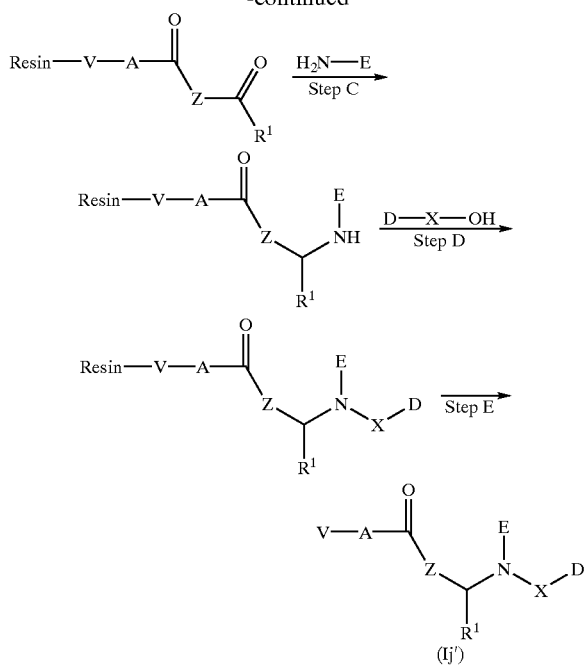

wherein
V, A, Z, $R^1$, E and D are as defined for formula (I), X is

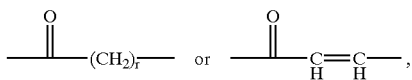

wherein r is as defined for formula (I), and

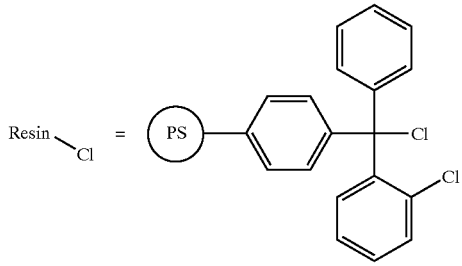

wherein PS is polystyrene.

Step A:

The reaction is known (The combinatorial index, Ed. Bunin, B. A. 1998, Academic Press, p. 24) and is generally performed by shaking a suspension of the resin with a solution of a nucleophilic Fmoc protected amine (V-A-Fmoc) or (IV) in the presence of a base such as triethylamine, diisopropylethylamine, dicyclohexylmethylamine or any other tertiary amine. Typical solvents are pyridine, dichloromethane, 1,2-dichloroethane, DMF, NMP, THF, DMSO or mixtures of two or more of these. The reaction is performed between 20° C. and 120° C., preferably at 25° C. Excess reagents are filtered off and the resin is washed with any solvent mentioned above including mixtures hereof, containing a base as mentioned above and an alcohol, typically methanol, as a scavenger of unreacted resin bound 2-chlorotritylchloride.

344

Step B:
Step B is identical to step B of general procedure (S).
Step C:
Step C is identical to step C of general procedure (S).
Step D:
The acylation (The combinatorial index, Ed. Bunin, B. A. 1998, Academic Press, p. 78) is performed by adding an excess of D-X—OH in a solvent such as DMF, N-methylpyrrolidinone, THF, dichloromethane, 1,2-dichloroethane, 1,2-dichloropropane, acetonitrile, DMSO or a mixture of two or more of these, optionally in the presence of a base such as N-methyl-morpholine, triethylamine, diisopropylethylamine, dicyclohexylmethylamine or another tertiary amine, followed by a coupling reagent such as dicyclohexylcarbodiimide, diisopropylcarbodiimide, 1,1'-carbonyldiimidazole, 2-(1H-9-azabenzotriazole-1-yl)-1,1,3,3-tetramethyluronium hexafluorophosphate (PyBrOP) or bromo-tris-pyrrolidinophosphonium hexafluorophosphate in a solvent such as DMF, N-methylpyrrolidinone, THF, dichloromethane, 1,2-dichloroethane, 1,2-dichloropropane, acetonitrile, DMSO or a mixture of two or more of these, optionally in the presence of a side reaction inhibitor such as 3-hydroxy-4-oxo-3,4-dihydro-1,2,3-benzotriazine, N-hydroxybenzotriazole or 1-hydroxy-7-azabenzotriazole. The reaction is performed between 20° C. and 60° C., preferably at 50° C. Excess reagents are filtered off and the resin is washed several times with the solvent used during the reaction.
Step E:
Step E is identical to step E of general procedure (S).

EXAMPLE 473

General Procedure (V)

Benzo[b]thiophene-2-carboxylic acid (4-tert-butylcyclohexyl)-[4-(2H-tetrazol-5-ylcarbamoyl)benzyl]amide

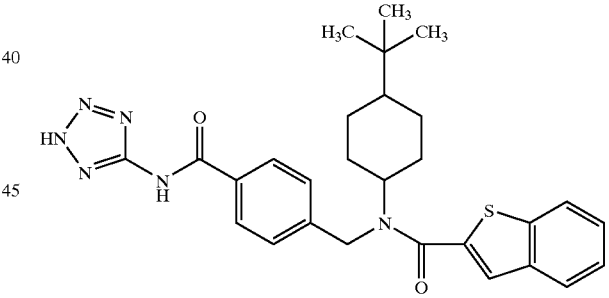

Step A: Resin bound 4-formyl-N-(2H-tetrazol-5-yl)benzamide

150 µmol 4-formyl-N-(2H-tetrazol-5-yl)benzamide was dissolved in a mixture of 250 µL dichloromethane, 250 µL DMF and 100 µL diisopropylethylamine and added to 50 mg polystyrene resin functionalized with 2-chlorotrityl chloride. After shaking the suspension for 4 hours at 25° C., the resin was isolated by filtration and washed with 2×1 mL dichloromethane: methanol:diisopropylethylamine 17:2:1 and 2×1 mL DMF.

Step C: Resin bound 4-[(4-tert-butylcyclohexylamino)methyl]-N-(2H-tetrazol-5-yl)benzamide The above resin bound 4-formyl-N-(2H-tetrazol-5-yl)benzamide (50 mg) was treated with a 0.5 M solution of 4-tert-butylcyclohexylamine (0.25 mmol, 38.75 mg) in a mixture of NMP and trimethylorthoformate (1:1, 0.5 mL) and glacial acetic acid (50 µL) for 1 hour at 25° C. followed by sodium cyanoborohydride (250 μmol, 16 mg) dissolved in a mixture of NMP and methanol (1:1, 0.25 mL). Shaking at 25° C. for 4 hours followed by filtration and washing with a mixture of NMP and methanol (1:1, 2×1 mL), NMP (3×1 mL) and a mixture of 1,2-dichloropropane (DCP) and diisopropylethylamine (7:1, 2×1 mL) afforded the desired product.

Step D: Resin bound benzo[b]thiophene-2-carboxylic acid (4-tert-butylcyclohexyl)-[4-(2H-tetrazol-5-ylcarbamoyl)benzyl]amide To the above resin bound 4-[(4-tert-butylcyclohexylamino)methyl]-N-(2H-tetrazol-5-yl)benzamide was added a solution of benzo[b]thiophene-2-carboxylic acid (400 μmol) in a mixture of NMP, DCP and diisopropylethylamine (4.5:4.5:1, 1 mL) followed by a solution of PyBrOP (400 μmol) in DCP (500 μL). The mixture was allowed to react 3 hours at 50° C. The resin was cooled to 25° C. while washed with NMP (4×1 mL), and DCM (10×1 mL).

Step E: Benzo[b]thiophene-2-carboxylic acid (4-tert-butylcyclohexyl)-[4-(2H-tetrazol-5-ylcarbamoyl)benzyl]amide The above resin bound benzo[b]thiophene-2-carboxylic acid (4-tert-butylcyclohexyl)-[4-(2H-tetrazol-5-ylcarbamoyl)benzyl]amide (50 mg) was treated with 1.2 mL 20% trifluoroacetic acid in dichloromethane for 1 hour at 25° C. The product was filtered off and concentrated in vacuo to afford the title compound.

$^1$H NMR (DMSO): δ 8.14 (d, 2H); 8.1–7.9 (m, 2H); 7.81 (s, 2H); 7.60–7.50 (m, 3H); 3H); 4.96 (s, 1H); 4.89 (s br, 1H).

HPLC-MS (Method D): m/z=517 (M+1). $R_t$=5.80 min.

The following examples can be made as described above.

EXAMPLE 474

General Procedure (V)

3H-Indene-1-carboxylic acid (4-tert-butylcyclohexyl)-[4-(2H-tetrazol-5-ylcarbamoyl)benzyl]amide

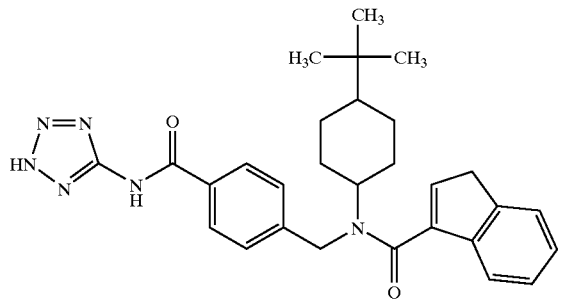

$^1$H NMR (DMSO): δ 8.15 (d, 2H); 7.70–7.30 (m, 6H); 6.82 (d, 1H).

HPLC-MS (Method E): m/z=499 (M+1). $R_t$=3.07 min.

EXAMPLE 475

General Procedure (V)

Benzofuran-2-carboxylic acid (4-tert-butylcyclohexyl)-[4-(2H-tetrazol-5-ylcarbamoyl)benzyl]amide

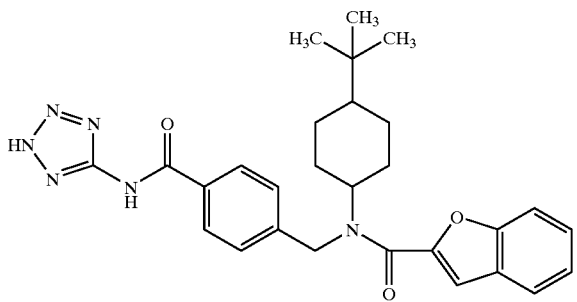

$^1$H NMR (DMSO. Isomers ca 1:1): δ 8.13 (d, 2H); 7.95–7.65 (m, 2H); 7.56 (d, 2H); 7.55–7.30 (m, 2H); 4.88 (s br, 2H); 4.23 (s br, 1H).

HPLC-MS (Method E): m/z=501 (M+1). $R_t$=3.20 min.

EXAMPLE 476

General Procedure (V)

4-{[(4-tert-Butylcyclohexyl)-(3-thiophen-2-ylacryloyl)amino]methyl}-N-(2H-tetrazol-5-yl)benzamide

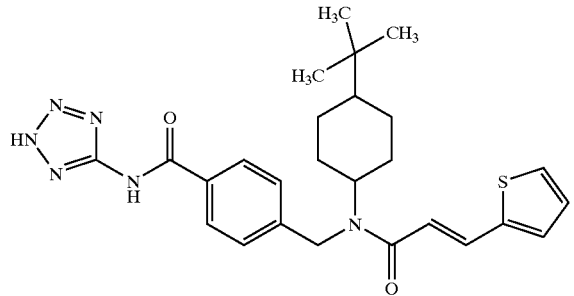

$^1$H NMR (DMSO. Isomers ca 1:1): δ 8.20–8.05 (m, 2H); 7.80–7.40 (m, 4H); 7.40–6.85 (2H); 4.87 (s, 1H); 4.75 (s, 1H).

HPLC-MS (Method E): m/z=495 (M+1). $R_t$=3.07 min.

EXAMPLE 477

General Procedure (V)

4-({(4-tert-Butylcyclohexyl)-[3-(2,6-dichlorophenyl)acryloyl]amino}methyl)-N-(2H-tetrazol-5-yl)benzamide

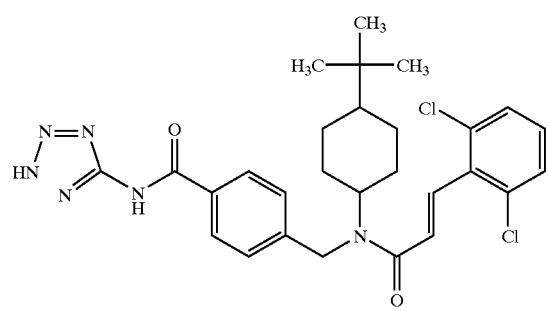

$^1$H NMR (DMSO. Isomers ca 1:1): δ 8.20 (m, 2H); 7.60 (m, 6H); 6.84 (d, 1H); 4.88 (s, 1H); 4.78 (s, 1H).

HPLC-MS (Method E): m/z=555 (M+1). $R_t$=3.39, 3.45 min.

EXAMPLE 478

General Procedure (V)

4-{[[3-(2,6-Dichlorophenyl)acryloyl]-(2,2-diphenylethyl)amino]methyl}-N-(2H-tetrazol-5-yl)benzamide

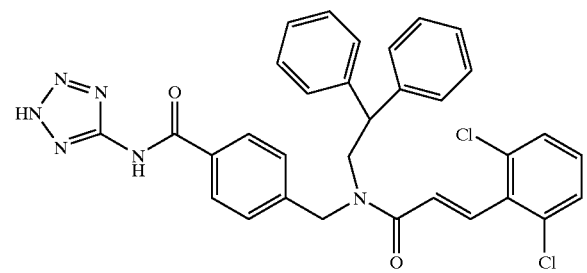

$^1$H NMR (DMSO. Isomers ca 1:1): δ 8.11 (s, 2H); 7.70–7.25 (m, 16H); 7.20 (d, 1H); 6.93 (d, 1H); 4.63 (s, 1H); 4.57 (s, 1H); 4.50 (t, 1H); 4.26 (d, 2H).

HPLC-MS (Method E): m/z=598 (M+1). $R_t$=3.09 min.

EXAMPLE 479

General Procedure (V)

4-({(4-tert-butylphenyl)-[3-(2,6-dichlorophenyl)acryloyl]amino}methyl)-N-(2H-tetrazol-5-yl)benzamide

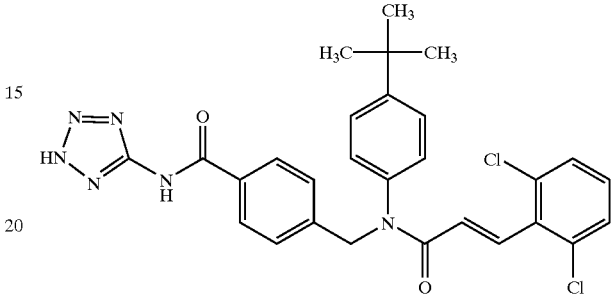

$^1$H NMR (DMSO): δ 8.10 (d, 2H); 7.68 (d, 1H); 7.56–7.48 (m, 6H); 7.41 (t, 1H); 7.26 (d, 2H); 6.56 (d, 1H); 5.17 (s, 2H).

HPLC-MS (Method E): m/z=549 (M+1). $R_t$=3.47 min.

EXAMPLE 480

General Procedure (V)

4-({(4-Cyclohexylphenyl)-[3-(2,6-dichlorophenyl)acryloyl]amino}methyl)-N-(2H-tetrazol-5-yl)benzamide

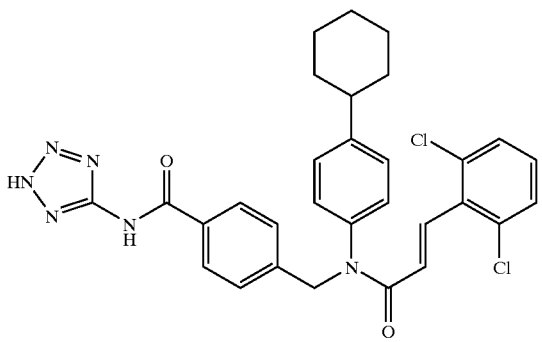

$^1$H NMR (DMSO): δ 8.07 (d, 2H); 7.67 (d, 1H); 7.55 (d, 2H); 7.49 (d, 2H); 7.40 (t, 1H); 7.32 (d, 2H); 7.23 (d, 2H); 6.55 (d, 1H); 5.16 (d, 2H).

HPLC-MS (Method E): m/z=575 (M+1). $R_t$=3.76 min.

EXAMPLE 481

General Procedure (V)

4-{[(4-Cyclohexylphenyl)-(3-nitrobenzoyl)amino]methyl}-N-(2H-tetrazol-5-yl)benzamide

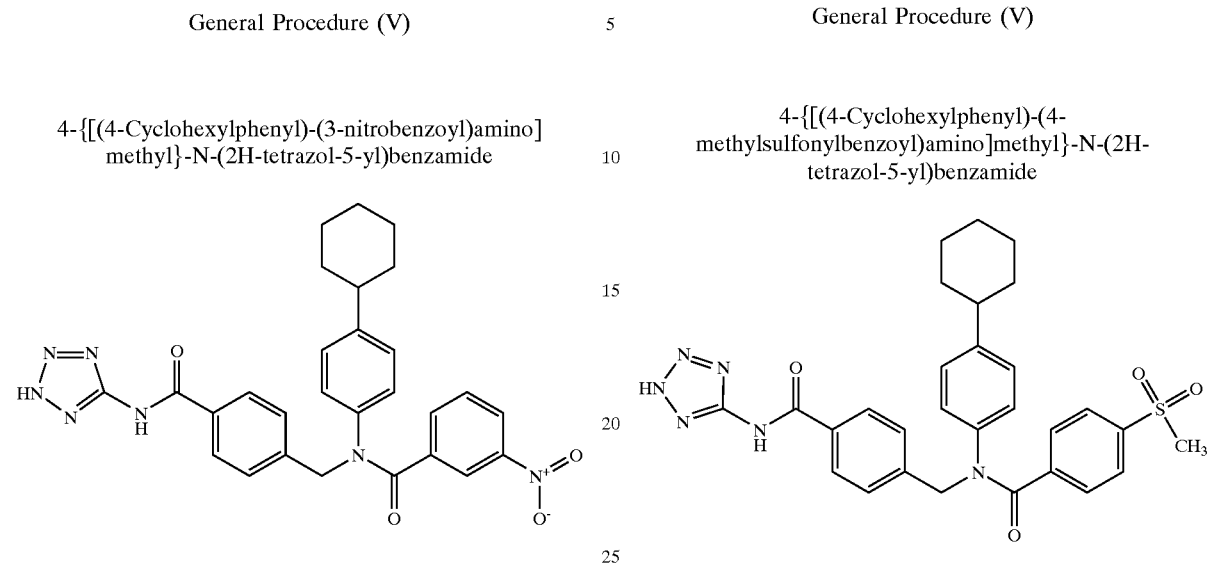

¹H NMR (DMSO): δ 8.20 (d, 1H); 8.17 (s, 1H); 8.09 (d, 2H); 7.81 (d, 1H); 7.60 (m, 3H); 7.14 (dd, 4H); 5,29 (s, 2H).

HPLC-MS (Method E): m/z=526 (M+1). R$_t$=3.18 min.

EXAMPLE 482

General Procedure (V)

4-{[(4-Cyclohexylphenyl)-(2-hydroxy-6-methylsulfanylbenzoyl)amino]methyl}-N-(2H-tetrazol-5-yl)benzamide

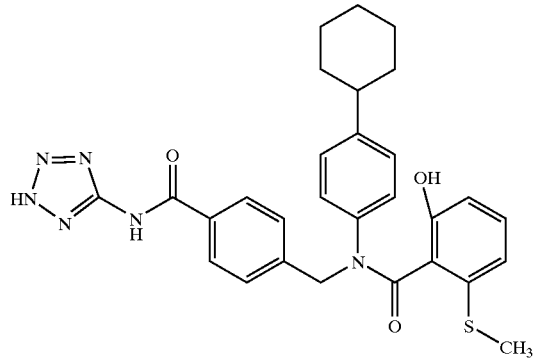

HPLC-MS (Method E): m/z=543 (M+1). R$_t$=3.25 min.

EXAMPLE 483

General Procedure (V)

4-{[(4-Cyclohexylphenyl)-(4-methylsulfonylbenzoyl)amino]methyl}-N-(2H-tetrazol-5-yl)benzamide ¹H NMR (DMSO): δ 8.09 (d, 2H); 8.09 (d, 4h); 7.84 (d, 2H); 7.65 (d, 2H); 7.57 (m, 3–4H); 7.12 (s, 4H); 5.24 (s, 2H).

HPLC-MS (Method E): m/z=559 (M+1). R$_t$=2.77 min.

EXAMPLE 484

General Procedure (V)

4-{[(4-Cyclohexylphenyl)-(4-cyclohexylbenzoyl)amino]methyl}-N-(2H-tetrazol-5-yl)benzamide

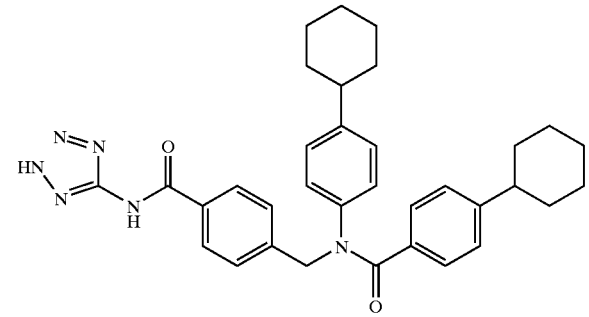

¹H NMR (DMSO): δ 8.08 (d, 2H) 7.53 (d, 2H); 7.30 (d, 2H); 7.15–7.05 (m, 6H); 5.21 (s, 2H).

HPLC-MS (Method E): m/z=563 (M+1). R$_t$=3.99 min.

EXAMPLE 485

General Procedure (V)

4-{[(4-Cyclohexylphenyl)-(4-triflourmethoxybenzoyl)amino]methyl}-N-(2H-tetrazol-5-yl)benzamide

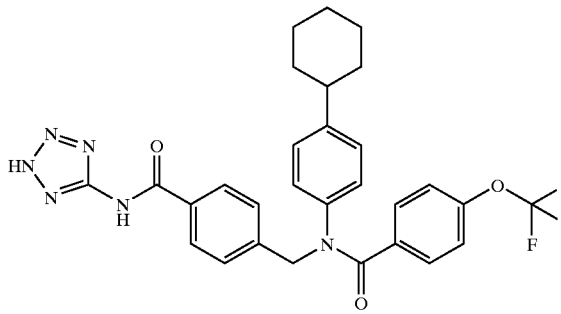

$^1$H NMR (DMSO): δ 8.09 (d, 2H); 7.56 (d, 2H); 7.51 (d, 2H); 7.28 (d, 2H); 7.10 (dd, 4H); 5.24 (s, 2H).

HPLC-MS (Method E): m/z=565(M+1). R$_t$=3.52 min.

EXAMPLE 486

General Procedure (V)

Naphtalene-2-carboxylic acid (4-tert-butylcyclohexyl)-[4-(2H-tetrazol-5-ylcarbamoyl)benzyl]amide

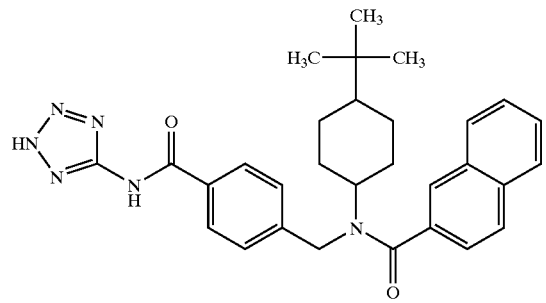

HPLC-MS (Method E): m/z=511 (M+1). R$_t$=3.47 min.

EXAMPLE 487

General Procedure (V)

Biphenyl-4-carboxylic acid (4-tert-butylcyclohexyl)-[4-(2H-tetrazol-5-ylcarbamoyl)benzyl]amide

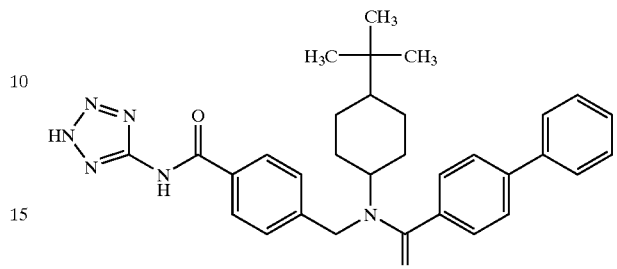

$^1$H NMR (DMSO): δ 8.15 (d, 2H); 7.90–7.40 (m, 9H); 4.84 (s, 2H).

HPLC-MS (Method D): m/z=537 (M+1). R$_t$=6.13 min.

EXAMPLE 488

General Procedure (V)

4-{[(4-tert-Butylcyclohexyl)-(4-cyclohexylbenzoyl)amino]methyl}-N-(2H-tetrazol-5-yl)benzamide

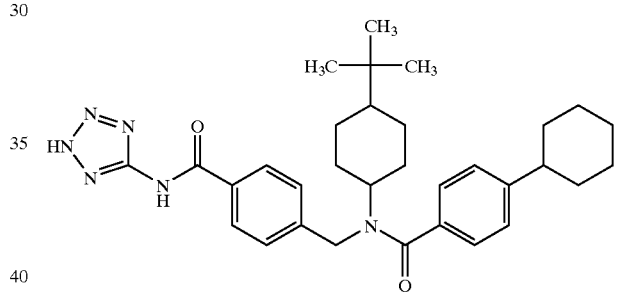

$^1$H NMR (DMSO): δ 8.13 (d, 2H); 7.70–7.30 (m, 6H); 4.79 (s, 1H).

EXAMPLE 489

General Procedure (V)

4-{[(4-tert-Butylcyclohexyl)-(4-triflourmethoxybenzoyl)amino]methyl}-N-(2H-tetrazol-5-yl)benzamide

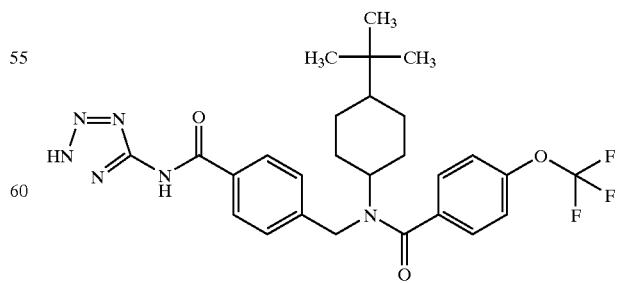

$^1$H NMR (DMSO): δ 8.14 (d, 2H); 7.70–7.40 (m, 6H); 4.82 (s, 2H).

HPLC-MS (Method D): m/z=545 (M+1). R$_t$=5.70 min.

EXAMPLE 490

General Procedure (V)

5-Chlorobenzofuran-2-carboxylic acid (4-tert-butylcyclohexyl)-[4-(2H-tetrazol-5-ylcarbamoyl)benzyl]amide

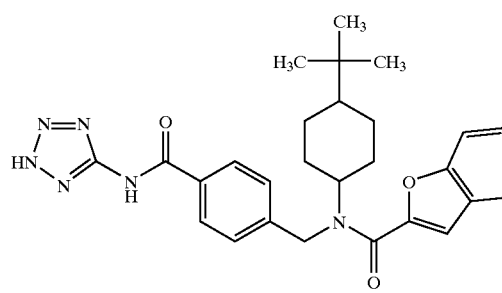

$^1$H NMR (DMSO): δ 8.13 (d, 2H); 7.90 (s, 1H); 7.54 (dd, 4H); 4.98 (s, 1H).

HPLC-MS (Method D): m/z=535 (M+1). R$_t$=6.10 min.

EXAMPLE 491

General Procedure (V)

4-{[[2-(4-Chlorophenoxy)propionyl]-(4-cyclohexylphenyl)amino]methyl}-N-(2H-tetrazol-5-yl)benzamide

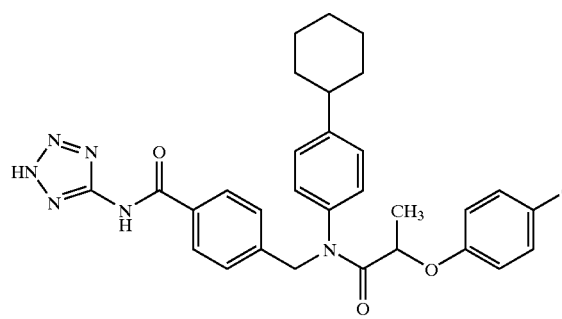

$^1$H NMR (DMSO): δ 8.09 (d, 2H); 7.41 (d, 2H); 7.34 (d, 2H); 7.25 (dd, 4H); 6.75 (d, 2H); 5.00 (d, 2H); 4.61 (d, 1H).

HPLC-MS (Method D): m/z=559 (M+1). R$_t$=6.10 min.

EXAMPLE 492

General Procedure (V)

4-({(4-Cyclohexylphenyl)-[2-(3-trifluoromethoxyphenyl)acetyl]amino}methyl)-N-(2H-tetrazol-5-yl)benzamide

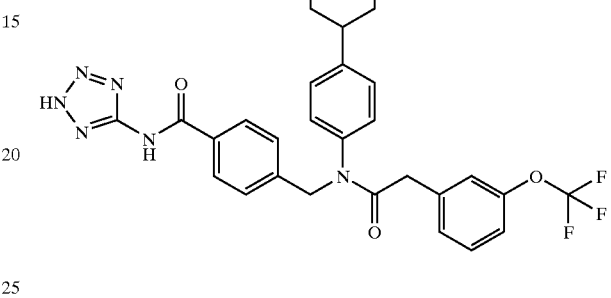

$^1$H NMR (DMSO): δ 8.10 (d, 2H); 7.45 (m, 3H); 7.30 (m, 3H); 7.20 (m, 3H); 7.08 (s, 1H); 5.03 (s, 1H).

HPLC-MS (Method D): m/z=579 (M+1). R$_t$=6.23 min.

EXAMPLE 493

General Procedure (V)

4-({(4-Cyclohexylphenyl)-[2-(4-trifluoromethylphenoxy)propionyl]amino}methyl)-N-(2H-tetrazol-5-yl)benzamide

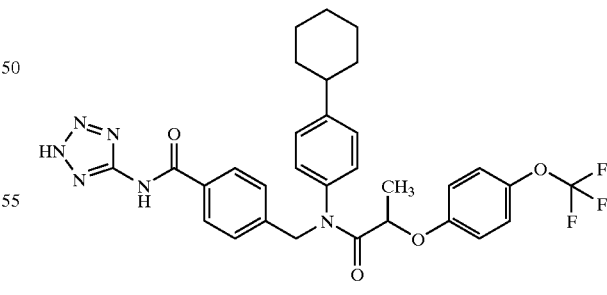

$^1$H NMR (DMSO): δ 8.10 (d, 2H); 7.43 (d, 2H); 7.31 (d, 2H); 7.25 (s, 4H); 6.83 (d, 2H); 5.01 (dd, 2H); 4.83 (q, 1H).

HPLC-MS (Method D): m/z=609 (M+1). R$_t$=6.27 min.

EXAMPLE 494

General Procedure (V)

4-({(4-Cyclohexylphenyl)-[2-(4-trifluoromethoxyphenyl)acetyl]amino}methyl)-N-(2H-tetrazol-5-yl)benzamide

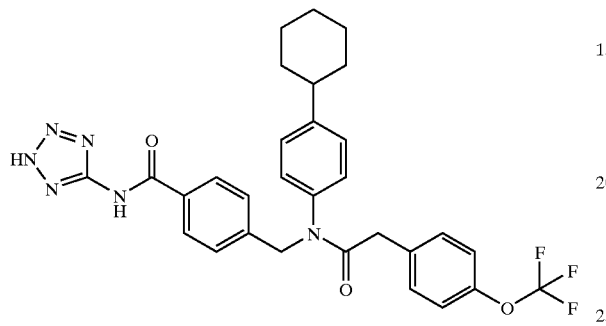

¹H NMR (DMSO): δ 8.09 (d, 2H); 7.47 (d, 2H); 7.33–7.22 (m, 8H); 5.03 (s, 2H).

HPLC-MS (Method D): m/z=579 (M+1). R$_t$=6.27 min.

EXAMPLE 495

4-({(4-Cyclohex-1-enylphenyl)-(3-chlorobenzoyl)amino}methyl)-N-(2H-tetrazol-5-yl)benzamide

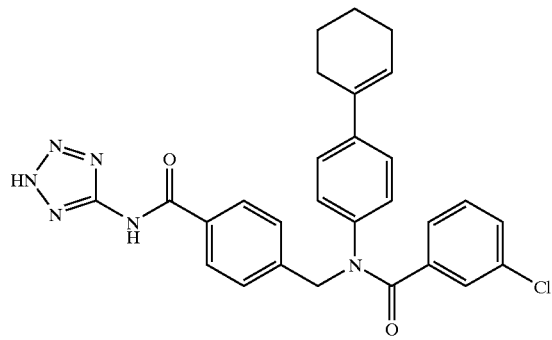

¹H NMR (DMSO): δ 12.4 (S, 1H), 8.02 (d, 2H), 7.50 (d, 2H), 7.35 (m, 1H), 7.42 (s, 1H), 7.25 (m, 4H), 7.06 (d, 2H), 6.12 (t, 1H), 5.19 (s, 2H), 2.22 (m, 2H), H), 2.12 (m, 2H), 1.65 (m, 2H), 1.55 (m, 2H)

EXAMPLE 496

General Procedure (V)

4-({(4-Cyclohexylphenyl)-[2-(2,4-difluorophenyl)acetyl]amino}methyl)-N-(2H-tetrazol-5-yl)benzamide

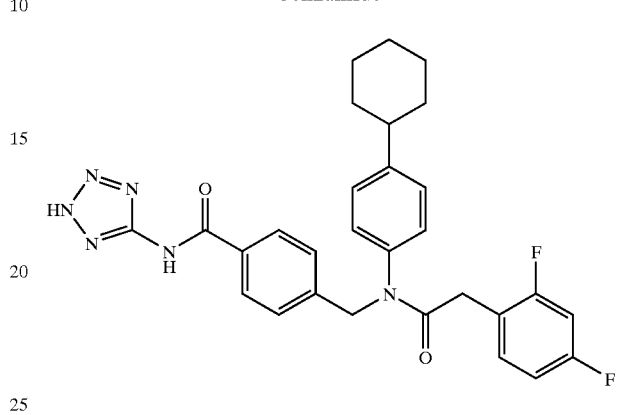

¹H NMR (DMSO): δ 8.11 (d, 2H); 7.48 (d, 2H); 7.38–7.32 (m, 3H); 7.27–7.20 (m, 3H); 7.08 (t, 1H); 5.03 (s, 2H).

HPLC-MS (Method D): m/z=531 (M+1). R$_t$=5.87 min.

EXAMPLE 497

General Procedure (V)

4-{[(2-Biphenyl-4-yl-acetyl)-(4-cyclohexylphenyl)amino]methyl}-N-(2H-tetrazol-5-yl)benzamide ¹H NMR (DMSO): δ 8.10 (d, 2H); 7.72 (d, 2H); 7.64 (d, 2H); 7.54 (t, 2H); 7.48 (d, 2H); 7.43 (t, 1H); 7.34 (d, 2H); 7.26–7.21 (m, 4H); 5.02 (s, 2H).

HPLC-MS (Method D): m/z=571 (M+1). R$_t$=6.50 min.

EXAMPLE 498

General Procedure (V)

4-{[[2-(3-Chlorophenoxy)propionyl]-(4-cyclohexylphenyl)amino]methyl}-N-(2H-tetrazol-5-yl)benzamide

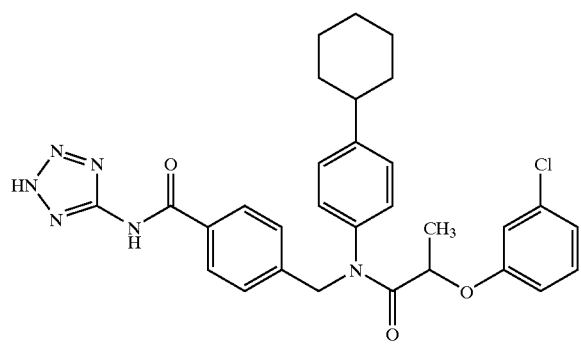

$^1$H NMR (DMSO): δ 8.09 (d, 2H); 7.41 (d, 2H); 7.33 (t, 1H); 7.29 (d, 2H); 7.23 (d, 2H); 7.08 (d, 1H); 6.75, (m, 2H); 5.10 (d, 1H); 4.92 (d, 1H); 4.82 (q, 1H).

HPLC-MS (Method D): m/z=559 (M+1). $R_t$=6.10 min.

EXAMPLE 499

General Procedure (V)

4-{[(4-Cyclohexylphenyl)-(2-naphth-2-ylacetyl)amino]methyl}-N-(2H-tetrazol-5-yl)benzamide

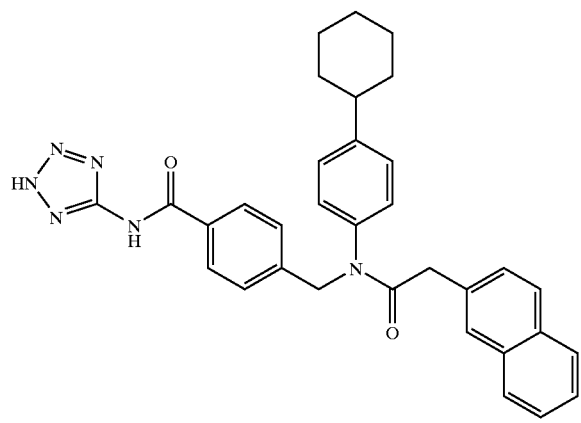

$^1$H NMR (DMSO): δ 8.09 (d, 2H); 9.95 (m, 1H); 7.92–7.85 (m, 2H); 7.58–7.54 (m, 3H); 7.48 (d, 2H); 7.32 (d, 3H); 7.24 (d, 2H); 5.05 (s, 2H).

HPLC-MS (Method D): m/z=545 (M+1). $R_t$=6.23 min.

EXAMPLE 500

General Procedure (V)

4-{[[3-(2-Chlorophenyl)acryloyl]-(4-cyclohexylphenyl)amino]methyl}-N-(2H-tetrazol-5-yl)benzamide

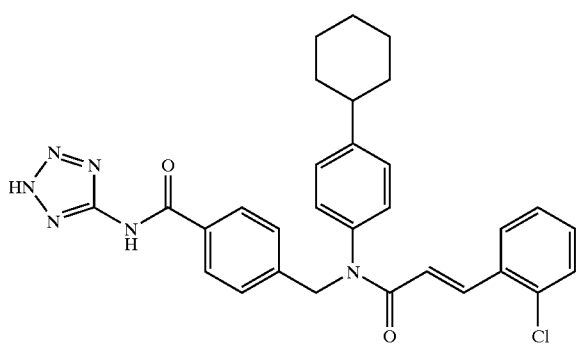

$^1$H NMR (DMSO): δ 8.11 (d, 2H); 7.94 (d, 1H); 7.59 (d, 1H); 7.51 (d, 2H); 7.53 (t, 2H); 7.40 (d, 1H); 7.36 (d, 2H); 7.28 (d, 2H); 6.55 (d, 1H); 5.19 (s, 2H).

HPLC-MS (Method D): m/z=541 (M+1). $R_t$=6.13 min.

EXAMPLE 501

General Procedure (V)

4-{[[3-(2-Bromophenyl)acryloyl]-(4-cyclohexylphenyl)amino]methyl}-N-(2H-tetrazol-5-yl)benzamide

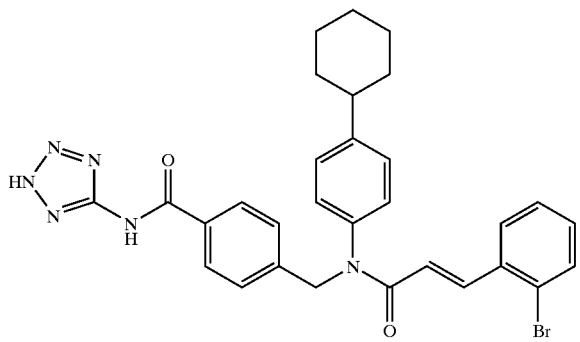

$^1$H NMR (DMSO): δ 8.11 (d, 2H); 7.91 (d, 1H); 7.76 (d, 1H); 7.52 (d, 2H); 7.43–7.30 (m, 5H); 7.28 (d, 2H); 6.50 (d br, 1H); 5.19 (s, 2H);

HPLC-MS (Method D): m/z=587 (M+1). $R_t$=6.23 min.

EXAMPLE 502

General Procedure (V)

4-({(4-tert-Butylcyclohexyl)-[2-(4-trifluoromethoxyphenyl)acetyl]amino}methyl)-N-(2H-tetrazol-5-yl)benzamide

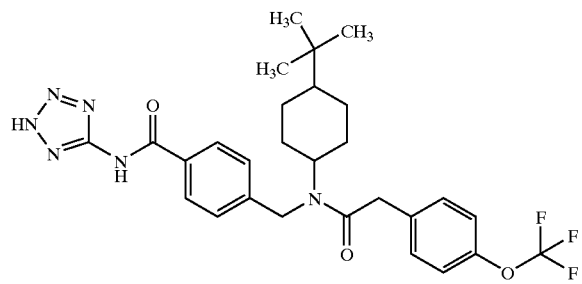

¹H NMR (DMSO. Isomers 2:1): δ 8.17+8.07 (d, 2H); 7.55–7.45 (m, 2H); 7.45–7.30 (m, 4H); 4.80+4.64 (s, 2H).

HPLC-MS (Method D): m/z=559 (M+1). $R_t$=5.97 min.

EXAMPLE 503

General Procedure (V)

4-({(4-tert-Butylcyclohexyl)-[3-(2,6-dichlorophenyl)acryloyl]amino}methyl)-N-(2H-tetrazol-5-yl)benzamide

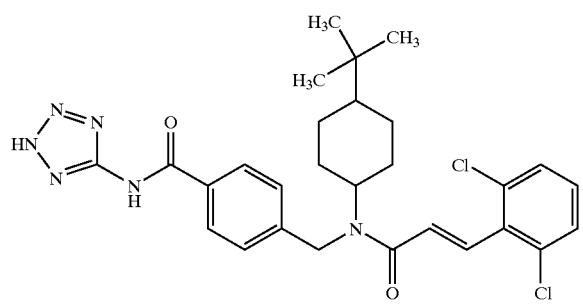

¹H NMR (DMSO. Isomers 1:1): δ 8.18–8.12 (m, 2H); 7.68–7.30 (m, 7H); 6.85 (d, 1H); 4.88 (s, 1H); 4.79 (s, 1H).

HPLC-MS (Method D): m/z=555 (M+1). $R_t$=6.13 min.

EXAMPLE 504

General Procedure (V)

3-[4-({(2,2-Diphenylethyl)-[2-(4-trifluoromethoxyphenyl)acetyl]amino}methyl)benzoylamino]propionic acid

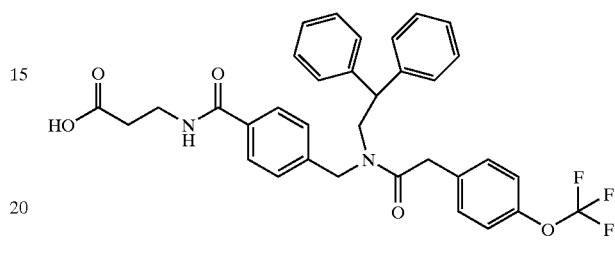

¹H NMR (DMSO): δ 8.58 (t, 1H); 8.53 (t, 1H); 7.88 (d, 2H); 7.82 (d, 2H); 7.47–7.26 (m, 28H); 7.20 (d, 2H); 7.15 (d, 2H); 4.62 (s, 2H); 4.52 (t, 2H); 4.41 (s, 2H); 4.08 (d, 2H); 4.03 (d, 2H).

HPLC-MS (Method D): m/z=605 (M+1). $R_t$=5.33 min.

EXAMPLE 505

General Procedure (V)

3-(4-{[[3-(2,6-Dichlorophenyl)acryloyl]-(2,2-diphenylethyl)amino]methyl}benzoylamino)propionic acid

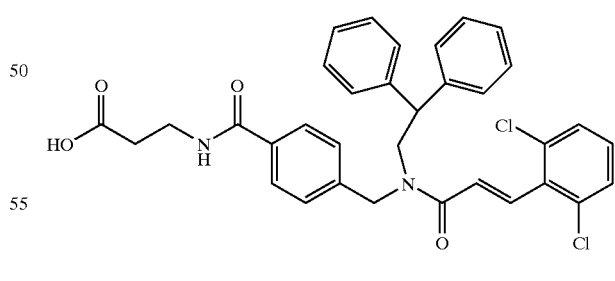

¹H NMR (DMSO): δ 8.55 (t, 1H); 7.84 (dd, 2H); 7.83–7.24 (m, 16); 7.18+6.95 (d, 1H); 4.70–4.50 (m, 3H); 4.21 (t, 2H).

HPLC-MS (Method D): m/z=601 (M+1). $R_t$=5.33 min.

EXAMPLE 506

General Procedure (V)

3-[4-({(4-tert-Butylcyclohexyl)-[2-(4-trifluoromethoxyphenyl)acetyl]amino}methyl)benzoylamino]propionic acid

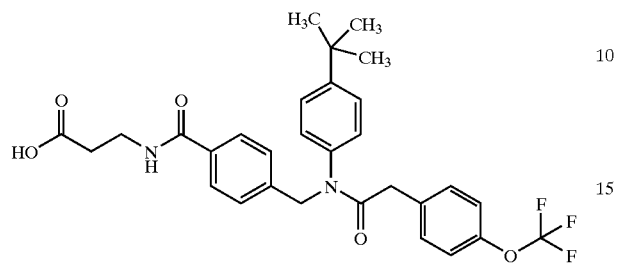

¹H NMR (DMSO. Isomers): δ 8.57+8.51 (t, 1H); 7.90+7.79 (d, 2H); 7.50–7.30 (m, 6H); 4.74–4.60 (s, 2H).

HPLC-MS (Method D): m/z=563 (M+1). R$_t$=5.73 min.

EXAMPLE 507

General Procedure (V)

4-{[(4-Cyclohexylphenyl)-(4-isobutylbenzoyl)amino]methyl}-N-(2H-tetrazol-5-yl)benzamide

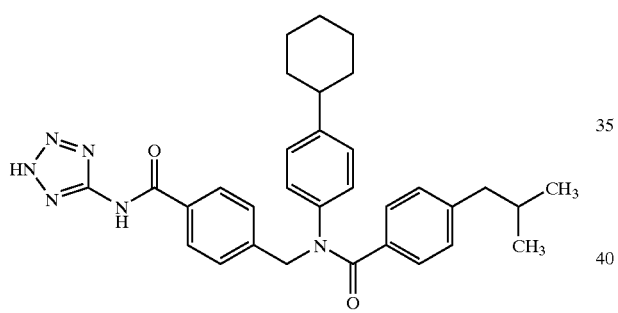

HPLC-MS (Method D): m/z=537 (M+1). R$_t$=6.57 min.

EXAMPLE 508

General Procedure (V)

4-{[(4-Cyclohexylphenyl)-(4-benzylbenzoyl)amino]methyl}-N-(2H-tetrazol-5-yl)benzamide

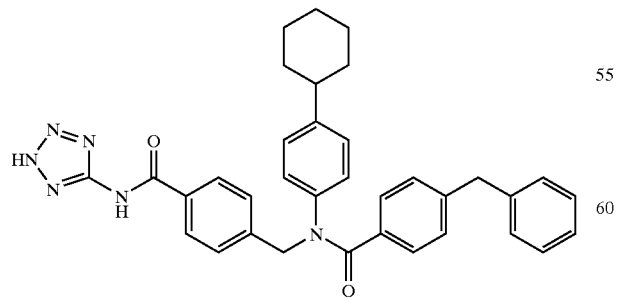

¹H NMR (DMSO): δ 8.09 (d, 2H); 7.55 (d, 2H); 7.34–7.30 (m, 4H); 7.26–7.04 (m, 9H); 5.20 (s, 2H).

HPLC-MS (Method D): m/z=571 (M+1). R$_t$=6.27 min.

EXAMPLE 509

General Procedure (V)

4-{[(4-Cyclohexylphenyl)-(9-oxo-9H-fluorene-4-carbonyl)amino]methyl}-N-(2H-tetrazol-5-yl)benzamide

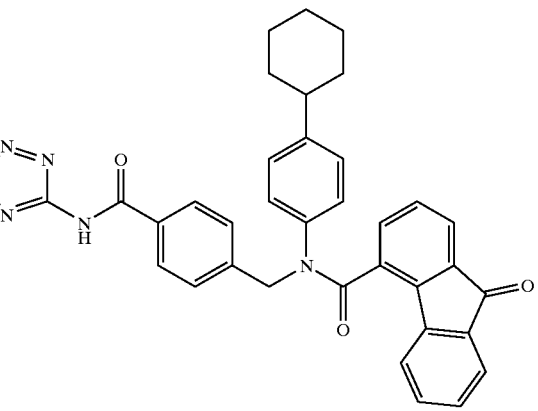

¹H NMR (DMSO): δ 8.17 (d, 2H); 7.72 (d, 1H); 7.68–7.62 (m, 3H); 7.55–7.50 (m, 2H); 7.45 (d, 1H); 7.25 (t, 1H); 7.05 (d, 2H); 7.02 (d, 2H); 5.30 (s, 2H).

HPLC-MS (Method D): m/z=583 (M+1). R$_t$=5.63 min.

EXAMPLE 510

General Procedure (V)

4-{[(4-Cyclohexylphenyl)-(3-trifluoromethylbenzoyl)amino]methyl}-N-(2H-tetrazol-5-yl)benzamide

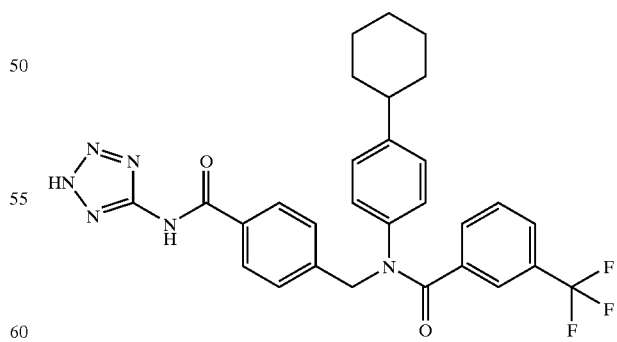

¹H NMR (DMSO): δ 8.09 (d, 2H); 7.76 (d, 1H); 7.71 (d, 1H); 7.59–7.55 (m, 4H); 7.12 (s, 4H); 5.30 (s, 2H).

HPLC-MS (Method D): m/z=549 (M+1). R$_t$=5.87 min.

EXAMPLE 511

General Procedure (V)

4-{[(4-tert-Butylcyclohexyl)-(4-isobutylbenzoyl)amino]methyl}-N-(2H-tetrazol-5-yl)benzamide

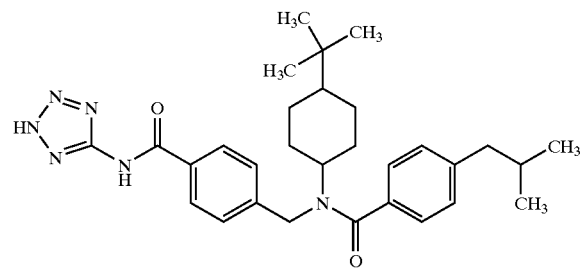

¹H NMR (DMSO): δ 8.12 (d, 2H); 7.60–7.28 (m, 6H); 4.80 (m, 2H).
HPLC-MS (Method D): m/z=517 (M+1). R$_t$=6.50 min.

EXAMPLE 512

General Procedure (V)

4-{[(4-tert-Butylcyclohexyl)-(4-benzylbenzoyl)amino]methyl}-N-(2H-tetrazol-5-yl)benzamide

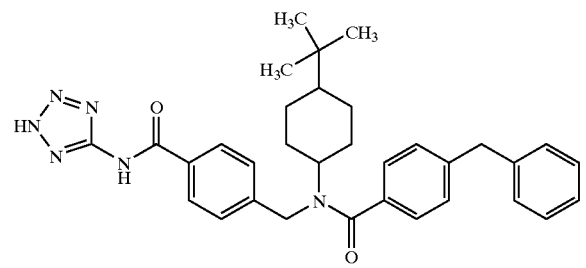

¹H NMR (DMSO): δ 8.07 (d, 2H); 7.60–7.15 (m, 11H).
HPLC-MS (Method D): m/z=551 (M+1). R$_t$=6.23 min.

EXAMPLE 513

General Procedure (V)

4-{[(4-tert-Butylcyclohexyl)-(4-isopropoxybenzoyl)amino]methyl}-N-(2H-tetrazol-5-yl)benzamide

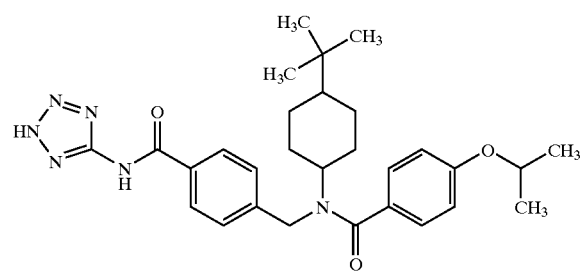

¹H NMR (DMSO): δ 8.10 (d, 2H); 7.60–7.40 (m, 4H); 4.80–4.70 (m, 3H).
HPLC-MS (Method D): m/z=519 (M+1). R$_t$=5.87 min.

EXAMPLE 514

General Procedure (V)

4-{[(4-tert-Butylcyclohexyl)-(3-trifluoromethylbenzoyl)amino]methyl}-N-(2H-tetrazol-5-yl)benzamide

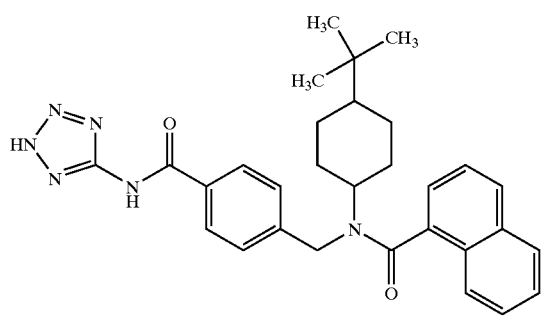

¹H NMR (DMSO): δ 8.11 (d, 2H); 8.00–7.70 (m, 3H); 7.65–7.40 (m, 3H); 4.70 (s, 2H).

HPLC-MS (Method D): m/z=529 (M+1). R$_t$=5.77 min.

EXAMPLE 515

General Procedure (V)

4-{[(4-tert-Butylcyclohexyl)-(naphth-1-ylcarbonyl)amino]methyl}-N-(2H-tetrazol-5-yl)benzamide HPLC-MS (Method D): m/z=511 (M+1). R$_t$=5.77 min.

EXAMPLE 516

General Procedure (V)

4-{[(4-tert-Butylcyclohexyl)-(1H-indol-4-ylcarbonyl)amino]methyl}-N-(2H-tetrazol-5-yl)benzamide

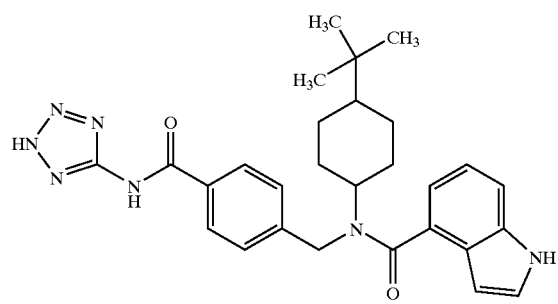

$^1$H NMR (DMSO): δ 8.20–8.05 (m, 2H); 7.70–7.60 (m, 1H); 7.60–7.45 (m, 3H); 7.28–7.12 (m, 1H); 7.08 (d, 1H); 6.40 (m, 1H); 4.70 (s br 2H).

HPLC-MS (Method D): m/z=500 (M+1). R$_t$=5.03 min.

EXAMPLE 517

General Procedure (V)

4-({(4-tert-Butylcyclohexyl)-[2-(4-methylsulfonylphenyl)acetyl]amino}methyl)-N-(2H-tetrazol-5-yl)benzamide

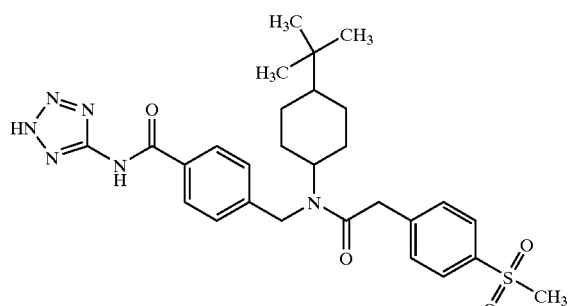

$^1$H NMR (DMSO. Isomers 2:1):

Set 1 (minor isomer): δ 8.16 (d, 2H); 7.88 (d, 2H); 7.52 (d, 2H); 7.47 (d, 2H); 4.80 (s, 2H).

Set 2 (major isomer): δ 8.06 (d, 2H); 7.96 (d, 2H); 7.64 (d, 2H); 7.42 (d, 2H); 4.70 (s, 2H).

HPLC-MS (Method D): m/z=553 (M+1). R$_t$=4.83 min.

EXAMPLE 518

General Procedure (V)

4-{[(4-Isobutylbenzoyl)-(4-piperidin-1-ylphenyl)amino]methyl}-N-(2H-tetrazol-5-yl)benzamide

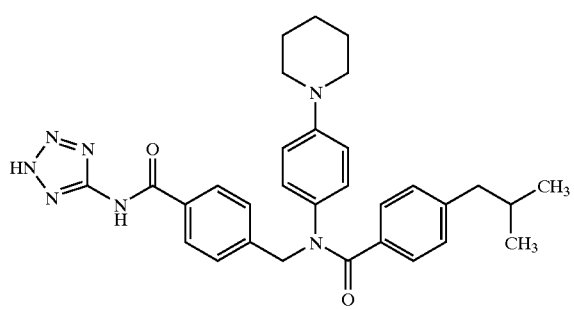

$^1$H NMR (DMSO): δ 8.11 (d, 2H); 7.55 (d, 2H); 7.31 (d, 2H); 7.08 (d, 2H); 6.96 (d, 2H); 6.80 (d, 2H); 5.10 (s, 2H).

HPLC-MS (Method D): m/z=538 (M+1). R$_t$=4.23 min.

EXAMPLE 519

General Procedure (V)

4-{[(4-Benzylbenzoyl)-(4-piperidin-1-ylphenyl)amino]methyl}-N-(2H-tetrazol-5-yl)benzamide

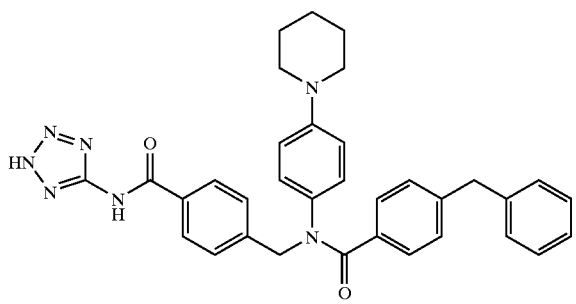

$^1$H NMR (DMSO): δ 8.07 (d, 2H); 7.51 (d, 2H); 7.32–7.28 (m, 4H); 7.25–7.18 (m, 3H); 7.13 (d, 2H); 6.93 (d, 2H); 6.76 (d, 2H); 5.10 (s, 2H).

HPLC-MS (Method D): m/z=572 (M+1). R$_t$=4.17 min.

EXAMPLE 520

General Procedure (V)

3-(4-{[(4-Cyclohexylphenyl)-(4-isobutylbenzoyl)amino]methyl}benzoylamino)propionic acid

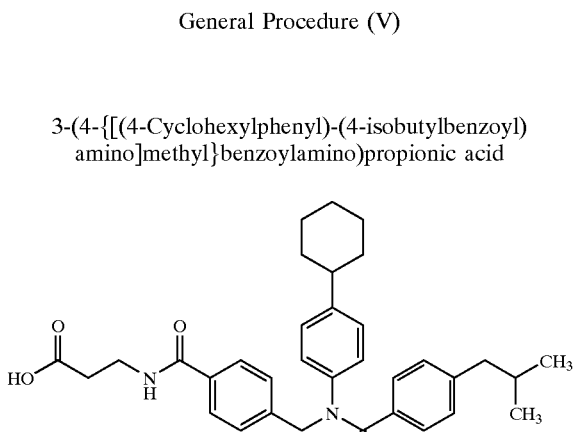

$^1$H NMR (DMSO): δ 8.54 (t, 1H); 7.83 (d, 2H); 7.44 (d, 2H); 7.26 (d, 2H); 7.09–7.04 (m, 4H); 7.00 (d, 2H); 5.18 (s, 2H).

HPLC-MS (Method D): m/z=541 (M+1). $R_t$=6.17 min.

EXAMPLE 521

General Procedure (V)

3-(4-{[(4-Benzylbenzoyl)-(4-cyclohexylphenyl)amino]methyl}benzoylamino)propionic acid

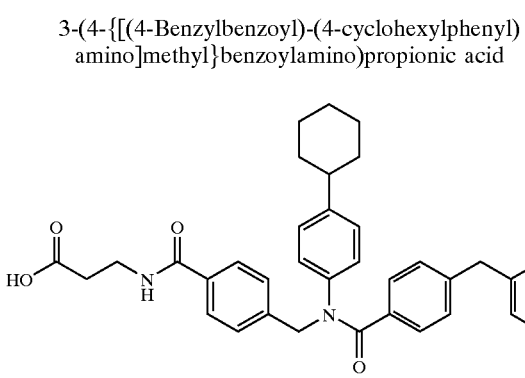

$^1$H NMR (DMSO): δ 8.53 (t, 1H); 7.82 (d, 2H); 7.42 (d, 2H); 7.33–7.20 (m, 9H); 7.08 (d, 2H); 7.00 (d, 2H); 5.10 (s, 2H).

HPLC-MS (Method D): m/z=575 (M+1). $R_t$=6.00 min.

EXAMPLE 522

General Procedure (V)

3-(4-{[(4-Cyclohexylphenyl)-(9-oxo-9H-fluorene-3-carbonyl)amino]methyl}benzoylamino)propionic acid

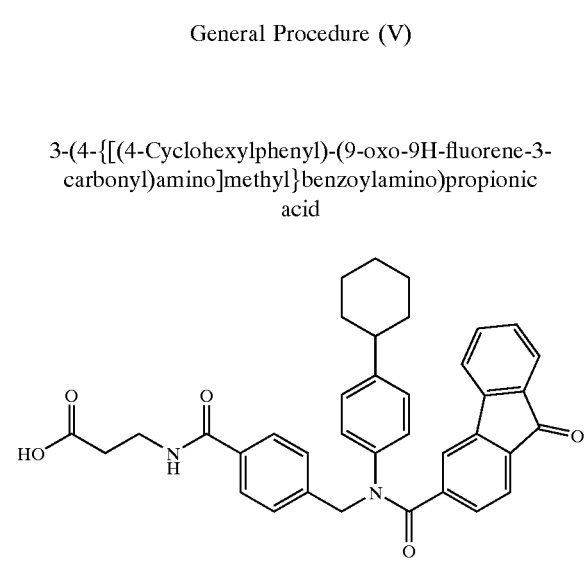

HPLC-MS (Method D): m/z=587 (M+1). $R_t$=5.40 min.

EXAMPLE 523

General Procedure (V)

3-(4-{[(4-Cyclohexylphenyl)-(4-isopropoxybenzoyl)amino]methyl}benzoylamino)propionic acid

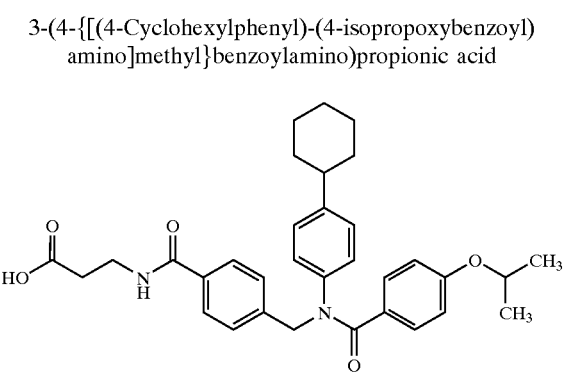

$^1$H NMR (DMSO): δ 8.52 (t, 1H); 7.78 (d, 2H); 7.40 (d, 2H); 7.27 (d, 2H); 7.09 (d, 2H); 7.00 (d, 2H); 6.76 (d, 2H); 5.15 (s, 2H).

HPLC-MS (Method D): m/z=543 (M+1). $R_t$=5.67 min.

EXAMPLE 524

General Procedure (V)

3-(4-{[(4-Cyclohexylphenyl)-(3-trifluoromethylbenzoyl)amino]methyl}benzoylamino)propionic acid

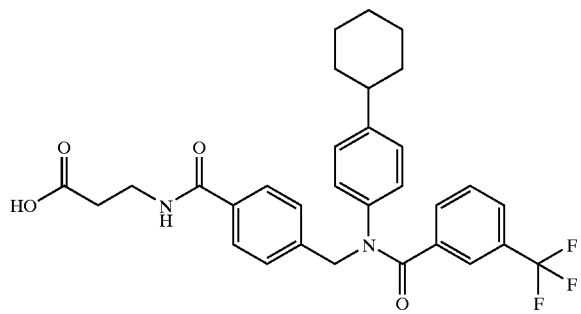

$^1$H NMR (DMSO): δ 8.54 (t, 1H); 7.82 (d, 2H); 7.75 (d, 1H); 7.70 (d, 1H); 7.56 (t, 1H); 7.53 (s, 1H); 7.46 (d, 2H); 7.10 (d, 2H); 7.07 (d, 2H); 5.20 (s, 2H).

HPLC-MS (Method D): m/z=553 (M+1). $R_t$=5.63 min.

EXAMPLE 525

General Procedure (V)

3-(4-{[(4-Benzylbenzoyl)-(4-tert-butylcyclohexyl)amino]methyl}benzoylamino)propionic acid

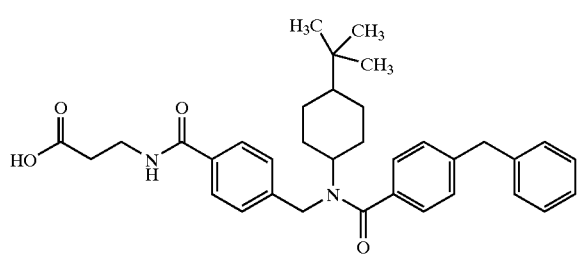

$^1$H NMR (DMSO): δ 8.54 (t, 1H); 7.84 (d, 2H); 7.50–7.20 (m, 11H);

HPLC-MS (Method D): m/z=555 (M+1). $R_t$=6.00 min.

EXAMPLE 526

General Procedure (V)

3-(4-{[(4-tert-Butylcyclohexyl)-(4-isopropoxybenzoyl)amino]methyl}benzoylamino)propionic acid

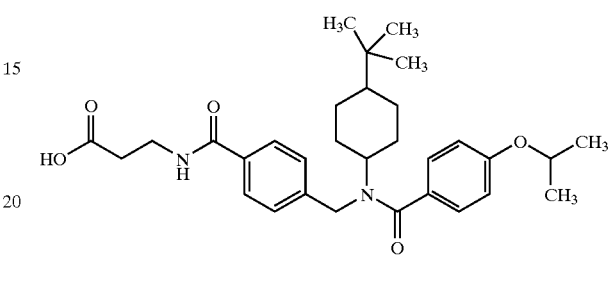

$^1$H NMR (DMSO): δ 8.52 (t, 1H); 7.82 (d, 2H); 7.45–7.37 (m, 4H); 7.07–6.97 (m, 2H).

HPLC-MS (Method D): m/z=523 (M+1). $R_t$=5.60 min.

EXAMPLE 527

General Procedure (V)

3-(4-{[(4-tert-Butylcyclohexyl)-(3-trifluormethylbenzoyl)amino]methyl}benzoylamino)propionic acid

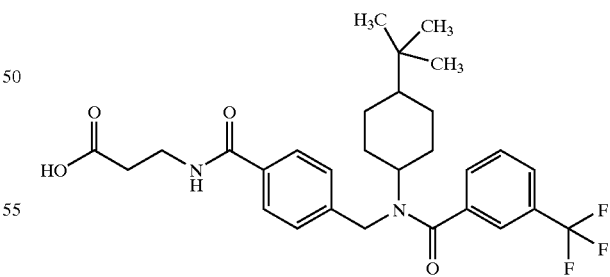

$^1$H NMR (DMSO): δ 8.54 (s, 1H); 8.00–7.70 (m, 6H); 7.60–7.30 (m 2H); 4.77 (s, 2H).

HPLC-MS (Method D): m/z=533 (M+1). $R_t$=5.53 min.

EXAMPLE 528

General Procedure (V)

3-(4-{[(4-tert-Butylcyclohexyl)-(1H-indole-4-carbonyl)amino]methyl}benzoylamino)propionic acid

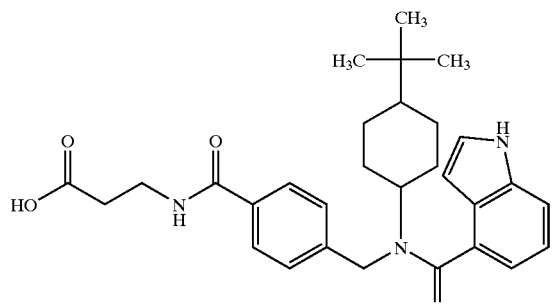

HPLC-MS (Method D): m/z=504 (M+1). $R_t$=5.00 min.

EXAMPLE 529

General Procedure (V)

4-({(2,2-Diphenylethyl)-[2-(3-trifluoromethoxyphenyl)acetyl]amino}methyl)-N-(2H-tetrazol-5-yl)benzamide

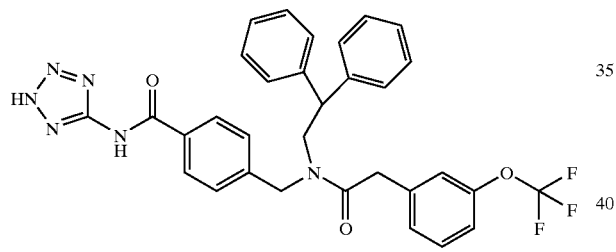

HPLC-MS (Method D): m/z=601 (M+1). $R_t$=5.60 min.

EXAMPLE 530

General Procedure (V)

4-({(2,2-Diphenylethyl)-[2-(4-trifluoromethoxyphenoxy)propionyl]amino}methyl)-N-(2H-tetrazol-5-yl)benzamide

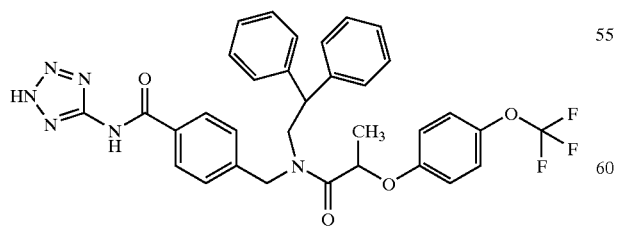

$^1$H NMR (DMSO): δ 8.15 (d, 1H); 8.08 (d, 1H); 7.50–7.20 (m, 12H); 6.74 (d, 1H); 6.64 (d, 1H); 5.27 (q, 1H); 5.16 (q, 1H); 4.80 (d, 1H); (4.68 (d, 1H); 4.60–4.49 (m, 2H);

HPLC-MS (Method D): m/z=631 (M+1). $R_t$=5.63 min.

EXAMPLE 531

General Procedure (V)

4-({(2,2-Diphenylethyl)-[2-(4-trifluoromethoxyphenyl)acetyl]amino{methyl)-N-(2H-tetrazol-5-yl)benzamide

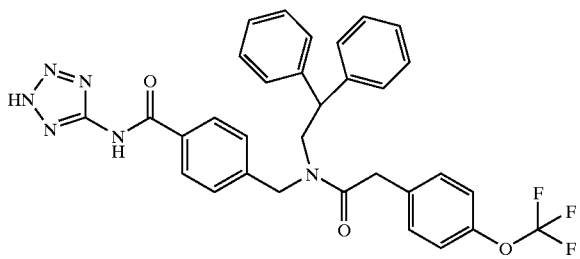

$^1$H NMR (DMSO): δ 8.13 (d, 1H); 8.08 (d, 1H); 7.50–7.28 (m, 14); 7.20 (d, 1H); 7.14 (d, 1H); 4.65 (s, 1H); 4.55 (t, 1H).

EXAMPLE 532

General Procedure (V)

4-{[(2-Benzylsulfanylacetyl)-(4-cyclohexylphenyl)amino]methyl}-N-(2H-tetrazol-5-yl)benzamide

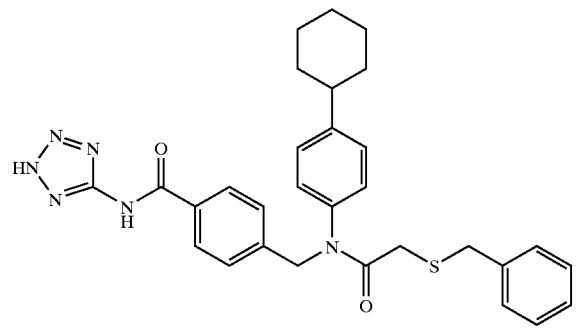

HPLC-MS (Method D): m/z=541 (M+1). $R_t$=6.03 min.

EXAMPLE 533

General Procedure (V)

4-{[(4-Cyclohexylphenyl)-(3-phenoxypropionyl)amino]methyl}-N-(2H-tetrazol-5-yl)benzamide

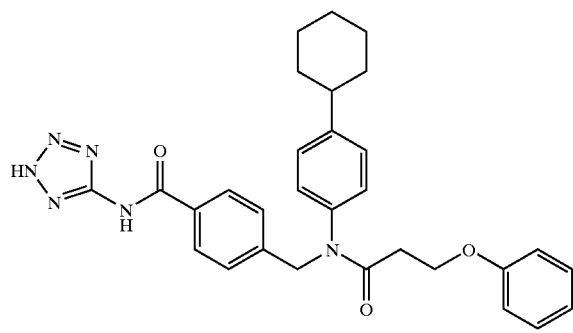

$^1$H NMR (DMSO): δ 8.11 (d, 2H); 7.51 (d, 2H); 7.39–7.30 (m, 3H); 7.26 (d, 2H); 7.03–6.97 (m, 4H); 5.20 (s, 2H); 4.25 (t, 2H).

HPLC-MS (Method D): m/z=525 (M+1). R$_t$=5.90 min.

EXAMPLE 534

General Procedure (V)

4-{[(4-Cyclohexylphenyl)-(3-naphthalen-1-ylacryloyl)amino]methyl}-N-(2H-tetrazol-5-yl)benzamide

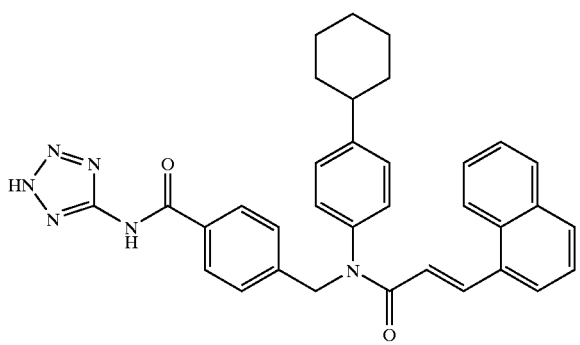

HPLC-MS (Method D): m/z=557 (M+1). R$_t$=6.50 min.

EXAMPLE 535

General Procedure (V)

4-{[(4-Cyclohexylphenyl)-(4-phenylbutyryl)amino]methyl}-N-(2H-tetrazol-5-yl)benzamide

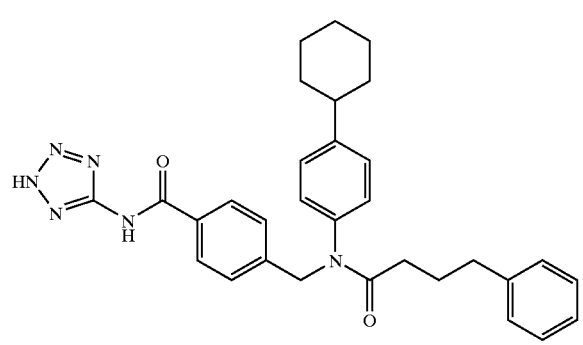

HPLC-MS (Method D): m/z=523 (M+1). R$_t$=6.13 min.

EXAMPLE 536

General Procedure (V)

4{[(4-tert-Butylcyclohexyl)-(2-phenylcyclopropanecarbonyl)amino]methyl}-N-(2H-tetrazol-5-yl)benzamide

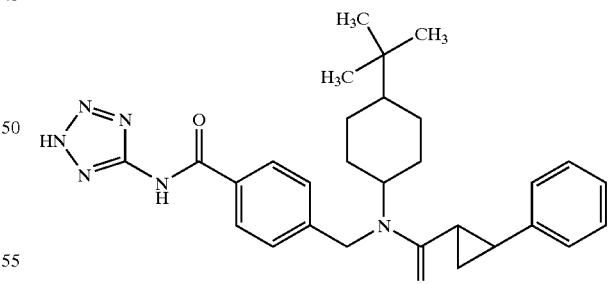

$^1$H NMR (DMSO): δ 8.09 (d, 2H); 8.04 (d, 2H); 7.44 (d, 4H); 7.40–7.10 (m, 8H); 7.01 (d, 2H); 4.92 (d, 1H); 4.77 (d, 1H); 4.72 (d, 1H); 4.68 (d, 1H); 4.44 (t, 1H); 4.13 (t, 1H).

HPLC-MS (Method D): m/z=501 (M+1). R$_t$=5.77 min.

EXAMPLE 537

General Procedure (V)

4-{[(2-Benzylsulfanylacetyl)-(4-tert-butylcyclohexyl)amino]methyl}-N-(2H-tetrazol-5-yl)benzamide

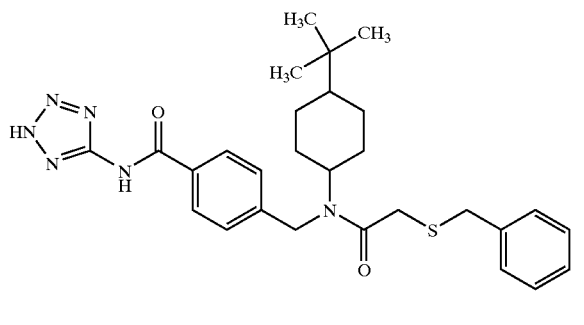

HPLC-MS (Method D): m/z=521 (M+1). $R_t$=5.87 min.

EXAMPLE 538

General Procedure (V)

4-{[(4-tert-Butylcyclohexyl)-(4-phenylbut-3-enoyl)amino]methyl}-N-(2H-tetrazol-5-yl)benzamide

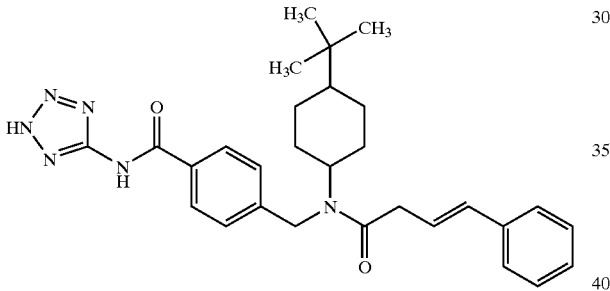

HPLC-MS (Method D): m/z=501 (M+1). $R_t$=5.83 min.

EXAMPLE 539

General Procedure (V)

4-({(4-tert-Butylcyclohexyl)-[2-(2,6-dichlorophenyl)acetyl]amino}methyl)-N-(2H-tetrazol-5-yl)benzamide

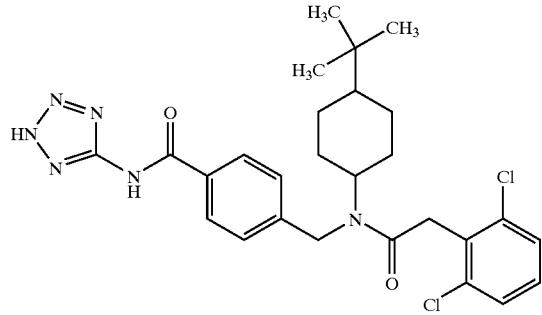

$^1$H NMR (DMSO) (molecule exists as isomers 1:2):
Minor isomer: δ 8.22 (d, 2H); 4.94 (s, 2H); 3.96 (s, 2H).
Major isomer: δ 8.10 (d, 2H); 4.68 (s, 2H); 4.30 (s, 2H).
Both isomers: δ 7.70–7.30 (m).

HPLC-MS (Method D): m/z=543 (M+1). $R_t$=6.20 min.

EXAMPLE 540

General Procedure (V)

4-({(4-tert-Butylcyclohexyl)-[4-(4-chlorophenyl)-4-oxobutyryl]amino}methyl)-N-(2H-tetrazol-5-yl)benzamide

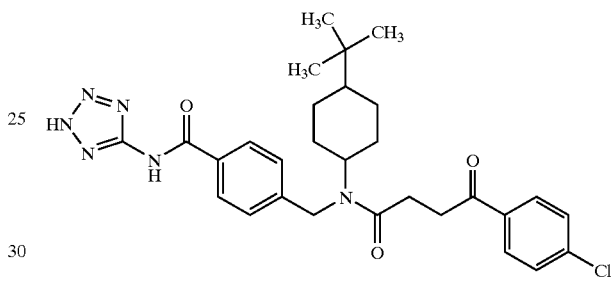

HPLC-MS (Method D): m/z=551 (M+1). $R_t$=5.93 min.

EXAMPLE 541

General Procedure (V)

4-({(4-tert-Butylcyclohexyl)-(4-oxo-4-phenylbutyryl)amino]methyl}-N-(2H-tetrazol-5-yl)benzamide

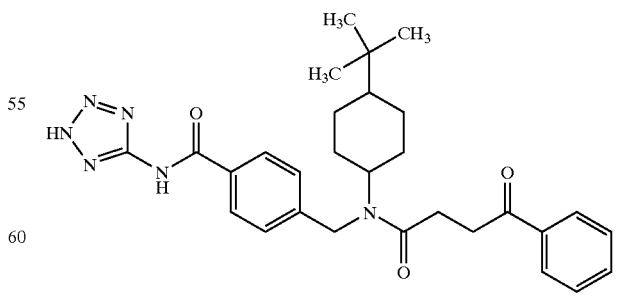

HPLC-MS (Method D): m/z=515 (M+1). $R_t$=5.60 min.

EXAMPLE 542

General Procedure (V)

4-({(4-tert-Butylcyclohexyl)-[2-(4-chlorophenoxy)
propionyl]amino}methyl)-N-(2H-tetrazol-5-yl)
benzamide

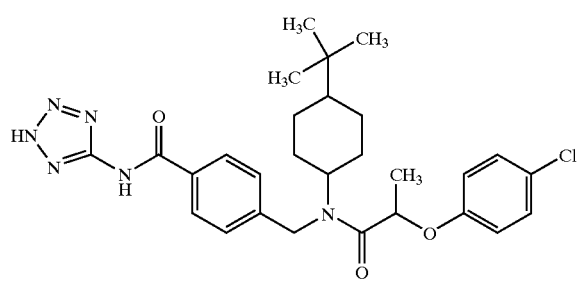

HPLC-MS (Method D): m/z=539 (M+1). $R_t$=5.97 min.

EXAMPLE 543

General Procedure (V)

4-({(4-tert-Butylcyclohexyl)-[2-(3-
trifluoromethoxyphenyl)acetyl]amino}methyl)-N-
(2H-tetrazol-5-yl)benzamide

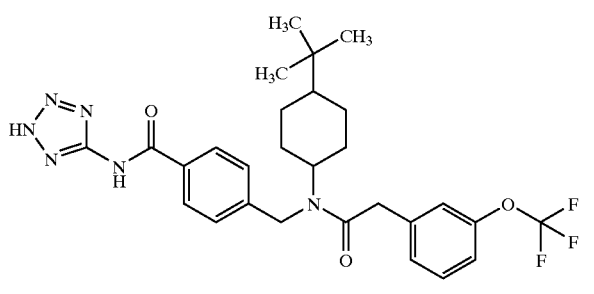

$^1$H NMR (DMSO) (isomers): δ 8.18–8.05 (two d, 2H);
7.60–7.15 (m, 6H); 4.90–4.60 (two s, 2H).
HPLC-MS (Method D): m/z=559 (M+1). $R_t$=6.03 min.

EXAMPLE 544

General Procedure (V)

4-({(4-tert-Butylcyclohexyl)-[2-(3-naphthalen-1yl-
acryloyl)amino]methyl}-N-(2H-tetrazol-5-yl)
benzamide

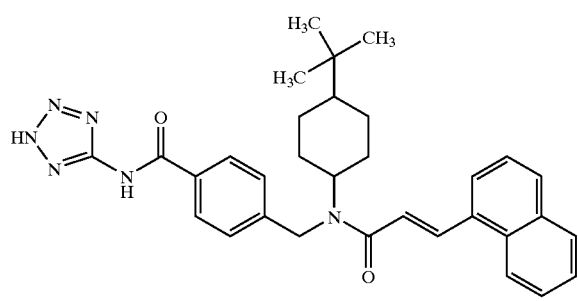

HPLC-MS (Method D): m/z=537 (M+1). $R_t$=6.23 min.

EXAMPLE 545

General Procedure (V)

4-([(4-tert-Butylcyclohexyl)-(4-phenylbutyryl)
amino]methyl}-N-(2H-tetrazol-5-yl)benzamide

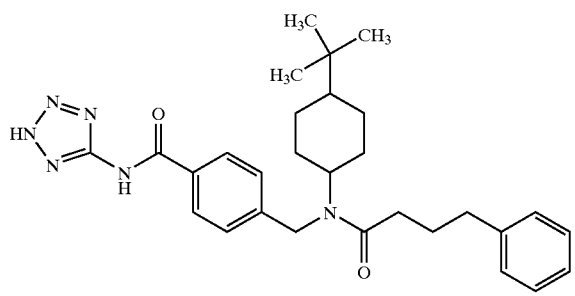

$^1$H NMR (DMSO) (isomers): δ 8.15, 8.11 (d, 2H);
7.45–7.15 (m, 7H); 4.68, 4.65 (s, 2H).
HPLC-MS (Method D): m/z=503 (M+1). $R_t$=5.97 min.

EXAMPLE 546

General Procedure (V)

4-([(4-tert-Butylcyclohexyl)-(3H-indene-1-carbonyl)
amino]methyl}-N-(2H-tetrazol-5-yl)benzamide

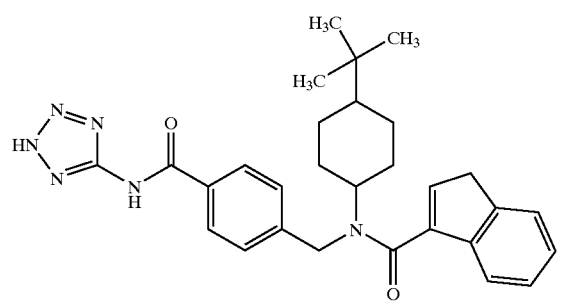

HPLC-MS (Method D): m/z=499 (M+1). $R_t$=5.67 min.

EXAMPLE 547

General Procedure (V)

4-{[(2-Biphenyl-4-ylacetyl)-(4-tert-butylcyclohexyl)
amino]methyl}-N-(2H-tetrazol-5-yl)benzamide

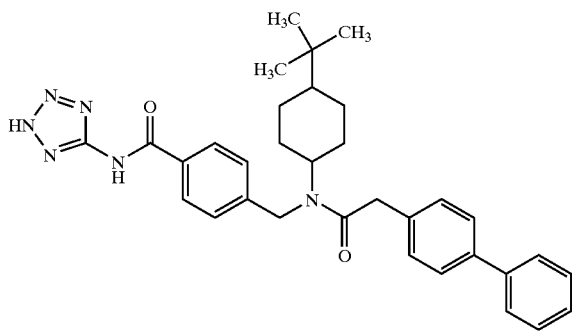

HPLC-MS (Method D): m/z=551 (M+l). $R_t$=6.27 min.

EXAMPLE 548

General Procedure (V)

4-({(4-tert-Butylcyclohexyl)-[2-(3-chlorophenoxy)propionyl]amino}methyl)-N-(2H-tetrazol-5-yl)benzamide

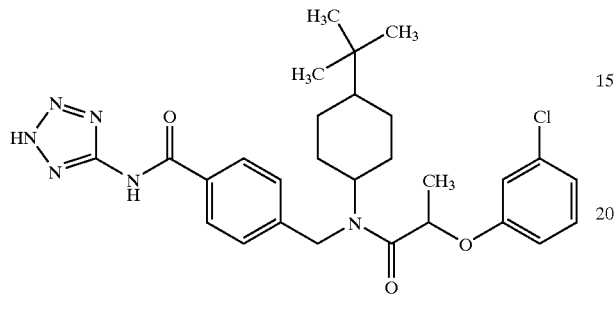

$^1$H NMR (DMSO): δ 8.05 (d, 2H); 7.44 (t, 1H); 7.34 (d, 2H); 7.13 (d, 1H); 7.10 (s, 1H); 7.01 (d, 1H); 5.70 (q, 1H); 4.60–4.70 (dd, 2H).

HPLC-MS (Method D): m/z=539 (M+1). $R_t$=5.97 min.

EXAMPLE 549

General Procedure (V)

4-({(4-tert-Butylcyclohexyl)-[3-(4-chlorophenyl)acroloyl]amino}methyl)-N-(2H-tetrazol-5-yl)benzamide

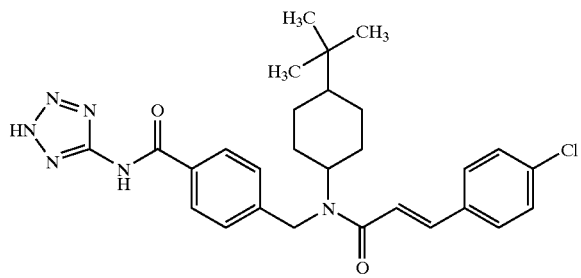

$^1$H NMR (DMSO) (isomers): δ 8.15 (d); 8.11(d); 7.90 (d); 7.70–7.62 (m); 7.58 (d); 7.55–7.42 (m); 7.03 (d); 5.15 (s); 5.00 (s).

HPLC-MS (Method D): m/z=521 (M+1). $R_t$=6.07 min.

EXAMPLE 550

General Procedure (V)

4-{[(4-tert-Butylcyclohexyl)-(2-Phenylpropionyl)amino]methyl}-N-(2H-tetrazol-5-yl)benzamide

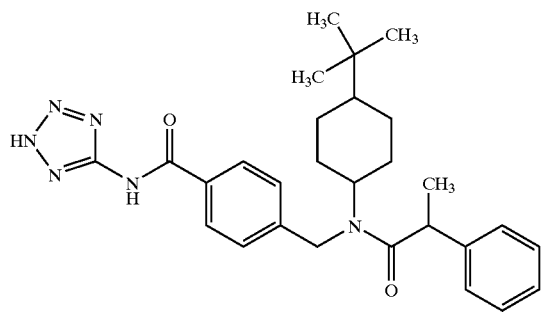

HPLC-MS (Method D): m/z=489 (M+1). $R_t$=5.83 min.

EXAMPLE 551

General Procedure (V)

4-({(4-tert-Butylcyclohexyl)-[3-(3-chlorophenyl)acroloyl]amino}methyl)-N-(2H-tetrazol-5-yl)benzamide

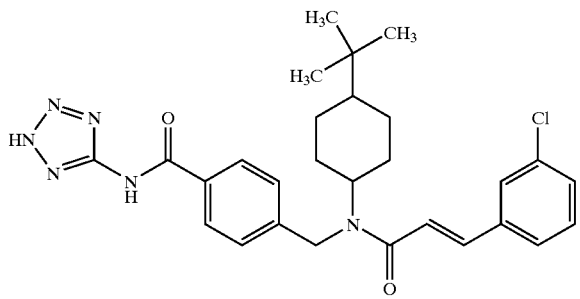

$^1$H NMR (DMSO) (isomers): δ 8.15 (d) 8.11 8(d) 8.00 (s); 7.85–7.75 (m); 7.70–7.40 (m); 7.11 (d); 5.05 (s); 4.85 (s).

HPLC-MS (Method D): m/z=521 (M+1). $R_t$=6.03 min.

EXAMPLE 552

General Procedure (V)

4-({(4-tert-Butylcyclohexyl)-[3-(2,6-dichlorophenyl)acryloyl]amino}methyl)-N-(2H-tetrazol-5-yl)benzamide

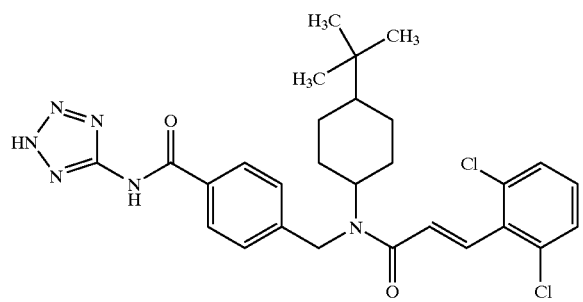

$^1$H NMR (DMSO): δ 8.16 (d); 8.13 (d); 7.70–7.30 (m); 6.84 (d).

HPLC-MS (Method D): m/z=555 (M+1). $R_t$=6.23 min.

EXAMPLE 553

General Procedure (V)

4-{[[2-(2,6-Dichlorophenyl)acetyl]-(4-piperidin-1-ylphenyl)amino]methyl}-N-(2H-tetrazol-5-yl)benzamide

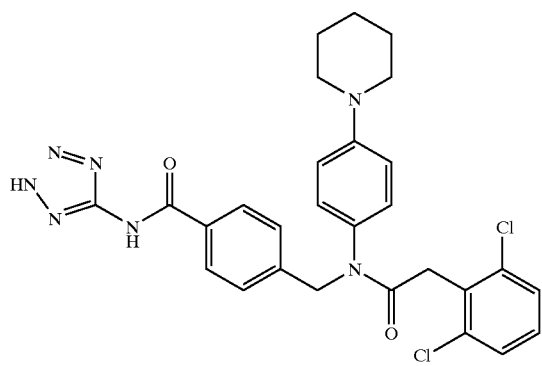

$^1$H NMR (DMSO): δ 8.13 (d, 2H); 7.48 (d, 2H); 7.41–7.36 (m, 2H); 7.34–7.30 (m, 3H); 7.05 (d, 2H); 6.93 (d, 2H); 5.00 (s, 2H).

HPLC-MS (Method D): m/z=479 (M+1). $R_t$=564 min.

EXAMPLE 554

General Procedure (V)

4-({(4-Piperidin-1-ylphenyl)-[2-(4-trifluoromethoxyphenoxy)propionyl]amino}methyl)-N-(2H-tetrazol-5-yl)benzamide

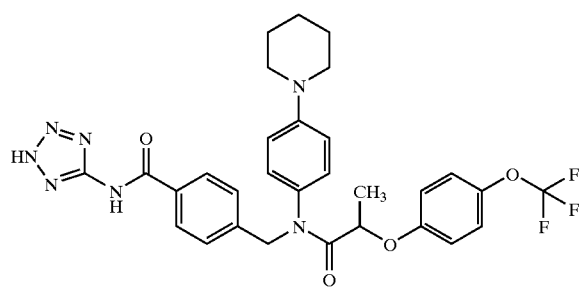

$^1$H NMR (DMSO): δ 8.10 (d, 2H); 7.40 (d, 2H); 7.36 (d, 2H); 7.13 (d, 2H); 6.95 (d, 2H); 6.90 (d, 2H); 5.05 (d, 1H); 4.95 (d,1H); 4.80 (q, 1H).

HPLC-MS (Method D): m/z=610 (M+1). $R_t$=4.83 min.

EXAMPLE 555

General Procedure (V)

4-{[[3-(2-Chlorophenyl)acryloyl]-(4-piperidin-1-ylphenyl)amino]methyl}-N-(2H-tetrazol-5-yl)benzamide

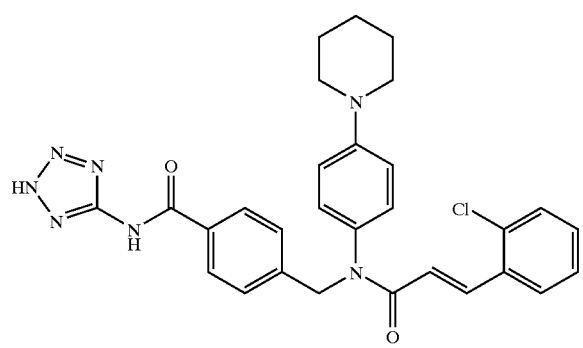

$^1$H NMR (DMSO): δ 8.13 (d, 2H); 7.95 (d, 1H); 7.60 (d, 1H); 7.54–7.45 (m, 5H); 7.15 (d, 2H); 7.01 (d, 2H); 6.58 (d, 1H); 5.13 (s, 2H).

HPLC-MS (Method D): m/z=542 (M+1). $R_t$=4.37 min.

EXAMPLE 556

General Procedure (V)

4-({(2,2-Diphenylethyl)-[2-(3-trifluoromethoxyphenyl)acetyl]amino}methyl)-N-(2H-tetrazol-5-yl)benzamide

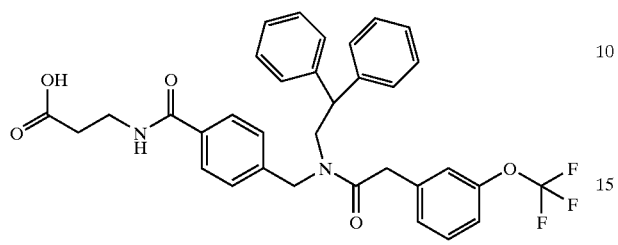

$^1$H NMR (DMSO) (isomers): δ 8.56 (t), 8.52 (t); 7.87 (d); 7.81 (d); 7.50–7.22 (m); 7.13 (s); 7.08 (t); 6.99 (s); 4.26 (s); 4.51 (q); 4.43 (s); 4.07 (d); 4.02 (d).
HPLC-MS (Method D): m/z=605 (M+1). $R_t$=5.37 min.

EXAMPLE 557

General Procedure (V)

5-Trifluoromethoxy-1H-indole-2-carboxylic acid (4-tert-butylcyclohexyl)-[4-(2H-tetrazol-5-ylcarbamoyl)benzyl]amide

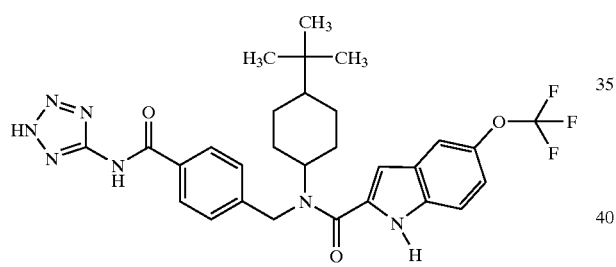

HPLC-MS (Method C): m/z=584 (M+1), $R_t$=8.07 min.

EXAMPLE 558

General Procedure (V)

5-Trifluoromethoxy-1H-indole-2-carboxylic acid (4-cyclohexylphenyl)-[4-(2H-tetrazol-5-ylcarbamoyl)benzyl]amide

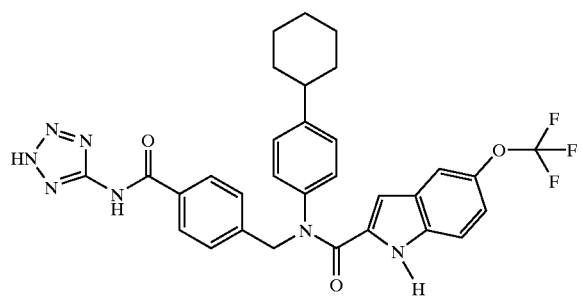

HPLC-MS (Method B): m/z=604 (M+1), $R_t$=8.33 min.

EXAMPLE 559

General Procedure (V)

5-Trifluoromethoxy-1H-indole-2-carboxylic acid (4-tert-butylphenyl)-[4-(2H-tetrazol-5-ylcarbamoyl)benzyl]amide

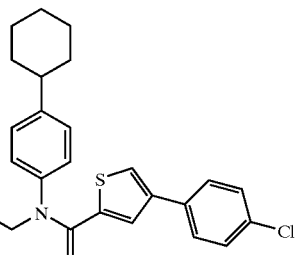

HPLC-MS (Method B): m/z=578 (M+1), $R_t$=7.78 min.

EXAMPLE 560

General Procedure (V)

3-(4-{[[4-(4-Chlorophenyl)thiophene-2-carbonyl]-(4-cyclohexylphenyl)amino]methyl}benzoylamino)propionic acid

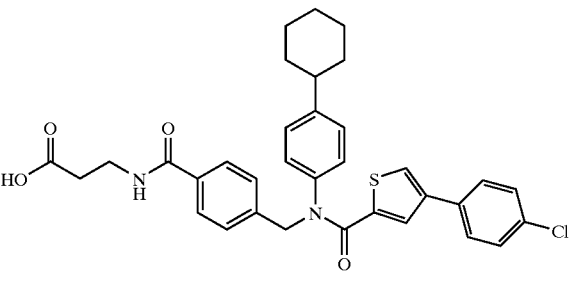

$^1$H NMR (DMSO-d$_6$): δ 12.25 (br s, 1H); 8.50 (t, 1H); 8.05 (s, 1H); 7.75 (d, 2H); 7.42–7.30 (m, 6H); 7.28 (d, 2H); 7.18 (d, 2H); 6.62 (s, 1H); 5.09 (s, 2H); 1.80–1.65 (m, 5H); 1.40–1.15 (m, 5H).
HPLC-MS (Method B): R=8.32 min, m/z=601 (M+1).

EXAMPLE 561

General Procedure (V)

3-(4-{[(5-Chlorobenzofuran-2-carbonyl)-(4-cyclohexylphenyl)amino]methyl}benzoylamino)propionic acid

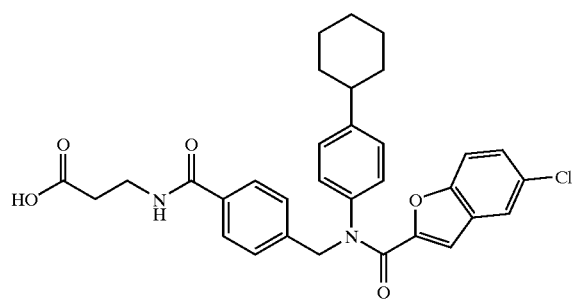

¹H NMR (DMSO-d₆): δ 8.51 (t, 1H); 7.78 (d, 2H); 7.67 (s, 1H); 7.49 (d, 1H); 7.42–7.32 (m, 3H); 7.21 (d, 2H); 7.14 (d, 2H); 6.47 (s, 1H); 5.11 (s, 2H); 1.80–1.65 (m, 5H); 1.45–1.10 (m, 5H).

HPLC-MS (Method B): m/z=559 (M+1), R$_t$=7.88 min.

EXAMPLE 562

General Procedure (V)

3-(4-{[(4-tert-Butylcyclohexyl)-(5-chlorobenzofuran-2-carbonyl)amino]methyl}benzoylamino)propionic acid

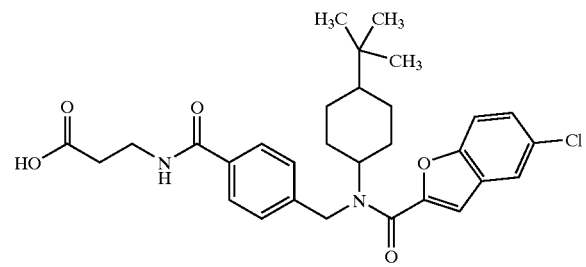

¹H NMR (DMSO-d₆): δ 12.25 (s, 1H); 8.52 (t, 1H); 7.92–7.70 (m, 4H); 7.50–7.15 (m, 4H); 4.80 (d br, 2H); 4.25–4.00 (d br, 1H); 3.50 (dd, 2H); 1.90–1.50 (m, 6H); 1.10–0.90 (m, 3H); 0.75 (s, 9H).

HPLC-MS (Method B): m/z=539 (M+1). R$_t$=7.85 min.

EXAMPLE 563

General Procedure (V)

3-(4-{[(5-Chlorobenzofuran-2-carbonyl)-(2,2-diphenylethyl)amino]methyl}benzoylamino)propionic acid ¹H NMR (DMSO-d₆): δ 8.52 (t, 1H); 7.80 (s, 3H); 7.58 (d, 1H); 7.50–7.05 (m, 14H); 4.65 (s, 2H); 4.50–4.05 (m, 2H).

HPLC-MS (Method B): m/z=581 (M+1). R$_t$=7.17 min.

EXAMPLE 564

General Procedure (V)

4-(4-Chlorophenyl)thiophene-2-carboxylic acid (4-tert-butylcyclohexyl)-[4-(2H-tetrazol-5-ylcarbamoyl)benzyl]amide

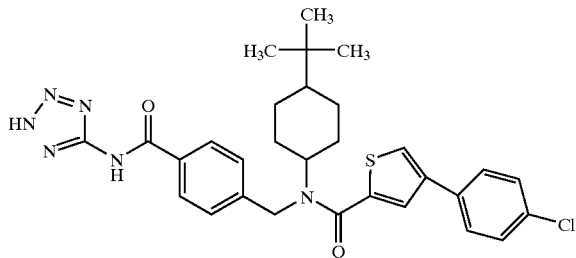

¹H NMR (DMSO-d₆): δ 12.40 (s, 1H); 8.10 (m, 3H); 7.85–7.65 (m, 3H); 7.50 (m, 4H); 4.85 (br d, 2H); 4.42+4.18 (m br, 1H); 1.95–1.48 (m, 7H); 1.20–1.00 (m, 2H); 0.80 (s, 9H).

HPLC-MS (Method B): m/z=577 (M+1). R$_t$=8.37 min.

EXAMPLE 565

General Procedure (V)

4-(4-Chlorophenyl)thiophene-2-carboxylic acid (4-cyclohexylphenyl)-[4-(2H-tetrazol-5-ylcarbamoyl)benzyl]amide

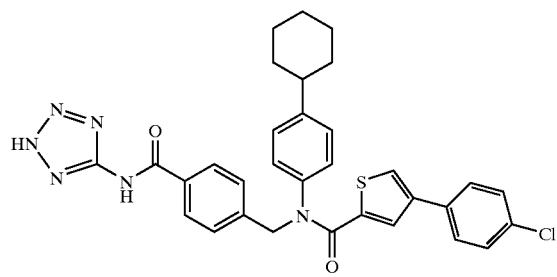

$^1$H NMR (DMSO-d$_6$): δ 12.40 (s, 1H); 8.05 (d+s, 3H); 7.52 (d, 2H); 7.35 (s, 4H); 7.28 (d, 2H); 7.18 (d, 2H); 6.61 (s, 1H); 5.11 (s, 2H); 1.90–1.65 (m, 5H); 1.60–1.15 (5H).

HPLC-MS (Method B): m/z=597 (M+1). R$_t$=8.65 min.

EXAMPLE 566

General Procedure (V)

4-(4-Chlorophenyl)thiophene-2-carboxylic acid (2,2-diphenyl-ethyl)-[4-(2H-tetrazol-5-ylcarbamoyl)benzyl]amide

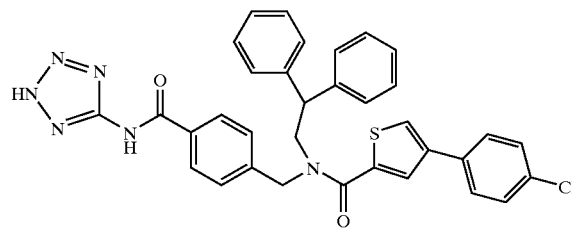

$^1$H NMR (DMSO-d$_6$): δ 12.44 (s, 1H); 8.10 (s+d, 3H); 7.60 (d, 2H); 7.45–7.15 (m, 15H); 4.62 (s, 2H); 4.59 (s br, 1H); 4.28 (br s, 2H).

HPLC-MS (Method B): m/z=619 (M+1). R$_t$=7.67 min.

EXAMPLE 567

General Procedure (V)

4-[1-(4-Cyclohexylphenyl)-3-(3-trifluoromethylphenyl)ureidomethyl]-N-(2H-tetrazol-5-yl)benzamide

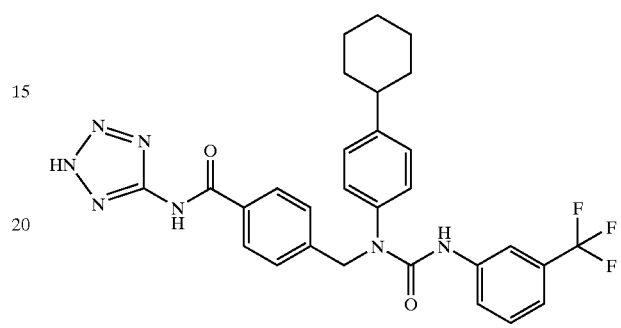

$^1$H NMR (DMSO-d$_6$): δ 12.30 (s, 1H); 8.60 (s, 1H); 8.03 (d, 2H); 7.88 (s, 1H); 7.72 (d, 1H); 7.48 (m, 3H); 7.38 (d, 1H); 7.20 (s, 4H); 5.00 (s, 2H); 1.85–1.65 (m, 5H); 1.50–1.20 (m, 5H).

HPLC-MS (Method B): m/z=564 (M+1), R$_t$=7.85 min.

The following library of compounds was made according to general procedure (V). All of the compounds are expected to be present in the library.

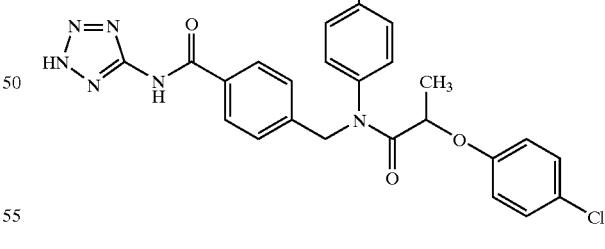

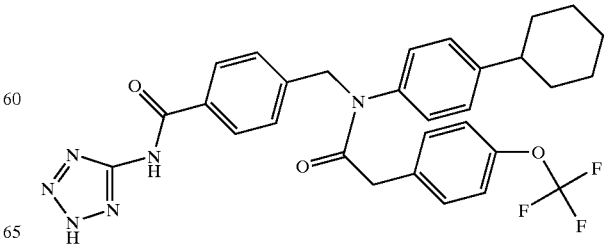

| 389 | 390 |
|---|---|
| -continued | -continued |
| 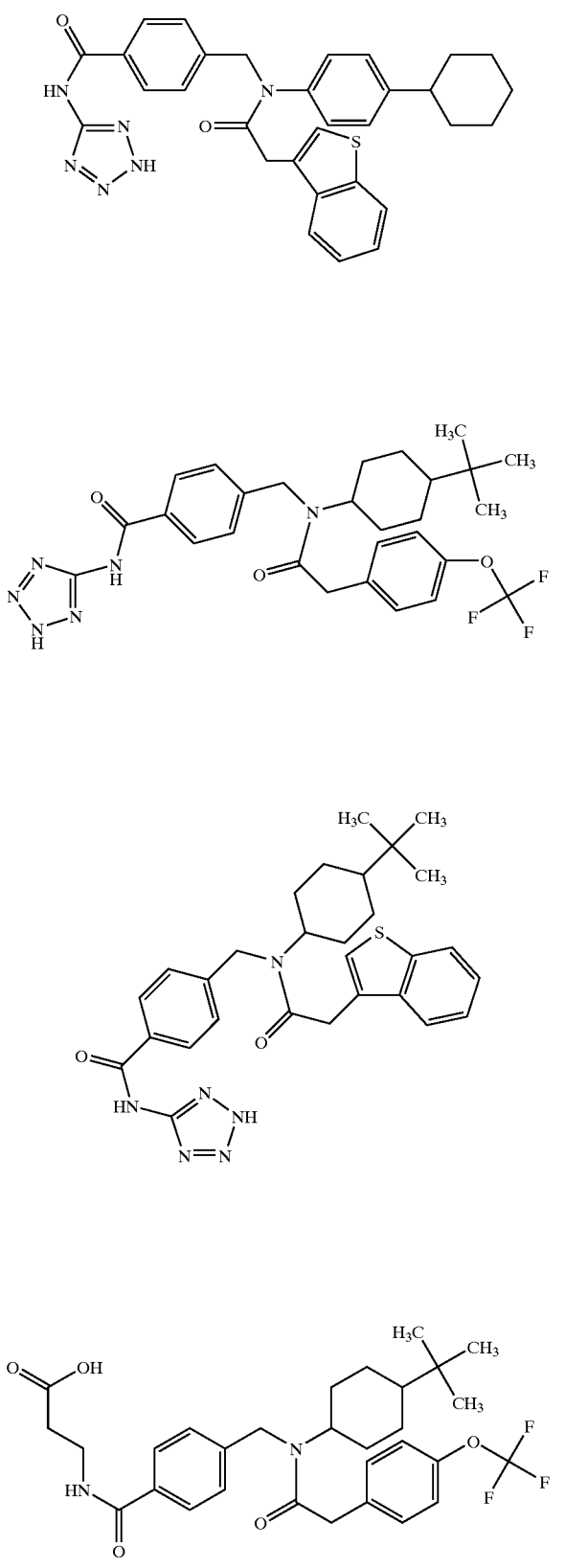 | 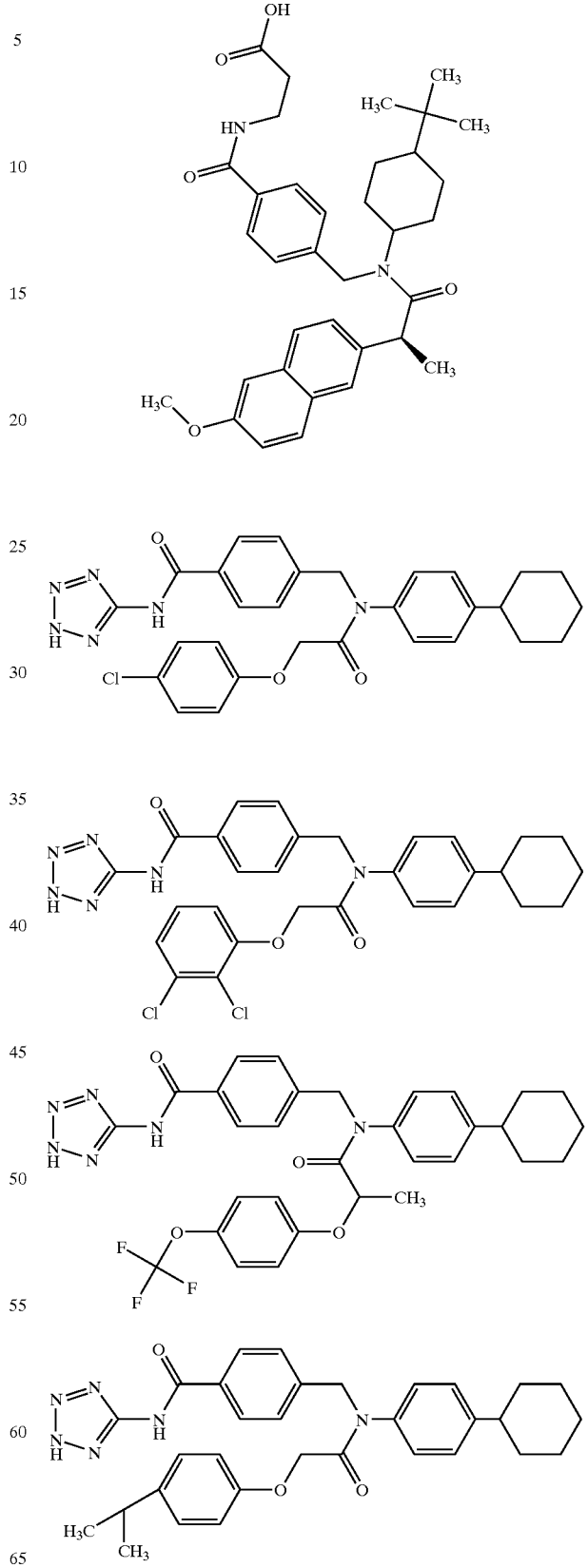 |

-continued
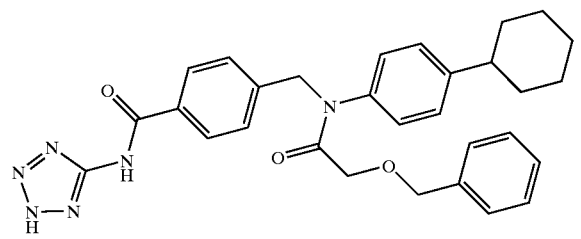
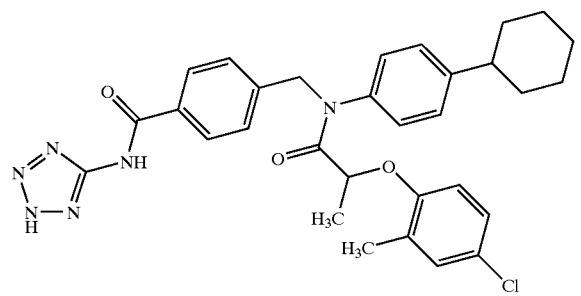
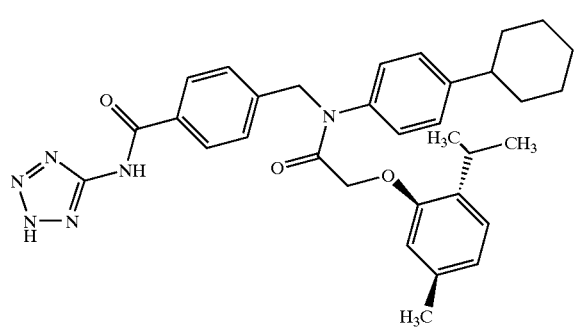
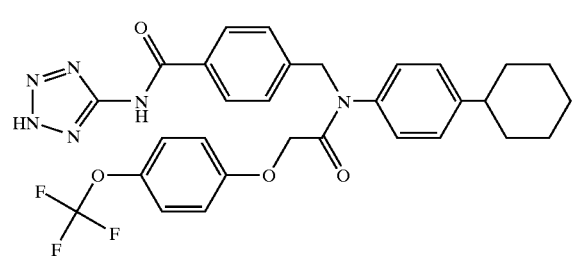
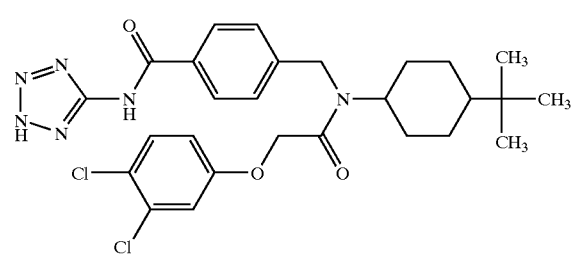
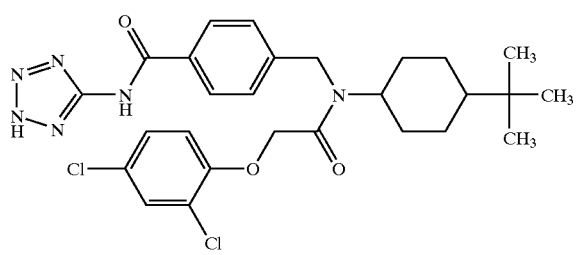
-continued
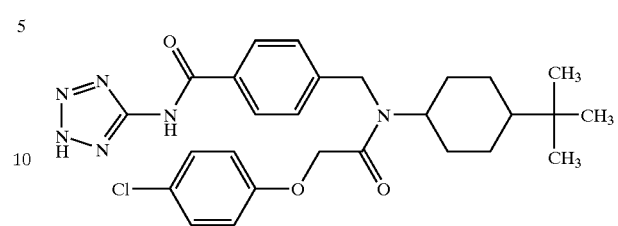
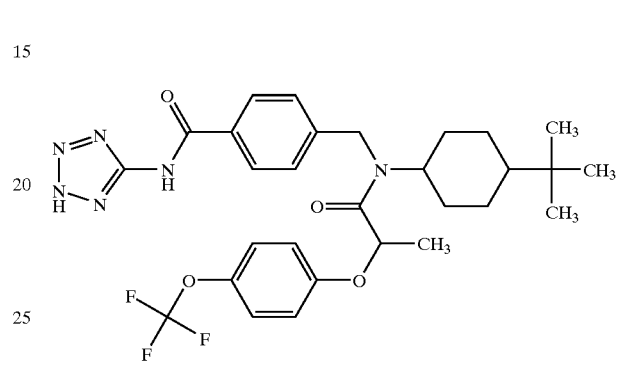
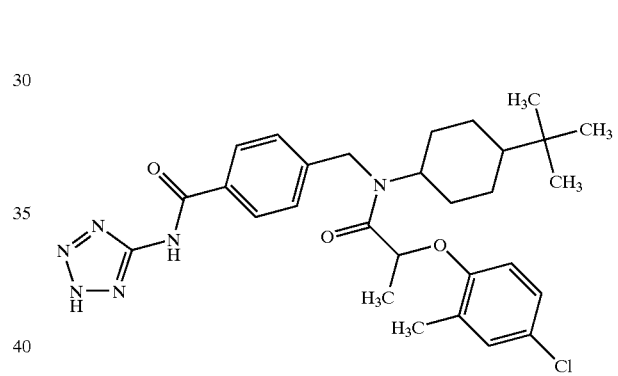
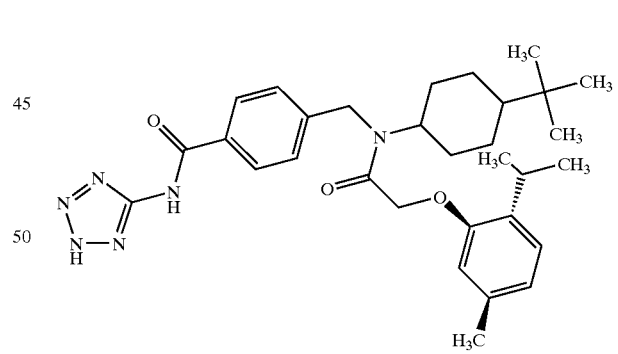
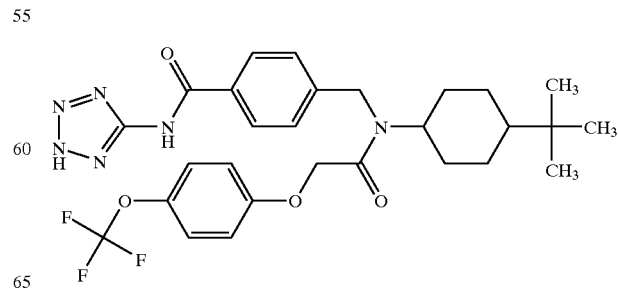

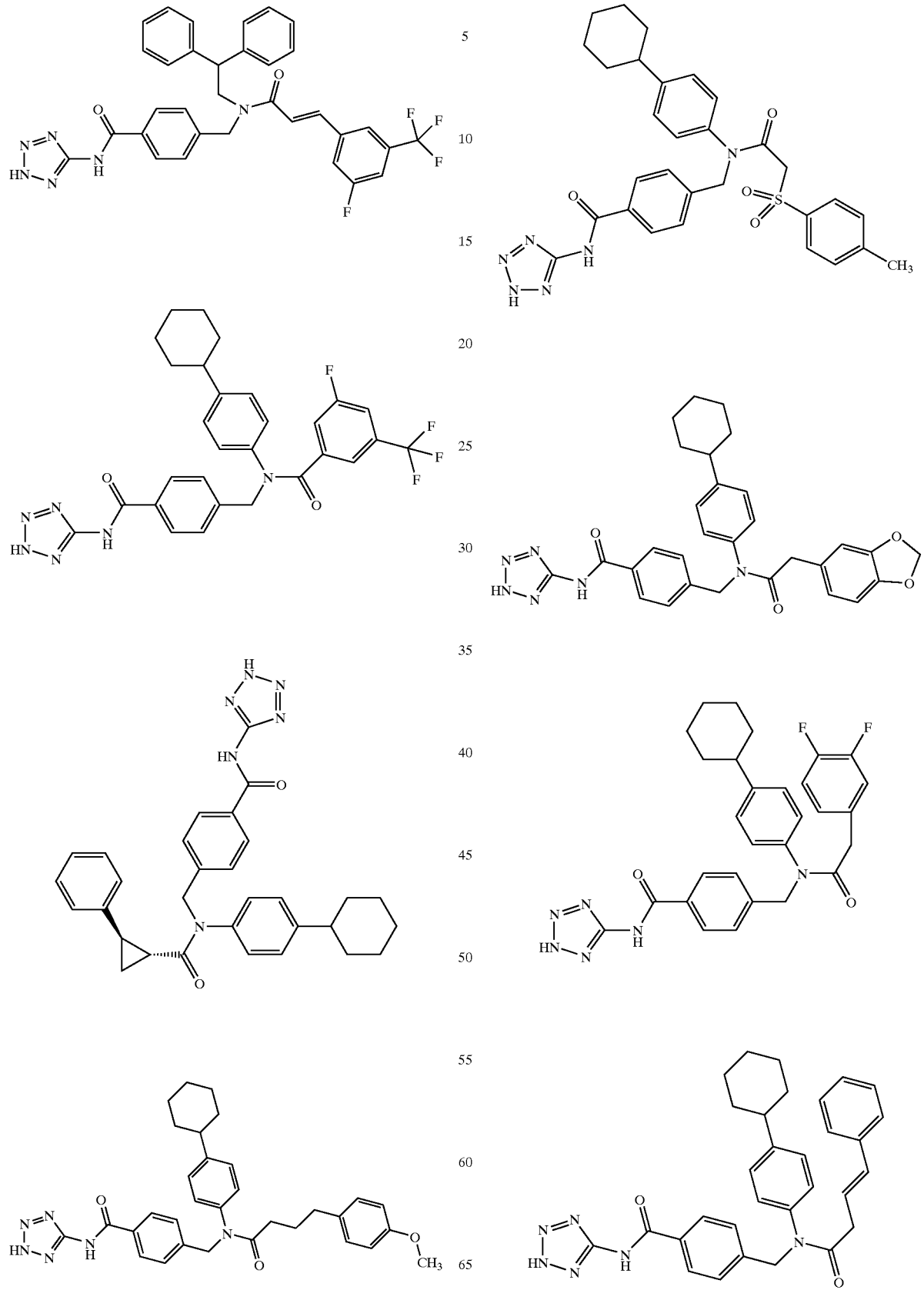

395
-continued
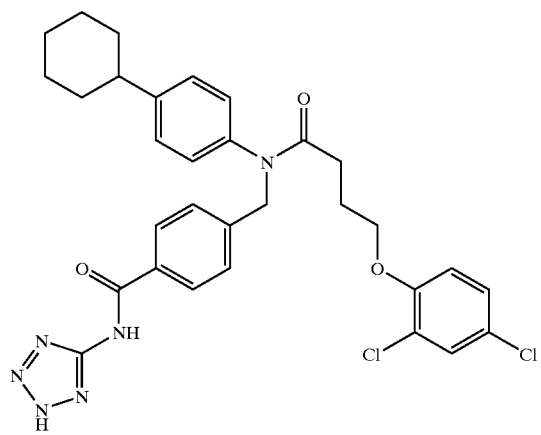
396
-continued
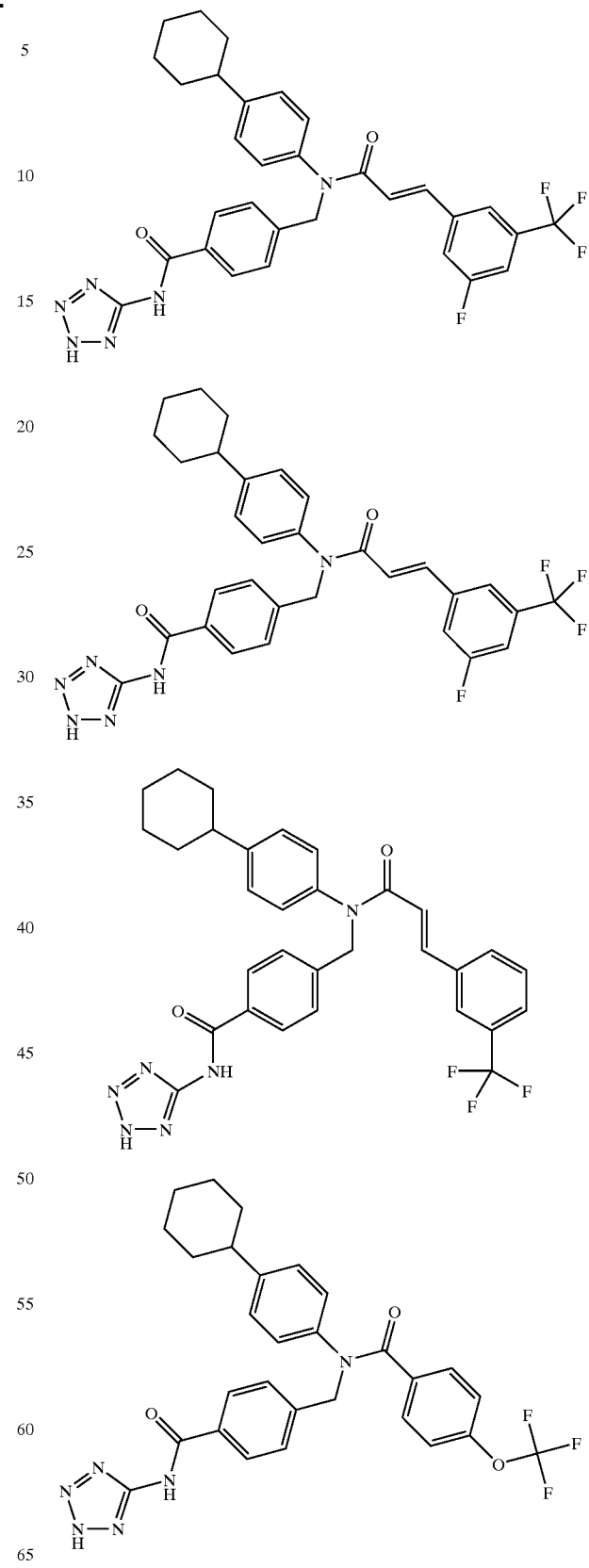

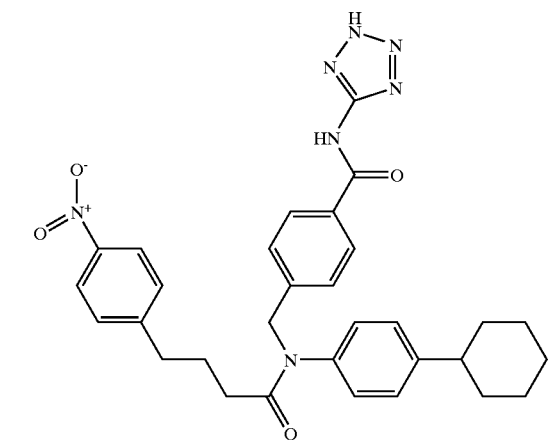
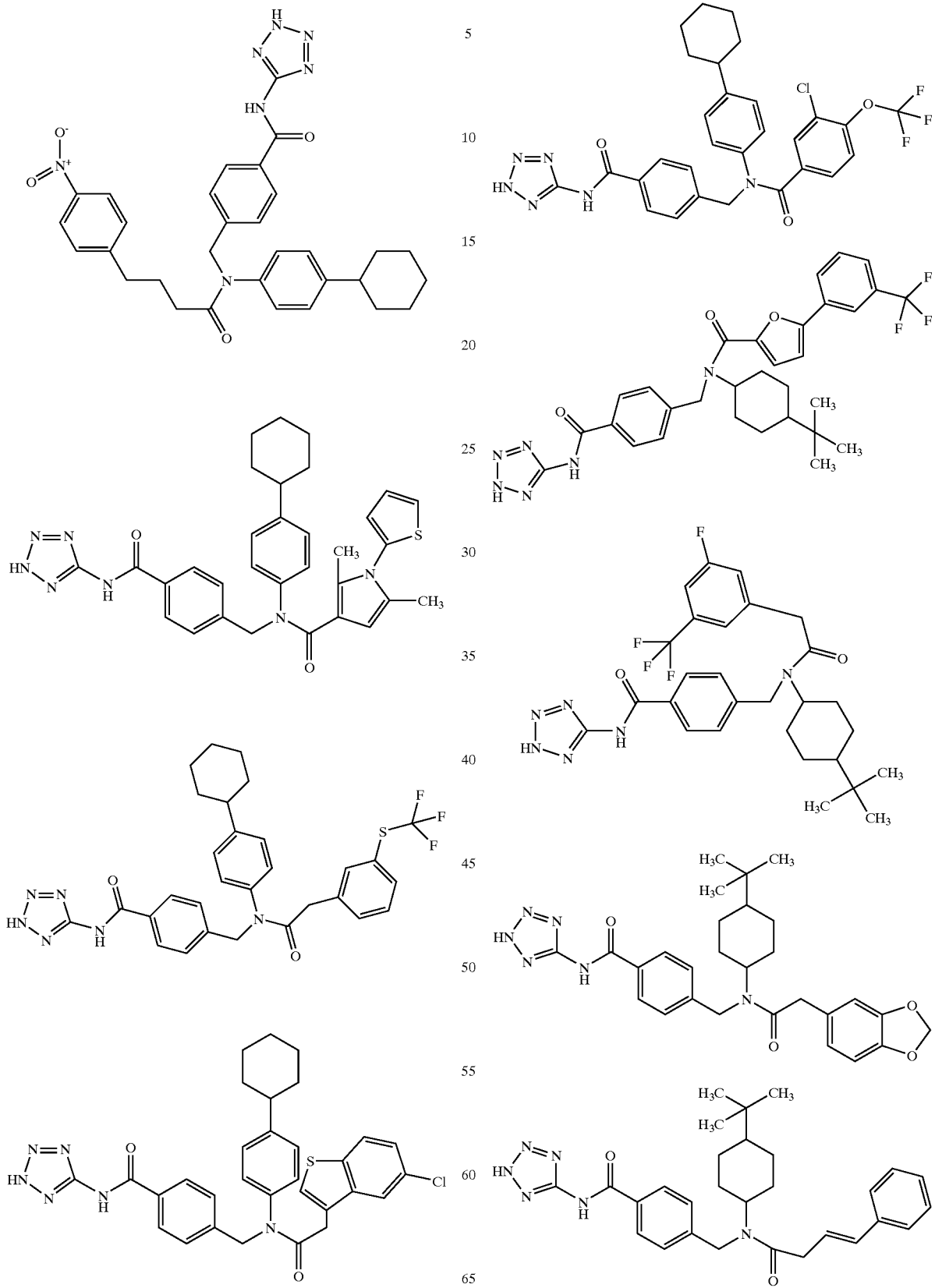

-continued
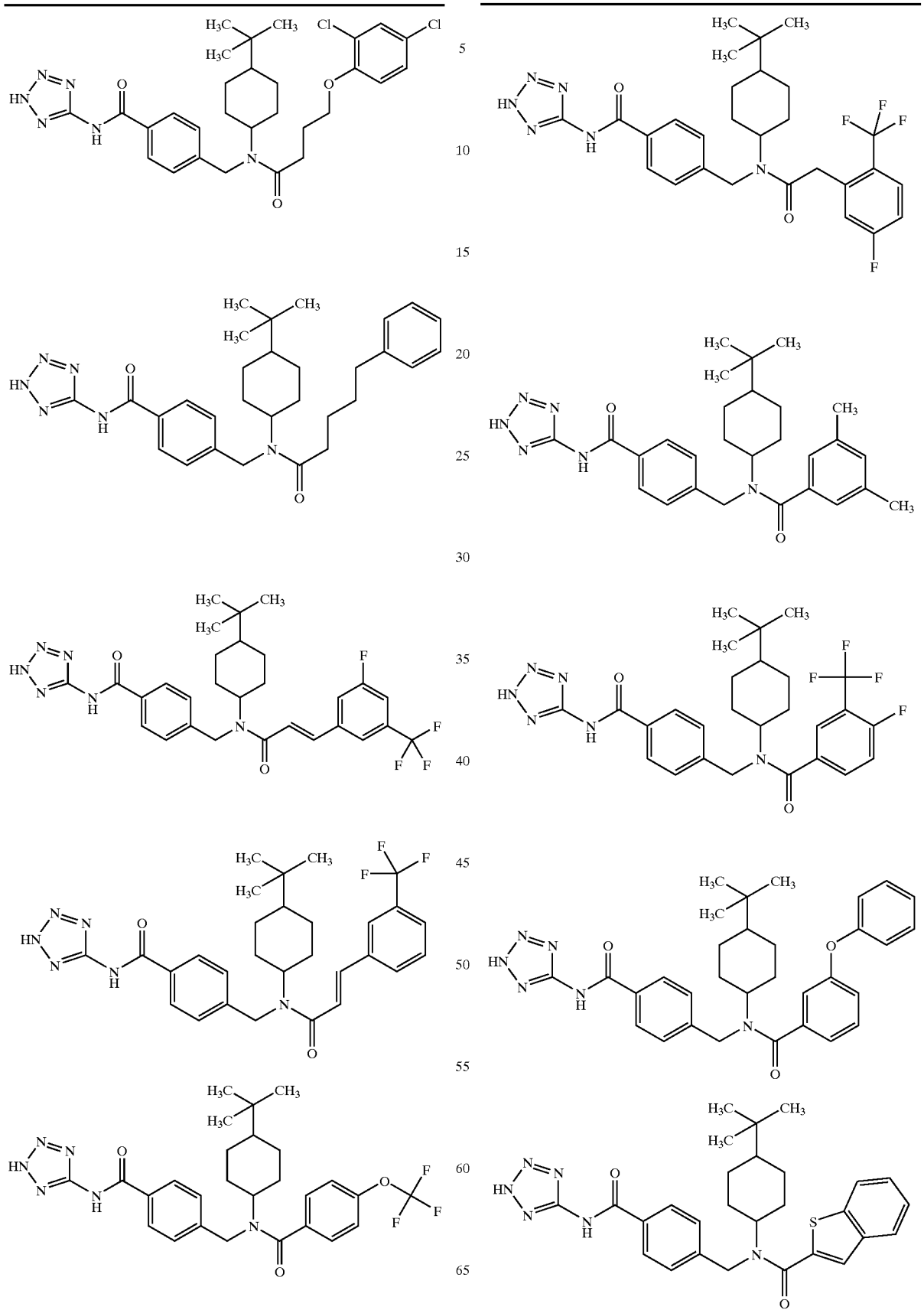

401
-continued
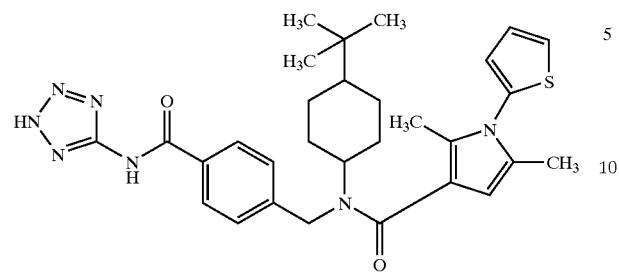
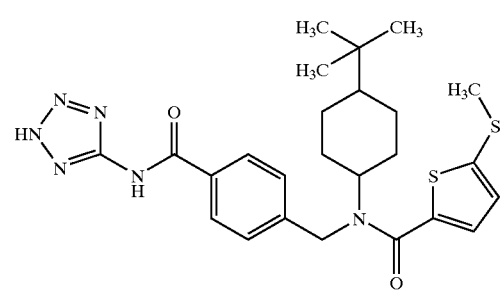
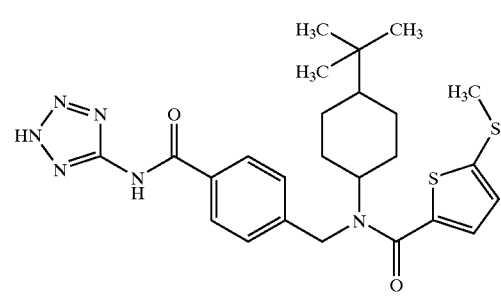
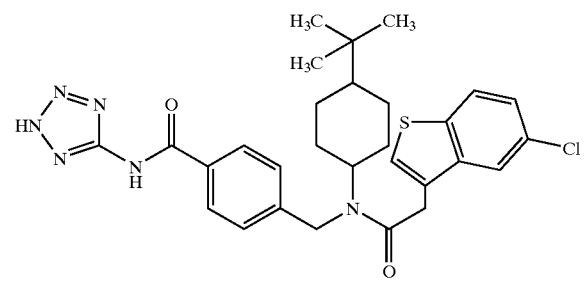
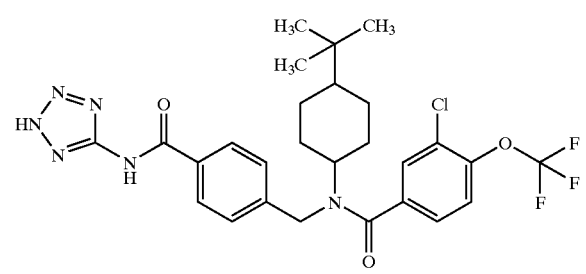
402
-continued
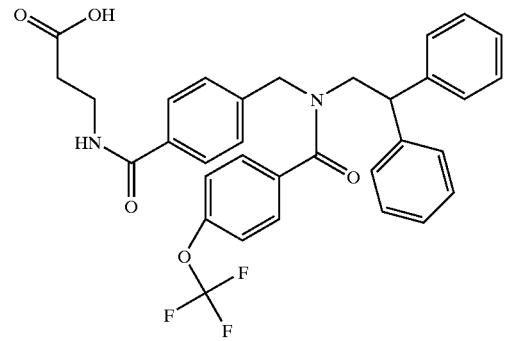
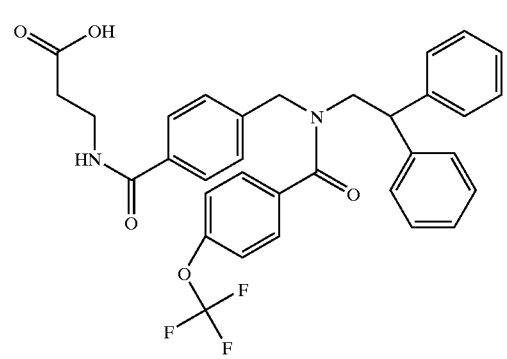
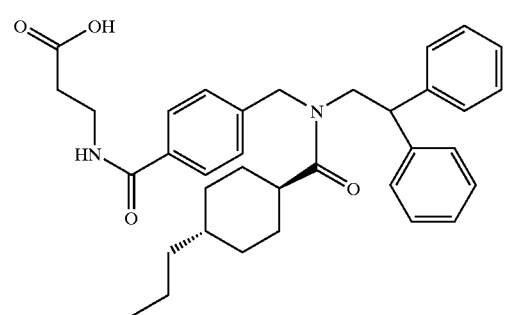
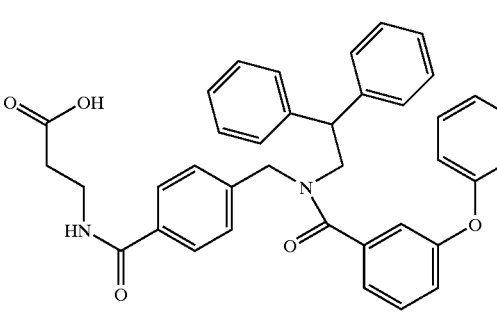

-continued
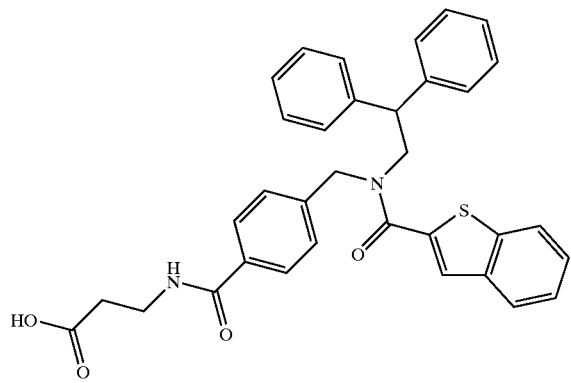
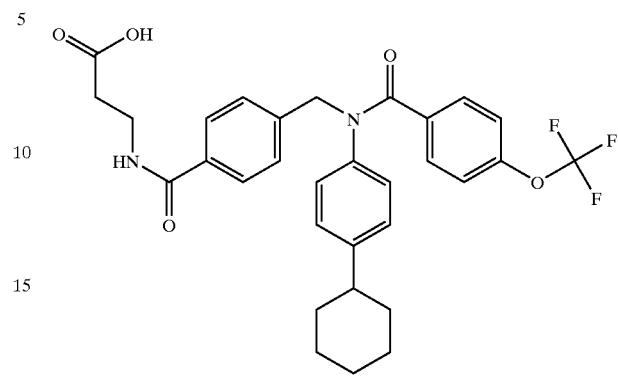
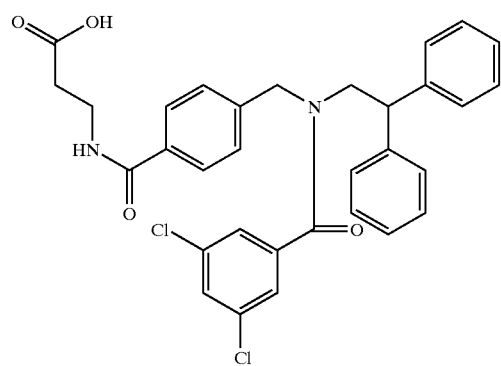
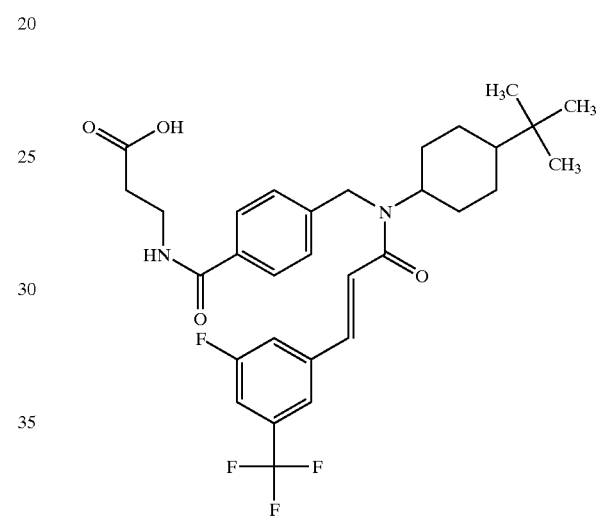
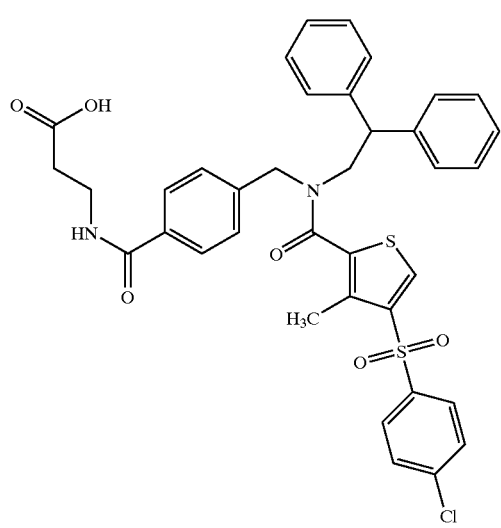
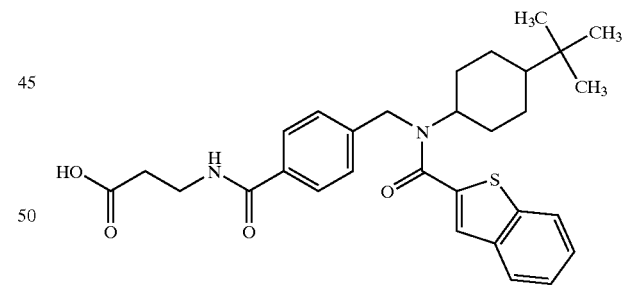
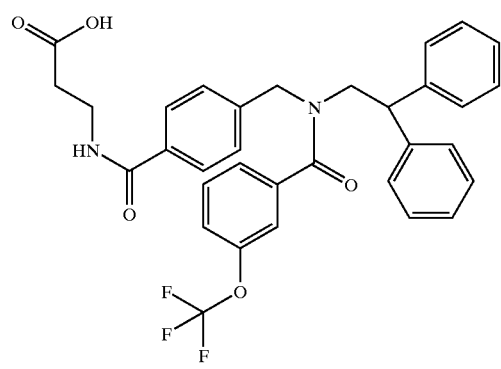
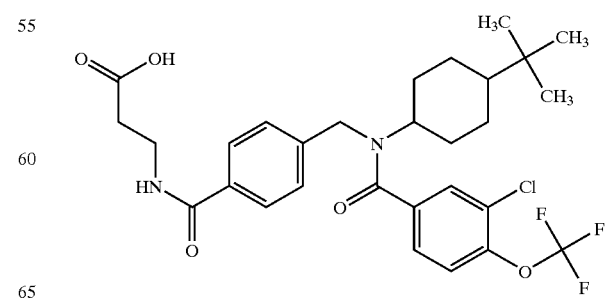

-continued

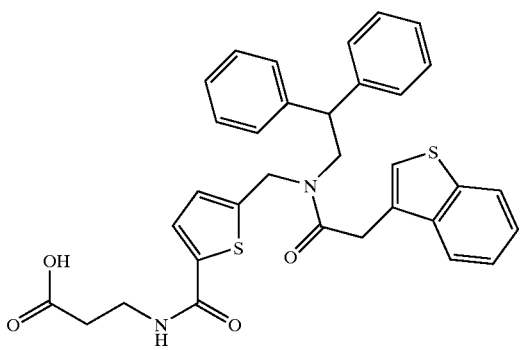

EXAMPLE 568

4-[1-(4-Cyclohexylphenyl)-3-(3-hydroxymethyl)-4-trifluoromethoxyphenyl)ureidomethyl]-N-(2H-tetrazol-5-yl)benzamide

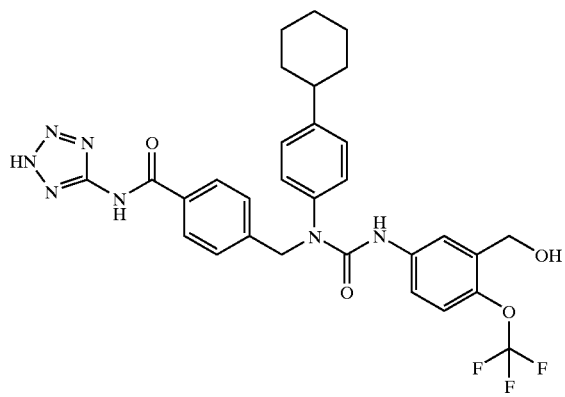

4-[3-[3-tert-Butyldimethylsilanyloxymethyl)-4-trifluoromethoxyphenyl]-1-(4-cyclohexylphenyl)ureidomethyl]-N-(2H-tetrazol-5-yl)benzamide (0.09 g, 0.12 mmol) (example 293) was dissolved in THF (2 mL) and a solution of tetrabutylammonium fluoride in THF (0,4 mL, 0,4 mmol, 1M) was added. The mixture was stirred for 6.5 hours and concentrated in vacuo. The residue was purified by column chromatography using 35 g of silica and dichloromethane and 10% ammonia in ethanol (80:20) as eluent to give 75 mg of the title compound.

$^1$H NMR (DMSO-$d_6$): δ 1.52–1.62 (6H, m), 1.68–1.83 (5H, m), 4.50 (2H, d), 4.98 (2H, s), 5.36 (1H, t), 7.16–7.22 (5H, m), 7.40 (2H, d), 7.53 (1H, dd), 7.64 (1H, d), 7.95 (2H, d), 8.44 (1H, s), 10.67 (1H, broad).

HPLC ms (method B): m/z: 610, $R_t$=7.34 min.

EXAMPLE 569

2-{4-[1-(4-tert-Butylphenyl)-3-(3-methylsulfonyl-4-methylphenyl)ureidomethyl]-benzoylamino}ethanesulfonic acid

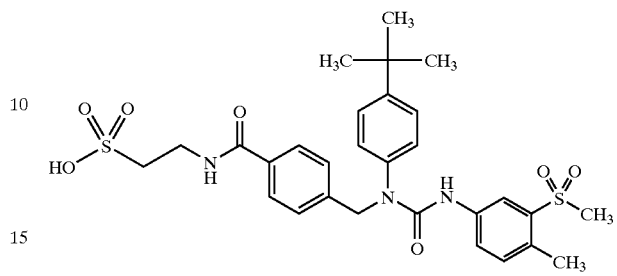

4-[1-(4-tert-Butylphenyl)-3-(3-methylsulfonyl-4-methylphenyl)ureidomethyl]benzoic acid (300 mg, 0.6 mmol) was dissolved in DMF (10 ml). Hydroxybenzotriazole (100 mg, 0.7 mmol), and N-(3-dimethylaminopropyl)-N'-ethylcarbodiimide hydrochloride (130 mg, 0.7 mmol) were added and the mixture was stirred for 30 minutes at room temperature followed by addition of 2-aminoethanesulfonic acid (110 mg, 0.9 mmol) and diisopropylethylamine (120 mg, 160 μl, 1.0 mmol). After 16 hours the reaction mixture was poured into water (40 mL), pH was adjusted to acidic reaction with sodium hydrogen sulphate and the solution was concentrated in vacuo. The residue was purified by flash chromatography (20 g Silica Gel) using methanol and dichloromethane (10:90) as eluent to give 0.2 g of the title compound.

$^1$H NMR (400 MHz, DMSO-$d_6$): δ 8.60 (s, 1H); 8.48 (t, 1H); 8.05 (s, 1H) 7.78 (d, 1H); 7.71 (d, 2H); 7.38 (d, 2H); 7.36 (d, 2H); 7.31 (d, 1H); 7.18 (d, 2H); 4.95 (s, 2H); 3.5 (q, 2H); 3.17 (s, 3H); 2.66 (t, 2H); 2.54 (s, 3H); 1.27 (s, 9H).

HPLC-MS (method B): m/z: 602, $R_t$=4.8 min.

EXAMPLE 570

3-(4-{[(cis-4-Cyclohexylcyclohexyl)-(4-trifluoromethoxybenzyl)amino]methyl}benzoylamino)propionic acid

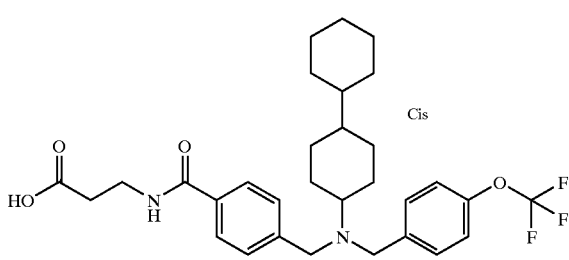

To a solution of 4-trifluoromethoxybenzylamine (2.76 g, 14.4 mmol) in methanol (150 mL) was added 4-(4-cyclohexyl)cyclohexanone (2.60 g, 14.4 mmol) and NaBH(OAc)$_3$ (3.64 g, 17.2 mmol). The mixture was stirred for 16 hours at room temperature, and filtered by suction. The filtrate was concentrated, the residue was dissolved in ethyl acetate (150 mL), washed with NaHCO$_3$ solution (100 mL), brine (100 mL), dried (Na$_2$SO$_4$), and concentrated. The cis- and trans-isomers were separated by flash chromatography. The cis-isomer together with a byproduct eluted with hexane, ethyl acetate (5:1) and was used without further purification and characterization in the next step. Pure trans-isomer was eluted with hexane, ethyl acetate (3:1). N-[4-(trans-4-Cyclohexyl)cyclohexyl)]-4-trifluoromethoxybenzylamine:

$^1$H NMR (CDCl$_3$): δ 0.82–1.17 (m, 11H), 1.59–1.76 (m, 7H), 1.86 (d, 2H), 2.41 (m, 1H), 3.81 (s, 2H), 7.16 (d, 2H), 7.34 (d, 2H). MS (APCl, pos.): 356.2 (M+1).

To a solution of crude N-4-(cis-4-cyclohexylcyclohexyl)-4-trifluoromethoxybenzylamine (760 mg) in dichloromethane (10 mL) was added ethyl 3-[(4-formylbenzoyl)amino]propionate (240 mg, 1.0 mmol) and NaBH(OAc)$_3$ (240 mg, 1.1 mmol). After stirring for 16 hours at room temperature, the mixture was diluted with ethyl acetate (20 mL), washed with NaHCO$_3$ solution (10 mL), and brine (10 mL), dried (MgSO$_4$), and concentrated. Flash chromatography (hexane, ethyl acetate, 3:1) afforded N-[4-({cis-4-cyclohexyl)cyclohexyl)]-[4-(trifluoromethoxy)benzyl]amino}methyl)benzoyl]-β-alanine ethyl ester (226 mg).

$^1$H NMR (CDCl$_3$): δ 0.82–1.86 (m, 23H), 2.49 (m, 1H), 2.64 (t, 2H), 3.62 (s, 2H), 3.66 (s, 2H), 3.70 (q, 2H), 4.15 (q, 2H), 6.84 (t, 1H), 7.12 (d, 2H), 7.35 (d, 2H), 7.40 (d, 2H), 7.68 (d, 2H).

MS (APCl, pos.): 589.2 (M+1).

The above ester was dissolved in THF (10 mL), and 1M LiOH (0.5 mL) was added. After stirring at room temperature for 16 hours, the solution was acidified with 1N HCl to pH=4, and concentrated. The residue was dissolved in acetone (15 mL), filtered by suction, and the filtrate was concentrated. The title compound was purified by HPLC.

$^1$H NMR (DMSO-d$_6$): δ 0.71–1.87 (m, 20H), 2.37 (t, 2H), 3.40 (t, 2H), 3.61 (s, 2H), 3.63 (s, 2H), 7.20 (d, 2H), 7.39 (d, 2H), 7.44 (d, 2H), 7.67 (d, 2H), 8.53 (t, 1H).

MS (APCl, pos.): 561.3 (M+1).

EXAMPLE 571

3-(4-{[(trans-4-Cyclohexylcyclohexyl)-(4-trifluoromethoxybenzyl)amino]methyl}benzoylamino)propionic acid

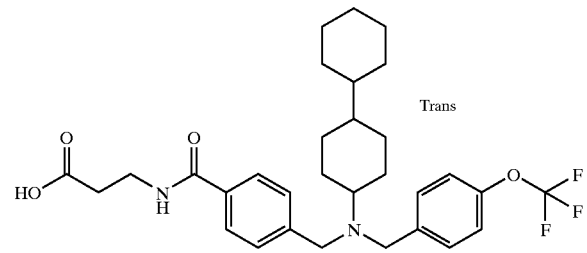

To a solution of N-[4-(trans-4-cyclohexylcyclohexyl)]-4-trifluoromethoxybenzylamine (149 mg, 0.42 mmol) in dichloromethane (10 mL) was added ethyl 3-[(4-formylbenzoyl)amino]propionate (104 mg, 0.42 mmol) and NaBH(OAc)$_3$ (132 mg, 0.62 mmol). After stirring for 16 hours at room temp. additional aldehyde (100 mg) and NaBH(OAc)$_3$ (132 mg) were added. After stirring for 72 hours at room temp., the mixture was diluted with ethyl acetate (20 mL), washed with NaHCO$_3$ solution (10 mL), brine (10 mL), dried (MgSO$_4$), and concentrated. Flash chromatography (hexane, ethyl acetate, 3:1) provided the title compound (74.2 mg).

$^1$H NMR (CDCl$_3$): δ 0.82–1.77 (m, 21H), 1.89 (d, 2H), 2.38 (tt, 1H), 2.64 (t, 2H), 3.60 (s, 2H), 3.64 (s, 2H), 3.72 (q, 2H), 4.16 (q, 2H), 6.82 (t, 1H), 7.12 (d, 2H), 7.35 (d, 2H), 7.40 (d, 2H), 7.68 (d, 2H).

MS (APCl, pos.): 589.2 (M+1).

The above ester was dissolved in THF, and excess 1M LiOH was added. After stirring at room temperature for 16 hours, the solution was acidified with 1N HCl to pH=4, and concentrated. The residue was dissolved in acetone (15 mL), filtered by suction, and the filtrate was concentrated. On addition of ethyl ether the title compound crystallized. Yield: 65 mg.

$^1$H NMR (DMSO-d$_6$, D$_2$O, NaOD): δ 0.80–1.82 (m, 20H), 2.13 (t, 2H), 2.60 (t, 1H), 3.33 (t, 2H), 3.55 (s, 2H), 3.57 (s, 2H), 7.22 (d, 2H), 7.36 (d, 2H), 7.42 (d, 2H), 7.68 (d, 2H).

MS (APCl, pos.): 561.2 (M+1).

EXAMPLE 572

4-({(4-cis-Cyclohexylcyclohexyl)-[4-(trifluoromethoxy)benzyl]amino}methyl)-N-(2H-tetrazol-5-yl)benzamide

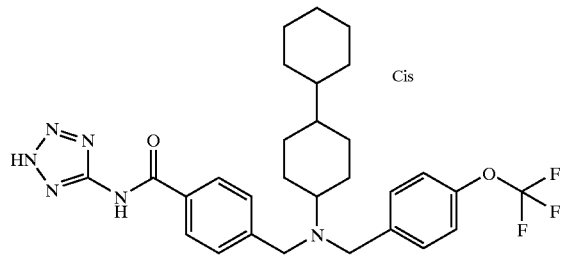

To a solution of crude cis-N-4-(4-cyclohexylcyclohexyl)-4-trifluoromethoxybenzylamine (1.70 g) in dichloromethane (10 mL) was added methyl 4-formylbenzoate (500 mg, 3.04 mmol) and NaBH(OAc)$_3$ (500 mg, 2.36 mmol). After stirring for 16 hours at room temperature, the mixture was diluted with dichloromethane (20 mL), washed with NaHCO$_3$ solution (2×20 mL) and brine (20 mL), dried (MgSO$_4$), and concentrated. Flash chromatography (hexane, ethyl acetate, 9:1) provided methyl 4-({(4-cis-cyclohexylcyclohexyl)-[4-(trifluoromethoxy)benzyl]amino}methyl)benzoate (836 mg).

$^1$H NMR (CDCl$_3$): δ 0.77–1.85 (m, 20H), 2.50 (m, 1H), 3.62 (s, 2H), 3.68 (s, 2H), 3.90 (s, 3H), 7.11 (d, 2H), 7.35 (d, 2H), 7.40 (d, 2H), 7.95 (d, 2H).

MS (APCl, pos.): 504.2 (M+1).

The above ester (836 mg, 1.66 mmol) was dissolved in THF (10 mL) and methanol (10 mL), and 1M KOH (4 mL) was added. The mixture was refluxed for 5 h, acidified with 1N HCl to pH=4, and concentrated. The residue was dissolved in ethyl acetate (20 mL), washed with brine (10 mL), dried (Na$_2$SO$_4$), and concentrated. The residue crystallized from hexanes and ethyl acetate. Yield: 786 mg of 4-({(4-cis-cyclohexylcyclohexyl)-[4-(trifluoromethoxy)benzyl]amino}methyl)benzoic acid as a white solid.

$^1$H NMR (CD$_3$OD): δ 0.70 (m, 2H), 1.13–1.22 (m, 8H), 1.61–2.00 (m, 10H), 3.38 (t, 1H), 4.26 (m, 2H), 4.54 (m, 2H), 7.34 (d, 2H), 7.67 (d, 2H), 7.75 (d, 2H), 7.87 (d, 2H). MS (APCl, pos.): 490.2 (M+1).

To a solution of above benzoic acid (250 mg, 0.51 mmol) in DMF (8 mL) was added diisopropylethylamine (0.18 mL, 130 mg, 0.61 mmol) and HBTU (228 mg, 0.61 mmol). After stirring for 15 min at room temperature, 5-aminotetrazole (105 mg, 1.01 mmol) was added. The mixture was stirred for 16 hours, and the solvent was evaporated. The residue was dissolved in ethyl acetate (20 mL), washed with water (2×10 mL), and brine (10 mL), dried (MgSO$_4$), and concentrated. The residue was dissolved in dichloromethane. On addition of ether and hexane, the title compound crystallized. Yield: 26 mg.

$^1$H NMR (DMSO-d$_6$): δ 0.70–0.84 (m, 2H), 1.00–1.80 (m, 18H), 2.40 (m, 1H), 3.65 (s, 2H), 3.70 (s, 2H), 7.27 (d, 2H), 7.46 (d, 2H), 7.50 (d, 2H), 8.01 (d, 2H).

MS (APCl, pos.): 557.2 (M+1).

EXAMPLE 573

4-({(4-cis-Cyclohexylcyclohexyl)-[4-(trifluoromethoxy)benzyl]amino}methyl)-N-(2H-tetrazol-5-ylmethyl)benzamide

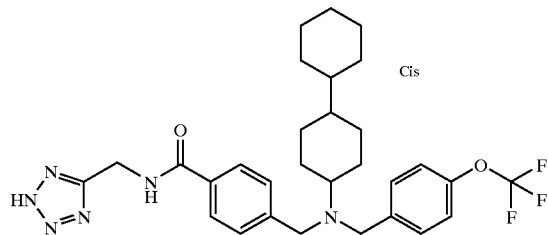

To a solution of the above 4-({(4-cis-cyclohexylcyclohexyl)-[4-(trifluoromethoxy)benzyl]amino}methyl)benzoic acid (242 mg, 0.49 mmol) in DMF (8 mL) was added diisopropylethylamine (0.18 mL, 130 mg, 0.61 mmol) and HBTU (220 mg, 0.59 mmol). After stirring for 15 minutes at room temperature, 5-aminomethyltetrazole (58 mg, 0.59 mmol) was added. The mixture was stirred for 16 hours, and the solvent was evaporated. The residue was dissolved in ethyl acetate (20 mL), washed with water (2×10 mL), and brine (10 mL), dried (MgSO$_4$), and concentrated. The residue was purified by HPLC to afford the title compound.

$^1$H NMR (DMSO-d$_6$): δ 0.75–1.80 (m, 20H), 2.45 (m, 1H), 3.63 (s, 2H), 3.65 (s, 2H), 4.67 (d, 2H), 7.28 (d, 2H), 7.43 (d, 2H), 7.46 (d, 2H), 7.82 (d, 2H), 8.96 (t, 1H).

MS (APCl, pos.): 571.2 (M+1).

EXAMPLE 574

4-({(trans-4-Cyclohexylcyclohexyl)-[4-(trifluoromethoxy)benzyl]amino}methyl)-N-(2H-tetrazol-5-yl)benzamide

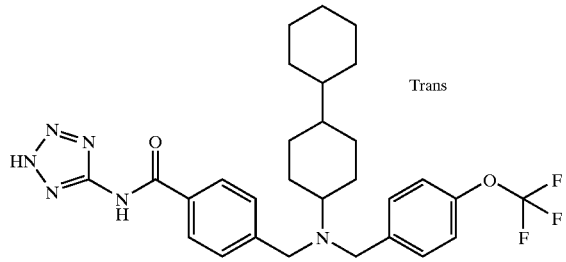

To a solution of trans-N-4-(4-cyclohexylcyclohexyl)-4-trifluoromethoxybenzylamine (350 mg, 0.98 mmol) in dichloromethane was added methyl 4-formylbenzoate (160 mg, 0.98 mmol) and NaBH(OAc)$_3$ (310 mg, 1.47 mmol). The mixture was stirred at room temperature for 16 hours.

Additional aldehyde (160 mg) and NaBH(OAc)$_3$ (360 mg) were added. Stirring was continued for 72 hours at room temperature. The mixture was diluted with ethyl acetate (20 mL), washed with NaHCO$_3$ solution (10 mL) and brine (10 mL), dried (Na$_2$SO$_4$), and concentrated. Flash chromatography (hexanes, ethyl acetate, 5:1) provided methyl 4-({(4-trans-cyclohexylcyclohexyl)-[4-(trifluoromethoxy)benzyl]amino}methyl)benzoate (290 mg).

$^1$H NMR (CDCl$_3$): δ 0.88–1.31 (m, 11H), 1.59–1.72 (m, 7H), 1.88 (d, 2H), 2.39 (m, 1H), 3.61 (s, 2H), 3.66 (s, 2H), 3.90 (s, 3H), 7.11 (d, 2H), 7.35 (d, 2H), 7.41 (d, 2H), 7.95 (d, 2H).

MS (APCl, pos.): 504.2 (M+1).

The above methyl benzoate (290 mg, 0.57 mmol) was dissolved in THF (5 mL) and methanol (5 mL) and 1M KOH (2 mL) were added. The mixture was refluxed for 90 minutes, acidified with 1N HCl to pH=4, and concentrated. The residue was dissolved in ethyl acetate (20 mL), washed with brine (10 mL), dried (Na$_2$SO$_4$), and concentrated. The residue crystallized from hexanes, ethyl acetate to afford 4-({(4-trans-cyclohexylcyclohexyl)-[4-(trifluoromethoxy)benzyl]amino}methyl)benzoic acid (252 mg) as a white solid.

$^1$H NMR (CD$_3$OD): δ 0.87–1.36 (m, 11H), 1.59–1.72 (m, 7H), 1.73 (d, 2H), 2.41 (m, 1H), 3.64 (s, 4H), 4.11 (s, 1H), 7.17 (d, 2H), 7.35 (d, 2H), 7.44 (d, 2H), 7.87 (d, 2H).

MS (APCl, pos.): 490.2.2 (M+1).

To a suspension of above benzoic acid (215 mg, 0.44 mmol) in DMF (10 mL) was added diisopropylethylamine (0.23 mL, 166 mg, 1.28 mmol) and HBTU (200 mg, 0.53 mmol). After stirring for 15 minutes at room temperature, 5-aminotetrazole (180 mg, 1.75 mmol) was added to the solution. After stirring for 16 hours, the solvent was evaporated. The residue was dissolved in ethyl acetate (30 mL), washed with water (3×10 mL), and brine (10 mL), dried (MgSO$_4$), and concentrated. Flash chromatography (CHCl$_3$, methanol, 95:5) gave 110 mg of the title compound, which was further purified by HPLC.

$^1$H NMR (CD$_3$OD): δ 0.98–1.27 (m, 9H), 1.64–1.85 (m, 7H), 1.93 (m, 2H), 2.14 (m, 2H), 3.23 (m, 1H), 4.52 (m, 4H), 7.36 (d, 2H), 7.53 (d, 2H), 7.60 (d, 2H), 8.10 (d, 2H).

MS (APCl, pos.): 557.3 (M+1).

EXAMPLE 575

4-[1-(4-cis-Cyclohexylcyclohexyl)-3-(4-trifluoromethoxyphenyl)ureidomethyl]-N-(2H-tetrazol-5-yl)benzamide

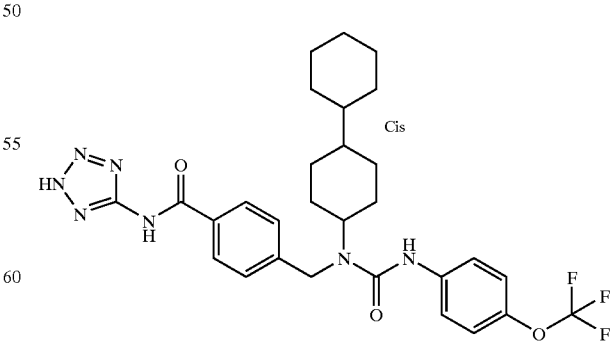

To a suspension of methyl 4-(aminomethyl)benzoate hydrochloride (2.0 g, 10 mmol) (prepared according to P. M. O'Brien et al., J. Med. Chem. 37, 1994, 1810–22) in ethanol (150 mL) was added 4-(4-cyclohexyl)cyclohexanone (1.8 g, 10 mmol) and NaBH(OAc)₃ (2.7 g, 12 mmol). The mixture was stirred for 16 hours at room temperature, and filtered by suction.

The filtrate was concentrated, and the residue was dissolved in ethyl acetate (150 mL), washed with NaHCO₃ solution (100 mL), brine (100 mL), dried (Na₂SO₄), and concentrated. Cis- and trans-isomers were separated by flash chromatography. The cis-isomer (340 mg) eluted with hexane, ethyl acetate, 5:1, the trans-isomer (338 mg) eluted with hexane, ethyl acetate, 1:1.

Methyl 4-[4-(cis-4-cyclohexyl)cyclohexyl)aminomethyl) benzoate:

¹H NMR (CDCl₃): δ 0.91–1.75 (m, 20H), 2.75 (m, 1H), 3.82 (s, 2H), 3.91 (s, 3H), 7.41 (d, 2H), 8.00 (d, 2H).

MS (APCl, pos.): 330.2 (M+1).

Methyl 4-[4-(trans-4-cyclohexyl)cyclohexyl)aminomethyl) benzoate:

¹H NMR (CDCl₃): δ 0.87–1.20 (m, 11H), 1.59–1.72 (m, 7H), 1.83 (d, 2H), 2.36 (m, 1H), 3.80 (s, 2H), 3.87 (s, 3H), 7.33 (d, 2H), 7.95 (d, 2H).

MS (APCl, pos.): 330.2 (M+1).

To a solution of methyl 4-[4-(cis-4-cyclohexyl) cyclohexyl)aminomethyl)benzoate (340 mg, 1.03 mmol) in dichloromethane (8 mL) was added 4-(trifluoromethoxy) phenylisocyanate (210 mg, 1.03 mmol). After stirring for 16 hours at room temperature, the mixture was diluted with dichloromethane (10 ml), washed with 1N HCl (5 mL), brine (5 mL), dried (MgSO₄), and concentrated. Recrystallisation from hexanes, ethyl acetate 1:1 provided 290 mg of 4-[1-(4-cis-cyclohexylcyclohexyl)-3-(4-trifluoromethoxyphenyl)ureidomethyl]benzoic acid methyl ester.

¹H NMR (CDCl₃): δ 0.79–1.95 (m, 20H), 3.93 (s, 3H), 4.48 (m, 1H), 4.55 (s, 2H), (6.15 (s, 1H), 7.07 (d, 2H), 7.20 (d, 2H), 7.45 (d, 2H), 8.08 (d, 2H).

MS (APCl, pos.): 533.2 (M+1).

The above ester (290 mg, 0.54 mmol) was dissolved in THF (5 mL) and methanol (5 mL) and 1M KOH (2 mL) was added. The mixture was refluxed for 1 hour, acidified with 1N HCl to pH=4, and concentrated. The residue was dissolved in ethyl acetate (20 mL), washed with brine (10 mL), dried (Na₂SO₄), and concentrated. The residue crystallized from hexane, ethyl acetate to afford 192 mg of 4-[1-(4-cis-cyclohexylcyclohexyl)-3-(4-trifluoromethoxy-phenyl) ureidomethyl]benzoic acid as a white solid.

¹H NMR (DMSO-d₆): δ 0.66–1.80 (m, 20H), 4.04 (m, 1H), 4.62 (s, 2H), 7.20 (d, 2H), 7.37 (d, 2H), 7.51 (d, 2H), 7.86 (d, 2H), 8.54 (s, 1H). MS (APCl, pos.): 519.1 (M+1).

To a solution of the above benzoic acid (192 mg, 0.36 mmol) in DMF (10 mL) was added diisopropylethylamine (0.19 mL, 137 mg, 0.72 mmol) and HBTU (190 mg, 0.51 mmol). After stirring for 15 minutes at room temperature, 5-aminotetrazole (74 mg, 0.72 mmol) was added. After stirring for 16 hours, the solvent was evaporated, the residue was dissolved in ethyl acetate (20 mL), washed with water (2×10 mL), brine (10 mL), dried (MgSO₄), and concentrated. The residue was purified by HPLC to afford the title compound.

¹H NMR (DMSO-d₆): δ 0.66–1.80 (m, 20H), 4.10 (m, 1H), 4.65 (s, 2H), 7.23 (d, 2H), 7.43 (d, 2H), 7.54 (d, 2H), 8.05 (d, 2H), 8.58 (s, 1H), 12.26 (s, 1H).

MS (APCl, pos.): 586.1 (M+1).

EXAMPLE 576

4-[1-(4-trans-Cyclohexylcyclohexyl)-3-(4-trifluoromethoxyphenyl)ureidomethyl]-N-(2H-tetrazol-5-yl)benzamide

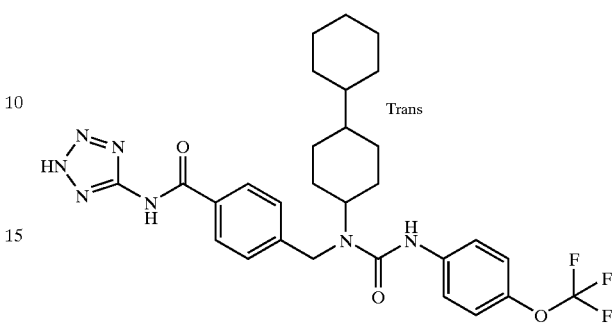

To a solution of methyl 4-[4-(trans-4-cyclohexyl) cyclohexyl)aminomethyl]benzoate (338 mg, 1.03 mmol) in dichloromethane (8 mL) was added at room temperature 4-(trifluoromethoxy)phenylisocyanate (210 mg, 1.03 mmol). After stirring for 16 hours at room temperature, the mixture was diluted with dichloromethane (10 mL), washed with 1N HCl (5 mL), brine (5 mL), dried (MgSO₄), and concentrated. After flash chromatography (hexanes, ethyl acetate, 5:1), 487 mg of 4-[1-(4-trans-cyclohexylcyclohexyl)-3-(4-trifluoromethoxyphenyl) ureidomethyl]benzoic acid methyl ester was obtained.

¹H NMR (CDCl₃): δ 0.91–1.41 (m, 12H), 1.61–1.90 (m, 8H), 3.93 (s, 3H), 4.19 (m, 1H), 4.55 (s, 2H), 6.18 (s, 1H), 7.07 (d, 2H), 7.20 (d, 2H), 7.45 (d, 2H), 8.06 (d, 2H).

MS (APCl, pos.): 533.2 (M+1).

The above ester (487 mg, 0.99 mmol) was dissolved in THF (10 mL) and methanol (5 mL) and 1M KOH (4 mL) was added. The mixture was stirred at 80° C. for 90 minutes, acidified with 1N HCl to pH=4, and concentrated. The residue was dissolved in ethyl acetate (20 mL), washed with brine (10 mL), dried (MgSO₄), and concentrated. The residue crystallized from hexane, ethyl acetate to afford 380 mg of 4-[1-(trans-4-cyclohexylcyclohexyl)-3-(4-trifluoromethoxyphenyl)ureidomethyl]benzoic acid white solid.

¹H NMR (DMSO-d₆): δ 0.91–1.15 (m, 10H), 1.37 (q, 2H), 1.63 (m, 8H), 4.04 (m, 1H), 4.60 (s, 2H), 7.21 (d, 2H), 7.34 (d, 2H), 7.53 (d, 2H), 7.86 (d, 2H), 8.54 (s, 1H).

MS (APCl, pos.): 519.1 (M+1).

To a solution of above benzoic acid (380 mg, 0.71 mmol) in DMF (10 mL) was added diisopropylethylamine (0.38 mL, 275 mg, 2.12 mmol) and HBTU (320 mg, 0.86 mmol). After stirring for 15 minutes at room temperature, 5-aminotetrazole (150 mg, 1.45 mmol) was added. The mixture was stirred for 16 hours, and the solvent was evaporated. The residue was dissolved in ethyl acetate (20 mL), washed with water (2×10 mL), brine (10 mL), dried (MgSO₄), and concentrated. The residue was dissolved in dichloromethane. On addition of ether, the title compound crystallized. Yield: 215 mg.

¹H NMR (DMSO-d₆): δ 0.82–1.18 (m, 10H), 1.40 (q, 2H), 1.63 (m, 8H), 4.03 (m, 1H), 4.63 (s, 2H), 7.21 (d, 2H), 7.41 (d, 2H), 7.57 (d, 2H), 8.03 (d, 2H), 8.56 (s, 1H), 12.32 (s, 1H), 15.95 (s, 1H).

MS (APCl, pos.): 586.1 (M+1).

EXAMPLE 577

3-{4-[1-(4-Cyclohexylcyclohexyl)-3-(4-trifluoromethoxyphenyl)ureidomethyl]benzoylamino}propionic acid

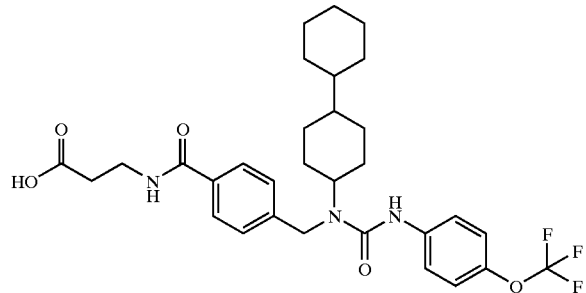

This compound was prepared similarly as described in examples 575 and 576 using the ethyl ester of 3-aminopropionate instead of 5-aminotetrazole followed by hydrolysis.

$^1$H NMR (DMSO-d$_6$): δ 0.07–0.08 (m, 2H), 1.05–1.13 (m, 5H), 1.32–1.50 (m, 6H), 1.64–1.91 (m, 7H), 2.51 (t, 2H), 3.48 (qt, 2H), 4.07 (brd m, 1H), 4.62 (s, 2H), 7.21 (d, 2H), 7.33 (d, 2H), 7.52 (d, 2H), 7.76 (d, 2H), 8.46 (brd t, 1H), 8.53 (brd s, 1H), 12.16 (brd s, 1H).

MS (APCl, pos): 590.3, 544.0, 518.2, 3.87.2, 388.2.

EXAMPLE 578

5-[1-(trans-4-tert-Butylcyclohexyl)-3-(4-trifluoromethoxyphenyl)ureidomethyl]thiophene-2-carboxylic acid (2H-tetrazol-5-yl)amide

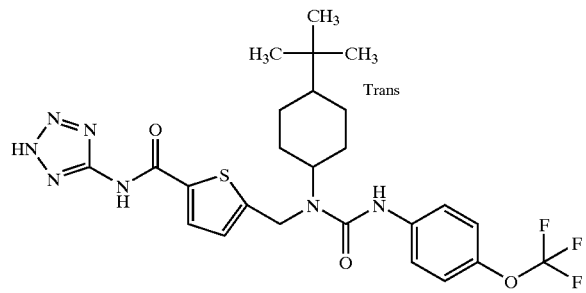

To as solution of methyl 5-formyl-thiophene-2-carboxylate (1.65 g, 9.6 mmol) (prepared according to C. Goddard, J. Heterocycl. Chem. 28, 1991, 17–28) in methanol (10 mL) was added 4-(tert-butylcyclohexyl)amine (cis/trans mixture). After standing at room temperature for 16 hours the precipitate was filtered off by suction to afford 1.82 g of 5-[(4-trans-tert-butylcyclohexylimino)methyl]thiophene-2-carboxylic acid methyl ester.

$^1$H NMR (CDCl$_3$): δ 0.87 (s, 9H), 1.07–1.17 (m, 3H), 1.51–1.63 (m, 2H), 1.77–1.88 (m, 4H), 3.13 (m, 1H), 3.88 (s, 3H), 7.25 (d, 1H), 7.72 (d, 1H), 8.36 (s, 1H).

The trans-imine from above (1.82 g, 5.9 mmol) was dissolved in dichloromethane (20 mL), and NaBH(OAc)$_3$ (1.5 g, 7.1 mmol) was added. The mixture was stirred for 16 hours at room temperature, diluted with water (20 mL), washed with NaHCO$_3$ solution (20 mL), brine (20 mL), dried (Na$_2$SO$_4$), and concentrated. Flash chromatography (hexanes, ethyl acetate, 2:1) provided 692 mg of 5-[(4-trans-tert-butylcyclohexylamino)methyl]thiophene-2-carboxylic acid methyl ester.

$^1$H NMR (CDCl$_3$): δ 0.85 (s, 9H), 1.00–1.15 (m, 5H), 1.80 (m, 2H), 2.00 (m, 2H), 2.44 (m, 1H), 3.88 (s, 3H), 4.04 (s, 2H), 6.92 (d, 1H), 7.68 (d, 1H).

MS (APCl, pos.): 310.1 (M+1).

The above amine (692 mg, 2.23 mmol) was dissolved in dichloromethane (12 mL), and 4-trifluoromethoxyphenylisocyanate (454 mg, 2.23 mmol) was added. After stirring for 16 hours at room temperature, the mixture was concentrated. Flash chromatography (hexanes, ethyl acetate, 5:1) provided 1.1 g of 5-[1-(4-trans-tert-butylcyclohexyl)-3-(4-trifluoromethoxyphenyl)ureidomethyl]thiophene-2-carboxylic acid methyl ester.

$^1$H NMR (CDCl$_3$): δ 0.87 (s, 9H), 0.98 (t, 1H), 1.12–1.27 (m, 2H), 1.48 (q, 2H), 1.88 (m, 4 H), 3.89 (s, 3H), 4.04 (s, 2H), 3.98 (m, 1H), 4.65 (s, 2H), 6.42 (s, 1H), 7.06 (d, 1H), 7.13 (d, 2H), 7.37 (d, 2H), 7.71 (d, 1H). MS (APCl, pos.): 513.1 (M+1).

The above ester (1.1 g, 2.14 mmol) was dissolved in THF (15 mL) and methanol (2 mL) and 2M LiOH (5 mL) was added. The mixture was stirred at room temperature for 16 hours, acidified with 1N HCl to pH=4, and concentrated. The residue was dissolved in ethyl acetate (20 mL), washed with brine (10 mL), dried (MgSO$_4$), and concentrated. The residue crystallized from hexane, ethyl acetate to afford 745 mg of 5-[1-(4-trans-tert-butylcyclohexyl)-3-(4-trifluoromethoxyphenyl)ureidomethyl]thiophene-2-carboxylic acid as a white solid.

$^1$H NMR (DMSO-d$_6$): δ 0.85 (s, 9H), 0.90 (q, 1H), 1.09 (q, 2H), 1.53 (q, 2H), 1.68 (m, 4H), 4.02 (m, 1H), 4.68 (s, 2H), 7.07 (d, 1H), 7.25 (d, 2H), 7.54 (d, 1H), 7.56 (d, 2H), 8.63 (s, 1H).

To a solution of above carboxylic acid (400 mg, 0.90 mmol) in DMF (7 mL) was added diisopropylethylamine (0.28 mL, 206 mg, 1.60 mmol) and HBTU (360 mg, 0.96 mmol). After stirring for 15 minutes at room temperature, 5-aminotetrazole (136 mg, 1.60 mmol) was added. After stirring for 72 hours, the solvent was evaporated. The residue was dissolved in ethyl acetate (20 mL), washed with water (2×10 mL), brine (10 mL), dried (MgSO$_4$), and concentrated. Flash chromatography (hexanes, ethyl acetate, 1:2) afforded 120 mg of the title compound.

$^1$H NMR (DMSO-d$_6$): δ 0.83 (s, 9H), 0.96 (q, 1H), 1.12 (q, 2H), 1.50 (q, 2H), 1.73 (m, 4H), 3.96 (m, 1H), 4.70 (s, 2H), 7.14 (d, 1H), 7.24 (d, 2H), 7.55 (d, 2H), 8.04 (d, 1H), 8.64 (s, 1H), 12.37 (s, 1H), 15.92 (s, 1H).

MS (APCl, pos.): 566.1 (M+1).

EXAMPLE 579

1-(4-tert-Butylcyclohexyl)-1-{4-[(2H-tetrazol-5-ylamino)methyl]benzyl}-3-(4-trifluoromethoxyphenyl)urea

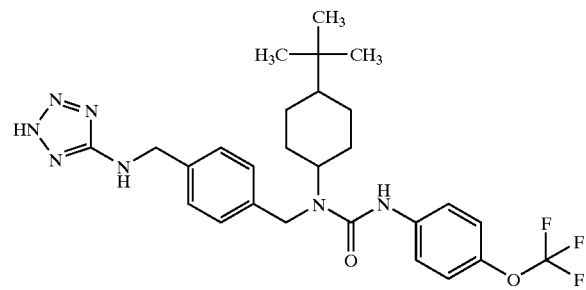

To a suspension of 5-aminotetrazole (4.25 g, 50 mmol) in ethanol (25 mL) was added triethylamine (6.9 mL, 5.05 g, 50 mmol). To the clear solution was added terephthaldehyde mono (diethyl acetal) (10.4 g, 50 mmol). After stirring for 2 hours at room temperature, platinum oxide (150 mg) was added, and the mixture was hydrogenated at 50 psi for 16 hours. The catalyst was filtered off, and the filtrate was concentrated. On addition of water and conc. HCl, the residue crystallized. The solid was filtered off to give 4-[(2H-tetrazol-5-ylamino)methyl]benzaldehyde hydrochloride.

$^1$H NMR (DMSO-d$_6$): δ 4.50 (d, 2H), 7.33 (s, 1H), 7.54 (d, 2H), 7.66 (t,1H) 7.88 (d, 2H), 9.98 (s, 1H).

MS (APCl, pos.): 204.0 (M+1).

To as suspension of above 4-[(2H-tetrazol-5-ylamino)methyl]benzaldehyde hydrochloride (1.0 g, 4.17 mmol) in methanol (10 mL) was added triethylamine, until a clear solution was obtained. 4-(tert-butylcyclohexyl)amine (cis/trans-mixture) (650 mg, 4.17 mmol) was added. Acetic acid was added to adjust the pH to 6. The mixture was stirred at room temperature for 16 hours, and NaBH(OAc)$_3$ (1.0 g, 4.7 mmol) was added. After stirring for 16 hours at room temperature, the mixture was filtered and concentrated. The crude {4-[(4-tert-butylcyclohexylamino)methyl]benzyl}-(2H-tetrazol-5-yl)amine was used without further purification in the next step.

MS (APCl, pos.): 343.2 (M+1).

To a solution of above amine (288 mg, 0.84 mmol) in dichloromethane (10 mL) was added 4-trifluoromethoxyphenylisocyanate (180 mg, 0.84 mmol). After stirring for 16 hours at room temperature, the title compound (75 mg) crystallized out as a mixture of cis and trans-isomers.

$^1$H NMR (DMSO-d$_6$): δ 0.80, 0.82 (2 s, 9H), 0.92 (m, 1H), 1.09 (q, 2H), 1.34–1.51 (m, 3H), 1.64–1.75 (m, 3H), 4.00 (m, 0.75H), 4.21 (m, 0.25H), 4.35 (d, 2H), 4.53 (s, 1.5H), 4.64 (s, 0.5H), 7.14 (d, 1H), 7.16–7.29 (m, 6H), 7.53 (d, 2H), 7.55 (s, 1H), 8.46 (s, 0.75H), 8.55 (s, 0.25H).

MS (APCl, pos.): 546.2 (M+1).

General Procedure (W) for the Solution Phase Synthesis of Compounds of General Formulae (Is) and (Is')

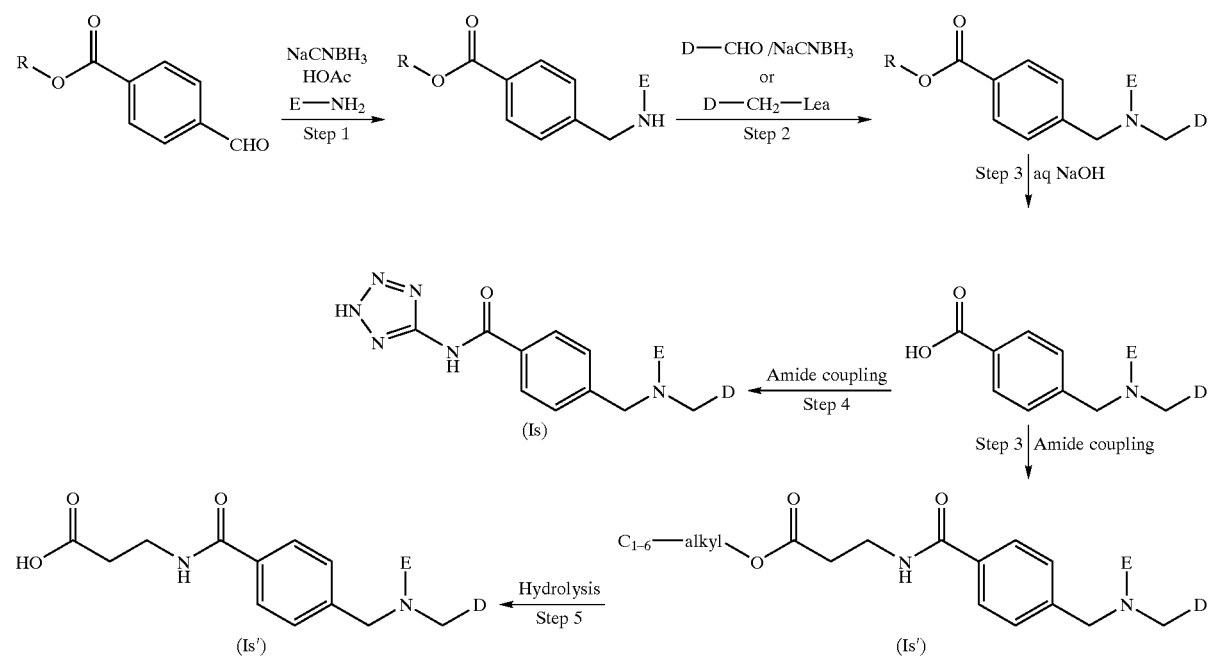

wherein R is C$_{1-6}$-alkyl,
D and E are as defined in general formula (I) and
Lea is a leaving group such as chloro, bromo, iodo, mesyl or tosyl, The general procedure (W) is illustrated by the following example.

EXAMPLE 580

General Procedure (W)

3-(4-{[(trans-4-tert-Butylcyclohexyl)-(3,5-dichlorobenzyl)amino]methyl}benzoylamino) propionic acid

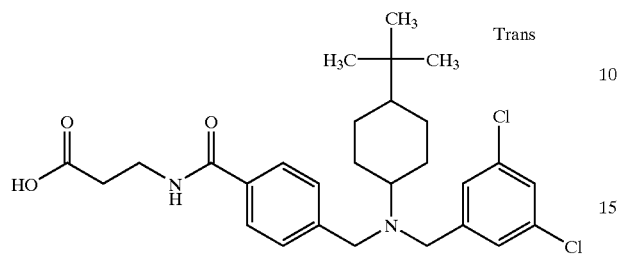

Step 1: This step is identical to that described in general procedure (K), step 1.

Step 2: To a solution of the product obtained from step 1 (1.15 g, 3.8 mmol) and 3,5-dichlorobenzylchloride (0.74 g, 3.8 mmol) in acetonitrile (50 mL) was added potassium carbonate (0.79 g 5.7 mmol). The mixture was refluxed overnight. After cooling to room temperature, water (100 mL) was added, and the mixture was extracted with diethyl ether. The organic extract was dried ($MgSO_4$) and concentrated to a give crude product, which was purified by column chromatography to afford 1.7 g (97%) of 4-{[(4-tert-butylcyclohexyl)-(3,5-dichlorobenzyl)amino]methyl}benzoic acid methyl ester.

$^1$H NMR ($CDCl_3$): δ 0.85(s, 9H), 1.22–1.59(m, 5H), 1.78–198(m, 4H), 2.41(m, 1H), 3.57(s, 2H)), 3.66(s, 2H), 3.87(s, 3H), 7.18(s, 1H), 7.24(s, 2H), 7.40(d, 2H), 9.08(d, 2H).

LC-MS (APCl, pos.): 463(M+1).

Alternatively, step 2 can be performed as a reductive alkylation using an aldehyde (D-CHO instead of D-$CH_2$-Lea) together with a reducing agent such as sodium cyanoborohydride.

Step 3: To a solution of the product from step 2 (1.7 g) in methanol (30 mL) was added 10% aqueous potassium hydroxide (10 mL) and the mixture was stirred at room temperature for 2 hours. The mixture was diluted with water and extracted with diethyl ether (2×30 mL). The aqueous layer was neutralised with dilute hydrochloric acid, and extracted with diethyl ether. The organic extract was dried ($MgSO_4$) and concentrated to give 1.6 g (100%) of 4-{[(4-tert-butylcyclohexyl)-(3,5-dichloro-benzyl)amino]methyl}benzoic acid.

$^1$H NMR ($CDCl_3$, δ): 8.01(s, 9H), 0.9–1.10(m, 4H), 1.66(m, 1H), 1.89(m, 2H), 2.32(m, 2H), 3.10(m, 1H), 4.21(s, 2H), 4.52(m, 2H), 7.58(s, 1H), 7.60–7.70(m, 3H), 7.88(d, 2H), 11.0(br, 1H).

LC-MS (APCl, pos.): 449 (M+1).

Step 4: To a solution of the product obtained in step 3 (1.6 g, 3.7 mmol) in DMF (30 mL) was added HBTU (1.5 g, 4.0 mmol) and diisopropylethylamine (1 g, 8 mmol). The mixture was stirred at 0° C. for 30 minutes, and then β-alanine ethyl ester hydrochloride (1.2 g, 8 mmol) was added at 0° C. The reaction was monitored by TLC, and DMF was evaporated in vacuo when the reaction was complete. The product from step 4 was used in the next step without further purification or characterisation.

Step 5: To a solution of the product from step 4 (1.7 g) in methanol (30 mL) was added 2M aqueous lithium hydroxide (10 mL). The mixture was stirred at room temperature for 30 minutes and then diluted with water and washed with diethyl ether (2×30 mL). The aqueous layer was acidified with dilute hydrochloric acid and extracted with diethyl ether. The organic extract was dried ($MgSO_4$) and concentrated to give a crude product, which was purified by HPLC to afford the title compound.

$^1$H NMR: (DMSO-$d_6$): δ 0.78 (s, 9H), 0.89 (m, 3H), 1.29 (qt, 2H), 1.77 (d, 2H), 1.85 (d, 2H), 2.31 (t,1H), 2.47 (t, 2H), 3.42 (qt, 2H), 3.60 (s, 2H), 3.62 (s, 2H), 7.36 (m, 3H), 7.40 (d, 2H), 7.76 (d, 2H), 8.47 (t, 1H).

MS (APCl, pos): 519.2, 521.1.

EXAMPLE 581

General Procedure (W)

3-(4-{[(3-Bromobenzyl)-(4-cyclohexylphenyl) amino]methyl}benzoylamino)propionic acid

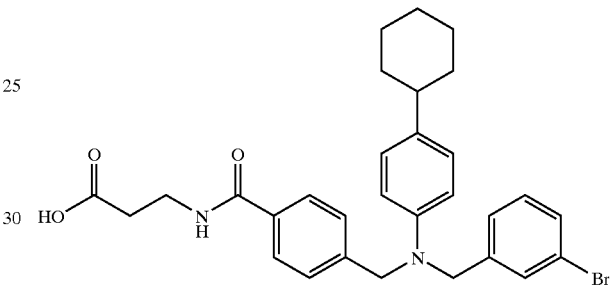

$^1$H NMR: (MeOH-$d_4$): δ 1.34–1.37 (m, 5H), 1.70–1.77 (m, 5H), 2.20 (m, 1H), 2.56 (t, 2H), 3.60 (t, 2H), 4.11 (s, 2H), 4.65 (s, 2H), 6.61 (d, 2H), 6.95 (d, 2H), 7.20 (d, 2H), 7.30 (m, 4H), 7.72 (d, 2H).

MS (APCl, pos): 551.1, 552.0.

EXAMPLE 582

General Procedure (W)

3-(4-{[(4-Cyclohexylphenyl)-(3,5-dichlorobenzyl) amino}methyl]benzoylamino)propionic acid

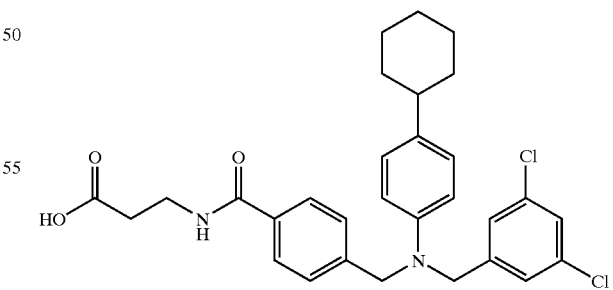

$^1$H NMR: (DMSO-$d_6$): δ 1.20–1.28 (m, 5H), 1.67–1.71 (m, 5H), 2.30 (m, 1H), 2.46 (t, 2H), 3.44 (qt, 2H), 4.69 (s, 2H), 4.73 (s, 2H), 6.53 (d, 2H), 6.94 (d, 2H), 7.28 (s, 2H), 7.31 (d, 2H), 7.47 (s, 1H), 7.77 (d, 2H), 8.49 (brd t, 1H).

MS (APCl, pos): 539.2, 541.0, 542.0.

EXAMPLE 583

General Procedure (W)

3-(4-{[(3-Chlorophenyl)-(4-cyclohexylphenyl)amino]methyl}benzoylamino)propionic acid

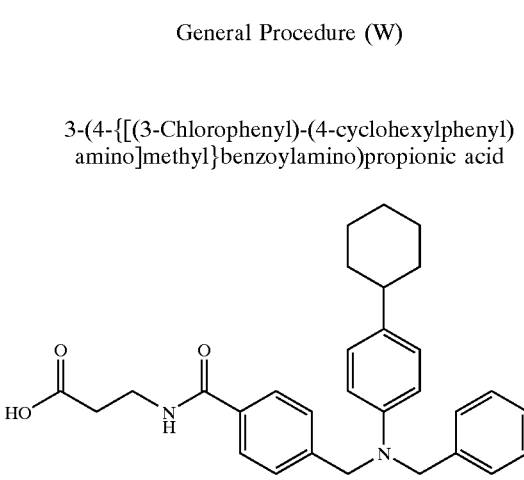

¹H NMR: (DMSO-d₆): δ 1.05–1.38 (m, 5H), 1.57–1.80 (m, 5H), 2.29 (br, 1H), 2.46 (t, 2H), 3.42 (q, 2H), 4.68 (d, 4H), 6.53 (d, 2H), 6.92 (d, 2H), 7.18–7.45 (m, 5H), 7.76 (d, 2H), 8.46 (t, 1H), 12.3 (br, 1H).

LC-MS (APCl, pos.): 505 (M+1).

EXAMPLE 584

General Procedure (W)

4-{[(3-Bromobenzyl)-(4-cyclohexylphenyl)amino]methyl}-N-(2H-tetrazol-5-yl)benzamide

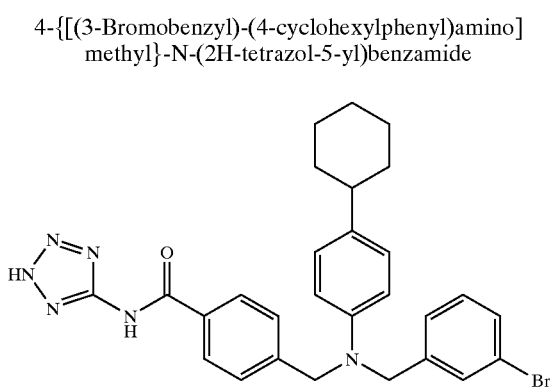

¹H NMR: (DMSO-d₆): δ 1.16–1.27 (m, 5H), 1.69–1.72 (m, 5H), 2.29 (brd m, 1H), 4.71 (s, 2H), 4.77 (s, 2H), 6.54 (d, 2H), 6.94 (d, 2H), 7.28 (s, 2H), 7.42 (m, 4H), 8.03 (d, 2H), 12.25 (brd s, 1H), 16.00 (brd s, 1H).

MS (APCl, pos): 545.2.

EXAMPLE 585

General Procedure (W)

4-{[(3-Chlorobenzyl)-(4-cyclohexylphenyl)amino]methyl}-N-(2H-tetrazol-5-yl)benzamide

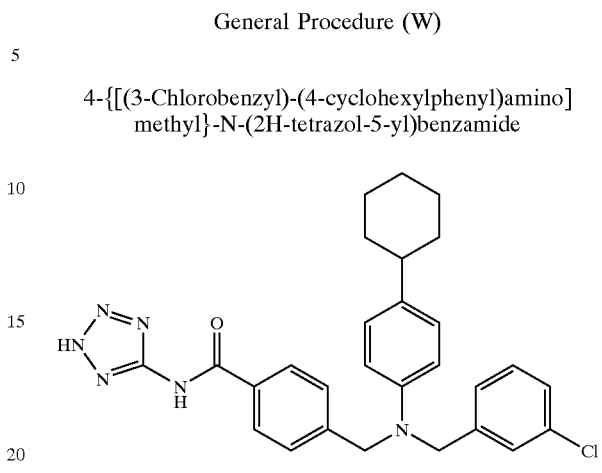

¹H NMR: (DMSO-d₆): δ 1.16–1.24 (m, 5H), 1.60–1.70 (m, 5H), 2.30 (m, 1H), 4.71 (s, 2H), 4.77 (d, 2H), 6.54 (d, 2H), 6.93 (d, 2H), 7.21 (d, 1H), 7.29 (m, 2H), 7.34 (d, 1H), 7.41 (d, 2H), 8.05 (d, 2H), 12.36 (s, 1H), 16.04 (brd s, 1H).

MS (APCl, pos): 501.2, 503.1.

EXAMPLE 586

3-(4-{[(trans-4-tert-Butylcyclohexyl)-(4-trifluoromethoxybenzoyl)amino]methyl}benzoylamino)propionic acid

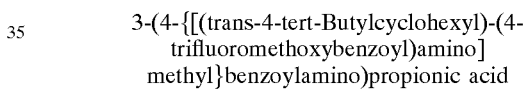
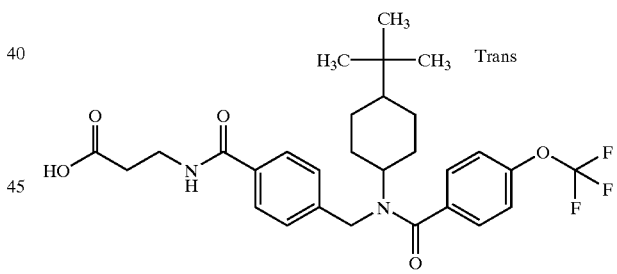

This compound was made from 3-{4-[(trans-4-tert-butylcyclohexylamino)methyl]benzoylamino}propionic acid methyl ester with trifluoromethoxybenzoyl chloride according to a typical acylation procedure, followed by hydrolysis.

¹H NMR: (CDCl₃): δ 0.76 (m, 10H), 1.46 (d, 2H), 1.60–1.80 (brd m, 6H), 2.60 (t, 2H), 3.56 (m, 1H), 3.63 (qt, 2H), 4.69 (s, 2H), 7.18 (m, 2H), 7.32 (m, 2H), 7.45 (m, 2H), 7.70 (d, 2H).

MS (APCl, pos): 549.2, 550.2.

General Procedure (X) for Solution Phase Synthesis of Compounds of the General Formula (It)

421 422

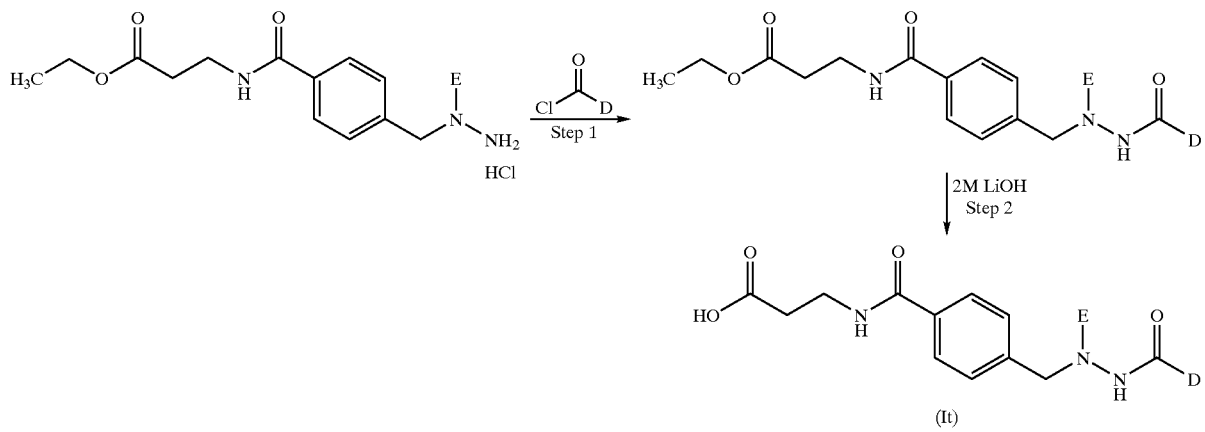

wherein D and E are as defined for formula (I).

Step 1: Solutions of the desired acid chloride (0.01 mmol) in dichloroethane are placed into the appropriate wells of a 1 mL deep-well plate. A solution of the hydrazide (0.01 mmol) in dichloroethane, and a solution of triethylamine (0.05 mmol) in dichloroethane are then added into all of the wells of the deep-well plate. The reaction mixtures are allowed to react for 12 hours.

Step 2: To the wells above are added excess aqueous 2M LiOH. After stirring the plates for at least three hours, the solvents are removed to afford the crude products.

The starting materials (hydrazines) can be prepared as follows:

Preparation of 3-{4-[N-4-cis-tert-butylcyclohexyl)hydrazinomethyl]benzoylamino}propionic acid ethyl ester hydrochloride:

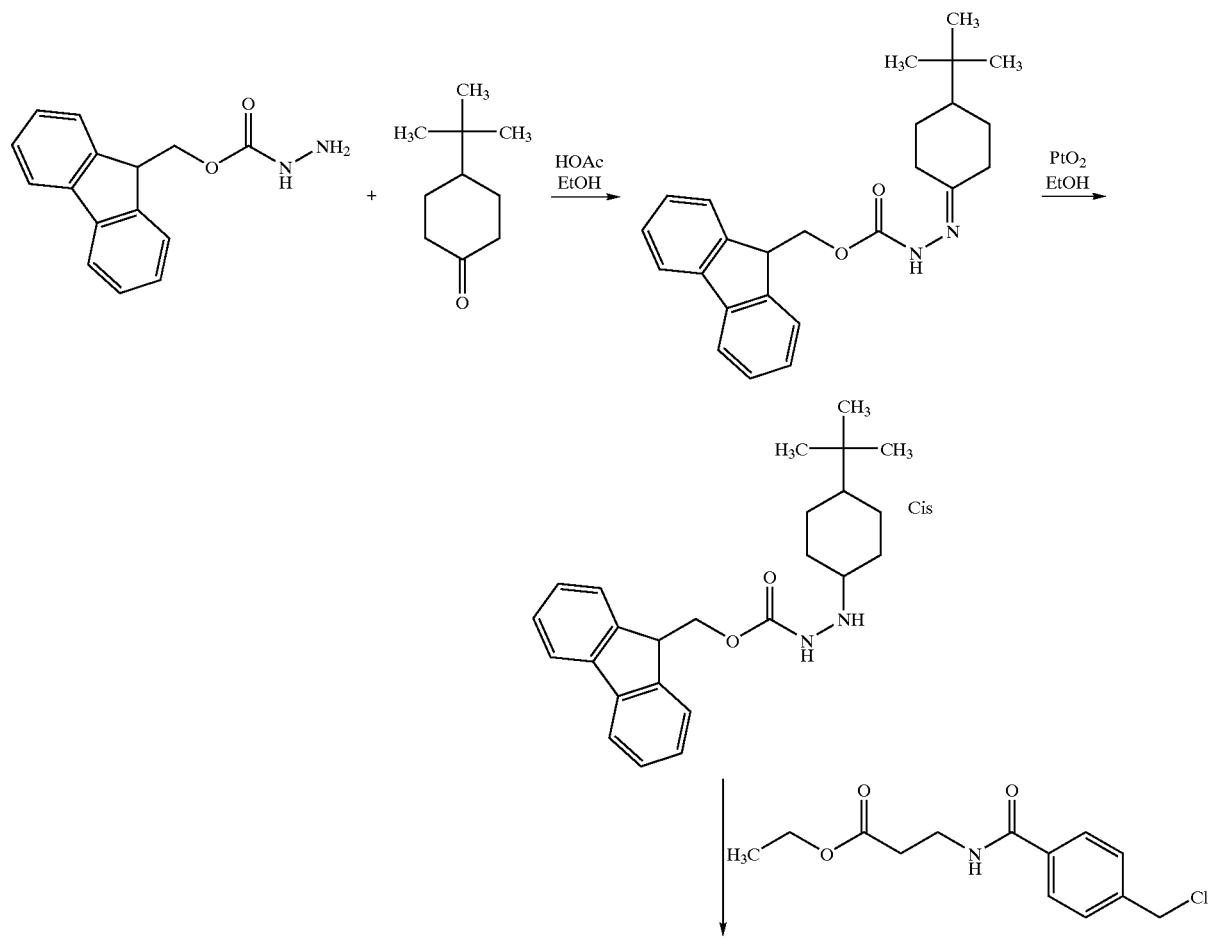

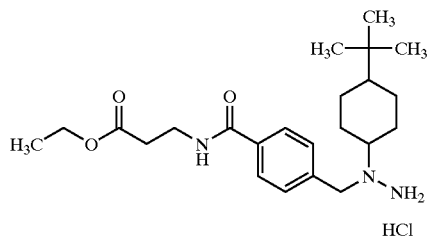 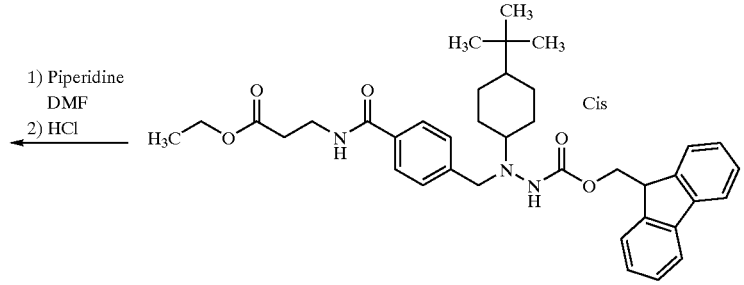

Fmoc-hydrazide (12 g, 47.2 mmol) was dissolved in ethanol (400 mL) and 4-tert-butyl-cyclohexanone (8.73 g, 56.6 mmol) was added. Glacial acetic acid (4 mL) was added and the solution stirred for 18 hours at room temperature. The solution was concentrated to ¼ its original volume and diluted with ethyl acetate (600 mL). The organic layer was washed with sat. aq NaHCO$_3$ (1×200 mL), brine (2×200 mL), dried over MgSO$_4$ and concentrated to give a yellow foam. Purification by silica gel flash chromatography eluting with 20% ethyl acetate/hexane to give N'-(4-tert-butylcyclohexylidene)hydrazinecarboxylic acid 9H-fluoren-9-ylethyl ester as a beige foam (16.9 g, 92% yield).

$^1$H NMR (300 MHz, DMSO-d$_6$): δ 9.98 (s, 1H), 7.89 (d, 2H), 7.48 (d, 2H), 7.43 (m, 2H), 7.31 (m, 2H), 4.29 (d, 2H), 2.12 (m, 1H), 1.80 (m, 4H), 1.12 (m, 4H), 0.86 (m, 10H).

APCl [M]$^+$=391.2.

The above cyclohexylidene compound (16.9 g, 43.3 mmol) was dissolved in anhydrous ethanol (400 mL) and PtO$_2$ (200 mg, 0.9 mmol) was added. The solution was stirred under a H$_2$ atmosphere (1 atm) at room temperature for 18 hours. The solution was passed through a bed of silica gel followed by two volumes of ethyl acetate and concentrated to give a yellow foam. Purification by silica gel flash chromatography eluting with 10% ethyl acetate/hexane afforded N'-(4-cis-tert-butylcyclohexyl)hydrazinecarboxylic acid 9H-fluoren-9-ylmethyl ester as a white foam (12 g, 71% yield). By eluting with 15% ethyl acetate/hexane the corresponding trans isomer, N'-(4-trans-tert-butylcyclohexyl)hydrazinecarboxylic acid 9H-fluoren-9-ylmethyl ester, is obtained (2 g, 12% yield) as a white foam.

cis isomer: $^1$H NMR (300 MHz) (CDCl$_3$): δ 7.78 (d, 2H), 7.59 (d, 2H), 7.43 (m, 2H), 7.34 (m, 2H), 4.48 (d, 2H), 4.25 (t, 1H), 3.21 (m, 1H), 1.80 (m, 2H), 1.36 (m, 6H), 1.01 (m, 1H), 0.87 (s, 9H).

APCl [M]$^+$=393.2.

The above cis isomer (8 g, 20 mmol) was dissolved in acetonitrile (200 mL) and the 3-(4-chloromethylbenzoylamino)propionic acid ethyl ester (6 g, 22.4 mmol), potassium carbonate (8.4 g, 61 mmol), and sodium iodide (catalytic) were added and the solution was stirred at 50° C. for 36 hours. The solution was diluted with ethyl acetate (800 mL) and washed with aqueous sat NaHCO$_3$ (3×300 mL), brine (3×300 mL), dried over MgSO$_4$ and concentrated to give a golden foam. Purification by silica gel flash chromatography eluting with 50% ethyl acetate/hexane afforded 3-{4-[N-(4-cis-tert-butylcyclohexyl)-N'-(9H-fluoren-9-ylmethyl-methoxycarbonyl)hydrazinomethyl]benzoylamino}propionic acid ethyl ester as a white foam (6 g, 47% yield).

$^1$H NMR (300 MHz, DMSO-d$_6$): δ 8.52 (t, 1H), 8.36 (s, 1H), 7.84 (d, 2H), 7.53 (d, 2H), 7.51 (t, 2H), 7.42 (m, 4H), 7.25 (t, 2H), 4.17 (d, 2H), 4.04 (m, 4H), 3.48 (m, 2H), 3.13 (m, 1H), 2.57 (d, 2H), 1.92 (m, 2H), 1.78 (m, 2H), 1.33 (m, 4H), 1.01 (m, 1H), 0.85 (s, 9H).

APCl [M]$^+$=626.3.

The above propionic acid ethyl ester (6 g, 9.6 mmol) was dissolved in DMF (15 mL) and piperidine (1.5 mL) was added while stirring at room temperature. TLC showed complete conversion after 10 minutes. The solution was diluted with ethyl acetate (350 mL) and washed with water (2×100 mL), brine (1×100 mL) and the organic layer was loaded directly onto a silica gel column packed with 20% ethyl acetate/hexane. 1 L of 20% ethyl acetate/hexane was flushed through the column followed by 50% ethyl acetate/hexane, followed by 80% ethyl acetate/hexane which eluded the product. To each 50 mL fraction that contained product, 4 mL of 1 M HCl/diethyl ether was added. The fractions were combined and concentrated to give 3-{4-[N-4-cis-tert-butylcyclohexyl)hydrazinomethyl]benzoylamino}propionic acid ethyl ester hydrochloride as an orange solid (3.6 g, 85.5% yield). The compound was used immediately in the next step.

APCl [M]$^+$=404.3.

Preparation of 3-{4-[N-(1-ethylpentyl)hydrazinomethyl]benzoylamino}propionic acid ethyl ester hydrochloride

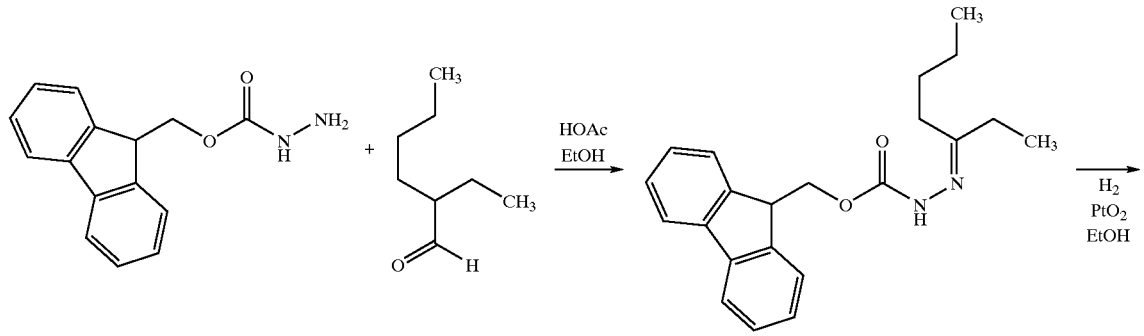

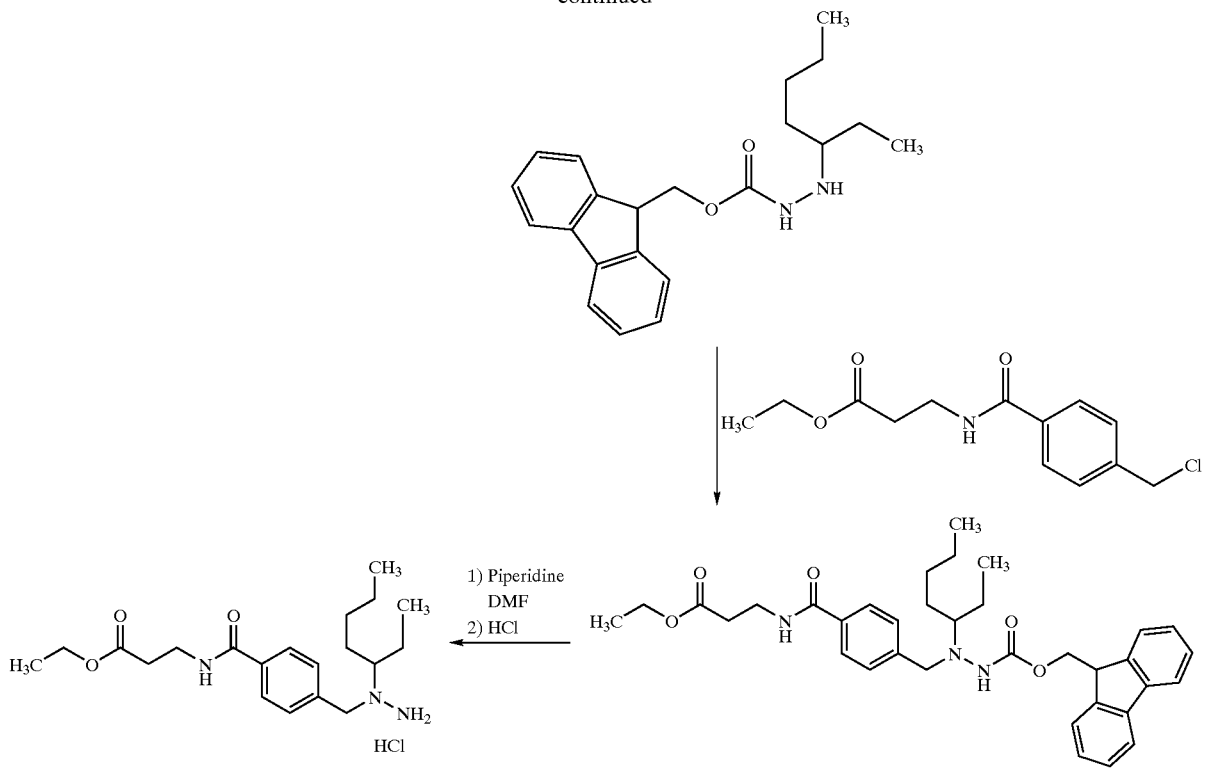

Fmoc-hydrazide (12 g, 47.2 mmol) was dissolved in ethanol (400 mL) and 2-ethylhexanal (7.3 g, 56.6 mmol) was added. Glacial acetic acid (4 mL) was added and the solution stirred for 18 h at room temperature. N'-(1-ethylpentylidene)hydrazinecarboxylic acid 9H-fluoren-9-ylmethyl ester precipitated out of solution, and was collected by vacuum filtration and rinsed with ethanol to give beige needles (8 g, 47% yield).

APCl [M]$^+$=365.2.

The above ethylpentylidene compound (8 g, 21.9 mmol) was dissolved in anhydrous ethanol (600 mL) and PtO$_2$ (150 mg, 0.68 mmol) was added. The solution was stirred under a H$_2$ atmosphere (1 atm) at room temperature for 6 hours. The solution was passed through a bed of silica gel followed by two volumes of ethyl acetate and concentrated to give a white foam. Purification by silica gel flash chromatography eluting with 15% ethyl acetate/hexane afforded N'-(1-ethylpentyl)hydrazinecarboxylic acd 9H-fluoren-9-ylmethyl ester as a white foam (7 g, 87% yield): APCl [M]$^+$=367.2.

The above ethylpentyl compound (7 g, 19.1 mmol) was dissolved in acetonitrile (200 mL) and the 3-(4-chloromethylbenzoylamino)propionic acid ethyl ester (5.7 g, 21 mmol) was added. Potassium carbonate (7.9 g, 57.3 mmol) and sodium iodide (catalytic) were added and the solution was stirred at 50° C. for 36 hours. The solution was diluted with ethyl acetate (800 mL) and washed with aqueous sat NaHCO$_3$ (3×300 mL), brine (3×300 mL), dried over MgSO$_4$ and concentrated to give a beige foam. Purification by silica gel flash chromatography eluting with 60% ethyl acetate/hexane to give 3-{4-[N-(1-ethylpentyl)-N'-(9H-fluoren-9-ylmethylmethoxycarbonyl)hydrazinomethyl]benzoylamino}propionic acid ethyl ester as a white foam (6 g, 52.4% yield).

$^1$H NMR (300 MHz, DMSO-d$_6$): δ 9.51 (t, 1H), 9.39 (s, 1H), 7.87 (d, 2H), 7.71 (d, 2H), 7.58 (d, 2H), 7.39 (m, 4H), 7.28 (m, 2H), 4.28 (m, 2H), 4.19 (d, 2H), 4.05 (q, 2H), 3.89 (s, 2H), 3.48 (q, 2H), 2.56 (m, 3H), 1.19 (m, 12H), 0.80 (m, 6H).

APCl [M]$^+$=600.3.

The above propionic acid ethyl ester compound (2.5 g, 4.2 mmol) was dissolved in DMF (15 mL) and piperidine (1.5 mL) was added while stirring at room temperature. TLC showed complete deprotection after 10 minutes. The solution was diluted with ethyl acetate (350 mL) and washed with H$_2$O (2×100 mL), brine (1×100 mL) and the organic layer was loaded directly onto a silica gel column packed with 20% ethyl acetate/hexane. 1 L of 20% ethyl acetate/hexane was flushed through the column followed by 50% ethyl acetate/hexane, followed by 80% ethyl acetate/hexane, which eluded the product. To each 50 mL fraction, which contained product, 4 mL of 1 M HCl/diethyl ether was added. The fractions were combined and concentrated to give 3-{4-[N-(1-ethylpentyl)hydrazinomethyl]benzoylamino}propionic acid ethyl ester hydrochloride as an orange solid (1.2 g, 69.6% yield). The compound was used immediately in the next step.

APCl [M]$^+$=378.2.

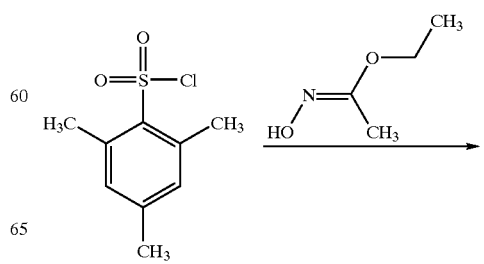

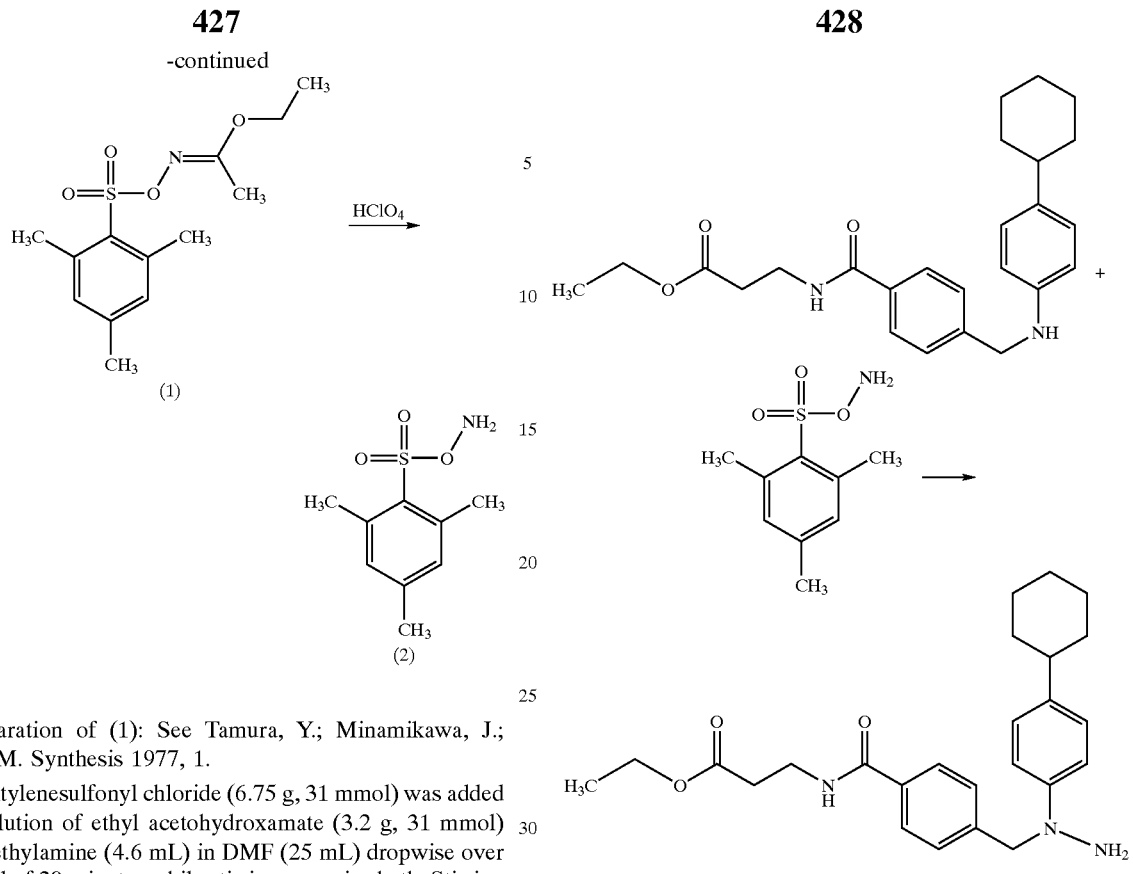

Preparation of (1): See Tamura, Y.; Minamikawa, J.; Ikeda, M. Synthesis 1977, 1.

Mesitylenesulfonyl chloride (6.75 g, 31 mmol) was added to a solution of ethyl acetohydroxamate (3.2 g, 31 mmol) and triethylamine (4.6 mL) in DMF (25 mL) dropwise over a period of 20 minutes while stirring on an ice bath. Stirring was continued for an additional 20 min at 0–10° C. and the reaction mixture was poured into ice/water (100 mL). The solution was stirred for 10 min and a white solid precipitated. The product was collected by vacuum filtration and washed with water (200 mL). The solid was dissolved in diethyl ether (200 mL) and dried over $MgSO_4$. The solution was concentrated to give an off white solid which was dissolved in hot hexane. White crystals formed by placing the solution in a −30° C. freezer overnight. The crystals were collected by filtration and dried with suction for one hour affording the product, (1) (6 g, 90% yield).

$^1$H NMR (300 MHz, DMSO-$d_6$): δ 7.71 (s, 2H), 3.84 (q, 2H), 2.56 (s, 6H), 2.29 (s, 3H), 2.01 (s, 3H), 1.12 (t, 3H).

APCl $[M]^+$=286.1.

Preparation of (2): See Tamura, Y.; Minamikawa, J.; Ikeda, M. Synthesis 1977, 1.

To a solution of (1) (2 g, 6.7 mmol) in dioxane (8 mL) was added 70% perchloric acid (1.2 mL) dropwise while stirring at 0° C. over a period of 10 minutes. The solution stirred for an additional 10 minutes at 0–10° C. and the reaction mixture was poured into ice/water (100 mL). The solution was stirred for 10 min and a white solid precipitated. The solid was collected by filtration, washed with cold water (200 mL) followed by cold hexane (100 mL) and dried by maintaining suction for 1 hour to give the product, (2), as a white powder (1.4 g, 97% yield).

$^1$H NMR (300 MHz, DMSO-$d_6$): δ 9.24 (bs, 2H), 6.78 (s, 2H), 2.51 (s, 6H), 2.18 (s, 3H).

APCl $[M-NH_2]^-$=199.0.

Preparation of 3-{4-[N-(4-cyclohexylphenyl) hydrazinomethyl]benzoylamino}propionic acid ethyl ester hydrochloride:

3-{4-[(4-Cyclohexylphenylamino)methyl] benzoylamino}propionic acid ethyl ester (0.6 g, 1.47 mmol) was dissolved in dichloromethane (12 mL) and O-mesitylenesulfonylhydroxylamine (0.79 g, 3.68 mmol) was added while stirring at 0° C. The solution stirred for 20 min. The solution was concentrated to ¼ its original volume and loaded onto a silica gel column packed with 25% ethyl acetate/hexane. The product was eluded with 5% methanol/ethyl acetate. To each 50 mL fraction, which contained product, 4 mL of 1 M HCl/diethyl ether was added. The fractions were combined and concentrated to give a rust colored solid. The solid was dissolved in ethyl acetate (10 mL) and hexane (20 mL) was added. A white precipitate formed and was collected by filtration followed by rinsing with ethyl acetate to give 3-{4-[N-(4-cyclohexylphenyl) hydrazinomethyl]benzoylamino}propionic acid ethyl ester hydrochloride as a white solid (0.1 g, 15% yield). The product was stored in a freezer at −70° C. until the next step.

APCl $[M]^+$=424.2.

Examples of Products Prepared According to General P procedure (X).

EXAMPLE 587
General Procedure (X)
3-{4-[N'-(4-Butoxybenzoyl)-N-indan-2-ylhydrazinomethyl]benzoylamino}propionic acid

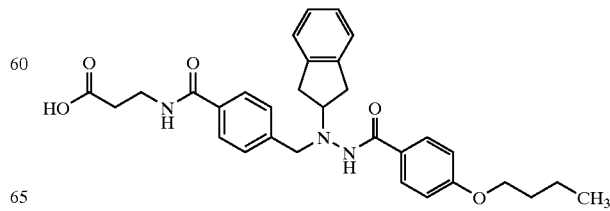

¹H NMR (DMSO-d₆): δ 0.91 (t, 3H), 1.41 (quintet, 2H), 1.67 (quintet, 2H), 2.49 (t, 2H), 3.96 (t, 2H), 4.15 (m, 2H), 6.88 (d, 2H), 7.09–7.18 (m, 2H), 7.10–7.20 (m, 2H), 7.50 (t, 4H), 7.72 (d, 2H), 8.47 (t, 1H), 9.13 (s, 1H).

MS (APCl, pos.): 530.2.

EXAMPLE 588

General Procedure (X)

3-{4-[N-(cis-4-tert-Butylcyclohexyl)-N'-(3,5-dichlorobenzoyl)hydrazinomethyl]benzoylamino}propionic acid

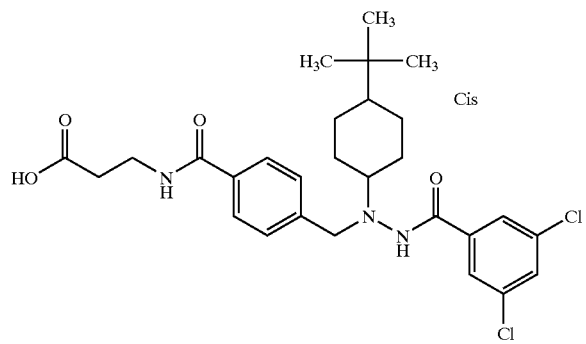

¹H NMR (DMSO-d₆): δ 0.85 (s, 9H), 1.04 (m, 1H), 1.37 (m, 4H), 1.58 (m, 2H), 1.92 (m, 2H), 2.44 (t, 2H), 3.42 (t, 2H), 4.16 (m, 3H), 7.44 (d, 2H), 7.58 (s, 2H), 7.74 (d, 2H), 7.75 (s, 1H), 8.48 (t, 1H), 9.42 (s, 1H).

MS (APCl, pos.): 548.2, 550.1.

EXAMPLE 589

General Procedure (X)

3-{4-[N-(cis-4-tert-Butylcyclohexyl)-N'-(3,4-difluorobenzoyl)hydrazinomethyl]benzoylamino}propionic acid

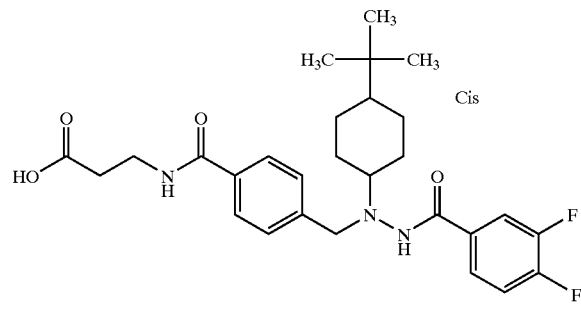

¹H NMR (DMSO-d₆): δ 0.85 (s, 9H), 1.03 (m, 1H), 1.36 (m, 4H), 1.59 (m, 2H), 1.92 (m, 2H), 2.44 (t, 2H), 3.41 (t, 2H), 4.04 (m, 3H), 7.46 (m, 4H), 7.60 (q, 1H), 7.72 (d, 2H), 8.47 (t, 1H), 9.30 (s, 1H).

MS (APCl, pos.): 516.2.

EXAMPLE 590

General Procedure (X)

3-{4-[N-(cis-4-tert-Butylcyclohexyl)-N'-(3-trifluoromethoxybenzoyl)hydrazinomethyl]benzoylamino}propionic acid

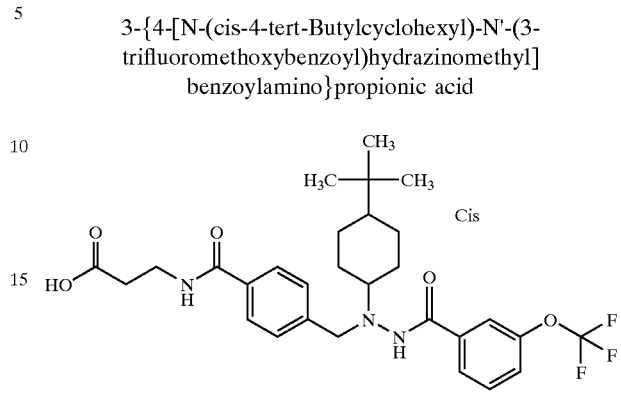

¹H NMR (DMSO-d₆): δ 0.87 (s, 9H), 1.08 (m, 1H), 1.38 (m, 4H), 1.61 (m, 2H), 1.95 (m, 2H), 3.41 (t, 2H), 4.10 (m, 2H), 7.45–7.53 (m, 3H), 7.62 (d, 1H), 7.74 (d, 1H), 8.44 (t, 1H), 9.38 (s, 1H), 12.19 (s, 1H).

MS (APCl, pos.): 564.2.

EXAMPLE 591

General Procedure (X)

3-(4-{N-(cis-4-tert-Butylcyclohexyl)-N'-[5-(2,4,6-trimethylbenzyl)furan-2-carbonyl]hydrazinomethyl}benzoylamino)propionic acid

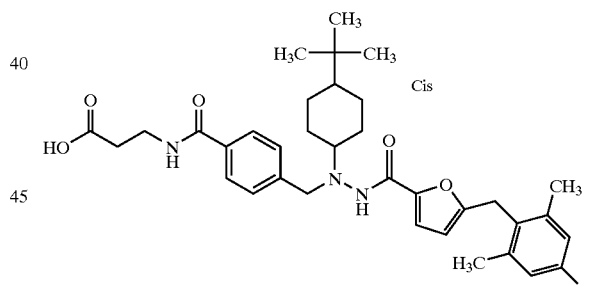

¹H NMR (DMSO-d₆): δ 0.86 (s, 9H), 1.10 (s, 1H), 1.25–1.35 (m, 4H), 1.57 (m, 2H), 1.91 (m, 2H), 2.20 (s, 9H), 2.47 (t, 2H), 3.31 (m, 1H), 3.42 (t, 2H), 3.90 (s, 2H), 4.08 (m, 2H), 7.79 (s, 1H), 6.83 (s, 2H), 6.85 (d, 1H), 7.47 (d, 1H), 7.73 (d, 1H), 8.48 (t, 1H), 8.90 (m, 2H), 12.18 (s, 1H).

Preparation of 5-(2,4,6-trimethylbenzyl)furan-2-carbonyl chloride:

Step A: 1,3,5-Trimethylbenzene (6.85 g, 57 mmol), methyl 5-chloromethyl-2-furanoate (2.48 g, 14.2 mmol) and aluminum trichloride (2.46 g, 18 mmol) were refluxed in dichloromethane (30 mL) for 4 h. The reaction was quenched with water, and the two layers were separated. The organic layer was concentrated and passed through a silica gel column. Hexane was used as the mobile phase to elute the product. The 5-(2,4,6-trimethylbenzyl)furan-2-carboxylic acid methyl ester was obtained as a yellow oil (86%).

Step B: The methyl ester (2.9 g, 11.6 mmol) from above was dissolved in methanol (50 mL) and 4 M NaOH (12 mL, 46.5 mmol) was added. The reaction was stirred overnight and made acidic using 1 N HCl. The reaction mixture was concentrated, dissolved in ethyl acetate, washed with brine, and dried over MgSO$_4$. Upon evaporation of the solvent, the corresponding carboxylic acid was obtained as a light yellow solid (2.7 g, 98%).

Step C: The furanyl carboxylic acid (2.59 g, 0.6 mmol) was dissolved in dichloromethane (20 mL) and thionyl chloride (10 mL, 106 mmol) was added dropwise. The reaction was refluxed for 3 hours and concentrated to dryness. The residue was passed through a silica gel plug-column using dichloromethane. The 5-(2,4,6-trimethylbenzyl)furan-2-carbonyl chloride was obtained as a yellow solid upon evaporation of the solvent (2.7 g, 97%).

MS (APCl, pos.): 602.3.

EXAMPLE 592

General Procedure (X)

3-(4-{N-(4-Cyclohexylphenyl)-N'-[5-(2,4,6-trimethylbenzyl)furan-2-carbonyl]hydrazinomethyl}benzoylamino)propionic acid

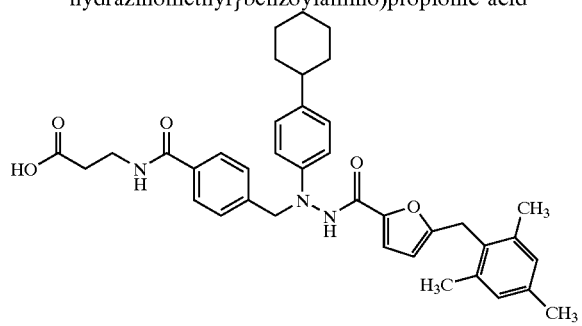

$^1$H NMR (acetone-d$_6$): δ 1.20–1.38 (m, 5H), 1.70–1.80 (m, 5H), 2.24 (s, 3H), 2.27 (s, 6H), 2.41 (m, 1H), 2.65 (t, 2H), 3.65 (qt, 2H), 3.94 (s, 2H), 4.84 (s, 2H), 5.92 (s, 1H), 6.81 (d, 2H), 6.85 (d, 2H), 7.04 (s, 1H), 7.06 (d, 2H), 7.58 (d, 2H), 7.84 (d, 2H), 9.61 (s, 1H).

MS (APCl, pos): 620.2, 621.3.

General Procedure (Y) for Solution Phase Preparation of Compounds of General Formula (Iu)

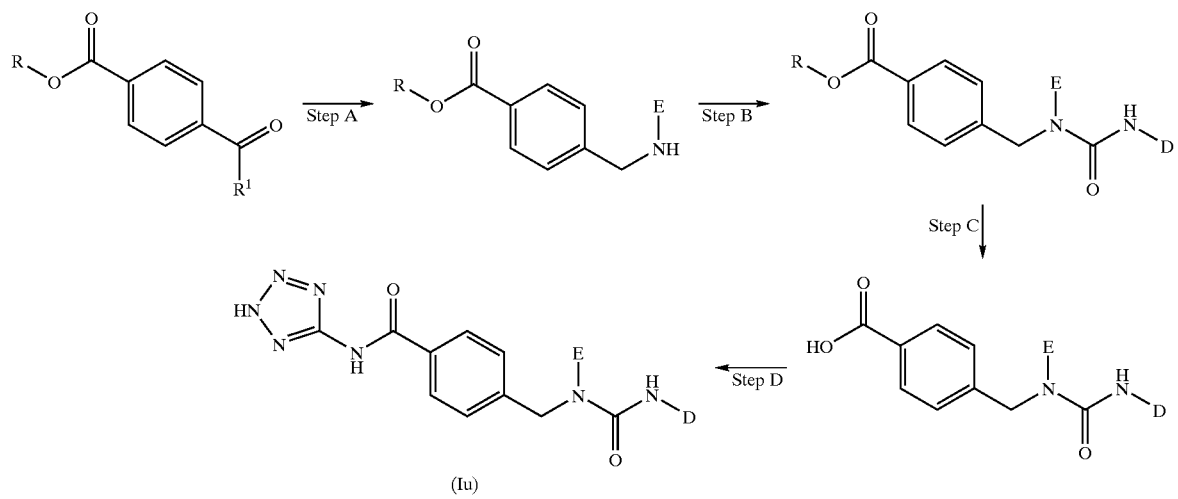

(Iu)

wherein
E and D are as defined for formula (I) and
R is C$_{1-6}$-alkyl.

Example 593

General Procedure (Y)

4-[1-(4-Cyclohex-1-enylphenyl)-3-(3,5-dichlorophenyl)ureidomethyl]-N-(2H-tetrazol-5-yl)benzamide

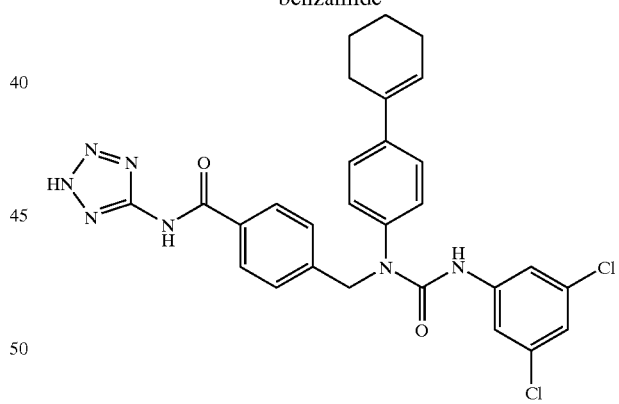

4-Cyclohex-1-enylaniline:

A mixture of cyclohexanone (50 g, 0.325 mol), and aniline (95 g, 1 mol) in 12 M HCl (100 mL), and ethanol (15 mL) was refluxed at 110° C. for four days. The solution was cooled and diluted with ethyl acetate. The aqueous layer was basified with 6 M NaOH. The organic layer was separate and washed with brine (3×), dried over MgSO$_4$, and concentrated to give a brown oil. Approximately half of the crude product was introduced into a silica gel column and eluted with 5% ethyl acetate/hexane to obtain the desired product along with aniline. The combined organic fractions were extracted with 1 N HCl and separated. Addition of brine to the aqueous layer precipitated the 4-cyclohex-1-enylaniline as a cream colored solid (9 g).

¹H NMR (DMSO-d₆): δ 1.50–1.60 (m, 2H), 1.60–1.70 (m, 2H), 2.10–2.15 (m, 2H), 2.20–2.30 (brd s, 2H), 5.00 (s, 2H), 5.90 (t, 1H), 6.50 (d, 2H), 7.10 (d, 2H).

Step A: To a solution of E-NH₂ (eg 4-cyclohexenylaniline, prepared as described above) (0.023 mol) and methyl 4-formylbenzoate (3.77 g, 0.023 mol) in dichloromethane (50 mL) and methanol (15 mL) was added a catalytic amount of acetic acid. After stirring the solution for 3 hours, Na(OAc)₃BH (24 g, 0.115 mol) was added. The reaction was allowed to stir at room temperature for 16 hours. The reaction mixture was diluted with ethyl acetate and washed with aqueous sodium bicarbonate (3×), brine (2×), dried over MgSO₄, filtered, and concentrated to give an orange solid. The crude product was introduced into a column of silica gel and eluted with ethyl acetate/hexane (5/95) to give 4-[(4-cyclohex-1-enylphenylamino)methyl]benzoic acid methyl ester (5 g, 0.015 mol).

¹H NMR (DMSO-d₆): δ 1.56 (m, 2H), 1.67 (m, 2H), 2.11 (m, 2H), 2.25 (m, 2H), 3.81 (s, 3H), 4.34 (d, 2H), 5.89 (t, 1H), 6.34 (t, 1H), 6.49 (d, 2H), 7.10 (d, 2H), 7.47 (d, 2H), 7.90 (d, 2H).

MS (APCl, pos): 322.1, 323.1.

Step B: The above 4-[(4-cyclohex-1-enylphenylamino)methyl]benzoic acid methyl ester (5 g, 0.015 mol) was dissolved in anhydrous dichloromethane and diisopropylethylamine (5.8 g, 0.045 mol) was added. To this solution was added an isocyanate (eg. 3,5-dichlorophenyl-isocyanate) (0.018 mol). After stirring the reaction mixture for 3 hours, the solution was diluted with ethyl acetate and washed with 1N HCl (2×), water, brine, dried over MgSO₄, filtered, and concentrated under reduced pressure. The residue was introduced into a silica gel column and eluted with ethyl acetate/hexane (10/90) to give 4-[3-(3,5-dichlorophenyl-1-(cyclohex-1-enylphenyl)ureidomethyl]benzoic acid methyl ester (4 g).

MS (APCl, pos): 509.0, 510.0, 511.1.

Step C: To a solution of the above 4-[3-(3,5-dichlorophenyl-1-(cyclohex-1-enylphenyl)ureido-methyl]benzoic acid methyl ester (1.5 g, 2 mmol) in THF (30 mL) and methanol (10 mL) was added an excess of 2 M LiOH (10 mL). After stirring the reaction mixture for 3 hours, the solution was concentrated. The residue was taken up in ethyl acetate and washed with 1 N HCl (2×), H₂O (2×), brine, and dried over MgSO₄. Evaporation of the solvent gave the product as an oil. The oil was taken up in dichloromethane. Upon sitting, 4-[3-(3,5-dichlorophenyl-1-(cyclohex-1-enylphenyl)ureidomethyl]benzoic acid (1.2 g, quantitative) crystallized out of solution.

Step D: To a solution of the above benzoic acid (0.4 g, 0.81 mmol) in DMF (4 mL) was added HBTU (0.37 g, 0.90 mmol), diisopropylethylamine (0.30 g, 2.4 mmol), and 5-aminotetrazole (0.24 g, 2.4 mmol). After stirring the solution for 16 hours, the reaction mixture was diluted with ethyl acetate and washed with 1N HCl (3×), brine (3×), dried over MgSO₄, filtered, and concentrated to a syrup. By addition of dichloromethane to the oil, the title compound precipitated as a creamy-white solid (200 mg, 0.36 mmol).

¹H NMR (DMSO-d₆): δ 1.52–1.78 (m, 4H), 2.08–2.25 (br, 2H), 2.26–2.40 (br, 2H), 5.00 (s, 2H), 6.19 (br, 1H), 7.14 (s, 1H), 7.22 (d, 2H), 7.36–7.50 (dd, 4H), 7.62 (s, 2H), 8.03 (d, 2H), 12.37 (s, 1H), 16.02 (s, 1H).

LC-MS (APCl, pos.): 562 (M+1).

Example 594

General Procedure (Y)

4-{1-(4-Cyclohexylphenyl)-3-(1H-indol-5-yl)ureidomethyl]-N-(2H-tetrazol-5-yl)benzamide

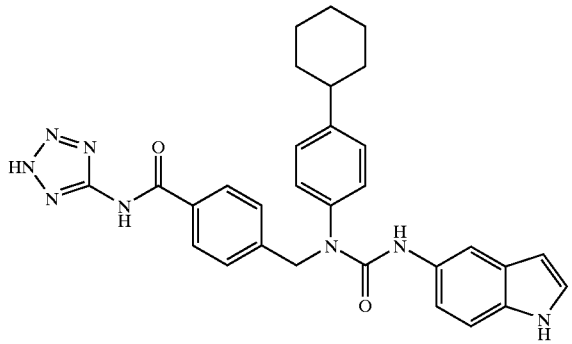

¹H NMR (DMSO-d₆): δ 1.12–1.46 (m, 5H), 1.62–1.83 (m, 5H), 5.01 (s, 1H), 6.32 (s, 1H), 7.05–7.08 (q, 1H), 7.17–7.29 (m, 6H), 7.48 (d, 2H), 7.55 (s, 1H), 7.85 (s, 1H), 8.05 (d, 2H), 10.9 (s, 1H), 12.36 (s, 1H), 16.0–16.2 (br, 1H).

MS (APCl, pos.): 535 (M+1).

Example 595

General Procedure (Y)

4-[1-(4-Cyclohexylphenyl)-3-(3,4-dichlorobenzyl)ureidomethyl}-N-(2H-tetrazol-5-yl)benzamide

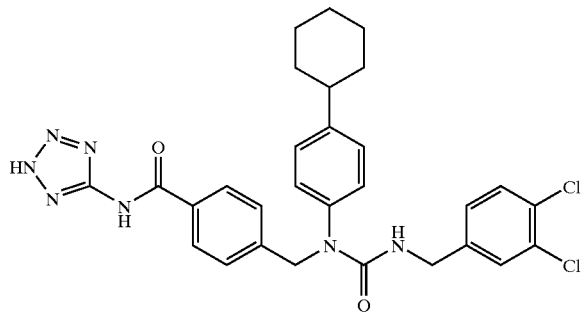

¹H NMR: (DMSO-d₆): δ 1.20 (m, 1H), 1.30–1.50 (m, 4H), 1.60–1.70 (m, 5H), 4.21 (s, 2H), 4.89 (s, 2H), 6.60 (m, 1H), 7.14 (d, 2H), 7.21 (d, 3H), 7.39 (d, 2H), 7.46 (s, 1H), 7.56 (d, 1H), 8.03 (d, 2H), 12.30 (s, 1H), 16.00 (brd s, 1H).

MS (APCl, pos): 578.1, 579.1, 580.1

Example 596

General Procedure (Y)

4-[1-(4-Cyclohexylphenyl)-3-((1S)-1-phenylethyl)ureidomethyl]-N-(2H-tetrazol-5-yl)benzamide

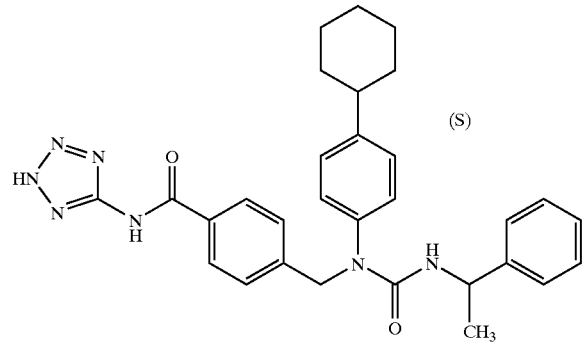

$^1$H NMR (DMSO-d$_6$): δ 1.15–1.45 (m, 9H), 1.64–1.80 (m, 5H), 4.82–4.98 (m, 3H), 6.16 (d, 2H), 7.08–7.38 (m, 11H), 7.98 (d, 2H), 11.0 (br, 1H).

LC-MS (APCl, pos.): 524 (M+1).

Example 597

General Procedure (Y)

4-[1-(4-Cyclohexylphenyl)-3-(4-cyano-3-trifluoromethylphenyl)ureidomethyl]-N-(2H-tetrazol-5-yl)benzamide

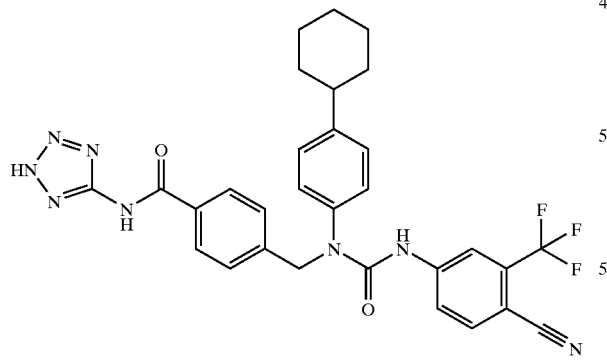

$^1$H NMR (DMSO-d$_6$): δ 1.10–1.90 (m, 10H), 2.30 (br, 1H), 5.02 (s, 2H), 7.18–7.40 (m, 4H), 7.45 (d, 2H), 7.95–8.20 (m, 5H), 9.14 (s, 1H), 12.34 (s, 1H).

LC-MS (APCl, pos.): 589 (M+1).

Example 598

General Procedure (Y)

4-[1-(4-Cyclohexylphenyl)-3-((1R)-1-phenylethyl)ureidomethyl]-N-(2H-tetrazol-5-yl)benzamide

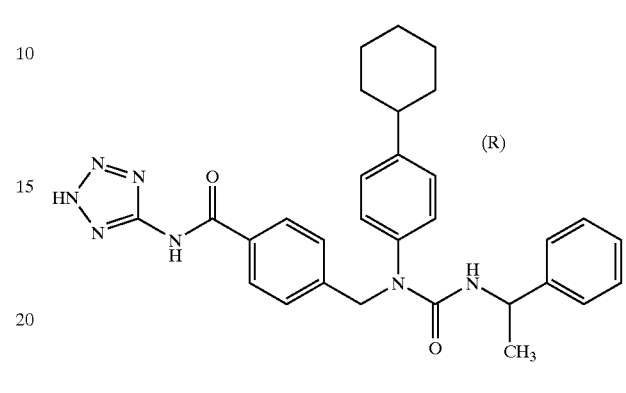

$^1$H NMR (acetone-d$_6$): δ 1.18–1.48 (m, 9H), 1.68–1.88 (m, 4H), 2.52 (m, 1H), 4.98 (s, 2H), 5.05 (m, 1H), 5.37 (d, 1H), 7.15–7.35 (m, 9H), 7.47 (d, 2H), 8.09 (d, 2H), 11.3 (br, 1H).

LC-MS (APCl, pos.): 524 (M+1).

EXAMPLE 599

General Procedure (Y)

4-[3-(4-Cyano-3-trifluoromethylphenyl)-1-(4-cyclohex-1-enylphenyl)ureidomethyl]-N-(2H-tetrazol-5-yl)benzamide

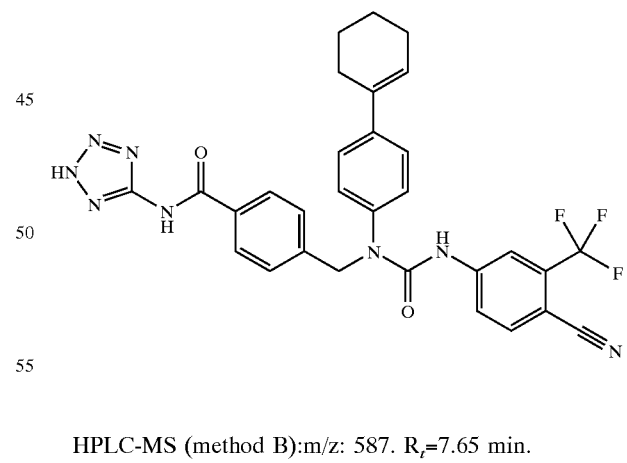

HPLC-MS (method B):m/z: 587. R$_t$=7.65 min.

$^1$H NMR (DMSO$_6$): δ 1.55–1.63 (2H,m), 1.68–1.76 (2H, m), 2.17 (2H, broad), 2.35 (2H, broad), 5.05 (2H, s), 6.20 (1H, broad), 7.28 (2H, d), 7.43 (4H, dd), 8.02 (5H, m), 8.18 (1H), 9.20 (1H, s), 12.35 (1H, s).

Microanalysis: calculated for C$_{30}$H$_{25}$F$_3$N$_8$O$_2$,0.5 mol H$_2$O: 60.50% C; 4.40% H; 18.81% N; Found: 60.80% C; 4.49% H; 18.51% N.

EXAMPLE 600

General Procedure (Y)

4-[1-(4-Cyclohexylphenyl)-3-(4-fluoro-3-trifluoromethylihenyl)ureidomethyl]-N-(2H-tetrazol-5-yl)benzamide

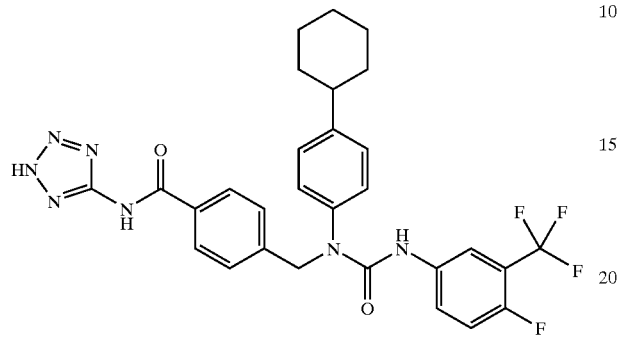

HPLC-MS (method B): m/z: 582. $R_t$=7.75 min.

$^1$H NMR (DMSO-$d_6$): δ 1.20–1.45 (5H, m), 1.65–1.85 (5H, m), 5.00 (2H, s), 7.22 (4H), 7.38 (1H, t), 7.48 (2H, d), 7.80 (1H, broad), 7.92 (1H, d), 8.03 (2H, d), 8.62 (1H, s), 12.4 (1H), broad).

EXAMPLE 601

General Procedure (Y)

4-[3-(4-Bromo-3-trifluoromethylphenyl)-1-(4-cyclohex-1-enylphenyl)ureidomethyl]-N-(2H-tetrazol-5-yl)benzamide

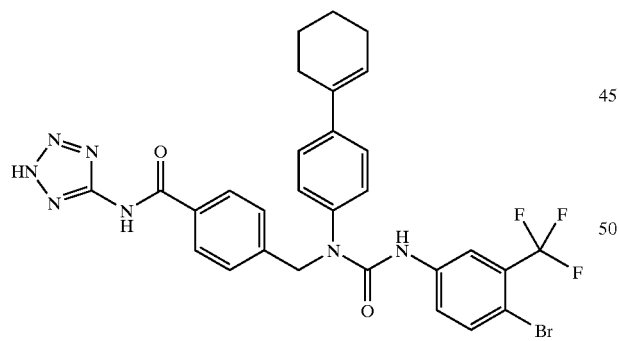

HPLC-MS (method B): m/z: 641, $R_t$=8.2 min.

$^1$H NMR (DMSO-$d_6$): δ 1.55–1.65 (m, 2H), 1.67–1.77 (m, 2H), 2.19 (broad, 2H), 2.35 (broad, 2H), 5.00 (s, 2H), 6.20 (s, 1H), 7.23 (d, 2H), 7.45 (dd, 4H), 7.72 (d, 1H), 7.75 (d, 1H), 8.04 (d, 2H), 8.05 (s, 1H), 8.72 (s, 1H), 12.4 (broad, 1H).

Microanalysis: calculated for $C_{29}H_{25}BrF_3N_7O_2$: 54.39% C; 3.93% H; 15.31% N. Found: 54.25% C; 4.02% H; 15.16% N.

EXAMPLE 602

General Procedure (Y)

4-[1-(4-tert-Butylcyclohexyl)-3-(3-methoxy-5-trifluoromethylphenyl)ureidomethyl]-N-(2H-tetrazol-5-yl)benzamide

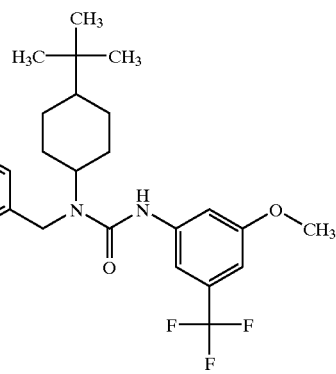

HPLC-MS (method B): m/z: 574, $R_t$=7.85 min.

$^1$H NMR (DMSO-$d_6$): δ 0.83 (9H, s), 0.96 (1H, m), 1.14 (2H, m), 1.44 (2H, m), 1.73 (4H, m), 3.80 (3H, s), 4.08 (1H, m), 4.68 (2H, s), 6.82 (1H, s), 7.42 (2H, d), 7.46 (1H, s), 7.53 (1H, s), 8.05 (2H, d), 8.71 (1H, s), 12.36 (1H, s).

Microanalysis: calculated for $C_{28}H_{34}F_3N_7O_3$: 58.63% C; 5.97% H; 17.09% N; Found: 58.45% C; 6.29% H; 17.04% N.

EXAMPLE 603

General Procedure (Y)

4-[3-(3,5-Bis(trifluoromethyl)phenyl)-1-(cis-4-tert-butylcyclohexyl)ureidomethyl]-N-(2H-tetrazol-5-yl)benzamide

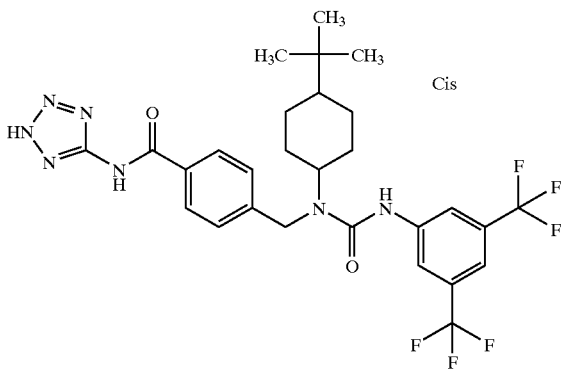

HPLC-MS (method B): m/z: 512, $R_t$=8.20 min.

$^1$H NMR (DMSO-d$_6$): δ 0.83 (9H, s), 1.20 (1H, m), 1.35 (2H, m), 1.55 (4H, m), 1.77 (2H, m), 4.31 (1H, m), 4.76 (2H, s), 7.42 (2H, d), 7.61 (1H, s), 8.05 (2H, d), 8.26 (2H, s), 9.12 (1H, s), 12.32 (1H, s).

EXAMPLE 604

4-[1-(4-Cyclopropylcyclohexyl)-3-(4-trifluoromethoxyphenyl)ureidomethyl]-N-(2H-tetrazol-5-yl)benzamide

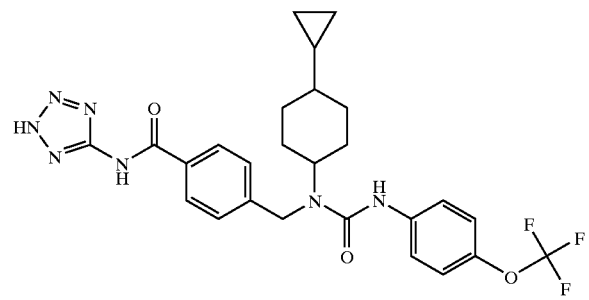

$^1$H NMR (DMSO-d$_6$): δ 12.2 (s, broad), 8.59 (1H, s), 8.03 (2H, d), 7.55 (2H, d), 7.42 (2H, d), 7.22 (2H, d), 4.63 (2H, broad), 4.12 (1H, m), 1.80–1.00 (9H, m), 0.49 (2H, m), 0.35 (2H, m).

HPLC-MS (method B): m/z: 544, $R_t$=7.70 min.

General Procedure (Z) for Solution Phase Preparation of Compounds of General Formula (Iv)

wherein
E and D are as defined for formula (I) and
R is $C_{1-6}$-alkyl.

Example 605
General Procedure (Z)

3-{4-[1-(4-Cyclohex-1-enylphenyl)-3-(3,5-dichlorophenyl)ureidomethyl]benzoylamino}propionic acid

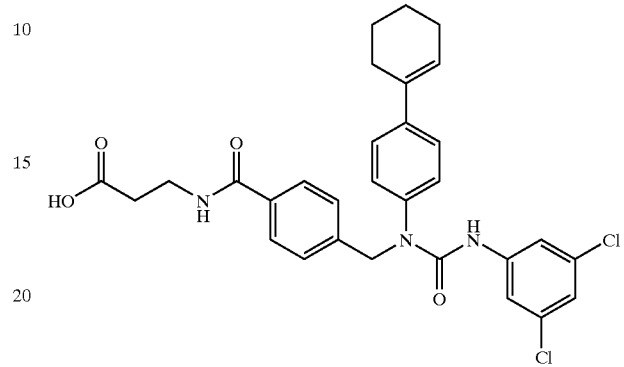

Steps A to C of this general procedure (Z) are similar to steps A to C of the general procedure (Y).

Step D: To a solution of the above benzoic acid (0.4 g, 0.81 mmol, prepared in step C) in DMF (4 mL) were added HBTU (0.37 g, 0.90 mmol), diisopropylethylamine (0.30 g, 2.4 mmol), and ethyl 3-aminopropanoate hydrochloride (0.30 g, 2.4 mmol). After stirring the solution for 16 hours, the reaction was diluted with ethyl acetate and washed with 1N HCl (3×), brine (3×), dried over MgSO$_4$, filtered, and concentrated to a syrup. The crude material was introduced

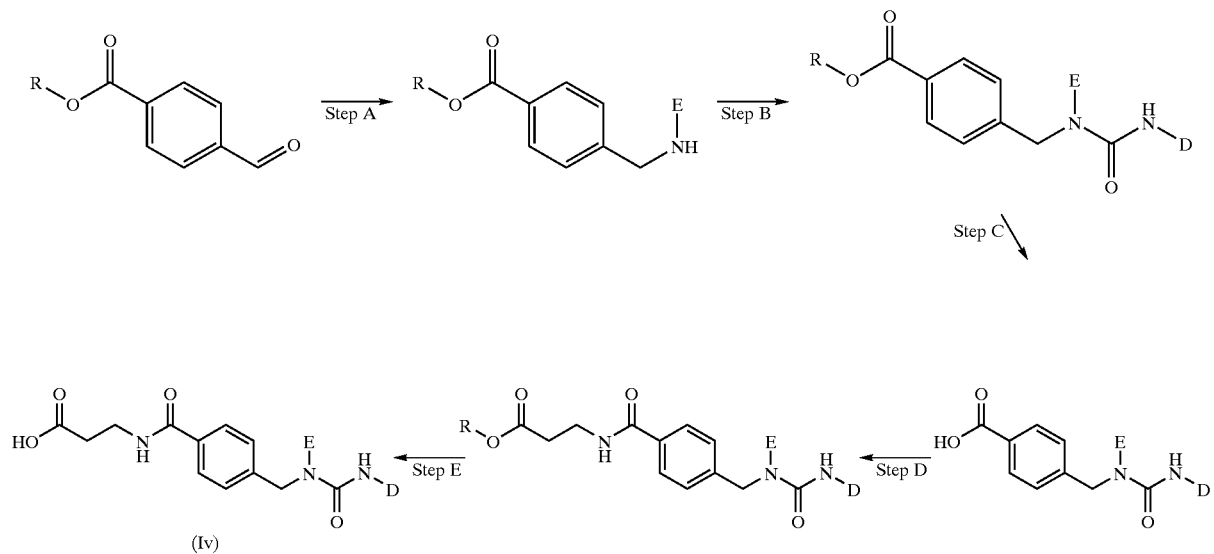

into a silica gel column and eluted with ethyl acetate/hexane (1/3 to 4/6) to afford 3-{4-[1-(4-cyclohex-1-enylphenyl)-3-(3,5-dichlorophenyl)ureidomethyl]benzoylamino}propionic acid ethyl ester in quantitative yield.

Step E: The propionic acid ethyl ester prepared in step D was dissolved in THF (6 mL) and MeOH (3 mL). A solution of 2 M LiOH (3 mL) was then added and the reaction was stirred at room temperature for 30 minutes. The solvents were evaporated under reduced pressure. The residue was

Example 606

General Procedure (Z)

3-{4-[1-(4-Cyclohexylphenyl)-3-(3,4-dichlorobenzyl)ureidomethyl]benzoylamino}propionic acid

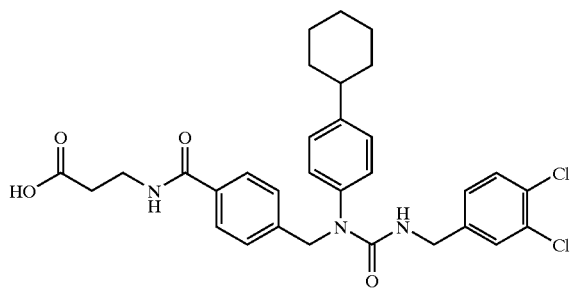

$^1$H NMR (DMSO-d$_6$): δ 1.15 (m, 1H), 1.34 (t, 4H), 1.70 (m, 1H), 1.75 (d, 4H), 2.45 (t, 2H), 3.45 (qt, 2H), 4.20 (d, 2H), 4.84 (s, 2H), 6.56 (t, 1H), 7.08 (d, 2H), 7.19–7.27 (m, 5H), 7.45 (s, 1H), 7.57 (d, 1H), 7.73 (d, 2H), 8.48 (t, 1H), 12.21 (s, 1H).

MS (APCl, pos): 582.1, 583.1, 584.1.

Example 607

General Procedure (Z)

3-{4-[1-(4-Cyclohexylphenyl)-3-(1H-indol-5-yl)ureidomethyl]benzoylamino}propionic acid

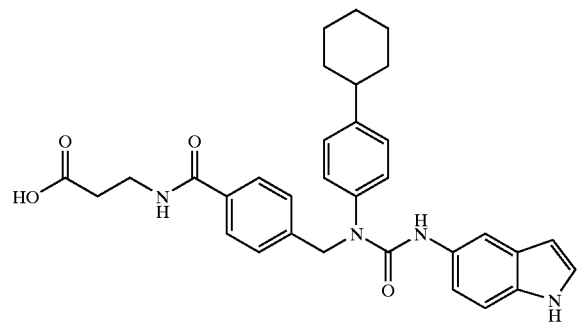

$^1$H NMR (DMSO-d$_6$): δ : 1.12–1.45 (m, 5H), 1.63–1.87 (m, 5H), 2.40–2.55 (br, 2H), 3.43 (q, 2H), 4.96 (s, 2H), 6.32 (s, 1H), 7.0–7.08 (q, 1H), 7.13–7.29 (m, 6H), 7.36 (d, 2H), 7.54 (s, 1H), 7.76 (m, 3H), 8.48 (t, 1H), 10.9 (s, 1H).

LC-MS (APCl, pos.): 539 (M+1).

taken up in ethyl acetate and washed with 1 N HCl (2×), brine (2×), dried over MgSO$_4$, filtered, and concentrated to a syrup. Addition of hexane followed by trituration precipitated the title compound (270 mg, 0.48 mmol) as a cream colored solid.

$^1$H NMR (acetone-d$_6$): δ : 1.58–1.85 (m, 4H), 2.15–2.28 (m, 2H), 2.32–2.44 (m, 2H), 2.65 (t, 2H), 3.63 (q, 2H), 5.01 (s, 2H), 6.24 (m,1H), 7.04 (m, 1H), 7.22 (d, 2H), 7.38–7.48 (m, 4H), 7.61 (d, 2H), 7.70–7.88 (m, 4H), 10.7 (br, 1H).

LC-MS (APCl, pos.): 567(M+1).

Example 608

General Procedure (Z)

3-{4-[1-(4-Cyclohexylphenyl)-3-((1R)-1-phenylethyl)ureidomethyl]benzoylamino}propionic acid

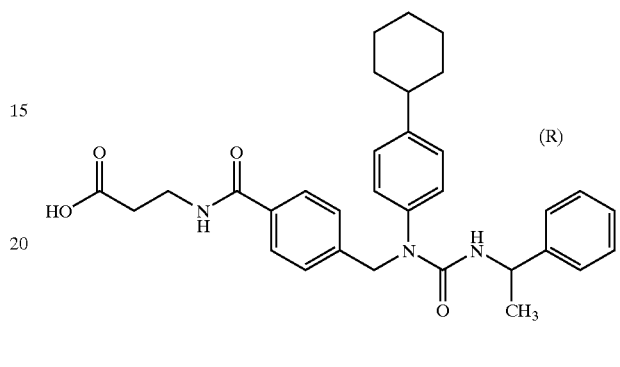

$^1$H NMR (acetone-d$_6$): δ 1.18–1.48 (m, 9H), 1.68–1.90 (m, 4), 2.51 (m, 1H), 2.65 (t, 2H), 3.63 (q, 2H), 4.91 (s, 2H), 5.03 (m, 1H), 5.28 (d, 1H), 7.08–7.35 (m, 11H), 7.70–7.82 (m, 3H), 10.7 (br, 1H).

LC-MS (APCl, pos.): 528 (M+1).

Example 609

General Procedure (Z)

3-{4-[1-(4-Cyclohexylphenyl)-3-((1S)-1-phenylethyl)ureidomethyl]benzoylamino}propionic acid

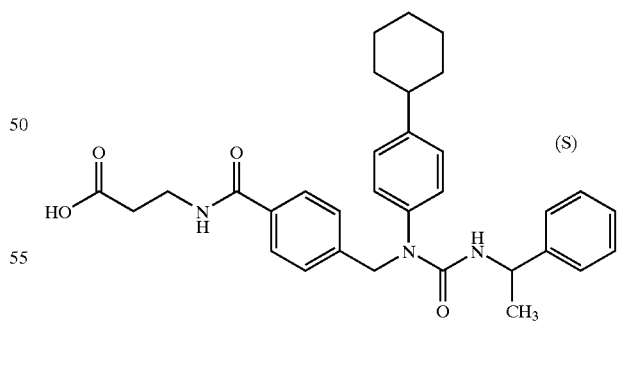

$^1$H NMR (DMSO-d$_6$): δ 1.12–1.40 (m, 9H), 1.62–1.85 (m, 5H), 2.50 (t, 2H), 3.43 (q, 2H), 4.78–4.95 (m, 3H), 6.09 (d, 2H), 7.07 (d, 2H), 7.14–7.34(m, 9H), 7.73 (d, 2H), 2H), 8.44 (s, 1H), 12.15 (s, 1H).

LC-MS: (APCl, pos.): 528 (M+1).

Example 610
General Procedure (Z)
3-{4-[1-(4-Cyclohexylphenyl)-3-[(1R)-1-(2-naphthyl)ethyl]ureidomethyl]benzoylamino}propionic acid
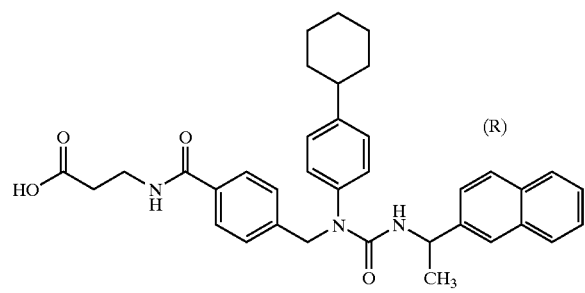
$^1$H NMR (DMSO-d$_6$): δ 1.15–1.86 (m, 14H), 2.50 (t, 2H), 3.44 (q, 2H), 4.87 (s, 2H), 5.06 (t, 1H), 6.26 (d, 2H), 7.10 (d, 2H), 7.19 (d, 2H), 7.26 (d, 2H), 7.43–7.50 (m, 3H), 7.68–7.76 (m, 3H), 7.80–7.91 (m, 3H), 8.44 (s, 1H), 12.13 (s, 1H).
LC-MS (APCl, pos.): 578 (M+1).
EXAMPLE 611
2-{4-[1-[4-(2-Carboxyethylcarbamoyl)benzyl]-3-(4-trifluoromethoxyphenyl)ureido]cyclohexyl}-2-methylpropionic acid ethyl ester
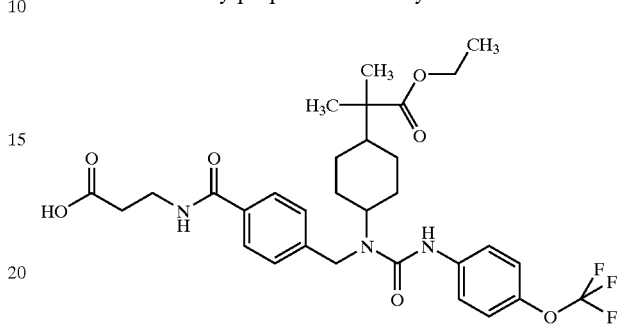
Reaction scheme
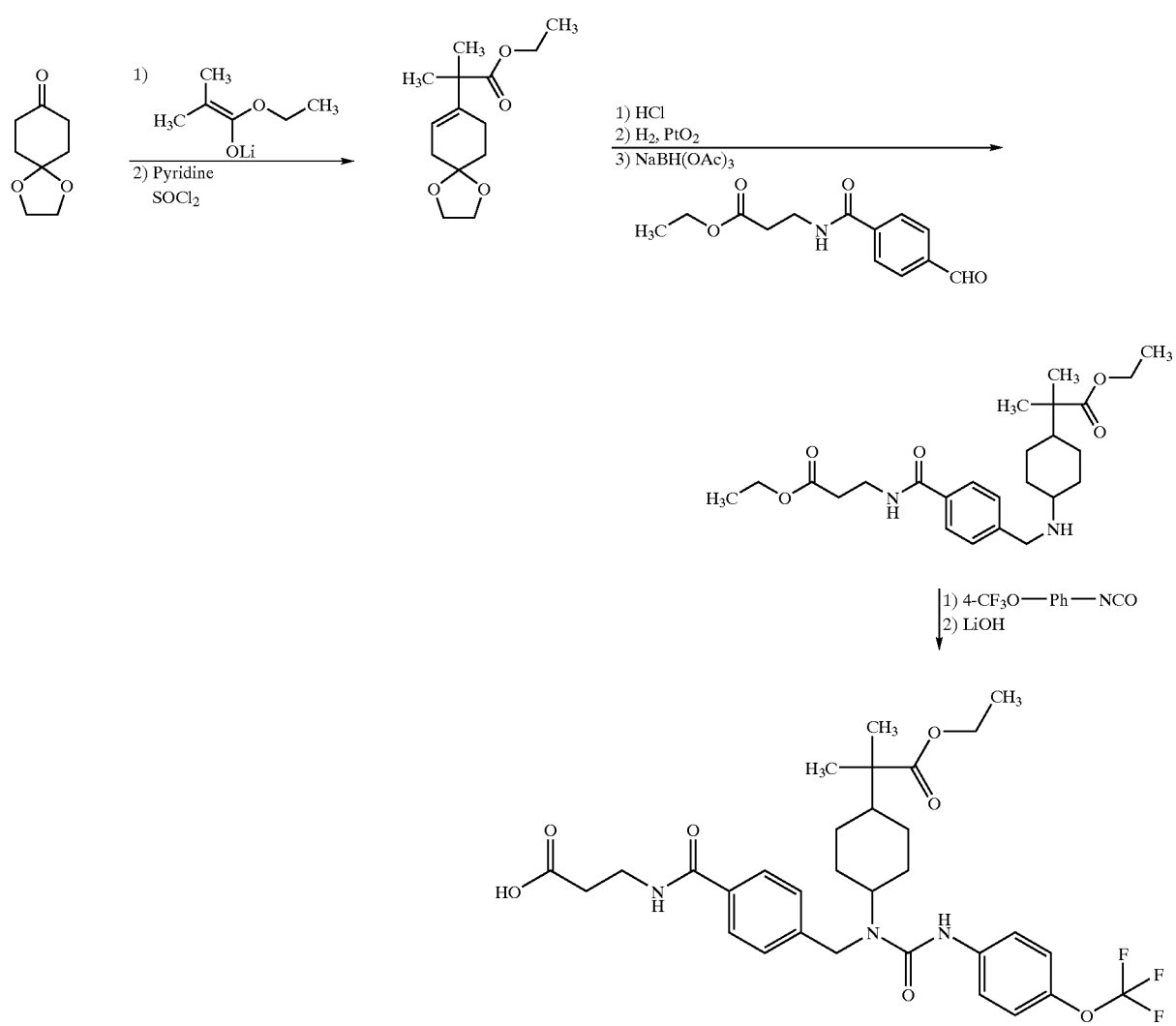

Ethyl 2-(1,4-dioxaspiro[4.5]dec-7-en-8-yl)-2-methylpropanoate:

To a solution of diisopropylamine (10.1 g, 0.1 mol) in THF (50 mL) at −78° C. was added n-butyl lithium (48 mL of a 2M solution in hexane) during a period of 15 min. After 15 min ethyl isobutyrate (11.6 g, 0.1 mol) was added dropwise during a period of 15 min. After additional 15 min at −78° C., a precooled solution of 1,4-cyclohexanedione monoethylene ketal in THF (80 mL) was added via cannula during a period of 15 min. After stirring for 2 hours at −78° C., the mixture was allowed to reach room temperature. It was poured onto ammonium chloride solution (100 mL), and extracted with ether (3×50 mL). The combined organic extracts were dried (MgSO$_4$) and concentrated to give 22 g colorless oil; GC-MS (pos.): 273, 255, 181.

The crude material was dissolved in pyridine (80 mL), and thionyl chloride (7.5 mL) was added dropwise with cooling in an ice bath. After stirring for 16 hours at room temperature, water (100 mL), and ether (300 mL) was added. The two layers were separated, the organic layer was washed with 1N HCl (3×50 mL), brine (2×50 mL), dried (MgSO$_4$), and concentrated to give 18.3 g of ethyl 2-(1,4-dioxaspiro[4,5]dec-7-en-8-yl)-2-methylpropanoate as a colourless oil.

$^1$H NMR (CDCl$_3$): δ 1.22 (t, 3H), 1.30 (s, 6H), 1.74 (t, 2H), 2.18 (m, 2H), 2.33 (s, 2H), 3.96 (m, 4H), 4.13 (q, 2H), 5.50 (s, 1H).

GC-MS (pos.): 255, 181.

N-{4-[([3-(2-ethoxy-1,1-dimethyl-2-oxoethyl)cyclohexyl]{[4-(trifluoromethoxy)anilino]carbonyl}amino)methyl]benzoylamino}propionic acid To a solution of ethyl 2-(1,4-dioxaspiro[4.5]dec-7-en-8-yl)-2-methylpropanoate (694 mg, 3.51 mmol) in THF (5 mL) was added 1N HCl. The mixture was stirred at room temperature for 72 hours, diluted with sodium bicarbonate solution (20 mL), and extracted with ether (3×30 mL). The combined organic extracts were dried (MgSO$_4$), and concentrated to give 666 mg colourless oil, GC-MS (pos.) 211, 138. The material was dissolved in ethanol (5 mL), and 20 mg Pd/C (10% Pd) was added. The mixture was stirred under a hydrogen atmosphere for 16 hours. The catalyst was filtered off by suction through celite, and the filtrate was concentrated to give 670 mg colorless oil. This material was dissolved in DMF (10 mL), and THF (10 mL), and N-[4-(aminomethyl)benzoylamino]propionic acid (700 mg, 3.14 mmol) was added followed by sodium triacetoxy borohydride (1.0 g, 4.7 mmol). The mixture was stirred at room temperature for five days, and filtered by suction. The filtrate was concentrated, and coevaporated with methanol and dichloromethane. The residue was dissolved in dichloromethane (5 mL), and triethylamine (1 mL) and 4-trifluoromethoxyphenyl isocyanate (650 mg, 3.20 mmol) was added. After stirring for 16 h at room temperature, the mixture was filtered by suction, and the filtrate was concentrated. The residue was dissolved in dichloromethane (100 mL), washed with 1N HCl (2×50 mL), brine (50 mL), dried (MgSO$_4$), and concentrated. Flash chromatography on silicagel eluting with chloroform/methanol, 9:1 provided the title compound.

$^1$H NMR (CD$_3$OD): δ 1.06 (s, 1H), 1.09 (s, 6H), 1.22 (t, 2H), 1.46–1.85 (m, 8H), 2.69 (t, 2H), 3.60 (t, 2H), 4.03–4.15 (m, 2H), 4.07 (s, 2H), 7.14 (d, 2H), 7.34–7.41 (m, 4H), 7.77 (d, 2H).

MS (APCl, pos.): 622.2

EXAMPLE 612

3-({6-[1-(4-tert-Butylcyclohexyl)-3-(4-trifluoromethoxyphenyl)ureidomethyl]pyridine-3-carbonyl}amino)propionic acid

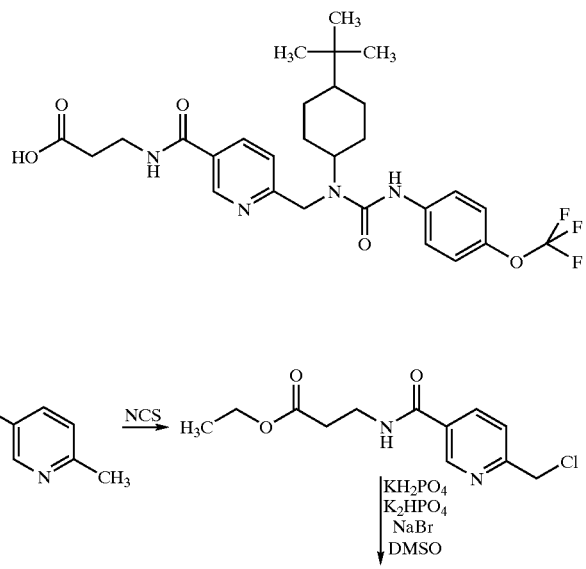

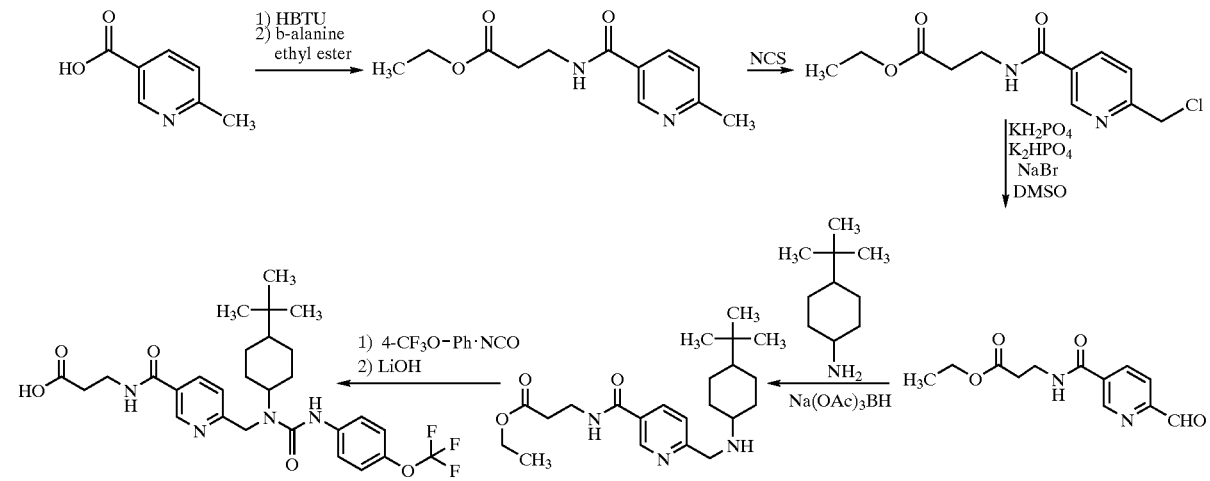

To solution of 6-methylnicotinic acid (4.9 g, 35.7 mmol) in DMF (50 mL) was added HBTU (16.2 g, 42.8 mmol) and diisopropylethylamine (11.0 g, 85 mmol). The mixture was stirred at 0° C. for 30 min, and β-alanine ethyl ester hydrochloride (6.57 g, 42.8 mmol) was added at 0° C. The reaction was monitored by TLC. The reaction mixture was concentrated in vacuo, and the residue was dissolved in carbon tetrachloride (200 mL). NCS (5.2 g, 38.9 mmol) and a catalytic amount of benzoyl peroxide were added. After refluxing for 2 hours, the solvent was removed in vacuo. Column chromatography on silica gel eluting with hexane/ethyl acetate, 1:1 provided ethyl 3-{[(6-chloromethyl-3-pyridinyl)carbonyl}aminopropanoate as a white solid (2.9 g, overall yield 30%).

$^1$H NMR (CDCl$_3$): δ: 1.20 (t, 3H), 2.55 (t, 2H), 3.70 (q, 2H), 4.13 (q, 2H), 4.68 (s, 2H), 7.52 (d, 1H), 7.57 (t, 1H), 8.15 (d, 1H), 8.94 (s, 1H).

To solution of ethyl 3-{[(6-chloromethyl-3-pyridinyl)carbonyl}aminopropanoate (4.0 g, 14.8 mmol) in DMSO (40 mL) was added KH$_2$PO$_4$ (2.6 g, 14.8 mmol), K$_2$HPO$_4$ (1.0 g, 7.4 mmol and sodium bromide (1.5 g, 14.8 mmol). The mixture was heated at 100° C. under nitrogen for 6 hours. TLC showed the starting material was completely consumed. The mixture was poured onto water (100 mL), and extracted with ethyl acetate (3×50 mL). The combined organic extracts were dried (MgSO$_4$), and concentrated. This material (aldehyde) was used without further purification in the next step.

The crude material (283 mg) was dissolved in dichloromethane (10 mL), and tert-butylcyclohexylamine (70 mg, 0.45 mmol) and sodium triacetoxy borohydride (190 mg, 0.89 mmol) were added. The mixture was stirred at room temperature for 16 hours, diluted with dichloromethane (20 mL), washed with sodium bicarbonate solution (20 mL), brine (20 mL), dried (MgSO$_4$), and concentrated. Flash chromatography on silicagel eluting with chloroform:methanol:ammonia:water, 90:10:0.5:0.5 provided the desired secondary amine (190 mg); MS (APCl, pos.): 390.2.

This material was dissolved in chloroform (5 mL), and 4-trifluoromethoxyphenyl isocyanate (150 mg, 0.73 mmol) was added. After stirring at room temperature for 16 hours, the mixture was concentrated. Flash chromatography on silica gel eluting with hexane:ethyl acetate, 1:1 afforded the ethyl ester of the title compound (225 mg).

$^1$H NMR (CDCl$_3$): δ 0.84 (s, 9H), 0.91–1.84 (m, 9H), 1.27 (t, 3H), 2.66 (t, 2H), 3.74 (q, 2H), 4.12 (m, 1H), 4.17 (q, 2H), 4.48 (s, 2H), 7.07 (t, 1H), 7.12 (d, 2H), 7.41 (d, 1H), 7.46 (d, 2H), 8.13 (d, 1H), 8.98 (d, 1H), 9.54 (s, 1H), 9.75 (s, 1H).

The above material was dissolved in THF (5 mL), and 1M LiOH (1 mL) was added. After stirring at room temperature for 3 hours, the solution was acidified with 1N HCl to pH=4, and concentrated. The residue was dissolved in chloroform (20 mL), washed with brine (10 mL), dried (MgSO$_4$) and concentrated. The title compound crystallized from dichloromethane on addition of hexane.

$^1$H NMR (DMSO-d$_6$): δ 0.82 (s, 9H), 0.93–1.75 (m, 9H), 2.50 (t, 2H), 3.43 (t, 2H), 4.63 (m, 1H), 4.63 (s, 2H), 7.24 (d, 2H), 7.38 (d, 1H), 7.55 (d, 2H), 8.13 (d, 1H), 8.73 (t, 1H), 8.93 (s, 1H), 9.05 (s, 1H).

MS (APCl, pos.): 565.1.

EXAMPLE 613

3-(4-{[(trans-4-tert-Butylcyclohexyl)-(3-methylsulfonylbenzyl)amino]methyl}benzoylamino)propionic acid

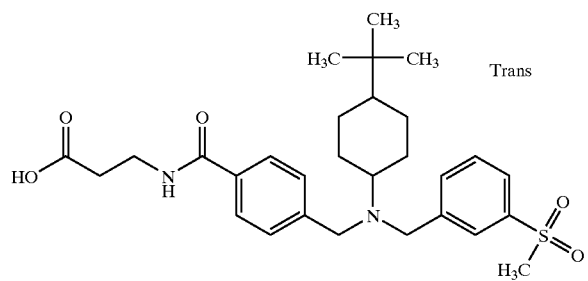

Reaction scheme

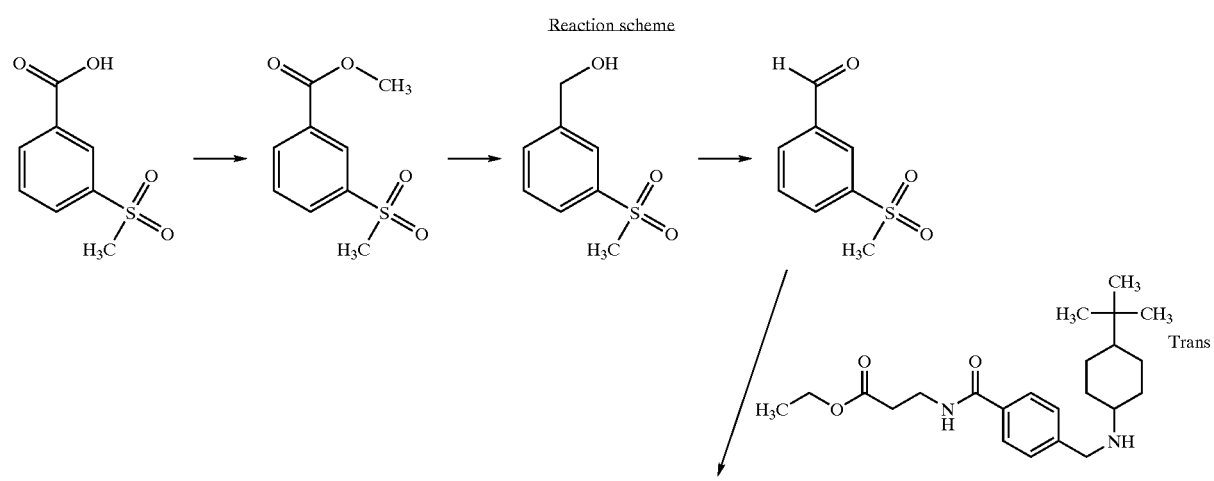

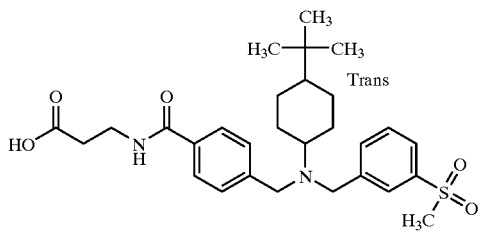

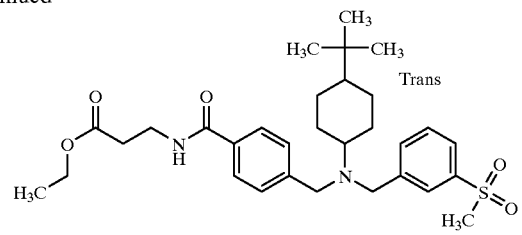

-continued

To a solution of 3-methylsulfonylbenzoic acid (10 g, 50 mmol) in anhydrous methanol (100 mL) was added conc. sulfuric acid (10 mL). The mixture was refluxed for 4 hours and then concentrated to one-third volume. Water (200 mL) was added, and the mixture was extracted with diethyl ether. The organic extract was washed with 10% sodium carbonate solution, and dried over $Na_2SO_4$. After concentration, 8.6 g (81%) of methyl 3-methylsulfonylbenzoate was obtained.

$^1$H NMR ($CDCl_3$) δ: 3.11 (s, 3H), 4.02 (s, 3H), 7.68 (t, 1H), 8.13 (d, 1H), 8.32 (d, 1H), 6.00 (s, 1H).

To a solution of methyl 3-methylsulfonylbenzoate (4.4 g, 20.3 mmol) in anhydrous THF (100 mL) was added lithium aluminum hydride (7 mL, 1.0 M solution in THF) via syringe at 0° C.

After stirring for 2 hours at room temperature, the mixture was diluted with water, and extracted with diethyl ether. The combined organic extracts were dried ($MgSO_4$), and concentrated to give 3-methylsulfonyl benzyl alcohol (3.5 g, 93%).

$^1$H NMR ($CDCl_3$) δ: 3.02 (s, 3H), 4.68 (s, 2H), 7.47 (t, 1H), 7.57 (d, 1H), 7.75 (d, 1H), 78.9 (s, 1H).

To a solution of 3-methylsulfonyl benzyl alcohol (3.5 g, 28.6 mmol) in dichloromethane (50 mL) was added pyridinium chloro chromate (PCC) (9.1 g, 42.2 mmol). The mixture was stirred at room temperature for 3 hours. After workup and column chromatography on silica gel eluting with hexane:ethyl acetate, 1:1, 3-methylsulfonylbenzaldehyde was obtained as white solid.

$^1$H NMR ($CDCl_3$) δ: 3.09 (s, 3H), 7.75 (t, 1H), 8.10–8.21 (2d, 2H), 8.40 (s, 1H), 10.11 (s, 1H).

To a solution of 3-methylsulfonylbenzaldehyde (0.93 g, 5.1 mmol) and ethyl 3-({[4-(tert-butyl)cyclohexyl] amino}methyl)benzoyl]amino}propanoate (1.9 g, 5.1 mmol) in dry DMF (50 mL) was added sodium triacetoxy borohydride (1.6 g, 7.5 mmol) and a catalytic amount of trifluoroacetic acid. The mixture was diluted with water and extracted with ethyl acetate. The combined organic extracts were dried ($MgSO_4$), and concentrated. The residue was dissolved in methanol, and saponified by 2M LiOH aqueous solution. After the reaction was complete, the mixture was acidified by 2M HCl, diluted with water, and extracted with ethyl acetate. The combined organic extracts were dried ($MgSO_4$), and concentrated. The residue was purified by HPLC to give the title compound.

$^1$H NMR ($CDCl_3$) δ: 0.78 (s, 9H), 0.81–0.96 (br, 3H), 1.18–1.39 (br, 2H), 1.71–1.98 (m, 4H), 2.40 (t, 1H), 2.56 (br, 2H), 3.53 (m, 6H), 7.25–7.86 (m, 8H).

LC-MS (APCl, pos.): 529(M+1).

EXAMPLE 614

3-{4-[3-(3,5-Bis(trifluoromethyl)phenyl)-1-spiro[5.5]undec-3-ylureidomethyl]benzoylamino}propionic acid

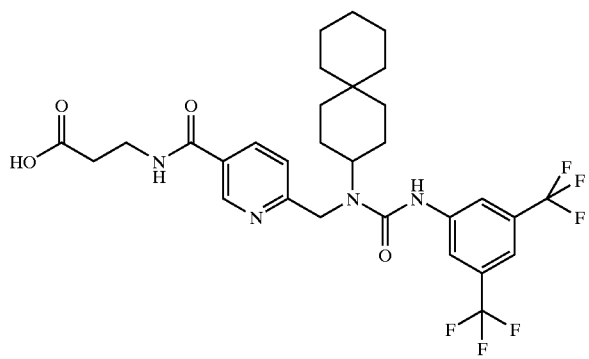

The title compound was made similarly as described in example 89.

$^1$H NMR (DMSO): δ 12.20 (s br, 1H); 9.05 (s, 1H); 8.48 (t, 1H); 8.22 (s, 2H); 7.72 (d, 2H); 7.55 (s, 1H); 7.32 (d, 2H); 4.65 (s, 2H); 4.08 (t br, 1H); 3.48 (q, 2H); 1.70–1.05 (m, 18H).

HPLC-MS (Method B): m/z=628 (M+1). $R_t$=8.30 min.

Spiro[5.5]undecan-3-one was Prepared as Described by Rice et al, *J. Org. Chem.*, 26, 2637–2640, (1964).

EXAMPLE 615

4-[1-(4-tert-Butylphenyl)-3-(6-trifluoromethoxy-benzothiazol-2-yl)ureidomethyl]-N-(2H-tetra-5-yl)benzamide

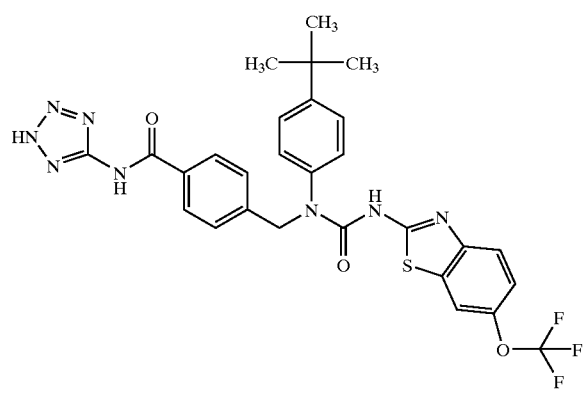

The title compound was made similarly as described in example 341.

$^1$H NMR (DMSO-d$_6$): δ 1.30 (9H, s), 5.14 (2H, s), 7.20–7.42, (7H, m), 7.48 (2H, d), 7.98 (1H, s), 8.08 (2H, d), 12.40 (1H, s).

EXAMPLE 616

4-[1-(4-Cyclohexylphenyl)-3-(6-methylsulfonylbenzothiazol-2-yl)ureidomethyl]-N-(2H-tetrazol-5-yl)benzamide

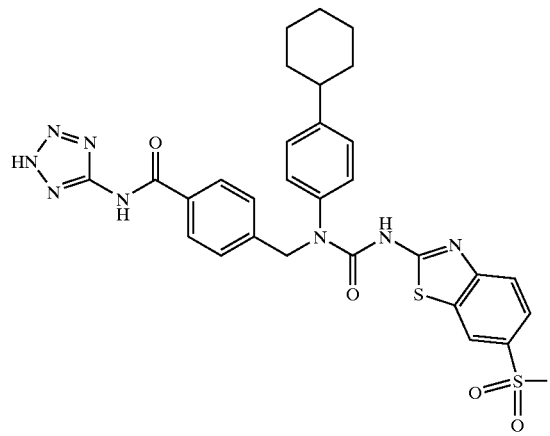

The title compound was made similarly as described in example 341.

HPLC-MS (Method C): R$_t$=5.07 min, m/z=631 (M+1).

EXAMPLE 617

4-[1-(4-Cyclohexylphenyl)-3-(6,7-(tetrafluoroethylenedioxy)benzothiazol-2-yl)ureidomethyl]-N-(2H-tetrazol-5-yl)benzamide

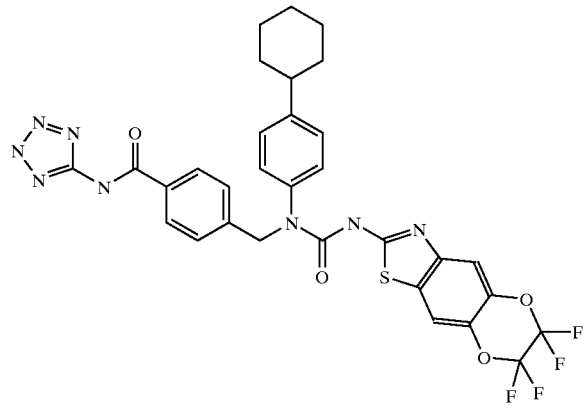

6,7-(Tetrafluoroethylenedioxy)benzothiazol-2-ylamine was Prepared from 6-amino-2,2,3,3-tetrafluoro-1,4-benzodioxene using the General Procedure Described in Stuckwisch C. G. *J. Am. Chem. Soc.* 1949 71, 3417:

To a suspension of 6-amino-2,2,3,3-tetrafluoro-1,4-benzodioxene (2 g, 9 mmol) and sodium thiocyanate (3.5 g, 43 mmol) in acetic acid (16 mL) was added dropwise, with stirring, bromine (1.4 g, 9 mmol) dissolved in acetic acid (7 mL) while the temperature was kept below 35° C. After all the bromine had been added the mixture was stirred for 16 hours and then filtered and the residue washed with water. The combined filtrate and the washings were neutralized with concentrated aqueous ammonia. The precipitate was collected on a filter, dried and recrystallized from toluene/hexane to yield 6,7-(tetrafluoroethylenedioxy)benzothiazol-2-ylamine.

The above 6,7-(tetrafluoroethylenedioxy)benzothiazol-2-ylamine was converted to the title compound using a similar method as described above.

$^1$H NMR (CDCl$_3$): δ 5.5 (2H, br s), 7.30 (1H, s), 7.37, (1H, s).

HPLC-MS (Method B): R$_t$=8.72 min, m/z=683 (M+1).

EXAMPLE 618

3-(4-{[(3-Fluoro-5-trifluoromethylbenzoyl)spiro[5.5]undec-3-yl-amino]methyl}benzoylamino)propionic acid

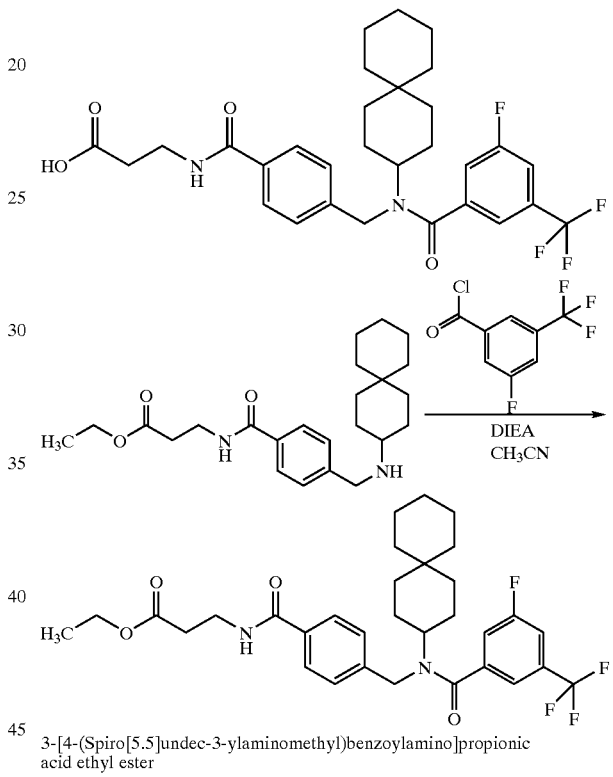

3-[4-(Spiro[5.5]undec-3-ylaminomethyl)benzoylamino]propionic acid ethyl ester

3-[4-(Spiro[5.5]undec-3-ylaminomethyl)benzoylamino] propionic acid ethyl ester was prepared by reductive alkylation of 3-(4-aminomethyl-benzoylamino)propionic acid ethyl ester with spiro[5.5]undecan-3-one. 3-[4-(Spiro[5.5]undec-3-ylaminomethyl)benzoylamino]propionic acid ethyl ester (200 mg, 499 μmol) was dissolved in acetonitrile (5 mL) and diisopropylethylamine (170 μL) and cooled on an ice bath. Commercially available 3-fluoro-5-(trifluoromethyl)benzoylchloride (136 mg, 602 μmol) dissolved in acetonitrile (5 mL) was added dropwise. The reaction was complete within one hour as shown by HPLC. The solvent was evaporated and water (10 mL) was added to the residue followed by saturated sodium bicarbonate (10 mL). The product was extracted using ethyl acetate (2×50 mL). The combined ethyl acetate extracts were washed with water (20 mL) and brine (20 mL). Drying the organic phases over MgSO$_4$ and evaporation of the solvent afforded 3-(4-{[(3-fluoro-5-trifluoromethylbenzoyl)spiro[5.5]undec-3-yl-amino]methyl}benzoylamino)propionic acid ethyl ester (295 mg) which was hydrolyzed using sodium hydroxide to afford the title compound.

¹H NMR (DMSO): δ 8.45 (t,1H); 7.75–7.15 (m, 7H); 4.70+4.50 (s+s, 2H); 2.30 (t, 2H); 1.70–0.70 (m, 18–20H).

HPLC-MS (Method D): m/z=563 (M+1). R$_t$=3.46 min.

EXAMPLE 619

3-(4-{[(Benzo[b]thiophene-2-carbonyl)spiro[5.5]undec-3-yl-amino]methyl}benzoylamino)propionic acid

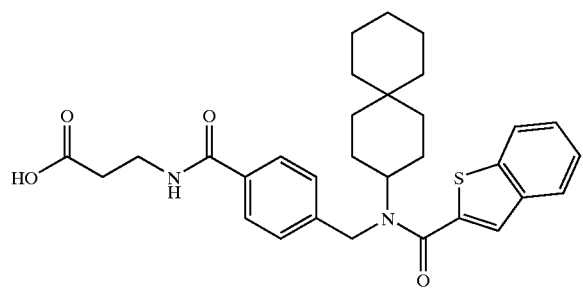

Prepared similarly as described in example 619.

¹H NMR (DMSO): δ 12.30 (s br, 1H); 8.51 (t, 1H); 8.05–7.55 (m, 5H); 7.50 (m 4H); 4.70 (s, 2H); 3.30 (s br, 2H); 1.80–0.90 (m, 18H).

HPLC-MS (Method D): m/z=533 (M+1). R$_t$=3.51 min.

The Benzo[b]thiophene-2-carbonyl chloride was prepared by adding toluene (2 mL), DMF (2 drops) and thionyl chloride (50 μL) to benzo[b]thiophene-2-carboxylic acid. Heating the mixture to reflux for 5 hours followed by removal of the solvent afforded the crude product, which was used without further purification.

EXAMPLE 620

4-[3-(3-Methylsulfonylphenyl)-1-spiro[5.5]undec-3-ylureidomethyl]-N-(2H-tetrazol-5-yl)benzamide

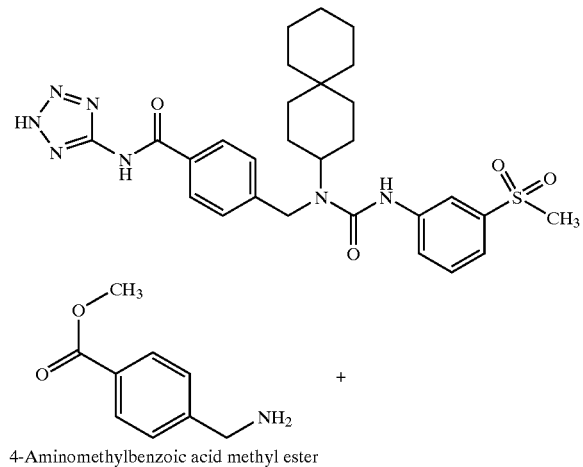

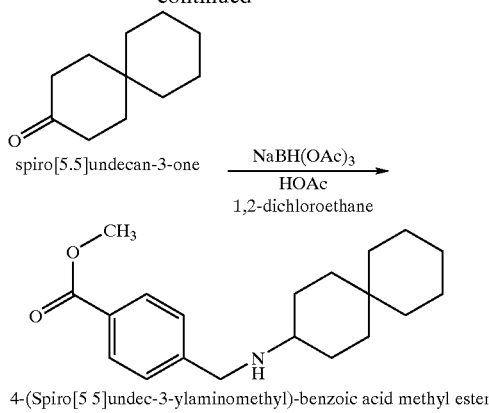

spiro[5.5]undecan-3-one 4-(Spiro[5 5]undec-3-ylaminomethyl)-benzoic acid methyl ester 4-Aminomethylbenzoic acid methyl ester hydrochloride (1.45 g, 7.2 mmol) was suspended in 1,2-dichloroethane (50 mL) and added saturated aqueous potassium carbonate. The phases were separated and the aqueous layer was extracted with another portion of 1,2-dichloroethane (50 mL). The combined organic phases were added glacial acetic acid (435 μL, 7.6 mmol) followed by spiro[5.5]undecan-3-one (1.2 g, 7.2 mmol). The suspension was stirred for 30 min at 25° C. and sodium triacetoxyborohydride (2.27 g, 10.7 μmol) was added. After stirring for 2 days at 25° C., water (100 mL) and saturated aqueous potassium carbonate (15 mL) were added. The phases were separated and the aqueous layer was extracted with 1,2-dichloroethane (2×100 mL). The combined organic phases were washed with water (100 mL) and brine (100 mL), dried over MgSO$_4$ and evaporated to afford 4-(spiro[5.5]undec-3-ylaminomethyl)benzoic acid methyl ester which was used in the subsequent steps without further purification.

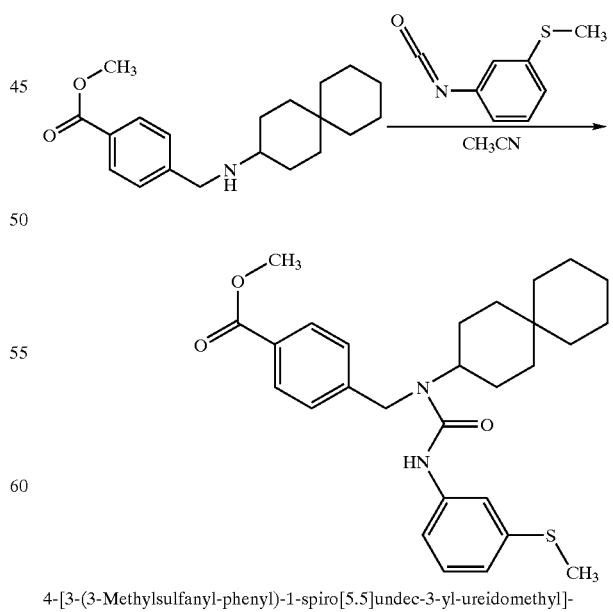

4-[3-(3-Methylsulfanyl-phenyl)-1-spiro[5.5]undec-3-yl-ureidomethyl]-benzoic acid methyl ester The above 4-(spiro[5.5]undec-3-ylaminomethyl)benzoic acid methyl ester (1.02 g, 3.2 mmol) was added acetonitrile (50 mL) and 3-(methylthio)phenylisocyanate (668 mg, 4 mmol). Upon stirring for 2 days, the reaction appeared incomplete as shown by HPLC, so another portion of 3-(methylthio)phenylisocyanate (240 mg) was added. After stirring for 2 hours the solvent was evaporated. The residue was taken up in dichloromethane (2 mL) and purified by chromatography on silica using dichloromethane as eluent affording 4-[3-(3-methylsulfanylphenyl)-1-spiro[5.5]undec-3-yl-ureidomethyl]benzoic acid methyl ester (680 mg).

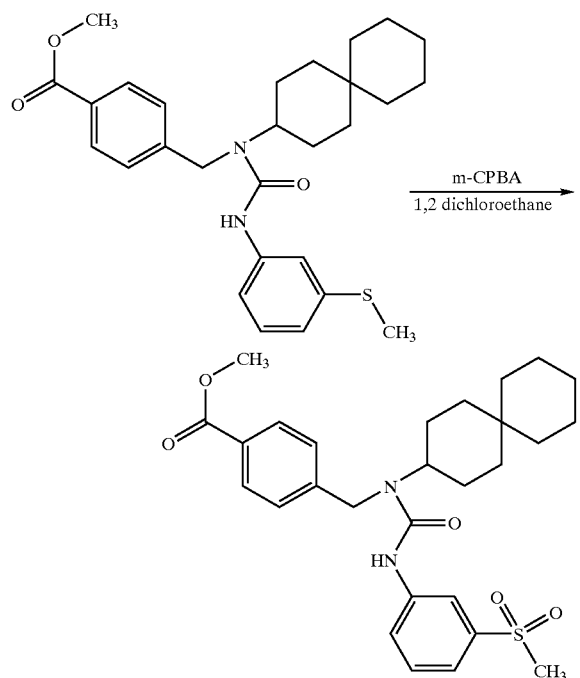

The above 4-[3-(3-methylsulfanylphenyl)-1-spiro[5.5] undec-3-yl-ureidomethyl]benzoic acid methyl ester (550 mg, 1.14 mmol) was dissolved in 1,2-dichloroethane (10 mL) and added m-chloroperbenzoic acid (611 mg). The reaction was monitored by HPLC. Upon completion, dichloromethane (20 mL) was added to dissolve any precipitate formed during the reaction. Water (20 mL) was added and the phases were separated. The aqueous phase was extracted with dichloromethane (20 mL) and the combined organic phases were washed with saturated aqueous potassium carbonate (20 mL), water (20 mL) and brine (20 mL), dried over MgSO$_4$ and evaporated. The residue was purified on silica (150 g) using a mixture of heptane and ethyl acetate (1:1) as eluent affording 4-[3-(3-methylsulfonylphenyl)-1-spiro[5.5]undec-3-yl-ureidomethyl]benzoic acid methyl ester (362 mg).

4-[3-(3-Methylsulfonylphenyl)-1-spiro[5.5]undec-3-yl-ureidomethyl]benzoic acid methyl ester was hydrolyzed to the corresponding carboxylic acid using 3 equiv. NaOH(aq) (4M) in dioxane.

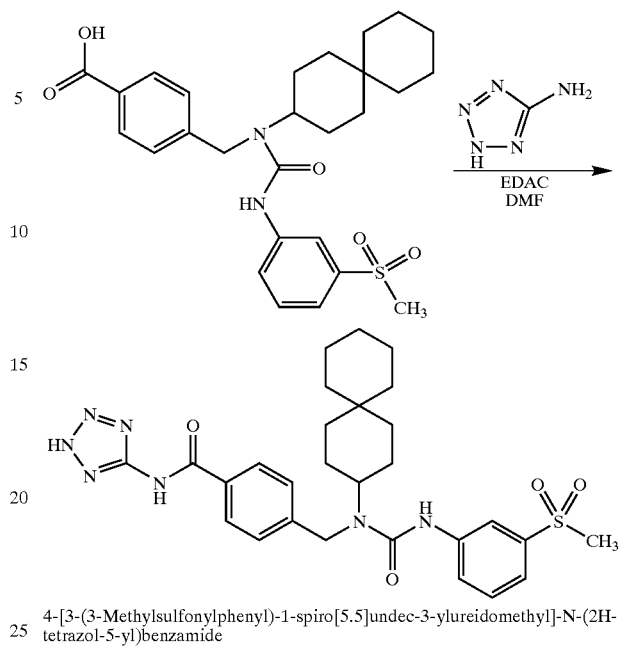

4-[3-(3-Methylsulfonylphenyl)-1-spiro[5.5]undec-3-ylureidomethyl]-N-(2H-tetrazol-5-yl)benzamide 4-[3-(3-Methylsulfonylphenyl)-1-spiro[5.5]undec-3-yl-ureidomethyl]benzoic acid (32.2 mg, 64.6 μmol) was dissolved in DMF (1 mL) and added N'-(3-dimethylaminopropyl)-N-ethylcarbodiimide hydrochloride (EDAC) (16.5 mg, 86 μmol) and 5-aminotetrazole.H$_2$O (16,5 mg, 160 μmol). The mixture was stirred at 25° C. for 1 day and concentrated in vacuo. Brine (5 mL) was added to the residue followed by a mixture of ethanol and chloroform (1:2, 10 mL). The phases were separated and the aqueous layer was extracted with a mixture of ethanol and chloroform (1:2, 2×10 mL). The combined organic extracts were dried over MgSO$_4$ and evaporated. The residue was purified by preparative HPLC affording the title compound.

$^1$H NMR (DMSO): δ 12.30 (s br, 1H); 8.80 (s, 1H); 8.11–8.02 (m, 3H); 7.85 (dt, 1H); 7.5–7.40 (m, 4H); 4.70 (s, 2H); 4.10 (m br 1H); 3.18 (s, 3H); 1.68–1.10 (m, 18H).

HPLC-MS (Method D): m/z=566 (M+1). R$_t$=3.03 min.

EXAMPLE 621

3-(4-{[(4-Cyclohexylphenyl)-(4-(methylsulfonyl) phenoxycarbonyl)amino]methyl}benzoylamino) propionic acid

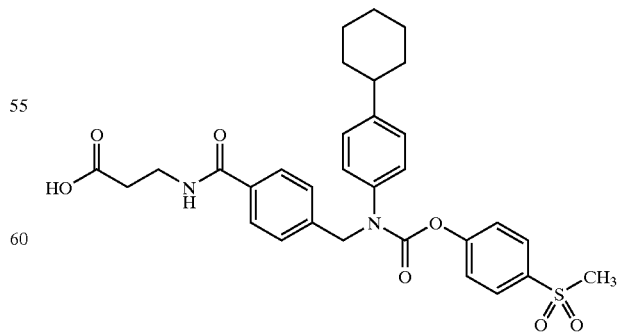

3-(4-{[(4-Cyclohexylphenyl)-(4-(methylsulfonyl) phenoxycarbonyl)amino]methyl}benzoylamino)propionic acid (0.05 mmol) assembled on 2-chlorotrityl resin (50 mg) as described in general procedure (Q) was treated overnight with 3-chloroperbenzoic acid (34.5 mg, 0.200 mmol) in NMP (0.50 mL). The solvent was drained off, and the resin washed with DMF (3×) followed by dichloromethane (10×). The product was cleaved from the support using 5% TFA in dichloromethane as described in general procedure (Q), and the pure product obtained as crystals after removal of solvent using speed vacuum. Yield: 5.0 mg.

HPLC-MS (method B): m/z=579, $R_t$=6.55 min.

EXAMPLE 622

4-Cyclohexylphenyl)-[4-(2H-tetrazol-5-ylcarbamoyl)benzyl]carbamic acid 4-(methylsulfonyl)phenyl ester

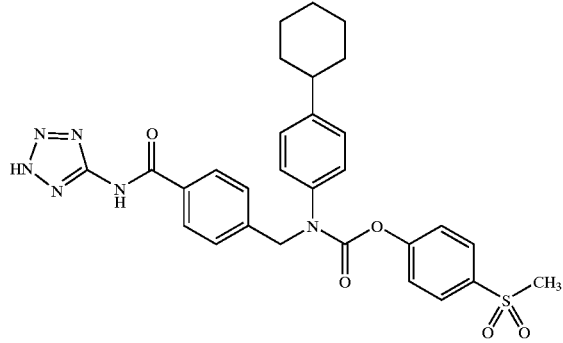

Prepared as described above in example 621. Yield: 15 mg.

HPLC-MS (method B): m/z=575, $R_t$=6.88 min.

EXAMPLE 623

4-tert-Butylcyclohexyl)-[4-(2H-tetrazol-5-ylcarbamoyl)benzyl]carbamic acid 4-(methylsulfonyl)phenyl ester

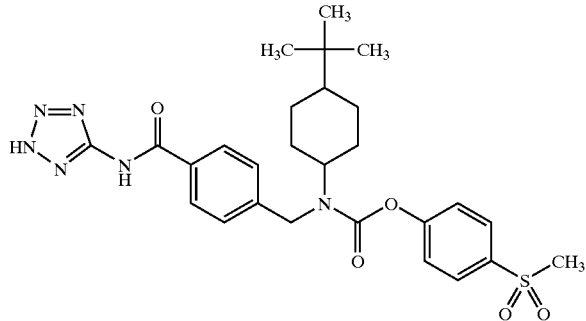

Prepared as described above in example 621. Yield: 15 mg.

HPLC-MS (method B): m/z=555, $R_t$=7.07 min.

EXAMPLE 624

4-tert-Butylphenyl)-[4-(2H-tetrazol-5-ylcarbamoyl)benzyl]carbamic acid 4-(methylsulfonyl)phenyl ester

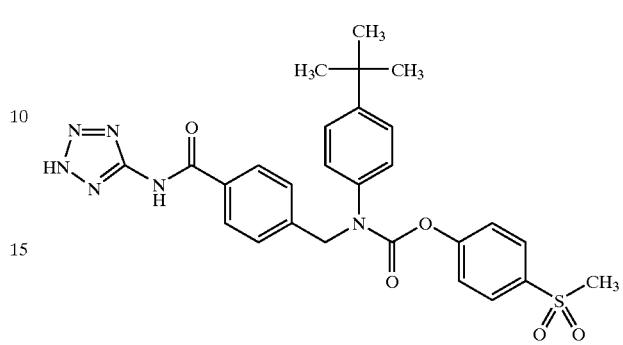

Prepared as described above in example 621. Yield: 15 mg.

HPLC-MS (method B): m/z=549, $R_t$=6.35 min.

Preparation of starting materials for phthalimide compounds of the invention:

N-Isopropylphthalimide-4-isocyanate

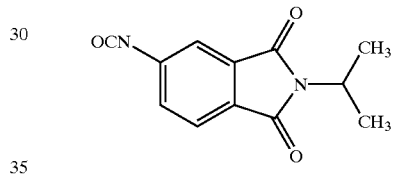

Step 1: 4-Nitroisophthalimide (25.0 g, 130.0 mmol) was dissolved in DMF (250 mL). Isopropyl bromide (61.0 mL, 650 mmol) and potassium carbonate (36.0 g, 260 mmol) were added and the mixture was heated to 60° C. overnight. Water (1.0 L) was added, and the precipitate formed was collected by filtration, washed twice with water and dried overnight in a vacuum oven to afford 21.3 g (70%) of pure N-isopropyl-4-nitrophthalimide.

$^1$H NMR (DMSO-d$_6$): δ 1.42 ppm (d, 6H); 4.44 (m, 1H); 8.07 (d, 1H); 8.45 (s, 1H); 8.61 (d, 1H).

Step 2: N-Isopropyl-4-nitrophthalimide (10.0 g, 43.0 mmol) was dissolved in a mixture of THF (200 mL) and DMF (100 mL). 10% Palladium catalyst on carbon (1,0 g, 50% wet weight) was added and the mixture was hydrogenated in a low-pressure apparatus (1 atm.) overnight. The catalyst was then removed by filtering the mixture through a short pad of celite. The filtrate was evaporated to dryness to afford a quantitative yield (8.70 g) of pure N-isopropyl-4-aminophthalimide.

$^1$H NMR (CDCl$_3$): δ 1.46 ppm (d, 6H); 4.47 (m, 1H); 6.82 (dd, 1H); 7.00 (d, 1H); 7.55 (d, 1H).

Step 3: N-Isopropyl-4-aminophthalimide (9.50 g, 47 mmol) was dissolved in THF (200 mL). While stirring, a solution of HCl in ethyl acetate (90 mL, 3.5 M, 315 mmol) was slowly added to form the anilinium hydrochloride. Solvent was removed, and the precipitate was re-suspended and evaporated twice from THF. The solid residue was then suspended in toluene (250 mL), and trichloromethyl chloroformate (60 mL, 500 mmol) was added. The suspension was heated to reflux and after 2 hours, a clear solution was obtained. Reflux was continued overnight. The solution was allowed to cool to room temperature before the solvent was removed by evaporation. The crystalline residue was stripped with toluene (2×200 mL) and acetonitrile (2×200 mL), and the obtained N-isopropylphthalimide-4-isocyanate was used for subsequent reactions without further purification. Yield: 10.7 g (99%).

$^1$H NMR (CDCl$_3$): δ 1.49 ppm (d, 6H); 4.50 (m, 1H); 7.37 (d, 1H); 7.51 (s, 1H); 7.76 (d, 1H).

N-Butylphthalimide-4-isocyanate

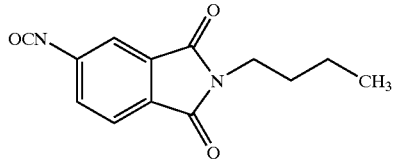

This material was prepared similarly as described for N-isopropylphthalimide-4-isocyanate.

N-(Cyclopropylmethyl)phthalimide-4-isocyanate

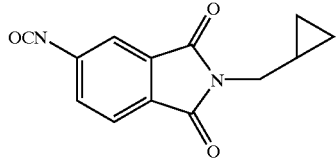

Step 1: 4-Nitrophthalimide (6.15 g, 32.0 mmol) was dissolved in DMF (60 mL). Cyclopropylmethyl bromide (9.3 mL, 96 mmol) and potassium carbonate (8.85 g, 64.0 mmol) were added and the mixture was heated to 100° C. for 4 hours. The mixture was allowed to cool to room temperature, and then partitioned between water (500 mL) and ethyl acetate (400 mL). The organic phase was collected, dried with Na$_2$SO$_4$, filtered and taken to dryness using rotary evaporation. The residue was dried overnight in a vacuum oven to afford 6.49 g (82%) of pure N-cyclopropylmethyl-4-nitrophthalimide as a powder.

$^1$H NMR (DMSO-d$_6$): δ 0.36 ppm (d, 2H); 0.50 (d, 2H); 1.12 (m, 1H); 3.51 (d, 2H); 8.13 (d, 1H); 8.50 (s, 1H); 8.62 (d, 1H).

Step 2: N-Cyclopropylmethyl-4-nitrophthalimide (6.0 g, 24 mmol) in methanol (200 mL) was added dropwise over 30 min to a solution of sodium dithionite (27.0 g, 156 mmol) and sodium carbonate (13.0 g, 125 mmol) in water (200 mL) while the temperature was maintained at 70° C. The mixture was stirred at 70° C. for an additional 50 min before it was allowed to cool to room temperature. The reaction volume was then reduced to one-third by rotary evaporation. Water (400 mL) was added, and the suspension extracted with ethyl acetate (2×450 mL). The combined organic solutions were dried with anhydrous MgSO$_4$. Solvent was then removed by rotary evaporation to afford 2.52 g (49%) of pure N-cyclopropylmethyl-4-aminophthalimide as a powder.

$^1$H NMR (DMSO-d$_6$): 0.25 ppm (d, 2H); 0.44 (d, 2H); 1.05 (m, 1H); 3.35 (d, 2H); 6.476 (s, 2H); 6.78 (d, 1H); 6.92 (s, 1H); 7.46 (d,1H).

HPLC-MS (method B): m/z=217, R$_t$=4.65 min.

Step 3: N-Cyclopropylmethyl-4-aminophthalimide (2.5 g, 11.6 mmol) was suspended in toluene (30 mL) and bis (trichloromethyl) carbonate (2.28 g, 7.71 mmol) was added. The mixture was heated to reflux under an inert atmosphere for 2 hours. The reaction mixture was cooled on an ice bath before filtering. The filtrate was then taken to dryness, and the oily residue suspended in petroleum ether (40 mL). The pure title material was obtained as a precipitate, which was collected by filtration and washed twice with cold petroleum ether to afford 1.50 g (54%) of N-(cyclopropylmethyl) phthalimide-4-isocyanate.

$^1$H NMR (CDCl$_3$): δ 0.37 ppm (m, 2H); 0.50 (m, 2H); 1.19 (m, 1H); 3.54 (d, 2H); 7.89 (d, 1H); 7.54 (s, 1H); 7.81 (d, 1H).

N-Cyclopropylphthalimide-4-isocyanate

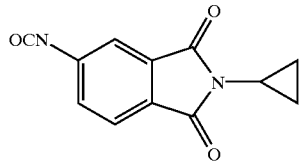

Step 1: 4-Nitrophthalic anhydride (5.60 g, 28.9 mmol) was dissolved in THF (50 mL), and cyclopropylamine (2.10 mL, 30 mmol) was added slowly while stirring under an inert atmosphere. After 30 min, a suspension was obtained. Triethylamine (8.2 mL, 60 mmol) and diisopropylcarbodiimide (5.50 mL, 35 mmol) were added followed by DMF (100 mL). The reaction mixture was then heated to 70° C. for 48 hours. The mixture was cooled to room temperature and the reaction volume was reduced to one-tenth of the original volume by rotary evaporation in vacuo. The precipitated N,N'-diisopropylurea was removed by filtration, and water (40 mL) was added to the mother liquor resulting in formation of a precipitate. The precipitate was collected by filtration and dried overnight in a vacuum oven to give 6.02 g (90%) of N-cyclopropyl-4-nitrophthalimide.

$^1$H NMR (DMSO-d$_6$): δ 0.92 ppm (m, 4H); 2.71 (s, 1H); 8.07 (d, 1H); 8.44 (d, 1H); 8.58 (dd, 1H).

HPLC-MS (method B): m/z=233, R$_t$=4.67 min.

Step 2: N-Cyclopropyl-4-nitrophthalimide (10.0 g, 43.0 mmol) was dissolved in ethanol (200 mL). Tin (II) chloride dihydrate (49.0 g, 215 mmol) was added, and the mixture was heated to reflux overnight. After cooling, the mixture was poured over crushed ice (1.0 L), and pH adjusted to 6.5 using 1 N NaOH. The mixture was passed through a small bed of celite, and the filtrate was subsequently extracted with ethyl acetate (1.2 L). The organic phase was dried using anhydrous MgSO$_4$, and solvent was removed by rotary evaporation in vacuo, to afford crystalline N-cyclopropyl-4-aminophthalimide. Yield: 6.0 g (69%).

$^1$H NMR (DMSO-d$_6$): δ 0.85 ppm (m, 4H); 2.55 (m, 1H); 6.41 (bs, 2H); 6.77 (d, 1H); 6.86 (d, 1H); 7.44 (dd, 1H).

Step 3: N-Cyclopropyl-4-aminophthalimide (3.00 g, 15.0 mmol) was dissolved in THF (50 mL). A 3.5 N HCl ethyl acetate solution (26 mL, 90.0 mmol) was added resulting in immediate precipitation of the hydrochloride salt. Solvent was removed, and the crystalline residue suspended in toluene (50 mL). Trichloromethyl chloroformate (22.0 mL, 180 mmol) was added and the suspension was heated to reflux. After 2 hours a clear solution was obtained. The solution was heated to reflux overnight. After cooling, solvent was removed and the residue was stripped twice with acetonitrile to remove traces of hydrochloric acid. The crystalline residue (N-cyclopropylphthalimide-4-isocyanate) was sufficiently pure for further synthesis.

¹H NMR (CDCl₃): δ 1.10 ppm (m, 4H); 2.66 (m, 1H); 7.39 (d, 1H); 7.75 (d, 1H); 7.78 (dd, 1H).

EXAMPLE 625

4-[3-(N'-Butylphthalimid-4-yl)-1-(4-cyclohex-1-enylphenyl)ureidomethyl]-N-(2H-tetrazol-5-yl)benzamide

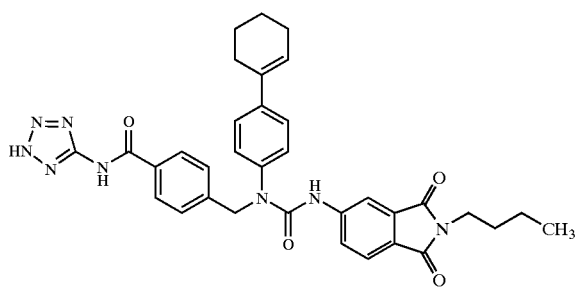

4-[(4-Cyclohex-1-enylphenylamino)methyl]-N-(2H-tetrazol-5-yl)benzamide (0.5 mmol) assembled on 2-chlorotrityl resin (500 mg) as described under general procedure (Q) was treated with a solution of N-butylphthalimide-4-isocyanate (1220 mg, 5.0 mmol) in NMP/1,2-dichloropropane (1:5, 10 mL) for 48 hours. Solvent was drained and the resin was washed with DMF (3×) and dichloromethane (10×). Standard cleavage with 10% TFA/dichloromethane and evaporation of solvent afforded a powder, which was further purified by recrystallization from acetonitrile to afford 227 mg (73%) of the title compound.

¹H NMR (DMSO-d₆): δ 0.89 ppm (t, 3H); 1.28 (q, 2H); 1.57 (m, 4H); 1.72 (m, 2H); 2.17 (m, 2H); 2.45 (m, 2H); 3.54 (t, 2H); 5.04 (s, 2H); 6.20 (t, 1H); 7.25 (d, 2H); 7.41 (d, 2H); 7.48 (d, 2H); 7.72 (d, 1H); 7.84 (dd, 1H); 8.01 (d, 1H); 8.03 (d, 2H), 8.92 (s, 1H); 12.35 (s, 1H).

HPLC-MS (method B): m/z=620, $R_t$=5.15 min.

EXAMPLE 626

3-{4-[3-(N'-Butylphthalimid-4-yl)-1-(4-tert-butylphenyl)ureidomethyl]benzoylamino}propionic acid

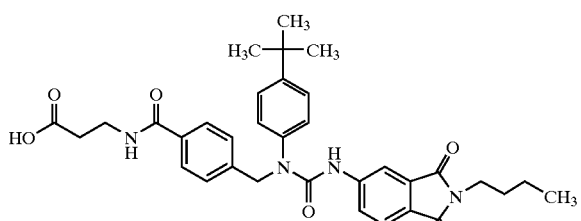

Prepared as described above using resin bound 3-{4-[(4-tert-butylphenylamino)methyl]benzoylamino}propionic acid. An oil was obtained after TFA cleavage and evaporation of solvent. The oil was taken up in ethanol (3 mL) and added dropwise to water (25 mL) while stirring. A fine white powder was obtained which was collected by filtration and dried overnight in a vacuum oven to afford 231 mg (77%) of the title compound.

¹H NMR (DMSO-d₆): 0.89 ppm (t, 3H); 1.26 (s, 9H); 1.28 (m, 2H); 1.54 (m, 2H); 2.48 (m, 2H); 3.42 (m, 2H); 3.53 (t, 2H); 7.20 (d, 2H); 7.35 (d, 2H); 7.39 (d, 2H); 7.71 (d, 1H), 7.76 (d, 2H); 7.80 (dd, 1H); 8.03 (d, 1H); 8.47 (t, 1H); 8.95 (s, 1H); 12.25 (bs, 1H).

HPLC-MS (method B): m/z=599, $R_t$=7.15 min.

The following examples 627 to 645 were prepared in a similar way:

EXAMPLE 627

4-[1-(4-Cyclohexylphenyl)-3-(N-isopropylphthalimid-4-yl)ureidomethyl]-N-(2H-tetrazol-5-yl)benzamide

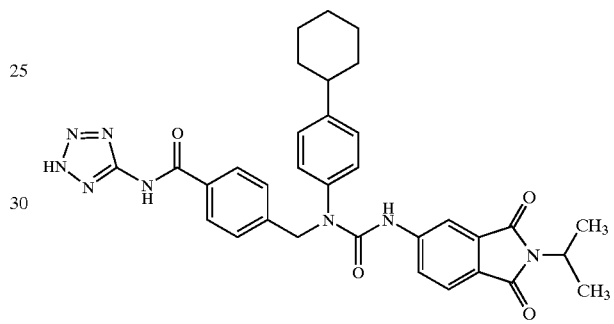

HPLC-MS (method B): m/z=607.0, $R_t$=7.62 min.

EXAMPLE 628

4-[1-(4-tert-Butyl-phenyl)-3-(N'-isopropylphthalimid-4-yl)ureidomethyl]-N-(2H-tetrazol-5-yl)benzamide

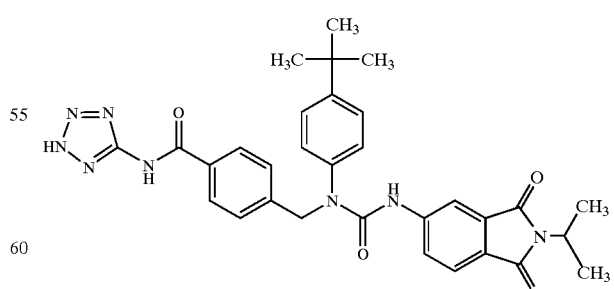

HPLC-MS (method B): m/z=581.0, $R_t$=7.62 min.

EXAMPLE 629

4-[1-(4-tert-Butylcyclohexyl)-3-(N'-isopropylphthalimid-5-yl)ureidomethyl]-N-(2H-tetrazol-5-yl)benzamide

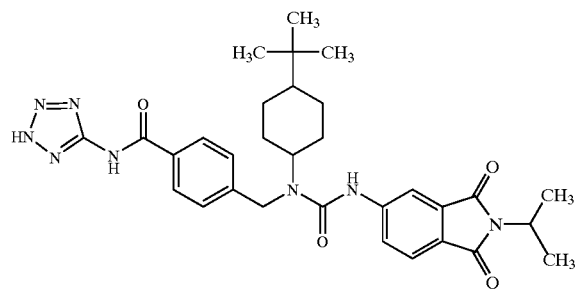

HPLC-MS (method B): m/z=531.0, $R_t$=7.52 min. (cis-isomer); $R_t$=7.62 min. (trans-isomer).

EXAMPLE 630

3-{4-[1-(4-tert-Butylphenyl)-3-(N'-isopropylphthalimid-4-yl)ureidomethyl]benzoylamino}propionic acid

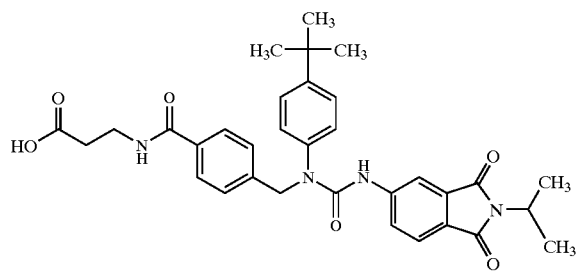

HPLC-MS (method B): m/z=585.0, $R_t$=6.83 min.

EXAMPLE 631

3-{4-[1-(4-Cyclohexyl-phenyl)-3-(N'-isopropylphthalimid-4-yl)ureidomethyl]benzoylamino}propionic acid

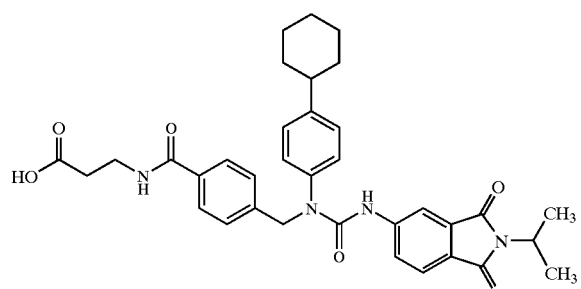

HPLC-MS (method B): m/z=611.0, $R_t$=7.42 min.

EXAMPLE 632

3-{4-[1-(4-tert-Butylcyclohexyl)-3-(N'-isopropylphthalimid-4-yl)ureidomethyl]benzoylamino}propionic acid

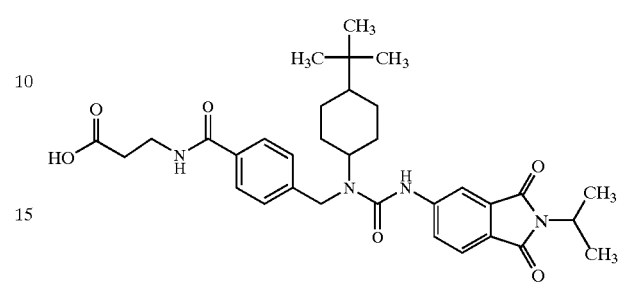

HPLC-MS (method B): m/z=591.0, $R_t$=7.35 min. (cis-isomer); $R_t$=7.45 min. (trans-isomer).

EXAMPLE 633

4-[1-(4-tert-Butylcyclohexyl)-3-(N'-butylphthalimid-4-yl)ureidomethyl]-N-(2H-tetrazol-5-yl)benzamide

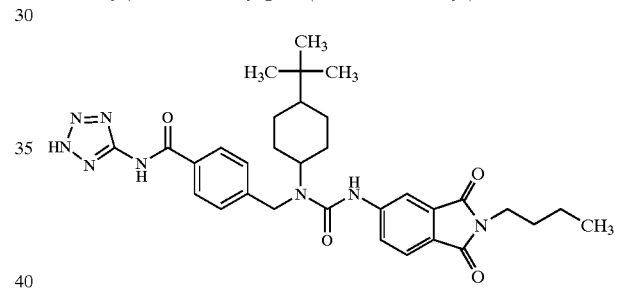

HPLC-MS (method B): m/z=601.0, $R_t$=7.68 min. (cis-isomer); $R_t$=7.83 min. (trans-isomer).

EXAMPLE 634

3-{4-[3-(N'-Butylphthalimid-4-yl)-1-(4-tert-butylphenyl)ureidomethyl]benzoylamino}propionic acid

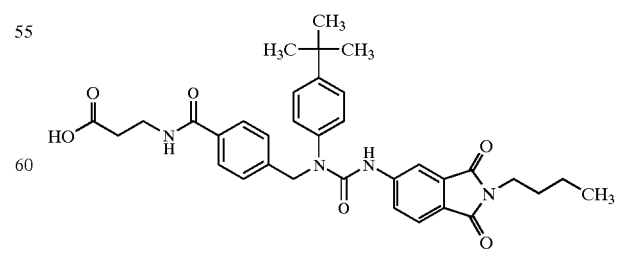

HPLC-MS (method B): m/z=599.0, $R_t$=7.15 min.

EXAMPLE 635

3-{4-[3-(N'-Butylphthalimid-4-yl)-1-(4-cyclohexylphenyl)ureidomethyl]benzoylamino}propionic acid

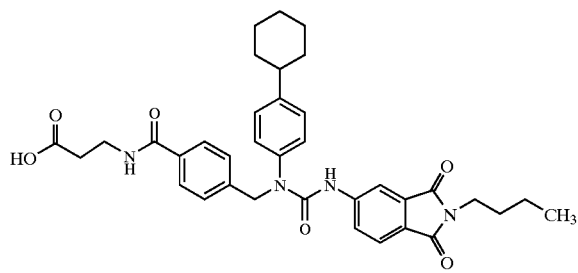

HPLC-MS (method B): m/z=625.0, $R_t$=7.68 min.

EXAMPLE 636

4-[3-(N'-Butylphthalimid-4-yl)-1-(4-cyclohexylphenyl)ureidomethyl]-N-(2H-tetrazol-5-yl)benzamide

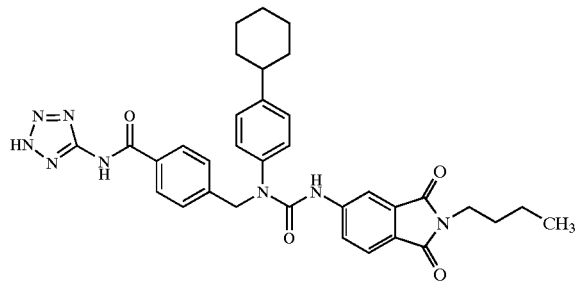

HPLC-MS (method B): m/z=621.0, $R_t$=7.92 min.

EXAMPLE 637

3-{4-[1-(4-tert-Butylcyclohexyl)-3-(N'-butylphthalimid-4-yl)ureidomethyl]benzoylamino}propionic acid

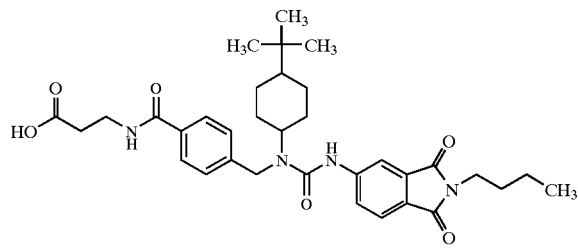

HPLC-MS (method B): m/z=605.0, $R_t$=7.58 min. (cis-isomer); $R_t$=7.68 min. (trans-isomer).

EXAMPLE 638

(4-tert-Butylcyclohexyl)-3-(N'-[cyclopropylmethyl]phthalimid-4-yl)ureidomethyl]-N-(2H-tetrazol-5-yl)benzamide

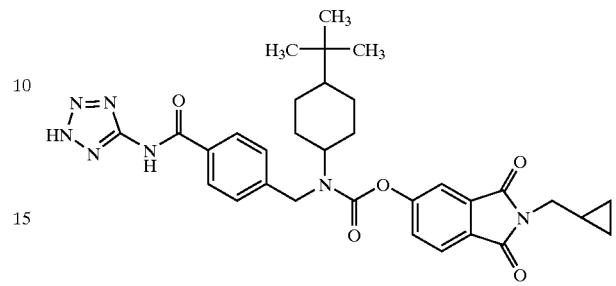

HPLC-MS (method B): m/z=599.0, $R_t$=7.52 min. (cis-isomer); $R_t$=7.72 min. (trans-isomer).

EXAMPLE 639

4-[1-(4-Cyclohexylphenyl)-3-(N'-[cyclopropylmethyl]phthalimid-4-yl)ureidomethyl]-N-(2H-tetrazol-5-yl)benzamide

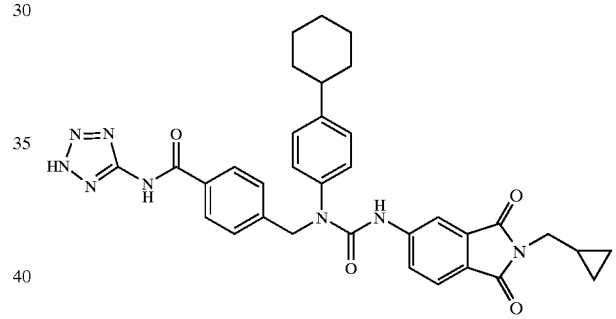

HPLC-MS (method B): m/z=619.0, $R_t$=7.73 min.

EXAMPLE 640

4-[1-(4-tert-Butylphenyl)-3-(N'-[cyclopropylmethyl]phthalimid-4-yl)ureidomethyl]-N-(2H-tetrazol-5-yl)benzamide

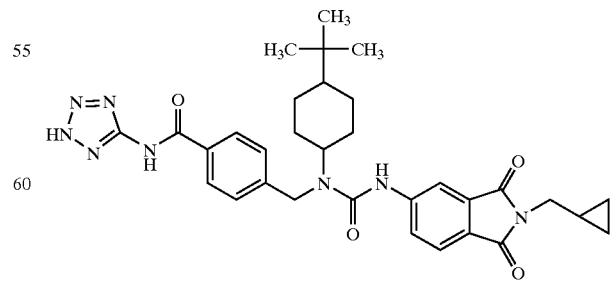

HPLC-MS (method B): m/z=593.0, $R_t$=7.20 min.

EXAMPLE 641

3-{4-[1-(4-tert-Butylcyclohexyl)-3-(N'-[cyclopropylmethyl]phthalimid-4-yl)ureidomethyl]benzoylamino}propionic acid

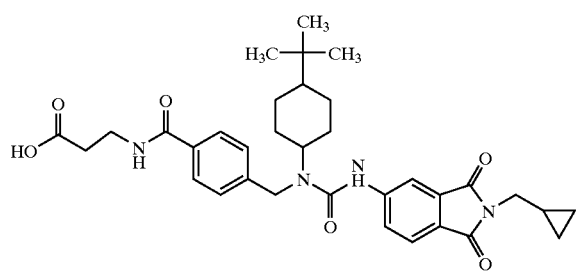

HPLC-MS (method B): m/z=603.0, R$_t$=7.38 min.

EXAMPLE 642

3-{4-[3-(N'-[Cyclopropylmethyl]phthalimid-4-yl)-1-(4-cyclohexylphenyl)ureidomethyl]benzoylamino}propionic acid

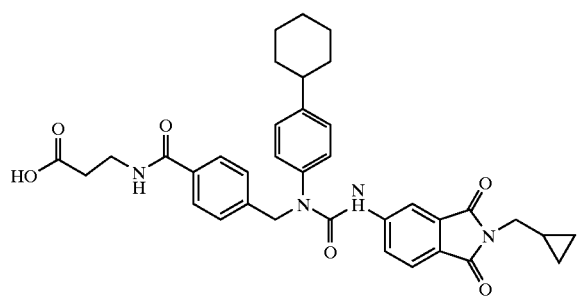

HPLC-MS (method B): m/z=623.0, R$_t$=7.45 min.

EXAMPLE 643

3-{4-[3-(N'-[Cyclopropylmethyl]phthalimid-4-yl)-1-(4-tert-butylphenyl)ureidomethyl]benzoylamino}propionic acid

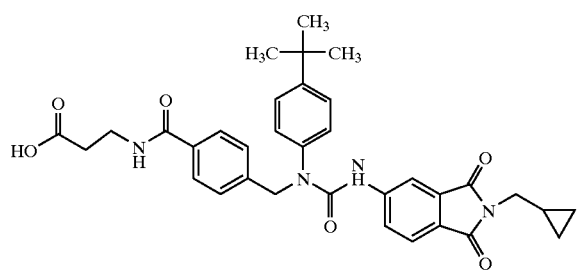

HPLC-MS (method B): m/z=597.0, R$_t$=6.89 min.

EXAMPLE 644

4-[3-(N'-[Cyclopropylmethyl]phthalimid-4-yl)-1-(4-cyclohex-1-enylphenyl)ureidomethyl]-N-(2H-tetrazol-5-yl)benzamide


HPLC-MS (method B): m/z=617.0, R$_t$=7.48 min.

EXAMPLE 645

3-{4-[1-(4-Cyclohex-1-enylphenyl)-3-(N'-[cyclopropylmethyl]phthalimid-4-yl)ureidomethyl]benzoylamino}propionic acid

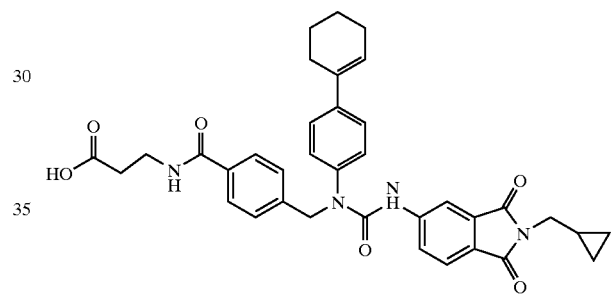

HPLC-MS (method B): m/z=621.0, R$_t$=7.32 min.

EXAMPLE 646

4-{1-[1-(4-tert-Butylphenyl)-3-(4-trifluoromethoxyphenyl)ureido]ethyl}-N-(2H-tetrazol-5-yl)benzamide

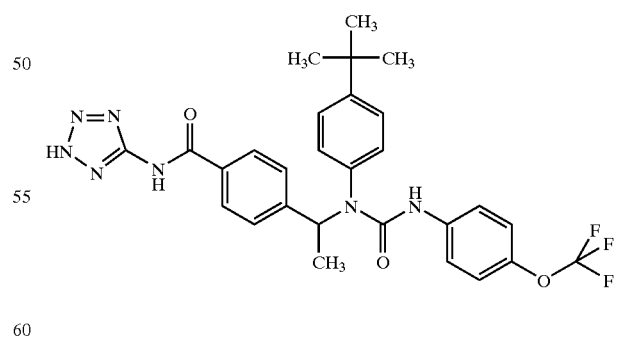

Step 1: 4-Acetylbenzoic acid (4.00 g, 24.4 mmol), 5-aminotetrazole monohydrate (3.00 g, 2.91 mmol) and ethyl dimethylaminopropyl carbodiimide hydrochloride (7.00 g, 3.55 mmol) were dissolved in DMF (25 mL) and stirred at ambient temperature for 48 hours. The reaction mixture was poured into ice-water, and the precipitate collected by filtration to afford 5.50 g (98%) of pure 4-acetyl-N-(2H-tetrazol-5-yl)benzamide after drying overnight in a vacuum oven.

$^1$H NMR (DMSO-$d_6$): δ 2.64 ppm (s, 3H); 8.12 (d, 2H), 8.20 (d, 2H). 12.60 (bs, 1H).

Step 2: 4-Acetyl-N-(2H-tetrazol-5-yl)benzamide (1.00 g, 4.32 mmol) and 4-tert-butylaniline were dissolved in THF (15 mL). Triethylamine (2.1 mL, 15.0 mmol) was added and the mixture was cooled to 0° C. on an ice bath. Neat titanium tetrachloride (0.25 mL, 2.25 mmol) was added dropwise using a syringe assuring that the temperature was maintained close to 0° C. The mixture was then stirred overnight at room temperature. A solution of sodium cyanoborohydride (0.88 g, 14 mmol) in methanol (10 mL) was slowly added, and the reaction mixture stirred for a further 60 min. The reaction mixture was then poured into ice water (100 mL) and pH adjusted to 2 using 1M aqueous hydrochloric acid. The crude product was collected by filtration and dried in a vacuum oven overnight. The crude product was taken up in DMF/ethyl acetate (1:1, 5 mL) and passed through a silica gel column using 5% acetic acid/ethyl acetate as eluent. Pure fractions were pooled and evaporated to dryness. The yield of 4-[1-(4-tert-butylphenylamino)ethyl]-N-(2H-tetrazol-5-yl)benzamide was 1.12 g (71%).

$^1$H NMR (DMSO-$d_6$): δ 1.15 ppm (s, 9H); 1.43 (d, 3H); 4.52 (q, 1H); 6.09 (bs, 1H); 6.41 (d, 2H); 7.00 (d, 2H); 7.56 (d, 2H); 8.04 (d, 2H); 12.30 (s, 1H).

Step 3: 4-[1-(4-tert-Butylphenylamino)ethyl]-N-(2H-tetrazol-5-yl)benzamide (100 mg, 0.28 mmol) and 4-trifluoromethoxyphenyl isocyanate (70 mg, 0.30 mmol) was dissolved in DMF (0.6 mL) and the solution was heated to 80° C. for 3 hours. The mixture was cooled to room temperature and subsequently taken to dryness using rotary evaporation. The residual oil was dissolved in a minimum of DMF/acetonitrile (1:1), and submitted to preparative HPLC purification. Pure fractions were pooled and concentrated to dryness to afford 10 mg (8%) of the title compound.

HPLC-MS (method B): m/z=568.0, $R_t$=5.31 min.

Furthermore, the following compounds according to the invention are preferred:

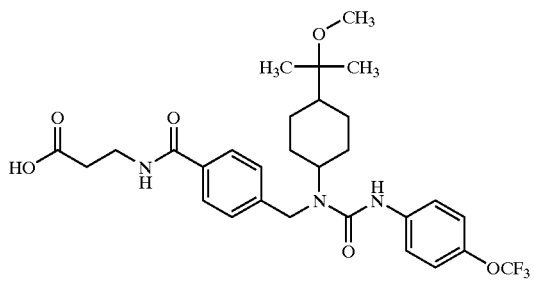

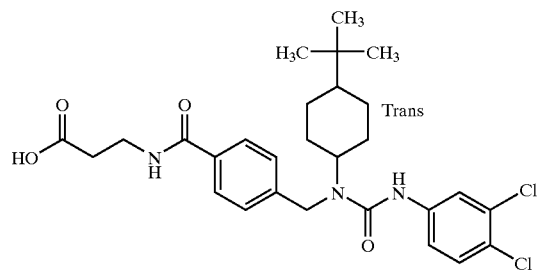

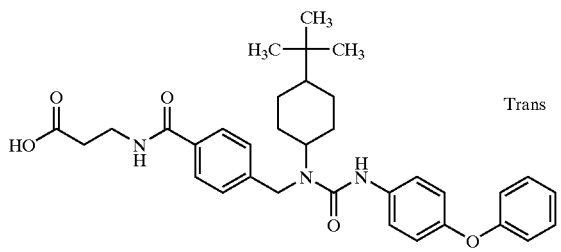

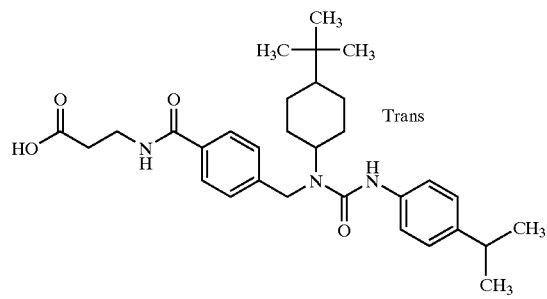

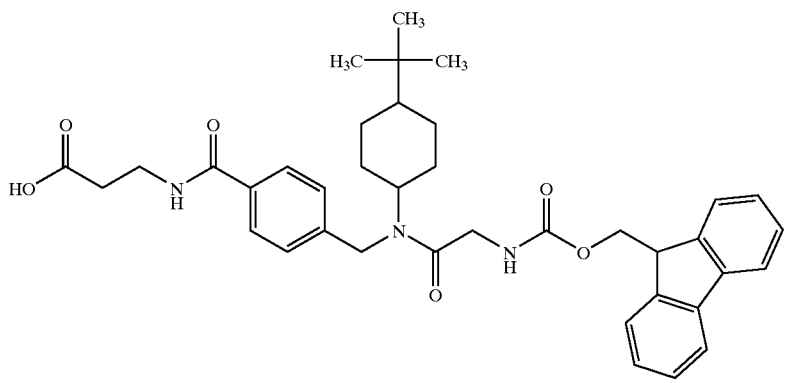

-continued
| 471 | 472 |
|---|---|
| 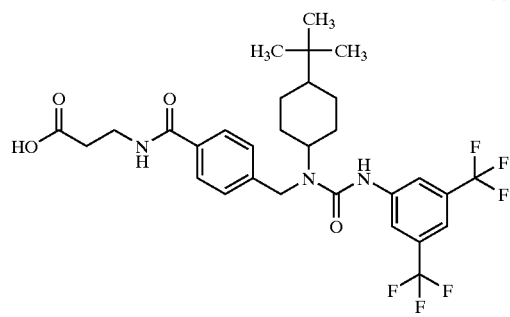 | 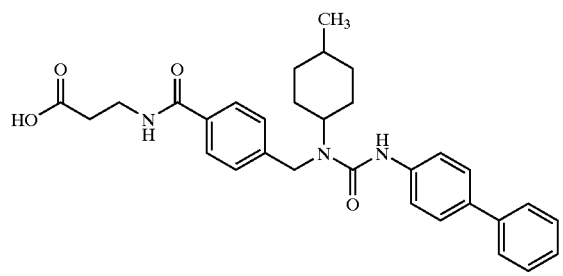 |
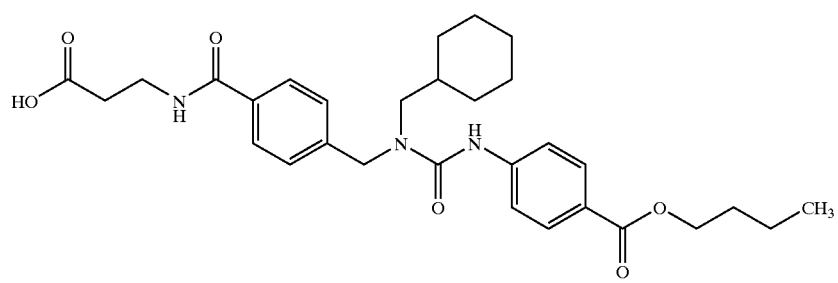
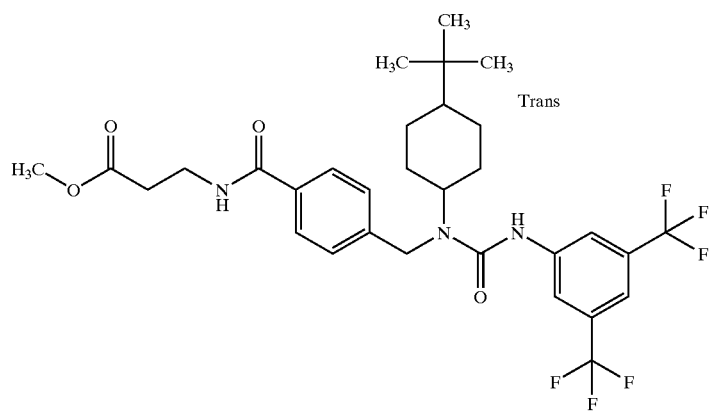
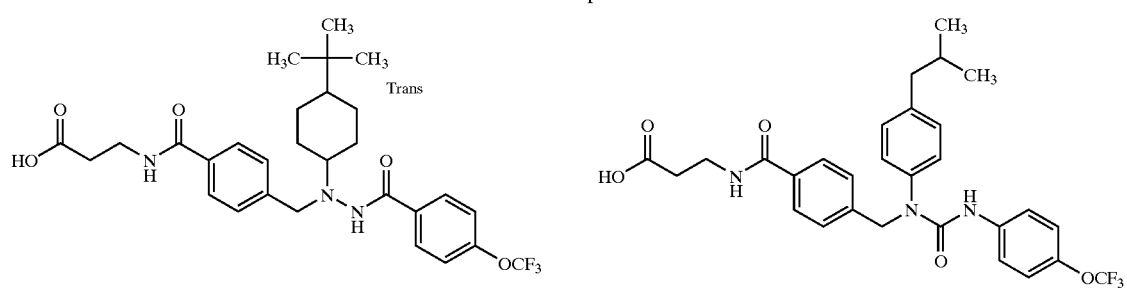
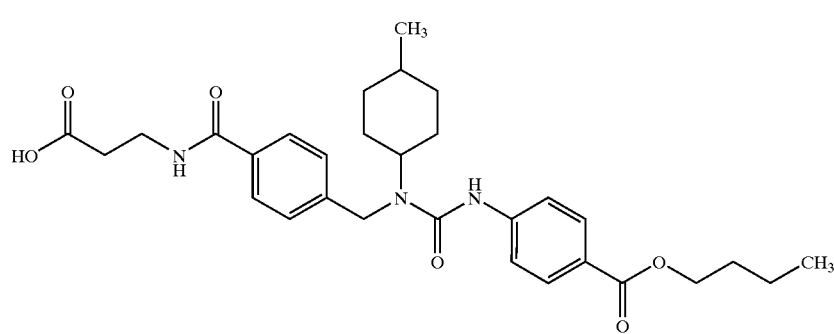

473                                                                                              474
-continued
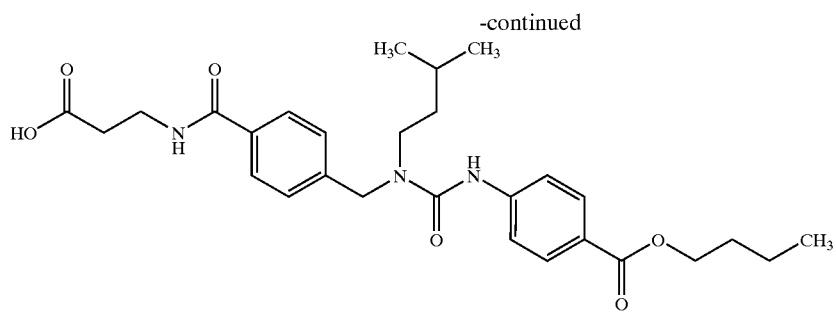
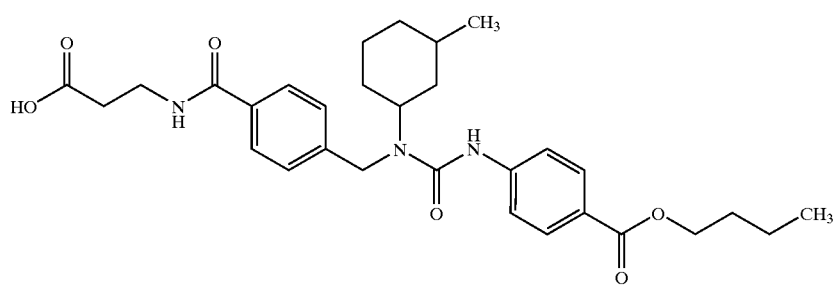
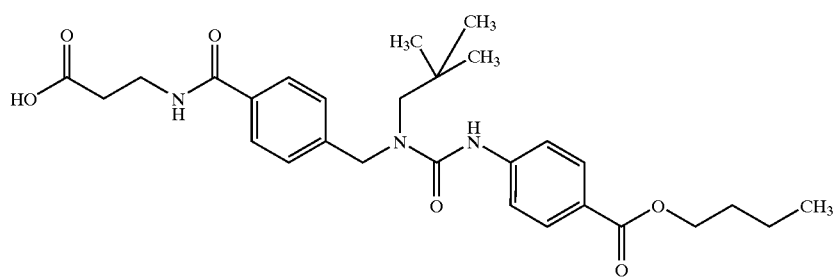
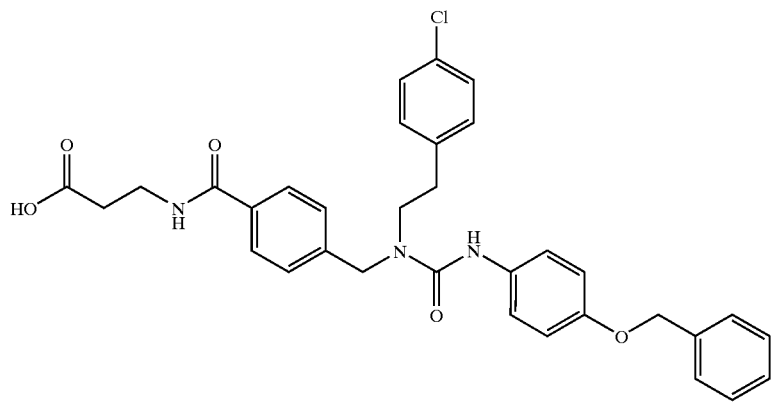
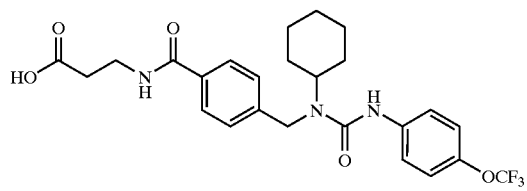
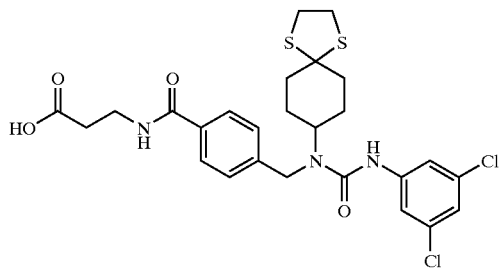

-continued
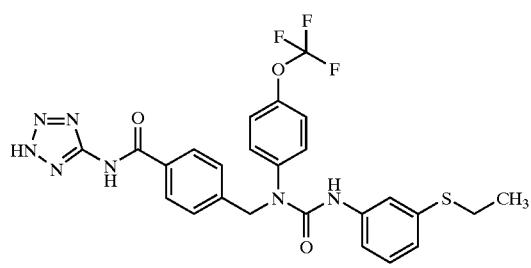
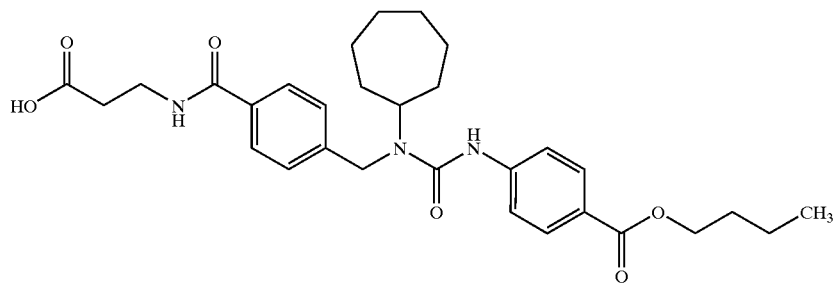
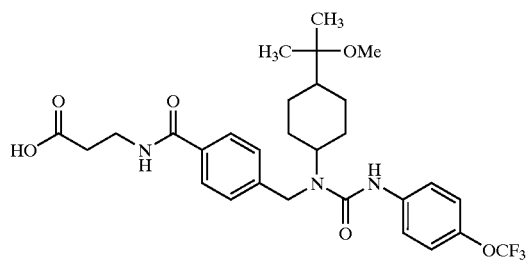
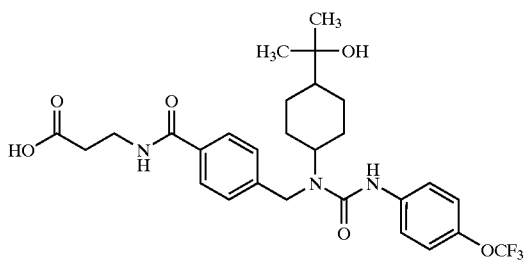
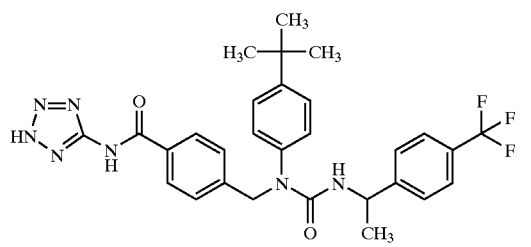
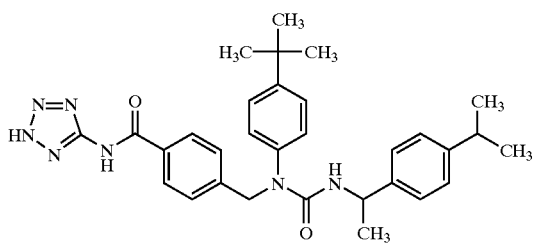
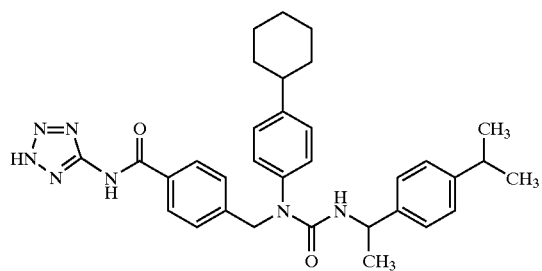
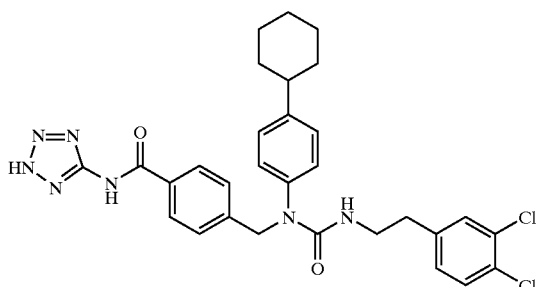
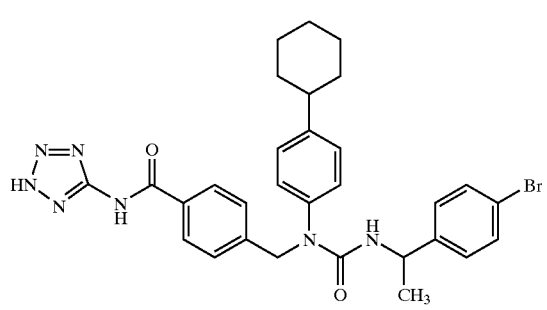
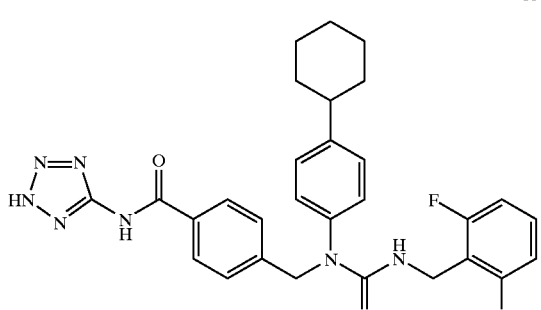

477
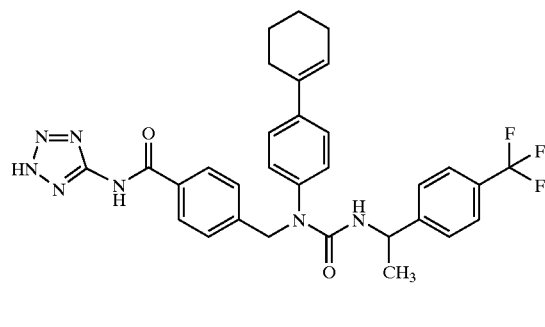
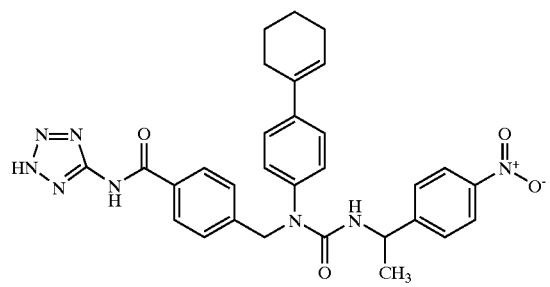
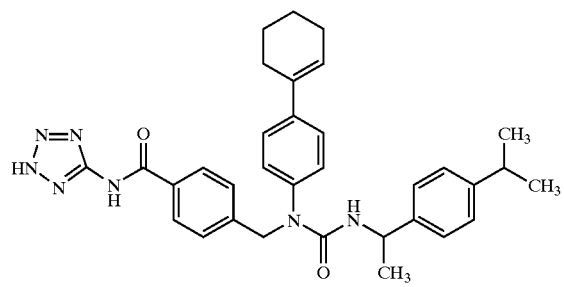
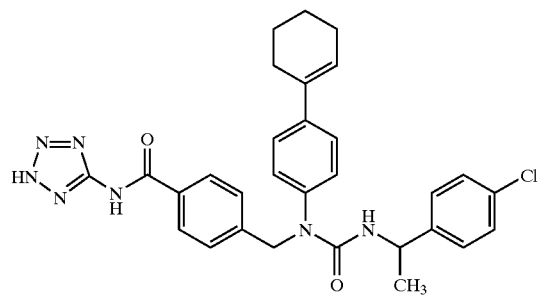
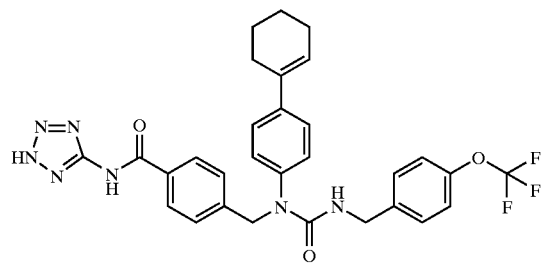
478
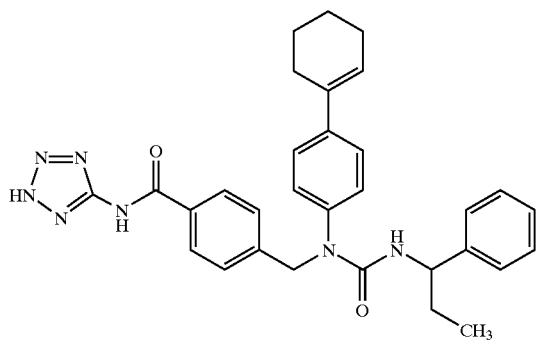
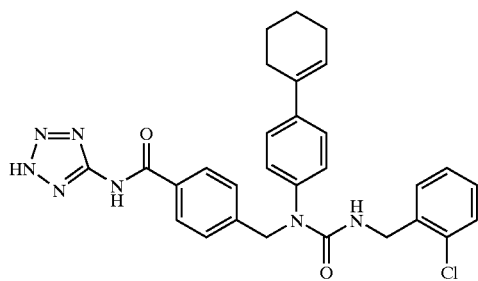
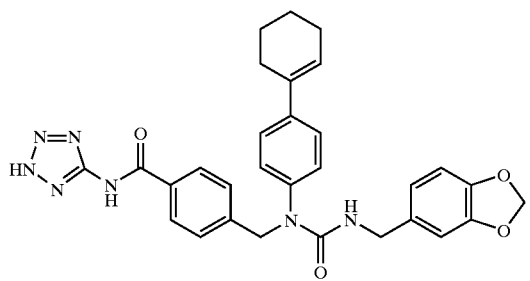
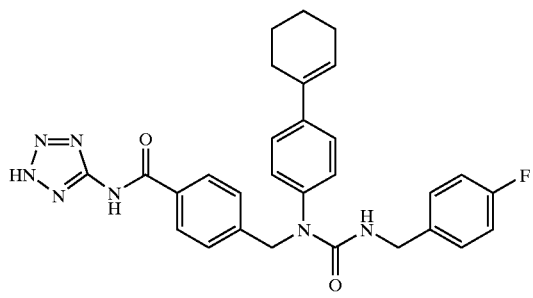
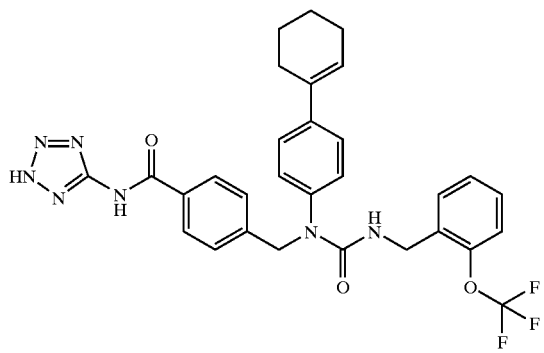

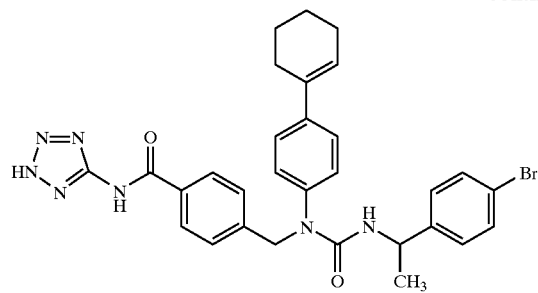
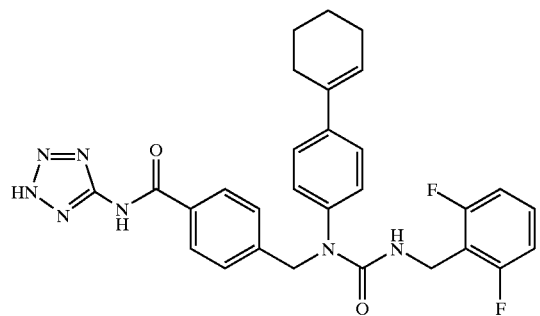
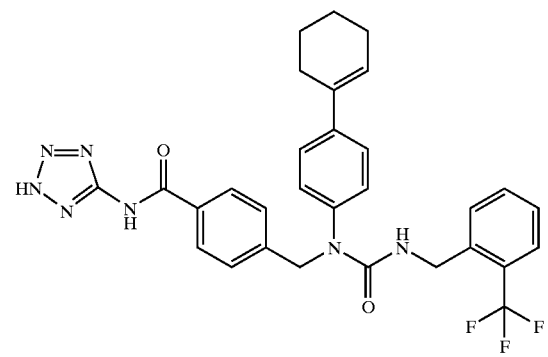
Furthermore, the following preferred compounds according to the invention may be prepared according to the general procedures set forth in the foregoing description:
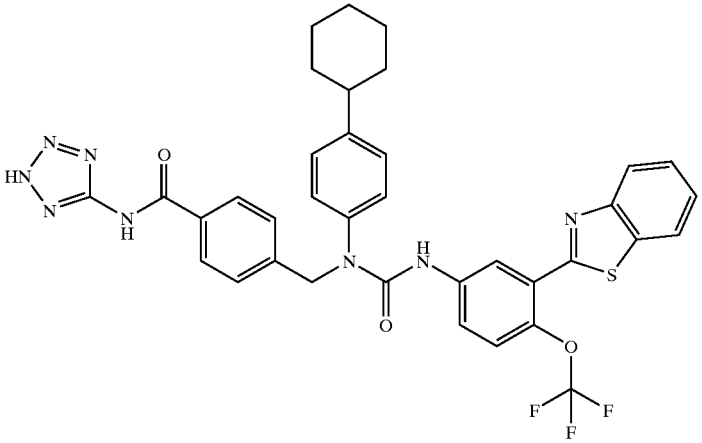
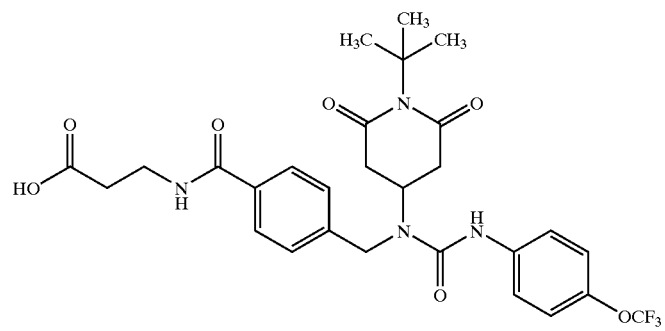

-continued
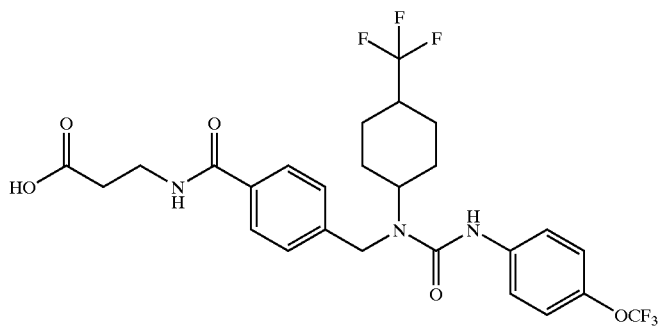
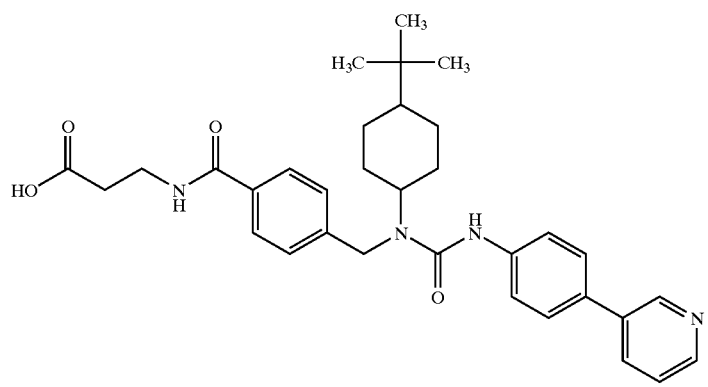
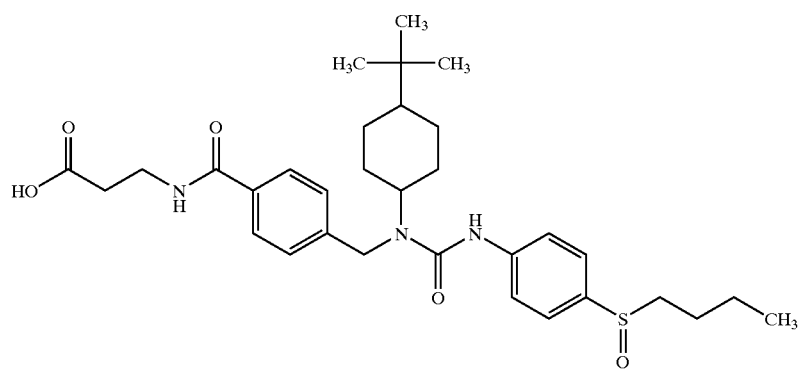
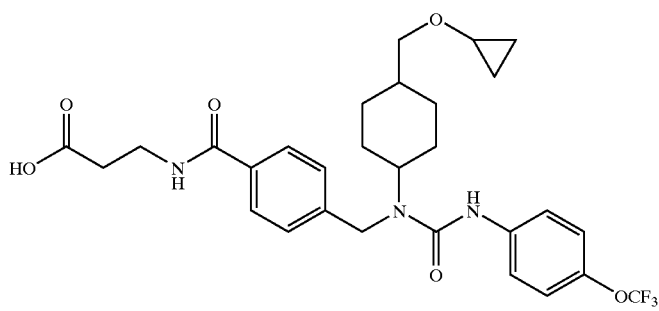

-continued
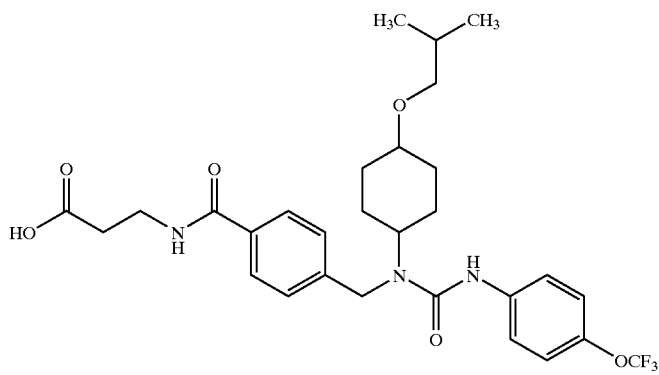
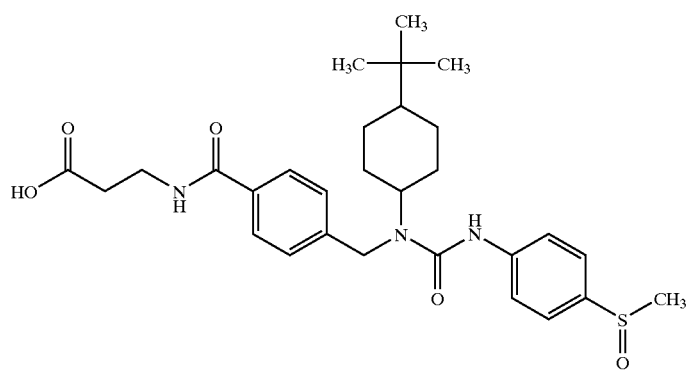
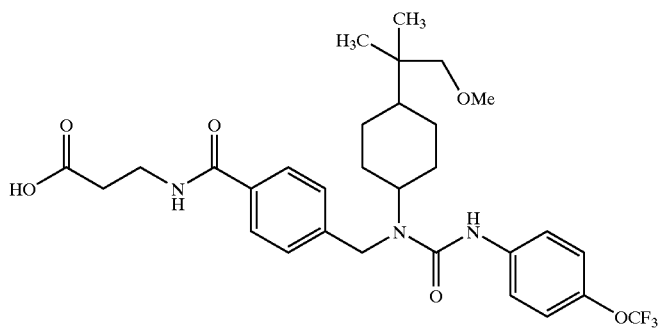
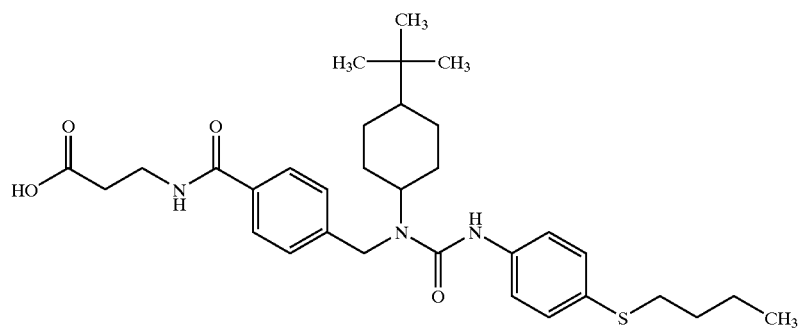

-continued
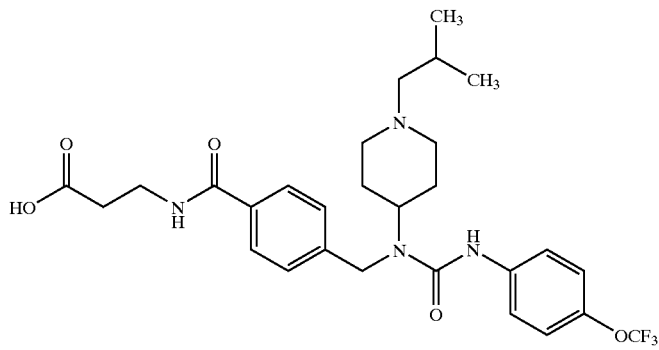
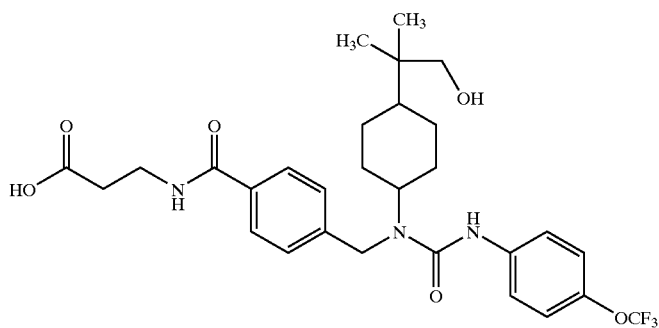
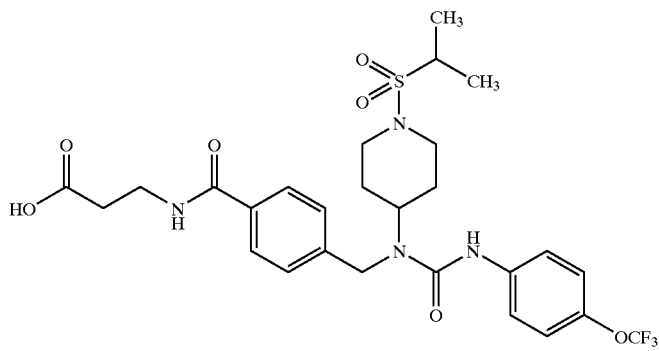
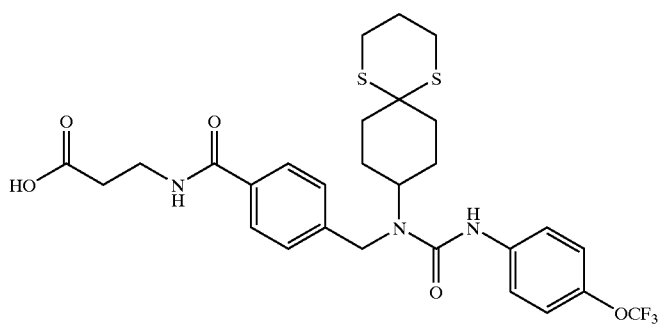

-continued
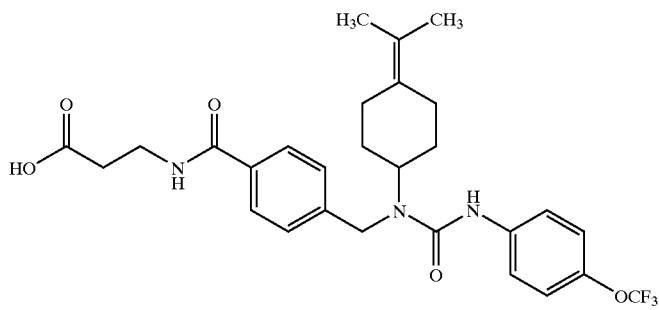
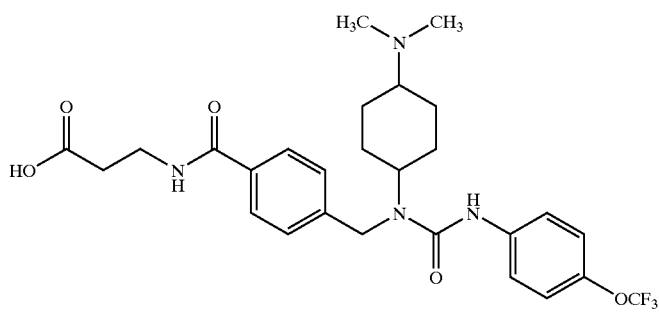
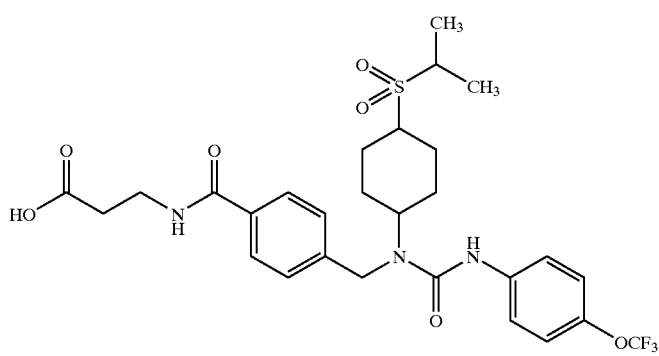
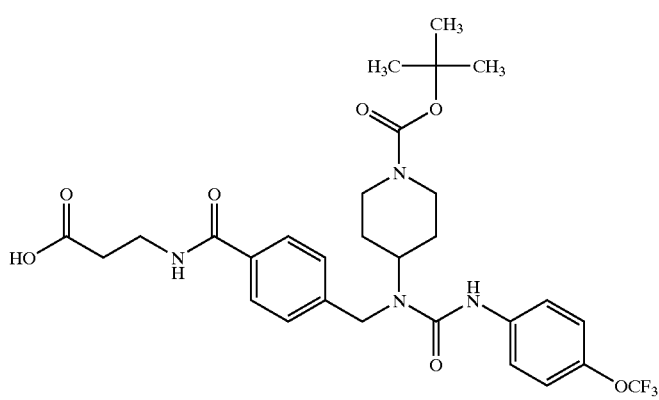

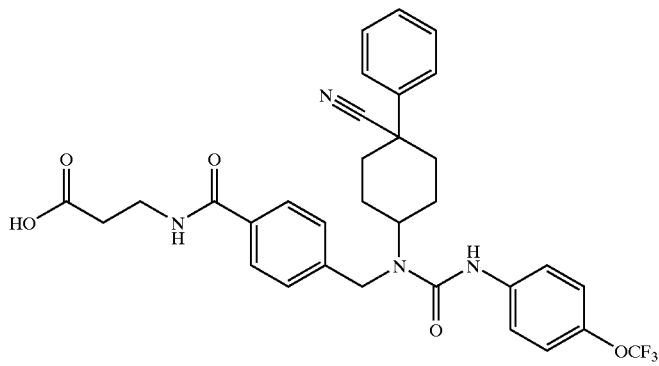
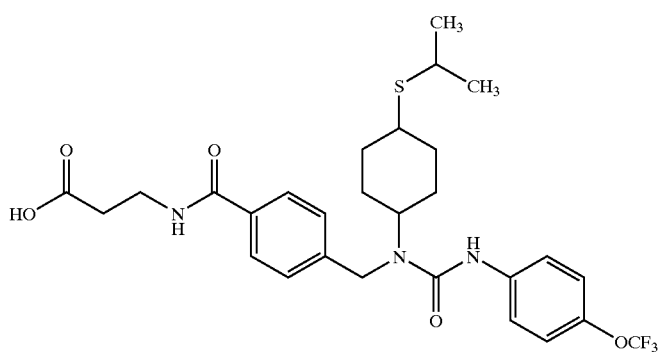
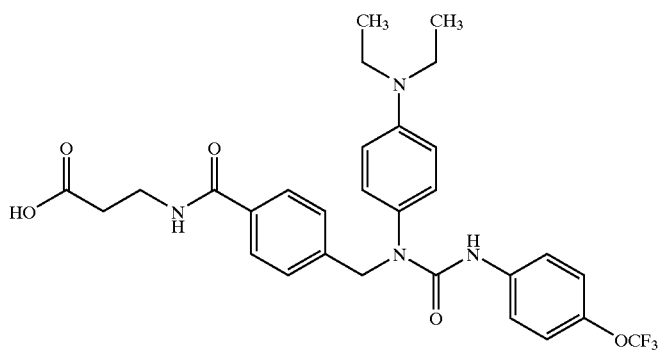
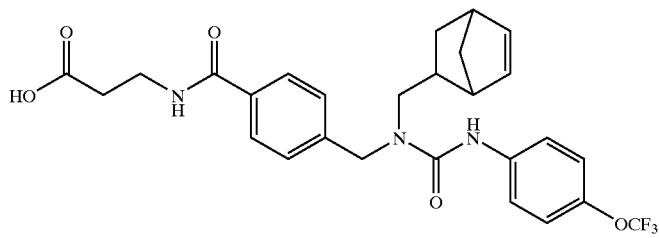
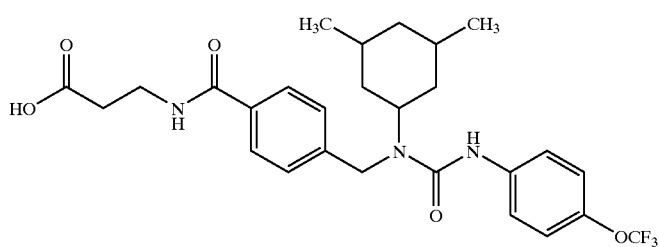

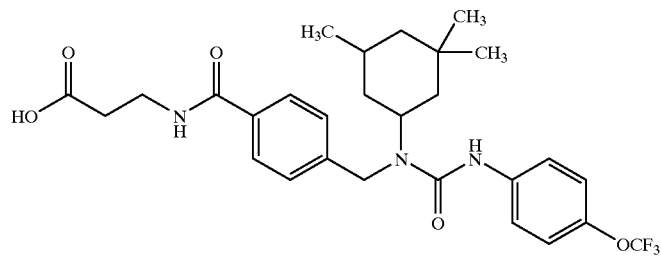
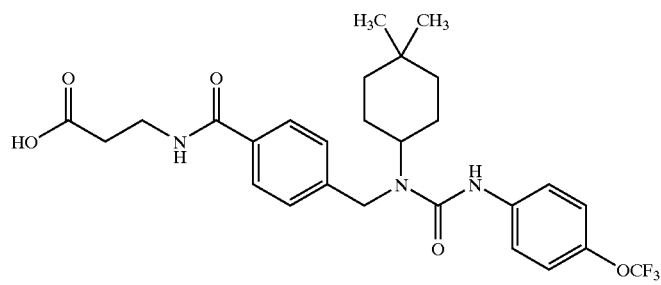
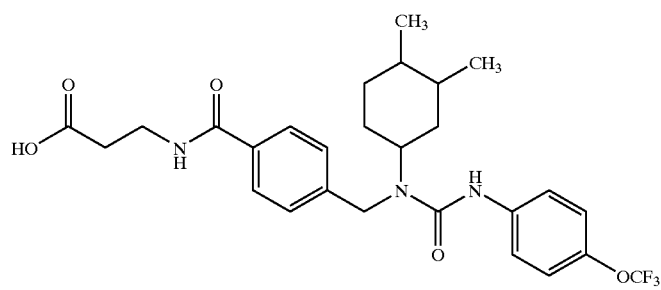
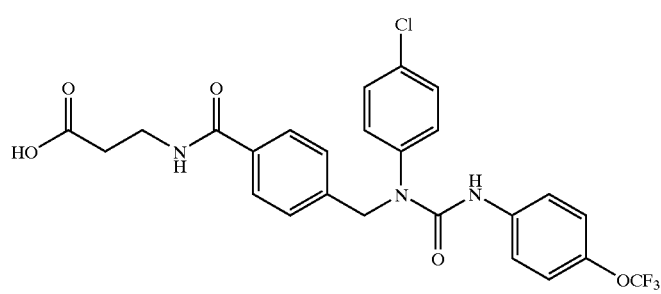
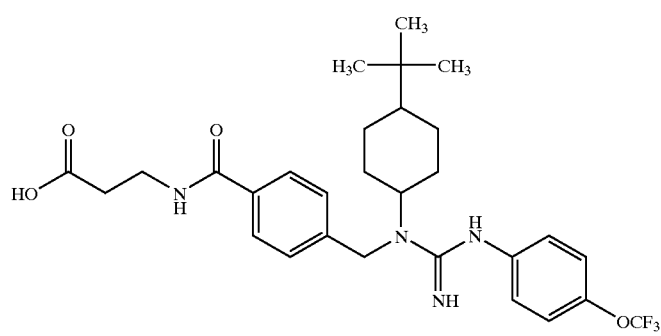

-continued
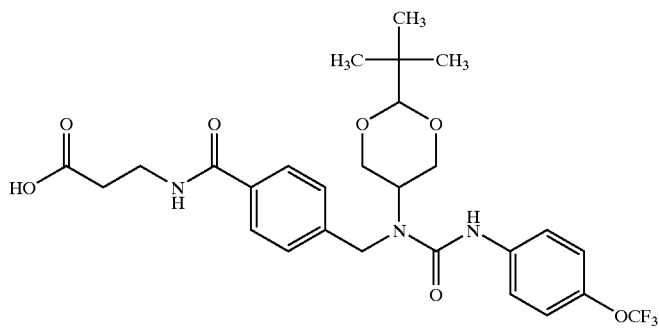
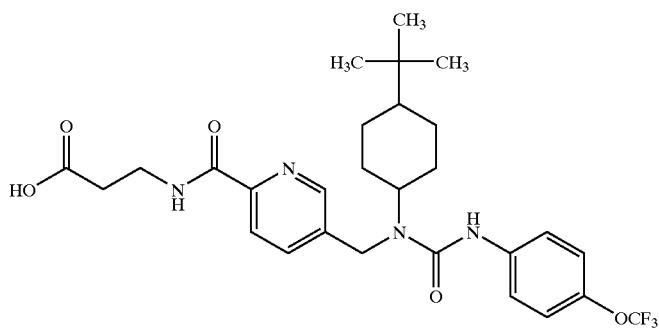
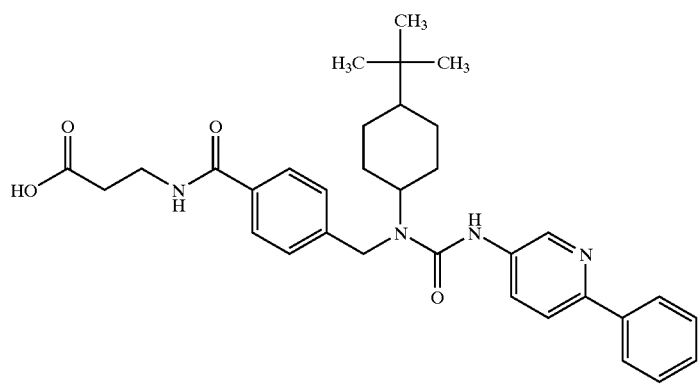
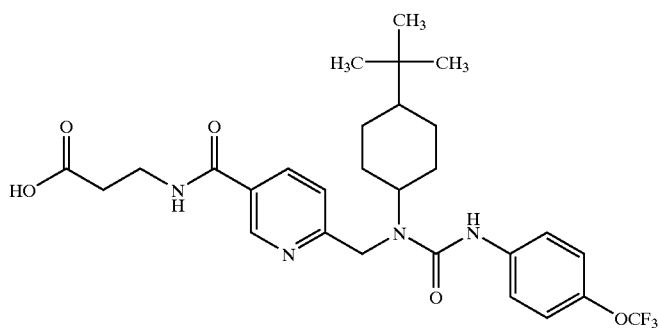

-continued
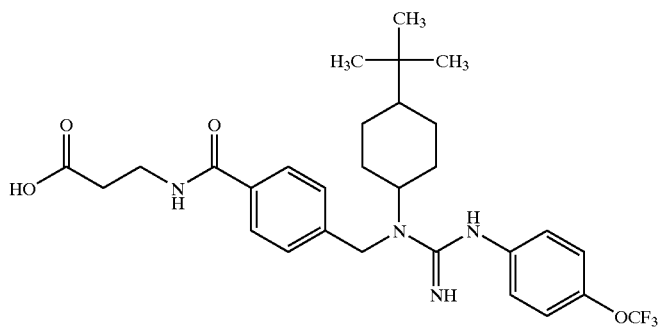
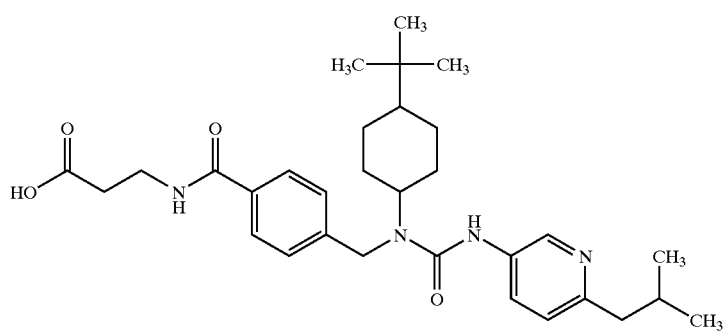
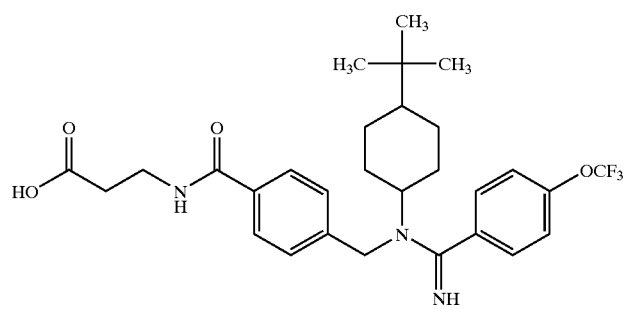
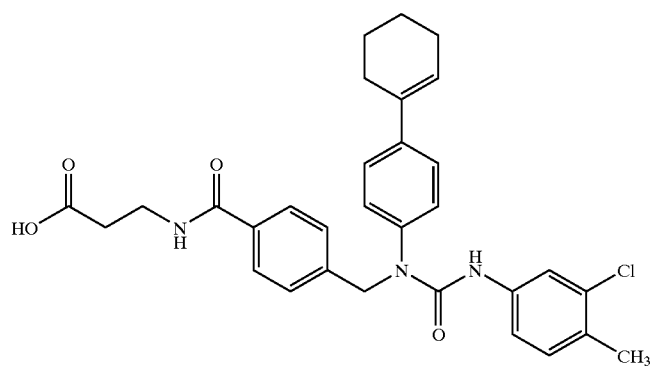

-continued
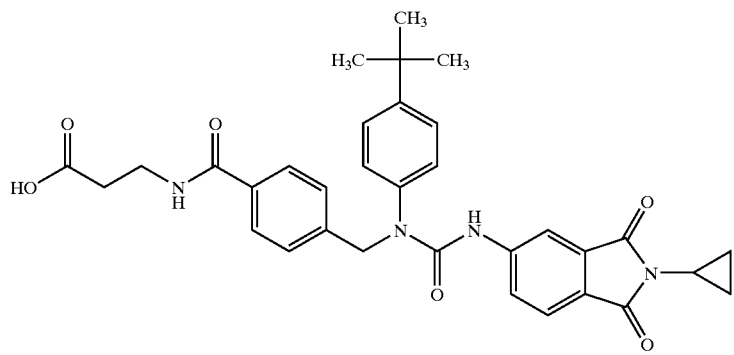
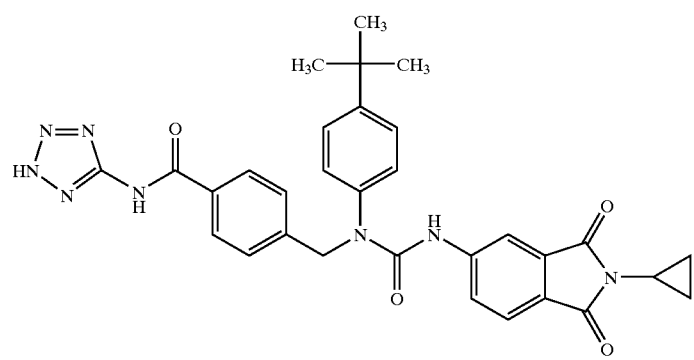
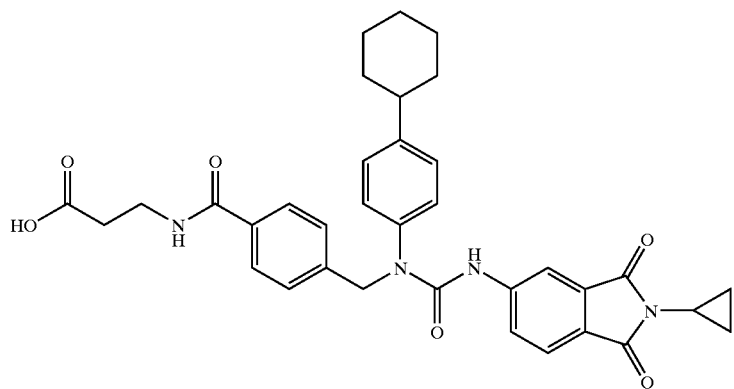
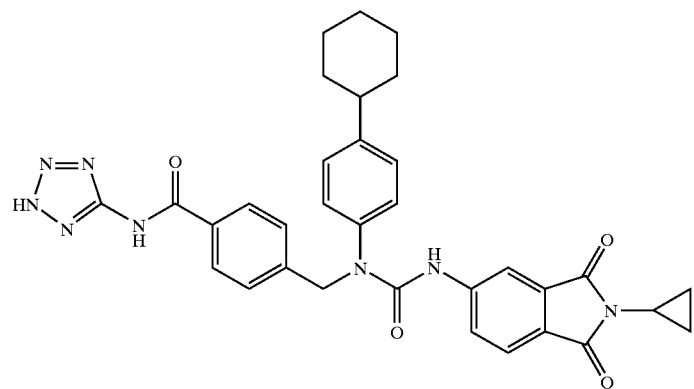

-continued
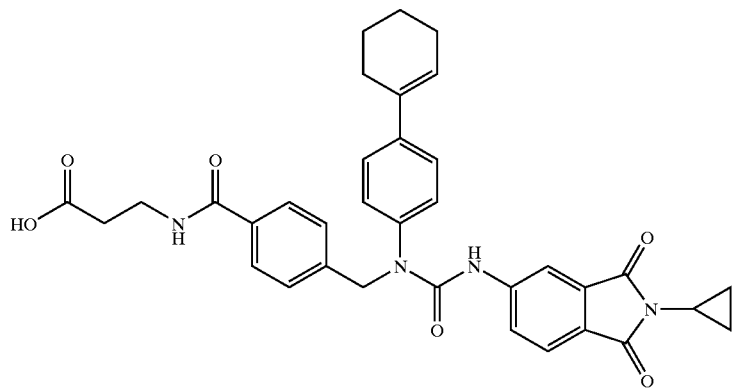
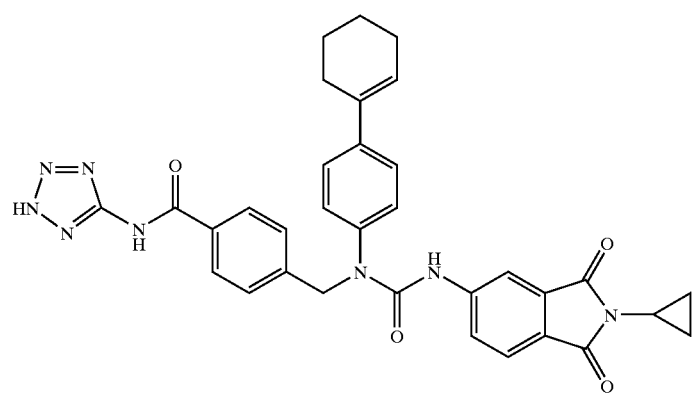
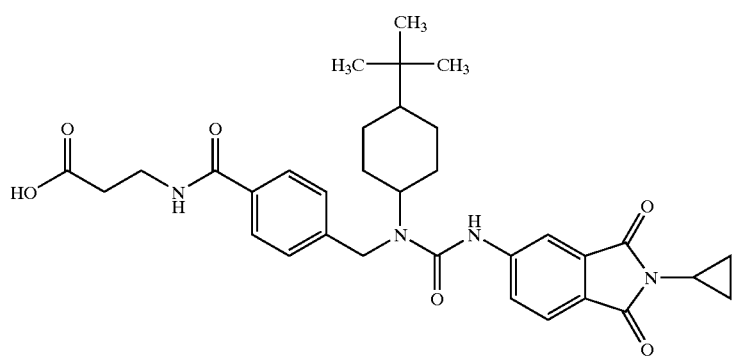
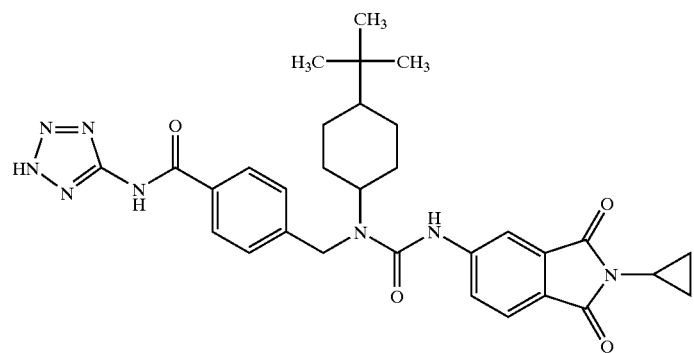

-continued
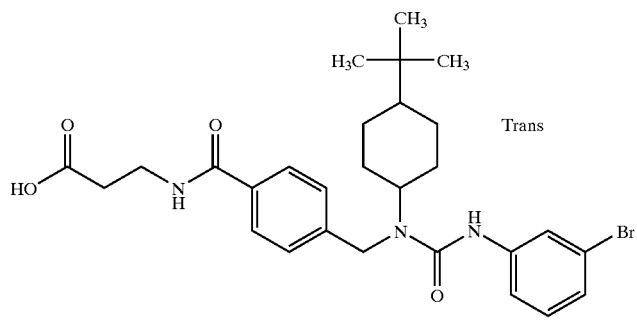
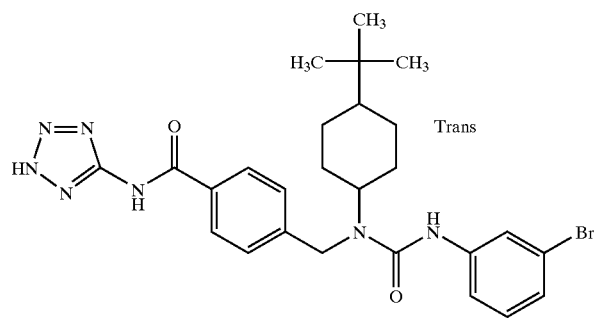
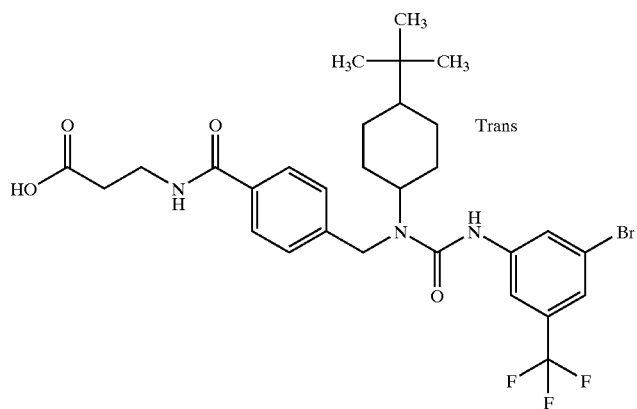
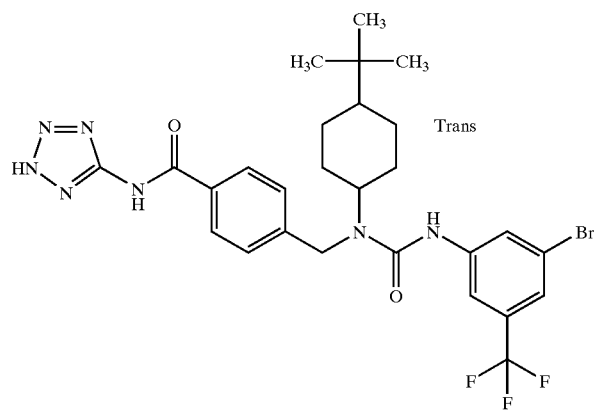

-continued
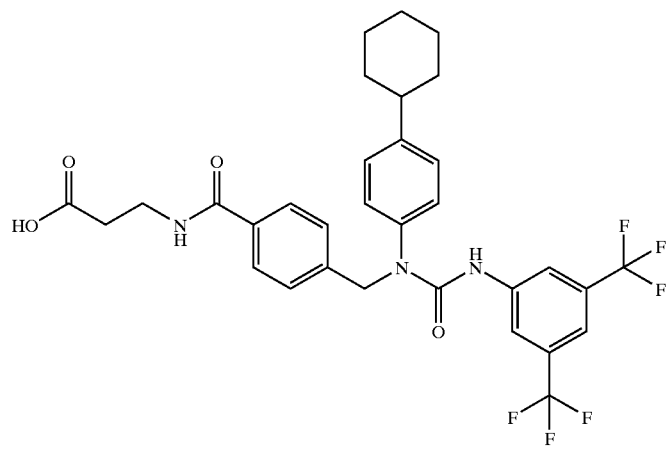
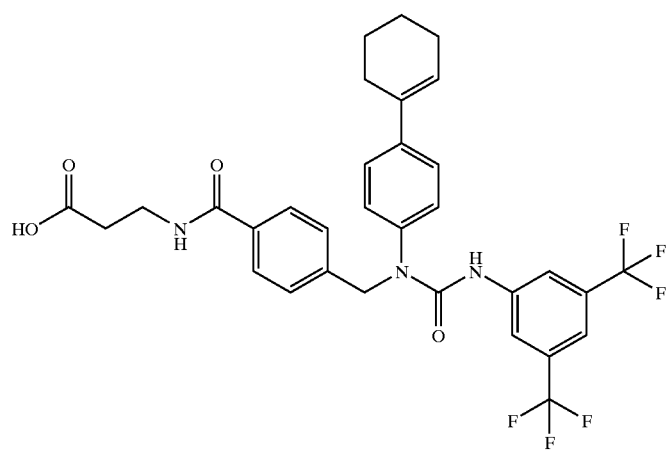
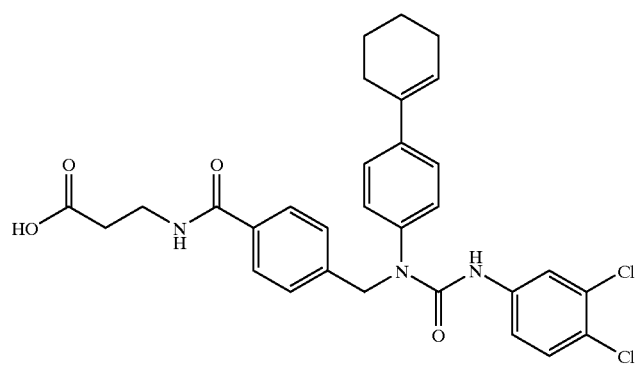
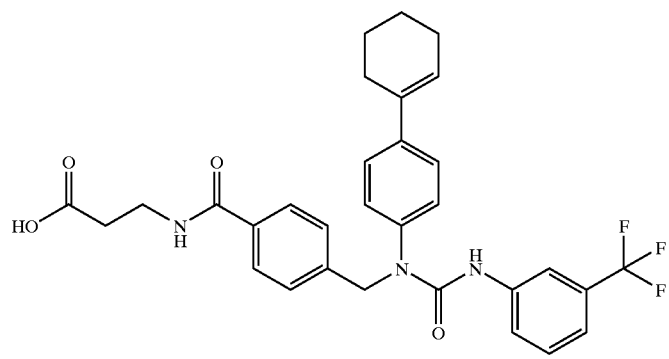

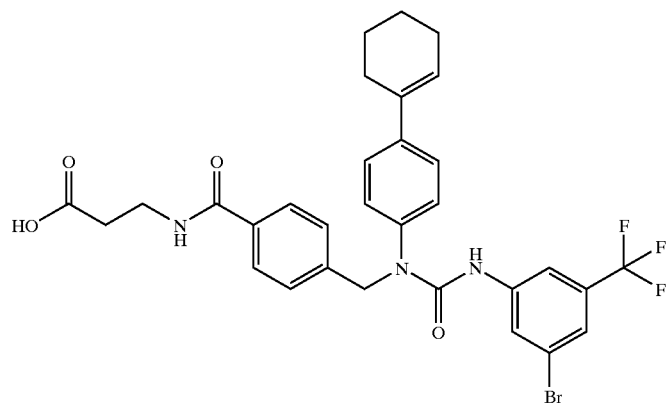
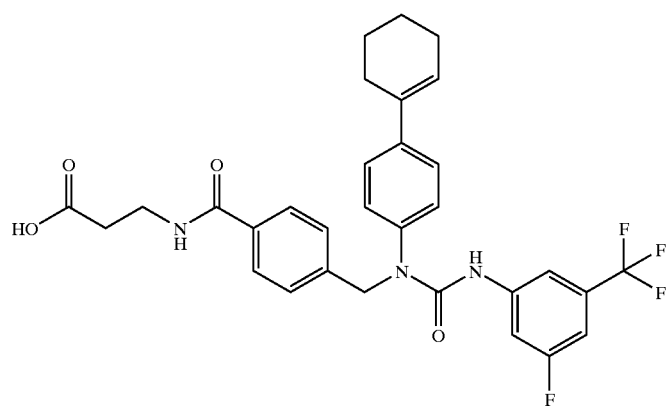
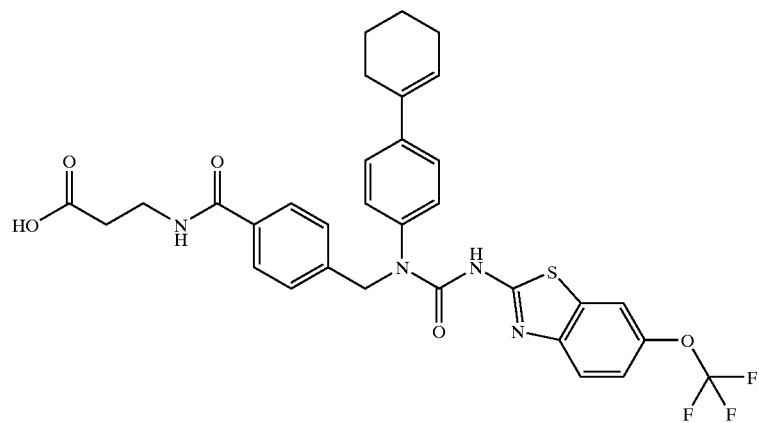

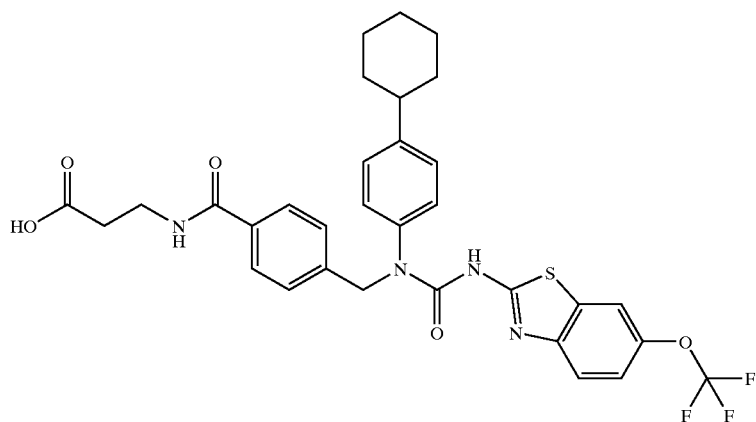
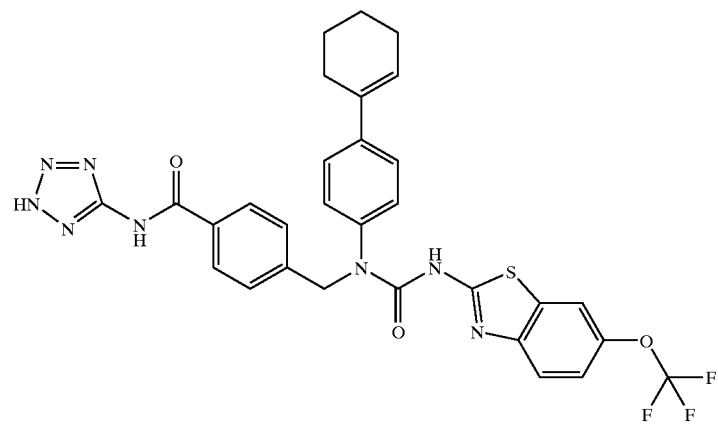
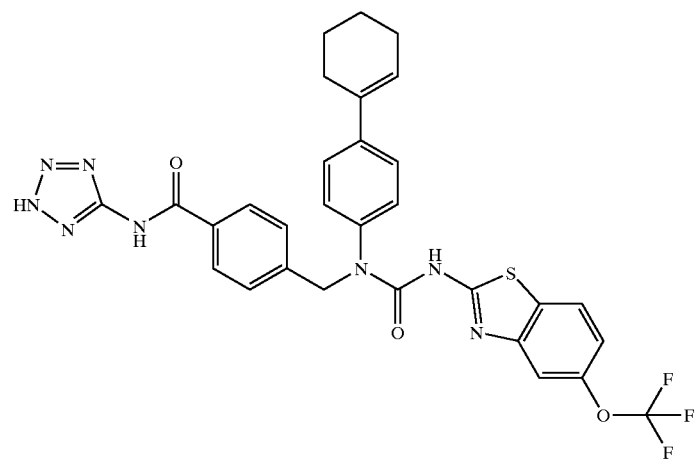

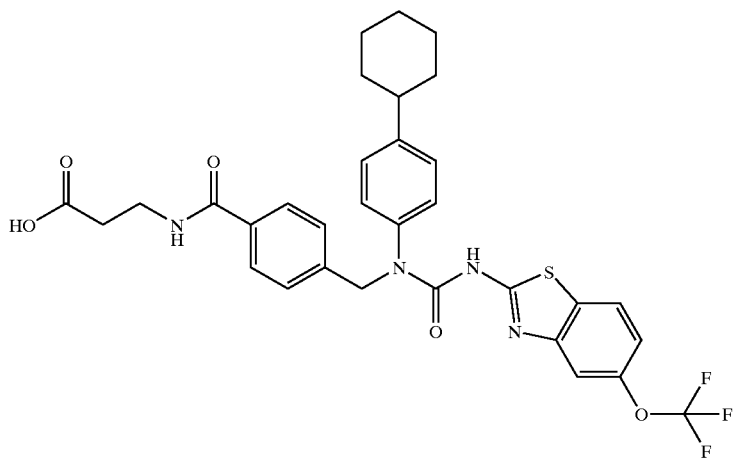
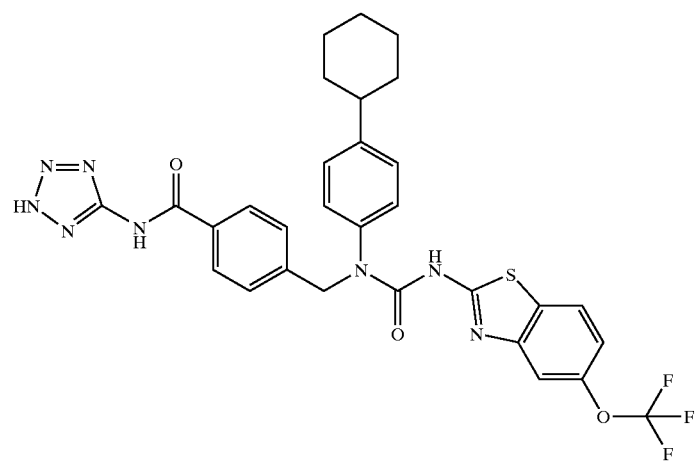
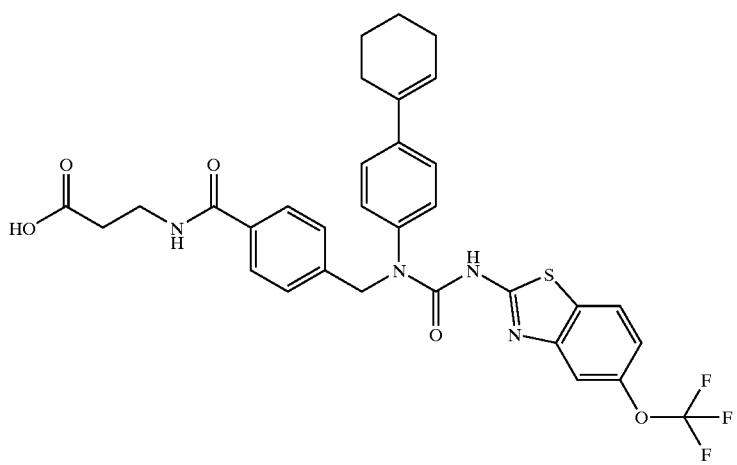

-continued
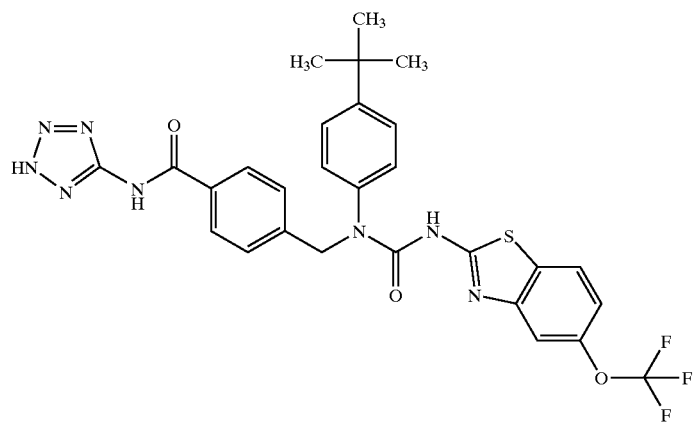
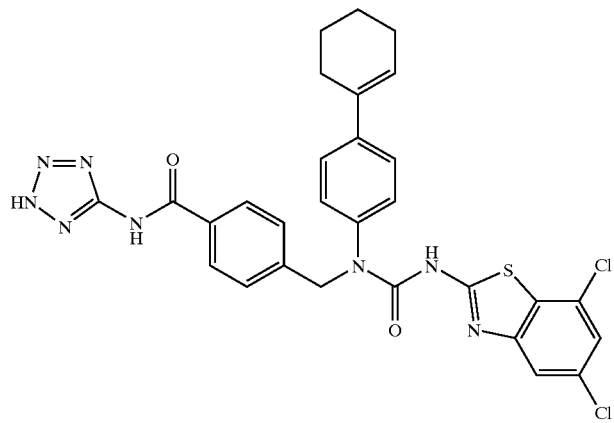
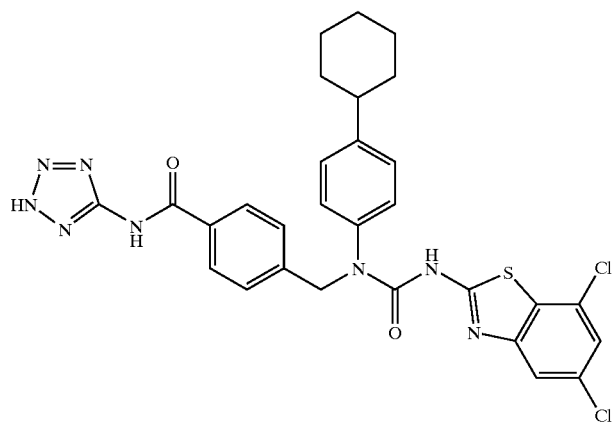

-continued
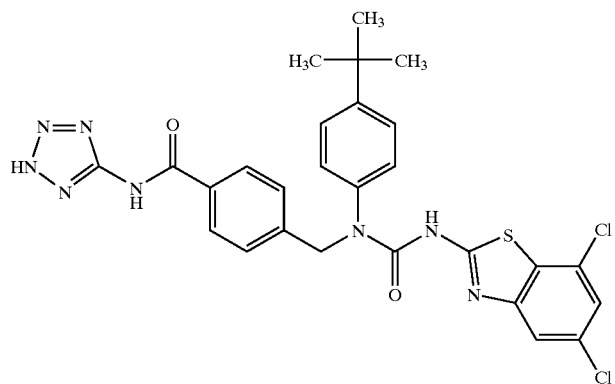
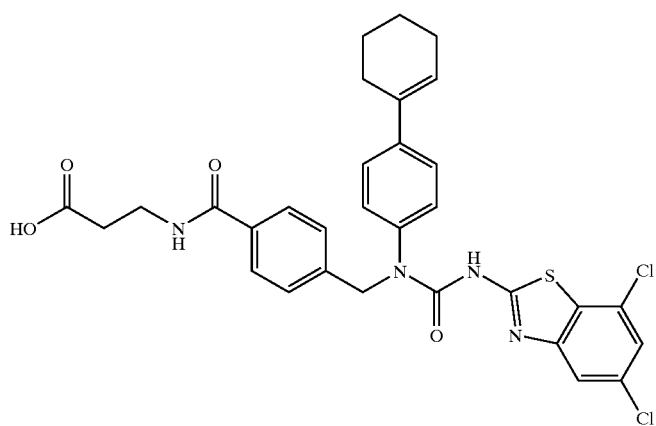
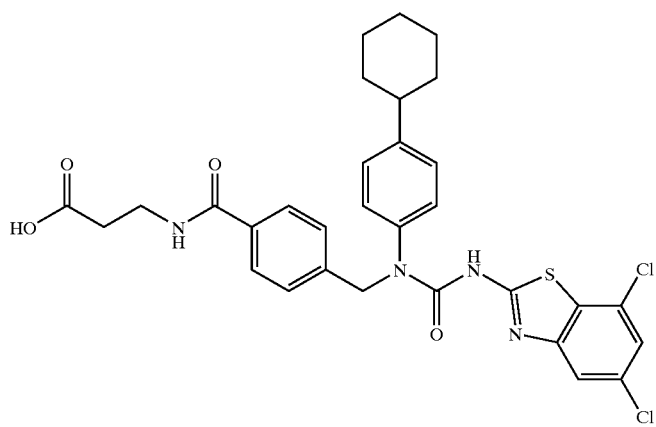

-continued
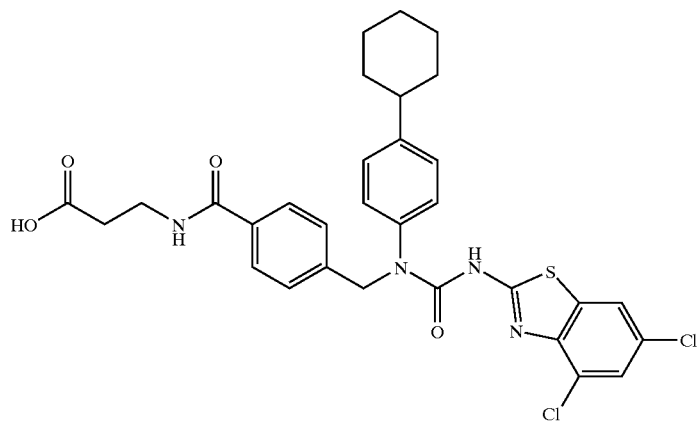
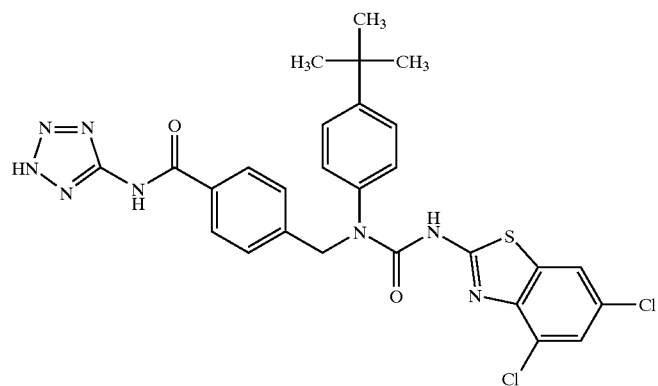
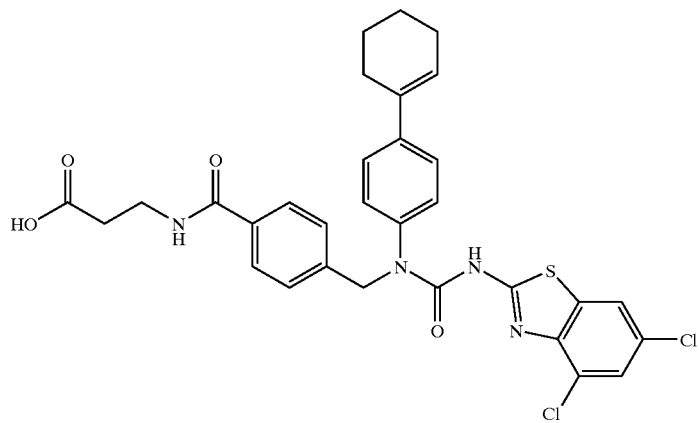

-continued
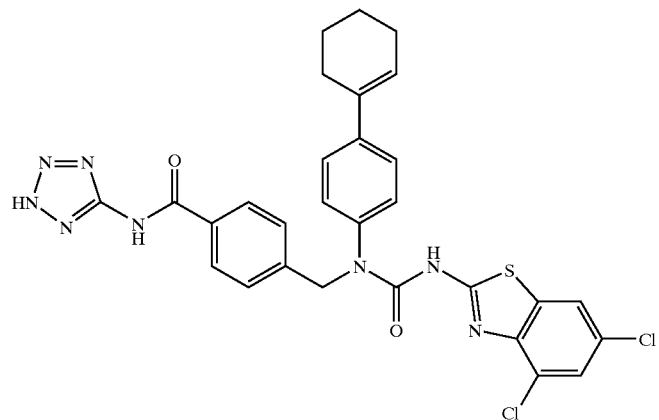
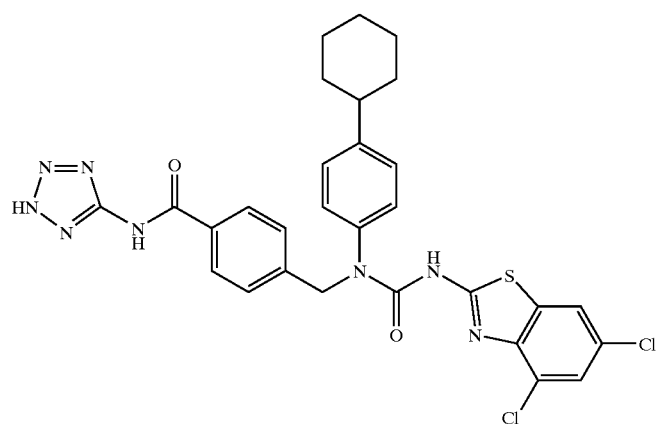
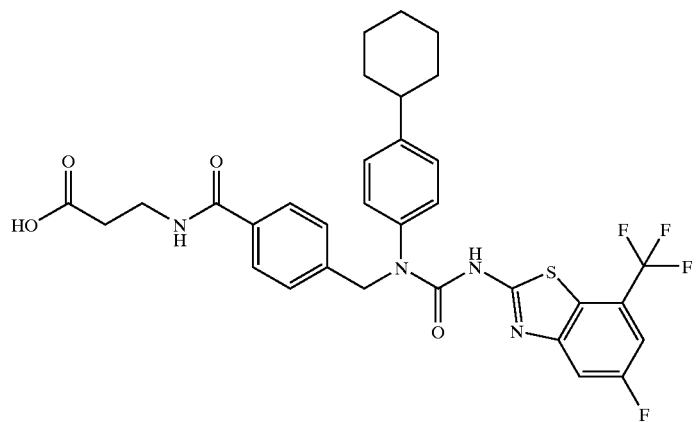
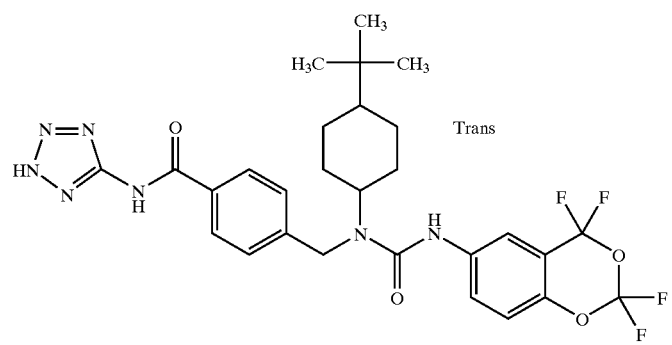

-continued
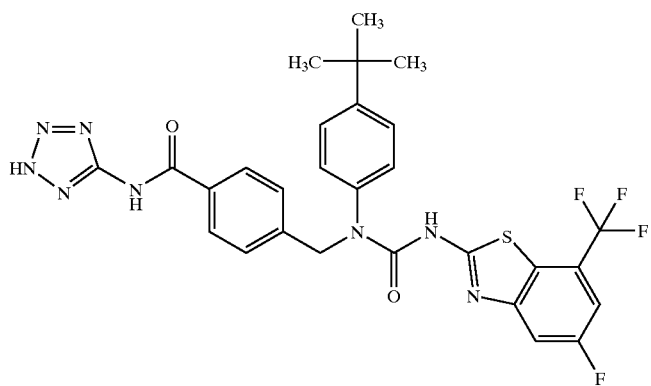
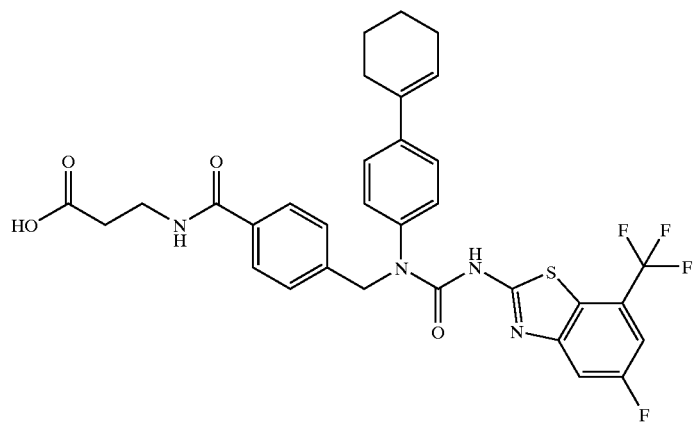
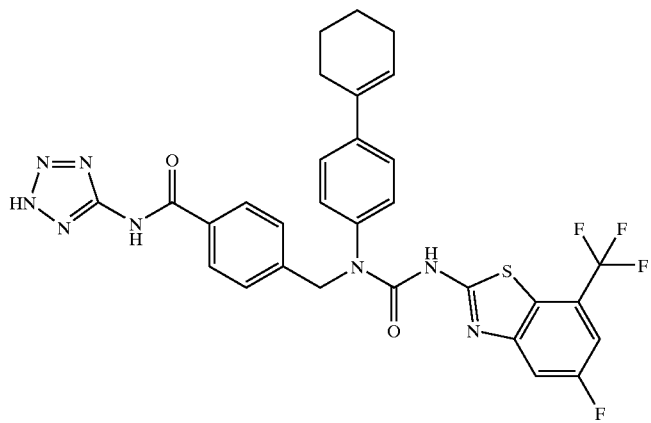

-continued
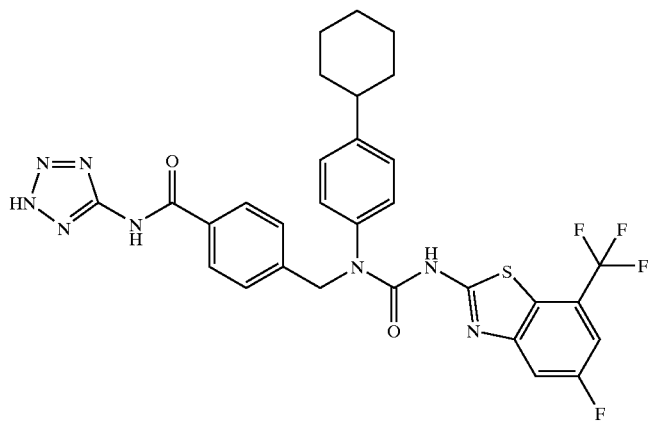
(R) and (S) enantiomers of
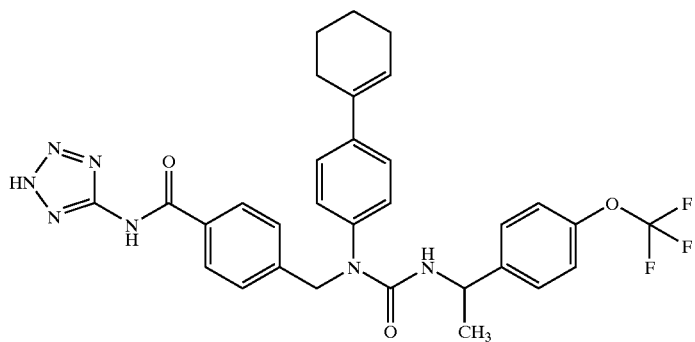
(R) and (S) enantiomers of
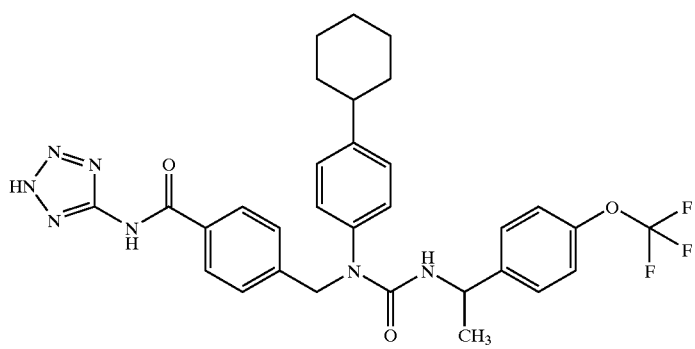
(R) and (S) enantiomers of
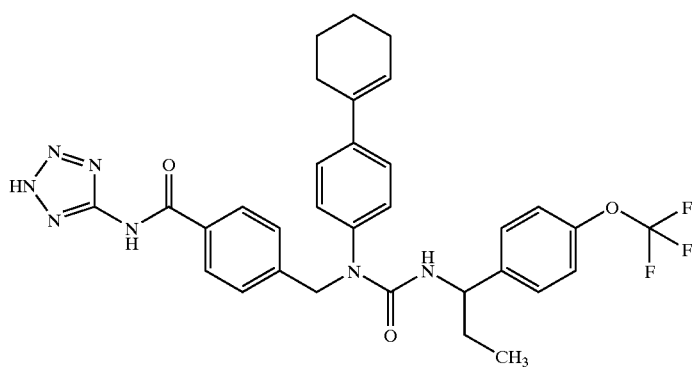

-continued
(R) and (S) enantiomers of
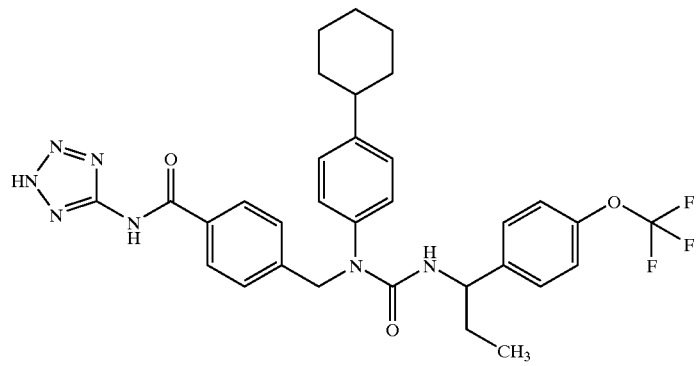
(R) and (S) enantiomers of
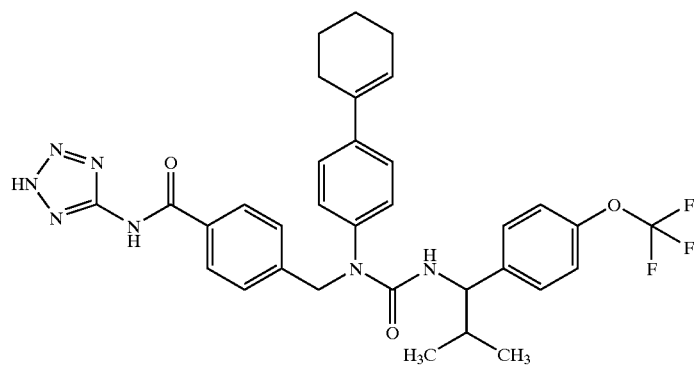
(R) and (S) enantiomers of
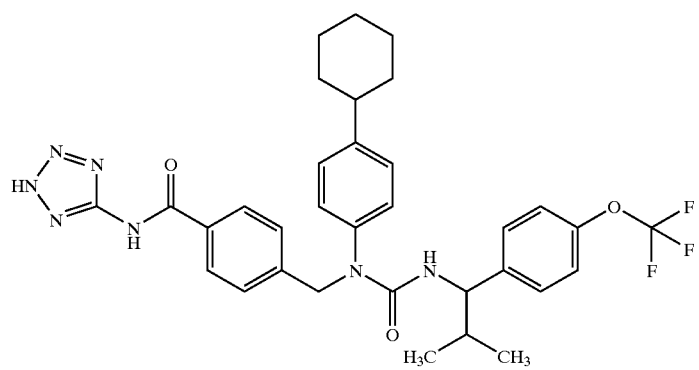

(R) and (S) enantiomers of
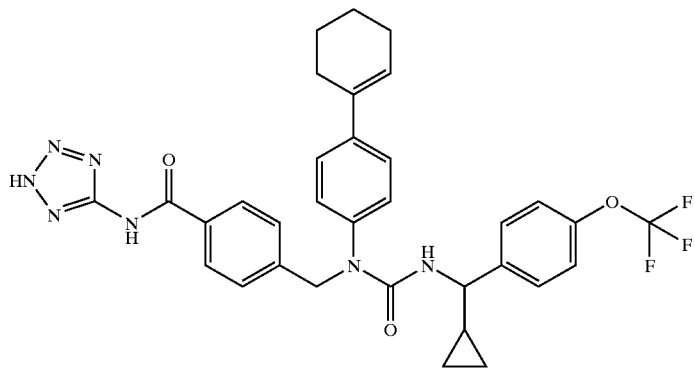
(R) and (S) enantiomers of
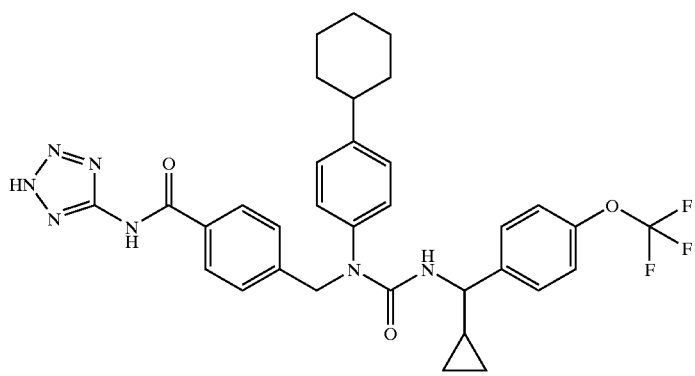
(R) and (S) enantiomers of
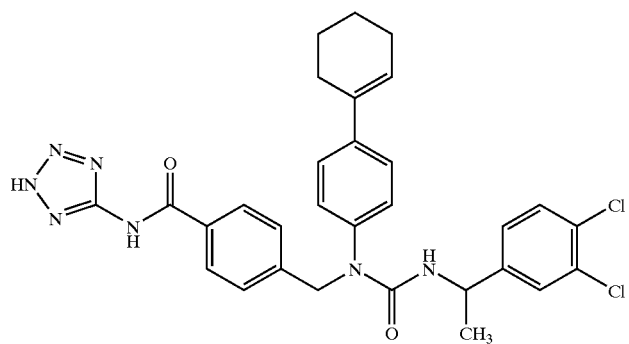

(R) and (S) enantiomers of
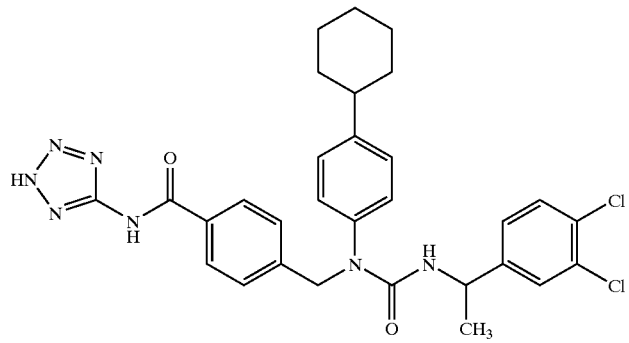
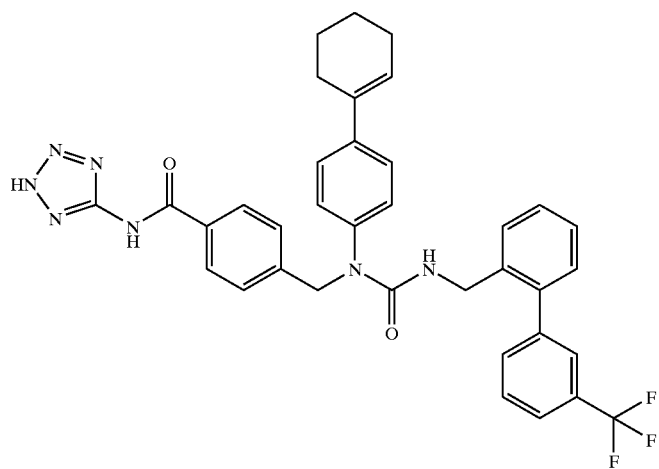
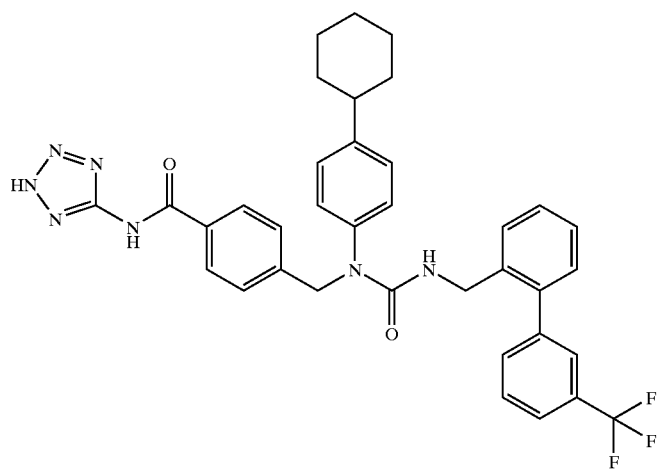

-continued
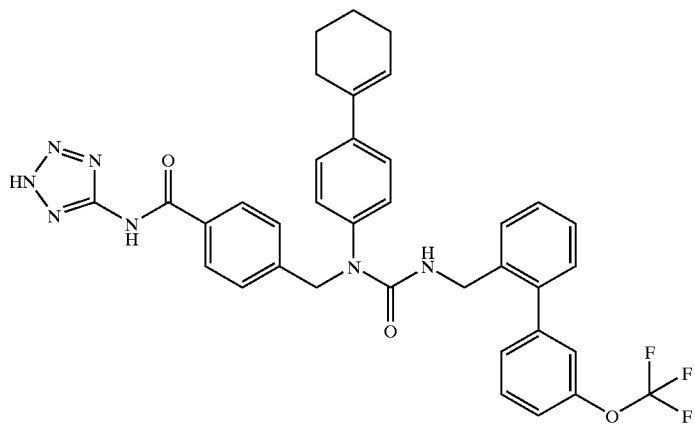
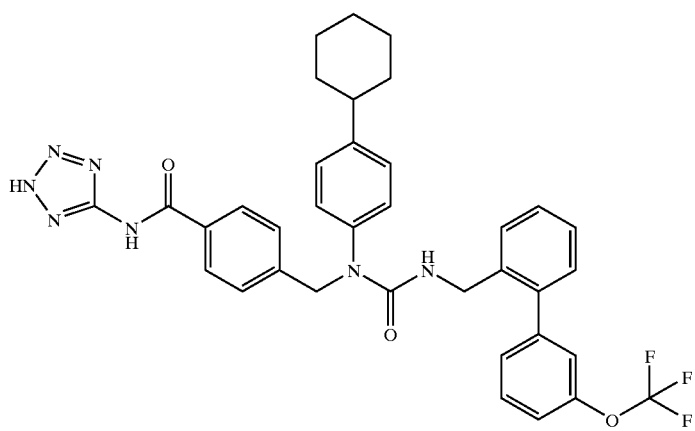
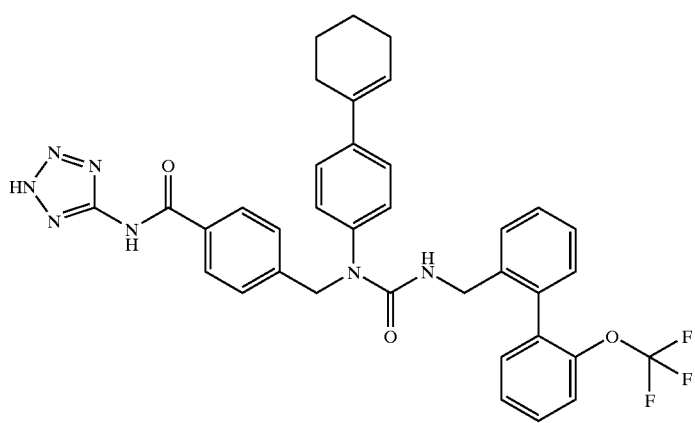

-continued
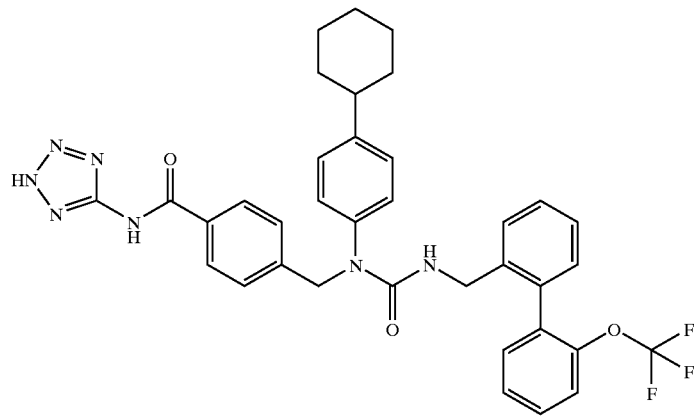
(R) and (S) enantiomers of
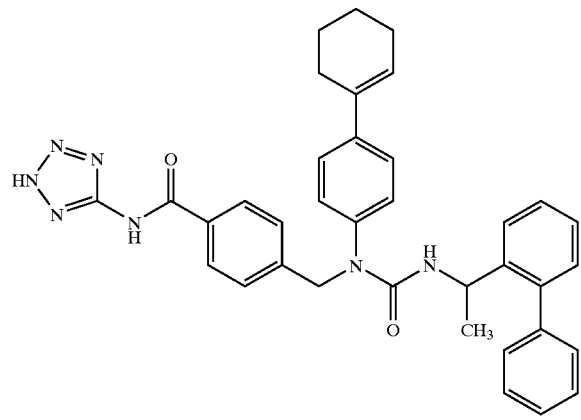
(R) and (S) enantiomers of
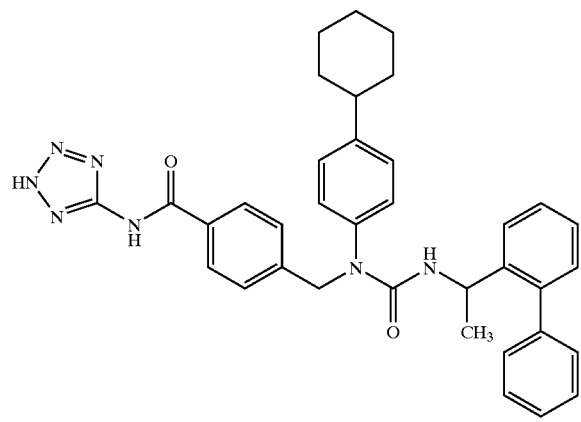

(R) and (S) enantiomers of
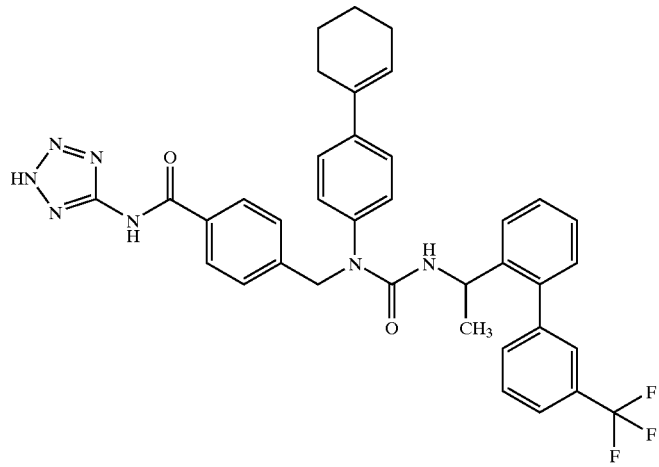
(R) and (S) enantiomers of
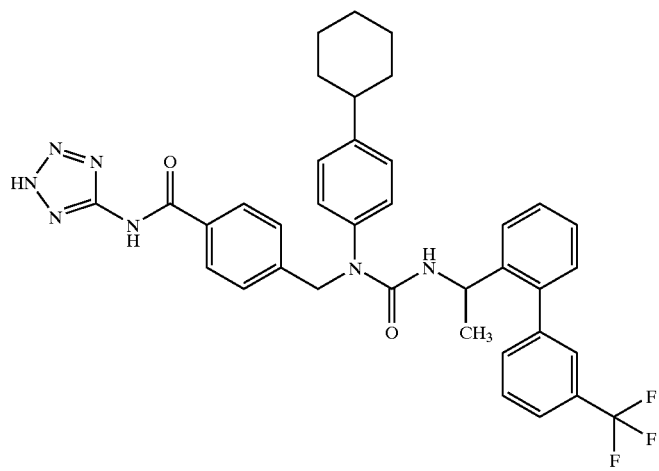
(R) and (S) enantiomers of
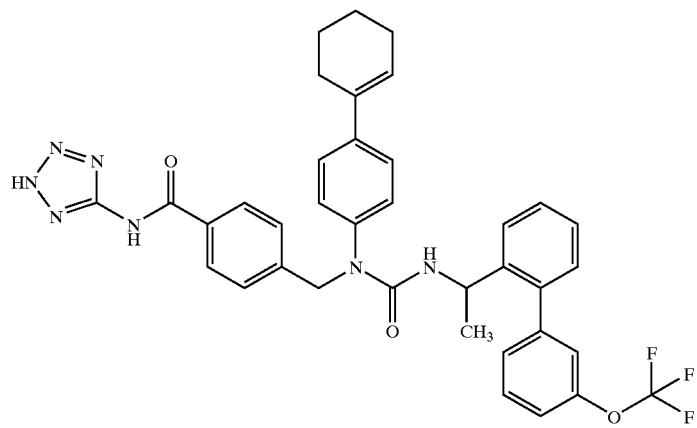

-continued
(R) and (S) enantiomers of
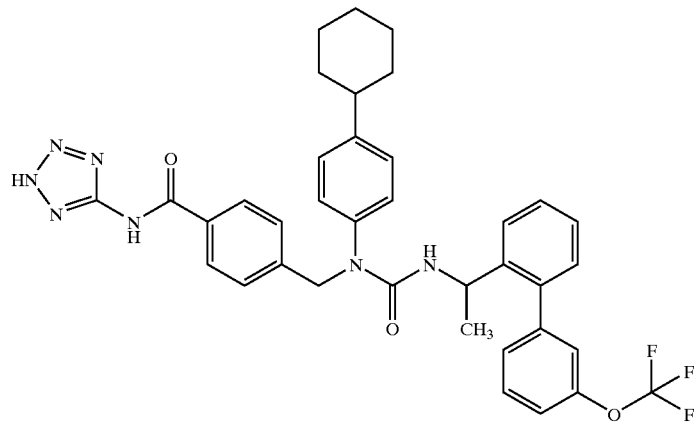
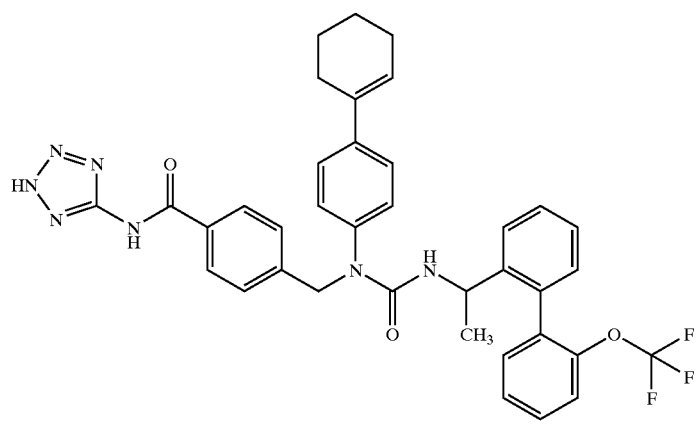
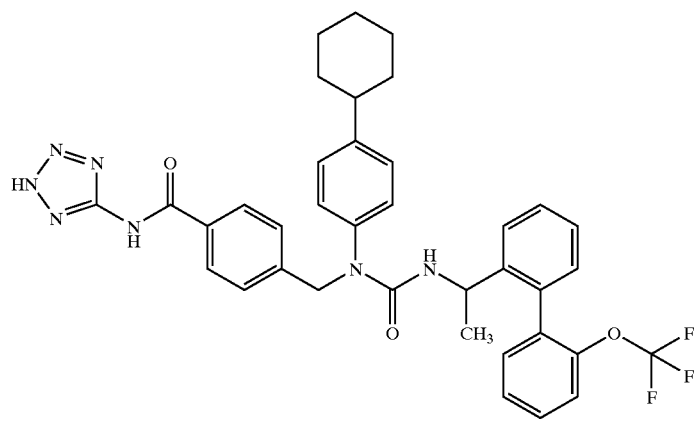

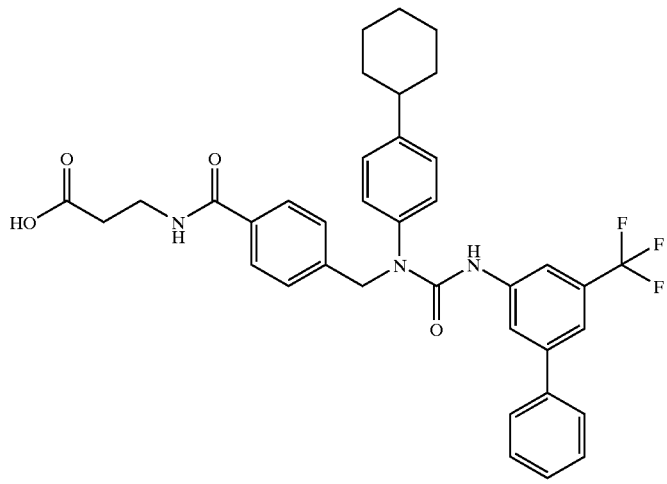
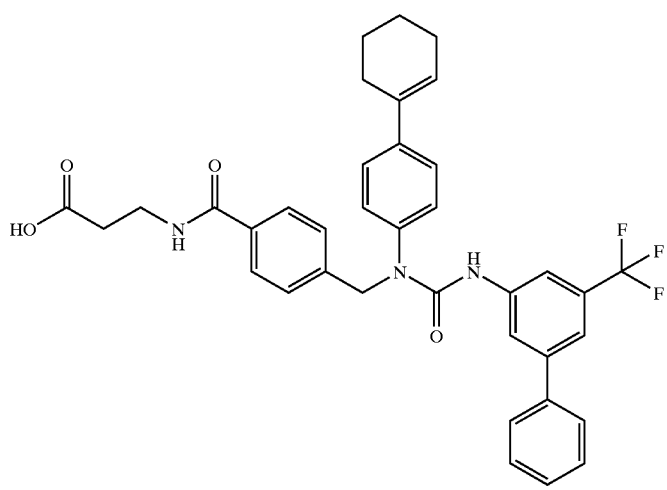
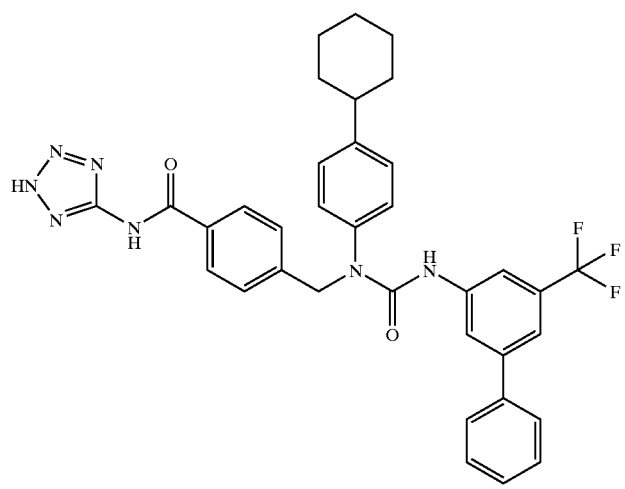

-continued
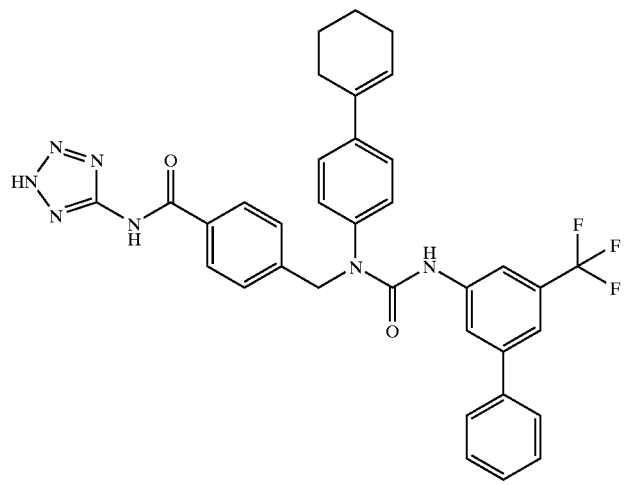
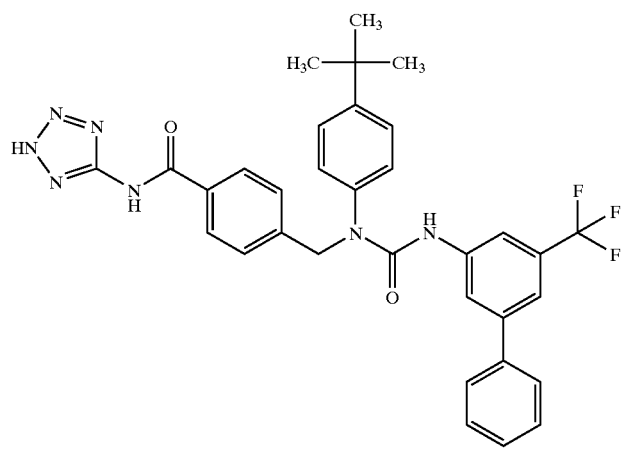
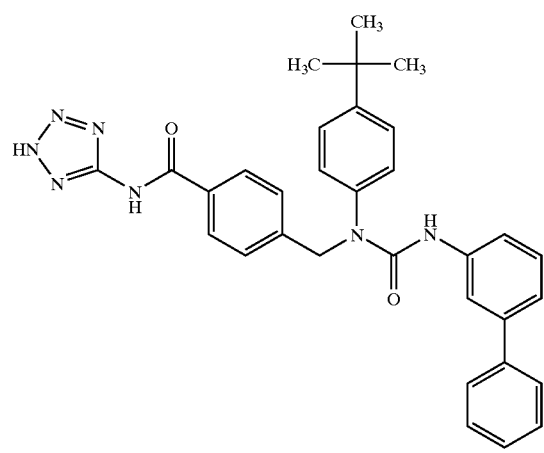

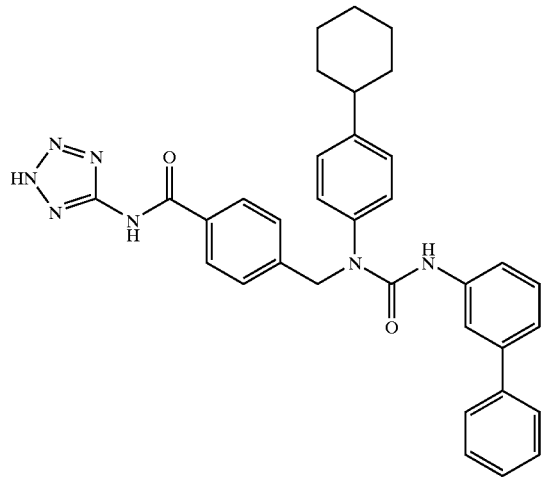
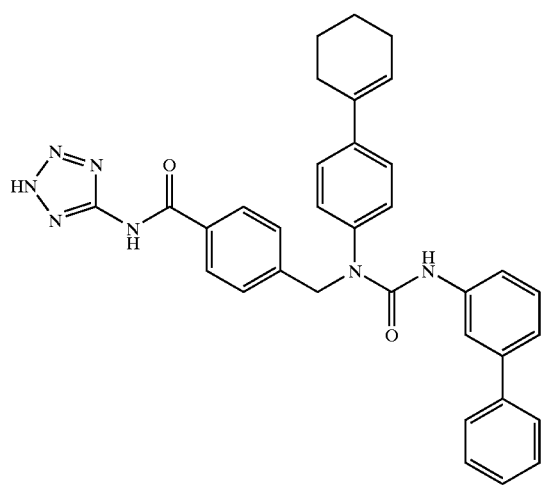
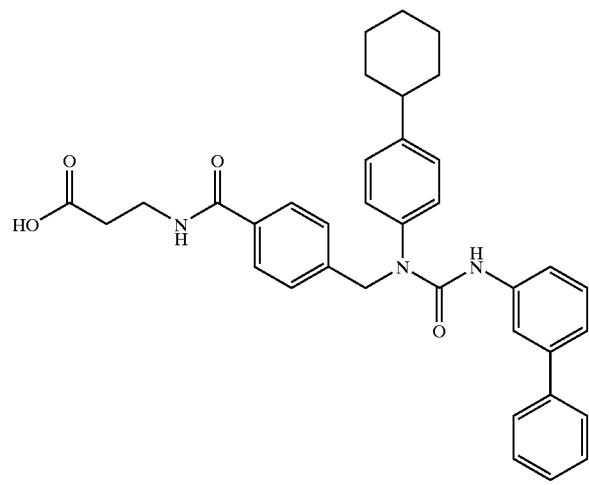

-continued
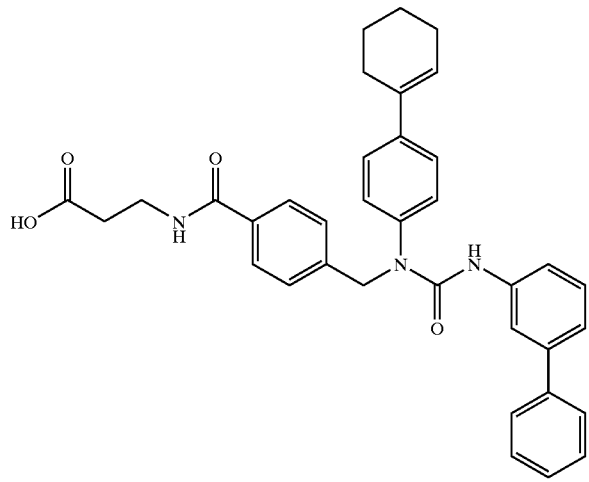
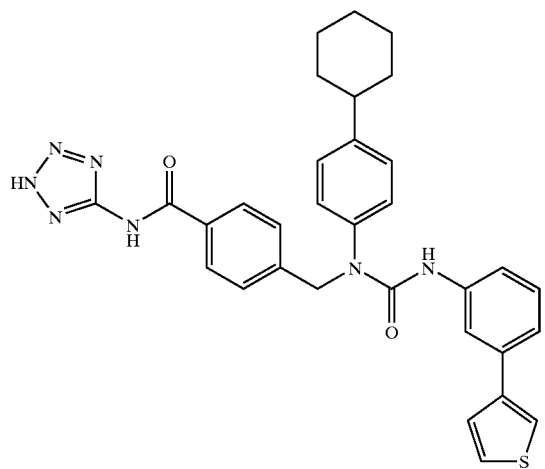
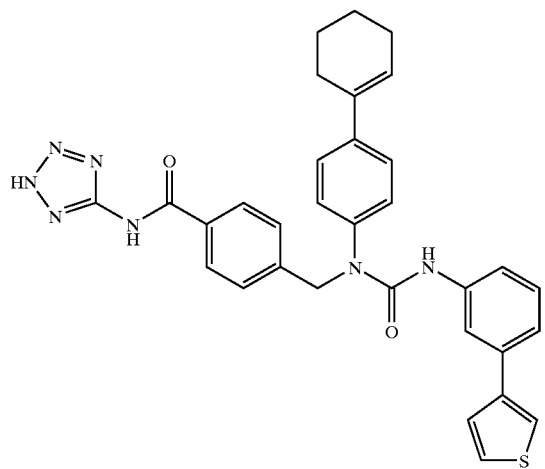

-continued
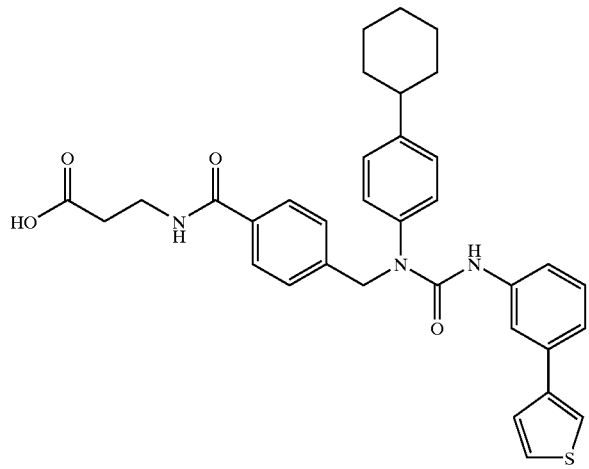
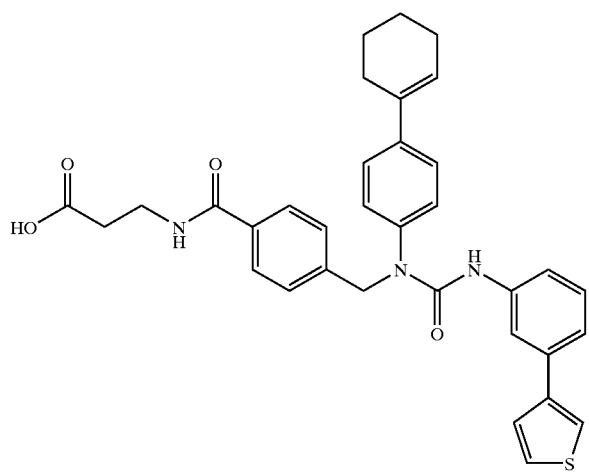
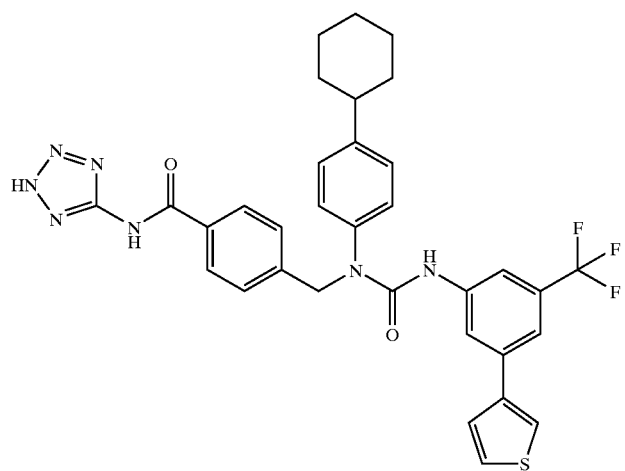

-continued
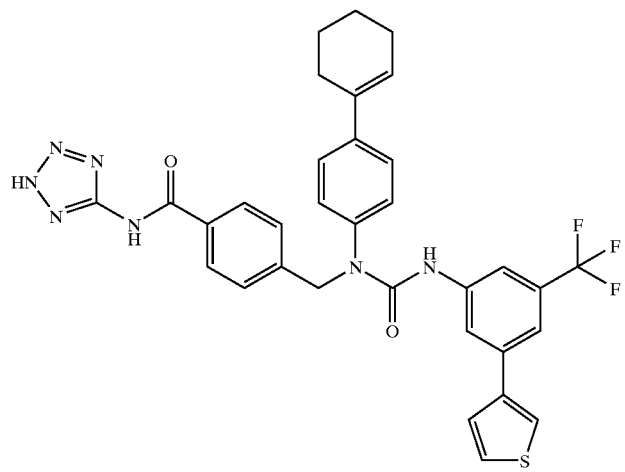
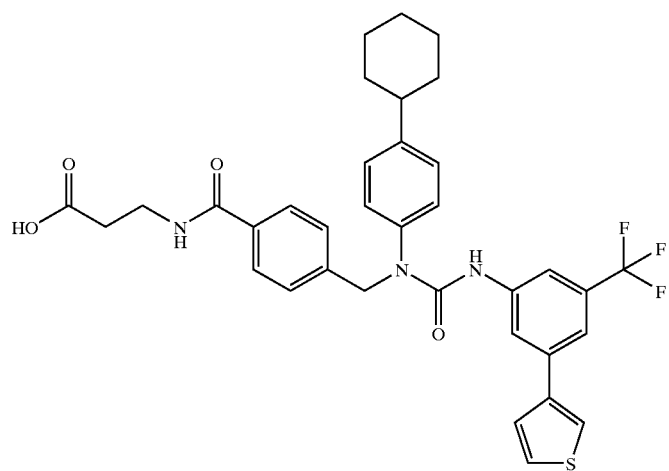
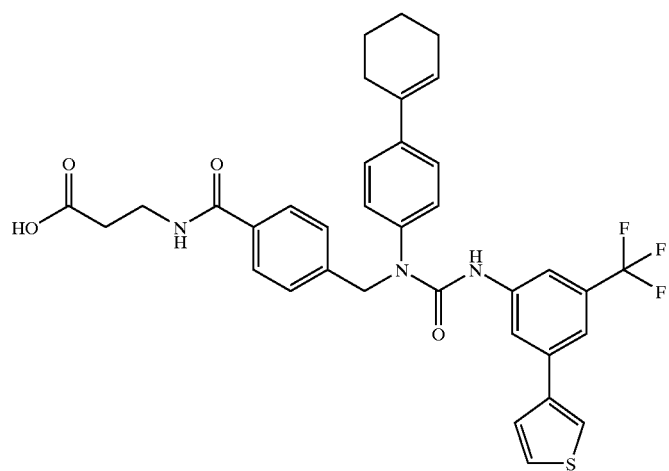

-continued
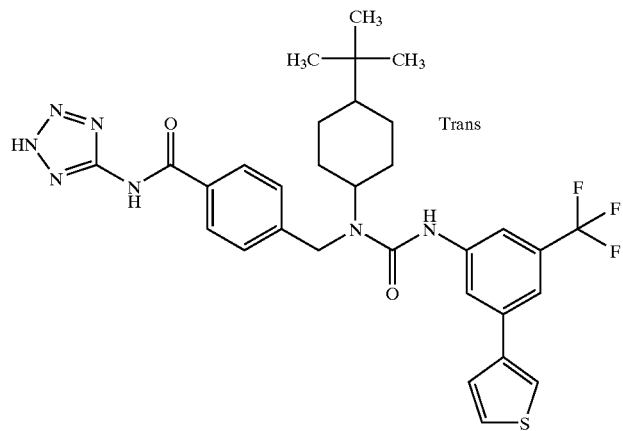
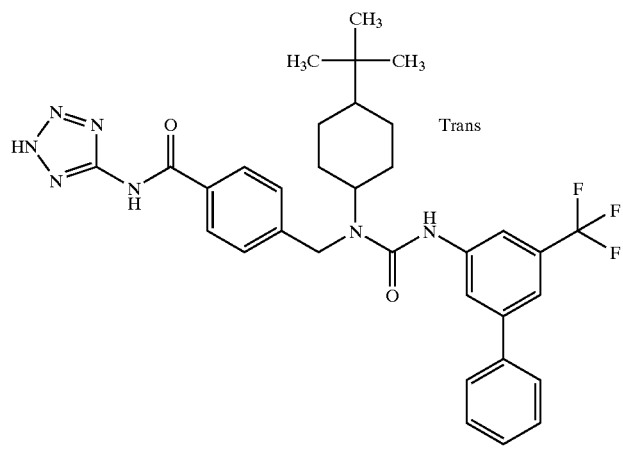
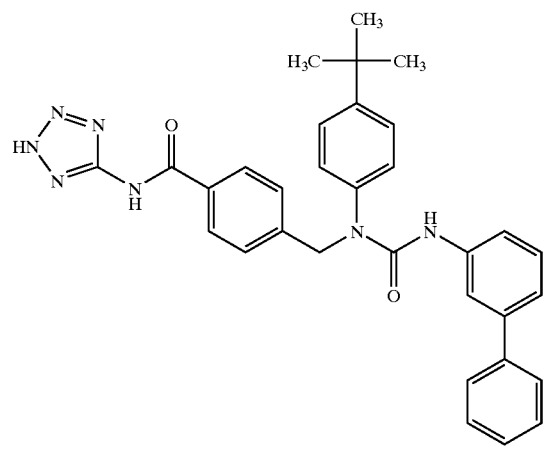

-continued
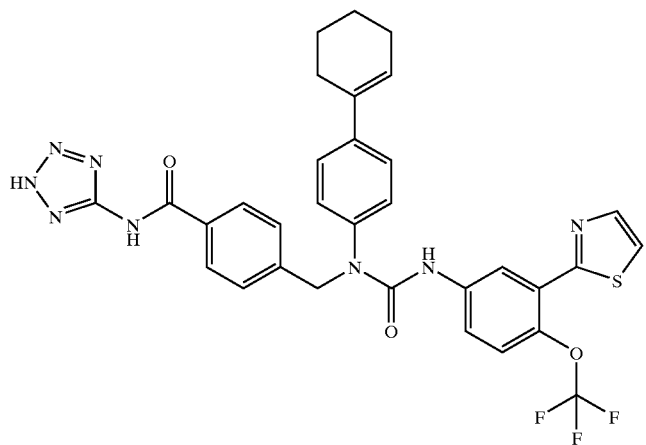
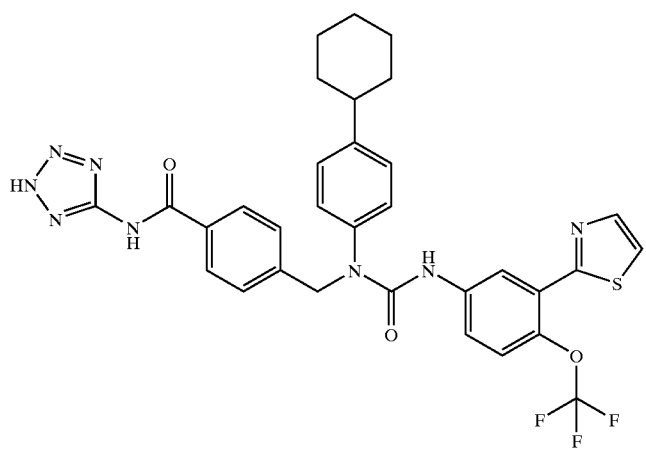
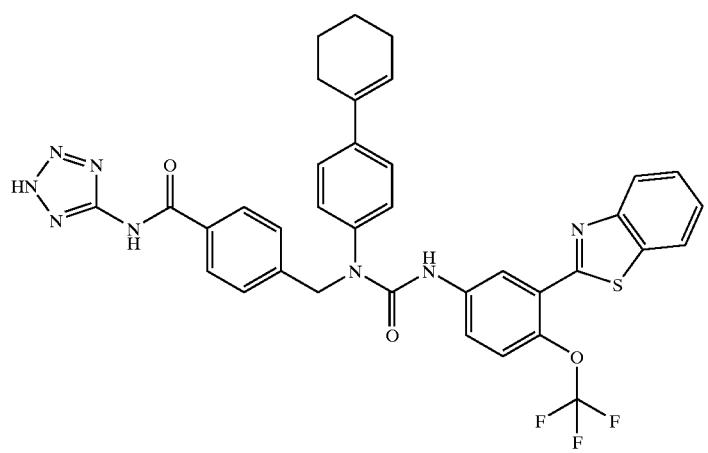

-continued
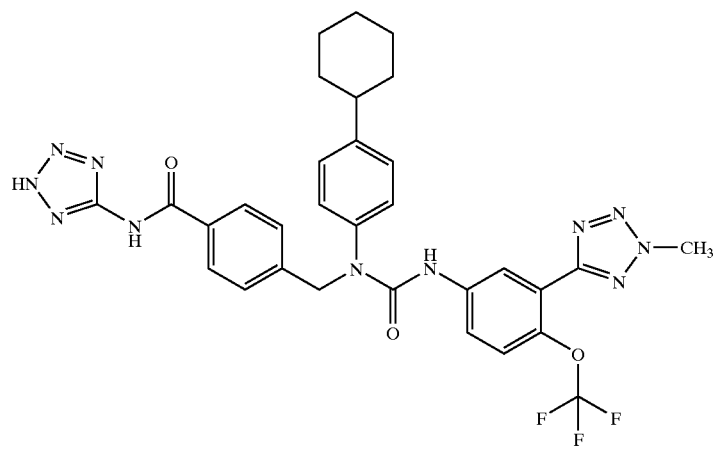
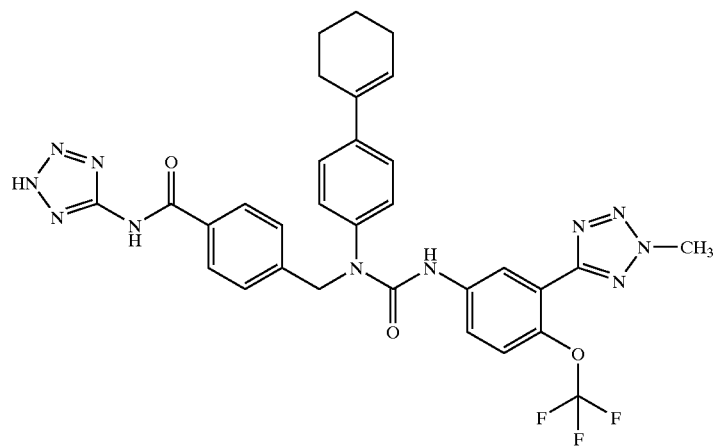
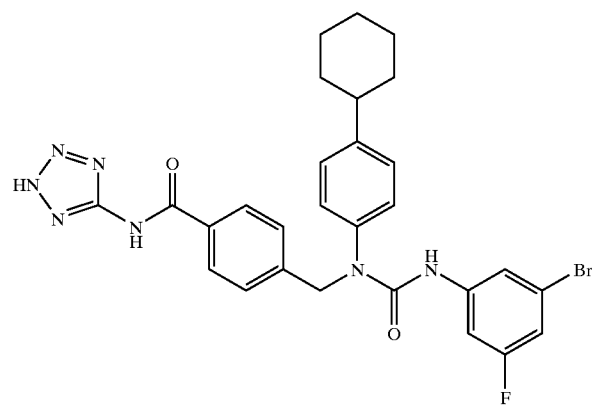

-continued
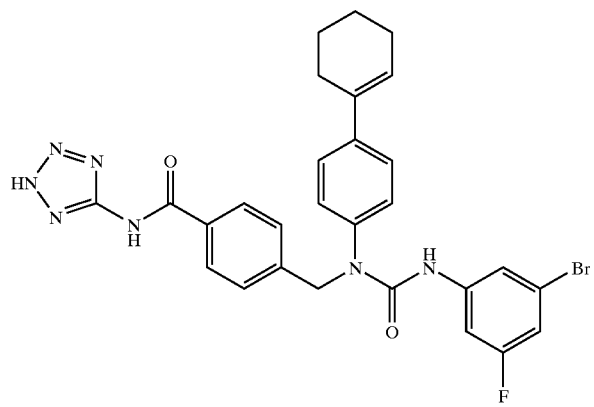
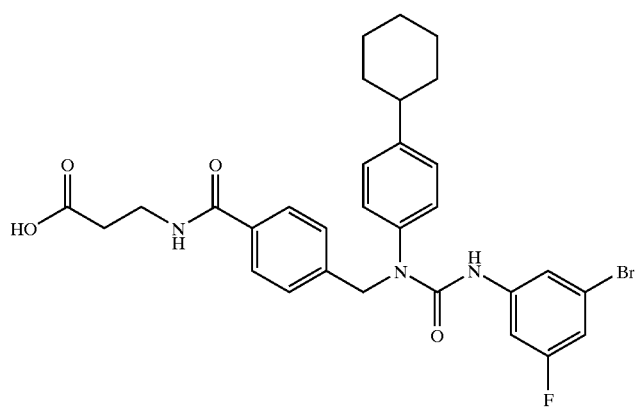
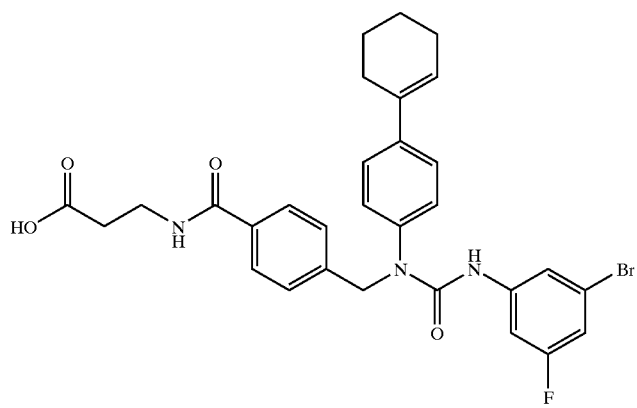
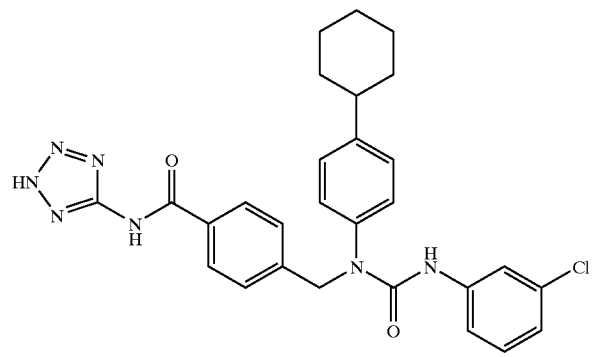

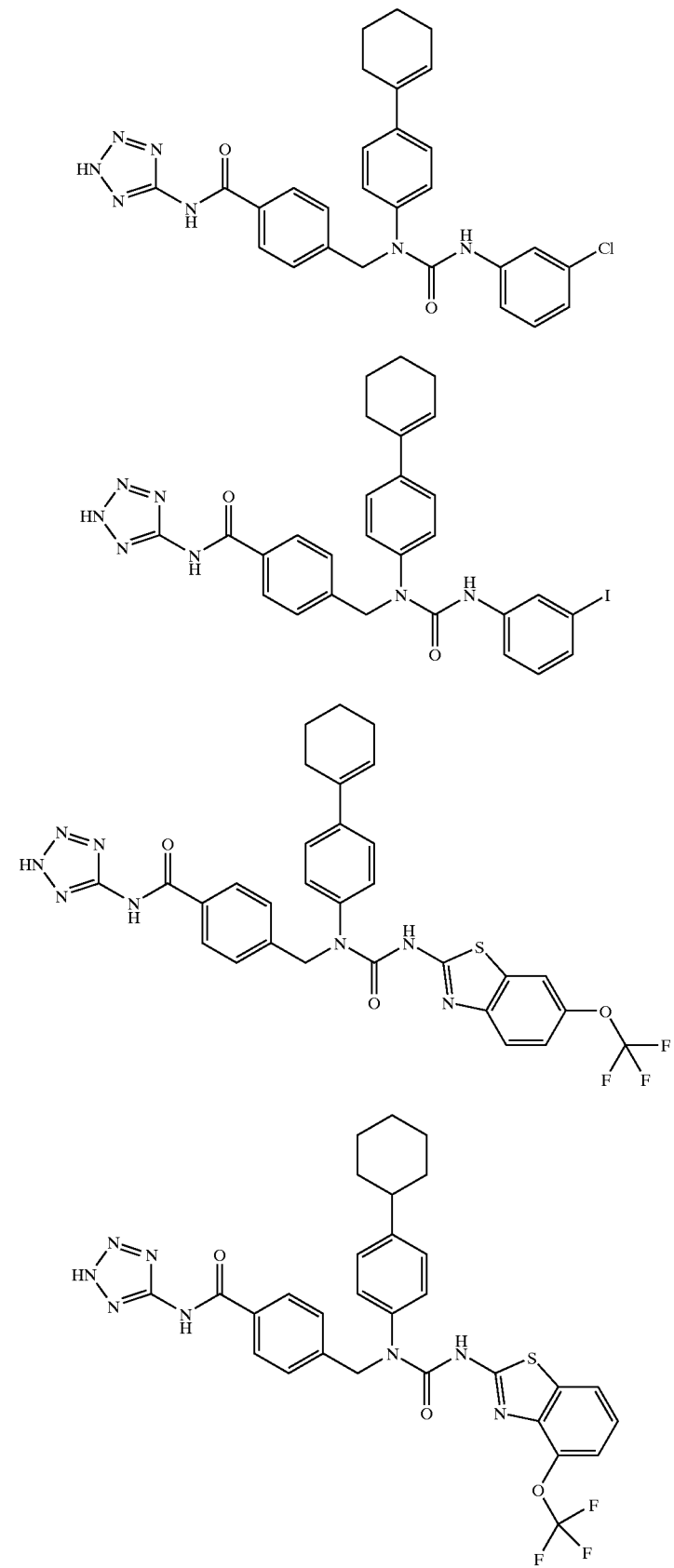

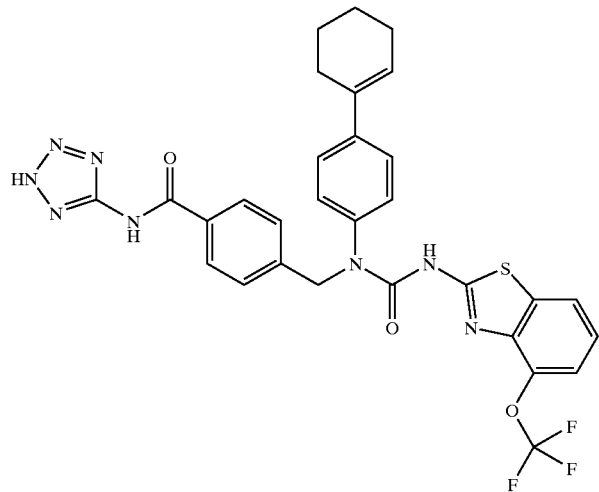
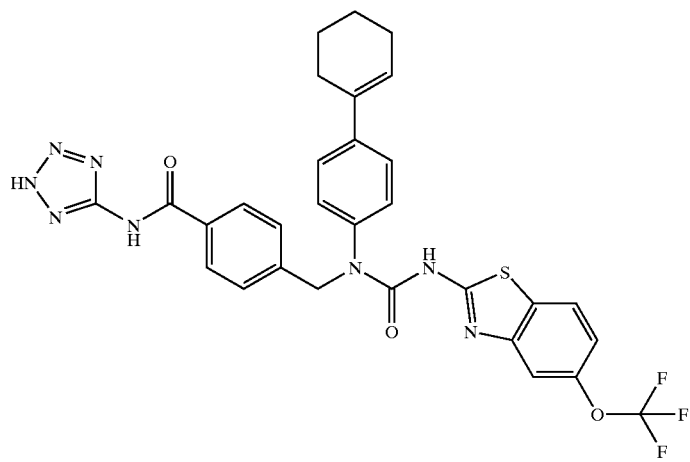
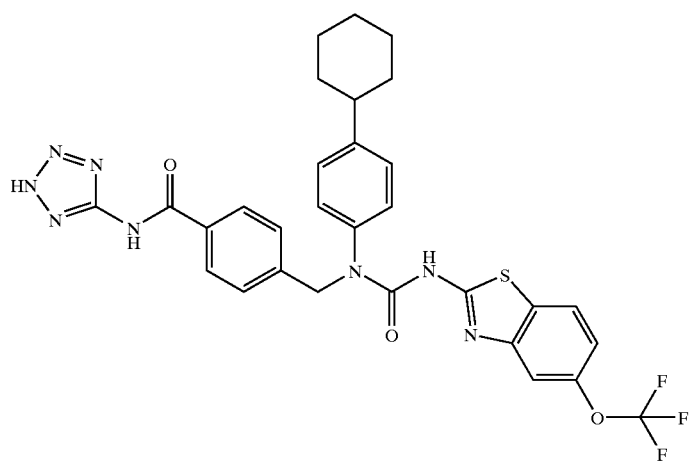

-continued
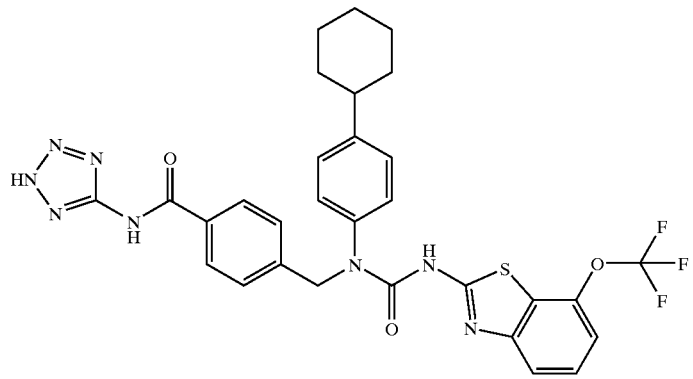
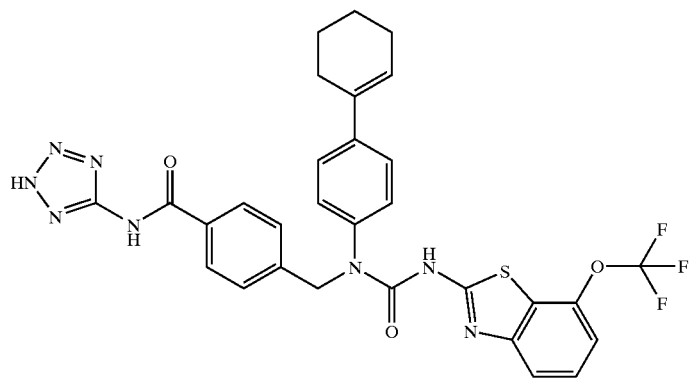
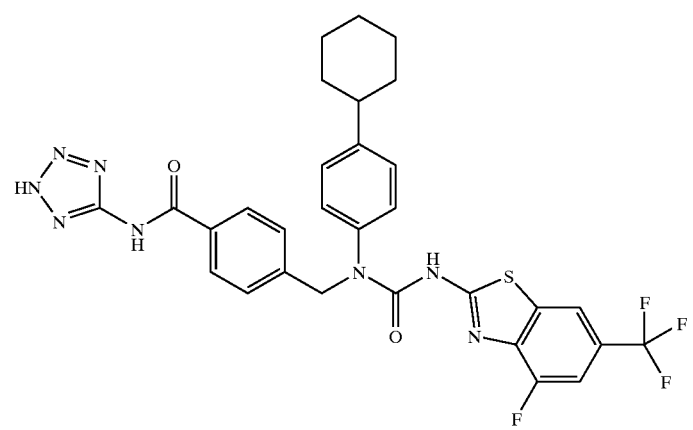
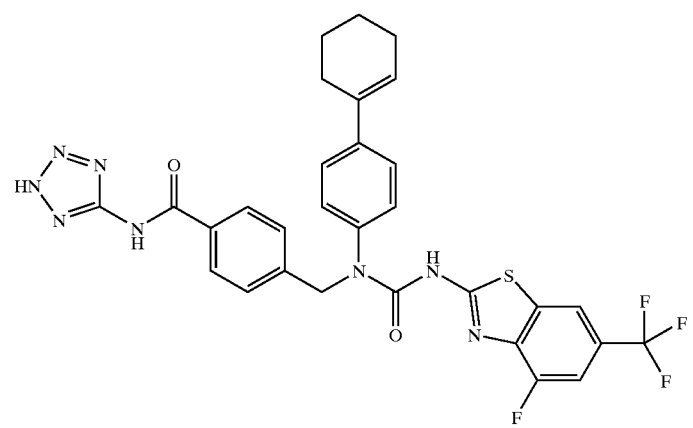

-continued
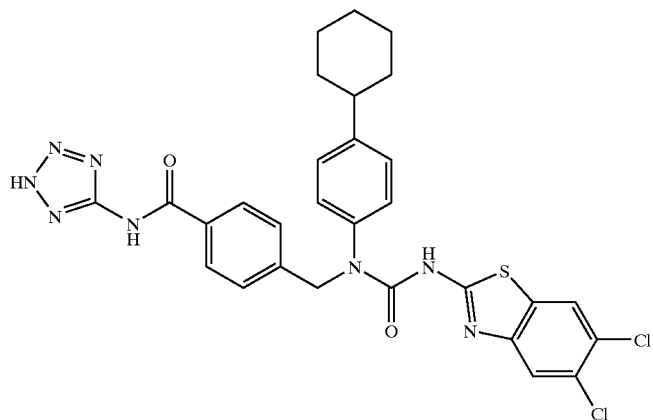
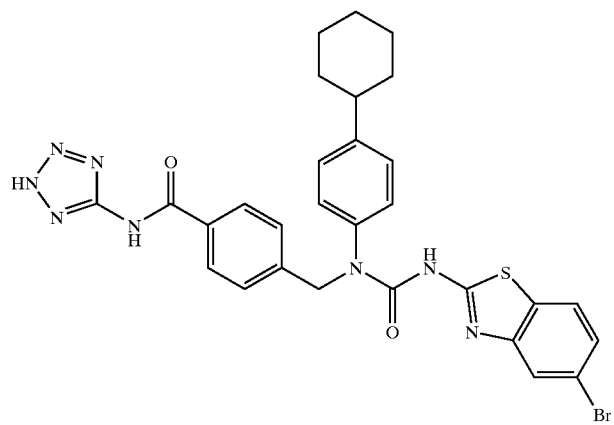
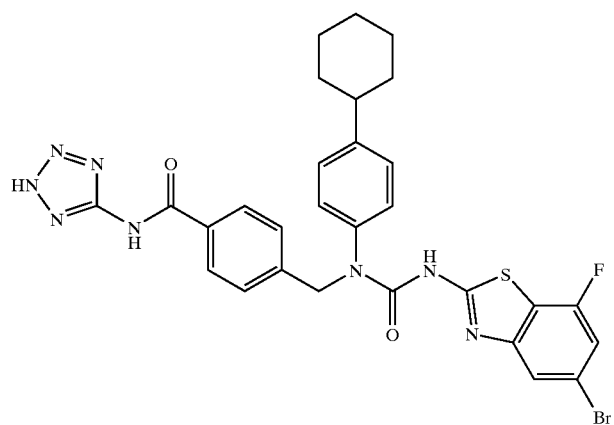

-continued
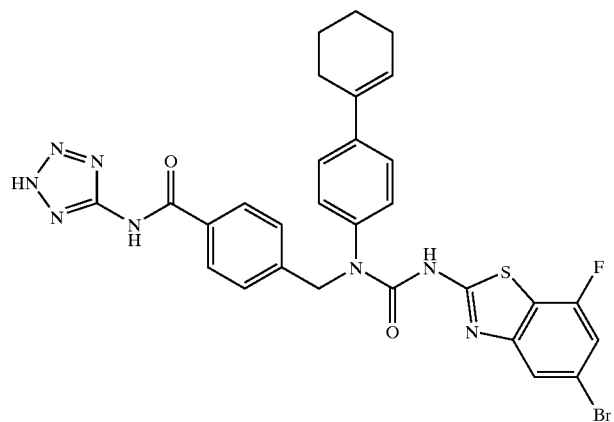
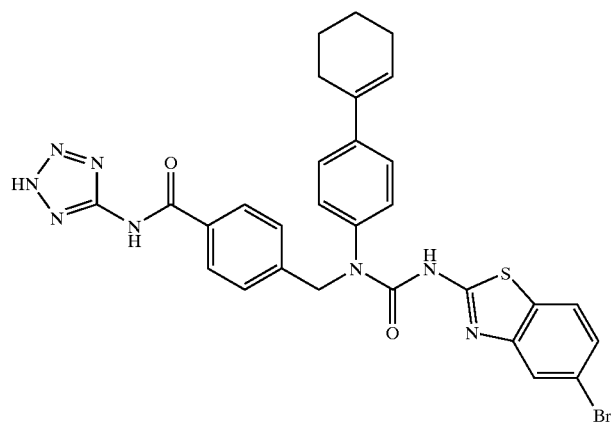
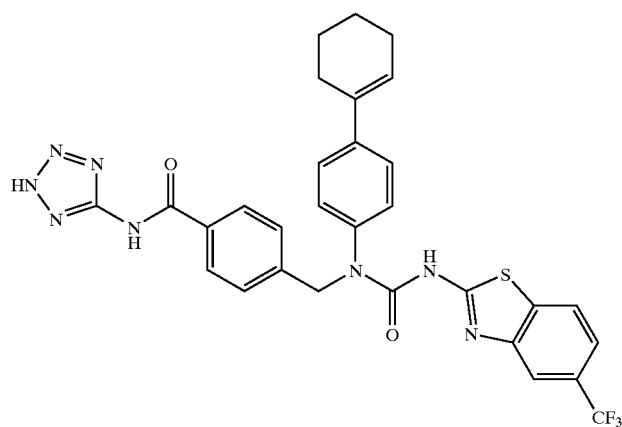

-continued
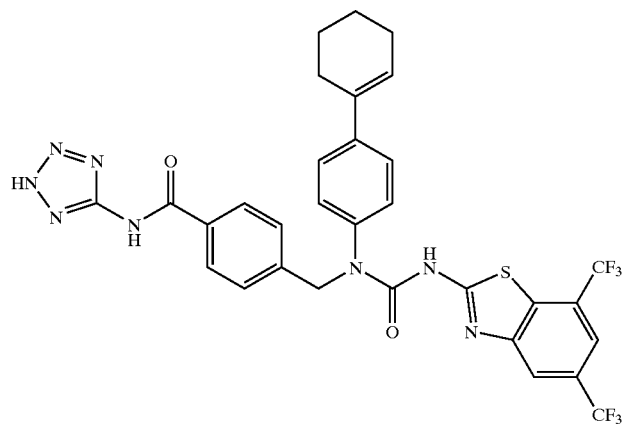
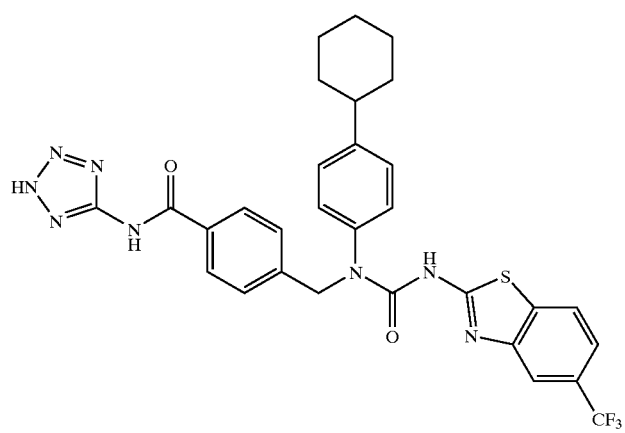
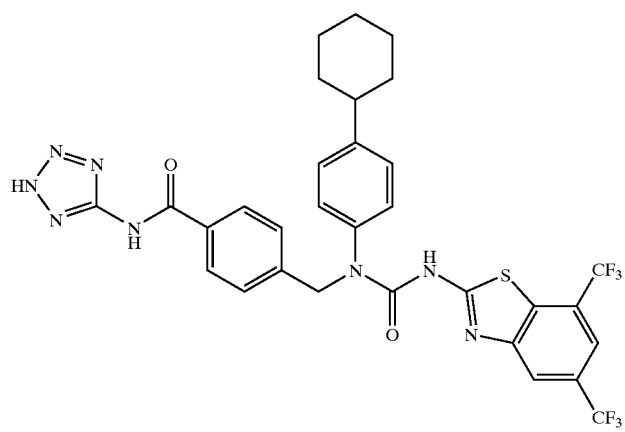

-continued
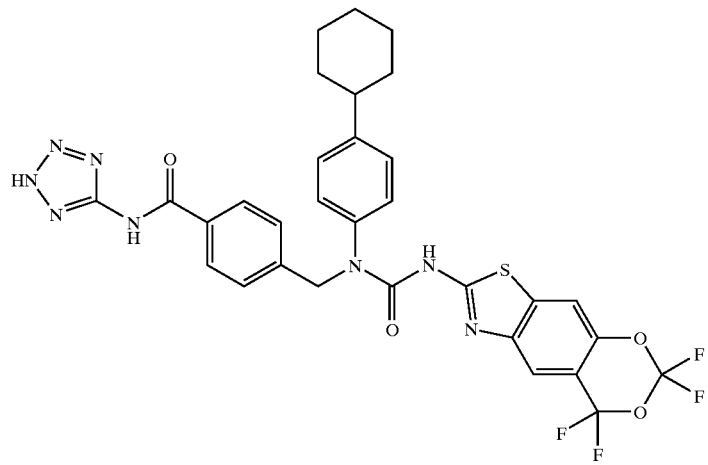
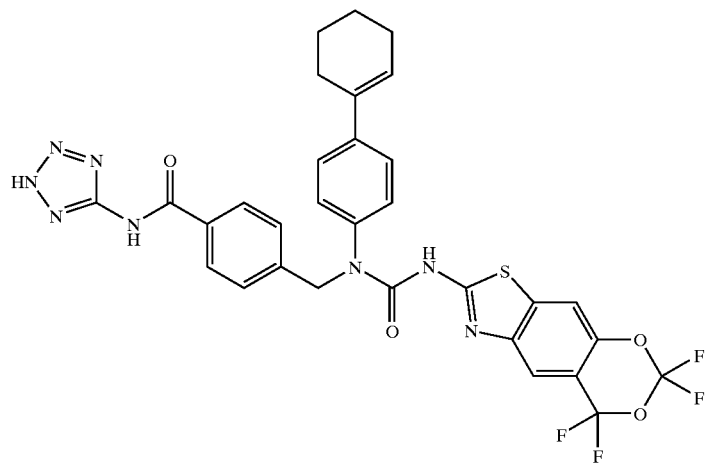
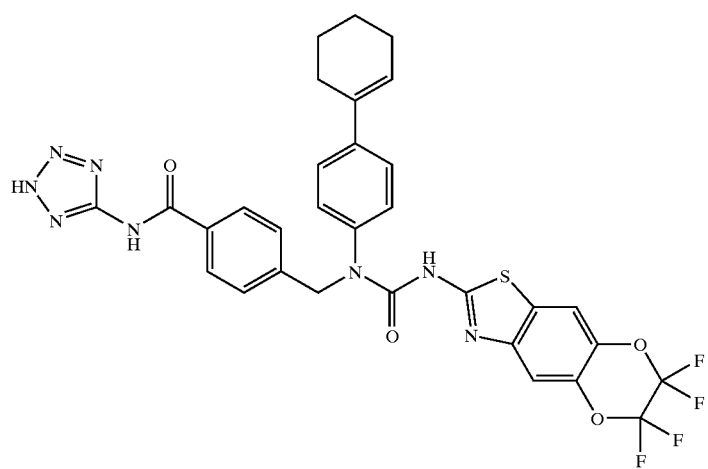

-continued
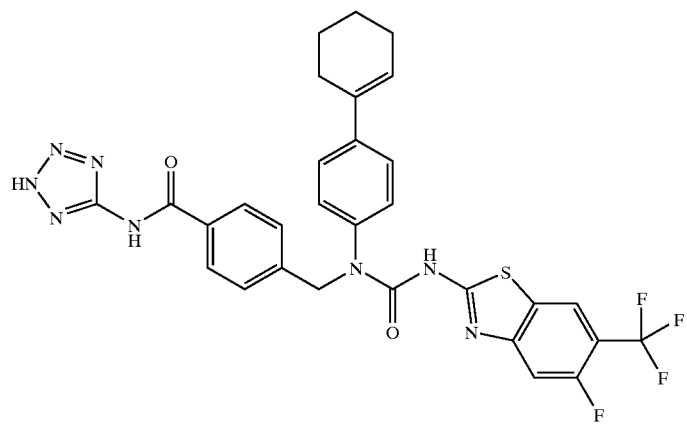
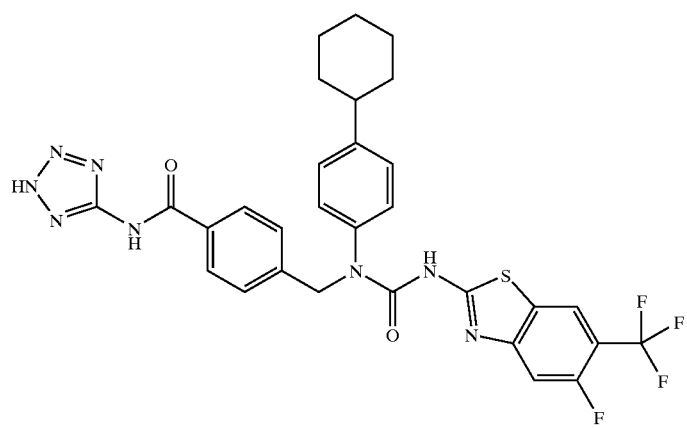
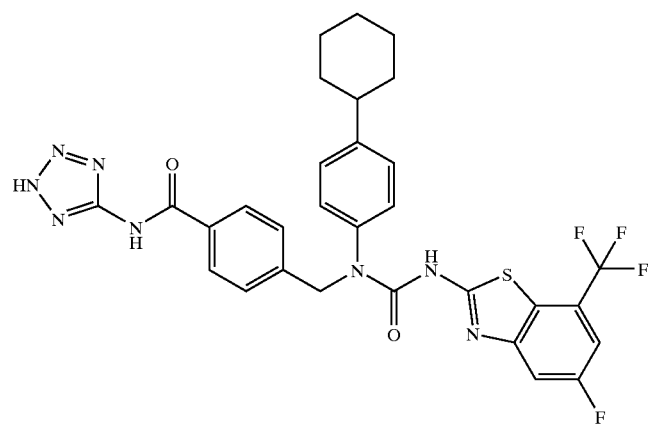

-continued
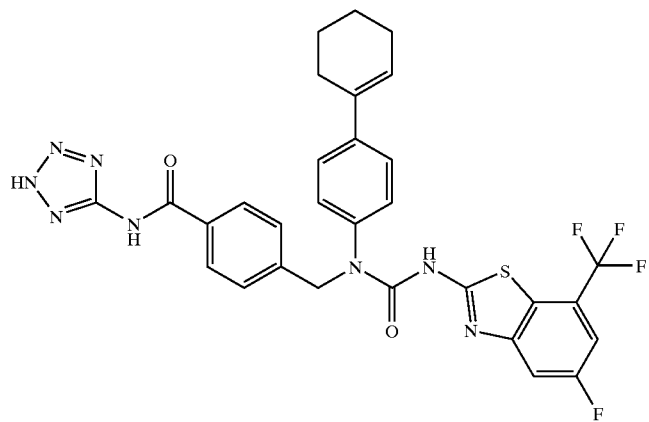
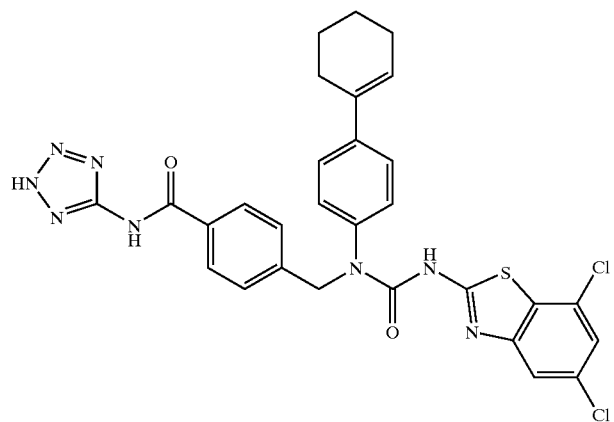
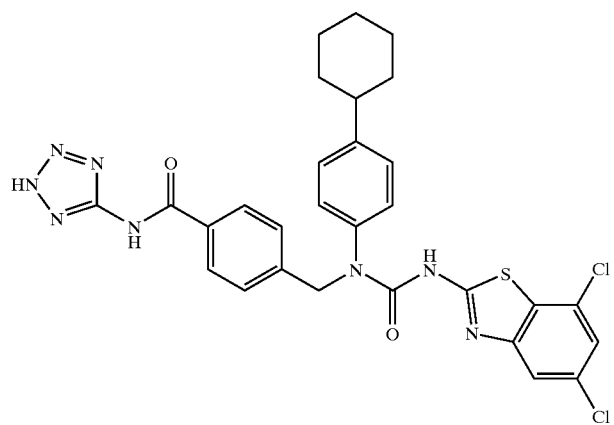

-continued
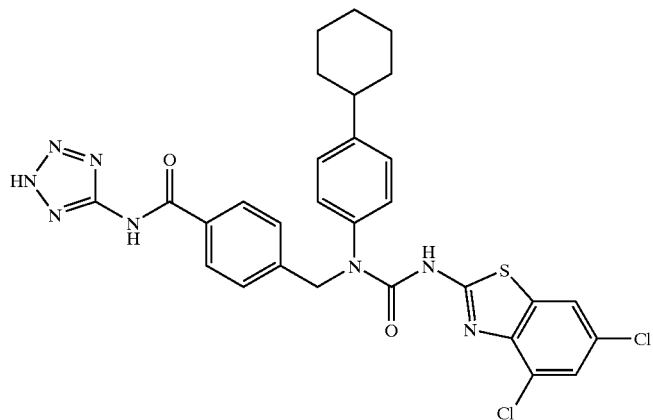
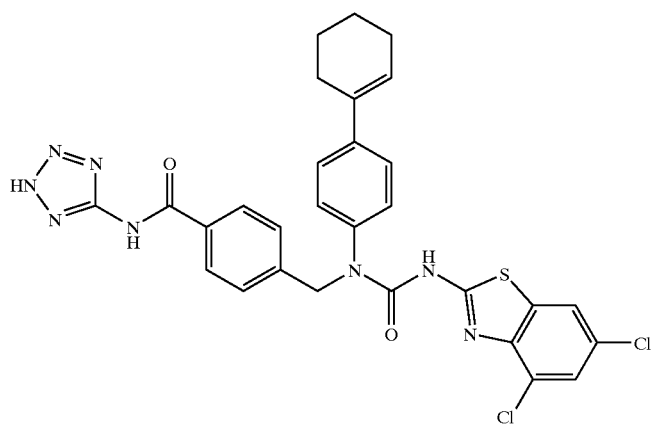
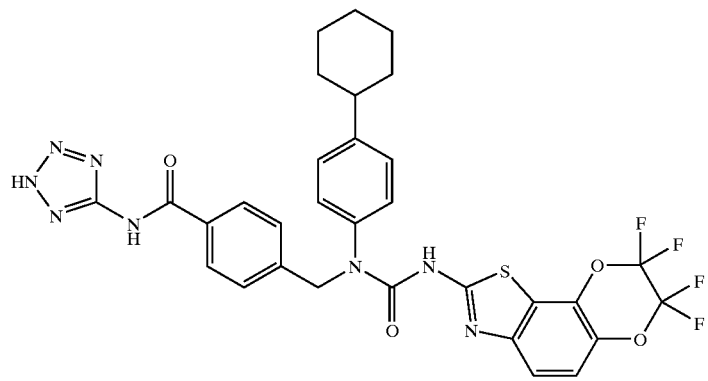
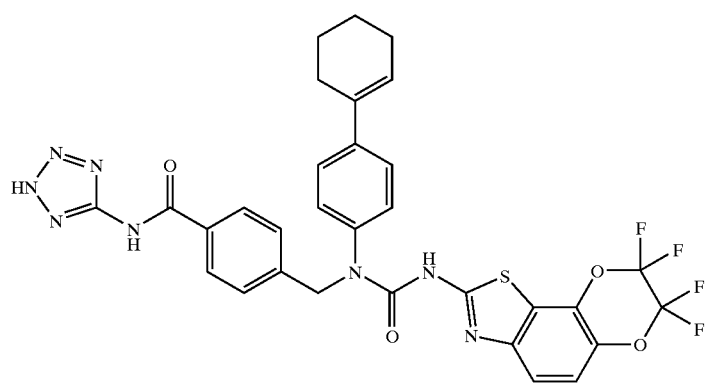

-continued
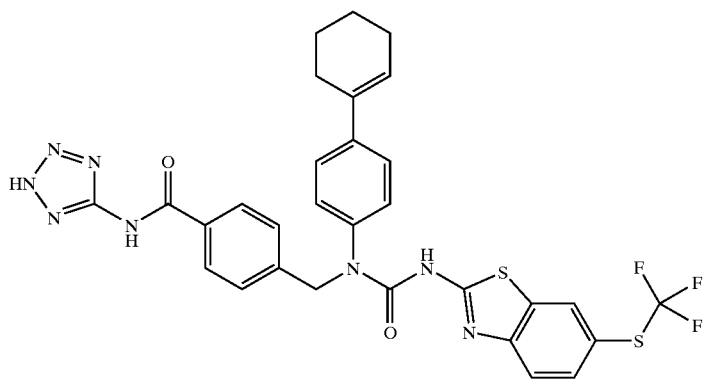
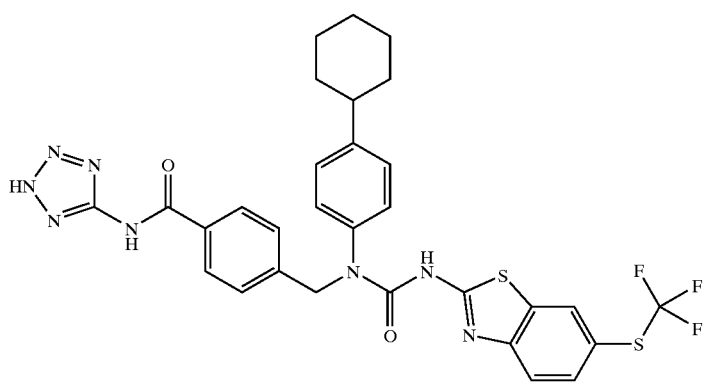
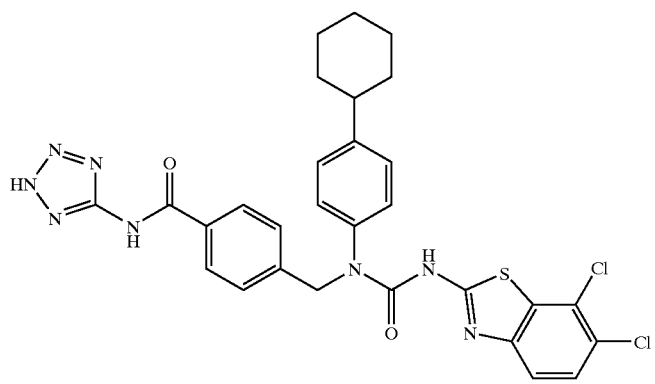
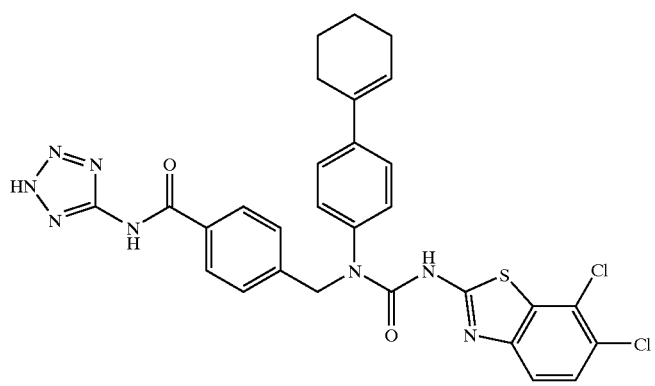

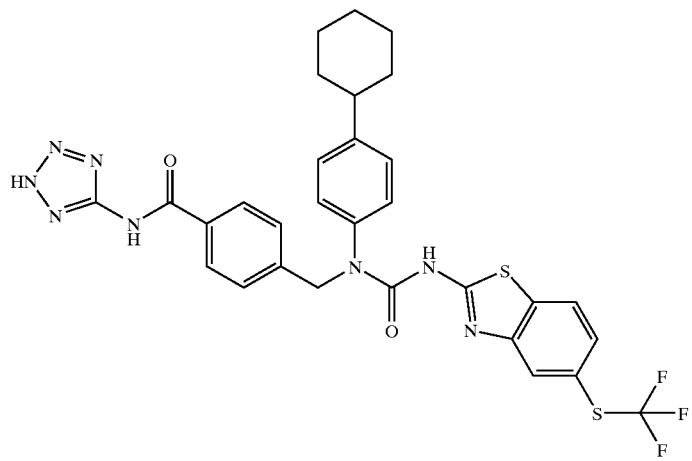
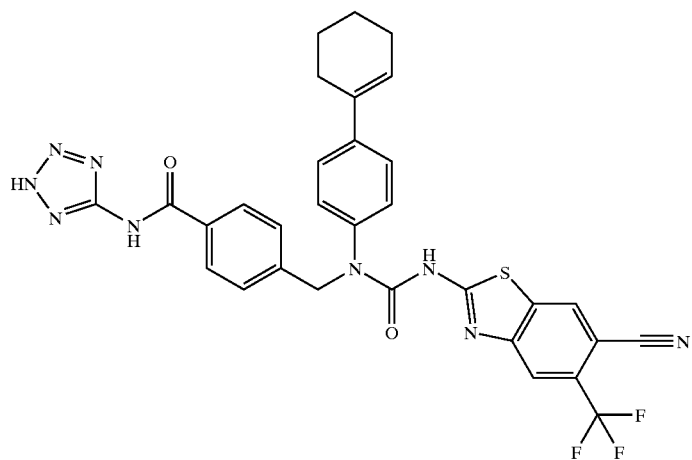
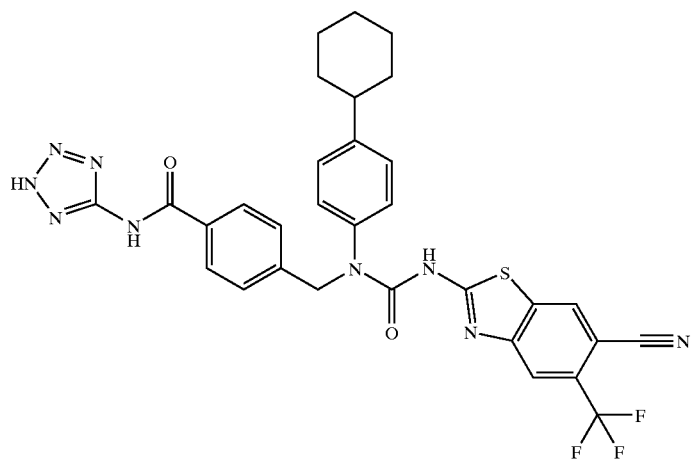

-continued
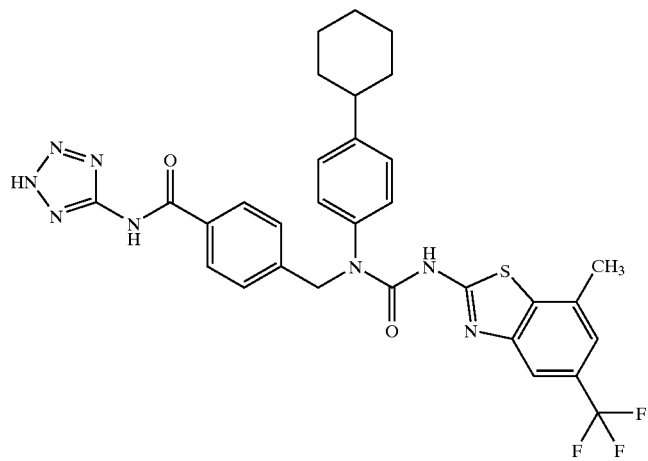
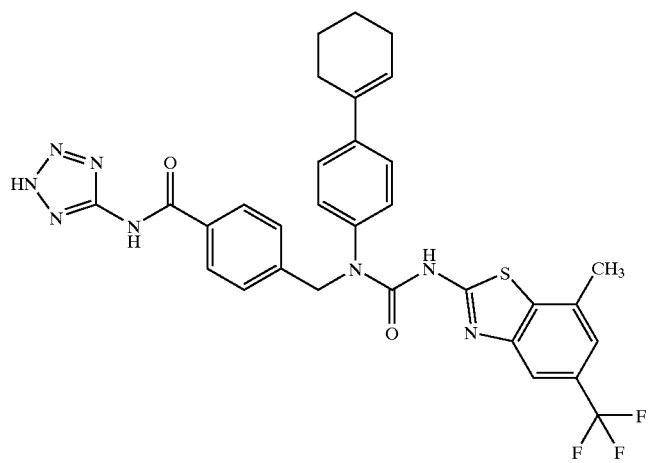
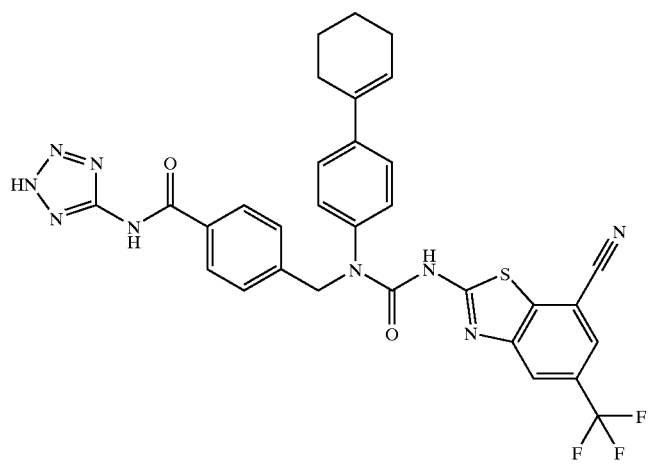

-continued
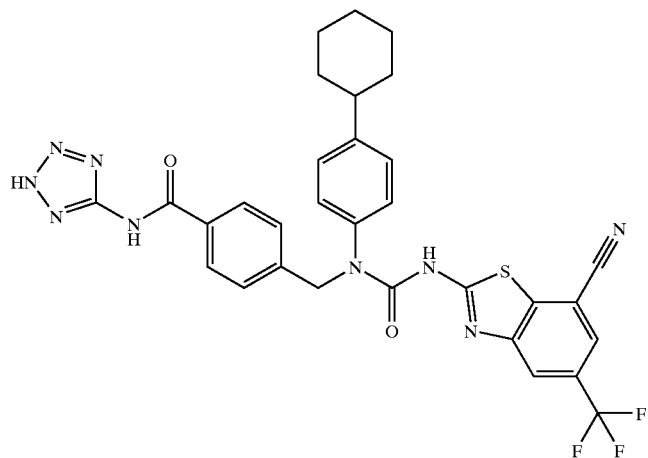
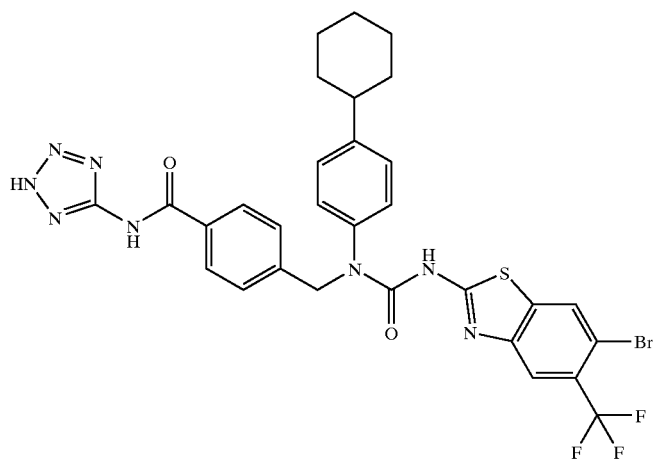
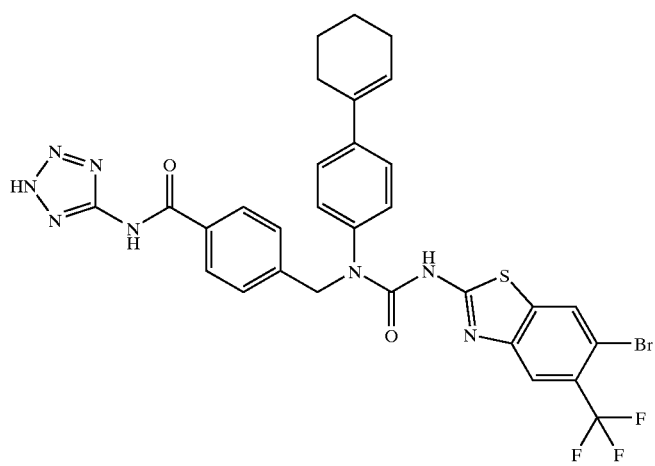

-continued
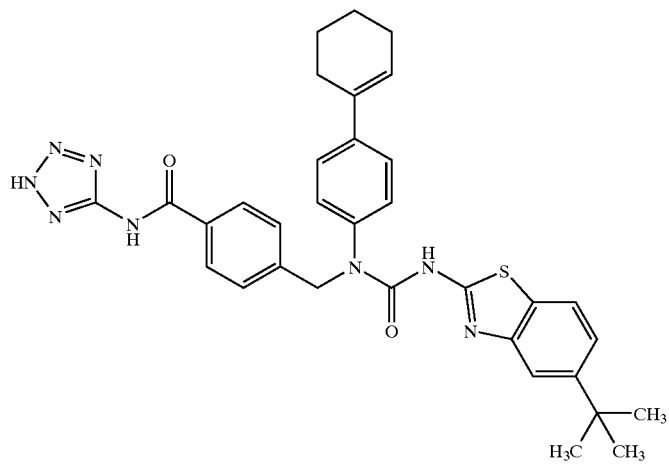
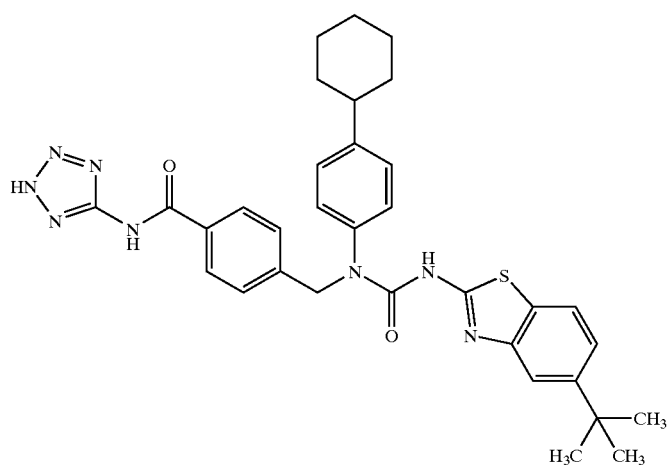
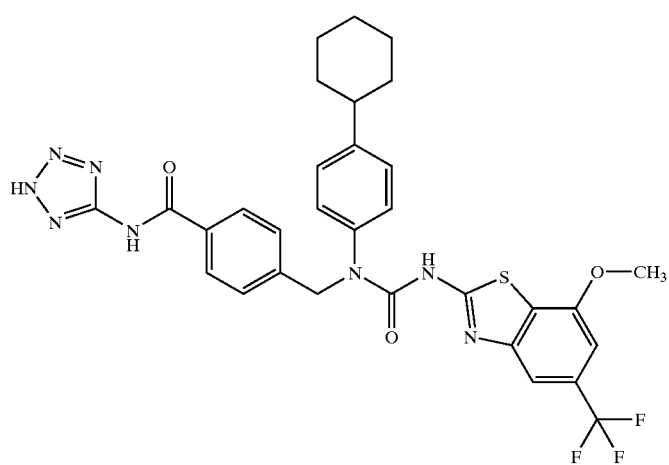

-continued
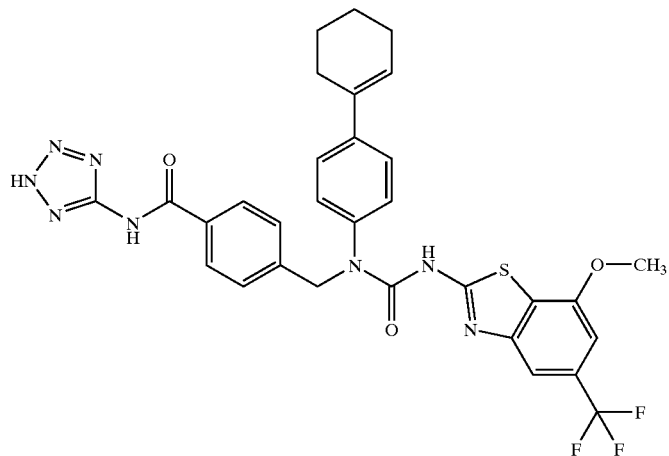
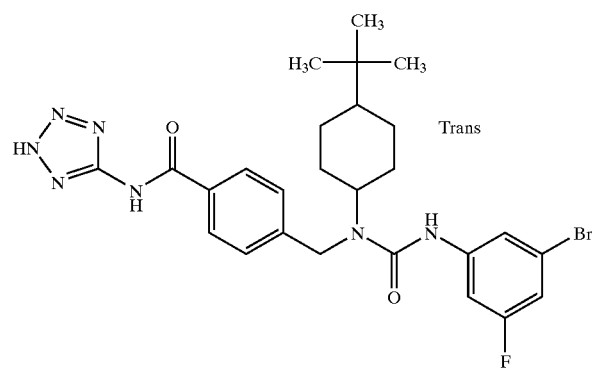
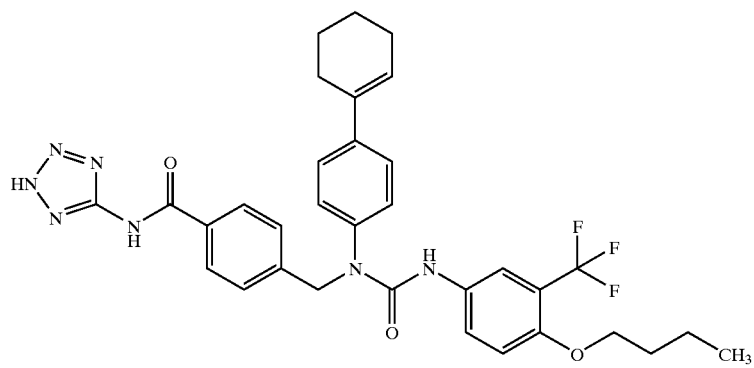
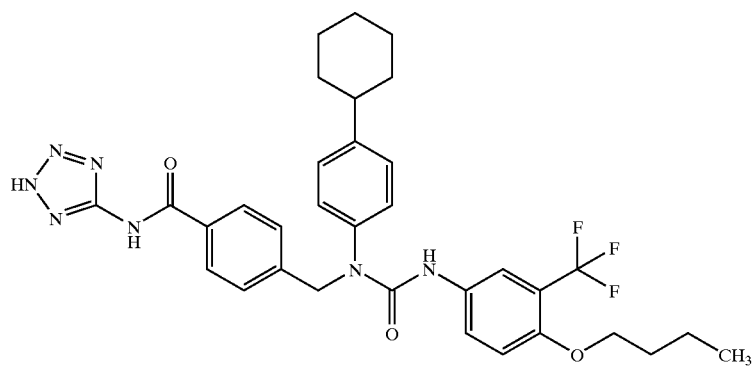

-continued
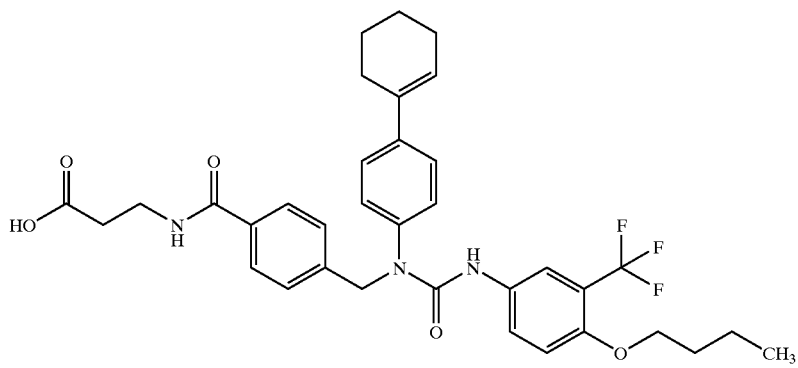
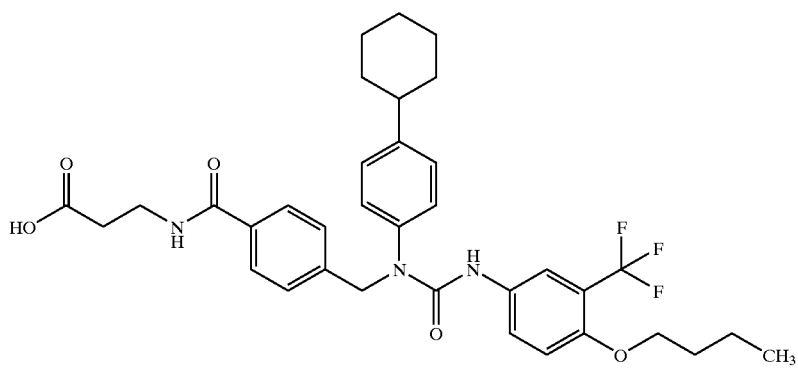
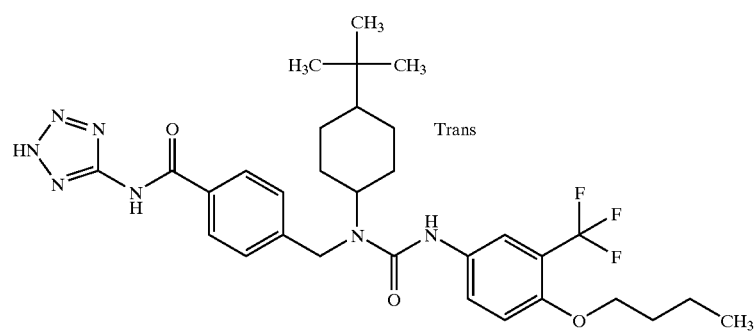
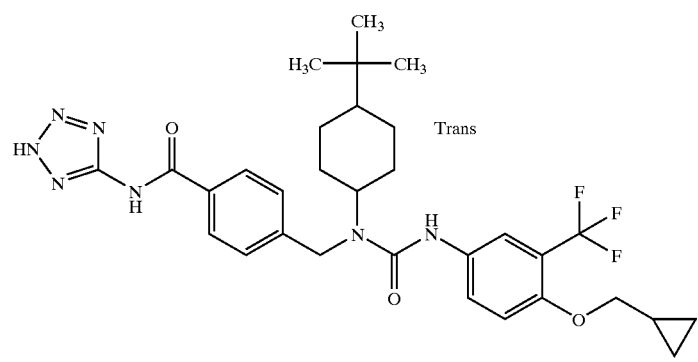

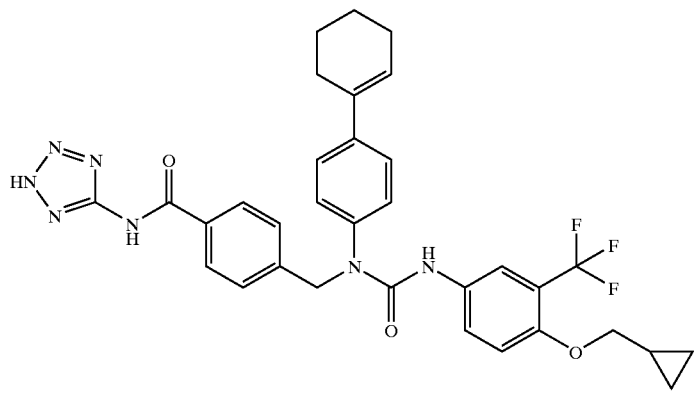
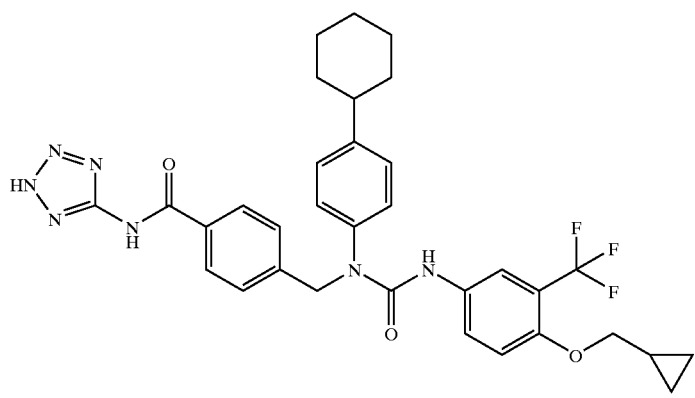
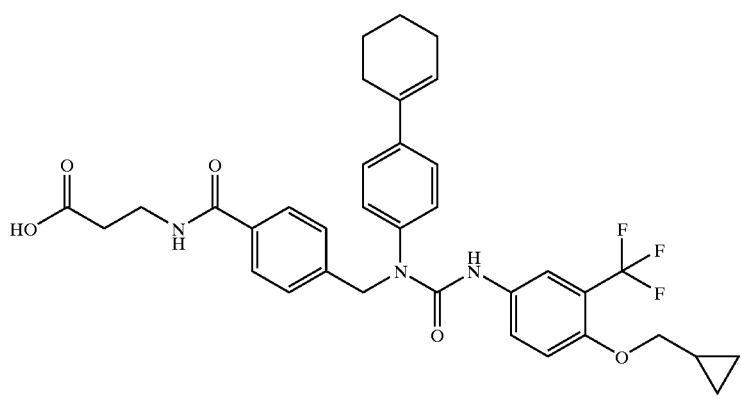
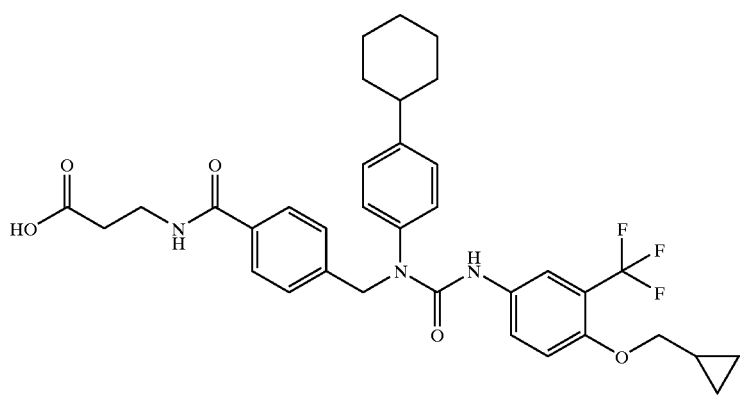

-continued
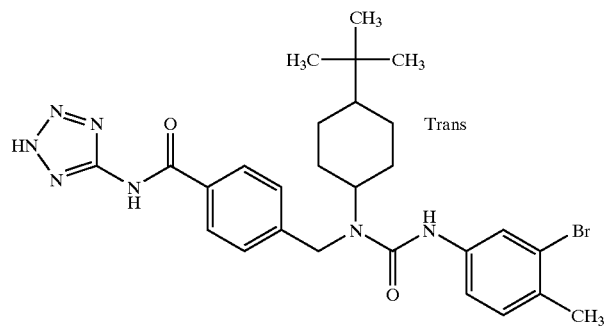
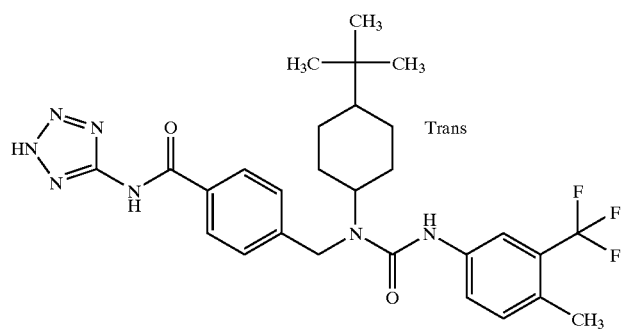
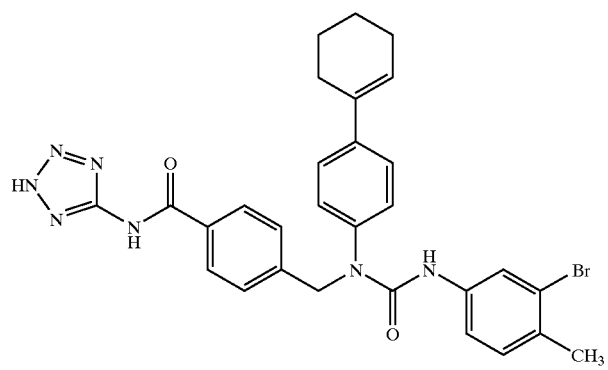
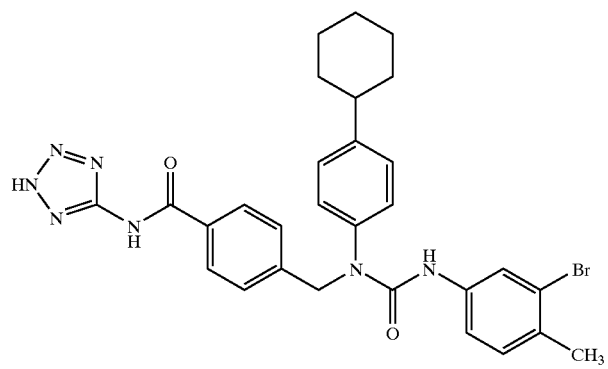

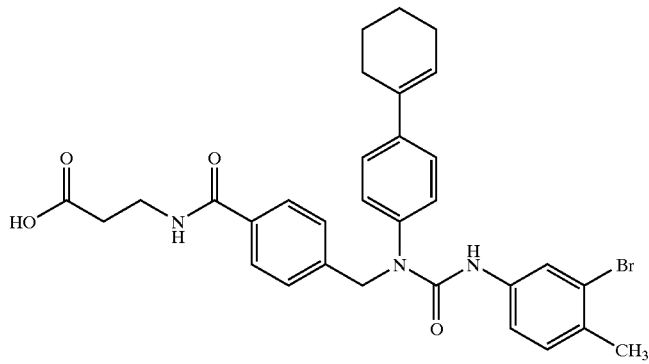
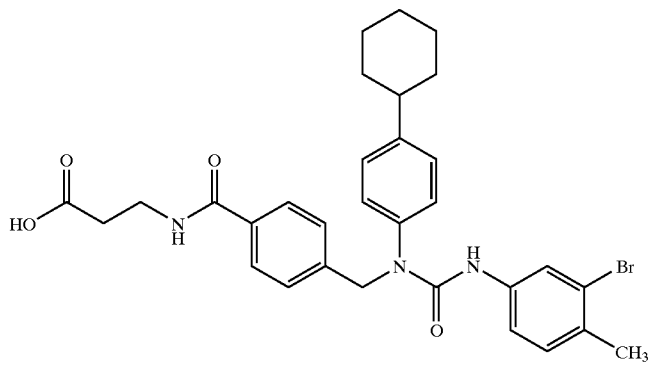
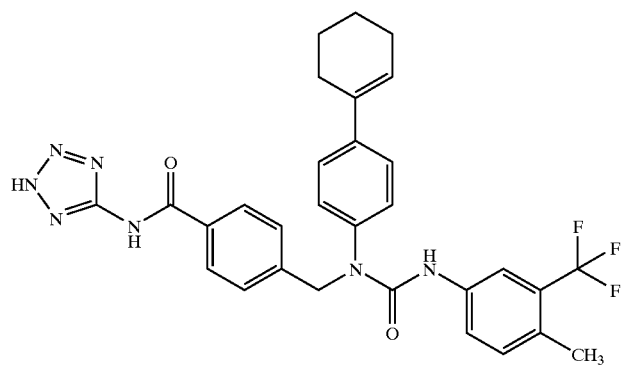
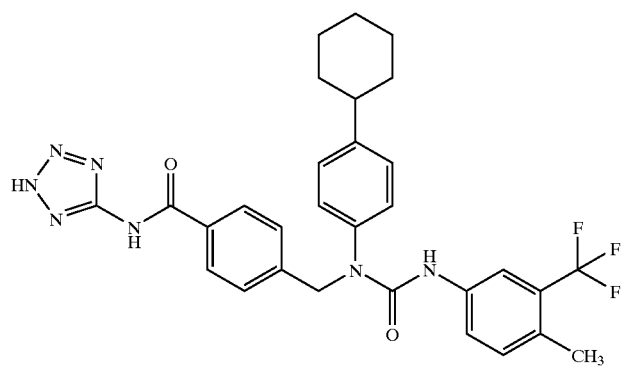

-continued
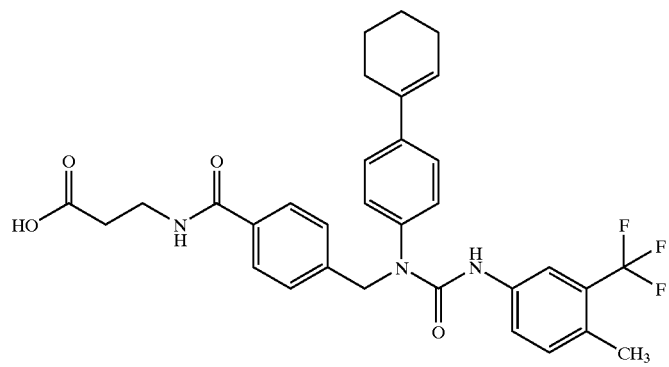
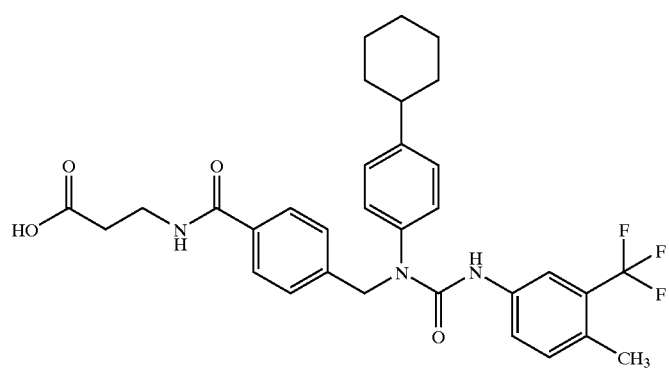
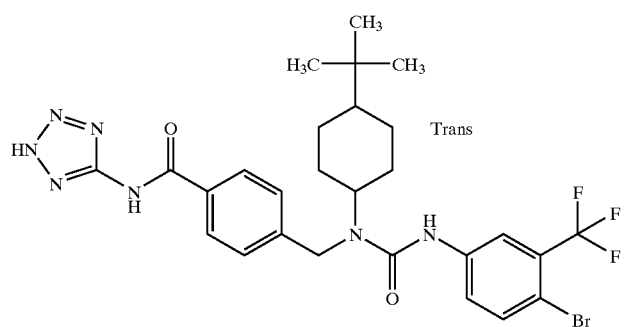
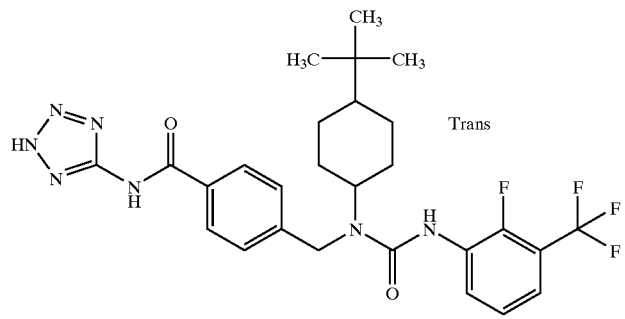

-continued
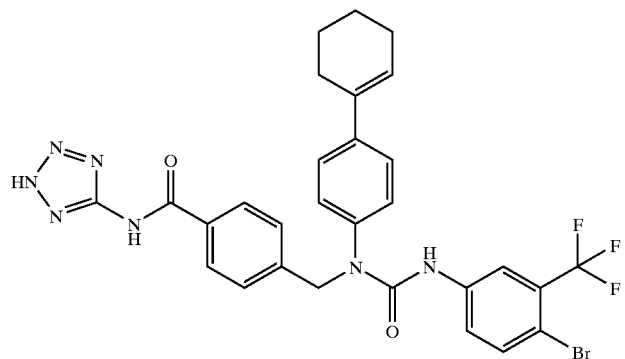
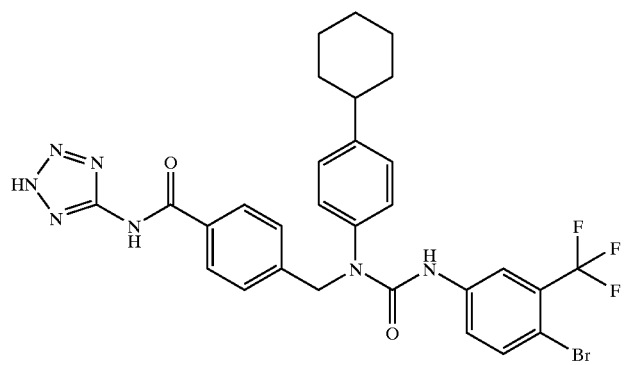
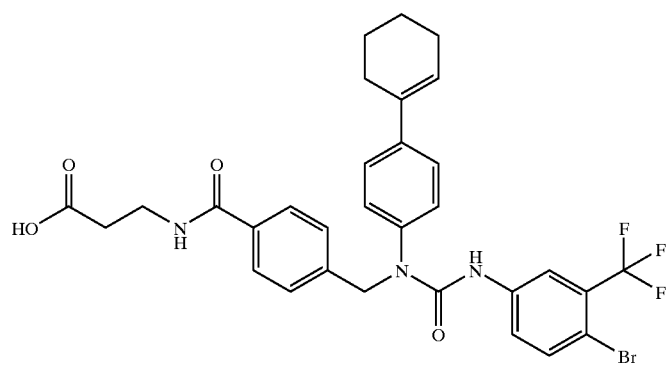
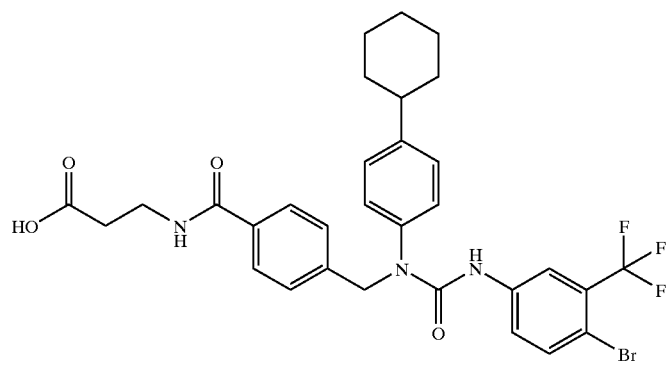

-continued
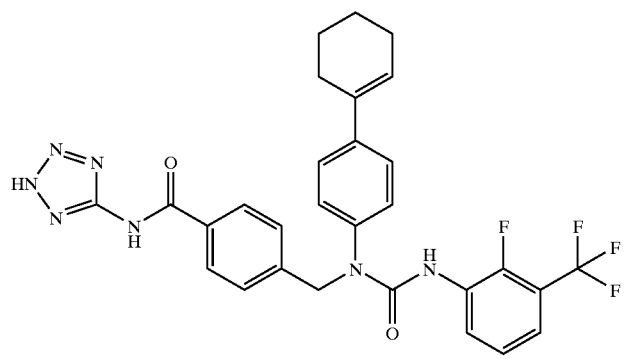
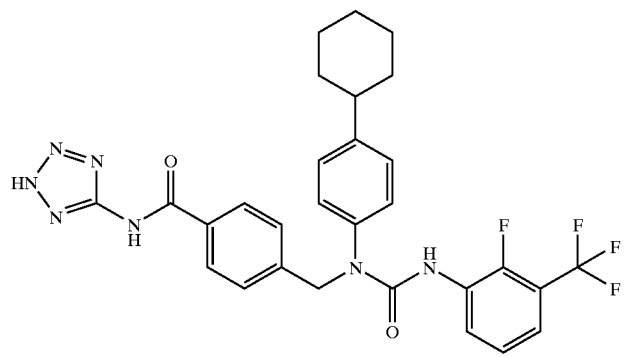
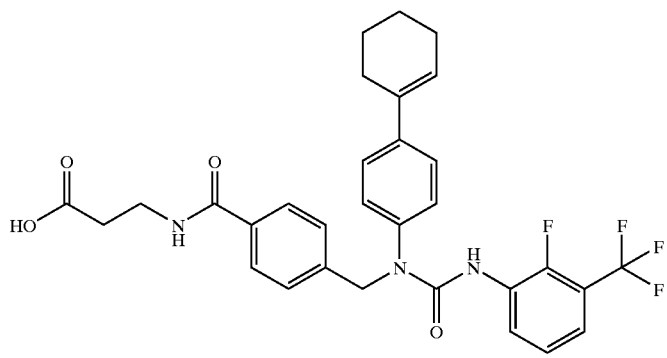
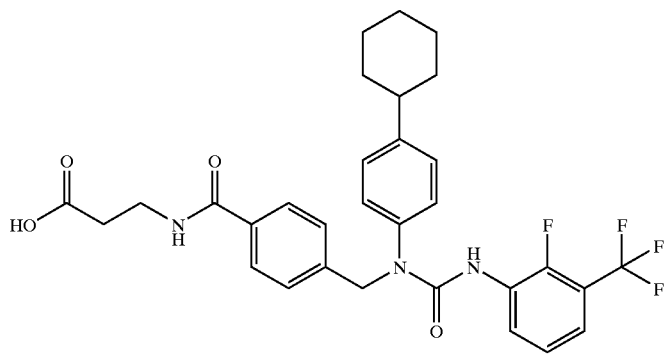

-continued
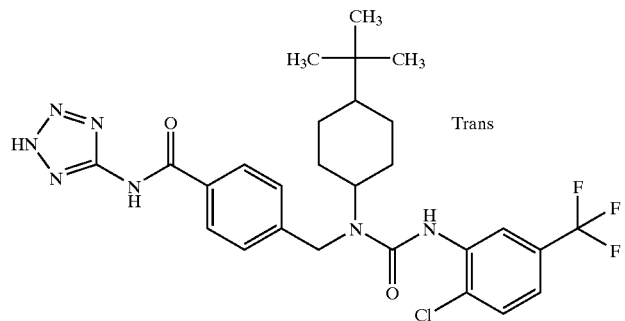
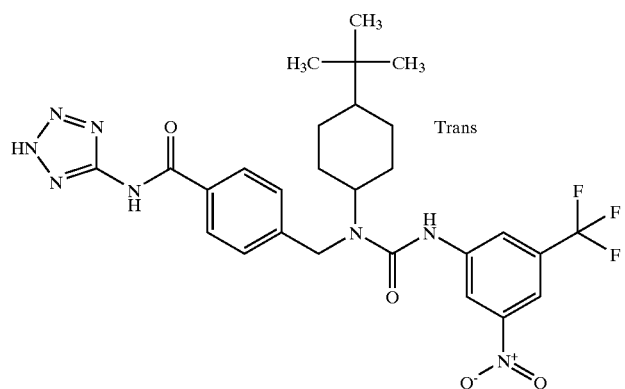
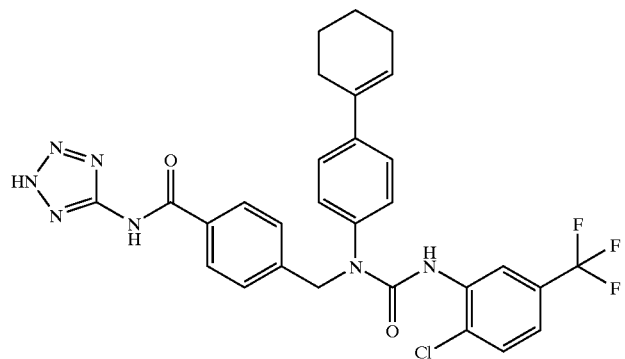
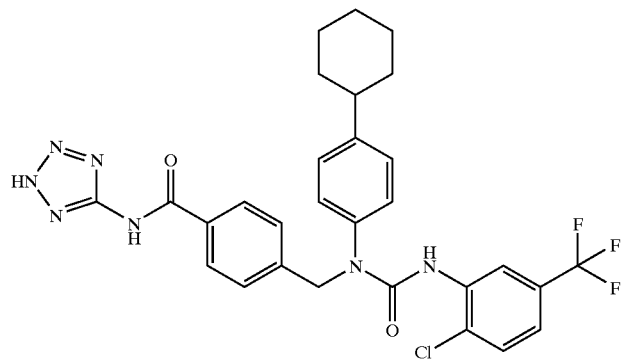

-continued
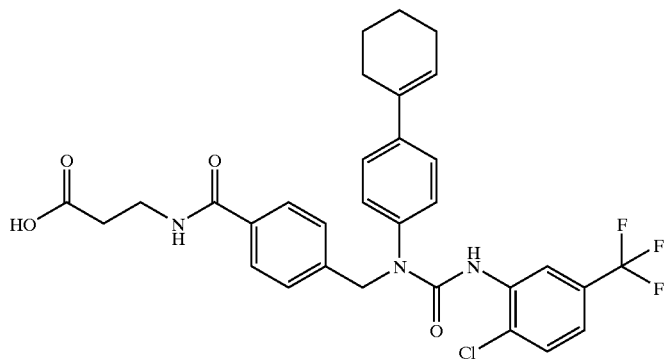
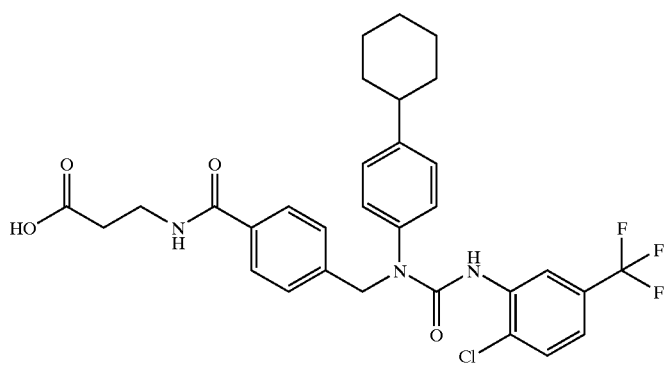
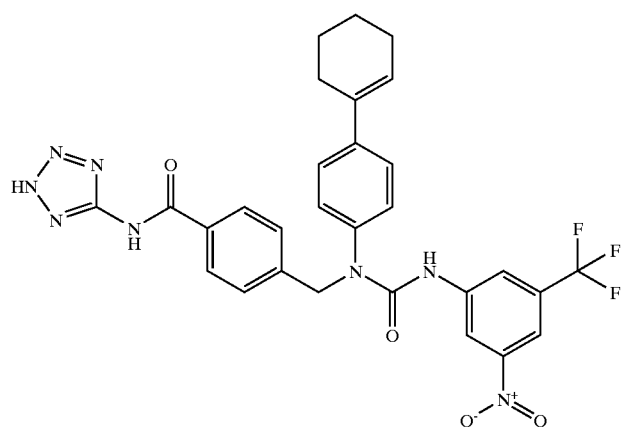
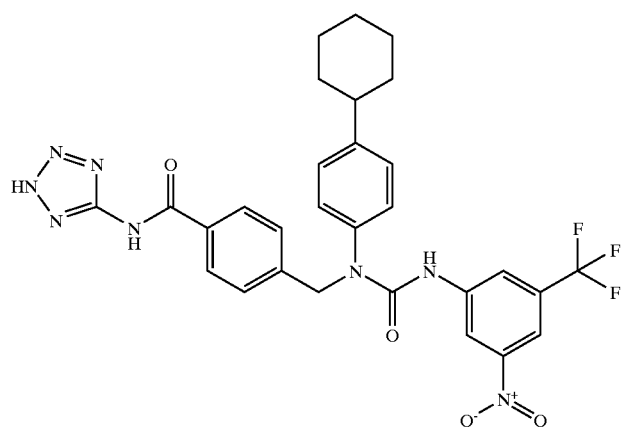

-continued
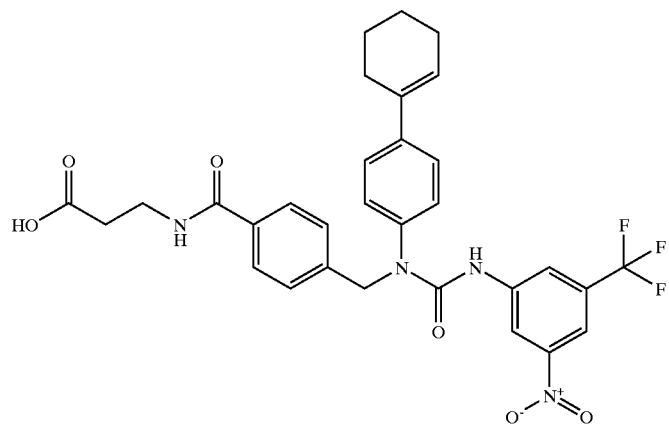
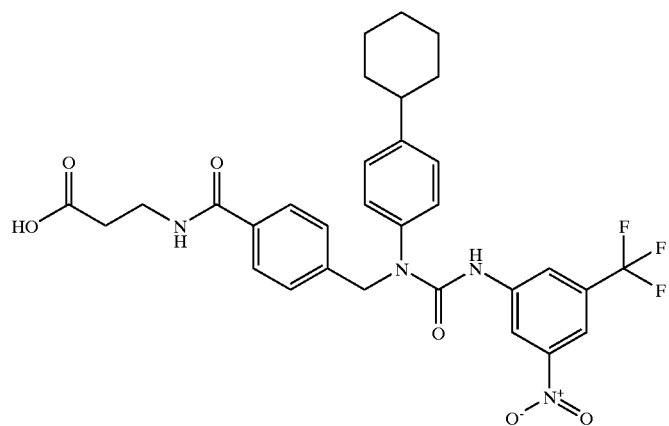
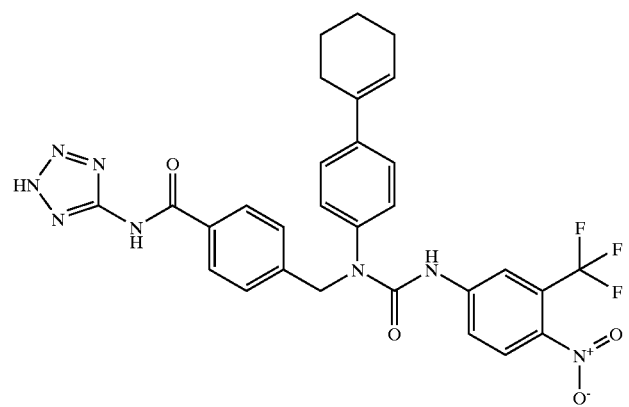

-continued
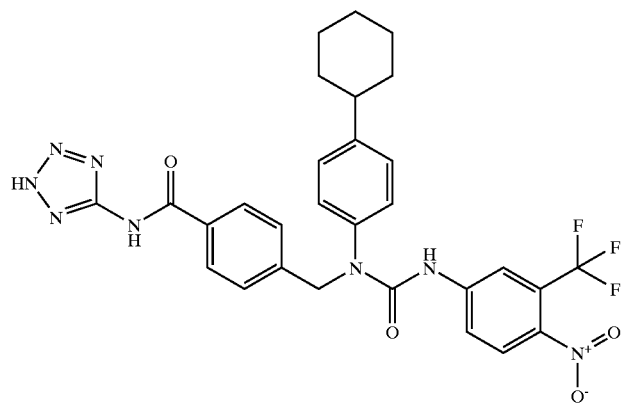
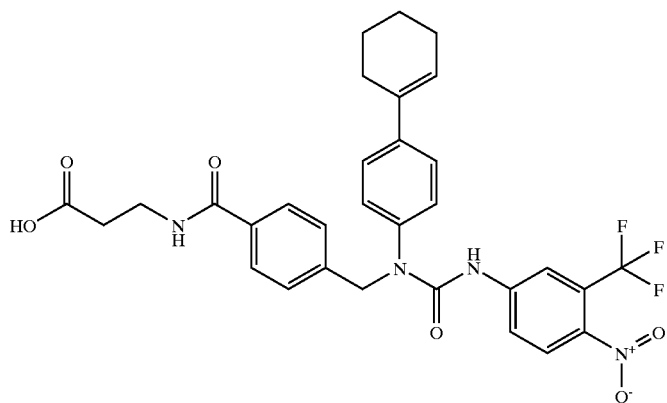
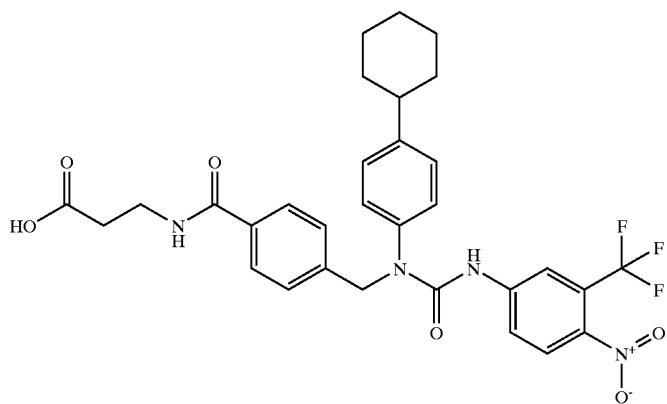
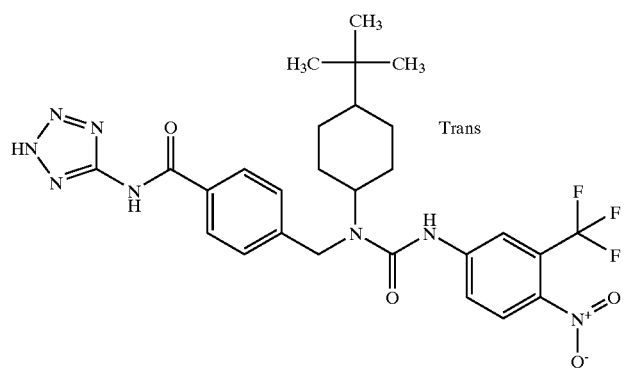

-continued
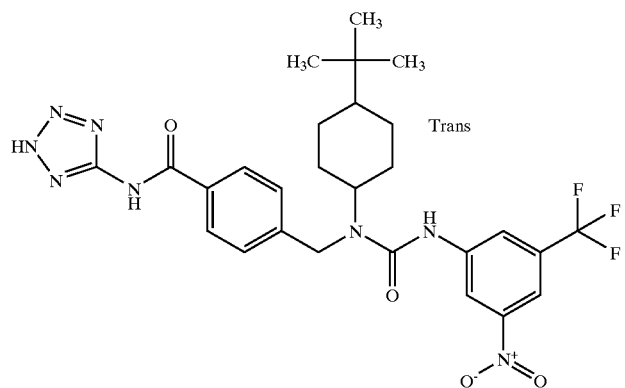
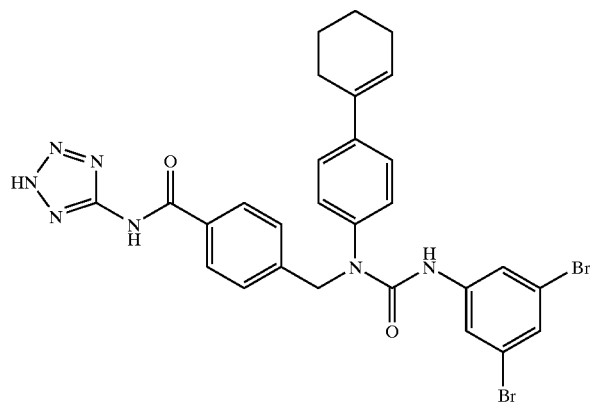
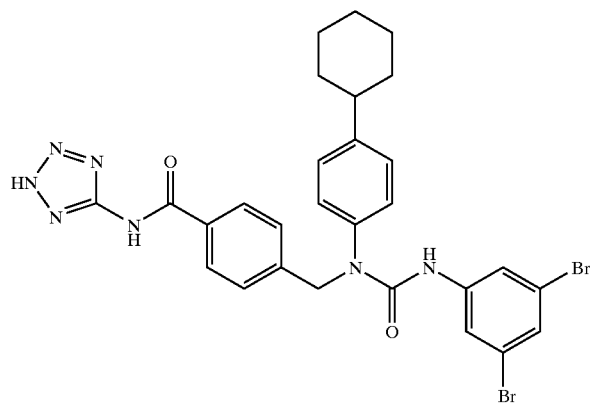
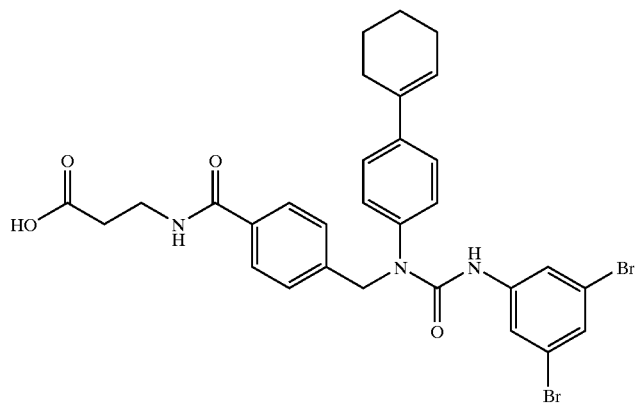

-continued
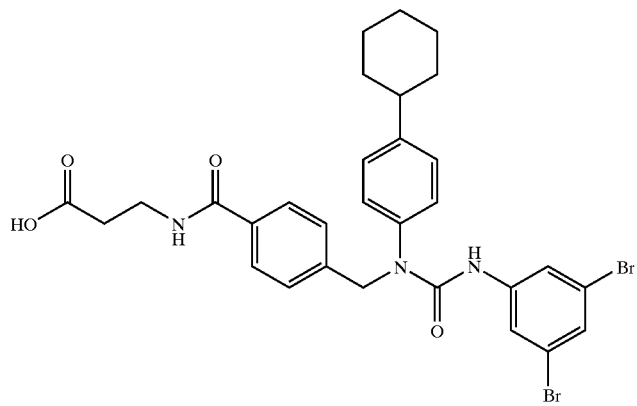
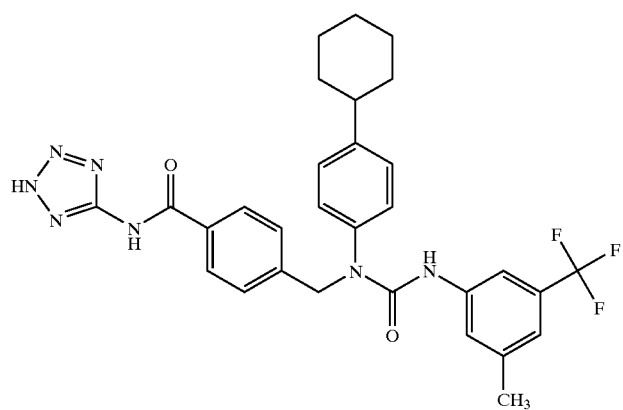
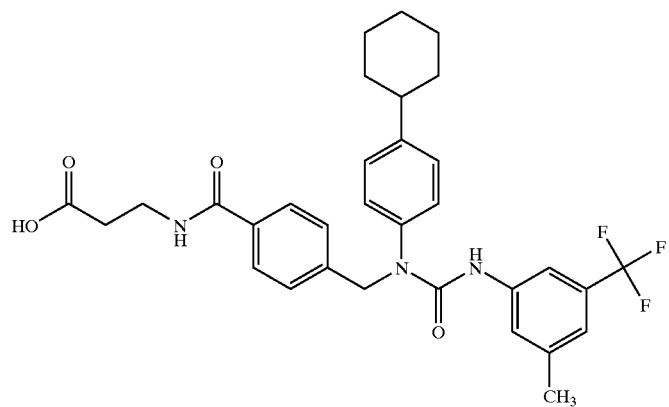
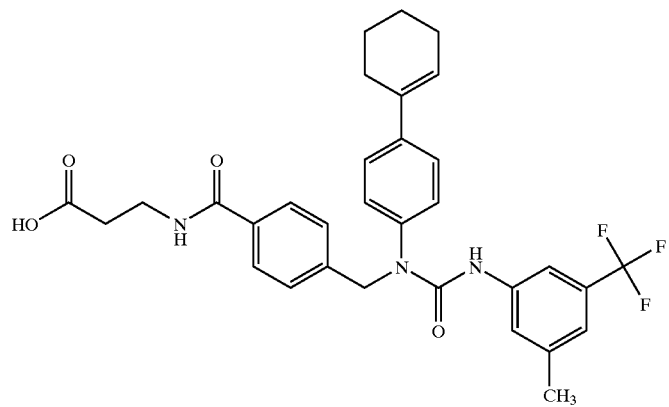

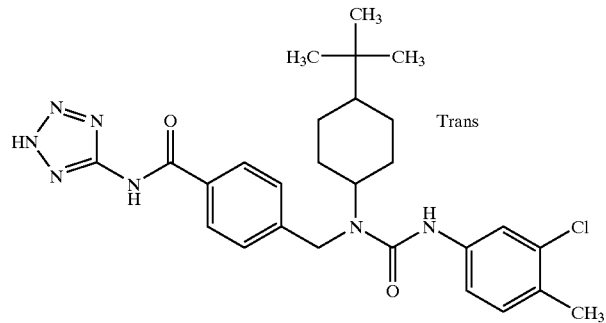
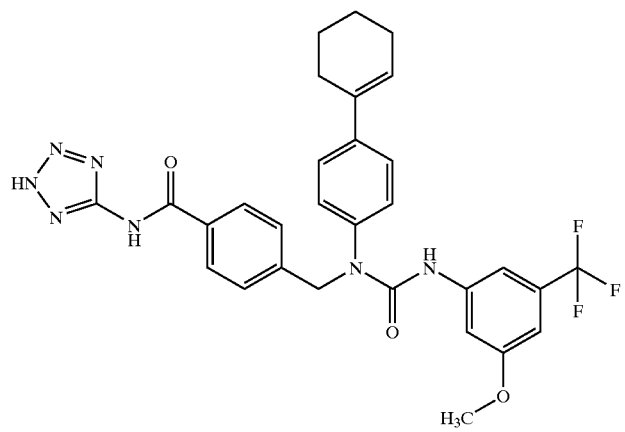
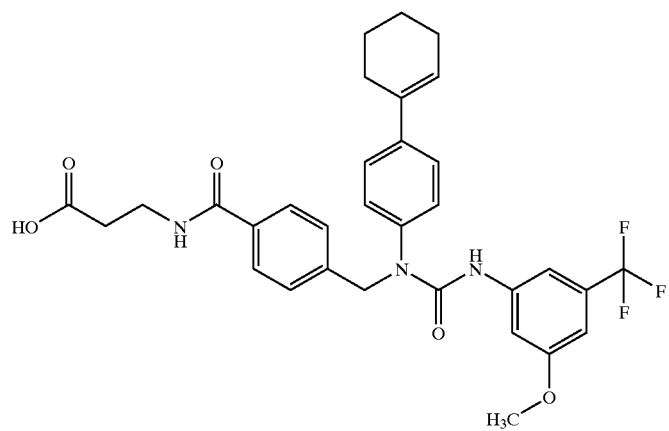

-continued
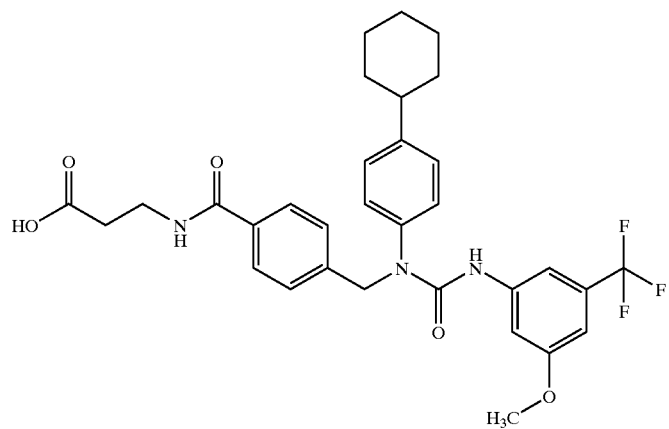
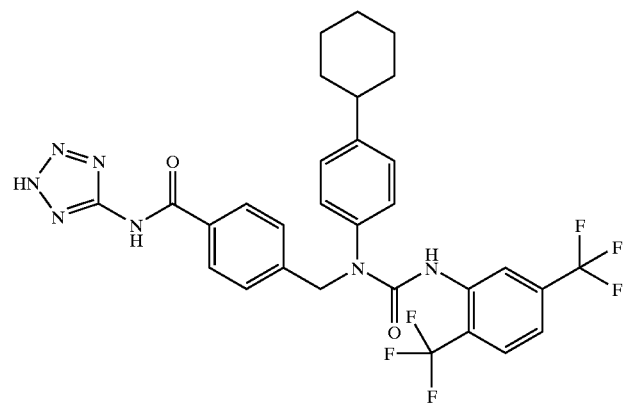
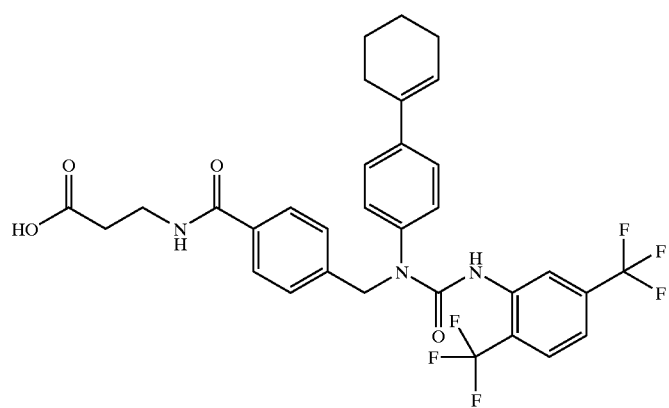

-continued
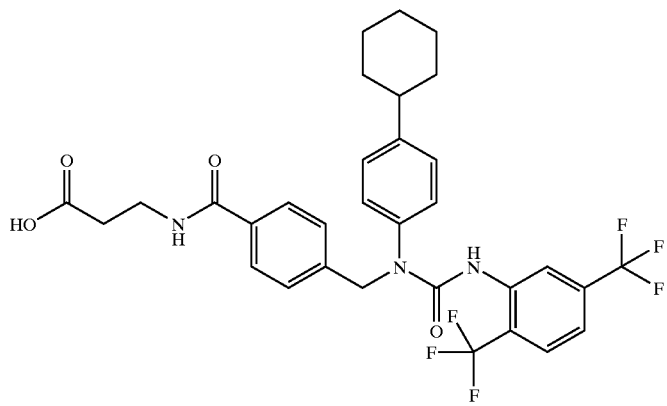
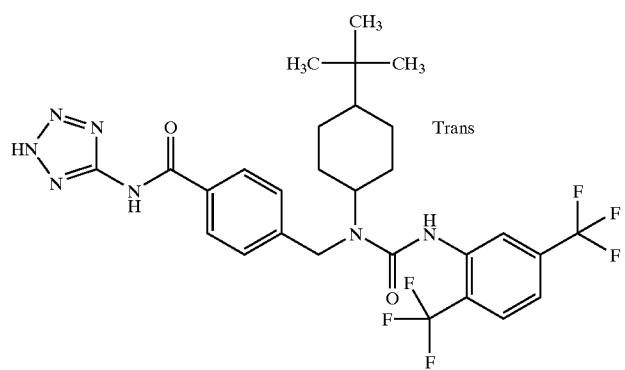
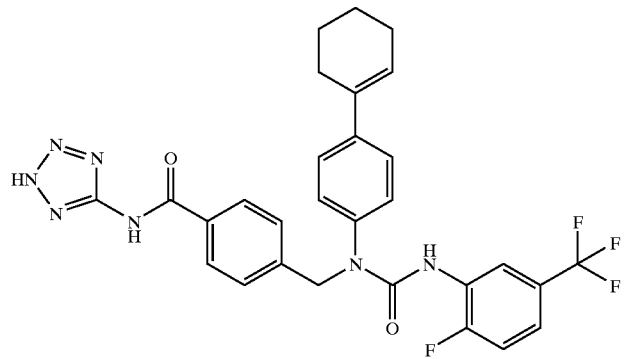
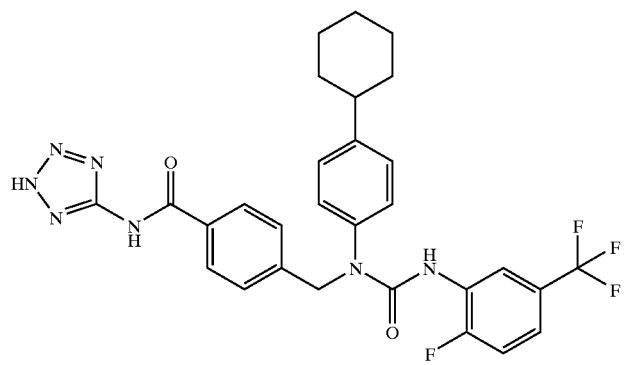

-continued
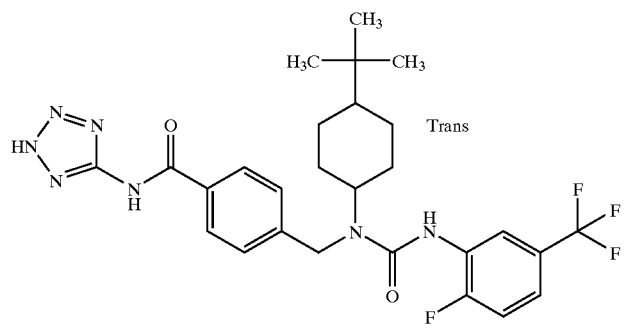
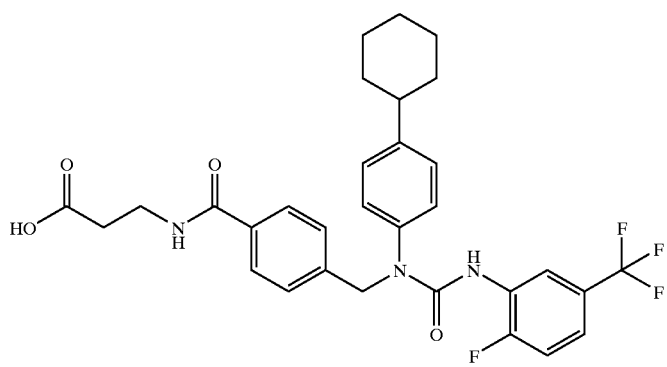
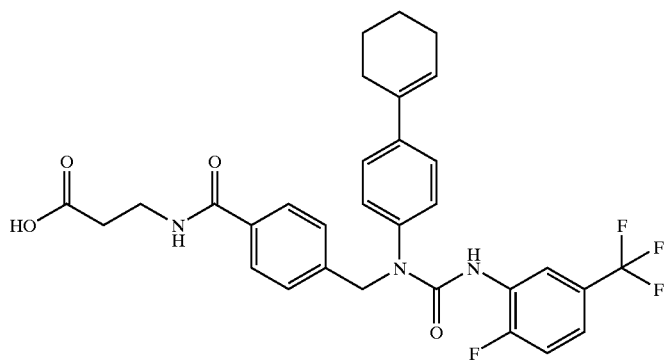
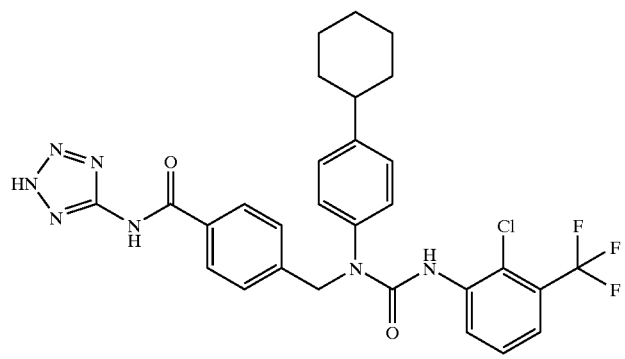

-continued
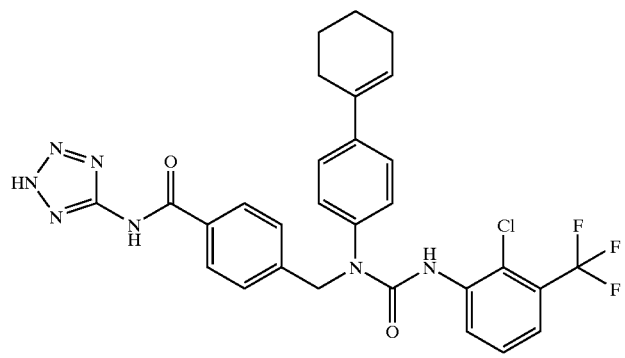
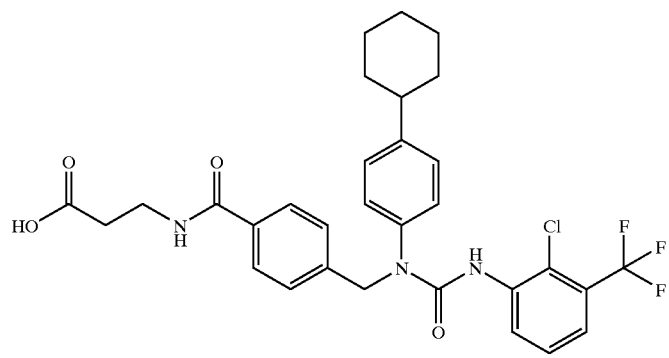
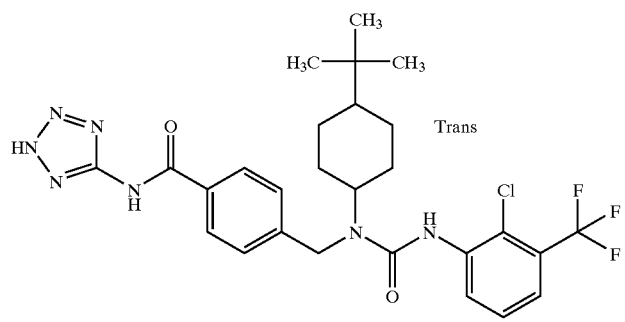
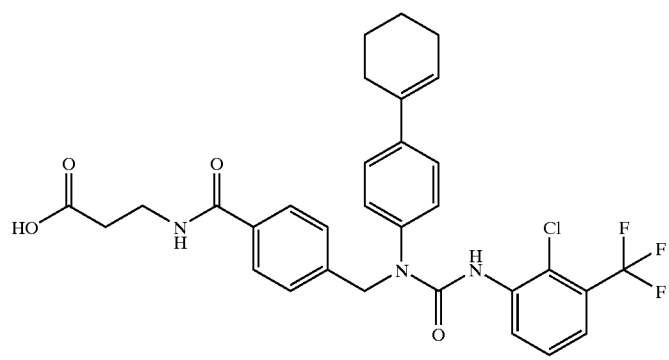

-continued
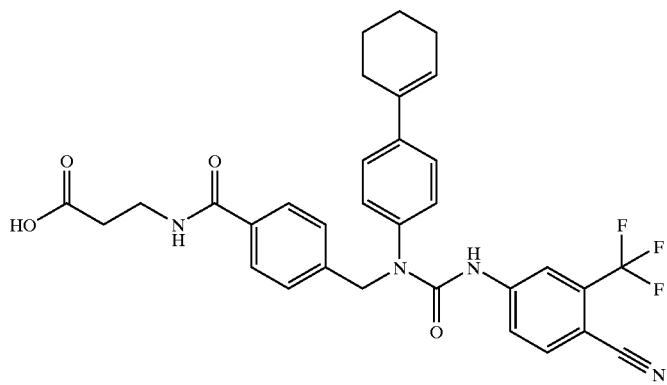
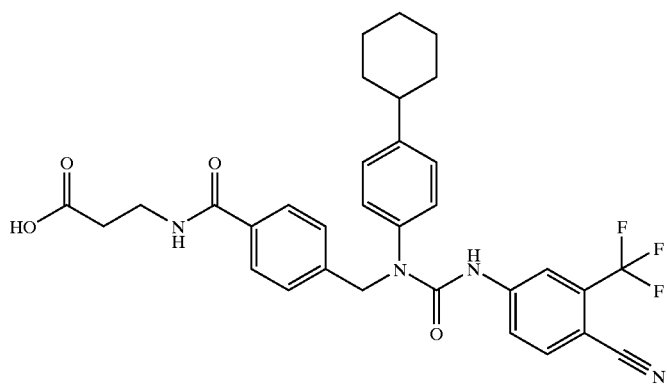
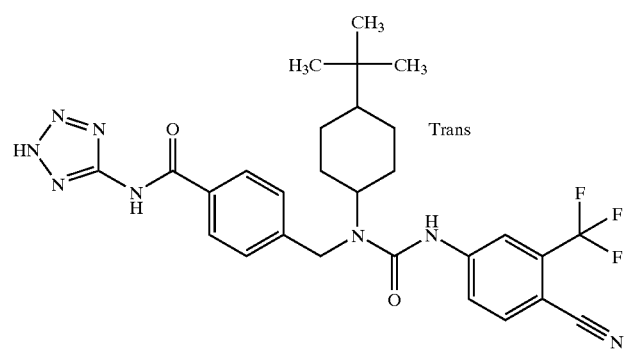
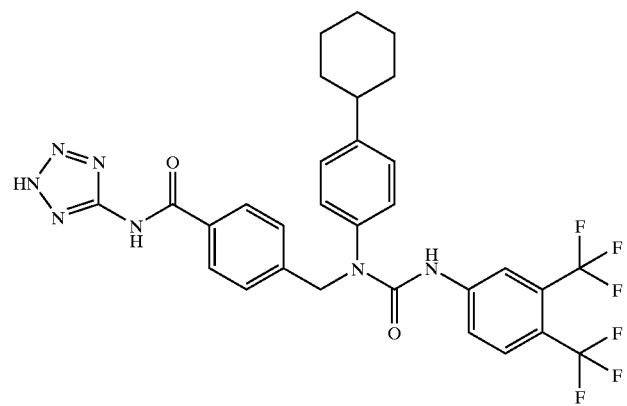

-continued
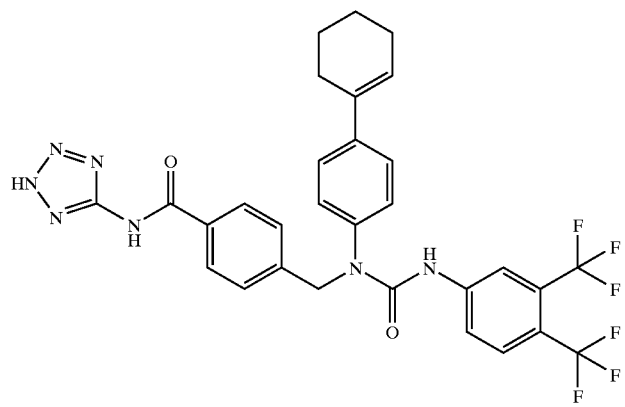
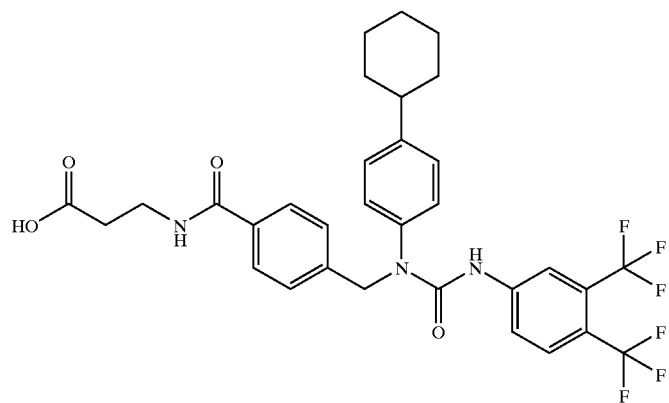
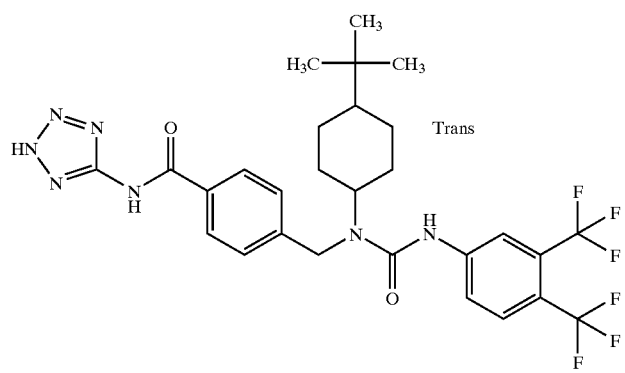
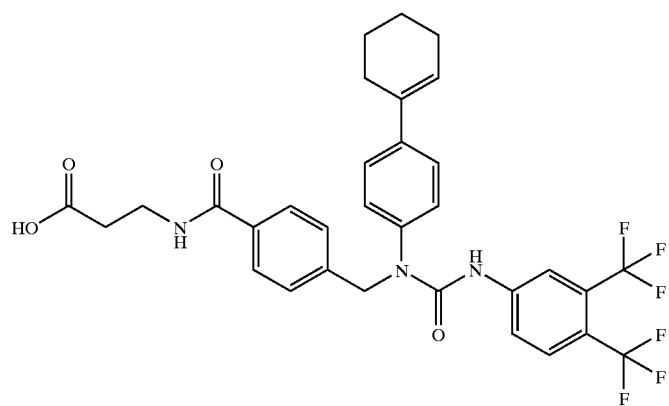

-continued
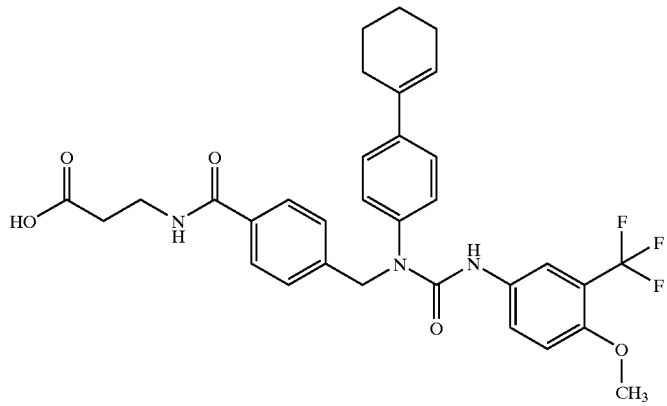
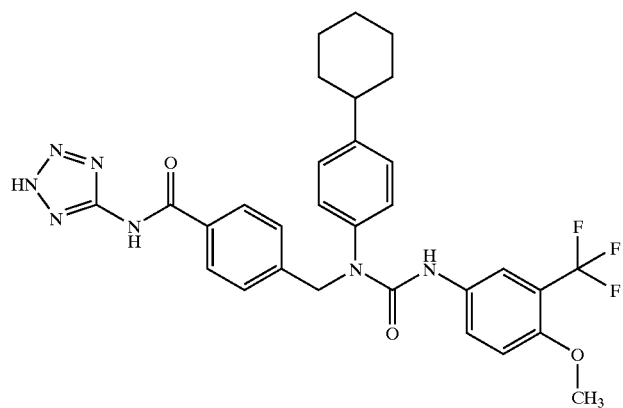
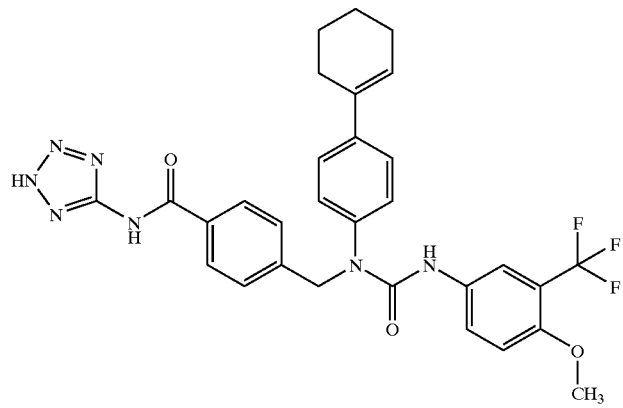
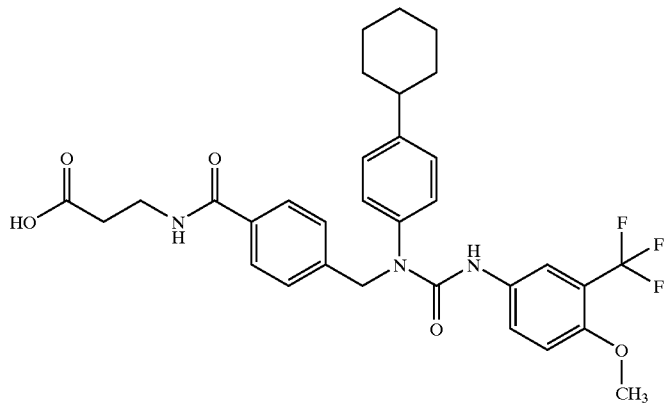

-continued
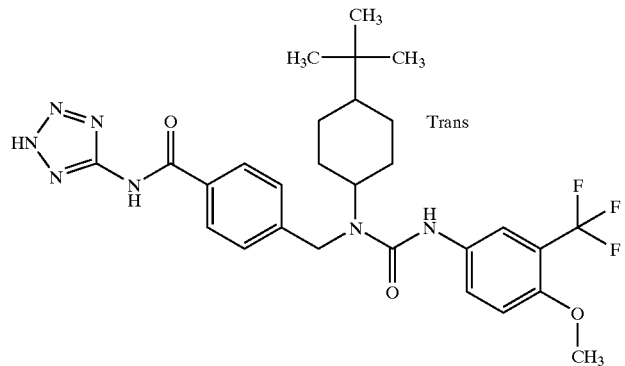
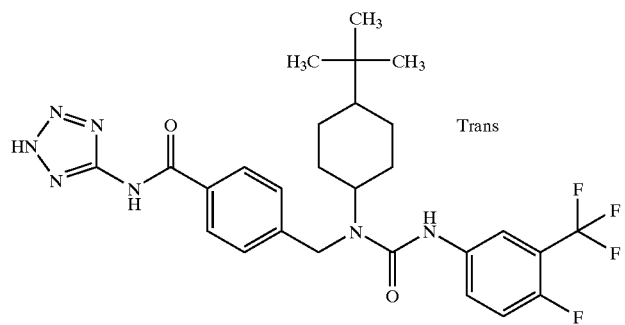
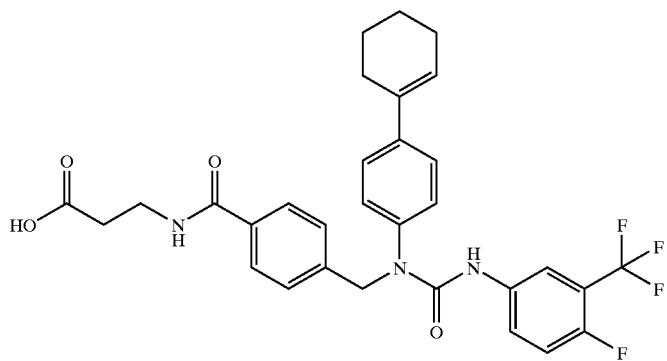
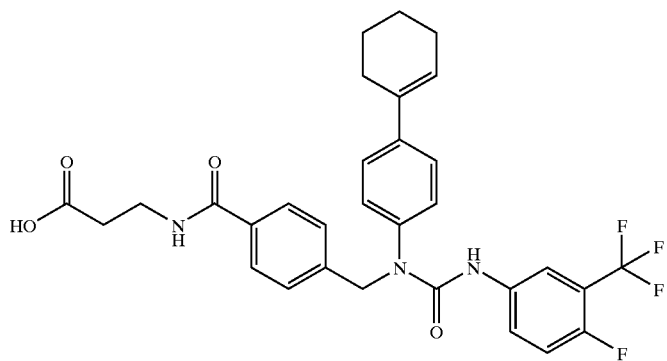

-continued
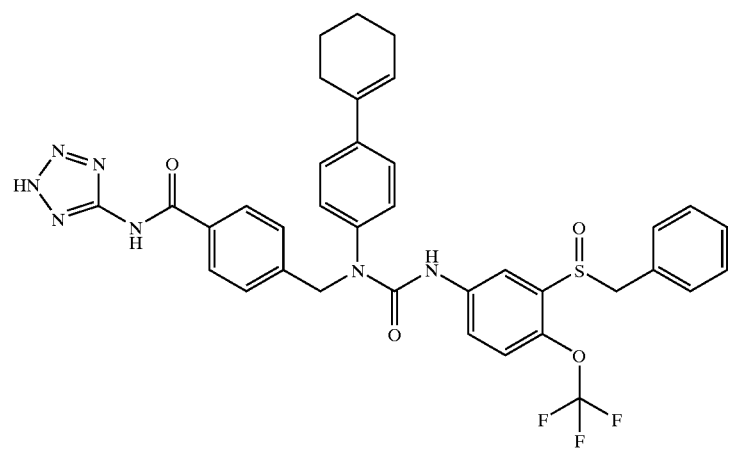
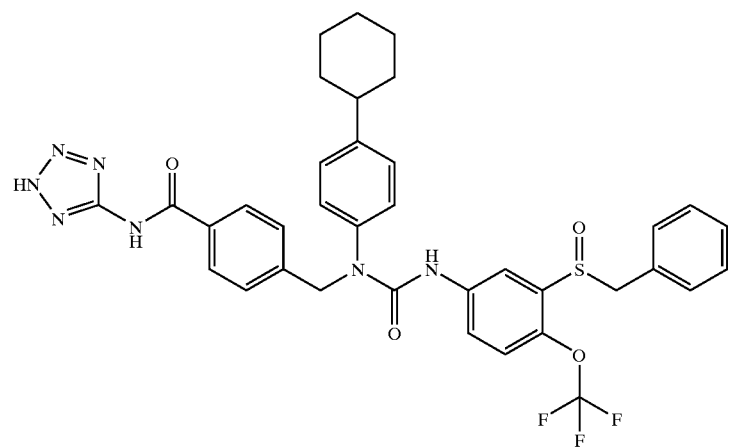
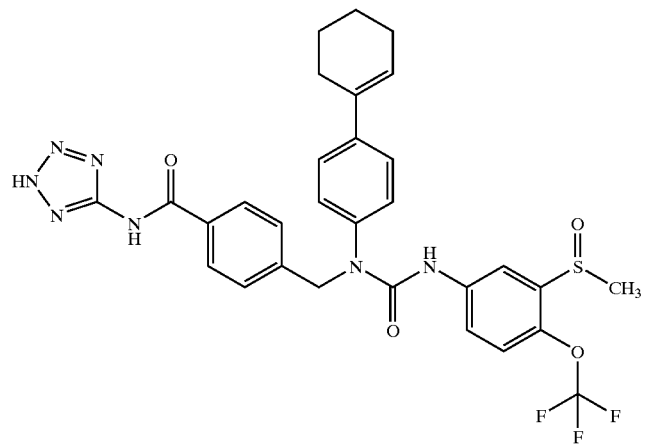

-continued
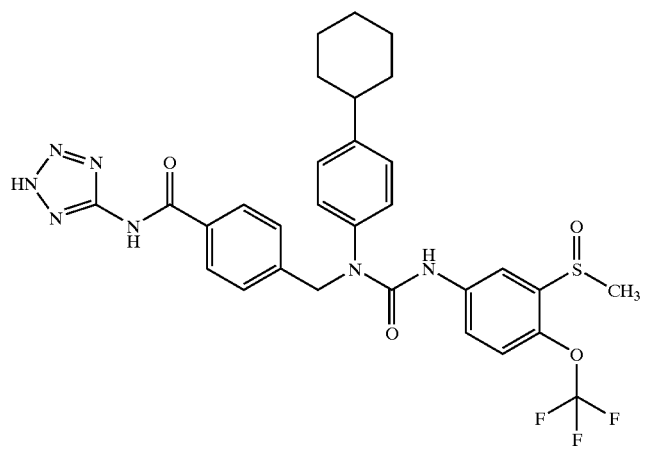
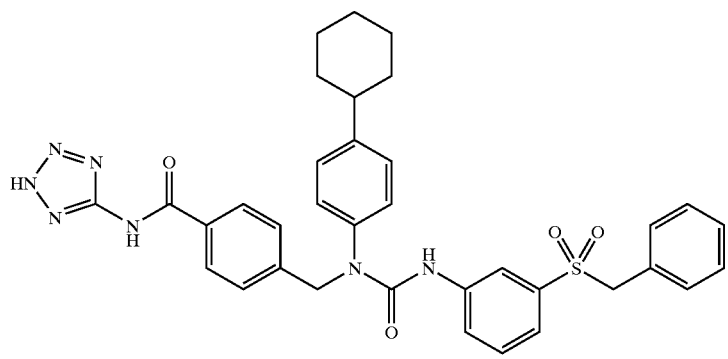
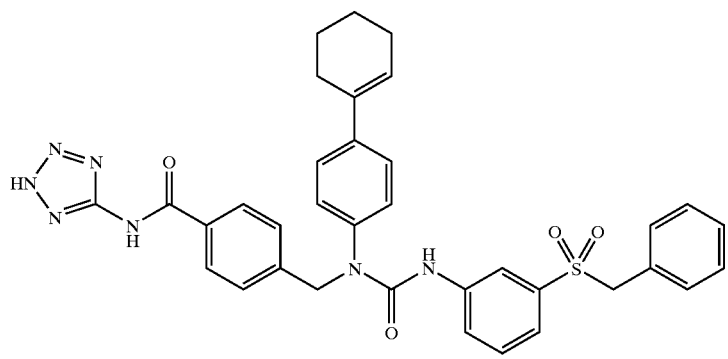
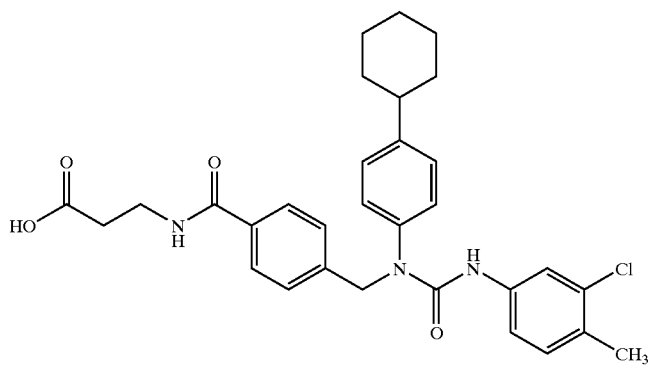

-continued
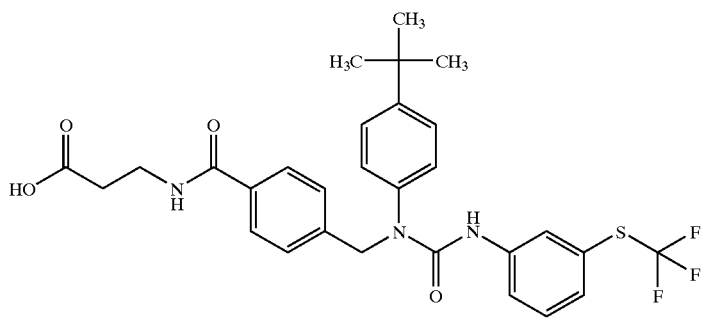
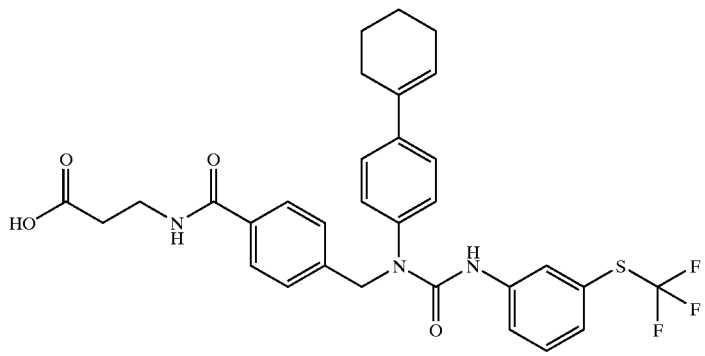
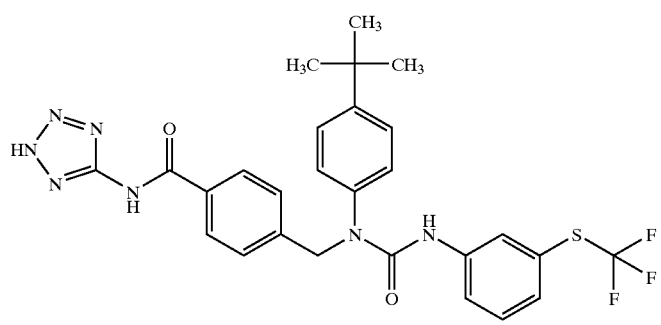
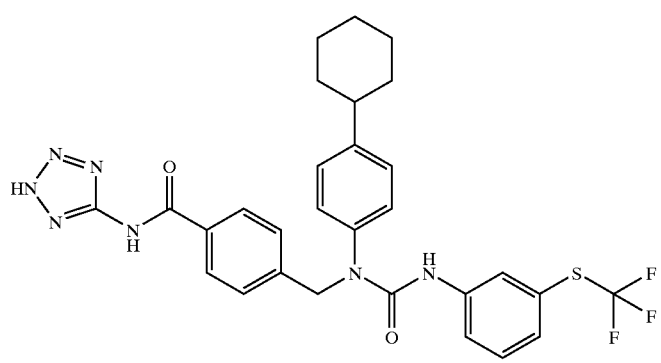

-continued
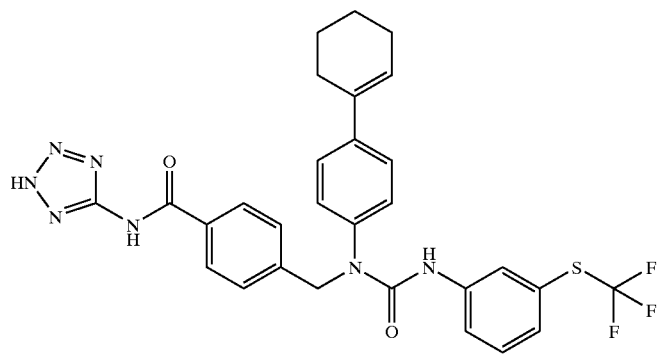
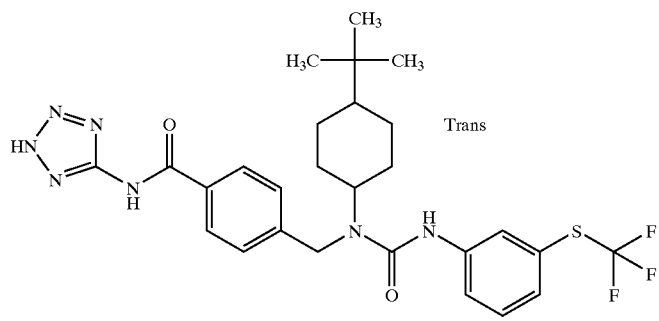
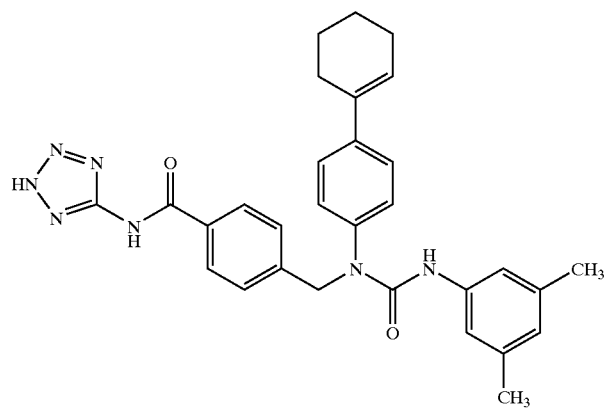
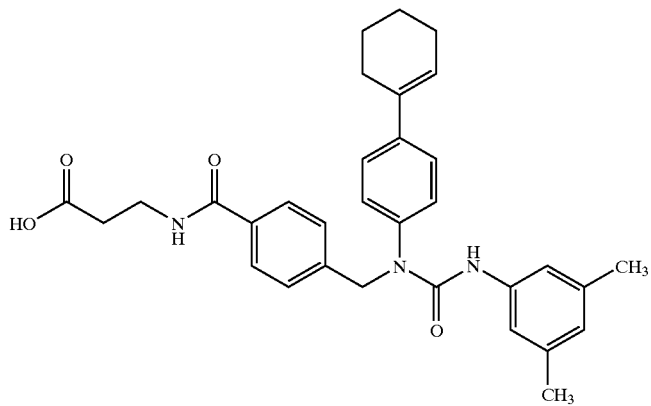

-continued
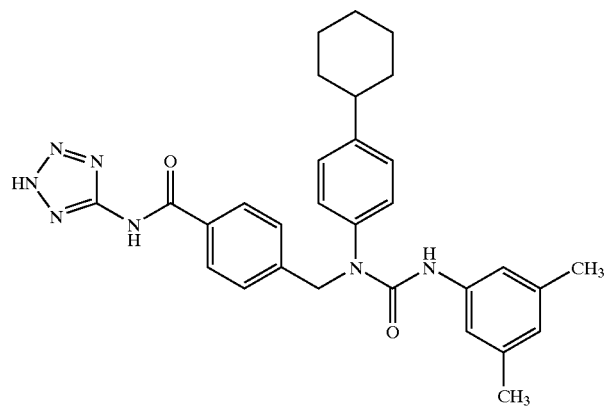
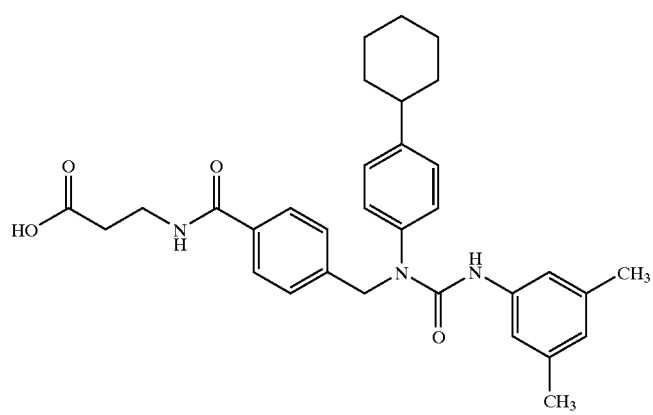
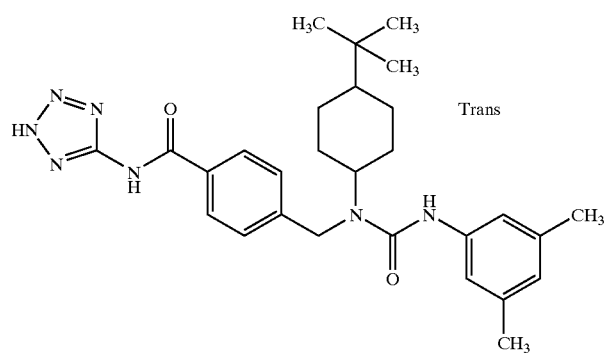
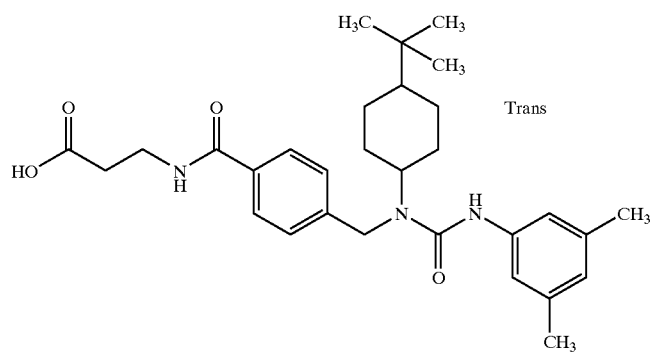

-continued
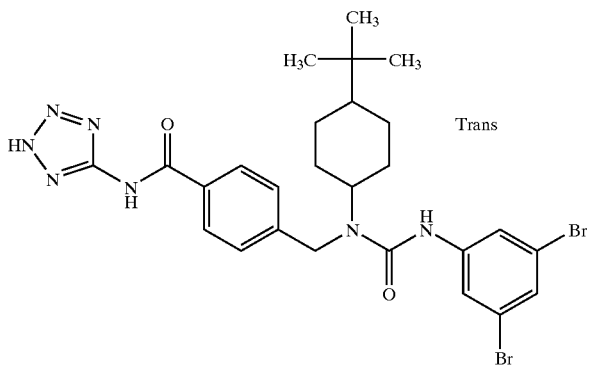
The following table shows activity data for the compounds according to the invention:
| Example No/Structure | Glu Bd Assay (I) $IC_{50}$ (nM); (Effect, 100-Residual binding (%) at 1 μM) | Glu Bd Assay (II) $IC_{50}$ (nM) | Glu Bd Assay (III) $IC_{50}$ (nM) |
|---|---|---|---|
| 1 | 120 | | |
| 2 | 1300 | | |
| 3 | 26.2% | | |
| 4 | 28.5% | | |
| 5 | 800; 31.1% | | |
| 6 | 1200; 29.5% | | |
| 7 | 845; 30.4% | | |
| 8 | 675; 37.8% | | |
| 9 | 56.4% (at 500 nM) | | |
| 10 | 42 | | |
| 11 | 27 | | |
| 12 | 20 | | |
| 13 | 78 | | |
| 14 | | | 184 |
| 15 | | | 826 |
| 16 | | | 39 |
| 17 | | | 27 |
| 18 | | | 126 |
| 19 | | | 201 |
| 20 | | | 2370 |
| 21 | | | 1500 |
| 22 | | | 1100 |
| 23 | | | 1800 |
| 24 | | | 1700 |
| 25 | | | 935 |
| 26 | | | 385 |
| 27 | | | 2000 |
| 28 | | | 266 |
| 29 | | | 149 |
| 30 | | | 139 |
| 31 | | | 2200 |
| 32 | | | 1680 |
| 33 | | | 104 |
| 34 | | | 462 |
| 35 | | | 352 |
| 36 | | | 151 |
| 37 | | | 145 |
| 38 | | | 928 |
| 39 | | | 227 |
| 40 | | | 821 |
| 41 | | | 299 |
| 42 | | | 117 |
| 43 | | | 1107 |
| 44 | | | 819 |
| 45 | | | 1191 |
| 46 | | | 456 |
| 47 | | | 1100 |

-continued

| | |
|---|---|
| 48 | 1075 |
| 49 | 1316 |
| 50 | 564 |
| 51 | 721 |
| 52 | 383 |
| 53 | 505 |
| 54 | 337 |
| 55 | 1000 |
| 56 | 59 |
| 57 | 90 |
| 58 | 139 |
| 59 | 3800 |
| 60 | 83 |
| 61 | 48 |
| 62 | 39 |
| 63 | 645 |
| 64 | 75 |
| 65 | 183 |
| 66 | 267 |
| 67 | 891 |
| 68 | 552 |
| 69 | 90 |
| 70 | 168 |
| 71 | 124 |
| 72 | 673 |
| 73 | 245 |
| 74 | 61 |
| 75 | 177 |
| 76 | 135 |
| 77 | 294 |
| 78 | 49 |
| 79 | 200 |
| 80 | 229 |
| 81 | 143 |
| 82 | 59 |
| 83 | 203 |
| 84 | 261 |
| 85 | 494 |
| 86 | 423 |
| 87 | 43 |
| 88 | 137 |
| 89 | 1206 |
| 90 | 4200 |
| 91 | 2800 |
| 92 | 47 |
| 93 | 47 |
| 94 | 1000 |
| 95 | 1700 |
| 96 | 137 |
| 97 | 1650 |
| 98 | 83 |
| 99 | 1045 |
| 100 | 50 |
| 101 | 119 |
| 102 | 167 |
| 103 | 150 |
| 104 | 50 |
| 105 | 446 |
| 106 | 468 |
| 107 | 1200 |
| 108 | 669 |
| 109 | 916 |
| 110 | 694 |
| 111 | 255 |
| 112 | 220 |
| 113 | 254 |
| 114 | 575 |
| 137 | 360 |
| 138 | 637 |
| 139 | 379 |
| 140 | 574 |
| 153 | 454 |
| 154 | 167 |
| 155 | 823 |
| 156 | 146 |
| 157 | 250 |
| 158 | 7 |
| 172 | 7 |
| 173 | 23 |

-continued

| | | |
|---|---|---|
| 174 | 11 | |
| 175 | 4 | |
| 176 | 641 | |
| 177 | 454 | |
| 178 | 999 | |
| 179 | 33 | 51 |
| 230 | 229 | |
| 231 | 349 | |
| 232 | 17 | 30 |
| 233 | 20 | |
| 234 | 112 | |
| 235 | 14 | |
| 236 | 29 | |
| 237 | | 56 |
| 238 | | 103 |
| 239 | | 1895 |
| 240 | | 2429 |
| 241 | | 140 |
| 242 | | 153 |
| 243 | | 1088 |
| 244 | | 528 |
| 245 | | 4047 |
| 246 | | 146 |
| 247 | | 215 |
| 248 | | 571 |
| 249 | | 320 |
| 250 | | 182 |
| 251 | | 56 |
| 252 | | 1319 |
| 253 | | 1169 |
| 254 | | 266 |
| 255 | | 80 |
| 256 | | 75 |
| 257 | | 684 |
| 258 | | 773 |
| 259 | | 1695 |
| 260 | | 149 |
| 261 | | 302 |
| 262 | | 18 |
| 263 | | 16 |
| 264 | | 9 |
| 265 | | 30 |
| 266 | | 15 |
| 267 | | 86 |
| 268 | | 21 |
| 269 | | 38 |
| 270 | | 64 |
| 271 | | 9 |
| 272 | | 192 |
| 273 | | 319 |
| 274 | | 94 |
| 275 | | 101 |
| 276 | | 313 |
| 277 | | 411 |
| 278 | | 88 |
| 279 | | 84 |
| 280 | | 252 |
| 281 | | 185 |
| 282 | 3 | 21 |
| 283 | | 57 |
| 284 | | 54 |
| 285 | | 151 |
| 286 | | 26 |
| 287 | | 52 |
| 288 | | 75 |
| 289 | | 27 |
| 290 | | 101 |
| 291 | | 42 |
| 292 | | 106 |
| 293 | | 45 |
| 294 | | 50 |
| 295 | | 279 |
| 296 | | 304 |
| 297 | | 87 |
| 298 | | 38 |
| 299 | | 171 |
| 300 | | 197 |
| 301 | | 35 |
| 302 | | 62 |

-continued

| | |
|---|---|
| 303 | 53 |
| 304 | 45 |
| 305 | 55 |
| 306 | 209 |
| 307 | 50 |
| 308 | 61 |
| 309 | 566 |
| 310 | 61 |
| 311 | 32 |
| 312 | 46 |
| 313 | 18 |
| 314 | 62 |
| 315 | 22 |
| 316 | 547 |
| 317 | 788 |
| 318 | 247 |
| 319 | 18 |
| 320 | 28 |
| 321 | 960 |
| 322 | 41 |
| 323 | 102 |
| 324 | 277 |
| 325 | 25 |
| 326 | 21 |
| 327 | 15 |
| 328 | 14 |
| 329 | 278 |
| 330 | 44 |
| 331 | 30 |
| 332 | 20 |
| 333 | 26 |
| 334 | 288 |
| 335 | 1087 |
| 336 | 58 |
| 337 | 22 |
| 338 | 169 |
| 339 | 797 |
| 340 | 179 |
| 341 | 56 |
| 342 | 376 |
| 343 | 99 |
| 344 | 16 |
| 345 | 64 |
| 346 | 25 |
| 347 | 79 |
| 348 | 73 |
| 349 | 6 |
| 350 | 271 |
| 351 | 368 |
| 352 | 21 |
| 353 | 22 |
| 354 | 11 |
| 355 | 112 |
| 356 | 16 |
| 357 | 17 |
| 358 | 19 |
| 359 | 16 |
| 360 | 8 |
| 361 | 119 |
| 362 | 13 |
| 363 | 23 |
| 364 | 2685 |
| 365 | 1426 |
| 366 | 12 |
| 367 | 34 |
| 368 | 37 |
| 369 | 558 |
| 370 | 87 |
| 371 | 52 |
| 372 | 90 |
| 373 | 96 |
| 374 | 10 |
| 375 | 29 |
| 376 | 391 |
| 377 | 2960 |
| 378 | 23 |
| 379 | 66 |
| 380 | 71 |
| 381 | 1984 |

-continued

| | | |
|---|---|---|
| 382 | | 781 |
| 383 | | 931 |
| 384 | | 324 |
| 385 | 33 | |
| 386 | 102 | |
| 387 | 111 | |
| 388 | 156 | |
| 389 | 337 | |
| 390 | | 6 |
| 391 | | 21 |
| 392 | | 36 |
| 393 | | 17 |
| 394 | | 17 |
| 395 | 153 | |
| 396 | 13 | |
| 397 | | 120 |
| 398 | | 135 |
| 399 | | 120 |
| 400 | | 533 |
| 401 | | 176 |
| 402 | | 176 |
| 403 | | 338 |
| 404 | | 346 |
| 405 | | 224 |
| 406 | | 751 |
| 407 | | 756 |
| 408 | | 580 |
| 409 | | 520 |
| 410 | | 386 |
| 411 | | 704 |
| 412 | | 604 |
| 413 | | 1201 |
| 414 | | 934 |
| 415 | | 2419 |
| 416 | | 634 |
| 417 | | 877 |
| 418 | | 472 |
| 419 | | 482 |
| 420 | | 729 |
| 421 | | 528 |
| 422 | | 536 |
| 423 | | 37 |
| 424 | | 61 |
| 425 | | 220 |
| 426 | | 338 |
| 427 | | 512 |
| 428 | | 410 |
| 429 | | 86 |
| 430 | | 1683 |
| 431 | | 2911 |
| 432 | | 1800 |
| 433 | | 1250 |
| 434 | | 126 |
| 435 | | 374 |
| 436 | | 1990 |
| 437 | | 207 |
| 438 | | 288 |
| 439 | | 184 |
| 440 | | 509 |
| 441 | | 3900 |
| 442 | | 4100 |
| 443 | | 167 |
| 444 | | 42 |
| 445 | | 204 |
| 446 | | 522 |
| 447 | | 327 |
| 448 | | 1482 |
| 449 | | 195 |
| 450 | | 1794 |
| 451 | | 3450 |
| 452 | | 1413 |
| 453 | | 72 |
| 454 | | 214 |
| 455 | | 53 |
| 456 | | 2806 |
| 457 | | 841 |
| 458 | | 1811 |
| 459 | | 2106 |
| 460 | | 1732 |

-continued

| | | |
|---|---|---|
| 461 | | 764 |
| 462 | | 1157 |
| 463 | | 256 |
| 464 | | 95 |
| 465 | | 606 |
| 466 | | 2667 |
| 467 | | 772 |
| 468 | | 23 |
| 469 | | 631 |
| 470 | | 116 |
| 471 | | 252 |
| 472 | | 255 |
| 473 | | 1500 |
| 474 | | 1261 |
| 475 | | 886 |
| 476 | | 955 |
| 477 | 224 | 464 |
| 478 | | 2940 |
| 479 | | 819 |
| 480 | | 276 |
| 481 | | 1984 |
| 482 | | 302 |
| 483 | | 1116 |
| 484 | | 505 |
| 485 | | 810 |
| 487 | | 523 |
| 488 | | 98 |
| 489 | | 150 |
| 490 | | 136 |
| 491 | | 264 |
| 492 | | 144 |
| 493 | | 880 |
| 495 | | 306 |
| 496 | | 566 |
| 497 | | 589 |
| 498 | | 621 |
| 499 | | 136 |
| 500 | | 140 |
| 501 | | 217 |
| 502 | | 28 |
| 503 | | 94 |
| 504 | | 235 |
| 505 | | 449 |
| 506 | | 108 |
| 507 | | 444 |
| 508 | | 198 |
| 510 | | 1098 |
| 511 | | 58 |
| 512 | | 111 |
| 513 | | 144 |
| 514 | | 667 |
| 515 | | 450 |
| 516 | | 2488 |
| 517 | | 620 |
| 518 | | 1470 |
| 519 | | 908 |
| 520 | | 1976 |
| 521 | | 3417 |
| 522 | | 896 |
| 523 | | 2112 |
| 524 | | 293 |
| 525 | | 669 |
| 526 | | 1702 |
| 527 | | 660 |
| 529 | | 470 |
| 530 | | 3981 |
| 531 | | 627 |
| 532 | | 626 |
| 533 | | 1801 |
| 534 | | 282 |
| 535 | | 224 |
| 537 | | 280 |
| 538 | | 180 |
| 539 | | 386 |
| 540 | | 540 |
| 541 | | 805 |
| 542 | | 304 |
| 543 | | 201 |
| 544 | | 552 |

-continued

| | | |
|---|---|---|
| 545 | | 47 |
| 546 | | 1739 |
| 547 | | 88 |
| 548 | | 309 |
| 549 | | 55 |
| 550 | | 381 |
| 551 | | 136 |
| 552 | | 133 |
| 554 | | 788 |
| 555 | | 604 |
| 556 | | 660 |
| 557 | | 266 |
| 558 | | 1060 |
| 559 | | 1088 |
| 560 | | 1553 |
| 561 | | 372 |
| 562 | | 146 |
| 563 | | 407 |
| 564 | | 98 |
| 565 | | 948 |
| 566 | | 855 |
| 567 | | 5 |
| 568 | | 13 |
| 569 | | 1772 |
| 570 | 44 | |
| 571 | 111 | |
| 572 | 166 | |
| 573 | 152 | |
| 574 | 159 | |
| 575 | 15 | |
| 576 | 4 | |
| 577 | 18 | |
| 578 | | 226 |
| 579 | 242 | |
| 580 | 57 | |
| 581 | 142 | |
| 582 | 108 | |
| 583 | 205 | |
| 584 | 284 | |
| 585 | 322 | |
| 586 | 874 | |
| 587 | 692 | |
| 588 | 75 | |
| 589 | 541 | |
| 590 | 224 | |
| 591 | 4 | |
| 592 | 16 | |
| 593 | 8 | |
| 594 | 354 | |
| 595 | 39 | |
| 596 | 112 | |
| 597 | 7 | |
| 598 | 207 | |
| 599 | | 12 |
| 600 | | 9 |
| 601 | | 17 |
| 602 | | 26 |
| 603 | | 26 |
| 604 | | 222 |
| 605 | 15 | |
| 606 | 98 | |
| 607 | 1853 | |
| 608 | 677 | |
| 609 | 726 | |
| 610 | 118 | |
| 611 | 437 | |
| 612 | 161 | |
| 613 | 578 | |
| 614 | | 129 |
| 615 | | 105 |
| 616 | | 745 |
| 617 | | 104 |
| 618 | | 1073 |
| 619 | | 479 |
| 620 | | 542 |
| 621 | | 4600 |
| 622 | | 4600 |
| 623 | | 2700 |
| 624 | | 2000 |

-continued
| | |
|---|---|
| 625 | 7 |
| 626 | 38 |
| 627 | 8 |
| 628 | 35 |
| 629 | 45 |
| 630 | 73 |
| 631 | 23 |
| 632 | 91 |
| 633 | 19 |
| 634 | 38 |
| 635 | 18 |
| 636 | 5 |
| 637 | 116 |
| 638 | 11 |
| 639 | 4 |
| 640 | 6 |
| 641 | 21 |
| 642 | 7 |
| 643 | 38 |
| 644 | 4 |
| 645 | 7 |
| 646 | 22 |
687
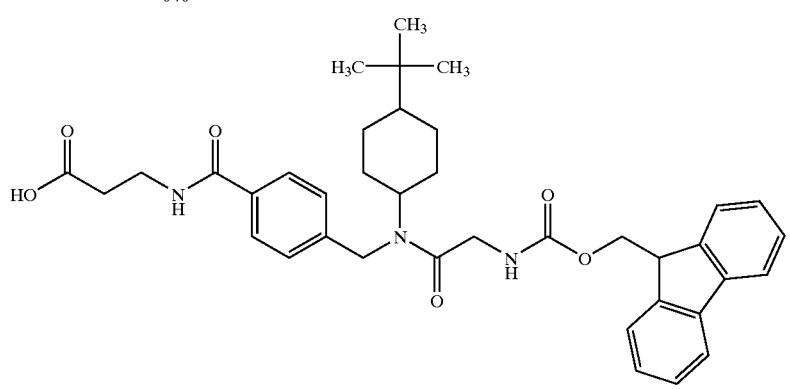
516
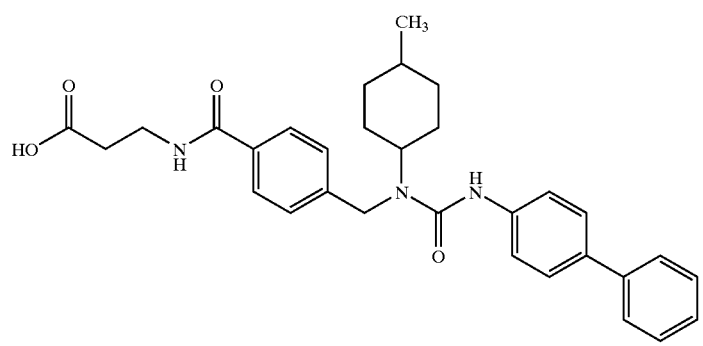
121
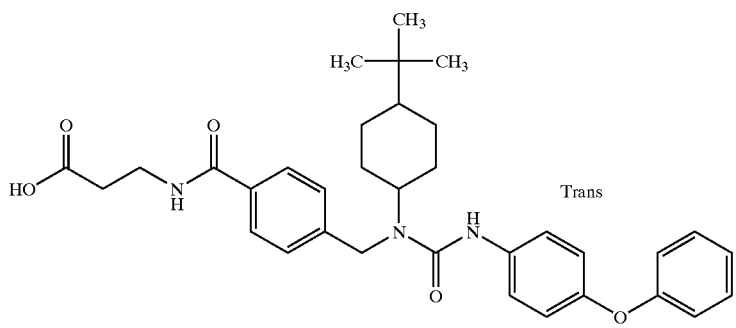

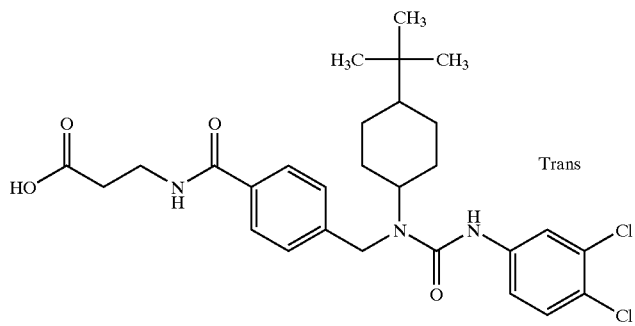
226
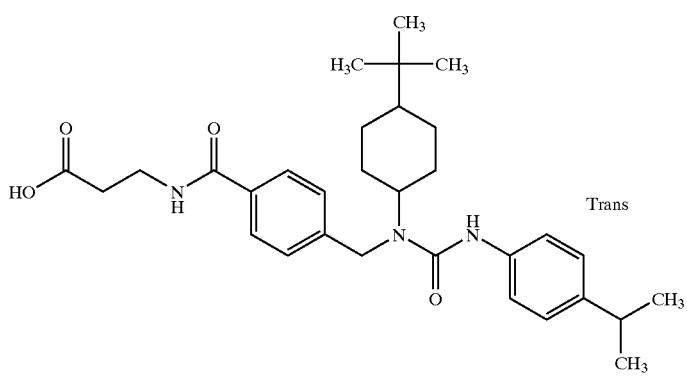
35
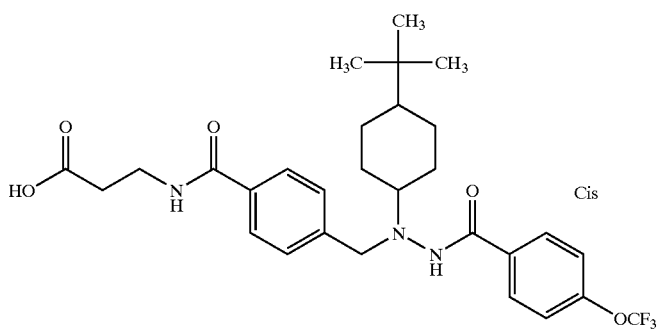
108
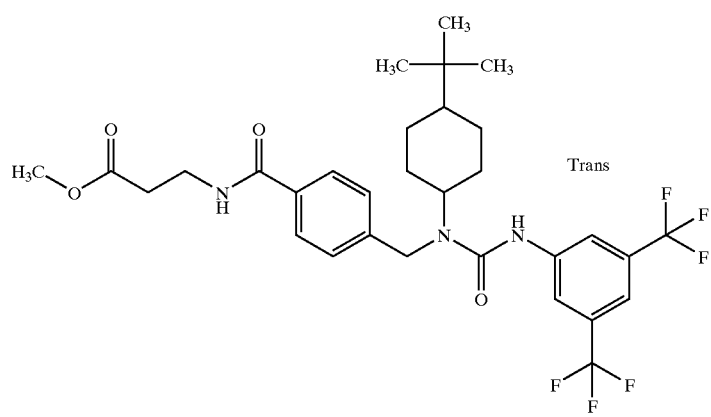
101

-continued
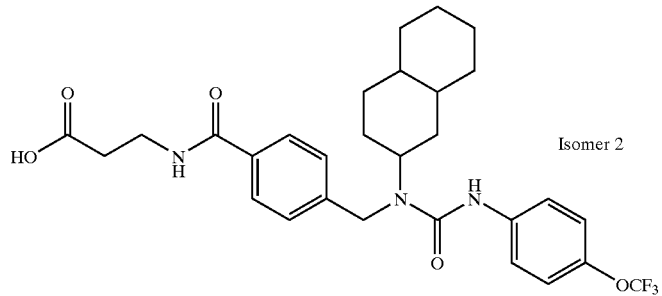 426
Isomer 2
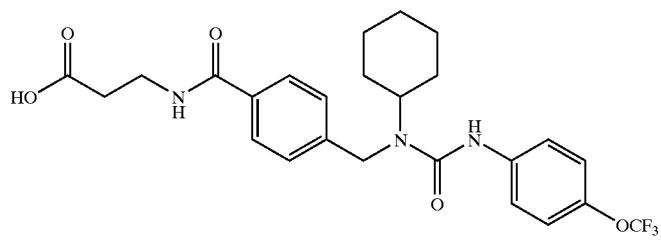 2700
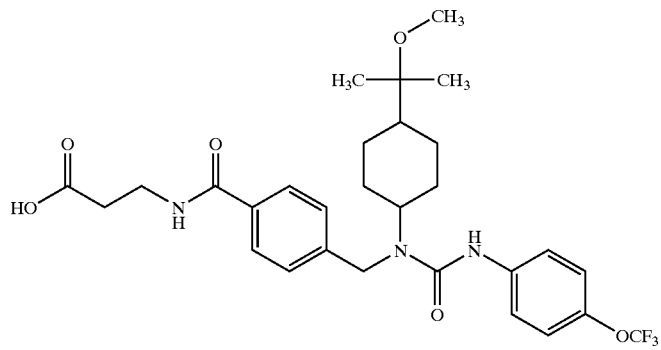 1285
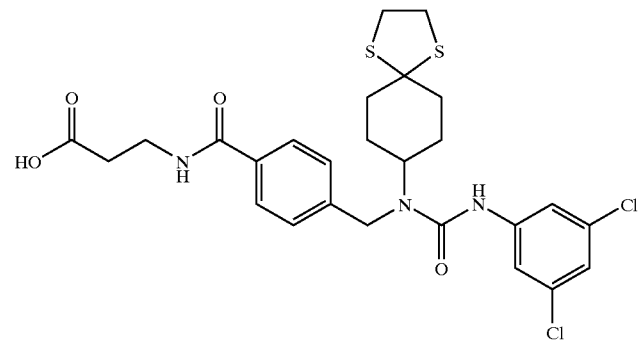 1336
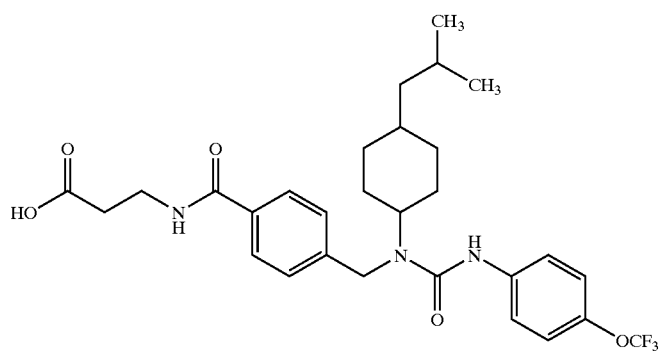 140

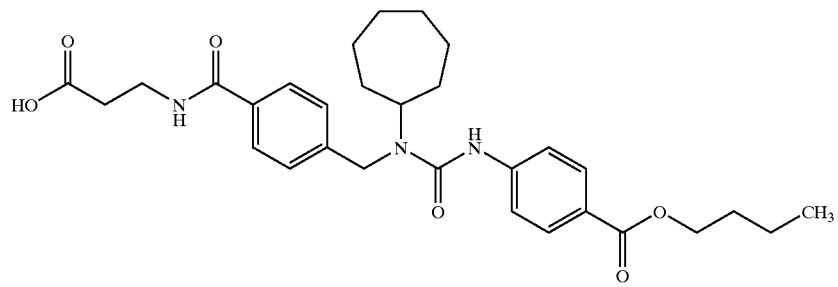
217
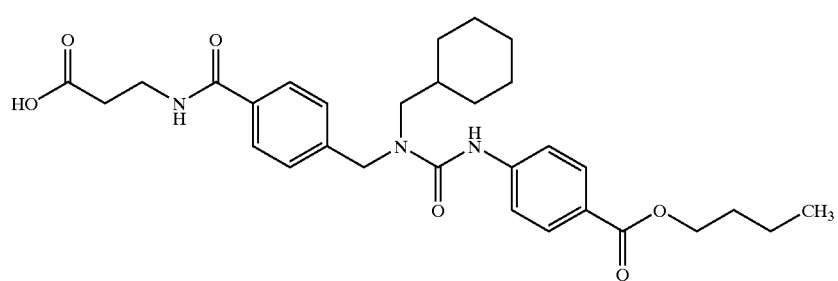
264
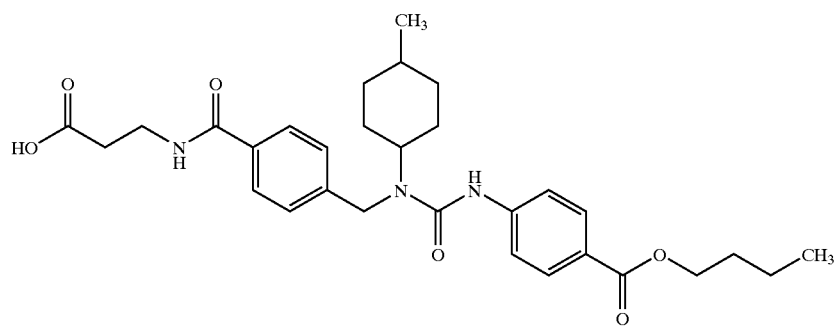
188
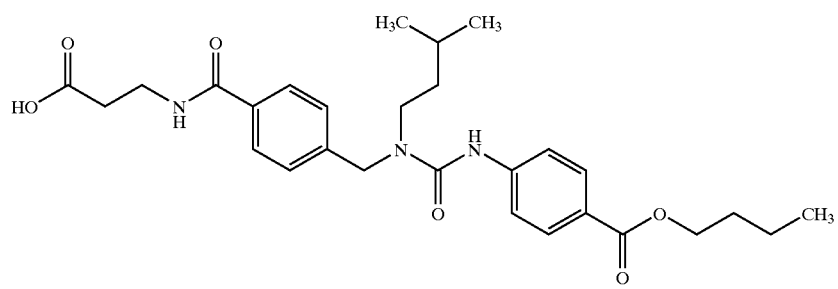
254
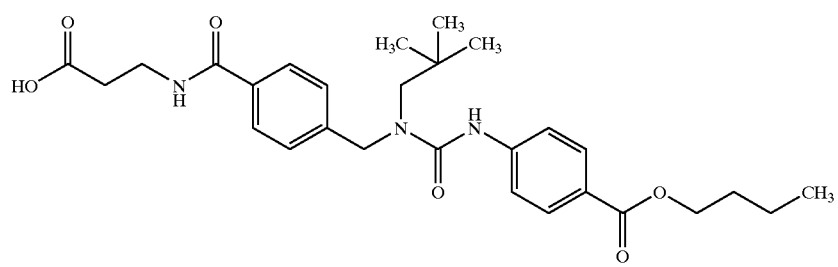
230

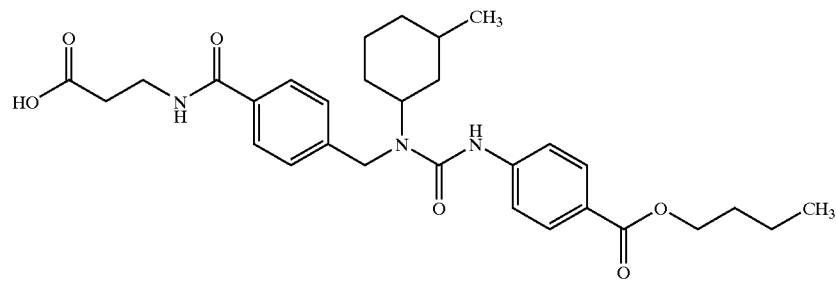
278
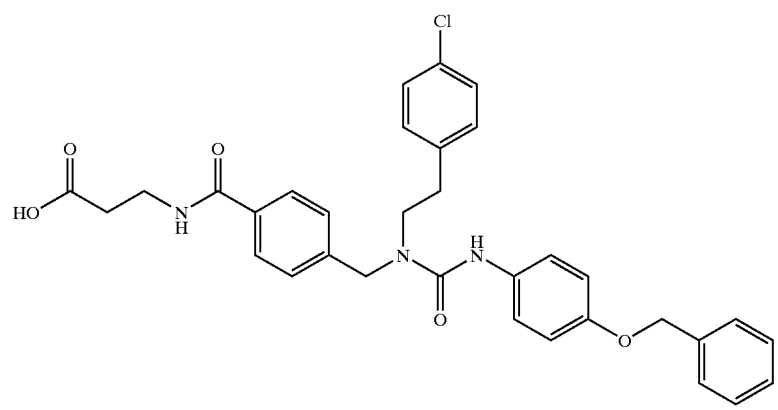
400
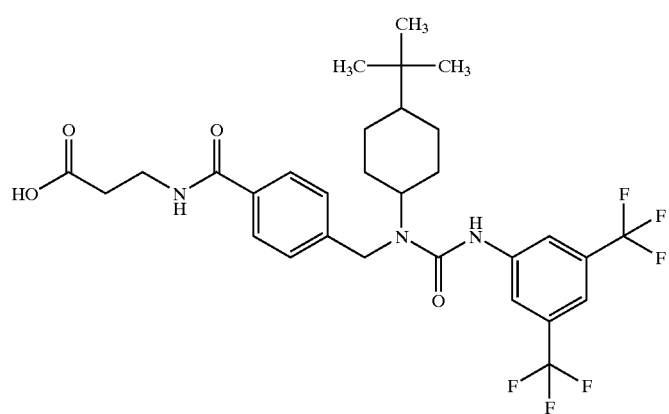
10
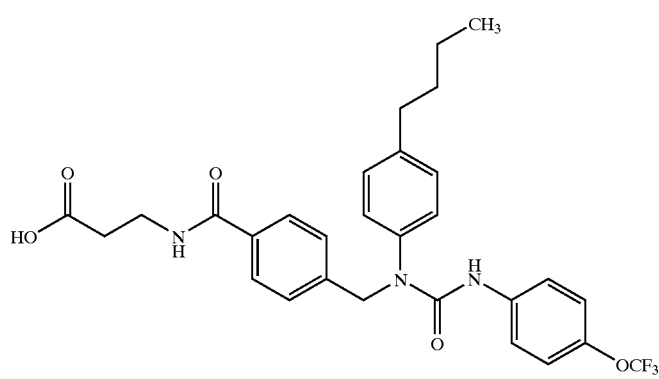
13

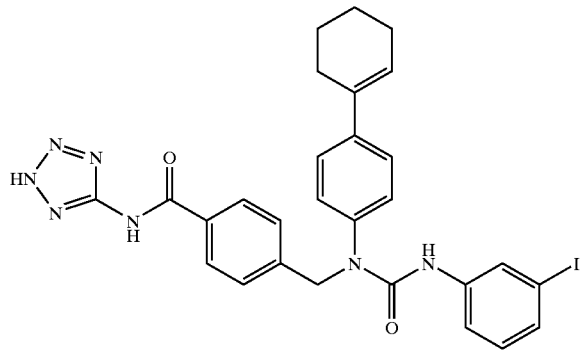

26 nM

It should be apparent from the foregoing that other starting materials and other intermediate compounds can be substituted in the above procedures to prepare all of the compounds of the invention. The methods disclosed herein are based on established chemical techniques, as will be apparent to those skilled in the art, and therefore all of the compounds of the invention are broadly enabled by the preceding disclosure.

Accordingly, the invention may be embodied in other specific forms without departing from its spirit or essential characteristics. The described embodiments are to be considered in all respects only as illustrative and not restrictive, and the scope of the invention is, therefore, indicated by the appending claims rather than by the foregoing description. All modifications, which come within the meaning and range of the lawful equivalency of the claims, are to be embraced within their scope.

What is claimed is:

1. A compound of formula ($I_6$):

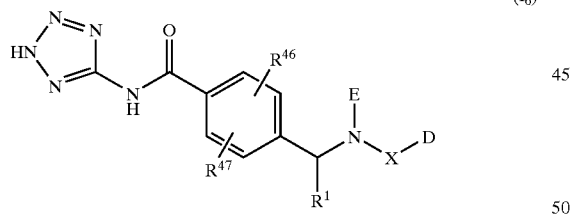

(I₆)

wherein $R^{46}$ and $R^{47}$ are selected from hydrogen, halogen, —CN, —CF$_3$, —OCF$_3$, —NO$_2$, —OR$^{10}$, —NR$^{10}$R$^{11}$ and C$_{1-6}$-alkyl,
  wherein $R^{10}$ and $R^{11}$ independently are hydrogen or C$_{1-6}$-alkyl;

$R^1$ is hydrogen or C$_{1-6}$-alkyl;

X is

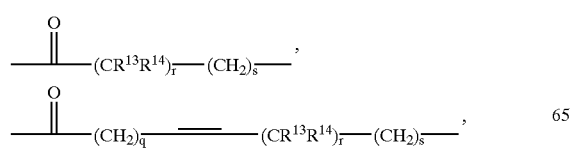

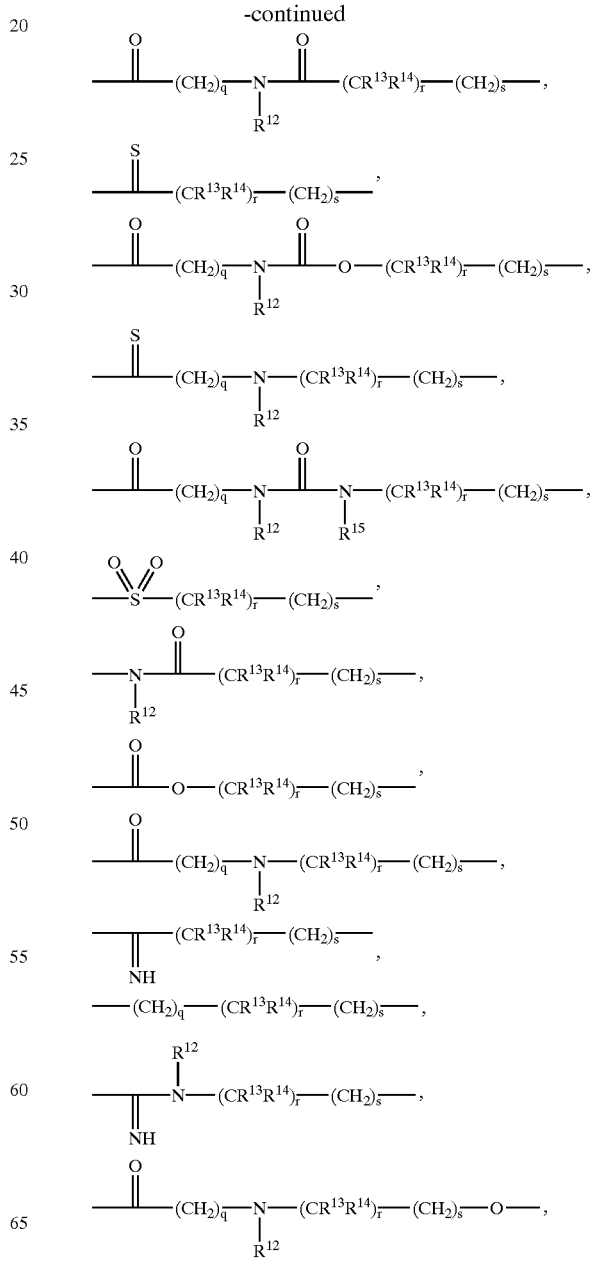

-continued

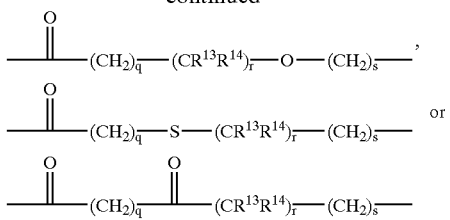

wherein
r is 0 or 1,
q and s independently are 0, 1, 2 or 3,
$R^{12}$, $R^{13}$, $R^{14}$ and $R^{15}$ independently are hydrogen or $C_{1-6}$-alkyl;
D is

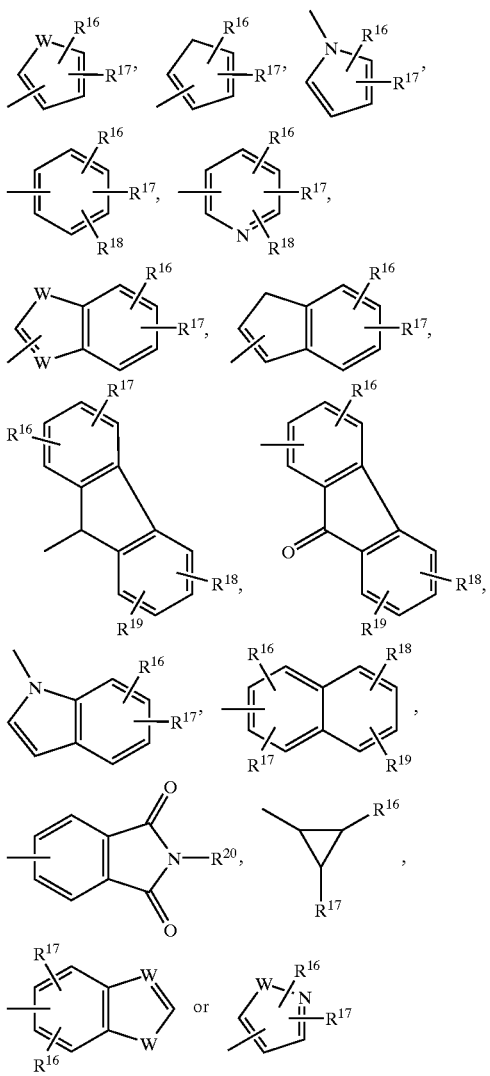

wherein
W is —O—, —S—, —S(O)$_2$— or —NR$^{20}$—,
W' is =CR$^{20'}$— or =N—,
$R^{16}$, $R^{17}$, $R^{18}$ and $R^{19}$ independently are
hydrogen, halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{21}$,
—NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ or —C(O)OR$^{21}$, $C_{1-6}$-alkyl, $C_{2-6}$-alkenyl or $C_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, $C_{3-8}$-cycloalkyl, $C_{4-8}$-cycloalkenyl, heterocyclyl, $C_{3-8}$-cycloalkyl-$C_{1-6}$-alkyl, $C_{3-8}$-cycloalkyl-$C_{1-6}$-alkoxy, $C_{3-8}$-cycloalkyloxy, $C_{3-8}$-cycloalkyl-$C_{1-6}$-alkylthio, $C_{3-8}$-cycloalkylthio, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl or heterocyclyl-$C_{2-4}$-alkynyl,
of which the cyclic moieties optionally may be substituted with one or more substituents selected from
—CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, $C_{1-6}$-alkyl, $C_{2-6}$-alkenyl and $C_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, aryl, aryloxy, aryloxycarbonyl, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl,
of which the aryl and heteroaryl moieties optionally may be substituted with one or more substituents selected from
halogen, —CN, —CH$_2$CN, —CHF$_2$, —CF$_3$, —OCF$_3$, —OCHF$_2$, —OCH$_2$CF$_3$, —OCF$_2$CHF$_2$, —OS(O)$_2$CF$_3$, —SCF$_3$, —NO$_2$, —OR$^{21}$, —NR$^{21}$R$^{22}$, —SR$^{21}$, —NR$^{21}$S(O)$_2$R$^{22}$, —S(O)$_2$NR$^{21}$R$^{22}$, —S(O)NR$^{21}$R$^{22}$, —S(O)R$^{21}$, —S(O)$_2$R$^{21}$, —OS(O)$_2$R$^{21}$, —C(O)NR$^{21}$R$^{22}$, —OC(O)NR$^{21}$R$^{22}$, —NR$^{21}$C(O)R$^{22}$, —CH$_2$C(O)NR$^{21}$R$^{22}$, —OCH$_2$C(O)NR$^{21}$R$^{22}$, —CH$_2$OR$^{21}$, —CH$_2$NR$^{21}$R$^{22}$, —OC(O)R$^{21}$, —C(O)R$^{21}$ and —C(O)OR$^{21}$, $C_{1-6}$-alkyl, $C_{2-6}$-alkenyl and $C_{2-6}$-alkynyl,
which may optionally be substituted with one or more substituents selected from —CHF$_2$, —CF$_3$, —OCF$_3$, —OCHF$_2$, —OCH$_2$CF$_3$, —OCF$_2$CHF$_2$, —SCF$_3$, —OR$^{21}$, —NR$^{21}$R$^{22}$, —SR$^{21}$, —S(O)R$^{21}$, —S(O)$_2$R$^{21}$, —C(O)NR$^{21}$R$^{22}$, —OC(O)NR$^{21}$R$^{22}$, —NR$^{21}$C(O)R$^{22}$, —OCH$_2$C(O)NR$^{21}$R$^{22}$, —C(O)R$^{21}$ and —C(O)OR$^{21}$, wherein $R^{21}$ and $R^{22}$ independently are hydrogen, —$CF_3$, $C_{1-6}$-alkyl, tri-$C_{1-6}$-alkylsilyl, $C_{3-8}$-cycloalkyl, $C_{3-8}$-cycloalkyl-$C_{1-6}$-alkyl, aryl, aryl-$C_{1-6}$-alkyl or heteroaryl, or $R^{21}$ and $R^{22}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, or two of the groups $R^{16}$ to $R^{19}$ when placed in adjacent positions together may form a bridge —$(CR^{16'}R^{17'})_a$—O—$(CR^{18'}R^{19'})_c$—O—, wherein a is 0, 1 or 2, c is 1 or 2, $R^{16'}$, $R^{17'}$, $R^{18'}$ and $R^{19'}$ independently are hydrogen, $C_{1-6}$-alkyl or halogen, $R^{20}$ and $R^{20'}$ independently are hydrogen, $C_{1-6}$-alkyl, $C_{3-8}$-cycloalkyl or $C_{3-8}$-cycloalkyl-$C_{1-6}$-alkyl;

E is a 3 to 9 membered mono- or bicyclic ring which may optionally contain one or two double bonds and which may optionally contain one or two heteroatoms selected from nitrogen, oxygen and sulfur, wherein one or two groups $R^{23}$ and $R^{24}$ may be attached to the same or different ring carbon atoms and wherein a group $R^{31}$ may be attached to a ring nitrogen atom when present, or

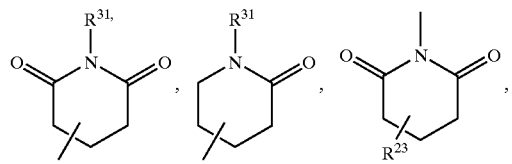

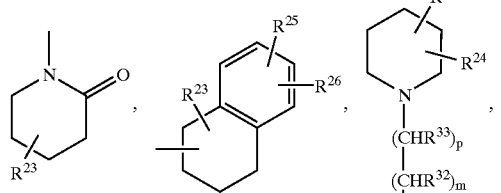

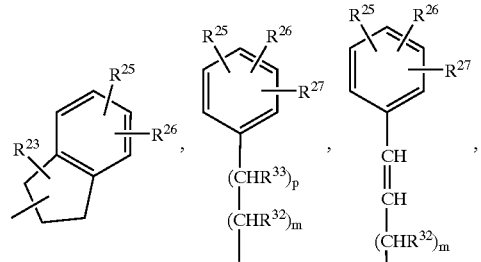

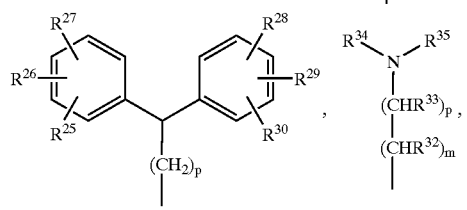

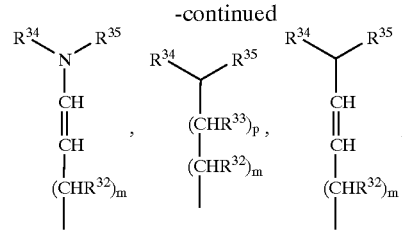

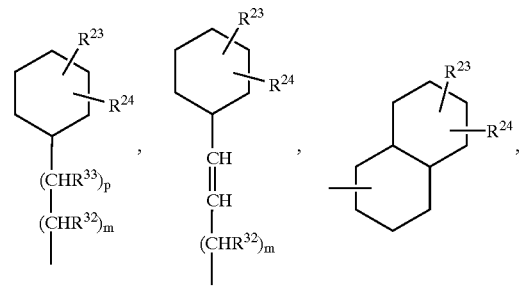

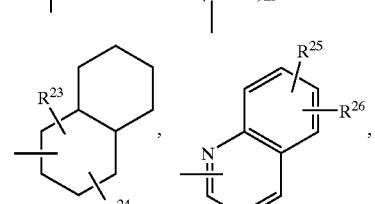

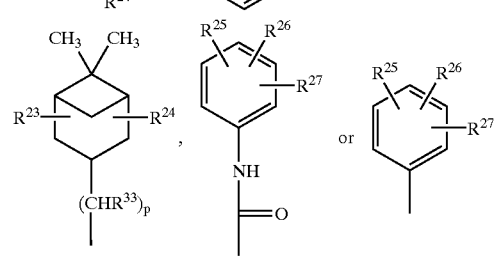

wherein m and p independently are 0, 1, 2, 3 or 4, with the proviso that when both m and p are present in the same formula at least one of m and p is different from 0, $R^{23}$ and $R^{24}$ independently are hydrogen, —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ or —$C(O)OR^{36}$, $C_{1-6}$-alkyl, $C_{2-6}$-alkenyl or $C_{2-6}$-alkynyl, which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, $C_{3-8}$-cycloalkyl, $C_{3-8}$-cycloalkylidene, $C_{4-8}$-cycloalkenyl, heterocyclyl, $C_{3-8}$-cycloalkyl-$C_{1-6}$-alkyl, $C_{3-8}$-cycloalkyl-$C_{2-6}$-alkenyl, $C_{3-8}$-cycloalkyl-$C_{2-6}$-alkynyl, $C_{4-8}$-cycloalkenyl-$C_{1-6}$-alkyl, $C_{4-8}$-cycloalkenyl-$C_{2-6}$-alkenyl, $C_{4-8}$-cycloalkenyl-$C_{2-6}$-alkynyl, heterocyclyl-$C_{1-6}$-alkyl, heterocyclyl-$C_{2-6}$-alkenyl or heterocyclyl-$C_{2-6}$-alkynyl, of which the cyclic moieties optionally may be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, $S(O)_2R^{36}$, $C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, $C_{1-6}$-alkyl, $C_{2-6}$-alkenyl and $C_{2-6}$-alkynyl,
which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, aryl, aryloxy, aroyl, aryl-$C_{1-6}$-alkoxy, aryl-$C_{1-6}$-alkyl, aryl-$C_{2-6}$-alkenyl, aryl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl,
of which the aryl and heteroaryl moieties optionally may be substituted with one or more substituents selected from halogen, —CN, —$CH_2CN$, —$CHF_2$, —$CF_3$, —$OCF_3$, —$OCHF_2$, —$OCH_2CF_3$, —$OCF_2CHF_2$, —$OS(O)_2CF_3$, —$SCF_3$, —$NO_2$, —$OR^{36}$, —$NR^{36}R^{37}$, —$SR^{36}$—$NR^{36}S(O)_2R^{37}$, —$S(O)_2NR^{36}R^{37}$, —$S(O)NR^{36}R^{37}$, —$S(O)R^{36}$, —$S(O)_2R^{36}$, —$OS(O)_2R^{36}$, —$C(O)NR^{36}R^{37}$, —$OC(O)NR^{36}R^{37}$, —$NR^{36}C(O)R^{37}$, —$CH_2C(O)NR^{36}R^{37}$, —$CH_2C(O)NR^{36}R^{37}$, —$CH_2OR^{36}$, —$CH_2NR^{36}R^{37}$, —$OC(O)R^{36}$, —$C(O)R^{36}$ and —$C(O)OR^{36}$, $C_{1-6}$-alkyl, $C_{2-6}$-alkenyl and $C_{2-6}$-alkynyl,
which may optionally be substituted with one or more substituents selected from —$CHF_2$, —$CF_3$, —$OCF_3$, —$OCHF_2$, —$OCH_2CF_3$, —$OCF_2CHF_2$, —$SCF_3$, —$OR^{36}$, —$NR^{36}R^{37}$, —$SR^{36}$, —$S(O)R^{36}$, —$S(O)_2R^{36}$, —$C(O)NR^{36}R^{37}$, —$OC(O)NR^{36}R^{37}$, —$NR^{36}C(O)R^{37}$, —$OCH_2C(O)NR^{36}R^{37}$, —$C(O)R^{36}$ and —$C(O)OR^{36}$, wherein $R^{36}$ and $R^{37}$ independently are hydrogen, $C_{1-6}$-alkyl or aryl,
of which the aryl moiety optionally may be substituted with one or more substituents selected from halogen, —CN, —$CF_3$, —$OCF_3$, —$NO_2$, —$OR^{38}$, —$NR^{38}R^{39}$ and $C_{1-6}$-alkyl,
wherein $R^{38}$ and $R^{39}$ independently are hydrogen or $C_{1-6}$-alkyl,
or $R^{36}$ and $R^{37}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds,
or $R^{23}$ and $R^{24}$ when attached to the same ring carbon atom or different ring carbon atoms together may form a radical —O—$(CH_2)_t$—$CR^{40}R^{41}$—$(CH_2)_l$—O—, —$(CH_2)_t$—$CR^{40}R^{41}$—$(CH_2)_l$— or —S—$(CH_2)_t$—$CR^{40}R^{41}$—$(CH_2)_l$—S—,
wherein
t and l independently are 0, 1, 2, 3, 4 or 5,
$R^{40}$ and $R^{41}$ independently are hydrogen or $C_{1-6}$-alkyl,
$R^{25}$ to $R^{30}$ independently are hydrogen, halogen, —CN, —$CF_3$, —$NO_2$, —$OR^{42}$, —$NR^{42}R^{43}$, $C_{1-6}$-alkyl, $C_{3-8}$-cycloalkyl or $C_{4-8}$-cycloalkenyl,
wherein $R^{42}$ and $R^{43}$ independently are hydrogen or $C_{1-6}$-alkyl, or
$R^{42}$ and $R^{43}$ when attached to the same nitrogen atom together with the said nitrogen atom may form a 3 to 8 membered heterocyclic ring optionally containing one or two further heteroatoms selected from nitrogen, oxygen and sulfur, and optionally containing one or two double bonds, $R^{31}$, $R^{32}$ and $R^{33}$ independently are hydrogen or $C_{1-6}$-alkyl, $R^{34}$ and $R^{35}$ independently are
hydrogen, $C_{1-6}$-alkyl, $C_{1-6}$-alkoxy, $C_{1-6}$-alkanoyl, —$C(O)NR^{44}R^{45}$ or —$S(O)_2R^{45}$,
aryl, aroyl, aryl-$C_{1-6}$-alkoxy, aryl-$C_{1-6}$-alkanoyl or aryl-$C_{1-6}$-alkyl,
of which the aryl moieties optionally may be substituted with one or more substituents selected from halogen, —CN, —$CF_3$, —$OCF_3$, —$OR^{44}$, —$NR^{44}R^{45}$ and $C_{1-6}$-alkyl,
wherein $R^{44}$ and $R^{45}$ independently are hydrogen or $C_{1-6}$-alkyl, or
$R^{34}$ and $R^{35}$ when attached to a carbon atom together with the said carbon atom may form a 3 to 8 membered cyclic ring optionally containing one or two heteroatoms selected from nitrogen, oxygen or sulfur, and optionally containing one or two double bonds, or
$R^{34}$ and $R^{35}$ when attached to a nitrogen atom together with the said nitrogen atom may form a 3 to 8 membered heterocyclic ring optionally containing one or two further heteroatoms selected from nitrogen, oxygen or sulfur, and optionally containing one or two double bonds, as well as any optical or geometric isomer or tautomeric form thereof including mixtures of these or a pharmaceutically acceptable salt thereof.

2. A compound according to claim 1, wherein $R^{46}$ and $R^{47}$ are hydrogen.

3. A compound according to claim 1, wherein $R^1$ is hydrogen.

4. A compound according to claim 1, wherein $R^1$ is methyl.

5. A compound according to claims 1, wherein X is

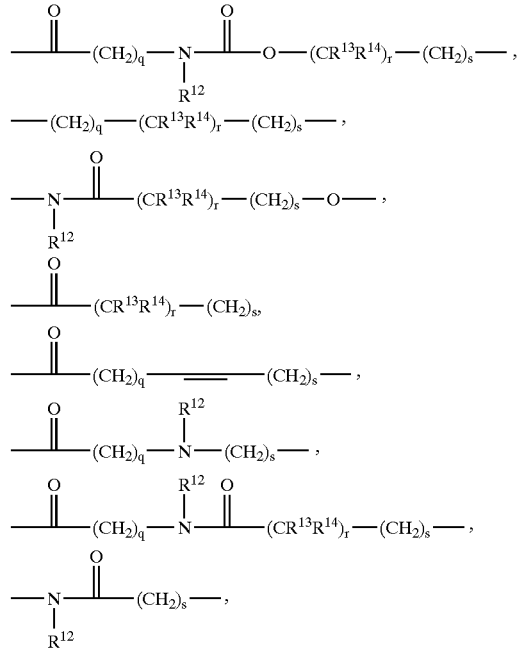

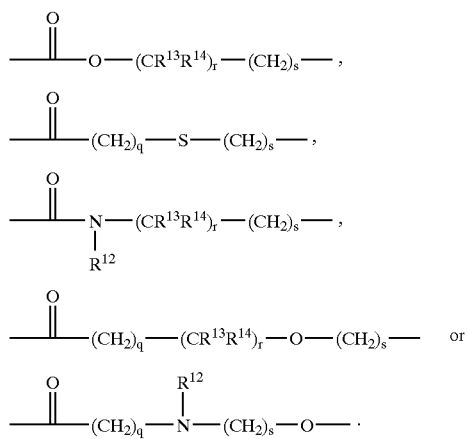

6. A compound according to claim 5, wherein X is

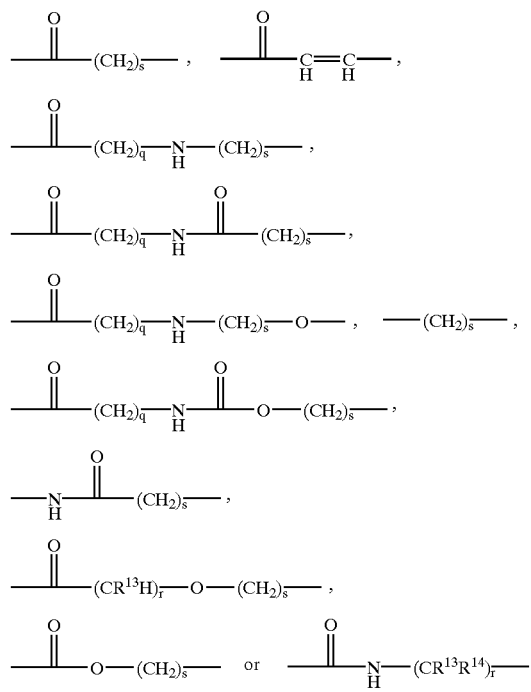

wherein q is 0 or 1, r is 0 or 1, s is 0, 1 or 2, and $R^{13}$ is hydrogen or $C_{1-6}$-alkyl.

7. A compound according to claim 6, wherein X is —C(O)NH—, —C(O)NHCH$_2$—, —C(O)NHCH(CH$_3$)—, —C(O)NHCH$_2$CH$_2$—, —C(O)CH$_2$—, —C(O)CH=CH—, —(CH$_2$)$_s$—, —C(O)—, —C(O)O— or —NHC(O)—, wherein s is 0 or 1.

8. A compound according to claim 7, wherein X is —C(O)NH—, —C(O)NHCH$_2$—, —C(O)NHCH(CH$_3$)—, —C(O)NHCH$_2$CH$_2$—, —C(O)CH$_2$—, —CH$_2$—, —C(O)— or —NHC(O)—.

9. A compound according to claim 8, wherein X is —C(O)NH—.

10. A compound according to claim 9, wherein X is —C(O)NHCH(CH$_3$)—.

11. A compound according to claim 1, wherein D is

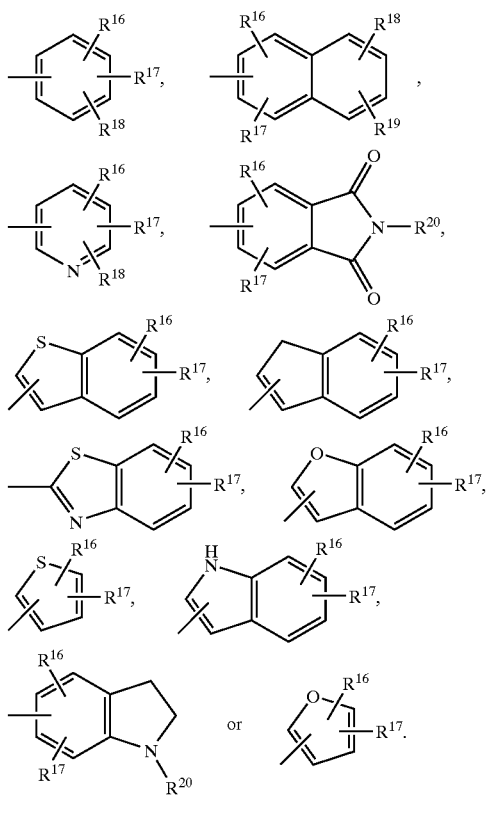

12. A compound according to claim 11, wherein D is

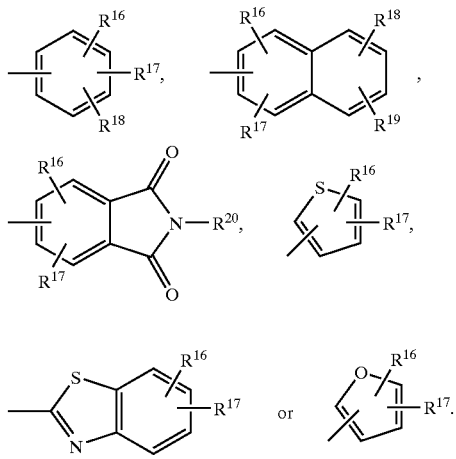

13. A compound according to claim 12, wherein D is

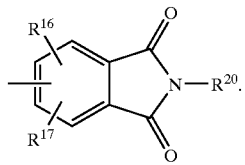

14. A compound according to claim 13, wherein $R^{16}$ and $R^{17}$ are both hydrogen and $R^{20}$ is $C_{1-6}$-alkyl or $C_{3-8}$-cycloalkyl-$C_{1-6}$-alkyl.

15. A compound according to claim 13, wherein $R^{20}$ is cyclopropylmethyl, butyl or isopropyl.

16. A compound according to claim 15, wherein $R^{20}$ is isopropyl.

17. A compound according to claim 12, wherein D is

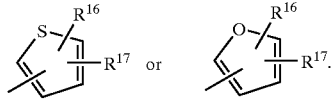

18. A compound according to claim 12, wherein D is

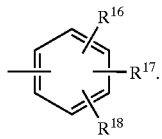

19. A compound according to claim 11, wherein $R^{16}$, $R^{17}$ and $R^{18}$ independently are hydrogen, halogen, —CN, —NO$_2$, —CF$_3$, —OCF$_3$, hydroxy, —SCF$_3$, C$_{1-6}$-alkyl, C$_{1-6}$-alkyl substituted with hydroxy, C$_{1-6}$-alkyl substituted with —S(O)$_2$R$^{21}$, C$_{1-6}$-alkoxy, —S—C$_{1-6}$-alkyl, —C(O)OR$^{21}$, —C(O)R$^{21}$, —CH$_2$(O)R$^{21}$, —C(O)NR$^{21}$R$^{22}$, —S(O)R$^{21}$, —S(O)$_2$R$^{21}$, —S(O)$_2$CF$_3$, —S(O)$_2$NR$^{21}$R$^{22}$, C$_{3-8}$-cycloalkyl, C$_{3-8}$-cycloalkyl-C$_{1-6}$-alkoxy, C$_{3-8}$-cycloalkyl-C$_{1-6}$-alkylthio or C$_{3-8}$-cycloalkylthio, wherein $R^{21}$ and $R^{22}$ independently are hydrogen, C$_{1-6}$-alkyl, tri-C$_{1-6}$-alkylsilyl, C$_{3-8}$-cycloalkyl, C$_{3-8}$-cycloalkyl-C$_{1-6}$-alkyl, phenyl, phenyl-C$_{1-6}$-alkyl, 2,3-dihydroindolyl or isoindolyl, or $R^{21}$ and $R^{22}$ together with the nitrogen atom to which they are attached form a piperidine ring, phenoxy, phenoxycarbonyl, phenyl, phenyl-C$_{1-6}$-alkoxy, phenyl-C$_{1-6}$-alkyl, furanyl, tetrazolyl, benzoxazolyl or oxadiazolyl, of which the ring systems optionally may be substituted with halogen, —CN, —CF$_3$, —OCF$_3$, —NO$_2$, —C(O)OR$^{21}$, —OR$^{21}$, —NR$^{21}$R$^{22}$ or C$_{1-6}$-alkyl, wherein $R^{21}$ and $R^{22}$ independently are hydrogen or C$_{1-6}$-alkyl, or wherein $R^{16}$ and $R^{17}$ in adjacent positions form the radical —O—CH$_2$—O—, —CF$_2$—O—CF$_2$—O— or —O—CF$_2$—CF$_2$—O—, and $R^{18}$ is hydrogen.

20. A compound according to claim 19, wherein $R^{16}$, $R^{17}$ and $R^{18}$ independently are hydrogen, halogen, —CN, —NO$_2$, —CF$_3$, —OCF$_3$, —SCF$_3$, C$_{1-6}$-alkyl, C$_{1-6}$-alkyl substituted with hydroxy, C$_{1-6}$-alkyl substituted with —S(O)$_2$R$^{21}$, C$_{1-6}$-alkoxy, —S—C$_{1-6}$-alkyl, —C(O)OR$^{21}$, —C(O)R$^{21}$, —CH$_2$(O)R$^{21}$, —C(O)NR$^{21}$R$^{22}$, —S(O)R$^{21}$, —S(O)$_2$R$^{21}$, —S(O)$_2$CF$_3$, —S(O)$_2$NR$^{21}$R$^{22}$, C$_{3-8}$-cycloalkyl-C$_{1-6}$-alkoxy, C$_{3-8}$-cycloalkyl-C$_{1-6}$-alkylthio or C$_{3-8}$-cycloalkylthio, wherein $R^{21}$ and $R^{22}$ independently are hydrogen, C$_{1-6}$-alkyl, tri-C$_{1-6}$-alkylsilyl, C$_{3-8}$-cycloalkyl, C$_{3-8}$-cycloalkyl-C$_{1-6}$-alkyl, phenyl or 2,3-dihydroindolyl, or $R^{21}$ and $R^{22}$ together with the nitrogen atom to which they are attached form a piperidine ring, phenoxy, phenyl, benzyl, furanyl, tetrazolyl, benzoxazolyl or oxadiazolyl, of which the ring systems optionally may be substituted with halogen, —C(O)OR$^{21}$ or C$_{1-6}$-alkyl, wherein $R^{21}$ is hydrogen or C$_{1-6}$-alkyl, or wherein $R^{16}$ and $R^{17}$ in adjacent positions form the radical —CF$_2$—O—CF$_2$—O— or —O—CF$_2$—CF$_2$—O—, and $R^{18}$ is hydrogen.

21. A compound according to claim 20, wherein $R^{16}$, $R^{17}$ and $R^{18}$ independently are hydrogen, halogen, —CN, —NO$_2$, —CF$_3$, —OCF$_3$, —SCF$_3$, C$_{1-6}$-alkyl, C$_{1-6}$-alkyl substituted with hydroxy, C$_{1-6}$-alkoxy, —S—C$_{1-6}$-alkyl, —C(O)OR$^{21}$, —C(O)R$^{21}$, —CH$_2$(O)R$^{21}$, —C(O)NR$^{21}$R$^{22}$, —S(O)$_2$R$^{21}$, —(O)$_2$CF$_3$ or —S(O)$_2$N R$^{21}$R$^{22}$, wherein $R^{21}$ and $R^{22}$ independently are hydrogen, C$_{1-6}$-alkyl, tri-C$_{1-6}$-alkylsilyl, phenyl or 2,3-dihydroindolyl, phenoxy, phenyl, benzyl, furanyl, tetrazolyl, benzoxazolyl or oxadiazolyl, of which the ring systems optionally may be substituted with halogen, —C(O)OR$^{21}$ or C$_{1-6}$-alkyl, wherein $R^{21}$ is hydrogen or C$_{1-6}$-alkyl, or wherein $R^{16}$ and $R^{17}$ in adjacent positions form the radical —CF$_2$—O—CF$_2$—O— or —O—CF$_2$—CF$_2$—O—, and $R^{18}$ is hydrogen.

22. A compound according to claim 21, wherein $R^{16}$, $R^{17}$ and $R^{18}$ independently are hydrogen, halogen, —CN, —NO$_2$, —CF$_3$, —OCF$_3$, —SCF$_3$, C$_{1-6}$-alkyl, C$_{1-6}$-alkoxy, —S—C$_{1-6}$-alkyl, —C(O)OC$_{1-6}$-alkyl, —S(O)$_2$C$_{1-6}$-alkyl, —S(O)$_2$CF$_3$, —C(O)N(C$_{1-6}$-alkyl)(C$_{1-6}$-alkyl), —S(O)$_2$N (phenyl)(C$_{1-6}$-alkyl), —C(=O)C$_{1-6}$-alkyl, —CH$_2$OH, —CH$_2$O(tri-C$_{1-6}$-alkylsilyl), 2,3-dihydro-indol-1-ylsulfonyl, phenoxy, phenyl, 4-chlorophenyl, 1,3,5-trimethylbenzyl, benzoxazolyl, 2-methyltetrazol-5-yl, 2-methyl-3-methoxycarbonylfuran-5-yl or 3-isopropyl-[1,2,4]oxadiazol-5-yl).

23. A compound according to claim 19, wherein one of $R^{16}$ to $R^{18}$ is hydrogen.

24. A compound according to claim 19, wherein two of $R^{16}$ to $R^{18}$ are hydrogen.

25. A compound according to claim 19, wherein $R^{16}$ and $R^{17}$ are both hydrogen and $R^{18}$ is —OCF$_3$, —SCF$_3$—CF$_3$, —S(O)$_2$CH$_3$, phenyl, halogen, C$_{1-6}$-alkyl, nitro, —S—C$_{1-6}$-alkyl or —S(O)$_2$NR$^{21}$R$^{22}$, wherein $R^{21}$ is C$_{1-6}$-alkyl and $R^{22}$ is phenyl.

26. A compound according to claim 19, wherein $R^{16}$ and $R^{17}$ are both hydrogen and $R^{18}$ is —OCF$_3$ or halogen.

27. A compound according to claim 19, wherein $R^{16}$ is hydrogen and $R^{17}$ and $R^{18}$ are both halogen or are both —CF$_3$.

28. A compound according to claim 19, wherein $R^{16}$ is hydrogen, $R^{17}$ is —CF$_3$ and $R^{18}$ is halogen, —CN, C$_{1-6}$-alkoxy or —OCF$_3$.

29. A compound according to claim 19, wherein $R^{16}$ is hydrogen, $R^{17}$ is —OCF$_3$ and $R^{18}$ is —S(O)$_2$CH$_3$, —CH$_2$O-tri-C$_{1-6}$-alkylsilyl, benzoxazolyl or —CH$_2$OH.

30. A compound according to claim 19, wherein $R^{16}$ is hydrogen, $R^{17}$ is C$_{1-6}$-alkyl and $R^{18}$ is —S(O)$_2$NR$^{21}$R$^{22}$, wherein $R^{21}$ is C$_{1-6}$-alkyl and $R^{22}$ is phenyl.

31. A compound according to claim 19, wherein $R^{16}$, $R^{17}$ and $R^{18}$ are selected from hydrogen, —OCF$_3$, —CF$_3$, —Br, —F and —Cl.

32. A compound according to claim 1, wherein E is

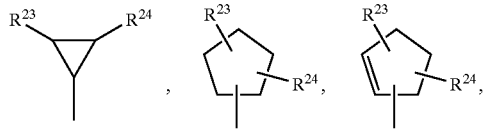

-continued
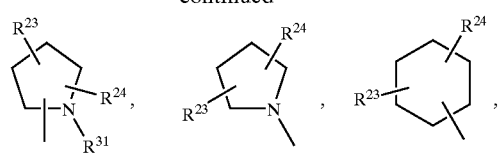
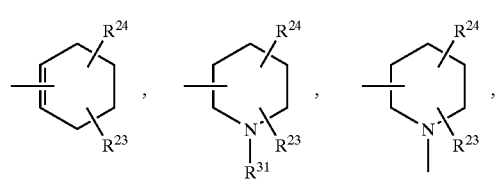
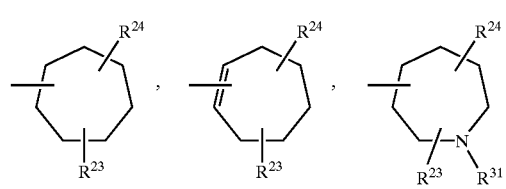
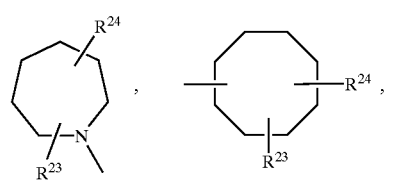
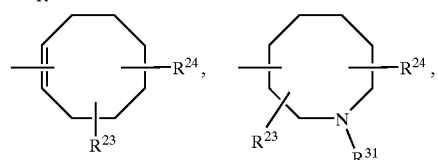
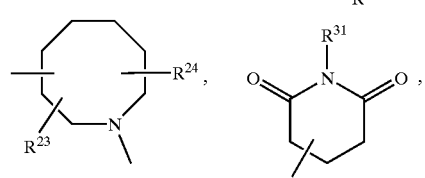
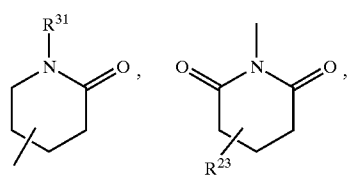
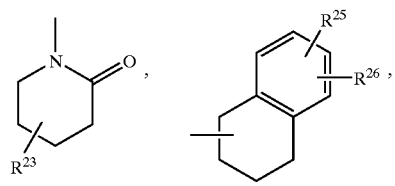
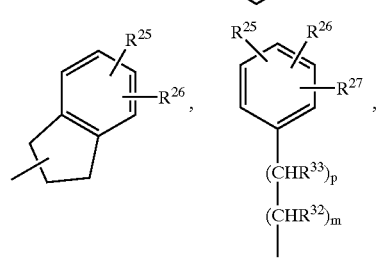
-continued
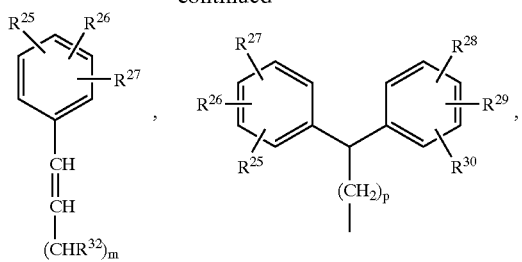
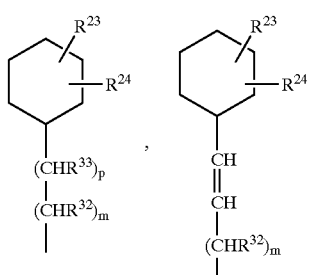
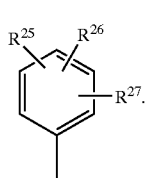
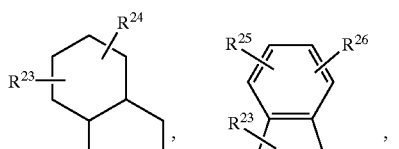
33. A compound according to claim 32, wherein E is
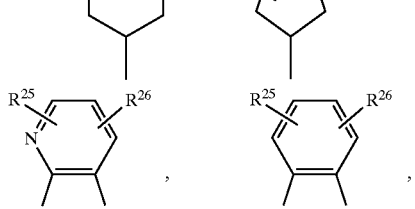
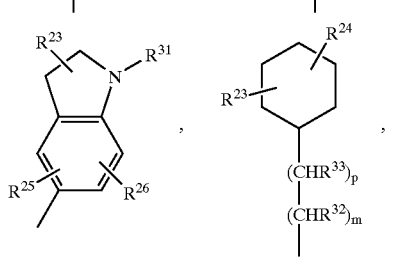

-continued
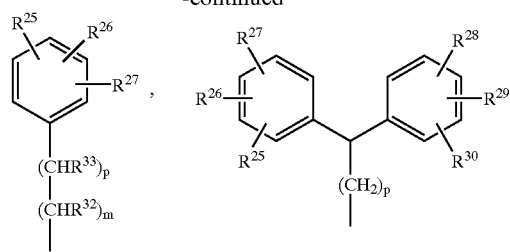
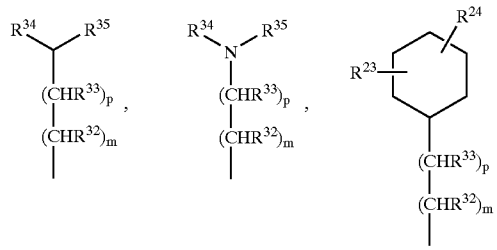
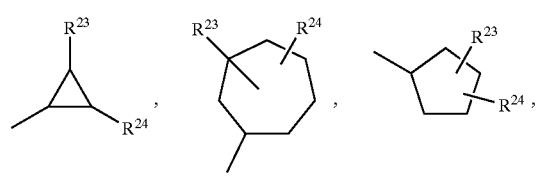
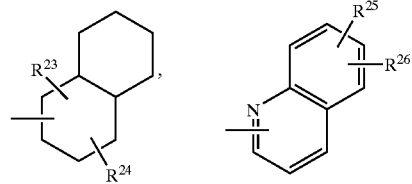
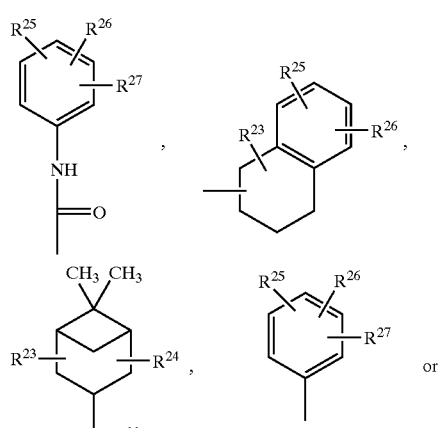
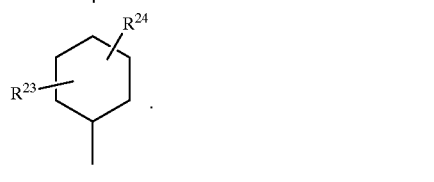
34. A compound according to claim 33, wherein E is
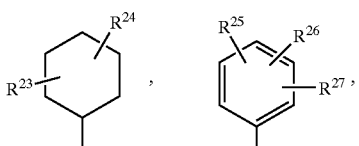
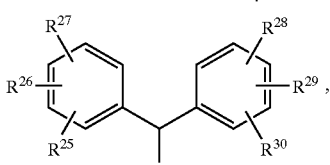
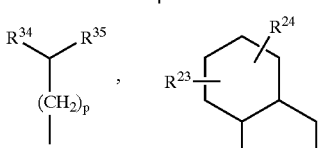
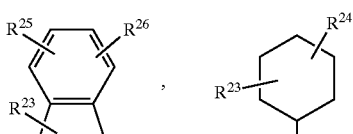
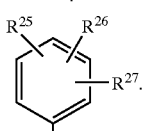
35. A compound according to claim 34, wherein E is
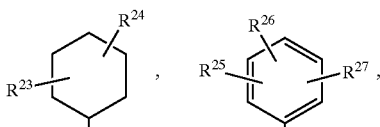
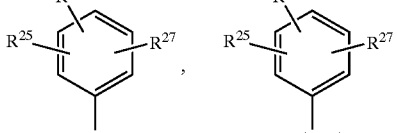
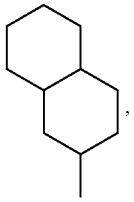

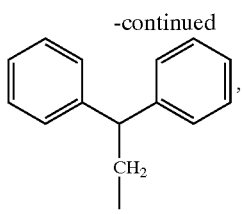

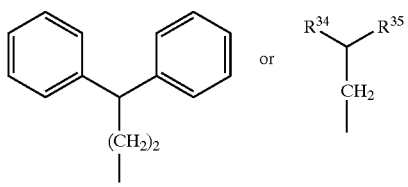

36. A compound according to claim 35, wherein $R^{34}$ and $R^{35}$ independently are $C_{1-6}$-alkyl, hydrogen or $C_{1-6}$-alkoxy.

37. A compound according to claim 36, wherein $R^{34}$ and $R^{35}$ are both $C_{1-6}$-alkyl.

38. A compound according to claim 37, wherein E is

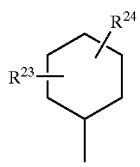

39. A compound according to claim 38, wherein E is

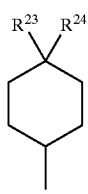

40. A compound according to claim 38, wherein $R^{23}$ and $R^{24}$ independently are selected from hydrogen, $C_{1-6}$-alkyl, $C_{3-8}$-cycloalkyl, $C_{3-8}$-cycloalkylidene, phenoxy, phenyl, —C(O)NR$^{36}$R$^{37}$ and —OC(O)NH-phenyl, of which the phenyl moiety optionally may be substituted with —OCF$_3$, or $R^{23}$ and $R^{24}$ together form the radical —(CH$_2$)$_r$—CR$^{40}$R$^{41}$—(CH$_2$)$_t$—, —O—(CH$_2$)$_r$—CR$^{40}$R$^{41}$—(CH$_2$)$_t$—O—, —S—(CH$_2$)$_r$—CR$^{40}$R$^{41}$—(CH$_2$)$_t$—S—.

41. A compound according to claim 40, wherein $R^{23}$ is hydrogen and $R^{24}$ is $C_{1-6}$-alkyl such as tert-butyl or $C_{3-8}$-cycloalkyl such as cyclohexyl, wherein $R^{23}$ and $R^{24}$ are both $C_{1-6}$-alkyl or wherein $R^{23}$ and $R^{24}$ together form the radical —(CH$_2$)$_5$—.

42. A compound according to claim 35, wherein E is

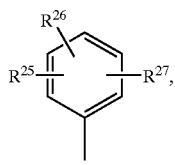

43. A compound according to claim 42, wherein E is

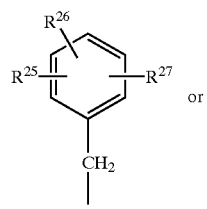

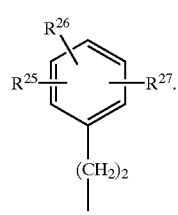

44. A compound according to claim 42, wherein $R^{25}$, $R^{26}$ and $R^{27}$ independently are selected from hydrogen, halogen, $C_{1-6}$-alkyl, $C_{1-6}$-alkoxy, $C_{3-8}$-cycloalkyl, $C_{4-8}$-cycloalkenyl, —CF$_3$, —OCF$_3$ or —NR$^{42}$R$^{43}$, wherein $R^{42}$ and $R^{43}$ are as defined in claim 1.

45. A compound according to claim 44, wherein E is

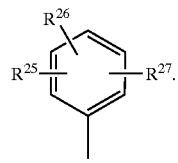

wherein $R^{25}$ is —OCF$_3$, —CF$_3$, $C_{1-6}$-alkyl such as tert-butyl, piperidyl, $C_{3-8}$-cycloalkyl such as cyclohexyl or $C_{4-8}$-cycloalkenyl such as cyclohexenyl.

46. A compound according to claim 45, wherein E is

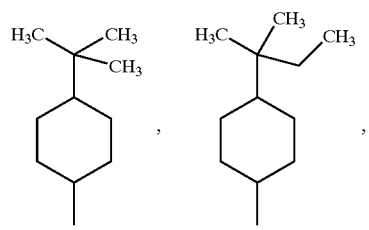

-continued

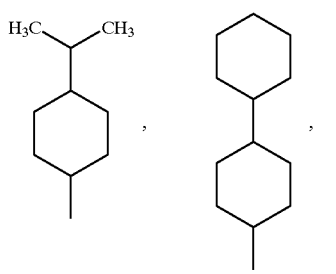

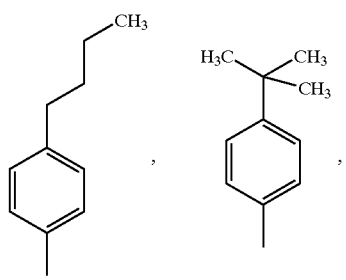

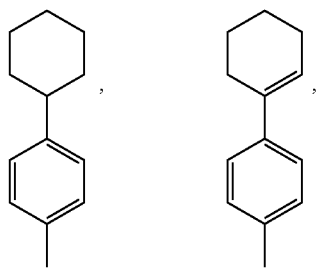

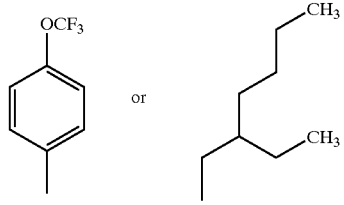

47. A compound according to claim 46, wherein E is

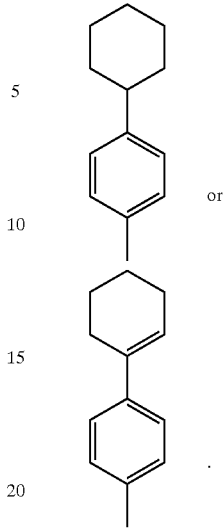

-continued or

48. A compound according to claim 1, which has an $IC_{50}$ value of no greater than 5 μM as determined by Glucagon Binding Assay (I), Glucagon Binding Assay (II) or Glucagon Binding Assay (III).

49. A compound according to claim 48, characterized by having a glucagon antagonistic activity as determined by Glucagon Binding Assay (I), Glucagon Binding Assay (II) or Glucagon Binding Assay (III) corresponding to an $IC_{50}$ value of less than 1 μM.

50. A compound according to claim 48 characterized by having a glucagon antagonistic activity as determined by Glucagon Binding Assay (I), Glucagon Binding Assay (II) or Glucagon Binding Assay (III) corresponding to an $IC_{50}$ value of less than 500 nM.

51. A compound according to claim 48 characterized by having a glucagon antagonistic activity as determined by Glucagon Binding Assay (I), Glucagon Binding Assay (II) or Glucagon Binding Assay (III) corresponding to an $IC_{50}$ value of less than 100 nM.

52. A compound according to claim 1, which is an agent useful for the treatment and/or prevention of an indication selected from the group consisting of hyperglycemia, impaired glucose tolerance, Type 2 diabetes, Type 1 diabetes and obesity.

53. A pharmaceutical composition comprising, as an active ingredient, at least one compound according to claim 1 together with one or more pharmaceutically acceptable carriers or excipients.

54. A pharmaceutical composition according to claim 53 in unit dosage form, said composition comprising from about 0.05 mg to about 1000 mg of said compound.

55. A pharmaceutical composition according to claim 53 in unit dosage form, said composition comprising from about 0.1 mg to about 500 mg of said compound.

56. A pharmaceutical composition according to claim 53 in unit dosage form, said composition comprising from about 0.5 mg to about 200 mg of said compound.

57. A method for the treatment of disorders or diseases mediated by a glucagon antagonistic action, said method comprising administering to a subject in need thereof an effective amount of a compound according to claim 1.

58. The method according to claim 57, wherein the effective amount of the compound is in the range of from about 0.05 mg to about 2000 mg per day.

59. The method according to claim 57, wherein the effective amount of the compound is in the range of from about 0.1 mg to about 1000 mg per day.

60. The method according to claim 57, wherein the effective amount of the compound is in the range of from about 0.5 mg to about 500 mg per day.

61. The method of claim 57, wherein the disorder or disease is selected from the group consisting of hyperglycemia, impaired glucose tolerance (IGT), Type 2 diabetes and Type 1 diabetes.

62. The method of claim 61, wherein said method further comprises administering to said subject an antidiabetic agent.

63. The method of claim 57, wherein the disorder or disease is obesity.

64. The method of claim 63, wherein said method further comprises administering to said subject an antiobesity agent.

65. A method for lowering blood glucose in a mammal, said method comprising administering to a mammal in need thereof an effective amount of a compound according to claim 1.

66. A method for delaying the progression from impaired glucose tolerance to Type 2 diabetes in a subject, said method comprising administering to said subject an effective amount of a compound according to claim 1.

67. A method for delaying the progression from non-insulin requiring Type 2 diabetes to insulin-requiring Type 2 diabetes in a subject, said method comprising administering to said subject an effective amount of a compound according to claim 1.

68. A compound according to claim 18, wherein $R^{16}$, $R^{17}$ and $R^{18}$ independently are hydrogen, halogen, —CN, —$NO_2$, —$CF_3$, —$OCF_3$, hydroxy, —$SCF_3$, $C_{1-6}$-alkyl, $C_{1-6}$-alkyl substituted with hydroxy, $C_{1-6}$-alkyl substituted with —$S(O)_2R^{21}$, $C_{1-6}$-alkoxy, —S—$C_{1-6}$-alkyl, —$C(O)OR^{21}$, —$C(O)R^{21}$, —$CH_2(O)R^{21}$, —$C(O)NR^{21}R^{22}$, —$S(O)R^{21}$, —$S(O)_2R^{21}$, —$S(O)_2CF_3$, —$S(O)_2NR^{21}R^{22}$, $C_{3-8}$-cycloalkyl, $C_{3-8}$-cycloalkyl-$C_{1-6}$-alkoxy, $C_{3-8}$-cycloalkyl-$C_{1-6}$-alkylthio or $C_{3-8}$-cycloalkylthio, wherein $R^{21}$ and $R^{22}$ independently are hydrogen, $C_{1-6}$-alkyl, tri-$C_{1-6}$-alkylsilyl, $C_{3-8}$-cycloalkyl, $C_{3-8}$-cycloalkyl-$C_{1-6}$-alkyl, phenyl, phenyl-$C_{1-6}$-alkyl, 2,3-dihydroindolyl or isoindolyl, or $R^{21}$ and $R^{22}$ together with the nitrogen atom to which they are attached form a piperidine ring, phenoxy, phenoxycarbonyl, phenyl, phenyl-$C_{1-6}$-alkoxy, phenyl-$C_{1-6}$-alkyl, furanyl, tetrazolyl, benzoxazolyl or oxadiazolyl, of which the ring systems optionally may be substituted with halogen, —CN, —$CF_3$, —$OCF_3$, —$NO_2$, —$C(O)OR^{21}$, —$OR^{21}$, —$NR^{21}R^{22}$ or $C_{1-6}$-alkyl, wherein $R^{21}$ and $R^{22}$ independently are hydrogen or $C_{1-6}$-alkyl, or wherein $R^{16}$ and $R^{17}$ in adjacent positions form the radical —O—$CH_2$—O—, —$CF_2$—O—$CF_2$—O— or —O—$CF_2$—$CF_2$—O—, and $R^{18}$ is hydrogen.

69. A compound according to claim 68, wherein $R^{16}$, $R^{17}$ and $R^{18}$ independently are hydrogen, halogen, —CN, —$NO_2$, —$CF_3$, —$OCF_3$, —$SCF_3$, $C_{1-6}$-alkyl, $C_{1-6}$-alkyl substituted with hydroxy, $C_{1-6}$-alkyl substituted with —$S(O)_2R^{21}$, $C_{1-6}$-alkoxy, —S—$C_{1-6}$-alkyl, —$C(O)OR^{21}$, —$C(O)R^{21}$, —$CH_2(O)R^{21}$, —$C(O)NR^{21}R^{22}$, —$S(O)R^{21}$, —$S(O)_2R^{21}$, —$S(O)_2CF_3$, —$S(O)_2NR^{21}R^{22}$, $C_{3-8}$-cycloalkyl-$C_{1-6}$-alkoxy, $C_{3-8}$-cycloalkyl-$C_{1-6}$-alkylthio or $C_{3-8}$-cycloalkylthio, wherein $R^{21}$ and $R^{22}$ independently are hydrogen, $C_{1-6}$-alkyl, tri-$C_{1-6}$-alkylsilyl, $C_{3-8}$-cycloalkyl, $C_{3-8}$-cycloalkyl-$C_{1-6}$-alkyl, phenyl or 2,3-dihydroindolyl, or $R^{21}$ and $R^{22}$ together with the nitrogen atom to which they are attached form a piperidine ring, phenoxy, phenyl, benzyl, furanyl, tetrazolyl, benzoxazolyl or oxadiazolyl, of which the ring systems optionally may be substituted with halogen, —$C(O)OR^{21}$ or $C_{1-6}$-alkyl, wherein $R^{21}$ is hydrogen or $C_{1-6}$-alkyl, or wherein $R^{16}$ and $R^{17}$ in adjacent positions form the radical —$CF_2$—O—$CF_2$—O— or —O—$CF_2$—$CF_2$—O—, and $R^{18}$ is hydrogen.

70. A compound according to claim 69, wherein $R^{16}$, $R^{17}$ and $R^{18}$ independently are hydrogen, halogen, —CN, —$NO_2$, —$CF_3$, —$OCF_3$, —$SCF_3$, $C_{1-6}$-alkyl, $C_{1-6}$-alkyl substituted with hydroxy, $C_{1-6}$-alkoxy, —S—$C_{1-6}$-alkyl, —$C(O)OR^{21}$, —$C(O)R^{21}$, —$CH_2(O)R^{21}$, —$C(O)NR^{21}R^{22}$, —$S(O)R^{21}$, —$(O)_2R^{21}$, or —$S(O)_2R^{2122}$, wherein $R^{21}$ and $R^{22}$ independently are hydrogen, $C_{1-6}$-alkyl, tri-$C_{1-6}$-alkylsilyl, phenyl or 2,3-dihydroindolyl, phenoxy, phenyl, benzyl, furanyl, tetrazolyl, benzoxazolyl or oxadiazolyl, of which the ring systems optionally may be substituted with halogen, —$C(O)OR^{21}$ or $C_{1-6}$-alkyl, wherein $R^{21}$ is hydrogen or $C_{1-6}$-alkyl, or wherein $R^{16}$ and $R^{17}$ in adjacent positions form the radical —$CF_2$—O—$CF_2$—O— or —O—$CF_2$—$CF_2$—O—, and $R^{18}$ is hydrogen.

71. A compound according to claim 70, wherein $R^{16}$, $R^{17}$ and $R^{18}$ independently are hydrogen, halogen, —CN, —$NO_2$, —$CF_3$, —$OCF_3$, —$SCF_3$, $C_{1-6}$-alkyl, $C_{1-6}$-alkoxy, —S—$C_{1-6}$-alkyl, —$C(O)OC_{1-6}$-alkyl, —$S(O)_2C_{1-6}$-alkyl, —$S(O)_2CF_3$, —$C(O)N(C_{1-6}$-alkyl)($C_{1-6}$-alkyl), —$S(O)_2N$(phenyl)($C_{1-6}$-alkyl), —C(=O)$C_{1-6}$-alkyl, —$CH_2OH$, —$CH_2O$(tri-$C_{1-6}$-alkylsilyl), 2,3-dihydro-indol-1-ylsulfonyl, phenoxy, phenyl, 4-chlorophenyl, 1,3,5-trimethylbenzyl, benzoxazolyl, 2-methyltetrazol-5-yl, 2-methyl-3-methoxycarbonylfuran-5-yl or 3-isopropyl-[1,2,4]oxadiazol-5-yl).

72. A compound according to claim 68, wherein one of $R^{16}$ to $R^{18}$ is hydrogen.

73. A compound according to claim 68, wherein two of $R^{16}$ to $R^{18}$ are hydrogen.

74. A compound according to claim 68, wherein $R^{16}$ and $R^{17}$ are both hydrogen and $R^{18}$ is —$OCF_3$, —$SCF_3$—$CF_3$, —$S(O)_2CH_3$, phenyl, halogen, $C_{1-6}$-alkyl, nitro, —S—$C_{1-6}$-alkyl or —$S(O)_2NR^{21}R^{22}$, wherein $R^{21}$ is $C_{1-6}$-alkyl and $R^{22}$ is phenyl.

75. A compound according to claim 68, wherein $R^{16}$ and $R^{17}$ are both hydrogen and $R^{18}$ is —$OCF_3$ or halogen.

76. A compound according to claim 68, wherein $R^{16}$ is hydrogen and $R^{17}$ and $R^{18}$ are both halogen or are both —$CF_3$.

77. A compound according to claim 68, wherein $R^{16}$ is hydrogen, $R^{17}$ is —$CF_3$ and $R^{18}$ is halogen, —CN, $C_{1-6}$-alkoxy or —$OCF_3$.

78. A compound according to claim 68, wherein $R^{16}$ is hydrogen, $R^{17}$ is —$OCF_3$ and $R^{18}$ is —$S(O)_2CH_3$, —$CH_2O$-tri-$C_{1-6}$-alkylsilyl, benzoxazolyl or —$CH_2OH$.

79. A compound according to claim 68, wherein $R^{16}$ is hydrogen, $R^{17}$ is $C_{1-6}$-alkyl and $R^{18}$ is —$S(O)_2NR^{21}R^{22}$, wherein $R^{21}$ is $C_{1-6}$-alkyl and $R^{22}$ is phenyl.

80. A compound according to claim 68, wherein $R^{16}$, $R^{17}$ and $R^{18}$ are selected from hydrogen, —$OCF_3$, —$CF_3$, —Br, —F and —Cl.

* * * * *